US012280103B2

(12) United States Patent
Liang et al.

(10) Patent No.: US 12,280,103 B2
(45) Date of Patent: *Apr. 22, 2025

(54) CORONAVIRUS VACCINE COMPOSITIONS, METHODS, AND USES THEREOF

(71) Applicant: Sichuan Clover Biopharmaceuticals, Inc., Sichuan (CN)

(72) Inventors: Peng Liang, Chengdu Sichuan (CN); Joshua Liang, Chengdu Sichuan (CN)

(73) Assignee: Sichuan Clover Biopharmaceuticals, Inc., Chengdu (CN)

( * ) Notice: Subject to any disclaimer, the term of this patent is extended or adjusted under 35 U.S.C. 154(b) by 9 days.

This patent is subject to a terminal disclaimer.

(21) Appl. No.: 17/832,664

(22) Filed: Jun. 5, 2022

(65) Prior Publication Data

US 2023/0096093 A1 Mar. 30, 2023

Related U.S. Application Data

(63) Continuation of application No. 17/489,572, filed on Sep. 29, 2021, now Pat. No. 11,389,528, which is a continuation of application No. PCT/CN2021/099285, filed on Jun. 10, 2021.

(30) Foreign Application Priority Data

Jun. 10, 2020 (WO) ................ PCT/CN2020/095269
Apr. 13, 2021 (WO) ................ PCT/CN2021/087066
May 14, 2021 (WO) ................ PCT/CN2021/093895

(51) Int. Cl.

| | |
|---|---|
| *A61K 39/215* | (2006.01) |
| *A61K 39/00* | (2006.01) |
| *A61P 31/14* | (2006.01) |
| *A61P 37/04* | (2006.01) |
| *C07K 14/005* | (2006.01) |
| *C07K 14/78* | (2006.01) |

(52) U.S. Cl.
CPC ............ *A61K 39/215* (2013.01); *A61P 37/04* (2018.01); *C07K 14/005* (2013.01); *C07K 14/78* (2013.01); *A61K 2039/54* (2013.01); *A61K 2039/543* (2013.01); *A61K 2039/545* (2013.01); *C07K 2319/00* (2013.01); *C12N 2770/20022* (2013.01); *C12N 2770/20034* (2013.01); *C12N 2770/20071* (2013.01)

(58) Field of Classification Search
CPC ....... G01N 2333/165; G01N 33/56983; A61K 2039/6031; A61K 39/12; A61K 39/215
See application file for complete search history.

(56) References Cited

U.S. PATENT DOCUMENTS

| | | | |
|---|---|---|---|
| 5,605,690 | A | 2/1997 | Jacobs et al. |
| 6,171,827 | B1 | 1/2001 | Bulleid et al. |
| 6,190,886 | B1 | 2/2001 | Hoppe et al. |
| 6,277,600 | B1 | 8/2001 | Tomita et al. |
| 6,617,431 | B1 | 9/2003 | Gruber et al. |
| 7,268,116 | B2 | 9/2007 | Liang |
| 7,666,837 | B2 | 2/2010 | Liang |
| 7,691,815 | B2 | 4/2010 | Liang |
| 10,906,944 | B2 | 2/2021 | He et al. |
| 10,960,070 | B2 | 3/2021 | Graham et al. |
| 11,111,284 | B2 | 9/2021 | Faustman et al. |
| 2003/0143564 | A1 | 7/2003 | Burgeson et al. |
| 2003/0148466 | A1 | 8/2003 | Fox et al. |
| 2004/0197876 | A1 | 10/2004 | Tschopp et al. |
| 2005/0202537 | A1 | 9/2005 | Liang |
| 2007/0087413 | A1 | 4/2007 | Liang |
| 2007/0117755 | A1 | 5/2007 | Liang |
| 2020/0009244 | A1 | 1/2020 | He et al. |
| 2021/0246170 | A1 | 8/2021 | Langedijk et al. |

(Continued)

FOREIGN PATENT DOCUMENTS

| | | | |
|---|---|---|---|
| CN | 106928326 | A | 7/2017 |
| CN | 111592602 | A | 8/2020 |

(Continued)

OTHER PUBLICATIONS

Addetia et al., "Neutralizing Antibodies Correlate with Protection from SARS-CoV-2 in Humans during a Fishery Vessel Outbreak with a High Attack Rate," J Clin Microbiol. (2020) 58(11):e02107-20.

Baker et al., "Structures of bovine and human papillomaviruses. Analysis by cryoelectron microscopy and three-dimensional image reconstruction," Biophys J. (1991) 60(6):1445-56.

Barouch et al., "A human T-cell leukemia virus type 1 regulatory element enhances the immunogenicity of human immunodeficiency virus type 1 DNA vaccines in mice and nonhuman primates," J Virol. (2005) 79(14):8828-34.

Bode et al., "CpG DNA as a vaccine adjuvant," Expert Rev Vaccines. (2011) 10(4):499-511.

(Continued)

*Primary Examiner* — Barry A Chestnut
(74) *Attorney, Agent, or Firm* — Knobbe, Martens, Olson & Bear, LLP

(57) ABSTRACT

The present disclosure relates in some aspects to immunogenic compositions including recombinant peptides and proteins comprising coronavirus viral antigens and immunogens, e.g., coronavirus S protein peptides. In some aspects, the immunogenic composition comprises a secreted fusion protein comprising a soluble coronavirus viral antigen joined by in-frame fusion to a C-terminal portion of a collagen which is capable of self-trimerization to form a disulfide bond-linked trimeric fusion protein. In some aspects, the immunogenic compositions provided herein are useful for generating an immune response, e.g., for treating or preventing a coronavirus infection. In some aspects, the immunogenic compositions provided herein may be used in a vaccine composition, e.g., as part of a prophylactic and/or therapeutic vaccine. Also provided herein are methods for producing the recombinant peptides and proteins, prophylactic, therapeutic, and/or diagnostic methods, and related kits.

20 Claims, 18 Drawing Sheets

Specification includes a Sequence Listing.

(56) References Cited

U.S. PATENT DOCUMENTS

| | | |
|---|---|---|
| 2021/0268102 A1 | 9/2021 | Yan et al. |
| 2021/0275665 A1 | 9/2021 | Cho et al. |
| 2021/0308257 A1 | 10/2021 | Kuo et al. |
| 2021/0355170 A1 | 11/2021 | Whitehead et al. |

FOREIGN PATENT DOCUMENTS

| | | |
|---|---|---|
| CN | 112220920 | 1/2021 |
| CN | 112266411 | 1/2021 |
| CN | 112480217 | 3/2021 |
| CN | 113185613 | 4/2021 |
| CN | 113234170 | 4/2021 |
| CN | 113480618 | 10/2021 |
| WO | WO 1997/017988 | 5/1997 |
| WO | WO 2016/029043 | 2/2016 |
| WO | WO 2021/154812 | 8/2021 |
| WO | WO 2021/160346 | 8/2021 |
| WO | WO 2021/163365 | 8/2021 |
| WO | WO 2021/170131 | 9/2021 |
| WO | WO 2021/174128 | 9/2021 |
| WO | WO 2021/178318 | 9/2021 |
| WO | WO 2021/178321 | 9/2021 |
| WO | WO 2021/178971 | 9/2021 |
| WO | WO 2021/189056 | 9/2021 |
| WO | WO 2021/198706 | 10/2021 |
| WO | WO 2021/204179 | 10/2021 |
| WO | WO 2021/205455 | 10/2021 |
| WO | WO 2021/214703 | 10/2021 |
| WO | WO 2021/216743 | 10/2021 |
| WO | WO 2021/226436 | 11/2021 |
| WO | WO 2021/228842 | 11/2021 |
| WO | WO 2021/243122 | 12/2021 |
| WO | WO 2021/245611 | 12/2021 |
| WO | WO 2021/249012 | 12/2021 |
| WO | WO 2021/249116 | 12/2021 |
| WO | WO 2021/249451 | 12/2021 |

OTHER PUBLICATIONS

Bradley et al., "Hepatitis A virus: growth characteristics of in vivo and in vitro propagated wild and attenuated virus strains," J Med Virol. (1984) 14(4): 373-86. (Abstract only).

Braun et al., "Immunogenic duplex nucleic acids are nuclease resistant," J Immunol. (1988) 141(6): 2084-9. (Abstract only).

Brito et al., "Self-amplifying mRNA vaccines," Adv Genet. (2015); 89:179-233. (Abstract only).

Cai et al., "Distinct conformational states of SARS-CoV-2 spike protein," Science. (2020) 369(6511): 1586-1592.

Clover Biopharmaceuticals & GSK, "Clover and GSK announce research collaboration to evaluate coronavirus (COVID-19) vaccine candidate with pandemic adjuvant system,", Feb. 24, 2020 (Feb. 24, 2020).

Clover Biopharmaceuticals & GSK, "GlaxoSmithKline and Clover collaborate to evaluate the combination of novel coronavirus vaccine candidate and pandemic vaccine adjuvant system,"Feb. 24, 2020 (Feb. 24, 2020).

Coffman et al., "Vaccine adjuvants: putting innate immunity to work," Immunity. (2010) 33(4):492-503.

De Felipe, "Skipping the co-expression problem: the new 2A "Chysel" technology," Genet Vaccines Ther Sep. 13, 2004;2(1):13.

De Felipe, "Targeting of proteins derived from self-processing polyproteins containing multiple signal sequences," Traffic (2004) 5(8):616-626.

Gao et al., "Development of an inactivated vaccine candidate for SARS-CoV-2," Science. (2020) 369(6499): 77-81.

Garcon et al., "Development and evaluation of AS03, an Adjuvant System containing α-tocopherol and squalene in an oil-in-water emulsion," Expert Rev Vaccines. (2012) 11(3):349-66.

Geall et al., "Nonviral delivery of self-amplifying RNA vaccines," Proc Natl Acad Sci U S A. (2012) 109(36): 14604-9.

Gil Carmen et al: "COVID-19: Drug Targets and Potential Treatments", Journal of Medicinal Chemistry, vol. 63, No. 21, Jun. 8, 2020 (Jun. 8, 2020), pp. 12359-12386, ISSN: 0022-2623, DOI: 10.1021/acs.jmedchem.Oc00606.

Hagansee et al., "Three-dimensional structure of vaccinia virus-produced human papillomavirus type 1 capsids," J Virol. (1994) 68(7): 4503-5.

Harbury et al., "A switch between two-, three-, and four-stranded coiled coils in GCN4 leucine zipper mutants," Science. (1993) 262(5138):1401-7.

Hoppe et al., "A parallel three stranded alpha-helical bundle at the nucleation site of collagen triple-helix formation," FEBS Lett. (1994) 344(2-3): 191-5.

James et al., "Safe administration of the measles vaccine to children allergic to eggs," N Engl J Med. (1995) 332(19):1262-6.

Kirchdoerfer et al., "Pre-fusion structure of a human coronavirus spike protein," Nature. (2016) 531(7592): 118-21.

Lanying Du et al: "The spike protein of SARS-CoV a target to vaccine and therapeutic development", Nature Reviews Microbiology, vol. 7, No. 3, Mar. 1, 2009 (Mar. 1, 2009), pp. 226-236, ISSN: 1740-1526, DOI: 10.1038/nrmicro2090.

Latimer et al., "Specificity of monoclonal antibodies produced against phosphorothioate and ribo modified DNAs," Mol Immunol. (1995) 32(14-15): 1057-64. (Abstract only).

Liang et al., "S-Trimer, a COVID-19 subunit vaccine candidate, induces protective immunity in nonhuman primates," Nat Commun. (2021) 12(1):1346.

Liu et al., "Improvement of Pharmacokinetic Profile of TRAIL via Trimer-Tag Enhances its Antitumor Activity in vivo," Sci Rep. (2017) 7(1): 8953.

Ma et al. "Cryo-EM structure of S-Trimer, a subunit vaccine candidate for COVID-19," bioRxiv 2020.09.21.306357. doi:10. 1101/2020.09.21.306357.

Ma et al., "Cryo-EM structure of S-Trimer, a subunit vaccine candidate for COVID-19," J Virol. (2021) 95(11): e00194-21. doi:10.1128/JVI.00194-21.

Magini et al., "Self-Amplifying mRNA Vaccines Expressing Multiple Conserved Influenza Antigens Confer Protection against Homologous and Heterosubtypic Viral Challenge," PLoS One. (2016) 11(8):e0161193.

McAlinden et al., "Alpha-helical coiled-coil oligomerization domains are almost ubiquitous in the collagen superfamily," J Biol Chem. (2003) 278(43): 42200-42207.

Miroshnikov et al., "Engineering trimeric fibrous proteins based on bacteriophage T4 adhesins," Protein Eng. (1998) 11(4):329-32.

Mohler et al., "Soluble Tumor Necrosis Factor (TNF) Receptors Are Effective Therapeutic Agents in Lethal Endotoxemia and Function Simultaneously as Both TNF Carriers and TNF Antagonists," J. of Immunology, vol. 151, No. 3, p. 1548-1561, 1993.

Morel et al., "Adjuvant System AS03 containing a-tocopherol modulates innate immune response and leads to improved adaptive immunity," Vaccine. (2011) 29(13): 2461-73.

Mowat et al., "ISCOMS—a novel strategy for mucosal immunization?," Immunol Today. (1991) 12(11): 383-5. (Abstract only).

Munster et al., Respiratory disease and virus shedding in rhesus macaques inoculated with SARS-CoV-2, Nature. (2020) 585: 268-272.

Newman et al., "Use of nonionic block copolymers in vaccines and therapeutics," Crit Rev Ther Drug Carrier Syst. (1998); 15(2): 89-142. (Abstract only).

O'Hagen et al., "The history of MF59(®) adjuvant: a phoenix that arose from the ashes," Expert Rev Vaccines. (2013) 12(1): 13-30.

Petsch et al., "Protective efficacy of in vitro synthesized, specific mRNA vaccines against influenza A virus infection," Nat Biotechnol. (2012) 30(12): 1210-6.

Pramanick et al., "Excipient Selection In Parenteral Formulation Development," Pharma Times. (2013) 45: 65-77.

Richmond et al., "Safety and immunogenicity of S-Trimer (SCB-2019), a protein subunit vaccine candidate for COVID-19 in healthy adults: a phase 1, randomised, double-blind, placebo-controlled trial," Lancet. (2021) ;397(10275): 682-694.

(56) References Cited

OTHER PUBLICATIONS

Shah et al., "Overview of Vaccine Adjuvants: Introduction, History, and Current Status," Methods Mol Biol. (2017) 1494:1-13. (Abstract only).
Shaw et al., "Heterologous prime-boost COVID-19 vaccination: initial reactogenicity data," Lancet. (2021) 397(10289): 2043-2046.
Stover et al., "New use of BCG for recombinant vaccines," Nature. (1991) 351(6326): 456-60.
Takahashi et al., "Induction of CD8+ cytotoxic T cells by immunization with purified HIV-1 envelope protein in ISCOMs," Nature. (1990) 344(6269): 873-875. (Abstract only).
Vatti et al., "Original antigenic sin: A comprehensive review," J Autoimmun. (2017) 83:12-21.
Walls et al., "Structure, Function, and Antigenicity of the SARS-CoV-2 Spike Glycoprotein," Cell. (2020) 181(2): 281-292.e6.
Wu et al., "Variant SARS-CoV-2 mRNA vaccines confer broad neutralization as primary or booster series in mice," bioRxiv. Oct. 7, 2021;2021.04.13.439482.
Wu et al., "Serum Neutralizing Activity Elicited by mRNA-1273 Vaccine," N Engl J Med. (2021) 384(15): 1468-1470.
Wu et al., "A new coronavirus associated with human respiratory disease in China," Nature. (2020) 579(7798): 265-269.

ID

SEQUENCE LISTING

<160> NUMBER OF SEQ ID NOS: 80

<210> SEQ ID NO 1
<211> LENGTH: 1509
<212> TYPE: PRT
<213> ORGANISM: Artificial Sequence
<220> FEATURE:
<223> OTHER INFORMATION: Synthetic construct

<400> SEQUENCE: 1

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140

```
Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
            195                 200                 205

Ala Leu Glu Pro Leu Val Asp Leu Pro Ile Gly Ile Asn Ile Thr Arg
210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Tyr Tyr Val Gly Tyr
                245                 250                 255

Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
            275                 280                 285

Thr Leu Lys Ser Phe Thr Val Glu Lys Gly Ile Tyr Gln Thr Ser Asn
290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
                340                 345                 350

Ser Val Leu Tyr Asn Ser Ala Ser Phe Ser Thr Phe Lys Cys Tyr Gly
                355                 360                 365

Val Ser Pro Thr Lys Leu Asn Asp Leu Cys Phe Thr Asn Val Tyr Ala
370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
            405                 410                 415

Thr Gly Cys Val Ile Ala Trp Asn Ser Asn Asn Leu Asp Ser Lys Val
            420                 425                 430

Gly Gly Asn Tyr Asn Tyr Leu Tyr Arg Leu Phe Arg Lys Ser Asn Leu
            435                 440                 445

Lys Pro Phe Glu Arg Asp Ile Ser Thr Glu Ile Tyr Gln Ala Gly Ser
450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
            485                 490                 495

Val Val Val Leu Ser Phe Glu Leu Leu His Ala Pro Ala Thr Val Cys
            500                 505                 510

Gly Pro Lys Lys Ser Thr Asn Leu Val Lys Asn Lys Cys Val Asn Phe
            515                 520                 525

Asn Phe Asn Gly Leu Thr Gly Thr Gly Val Leu Thr Glu Ser Asn Lys
            530                 535                 540

Lys Phe Leu Pro Phe Gln Gln Phe Gly Arg Asp Ile Ala Asp Thr Thr
545                 550                 555                 560
```

```
Asp Ala Val Arg Asp Pro Gln Thr Leu Glu Ile Leu Asp Ile Thr Pro
                565                 570                 575
Cys Ser Phe Gly Gly Val Ser Val Ile Thr Pro Gly Thr Asn Thr Ser
                580                 585                 590
Asn Gln Val Ala Val Leu Tyr Gln Asp Val Asn Cys Thr Glu Val Pro
                595                 600                 605
Val Ala Ile His Ala Asp Gln Leu Thr Pro Thr Trp Arg Val Tyr Ser
610                 615                 620
Thr Gly Ser Asn Val Phe Gln Thr Arg Ala Gly Cys Leu Ile Gly Ala
625                 630                 635                 640
Glu His Val Asn Asn Ser Tyr Glu Cys Asp Ile Pro Ile Gly Ala Gly
                645                 650                 655
Ile Cys Ala Ser Tyr Gln Thr Gln Thr Asn Ser Pro Arg Arg Ala Arg
                660                 665                 670
Ser Val Ala Ser Gln Ser Ile Ile Ala Tyr Thr Met Ser Leu Gly Ala
                675                 680                 685
Glu Asn Ser Val Ala Tyr Ser Asn Asn Ser Ile Ala Ile Pro Thr Asn
                690                 695                 700
Phe Thr Ile Ser Val Thr Thr Glu Ile Leu Pro Val Ser Met Thr Lys
705                 710                 715                 720
Thr Ser Val Asp Cys Thr Met Tyr Ile Cys Gly Asp Ser Thr Glu Cys
                725                 730                 735
Ser Asn Leu Leu Leu Gln Tyr Gly Ser Phe Cys Thr Gln Leu Asn Arg
                740                 745                 750
Ala Leu Thr Gly Ile Ala Val Glu Gln Asp Lys Asn Thr Gln Glu Val
                755                 760                 765
Phe Ala Gln Val Lys Gln Ile Tyr Lys Thr Pro Pro Ile Lys Asp Phe
770                 775                 780
Gly Gly Phe Asn Phe Ser Gln Ile Leu Pro Asp Pro Ser Lys Pro Ser
785                 790                 795                 800
Lys Arg Ser Phe Ile Glu Asp Leu Leu Phe Asn Lys Val Thr Leu Ala
                805                 810                 815
Asp Ala Gly Phe Ile Lys Gln Tyr Gly Asp Cys Leu Gly Asp Ile Ala
                820                 825                 830
Ala Arg Asp Leu Ile Cys Ala Gln Lys Phe Asn Gly Leu Thr Val Leu
835                 840                 845
Pro Pro Leu Leu Thr Asp Glu Met Ile Ala Gln Tyr Thr Ser Ala Leu
850                 855                 860
Leu Ala Gly Thr Ile Thr Ser Gly Trp Thr Phe Gly Ala Gly Ala Ala
865                 870                 875                 880
Leu Gln Ile Pro Phe Ala Met Gln Met Ala Tyr Arg Phe Asn Gly Ile
                885                 890                 895
Gly Val Thr Gln Asn Val Leu Tyr Glu Asn Gln Lys Leu Ile Ala Asn
                900                 905                 910
Gln Phe Asn Ser Ala Ile Gly Lys Ile Gln Asp Ser Leu Ser Ser Thr
                915                 920                 925
Ala Ser Ala Leu Gly Lys Leu Gln Asp Val Val Asn Gln Asn Ala Gln
                930                 935                 940
Ala Leu Asn Thr Leu Val Lys Gln Leu Ser Ser Asn Phe Gly Ala Ile
945                 950                 955                 960
Ser Ser Val Leu Asn Asp Ile Leu Ser Arg Leu Asp Lys Val Glu Ala
                965                 970                 975
Glu Val Gln Ile Asp Arg Leu Ile Thr Gly Arg Leu Gln Ser Leu Gln
```

-continued

```
                980             985             990
Thr Tyr Val Thr Gln Gln Leu Ile Arg Ala Ala Glu Ile Arg Ala Ser
            995                1000                1005
Ala Asn Leu Ala Ala Thr Lys Met Ser Glu Cys Val Leu Gly Gln Ser
    1010                1015                1020
Lys Arg Val Asp Phe Cys Gly Lys Gly Tyr His Leu Met Ser Phe Pro
1025                1030                1035                1040
Gln Ser Ala Pro His Gly Val Val Phe Leu His Val Thr Tyr Val Pro
                1045                1050                1055
Ala Gln Glu Lys Asn Phe Thr Thr Ala Pro Ala Ile Cys His Asp Gly
            1060                1065                1070
Lys Ala His Phe Pro Arg Glu Gly Val Phe Val Ser Asn Gly Thr His
        1075                1080                1085
Trp Phe Val Thr Gln Arg Asn Phe Tyr Glu Pro Gln Ile Ile Thr Thr
    1090                1095                1100
Asp Asn Thr Phe Val Ser Gly Asn Cys Asp Val Val Ile Gly Ile Val
1105                1110                1115                1120
Asn Asn Thr Val Tyr Asp Pro Leu Gln Pro Glu Leu Asp Ser Phe Lys
                1125                1130                1135
Glu Glu Leu Asp Lys Tyr Phe Lys Asn His Thr Ser Pro Asp Val Asp
            1140                1145                1150
Leu Gly Asp Ile Ser Gly Ile Asn Ala Ser Val Val Asn Ile Gln Lys
        1155                1160                1165
Glu Ile Asp Arg Leu Asn Glu Val Ala Lys Asn Leu Asn Glu Ser Leu
    1170                1175                1180
Ile Asp Leu Gln Glu Leu Gly Lys Tyr Glu Gln Tyr Ile Lys Arg Ser
1185                1190                1195                1200
Asn Gly Leu Pro Gly Pro Ile Gly Pro Pro Gly Pro Arg Gly Arg Thr
                1205                1210                1215
Gly Asp Ala Gly Pro Val Gly Pro Pro Gly Pro Pro Gly Pro Pro Gly
            1220                1225                1230
Pro Pro Gly Pro Pro Ser Ala Gly Phe Asp Phe Ser Phe Leu Pro Gln
        1235                1240                1245
Pro Pro Gln Glu Lys Ala His Asp Gly Gly Arg Tyr Tyr Arg Ala Asn
    1250                1255                1260
Asp Ala Asn Val Val Arg Asp Arg Asp Leu Glu Val Asp Thr Thr Leu
1265                1270                1275                1280
Lys Ser Leu Ser Gln Gln Ile Glu Asn Ile Arg Ser Pro Glu Gly Ser
            1285                1290                1295
Arg Lys Asn Pro Ala Arg Thr Cys Arg Asp Leu Lys Met Cys His Ser
        1300                1305                1310
Asp Trp Lys Ser Gly Glu Tyr Trp Ile Asp Pro Asn Gln Gly Cys Asn
    1315                1320                1325
Leu Asp Ala Ile Lys Val Phe Cys Asn Met Glu Thr Gly Glu Thr Cys
        1330                1335                1340
Val Tyr Pro Thr Gln Pro Ser Val Ala Gln Lys Asn Trp Tyr Ile Ser
1345                1350                1355                1360
Lys Asn Pro Lys Asp Lys Arg His Val Trp Phe Gly Glu Ser Met Thr
                1365                1370                1375
Asp Gly Phe Gln Phe Glu Tyr Gly Gly Gln Gly Ser Asp Pro Ala Asp
            1380                1385                1390
Val Ala Ile Gln Leu Thr Phe Leu Arg Leu Met Ser Thr Glu Ala Ser
        1395                1400                1405
```

Gln Asn Ile Thr Tyr His Cys Lys Asn Ser Val Ala Tyr Met Asp Gln
    1410                1415                1420

Gln Thr Gly Asn Leu Lys Lys Ala Leu Leu Leu Gln Gly Ser Asn Glu
1425                1430                1435                1440

Ile Glu Ile Arg Ala Glu Gly Asn Ser Arg Phe Thr Tyr Ser Val Thr
                1445                1450                1455

Val Asp Gly Cys Thr Ser His Thr Gly Ala Trp Gly Lys Thr Val Ile
                1460                1465                1470

Glu Tyr Lys Thr Thr Lys Thr Ser Arg Leu Pro Ile Ile Asp Val Ala
            1475                1480                1485

Pro Leu Asp Val Gly Ala Pro Asp Gln Glu Phe Gly Phe Asp Val Gly
        1490                1495                1500

Pro Val Cys Phe Leu
1505

<210> SEQ ID NO 2
<211> LENGTH: 1509
<212> TYPE: PRT
<213> ORGANISM: Artificial Sequence
<220> FEATURE:
<223> OTHER INFORMATION: Synthetic construct

<400> SEQUENCE: 2

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205

Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
                245                 250                 255

-continued

```
Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
        275                 280                 285

Thr Leu Lys Ser Phe Thr Val Glu Lys Gly Ile Tyr Gln Thr Ser Asn
    290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
            340                 345                 350

Ser Val Leu Tyr Asn Ser Ala Ser Phe Ser Thr Phe Lys Cys Tyr Gly
        355                 360                 365

Val Ser Pro Thr Lys Leu Asn Asp Leu Cys Phe Thr Asn Val Tyr Ala
    370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
            420                 425                 430

Gly Gly Asn Tyr Asn Tyr Leu Tyr Arg Leu Phe Arg Lys Ser Asn Leu
        435                 440                 445

Lys Pro Phe Glu Arg Asp Ile Ser Thr Glu Ile Tyr Gln Ala Gly Ser
    450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
                485                 490                 495

Val Val Val Leu Ser Phe Glu Leu Leu His Ala Pro Ala Thr Val Cys
            500                 505                 510

Gly Pro Lys Lys Ser Thr Asn Leu Val Lys Asn Lys Cys Val Asn Phe
        515                 520                 525

Asn Phe Asn Gly Leu Thr Gly Thr Gly Val Leu Thr Glu Ser Asn Lys
    530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
            580                 585                 590

Asn Gln Val Ala Val Leu Tyr Gln Asp Val Asn Cys Thr Glu Val Pro
        595                 600                 605

Val Ala Ile His Ala Asp Gln Leu Thr Pro Thr Trp Arg Val Tyr Ser
    610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Arg Arg Ala Ala
            660                 665                 670
```

-continued

```
Ser Val Ala Ser Gln Ser Ile Ile Ala Tyr Thr Met Ser Leu Gly Ala
            675                 680                 685
Glu Asn Ser Val Ala Tyr Ser Asn Asn Ser Ile Ala Ile Pro Thr Asn
        690                 695                 700
Phe Thr Ile Ser Val Thr Thr Glu Ile Leu Pro Val Ser Met Thr Lys
705                 710                 715                 720
Thr Ser Val Asp Cys Thr Met Tyr Ile Cys Gly Asp Ser Thr Glu Cys
                725                 730                 735
Ser Asn Leu Leu Leu Gln Tyr Gly Ser Phe Cys Thr Gln Leu Asn Arg
            740                 745                 750
Ala Leu Thr Gly Ile Ala Val Glu Gln Asp Lys Asn Thr Gln Glu Val
        755                 760                 765
Phe Ala Gln Val Lys Gln Ile Tyr Lys Thr Pro Pro Ile Lys Asp Phe
770                 775                 780
Gly Gly Phe Asn Phe Ser Gln Ile Leu Pro Asp Pro Ser Lys Pro Ser
785                 790                 795                 800
Lys Arg Ser Phe Ile Glu Asp Leu Leu Phe Asn Lys Val Thr Leu Ala
                805                 810                 815
Asp Ala Gly Phe Ile Lys Gln Tyr Gly Asp Cys Leu Gly Asp Ile Ala
            820                 825                 830
Ala Arg Asp Leu Ile Cys Ala Gln Lys Phe Asn Gly Leu Thr Val Leu
        835                 840                 845
Pro Pro Leu Leu Thr Asp Glu Met Ile Ala Gln Tyr Thr Ser Ala Leu
850                 855                 860
Leu Ala Gly Thr Ile Thr Ser Gly Trp Thr Phe Gly Ala Gly Ala Ala
865                 870                 875                 880
Leu Gln Ile Pro Phe Ala Met Gln Met Ala Tyr Arg Phe Asn Gly Ile
                885                 890                 895
Gly Val Thr Gln Asn Val Leu Tyr Glu Asn Gln Lys Leu Ile Ala Asn
            900                 905                 910
Gln Phe Asn Ser Ala Ile Gly Lys Ile Gln Asp Ser Leu Ser Ser Thr
        915                 920                 925
Ala Ser Ala Leu Gly Lys Leu Gln Asp Val Val Asn Gln Asn Ala Gln
930                 935                 940
Ala Leu Asn Thr Leu Val Lys Gln Leu Ser Ser Asn Phe Gly Ala Ile
945                 950                 955                 960
Ser Ser Val Leu Asn Asp Ile Leu Ser Arg Leu Asp Lys Val Glu Ala
                965                 970                 975
Glu Val Gln Ile Asp Arg Leu Ile Thr Gly Arg Leu Gln Ser Leu Gln
            980                 985                 990
Thr Tyr Val Thr Gln Gln Leu Ile Arg Ala Ala Glu Ile Arg Ala Ser
        995                 1000                1005
Ala Asn Leu Ala Ala Thr Lys Met Ser Glu Cys Val Leu Gly Gln Ser
1010                1015                1020
Lys Arg Val Asp Phe Cys Gly Lys Gly Tyr His Leu Met Ser Phe Pro
1025                1030                1035                1040
Gln Ser Ala Pro His Gly Val Val Phe Leu His Val Thr Tyr Val Pro
                1045                1050                1055
Ala Gln Glu Lys Asn Phe Thr Thr Ala Pro Ala Ile Cys His Asp Gly
            1060                1065                1070
Lys Ala His Phe Pro Arg Glu Gly Val Phe Val Ser Asn Gly Thr His
        1075                1080                1085
Trp Phe Val Thr Gln Arg Asn Phe Tyr Glu Pro Gln Ile Ile Thr Thr
```

```
              1090                1095                1100
Asp Asn Thr Phe Val Ser Gly Asn Cys Asp Val Val Ile Gly Ile Val
1105                1110                1115                1120

Asn Asn Thr Val Tyr Asp Pro Leu Gln Pro Glu Leu Asp Ser Phe Lys
                1125                1130                1135

Glu Glu Leu Asp Lys Tyr Phe Lys Asn His Thr Ser Pro Asp Val Asp
                1140                1145                1150

Leu Gly Asp Ile Ser Gly Ile Asn Ala Ser Val Val Asn Ile Gln Lys
                1155                1160                1165

Glu Ile Asp Arg Leu Asn Glu Val Ala Lys Asn Leu Asn Glu Ser Leu
                1170                1175                1180

Ile Asp Leu Gln Glu Leu Gly Lys Tyr Glu Gln Tyr Ile Lys Arg Ser
1185                1190                1195                1200

Asn Gly Leu Pro Gly Pro Ile Gly Pro Gly Pro Arg Gly Arg Thr
                1205                1210                1215

Gly Asp Ala Gly Pro Val Gly Pro Pro Gly Pro Pro Gly Pro Pro Gly
                1220                1225                1230

Pro Pro Gly Pro Pro Ser Ala Gly Phe Asp Phe Ser Phe Leu Pro Gln
                1235                1240                1245

Pro Pro Gln Glu Lys Ala His Asp Gly Gly Arg Tyr Tyr Arg Ala Asn
                1250                1255                1260

Asp Ala Asn Val Val Arg Asp Arg Asp Leu Glu Val Asp Thr Thr Leu
1265                1270                1275                1280

Lys Ser Leu Ser Gln Gln Ile Glu Asn Ile Arg Ser Pro Glu Gly Ser
                1285                1290                1295

Arg Lys Asn Pro Ala Arg Thr Cys Arg Asp Leu Lys Met Cys His Ser
                1300                1305                1310

Asp Trp Lys Ser Gly Glu Tyr Trp Ile Asp Pro Asn Gln Gly Cys Asn
                1315                1320                1325

Leu Asp Ala Ile Lys Val Phe Cys Asn Met Glu Thr Gly Glu Thr Cys
                1330                1335                1340

Val Tyr Pro Thr Gln Pro Ser Val Ala Gln Lys Asn Trp Tyr Ile Ser
1345                1350                1355                1360

Lys Asn Pro Lys Asp Lys Arg His Val Trp Phe Gly Glu Ser Met Thr
                1365                1370                1375

Asp Gly Phe Gln Phe Glu Tyr Gly Gly Gln Gly Ser Asp Pro Ala Asp
                1380                1385                1390

Val Ala Ile Gln Leu Thr Phe Leu Arg Leu Met Ser Thr Glu Ala Ser
                1395                1400                1405

Gln Asn Ile Thr Tyr His Cys Lys Asn Ser Val Ala Tyr Met Asp Gln
1410                1415                1420

Gln Thr Gly Asn Leu Lys Lys Ala Leu Leu Leu Gln Gly Ser Asn Glu
1425                1430                1435                1440

Ile Glu Ile Arg Ala Glu Gly Asn Ser Arg Phe Thr Tyr Ser Val Thr
                1445                1450                1455

Val Asp Gly Cys Thr Ser His Thr Gly Ala Trp Gly Lys Thr Val Ile
                1460                1465                1470

Glu Tyr Lys Thr Thr Lys Thr Ser Arg Leu Pro Ile Ile Asp Val Ala
                1475                1480                1485

Pro Leu Asp Val Gly Ala Pro Asp Gln Glu Phe Gly Phe Asp Val Gly
                1490                1495                1500

Pro Val Cys Phe Leu
1505
```

```
<210> SEQ ID NO 3
<211> LENGTH: 1509
<212> TYPE: PRT
<213> ORGANISM: Artificial Sequence
<220> FEATURE:
<223> OTHER INFORMATION: Synthetic construct

<400> SEQUENCE: 3

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205

Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
                245                 250                 255

Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
        275                 280                 285

Thr Leu Lys Ser Phe Thr Val Glu Lys Gly Ile Tyr Gln Thr Ser Asn
    290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
            340                 345                 350

Ser Val Leu Tyr Asn Ser Ala Ser Phe Ser Thr Phe Lys Cys Tyr Gly
        355                 360                 365
```

-continued

```
Val Ser Pro Thr Lys Leu Asn Asp Leu Cys Phe Thr Asn Val Tyr Ala
    370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
            420                 425                 430

Gly Gly Asn Tyr Asn Tyr Leu Tyr Arg Leu Phe Arg Lys Ser Asn Leu
        435                 440                 445

Lys Pro Phe Glu Arg Asp Ile Ser Thr Glu Ile Tyr Gln Ala Gly Ser
    450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
                485                 490                 495

Val Val Val Leu Ser Phe Glu Leu Leu His Ala Pro Ala Thr Val Cys
            500                 505                 510

Gly Pro Lys Lys Ser Thr Asn Leu Val Lys Asn Lys Cys Val Asn Phe
        515                 520                 525

Asn Phe Asn Gly Leu Thr Gly Thr Gly Val Leu Thr Glu Ser Asn Lys
530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
            580                 585                 590

Asn Gln Val Ala Val Leu Tyr Gln Asp Val Asn Cys Thr Glu Val Pro
        595                 600                 605

Val Ala Ile His Ala Asp Gln Leu Thr Pro Thr Trp Arg Val Tyr Ser
    610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Arg Arg Ala Arg
            660                 665                 670

Ser Val Ala Ser Gln Ser Ile Ile Ala Tyr Thr Met Ser Leu Gly Ala
        675                 680                 685

Glu Asn Ser Val Ala Tyr Ser Asn Asn Ser Ile Ala Ile Pro Thr Asn
    690                 695                 700

Phe Thr Ile Ser Val Thr Thr Glu Ile Leu Pro Val Ser Met Thr Lys
705                 710                 715                 720

Thr Ser Val Asp Cys Thr Met Tyr Ile Cys Gly Asp Ser Thr Glu Cys
                725                 730                 735

Ser Asn Leu Leu Leu Gln Tyr Gly Ser Phe Cys Thr Gln Leu Asn Arg
            740                 745                 750

Ala Leu Thr Gly Ile Ala Val Glu Gln Asp Lys Asn Thr Gln Glu Val
        755                 760                 765

Phe Ala Gln Val Lys Gln Ile Tyr Lys Thr Pro Pro Ile Lys Asp Phe
770                 775                 780
```

```
Gly Gly Phe Asn Phe Ser Gln Ile Leu Pro Asp Pro Ser Lys Pro Ser
785                 790                 795                 800

Lys Arg Ser Phe Ile Glu Asp Leu Leu Phe Asn Lys Val Thr Leu Ala
                805                 810                 815

Asp Ala Gly Phe Ile Lys Gln Tyr Gly Asp Cys Leu Gly Asp Ile Ala
                820                 825                 830

Ala Arg Asp Leu Ile Cys Ala Gln Lys Phe Asn Gly Leu Thr Val Leu
                835                 840                 845

Pro Pro Leu Leu Thr Asp Glu Met Ile Ala Gln Tyr Thr Ser Ala Leu
850                 855                 860

Leu Ala Gly Thr Ile Thr Ser Gly Trp Thr Phe Gly Ala Gly Ala Ala
865                 870                 875                 880

Leu Gln Ile Pro Phe Ala Met Gln Met Ala Tyr Arg Phe Asn Gly Ile
                885                 890                 895

Gly Val Thr Gln Asn Val Leu Tyr Glu Asn Gln Lys Leu Ile Ala Asn
                900                 905                 910

Gln Phe Asn Ser Ala Ile Gly Lys Ile Gln Asp Ser Leu Ser Ser Thr
                915                 920                 925

Ala Ser Ala Leu Gly Lys Leu Gln Asp Val Val Asn Gln Asn Ala Gln
930                 935                 940

Ala Leu Asn Thr Leu Val Lys Gln Leu Ser Ser Asn Phe Gly Ala Ile
945                 950                 955                 960

Ser Ser Val Leu Asn Asp Ile Leu Ser Arg Leu Asp Pro Pro Glu Ala
                965                 970                 975

Glu Val Gln Ile Asp Arg Leu Ile Thr Gly Arg Leu Gln Ser Leu Gln
                980                 985                 990

Thr Tyr Val Thr Gln Gln Leu Ile Arg Ala Ala Glu Ile Arg Ala Ser
                995                 1000                1005

Ala Asn Leu Ala Ala Thr Lys Met Ser Glu Cys Val Leu Gly Gln Ser
        1010                1015                1020

Lys Arg Val Asp Phe Cys Gly Lys Gly Tyr His Leu Met Ser Phe Pro
1025                1030                1035                1040

Gln Ser Ala Pro His Gly Val Val Phe Leu His Val Thr Tyr Val Pro
        1045                1050                1055

Ala Gln Glu Lys Asn Phe Thr Thr Ala Pro Ala Ile Cys His Asp Gly
        1060                1065                1070

Lys Ala His Phe Pro Arg Glu Gly Val Phe Val Ser Asn Gly Thr His
        1075                1080                1085

Trp Phe Val Thr Gln Arg Asn Phe Tyr Glu Pro Gln Ile Ile Thr Thr
        1090                1095                1100

Asp Asn Thr Phe Val Ser Gly Asn Cys Asp Val Val Ile Gly Ile Val
1105                1110                1115                1120

Asn Asn Thr Val Tyr Asp Pro Leu Gln Pro Glu Leu Asp Ser Phe Lys
        1125                1130                1135

Glu Glu Leu Asp Lys Tyr Phe Lys Asn His Thr Ser Pro Asp Val Asp
        1140                1145                1150

Leu Gly Asp Ile Ser Gly Ile Asn Ala Ser Val Val Asn Ile Gln Lys
        1155                1160                1165

Glu Ile Asp Arg Leu Asn Glu Val Ala Lys Asn Leu Asn Glu Ser Leu
        1170                1175                1180

Ile Asp Leu Gln Glu Leu Gly Lys Tyr Glu Gln Tyr Ile Lys Arg Ser
1185                1190                1195                1200

Asn Gly Leu Pro Gly Pro Ile Gly Pro Pro Gly Pro Arg Gly Arg Thr
```

1205                1210                1215

Gly Asp Ala Gly Pro Val Gly Pro Gly Pro Pro Gly Pro Pro Gly
            1220                1225                1230

Pro Pro Gly Pro Pro Ser Ala Gly Phe Asp Phe Ser Phe Leu Pro Gln
        1235                1240                1245

Pro Pro Gln Glu Lys Ala His Asp Gly Gly Arg Tyr Tyr Arg Ala Asn
    1250                1255                1260

Asp Ala Asn Val Val Arg Asp Arg Asp Leu Glu Val Asp Thr Thr Leu
1265                1270                1275                1280

Lys Ser Leu Ser Gln Gln Ile Glu Asn Ile Arg Ser Pro Glu Gly Ser
                1285                1290                1295

Arg Lys Asn Pro Ala Arg Thr Cys Arg Asp Leu Lys Met Cys His Ser
            1300                1305                1310

Asp Trp Lys Ser Gly Glu Tyr Trp Ile Asp Pro Asn Gln Gly Cys Asn
        1315                1320                1325

Leu Asp Ala Ile Lys Val Phe Cys Asn Met Glu Thr Gly Glu Thr Cys
    1330                1335                1340

Val Tyr Pro Thr Gln Pro Ser Val Ala Gln Lys Asn Trp Tyr Ile Ser
1345                1350                1355                1360

Lys Asn Pro Lys Asp Lys Arg His Val Trp Phe Gly Glu Ser Met Thr
                1365                1370                1375

Asp Gly Phe Gln Phe Glu Tyr Gly Gly Gln Gly Ser Asp Pro Ala Asp
            1380                1385                1390

Val Ala Ile Gln Leu Thr Phe Leu Arg Leu Met Ser Thr Glu Ala Ser
        1395                1400                1405

Gln Asn Ile Thr Tyr His Cys Lys Asn Ser Val Ala Tyr Met Asp Gln
    1410                1415                1420

Gln Thr Gly Asn Leu Lys Lys Ala Leu Leu Leu Gln Gly Ser Asn Glu
1425                1430                1435                1440

Ile Glu Ile Arg Ala Glu Gly Asn Ser Arg Phe Thr Tyr Ser Val Thr
                1445                1450                1455

Val Asp Gly Cys Thr Ser His Thr Gly Ala Trp Gly Lys Thr Val Ile
            1460                1465                1470

Glu Tyr Lys Thr Thr Lys Thr Ser Arg Leu Pro Ile Ile Asp Val Ala
        1475                1480                1485

Pro Leu Asp Val Gly Ala Pro Asp Gln Glu Phe Gly Phe Asp Val Gly
    1490                1495                1500

Pro Val Cys Phe Leu
1505

<210> SEQ ID NO 4
<211> LENGTH: 1509
<212> TYPE: PRT
<213> ORGANISM: Artificial Sequence
<220> FEATURE:
<223> OTHER INFORMATION: Synthetic construct

<400> SEQUENCE: 4

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys

```
                50                  55                  60
Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
                100                 105                 110

Val Val Ile Lys Val Cys Glu Phe Gln Phe Cys Asn Asp Pro Phe Leu
                115                 120                 125

Gly Val Tyr Tyr His Lys Asn Asn Lys Ser Trp Met Glu Ser Glu Phe
                130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
                180                 185                 190

Lys His Thr Pro Ile Asn Leu Val Arg Asp Leu Pro Gln Gly Phe Ser
                195                 200                 205

Ala Leu Glu Pro Leu Val Asp Leu Pro Ile Gly Ile Asn Ile Thr Arg
                210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
                245                 250                 255

Leu Gln Pro Arg Thr Phe Leu Leu Lys Tyr Asn Glu Asn Gly Thr Ile
                260                 265                 270

Thr Asp Ala Val Asp Cys Ala Leu Asp Pro Leu Ser Glu Thr Lys Cys
                275                 280                 285

Thr Leu Lys Ser Phe Thr Val Glu Lys Gly Ile Tyr Gln Thr Ser Asn
                290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
                340                 345                 350

Ser Val Leu Tyr Asn Ser Ala Ser Phe Ser Thr Phe Lys Cys Tyr Gly
                355                 360                 365

Val Ser Pro Thr Lys Leu Asn Asp Leu Cys Phe Thr Asn Val Tyr Ala
                370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
                420                 425                 430

Gly Gly Asn Tyr Asn Tyr Leu Tyr Arg Leu Phe Arg Lys Ser Asn Leu
                435                 440                 445

Lys Pro Phe Glu Arg Asp Ile Ser Thr Glu Ile Tyr Gln Ala Gly Ser
                450                 455                 460

Thr Pro Cys Asn Gly Val Glu Gly Phe Asn Cys Tyr Phe Pro Leu Gln
465                 470                 475                 480
```

```
Ser Tyr Gly Phe Gln Pro Thr Asn Gly Val Gly Tyr Gln Pro Tyr Arg
                485                 490                 495

Val Val Val Leu Ser Phe Glu Leu Leu His Ala Pro Ala Thr Val Cys
                500                 505                 510

Gly Pro Lys Lys Ser Thr Asn Leu Val Lys Asn Lys Cys Val Asn Phe
                515                 520                 525

Asn Phe Asn Gly Leu Thr Gly Thr Gly Val Leu Thr Glu Ser Asn Lys
                530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
                580                 585                 590

Asn Gln Val Ala Val Leu Tyr Gln Asp Val Asn Cys Thr Glu Val Pro
                595                 600                 605

Val Ala Ile His Ala Asp Gln Leu Thr Pro Thr Trp Arg Val Tyr Ser
                610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Arg Arg Ala Ala
                660                 665                 670

Ser Val Ala Ser Gln Ser Ile Ile Ala Tyr Thr Met Ser Leu Gly Ala
                675                 680                 685

Glu Asn Ser Val Ala Tyr Ser Asn Asn Ser Ile Ala Ile Pro Thr Asn
                690                 695                 700

Phe Thr Ile Ser Val Thr Thr Glu Ile Leu Pro Val Ser Met Thr Lys
705                 710                 715                 720

Thr Ser Val Asp Cys Thr Met Tyr Ile Cys Gly Asp Ser Thr Glu Cys
                725                 730                 735

Ser Asn Leu Leu Leu Gln Tyr Gly Ser Phe Cys Thr Gln Leu Asn Arg
                740                 745                 750

Ala Leu Thr Gly Ile Ala Val Glu Gln Asp Lys Asn Thr Gln Glu Val
                755                 760                 765

Phe Ala Gln Val Lys Gln Ile Tyr Lys Thr Pro Pro Ile Lys Asp Phe
                770                 775                 780

Gly Gly Phe Asn Phe Ser Gln Ile Leu Pro Asp Pro Ser Lys Pro Ser
785                 790                 795                 800

Lys Arg Ser Phe Ile Glu Asp Leu Leu Phe Asn Lys Val Thr Leu Ala
                805                 810                 815

Asp Ala Gly Phe Ile Lys Gln Tyr Gly Asp Cys Leu Gly Asp Ile Ala
                820                 825                 830

Ala Arg Asp Leu Ile Cys Ala Gln Lys Phe Asn Gly Leu Thr Val Leu
                835                 840                 845

Pro Pro Leu Leu Thr Asp Glu Met Ile Ala Gln Tyr Thr Ser Ala Leu
                850                 855                 860

Leu Ala Gly Thr Ile Thr Ser Gly Trp Thr Phe Gly Ala Gly Ala Ala
865                 870                 875                 880

Leu Gln Ile Pro Phe Ala Met Gln Met Ala Tyr Arg Phe Asn Gly Ile
                885                 890                 895
```

-continued

```
Gly Val Thr Gln Asn Val Leu Tyr Glu Asn Gln Lys Leu Ile Ala Asn
                900                 905                 910
Gln Phe Asn Ser Ala Ile Gly Lys Ile Gln Asp Ser Leu Ser Ser Thr
            915                 920                 925
Ala Ser Ala Leu Gly Lys Leu Gln Asp Val Val Asn Gln Asn Ala Gln
        930                 935                 940
Ala Leu Asn Thr Leu Val Lys Gln Leu Ser Ser Asn Phe Gly Ala Ile
945                 950                 955                 960
Ser Ser Val Leu Asn Asp Ile Leu Ser Arg Leu Asp Pro Pro Glu Ala
                965                 970                 975
Glu Val Gln Ile Asp Arg Leu Ile Thr Gly Arg Leu Gln Ser Leu Gln
            980                 985                 990
Thr Tyr Val Thr Gln Gln Leu Ile Arg Ala Ala Glu Ile Arg Ala Ser
        995                 1000                1005
Ala Asn Leu Ala Ala Thr Lys Met Ser Glu Cys Val Leu Gly Gln Ser
        1010                1015                1020
Lys Arg Val Asp Phe Cys Gly Lys Gly Tyr His Leu Met Ser Phe Pro
1025                1030                1035                1040
Gln Ser Ala Pro His Gly Val Val Phe Leu His Val Thr Tyr Val Pro
            1045                1050                1055
Ala Gln Glu Lys Asn Phe Thr Thr Ala Pro Ala Ile Cys His Asp Gly
        1060                1065                1070
Lys Ala His Phe Pro Arg Glu Gly Val Phe Val Ser Asn Gly Thr His
        1075                1080                1085
Trp Phe Val Thr Gln Arg Asn Phe Tyr Glu Pro Gln Ile Ile Thr Thr
        1090                1095                1100
Asp Asn Thr Phe Val Ser Gly Asn Cys Asp Val Val Ile Gly Ile Val
1105                1110                1115                1120
Asn Asn Thr Val Tyr Asp Pro Leu Gln Pro Glu Leu Asp Ser Phe Lys
            1125                1130                1135
Glu Glu Leu Asp Lys Tyr Phe Lys Asn His Thr Ser Pro Asp Val Asp
        1140                1145                1150
Leu Gly Asp Ile Ser Gly Ile Asn Ala Ser Val Val Asn Ile Gln Lys
        1155                1160                1165
Glu Ile Asp Arg Leu Asn Glu Val Ala Lys Asn Leu Asn Glu Ser Leu
        1170                1175                1180
Ile Asp Leu Gln Glu Leu Gly Lys Tyr Glu Gln Tyr Ile Lys Arg Ser
1185                1190                1195                1200
Asn Gly Leu Pro Gly Pro Ile Gly Pro Pro Gly Pro Arg Gly Arg Thr
            1205                1210                1215
Gly Asp Ala Gly Pro Val Gly Pro Pro Gly Pro Pro Gly Pro Pro Gly
        1220                1225                1230
Pro Pro Gly Pro Pro Ser Ala Gly Phe Asp Phe Ser Phe Leu Pro Gln
        1235                1240                1245
Pro Pro Gln Glu Lys Ala His Asp Gly Gly Arg Tyr Tyr Arg Ala Asn
        1250                1255                1260
Asp Ala Asn Val Val Arg Asp Arg Asp Leu Glu Val Asp Thr Thr Leu
1265                1270                1275                1280
Lys Ser Leu Ser Gln Gln Ile Glu Asn Ile Arg Ser Pro Glu Gly Ser
            1285                1290                1295
Arg Lys Asn Pro Ala Arg Thr Cys Arg Asp Leu Lys Met Cys His Ser
        1300                1305                1310
Asp Trp Lys Ser Gly Glu Tyr Trp Ile Asp Pro Asn Gln Gly Cys Asn
```

```
                1315                1320                1325

Leu Asp Ala Ile Lys Val Phe Cys Asn Met Glu Thr Gly Glu Thr Cys
            1330                1335                1340

Val Tyr Pro Thr Gln Pro Ser Val Ala Gln Lys Asn Trp Tyr Ile Ser
1345                1350                1355                1360

Lys Asn Pro Lys Asp Lys Arg His Val Trp Phe Gly Glu Ser Met Thr
                1365                1370                1375

Asp Gly Phe Gln Phe Glu Tyr Gly Gly Gln Gly Ser Asp Pro Ala Asp
            1380                1385                1390

Val Ala Ile Gln Leu Thr Phe Leu Arg Leu Met Ser Thr Glu Ala Ser
                1395                1400                1405

Gln Asn Ile Thr Tyr His Cys Lys Asn Ser Val Ala Tyr Met Asp Gln
1410                1415                1420

Gln Thr Gly Asn Leu Lys Lys Ala Leu Leu Gln Gly Ser Asn Glu
1425                1430                1435                1440

Ile Glu Ile Arg Ala Glu Gly Asn Ser Arg Phe Thr Tyr Ser Val Thr
                1445                1450                1455

Val Asp Gly Cys Thr Ser His Thr Gly Ala Trp Gly Lys Thr Val Ile
            1460                1465                1470

Glu Tyr Lys Thr Thr Lys Thr Ser Arg Leu Pro Ile Ile Asp Val Ala
                1475                1480                1485

Pro Leu Asp Val Gly Ala Pro Asp Gln Glu Phe Gly Phe Asp Val Gly
            1490                1495                1500

Pro Val Cys Phe Leu
1505

<210> SEQ ID NO 5
<211> LENGTH: 836
<212> TYPE: PRT
<213> ORGANISM: Artificial Sequence
<220> FEATURE:
<223> OTHER INFORMATION: Synthetic construct

<400> SEQUENCE: 5

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
                20                  25                  30

Ser Val Leu His Ser Thr Gln Asp Leu Phe Leu Pro Phe Phe Ser Asn
            35                  40                  45

Val Thr Trp Phe His Ala Ile His Val Ser Gly Thr Asn Gly Thr Lys
        50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
```

-continued

```
            165                 170                 175
Arg Glu Phe Val Phe Lys Asn Ile Asp Gly Tyr Phe Lys Ile Tyr Ser
                180                 185                 190
Lys His Thr Pro Ile Asn Leu Val Arg Asp Leu Pro Gln Gly Phe Ser
                195                 200                 205
Ala Leu Glu Pro Leu Val Asp Leu Pro Ile Gly Ile Asn Ile Thr Arg
                210                 215                 220
Phe Gln Thr Leu Leu Ala Leu His Arg Ser Tyr Leu Thr Pro Gly Asp
225                 230                 235                 240
Ser Ser Ser Gly Trp Thr Ala Gly Ala Ala Ala Tyr Tyr Val Gly Tyr
                245                 250                 255
Leu Gln Pro Arg Thr Phe Leu Leu Lys Tyr Asn Glu Asn Gly Thr Ile
                260                 265                 270
Thr Asp Ala Val Asp Cys Ala Leu Asp Pro Leu Ser Glu Thr Lys Cys
                275                 280                 285
Thr Leu Lys Ser Phe Thr Val Glu Lys Gly Ile Tyr Gln Thr Ser Asn
                290                 295                 300
Phe Arg Val Gln Pro Thr Glu Ser Ile Val Arg Phe Pro Asn Ile Thr
305                 310                 315                 320
Asn Leu Cys Pro Phe Gly Glu Val Phe Asn Ala Thr Arg Phe Ala Ser
                325                 330                 335
Val Tyr Ala Trp Asn Arg Lys Arg Ile Ser Asn Cys Val Ala Asp Tyr
                340                 345                 350
Ser Val Leu Tyr Asn Ser Ala Ser Phe Ser Thr Phe Lys Cys Tyr Gly
                355                 360                 365
Val Ser Pro Thr Lys Leu Asn Asp Leu Cys Phe Thr Asn Val Tyr Ala
                370                 375                 380
Asp Ser Phe Val Ile Arg Gly Asp Glu Val Arg Gln Ile Ala Pro Gly
385                 390                 395                 400
Gln Thr Gly Lys Ile Ala Asp Tyr Asn Tyr Lys Leu Pro Asp Asp Phe
                405                 410                 415
Thr Gly Cys Val Ile Ala Trp Asn Ser Asn Asn Leu Asp Ser Lys Val
                420                 425                 430
Gly Gly Asn Tyr Asn Tyr Leu Tyr Arg Leu Phe Arg Lys Ser Asn Leu
                435                 440                 445
Lys Pro Phe Glu Arg Asp Ile Ser Thr Glu Ile Tyr Gln Ala Gly Ser
                450                 455                 460
Thr Pro Cys Asn Gly Val Glu Gly Phe Asn Cys Tyr Phe Pro Leu Gln
465                 470                 475                 480
Ser Tyr Gly Phe Gln Pro Thr Asn Gly Val Gly Tyr Gln Pro Tyr Arg
                485                 490                 495
Val Val Val Leu Ser Phe Glu Leu Leu His Ala Pro Ala Thr Val Cys
                500                 505                 510
Gly Pro Lys Lys Ser Thr Asn Leu Val Lys Asn Lys Cys Arg Ser Asn
                515                 520                 525
Gly Leu Pro Gly Pro Ile Gly Pro Gly Pro Arg Gly Arg Thr Gly
                530                 535                 540
Asp Ala Gly Pro Val Gly Pro Pro Gly Pro Gly Pro Pro Gly Pro
545                 550                 555                 560
Pro Gly Pro Pro Ser Ala Gly Phe Asp Phe Ser Phe Leu Pro Gln Pro
                565                 570                 575
Pro Gln Glu Lys Ala His Asp Gly Gly Arg Tyr Tyr Arg Ala Asn Asp
                580                 585                 590
```

```
Ala Asn Val Val Arg Asp Arg Asp Leu Glu Val Asp Thr Thr Leu Lys
            595                 600                 605

Ser Leu Ser Gln Gln Ile Glu Asn Ile Arg Ser Pro Glu Gly Ser Arg
    610                 615                 620

Lys Asn Pro Ala Arg Thr Cys Arg Asp Leu Lys Met Cys His Ser Asp
625                 630                 635                 640

Trp Lys Ser Gly Glu Tyr Trp Ile Asp Pro Asn Gln Gly Cys Asn Leu
                645                 650                 655

Asp Ala Ile Lys Val Phe Cys Asn Met Glu Thr Gly Glu Thr Cys Val
            660                 665                 670

Tyr Pro Thr Gln Pro Ser Val Ala Gln Lys Asn Trp Tyr Ile Ser Lys
        675                 680                 685

Asn Pro Lys Asp Lys Arg His Val Trp Phe Gly Glu Ser Met Thr Asp
        690                 695                 700

Gly Phe Gln Phe Glu Tyr Gly Gly Gln Gly Ser Asp Pro Ala Asp Val
705                 710                 715                 720

Ala Ile Gln Leu Thr Phe Leu Arg Leu Met Ser Thr Glu Ala Ser Gln
                725                 730                 735

Asn Ile Thr Tyr His Cys Lys Asn Ser Val Ala Tyr Met Asp Gln Gln
            740                 745                 750

Thr Gly Asn Leu Lys Lys Ala Leu Leu Leu Gln Gly Ser Asn Glu Ile
        755                 760                 765

Glu Ile Arg Ala Glu Gly Asn Ser Arg Phe Thr Tyr Ser Val Thr Val
    770                 775                 780

Asp Gly Cys Thr Ser His Thr Gly Ala Trp Gly Lys Thr Val Ile Glu
785                 790                 795                 800

Tyr Lys Thr Thr Lys Thr Ser Arg Leu Pro Ile Ile Asp Val Ala Pro
                805                 810                 815

Leu Asp Val Gly Ala Pro Asp Gln Glu Phe Gly Phe Asp Val Gly Pro
            820                 825                 830

Val Cys Phe Leu
        835

<210> SEQ ID NO 6
<211> LENGTH: 979
<212> TYPE: PRT
<213> ORGANISM: Artificial Sequence
<220> FEATURE:
<223> OTHER INFORMATION: Synthetic construct

<400> SEQUENCE: 6

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
                20                  25                  30

Ser Val Leu His Ser Thr Gln Asp Leu Phe Leu Pro Phe Phe Ser Asn
            35                  40                  45

Val Thr Trp Phe His Ala Ile His Val Ser Gly Thr Asn Gly Thr Lys
        50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110
```

```
Val Val Ile Lys Val Cys Glu Phe Gln Phe Cys Asn Asp Pro Phe Leu
            115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
                180                 185                 190

Lys His Thr Pro Ile Asn Leu Val Arg Asp Leu Pro Gln Gly Phe Ser
            195                 200                 205

Ala Leu Glu Pro Leu Val Asp Leu Pro Ile Gly Ile Asn Ile Thr Arg
            210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
                245                 250                 255

Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
            275                 280                 285

Thr Leu Lys Ser Phe Thr Val Glu Lys Gly Ile Tyr Gln Thr Ser Asn
            290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
                340                 345                 350

Ser Val Leu Tyr Asn Ser Ala Ser Phe Ser Thr Phe Lys Cys Tyr Gly
            355                 360                 365

Val Ser Pro Thr Lys Leu Asn Asp Leu Cys Phe Thr Asn Val Tyr Ala
            370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
                420                 425                 430

Gly Gly Asn Tyr Asn Tyr Leu Tyr Arg Leu Phe Arg Lys Ser Asn Leu
            435                 440                 445

Lys Pro Phe Glu Arg Asp Ile Ser Thr Glu Ile Tyr Gln Ala Gly Ser
            450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
                485                 490                 495

Val Val Val Leu Ser Phe Glu Leu Leu His Ala Pro Ala Thr Val Cys
            500                 505                 510

Gly Pro Lys Lys Ser Thr Asn Leu Val Lys Asn Lys Cys Val Asn Phe
            515                 520                 525
```

-continued

```
Asn Phe Asn Gly Leu Thr Gly Thr Gly Val Leu Thr Glu Ser Asn Lys
            530                 535                 540
Lys Phe Leu Pro Phe Gln Gln Phe Gly Arg Asp Ile Ala Asp Thr Thr
545                 550                 555                 560
Asp Ala Val Arg Asp Pro Gln Thr Leu Glu Ile Leu Asp Ile Thr Pro
                565                 570                 575
Cys Ser Phe Gly Gly Val Ser Val Ile Thr Pro Gly Thr Asn Thr Ser
            580                 585                 590
Asn Gln Val Ala Val Leu Tyr Gln Asp Val Asn Cys Thr Glu Val Pro
                595                 600                 605
Val Ala Ile His Ala Asp Gln Leu Thr Pro Thr Trp Arg Val Tyr Ser
            610                 615                 620
Thr Gly Ser Asn Val Phe Gln Thr Arg Ala Gly Cys Leu Ile Gly Ala
625                 630                 635                 640
Glu His Val Asn Asn Ser Tyr Glu Cys Asp Ile Pro Ile Gly Ala Gly
                645                 650                 655
Ile Cys Ala Ser Tyr Gln Thr Gln Thr Asn Ser Pro Arg Ser Asn Gly
            660                 665                 670
Leu Pro Gly Pro Ile Gly Pro Gly Pro Arg Gly Arg Thr Gly Asp
            675                 680                 685
Ala Gly Pro Val Gly Pro Pro Gly Pro Pro Gly Pro Pro Gly Pro Pro
690                 695                 700
Gly Pro Pro Ser Ala Gly Phe Asp Phe Ser Phe Leu Pro Gln Pro Pro
705                 710                 715                 720
Gln Glu Lys Ala His Asp Gly Gly Arg Tyr Tyr Arg Ala Asn Asp Ala
                725                 730                 735
Asn Val Val Arg Asp Arg Asp Leu Glu Val Asp Thr Thr Leu Lys Ser
            740                 745                 750
Leu Ser Gln Gln Ile Glu Asn Ile Arg Ser Pro Glu Gly Ser Arg Lys
            755                 760                 765
Asn Pro Ala Arg Thr Cys Arg Asp Leu Lys Met Cys His Ser Asp Trp
            770                 775                 780
Lys Ser Gly Glu Tyr Trp Ile Asp Pro Asn Gln Gly Cys Asn Leu Asp
785                 790                 795                 800
Ala Ile Lys Val Phe Cys Asn Met Glu Thr Gly Glu Thr Cys Val Tyr
                805                 810                 815
Pro Thr Gln Pro Ser Val Ala Gln Lys Asn Trp Tyr Ile Ser Lys Asn
            820                 825                 830
Pro Lys Asp Lys Arg His Val Trp Phe Gly Glu Ser Met Thr Asp Gly
            835                 840                 845
Phe Gln Phe Glu Tyr Gly Gly Gln Gly Ser Asp Pro Ala Asp Val Ala
            850                 855                 860
Ile Gln Leu Thr Phe Leu Arg Leu Met Ser Thr Glu Ala Ser Gln Asn
865                 870                 875                 880
Ile Thr Tyr His Cys Lys Asn Ser Val Ala Tyr Met Asp Gln Gln Thr
                885                 890                 895
Gly Asn Leu Lys Lys Ala Leu Leu Leu Gln Gly Ser Asn Glu Ile Glu
            900                 905                 910
Ile Arg Ala Glu Gly Asn Ser Arg Phe Thr Tyr Ser Val Thr Val Asp
                915                 920                 925
Gly Cys Thr Ser His Thr Gly Ala Trp Gly Lys Thr Val Ile Glu Tyr
            930                 935                 940
Lys Thr Thr Lys Thr Ser Arg Leu Pro Ile Ile Asp Val Ala Pro Leu
```

```
                945                 950                 955                 960
Asp Val Gly Ala Pro Asp Gln Glu Phe Gly Phe Asp Val Gly Pro Val
                    965                 970                 975

Cys Phe Leu

<210> SEQ ID NO 7
<211> LENGTH: 837
<212> TYPE: PRT
<213> ORGANISM: Artificial Sequence
<220> FEATURE:
<223> OTHER INFORMATION: Synthetic construct

<400> SEQUENCE: 7

Ser Val Ala Ser Gln Ser Ile Ile Ala Tyr Thr Met Ser Leu Gly Ala
1               5                   10                  15

Glu Asn Ser Val Ala Tyr Ser Asn Asn Ser Ile Ala Ile Pro Thr Asn
                20                  25                  30

Phe Thr Ile Ser Val Thr Thr Glu Ile Leu Pro Val Ser Met Thr Lys
            35                  40                  45

Thr Ser Val Asp Cys Thr Met Tyr Ile Cys Gly Asp Ser Thr Glu Cys
50                  55                  60

Ser Asn Leu Leu Leu Gln Tyr Gly Ser Phe Cys Thr Gln Leu Asn Arg
65                  70                  75                  80

Ala Leu Thr Gly Ile Ala Val Glu Gln Asp Lys Asn Thr Gln Glu Val
                85                  90                  95

Phe Ala Gln Val Lys Gln Ile Tyr Lys Thr Pro Pro Ile Lys Asp Phe
            100                 105                 110

Gly Gly Phe Asn Phe Ser Gln Ile Leu Pro Asp Pro Ser Lys Pro Ser
        115                 120                 125

Lys Arg Ser Phe Ile Glu Asp Leu Leu Phe Asn Lys Val Thr Leu Ala
130                 135                 140

Asp Ala Gly Phe Ile Lys Gln Tyr Gly Asp Cys Leu Gly Asp Ile Ala
145                 150                 155                 160

Ala Arg Asp Leu Ile Cys Ala Gln Lys Phe Asn Gly Leu Thr Val Leu
                165                 170                 175

Pro Pro Leu Leu Thr Asp Glu Met Ile Ala Gln Tyr Thr Ser Ala Leu
            180                 185                 190

Leu Ala Gly Thr Ile Thr Ser Gly Trp Thr Phe Gly Ala Gly Ala Ala
        195                 200                 205

Leu Gln Ile Pro Phe Ala Met Gln Met Ala Tyr Arg Phe Asn Gly Ile
210                 215                 220

Gly Val Thr Gln Asn Val Leu Tyr Glu Asn Gln Lys Leu Ile Ala Asn
225                 230                 235                 240

Gln Phe Asn Ser Ala Ile Gly Lys Ile Gln Asp Ser Leu Ser Ser Thr
                245                 250                 255

Ala Ser Ala Leu Gly Lys Leu Gln Asp Val Val Asn Gln Asn Ala Gln
            260                 265                 270

Ala Leu Asn Thr Leu Val Lys Gln Leu Ser Ser Asn Phe Gly Ala Ile
        275                 280                 285

Ser Ser Val Leu Asn Asp Ile Leu Ser Arg Leu Asp Lys Val Glu Ala
        290                 295                 300

Glu Val Gln Ile Asp Arg Leu Ile Thr Gly Arg Leu Gln Ser Leu Gln
305                 310                 315                 320

Thr Tyr Val Thr Gln Gln Leu Ile Arg Ala Ala Glu Ile Arg Ala Ser
                325                 330                 335
```

```
Ala Asn Leu Ala Ala Thr Lys Met Ser Glu Cys Val Leu Gly Gln Ser
                340                 345                 350

Lys Arg Val Asp Phe Cys Gly Lys Gly Tyr His Leu Met Ser Phe Pro
        355                 360                 365

Gln Ser Ala Pro His Gly Val Val Phe Leu His Val Thr Tyr Val Pro
370                 375                 380

Ala Gln Glu Lys Asn Phe Thr Thr Ala Pro Ala Ile Cys His Asp Gly
385                 390                 395                 400

Lys Ala His Phe Pro Arg Glu Gly Val Phe Val Ser Asn Gly Thr His
                405                 410                 415

Trp Phe Val Thr Gln Arg Asn Phe Tyr Glu Pro Gln Ile Ile Thr Thr
            420                 425                 430

Asp Asn Thr Phe Val Ser Gly Asn Cys Asp Val Val Ile Gly Ile Val
            435                 440                 445

Asn Asn Thr Val Tyr Asp Pro Leu Gln Pro Glu Leu Asp Ser Phe Lys
        450                 455                 460

Glu Glu Leu Asp Lys Tyr Phe Lys Asn His Thr Ser Pro Asp Val Asp
465                 470                 475                 480

Leu Gly Asp Ile Ser Gly Ile Asn Ala Ser Val Val Asn Ile Gln Lys
                485                 490                 495

Glu Ile Asp Arg Leu Asn Glu Val Ala Lys Asn Leu Asn Glu Ser Leu
            500                 505                 510

Ile Asp Leu Gln Glu Leu Gly Lys Tyr Glu Gln Tyr Ile Lys Arg Ser
        515                 520                 525

Asn Gly Leu Pro Gly Pro Ile Gly Pro Pro Gly Pro Arg Gly Arg Thr
        530                 535                 540

Gly Asp Ala Gly Pro Val Gly Pro Pro Gly Pro Pro Gly Pro Pro Gly
545                 550                 555                 560

Pro Pro Gly Pro Pro Ser Ala Gly Phe Asp Phe Ser Phe Leu Pro Gln
                565                 570                 575

Pro Pro Gln Glu Lys Ala His Asp Gly Gly Arg Tyr Tyr Arg Ala Asn
            580                 585                 590

Asp Ala Asn Val Val Arg Asp Arg Asp Leu Glu Val Asp Thr Thr Leu
        595                 600                 605

Lys Ser Leu Ser Gln Gln Ile Glu Asn Ile Arg Ser Pro Glu Gly Ser
610                 615                 620

Arg Lys Asn Pro Ala Arg Thr Cys Arg Asp Leu Lys Met Cys His Ser
625                 630                 635                 640

Asp Trp Lys Ser Gly Glu Tyr Trp Ile Asp Pro Asn Gln Gly Cys Asn
                645                 650                 655

Leu Asp Ala Ile Lys Val Phe Cys Asn Met Glu Thr Gly Glu Thr Cys
            660                 665                 670

Val Tyr Pro Thr Gln Pro Ser Val Ala Gln Lys Asn Trp Tyr Ile Ser
        675                 680                 685

Lys Asn Pro Lys Asp Lys Arg His Val Trp Phe Gly Glu Ser Met Thr
        690                 695                 700

Asp Gly Phe Gln Phe Glu Tyr Gly Gly Gln Gly Ser Asp Pro Ala Asp
705                 710                 715                 720

Val Ala Ile Gln Leu Thr Phe Leu Arg Leu Met Ser Thr Glu Ala Ser
                725                 730                 735

Gln Asn Ile Thr Tyr His Cys Lys Asn Ser Val Ala Tyr Met Asp Gln
            740                 745                 750
```

```
Gln Thr Gly Asn Leu Lys Lys Ala Leu Leu Gln Gly Ser Asn Glu
            755                 760                 765

Ile Glu Ile Arg Ala Glu Gly Asn Ser Arg Phe Thr Tyr Ser Val Thr
    770                 775                 780

Val Asp Gly Cys Thr Ser His Thr Gly Ala Trp Gly Lys Thr Val Ile
785                 790                 795                 800

Glu Tyr Lys Thr Thr Lys Thr Ser Arg Leu Pro Ile Ile Asp Val Ala
                805                 810                 815

Pro Leu Asp Val Gly Ala Pro Asp Gln Glu Phe Gly Phe Asp Val Gly
            820                 825                 830

Pro Val Cys Phe Leu
            835

<210> SEQ ID NO 8
<211> LENGTH: 827
<212> TYPE: PRT
<213> ORGANISM: Artificial Sequence
<220> FEATURE:
<223> OTHER INFORMATION: Synthetic construct

<400> SEQUENCE: 8

Thr Met Ser Leu Gly Ala Glu Asn Ser Val Ala Tyr Ser Asn Asn Ser
1               5                   10                  15

Ile Ala Ile Pro Thr Asn Phe Thr Ile Ser Val Thr Thr Glu Ile Leu
            20                  25                  30

Pro Val Ser Met Thr Lys Thr Ser Val Asp Cys Thr Met Tyr Ile Cys
        35                  40                  45

Gly Asp Ser Thr Glu Cys Ser Asn Leu Leu Leu Gln Tyr Gly Ser Phe
    50                  55                  60

Cys Thr Gln Leu Asn Arg Ala Leu Thr Gly Ile Ala Val Glu Gln Asp
65                  70                  75                  80

Lys Asn Thr Gln Glu Val Phe Ala Gln Val Lys Gln Ile Tyr Lys Thr
                85                  90                  95

Pro Pro Ile Lys Asp Phe Gly Gly Phe Asn Phe Ser Gln Ile Leu Pro
            100                 105                 110

Asp Pro Ser Lys Pro Ser Lys Arg Ser Phe Ile Glu Asp Leu Leu Phe
        115                 120                 125

Asn Lys Val Thr Leu Ala Asp Ala Gly Phe Ile Lys Gln Tyr Gly Asp
130                 135                 140

Cys Leu Gly Asp Ile Ala Ala Arg Asp Leu Ile Cys Ala Gln Lys Phe
145                 150                 155                 160

Asn Gly Leu Thr Val Leu Pro Pro Leu Leu Thr Asp Glu Met Ile Ala
                165                 170                 175

Gln Tyr Thr Ser Ala Leu Leu Ala Gly Thr Ile Thr Ser Gly Trp Thr
            180                 185                 190

Phe Gly Ala Gly Ala Ala Leu Gln Ile Pro Phe Ala Met Gln Met Ala
        195                 200                 205

Tyr Arg Phe Asn Gly Ile Gly Val Thr Gln Asn Val Leu Tyr Glu Asn
    210                 215                 220

Gln Lys Leu Ile Ala Asn Gln Phe Asn Ser Ala Ile Gly Lys Ile Gln
225                 230                 235                 240

Asp Ser Leu Ser Ser Thr Ala Ser Ala Leu Gly Lys Leu Gln Asp Val
                245                 250                 255

Val Asn Gln Asn Ala Gln Ala Leu Asn Thr Leu Val Lys Gln Leu Ser
            260                 265                 270
```

```
Ser Asn Phe Gly Ala Ile Ser Ser Val Leu Asn Asp Ile Leu Ser Arg
            275                 280                 285

Leu Asp Lys Val Glu Ala Glu Val Gln Ile Asp Arg Leu Ile Thr Gly
290                 295                 300

Arg Leu Gln Ser Leu Gln Thr Tyr Val Thr Gln Gln Leu Ile Arg Ala
305                 310                 315                 320

Ala Glu Ile Arg Ala Ser Ala Asn Leu Ala Ala Thr Lys Met Ser Glu
                325                 330                 335

Cys Val Leu Gly Gln Ser Lys Arg Val Asp Phe Cys Gly Lys Gly Tyr
            340                 345                 350

His Leu Met Ser Phe Pro Gln Ser Ala Pro His Gly Val Val Phe Leu
            355                 360                 365

His Val Thr Tyr Val Pro Ala Gln Glu Lys Asn Phe Thr Thr Ala Pro
            370                 375                 380

Ala Ile Cys His Asp Gly Lys Ala His Phe Pro Arg Glu Gly Val Phe
385                 390                 395                 400

Val Ser Asn Gly Thr His Trp Phe Val Thr Gln Arg Asn Phe Tyr Glu
                405                 410                 415

Pro Gln Ile Ile Thr Thr Asp Asn Thr Phe Val Ser Gly Asn Cys Asp
            420                 425                 430

Val Val Ile Gly Ile Val Asn Asn Thr Val Tyr Asp Pro Leu Gln Pro
            435                 440                 445

Glu Leu Asp Ser Phe Lys Glu Glu Leu Asp Lys Tyr Phe Lys Asn His
            450                 455                 460

Thr Ser Pro Asp Val Asp Leu Gly Asp Ile Ser Gly Ile Asn Ala Ser
465                 470                 475                 480

Val Val Asn Ile Gln Lys Glu Ile Asp Arg Leu Asn Glu Val Ala Lys
                485                 490                 495

Asn Leu Asn Glu Ser Leu Ile Asp Leu Gln Glu Leu Gly Lys Tyr Glu
            500                 505                 510

Gln Tyr Ile Lys Arg Ser Asn Gly Leu Pro Gly Pro Ile Gly Pro Pro
            515                 520                 525

Gly Pro Arg Gly Arg Thr Gly Asp Ala Gly Pro Val Gly Pro Pro Gly
530                 535                 540

Pro Pro Gly Pro Pro Gly Pro Pro Gly Pro Pro Ser Ala Gly Phe Asp
545                 550                 555                 560

Phe Ser Phe Leu Pro Gln Pro Pro Gln Glu Lys Ala His Asp Gly Gly
                565                 570                 575

Arg Tyr Tyr Arg Ala Asn Asp Ala Asn Val Val Arg Asp Arg Asp Leu
            580                 585                 590

Glu Val Asp Thr Thr Leu Lys Ser Leu Ser Gln Gln Ile Glu Asn Ile
            595                 600                 605

Arg Ser Pro Glu Gly Ser Arg Lys Asn Pro Ala Arg Thr Cys Arg Asp
610                 615                 620

Leu Lys Met Cys His Ser Asp Trp Lys Ser Gly Glu Tyr Trp Ile Asp
625                 630                 635                 640

Pro Asn Gln Gly Cys Asn Leu Asp Ala Ile Lys Val Phe Cys Asn Met
                645                 650                 655

Glu Thr Gly Glu Thr Cys Val Tyr Pro Thr Gln Pro Ser Val Ala Gln
            660                 665                 670

Lys Asn Trp Tyr Ile Ser Lys Asn Pro Lys Asp Lys Arg His Val Trp
            675                 680                 685

Phe Gly Glu Ser Met Thr Asp Gly Phe Gln Phe Glu Tyr Gly Gly Gln
```

```
                690                 695                 700
Gly Ser Asp Pro Ala Asp Val Ala Ile Gln Leu Thr Phe Leu Arg Leu
705                 710                 715                 720

Met Ser Thr Glu Ala Ser Gln Asn Ile Thr Tyr His Cys Lys Asn Ser
                725                 730                 735

Val Ala Tyr Met Asp Gln Gln Thr Gly Asn Leu Lys Lys Ala Leu Leu
                740                 745                 750

Leu Gln Gly Ser Asn Glu Ile Glu Ile Arg Ala Glu Gly Asn Ser Arg
                755                 760                 765

Phe Thr Tyr Ser Val Thr Val Asp Gly Cys Thr Ser His Thr Gly Ala
                770                 775                 780

Trp Gly Lys Thr Val Ile Glu Tyr Lys Thr Thr Lys Thr Ser Arg Leu
785                 790                 795                 800

Pro Ile Ile Asp Val Ala Pro Leu Asp Val Gly Ala Pro Asp Gln Glu
                805                 810                 815

Phe Gly Phe Asp Val Gly Pro Val Cys Phe Leu
                820                 825

<210> SEQ ID NO 9
<211> LENGTH: 707
<212> TYPE: PRT
<213> ORGANISM: Artificial Sequence
<220> FEATURE:
<223> OTHER INFORMATION: Synthetic construct

<400> SEQUENCE: 9

Ser Phe Ile Glu Asp Leu Leu Phe Asn Lys Val Thr Leu Ala Asp Ala
1               5                   10                  15

Gly Phe Ile Lys Gln Tyr Gly Asp Cys Leu Gly Asp Ile Ala Ala Arg
                20                  25                  30

Asp Leu Ile Cys Ala Gln Lys Phe Asn Gly Leu Thr Val Leu Pro Pro
                35                  40                  45

Leu Leu Thr Asp Glu Met Ile Ala Gln Tyr Thr Ser Ala Leu Leu Ala
            50                  55                  60

Gly Thr Ile Thr Ser Gly Trp Thr Phe Gly Ala Gly Ala Ala Leu Gln
65              70                  75                  80

Ile Pro Phe Ala Met Gln Met Ala Tyr Arg Phe Asn Gly Ile Gly Val
                85                  90                  95

Thr Gln Asn Val Leu Tyr Glu Asn Gln Lys Leu Ile Ala Asn Gln Phe
                100                 105                 110

Asn Ser Ala Ile Gly Lys Ile Gln Asp Ser Leu Ser Ser Thr Ala Ser
                115                 120                 125

Ala Leu Gly Lys Leu Gln Asp Val Val Asn Gln Asn Ala Gln Ala Leu
            130                 135                 140

Asn Thr Leu Val Lys Gln Leu Ser Ser Asn Phe Gly Ala Ile Ser Ser
145                 150                 155                 160

Val Leu Asn Asp Ile Leu Ser Arg Leu Asp Lys Val Glu Ala Glu Val
                165                 170                 175

Gln Ile Asp Arg Leu Ile Thr Gly Arg Leu Gln Ser Leu Gln Thr Tyr
                180                 185                 190

Val Thr Gln Gln Leu Ile Arg Ala Ala Glu Ile Arg Ala Ser Ala Asn
                195                 200                 205

Leu Ala Ala Thr Lys Met Ser Glu Cys Val Leu Gly Gln Ser Lys Arg
            210                 215                 220

Val Asp Phe Cys Gly Lys Gly Tyr His Leu Met Ser Phe Pro Gln Ser
```

```
            225                 230                 235                 240
        Ala Pro His Gly Val Val Phe Leu His Val Thr Tyr Val Pro Ala Gln
                        245                 250                 255
        Glu Lys Asn Phe Thr Thr Ala Pro Ala Ile Cys His Asp Gly Lys Ala
                        260                 265                 270
        His Phe Pro Arg Glu Gly Val Phe Val Ser Asn Gly Thr His Trp Phe
                        275                 280                 285
        Val Thr Gln Arg Asn Phe Tyr Glu Pro Gln Ile Ile Thr Thr Asp Asn
                        290                 295                 300
        Thr Phe Val Ser Gly Asn Cys Asp Val Val Ile Gly Ile Val Asn Asn
        305                 310                 315                 320
        Thr Val Tyr Asp Pro Leu Gln Pro Glu Leu Asp Ser Phe Lys Glu Glu
                        325                 330                 335
        Leu Asp Lys Tyr Phe Lys Asn His Thr Ser Pro Asp Val Asp Leu Gly
                        340                 345                 350
        Asp Ile Ser Gly Ile Asn Ala Ser Val Val Asn Ile Gln Lys Glu Ile
                        355                 360                 365
        Asp Arg Leu Asn Glu Val Ala Lys Asn Leu Asn Glu Ser Leu Ile Asp
                        370                 375                 380
        Leu Gln Glu Leu Gly Lys Tyr Glu Gln Tyr Ile Lys Arg Ser Asn Gly
        385                 390                 395                 400
        Leu Pro Gly Pro Ile Gly Pro Pro Gly Pro Arg Gly Arg Thr Gly Asp
                        405                 410                 415
        Ala Gly Pro Val Gly Pro Pro Gly Pro Pro Gly Pro Pro Gly Pro Pro
                        420                 425                 430
        Gly Pro Pro Ser Ala Gly Phe Asp Phe Ser Phe Leu Pro Gln Pro Pro
                        435                 440                 445
        Gln Glu Lys Ala His Asp Gly Gly Arg Tyr Tyr Arg Ala Asn Asp Ala
                        450                 455                 460
        Asn Val Val Arg Asp Arg Asp Leu Glu Val Asp Thr Thr Leu Lys Ser
        465                 470                 475                 480
        Leu Ser Gln Gln Ile Glu Asn Ile Arg Ser Pro Glu Gly Ser Arg Lys
                        485                 490                 495
        Asn Pro Ala Arg Thr Cys Arg Asp Leu Lys Met Cys His Ser Asp Trp
                        500                 505                 510
        Lys Ser Gly Glu Tyr Trp Ile Asp Pro Asn Gln Gly Cys Asn Leu Asp
                        515                 520                 525
        Ala Ile Lys Val Phe Cys Asn Met Glu Thr Gly Glu Thr Cys Val Tyr
        530                 535                 540
        Pro Thr Gln Pro Ser Val Ala Gln Lys Asn Trp Tyr Ile Ser Lys Asn
        545                 550                 555                 560
        Pro Lys Asp Lys Arg His Val Trp Phe Gly Glu Ser Met Thr Asp Gly
                        565                 570                 575
        Phe Gln Phe Glu Tyr Gly Gly Gln Gly Ser Asp Pro Ala Asp Val Ala
                        580                 585                 590
        Ile Gln Leu Thr Phe Leu Arg Leu Met Ser Thr Glu Ala Ser Gln Asn
                        595                 600                 605
        Ile Thr Tyr His Cys Lys Asn Ser Val Ala Tyr Met Asp Gln Gln Thr
                        610                 615                 620
        Gly Asn Leu Lys Lys Ala Leu Leu Leu Gln Gly Ser Asn Glu Ile Glu
        625                 630                 635                 640
        Ile Arg Ala Glu Gly Asn Ser Arg Phe Thr Tyr Ser Val Thr Val Asp
                        645                 650                 655
```

```
Gly Cys Thr Ser His Thr Gly Ala Trp Gly Lys Thr Val Ile Glu Tyr
            660                 665                 670

Lys Thr Thr Lys Thr Ser Arg Leu Pro Ile Ile Asp Val Ala Pro Leu
            675                 680                 685

Asp Val Gly Ala Pro Asp Gln Glu Phe Gly Phe Asp Val Gly Pro Val
            690                 695                 700

Cys Phe Leu
705

<210> SEQ ID NO 10
<211> LENGTH: 1509
<212> TYPE: PRT
<213> ORGANISM: Artificial Sequence
<220> FEATURE:
<223> OTHER INFORMATION: Synthetic construct

<400> SEQUENCE: 10

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205

Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
                245                 250                 255

Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
        275                 280                 285

Thr Leu Lys Ser Phe Thr Val Glu Lys Gly Ile Tyr Gln Thr Ser Asn
    290                 295                 300
```

```
Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
            325                 330                 335

Val Tyr Ala Trp Asn Arg Lys Arg Ile Ser Asn Cys Val Ala Asp Tyr
        340                 345                 350

Ser Val Leu Tyr Asn Ser Ala Ser Phe Ser Thr Phe Lys Cys Tyr Gly
                355                 360                 365

Val Ser Pro Thr Lys Leu Asn Asp Leu Cys Phe Thr Asn Val Tyr Ala
        370                 375                 380

Asp Ser Phe Val Ile Arg Gly Asp Glu Val Arg Gln Ile Ala Pro Gly
385                 390                 395                 400

Gln Thr Gly Asn Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
            420                 425                 430

Gly Gly Asn Tyr Asn Tyr Leu Tyr Arg Leu Phe Arg Lys Ser Asn Leu
        435                 440                 445

Lys Pro Phe Glu Arg Asp Ile Ser Thr Glu Ile Tyr Gln Ala Gly Ser
    450                 455                 460

Thr Pro Cys Asn Gly Val Lys Gly Phe Asn Cys Tyr Phe Pro Leu Gln
465                 470                 475                 480

Ser Tyr Gly Phe Gln Pro Thr Tyr Gly Val Gly Tyr Gln Pro Tyr Arg
                485                 490                 495

Val Val Val Leu Ser Phe Glu Leu Leu His Ala Pro Ala Thr Val Cys
            500                 505                 510

Gly Pro Lys Lys Ser Thr Asn Leu Val Lys Asn Lys Cys Val Asn Phe
        515                 520                 525

Asn Phe Asn Gly Leu Thr Gly Thr Gly Val Leu Thr Glu Ser Asn Lys
    530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
            580                 585                 590

Asn Gln Val Ala Val Leu Tyr Gln Gly Val Asn Cys Thr Glu Val Pro
        595                 600                 605

Val Ala Ile His Ala Asp Gln Leu Thr Pro Thr Trp Arg Val Tyr Ser
    610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Arg Arg Ala Arg
            660                 665                 670

Ser Val Ala Ser Gln Ser Ile Ile Ala Tyr Thr Met Ser Leu Gly Ala
        675                 680                 685

Glu Asn Ser Val Ala Tyr Ser Asn Asn Ser Ile Ala Ile Pro Thr Asn
    690                 695                 700

Phe Thr Ile Ser Val Thr Thr Glu Ile Leu Pro Val Ser Met Thr Lys
705                 710                 715                 720
```

```
Thr Ser Val Asp Cys Thr Met Tyr Ile Cys Gly Asp Ser Thr Glu Cys
            725                 730                 735

Ser Asn Leu Leu Leu Gln Tyr Gly Ser Phe Cys Thr Gln Leu Asn Arg
            740                 745                 750

Ala Leu Thr Gly Ile Ala Val Glu Gln Asp Lys Asn Thr Gln Glu Val
            755                 760                 765

Phe Ala Gln Val Lys Gln Ile Tyr Lys Thr Pro Pro Ile Lys Asp Phe
            770                 775                 780

Gly Gly Phe Asn Phe Ser Gln Ile Leu Pro Asp Pro Ser Lys Pro Ser
785                 790                 795                 800

Lys Arg Ser Phe Ile Glu Asp Leu Leu Phe Asn Lys Val Thr Leu Ala
            805                 810                 815

Asp Ala Gly Phe Ile Lys Gln Tyr Gly Asp Cys Leu Gly Asp Ile Ala
            820                 825                 830

Ala Arg Asp Leu Ile Cys Ala Gln Lys Phe Asn Gly Leu Thr Val Leu
            835                 840                 845

Pro Pro Leu Leu Thr Asp Glu Met Ile Ala Gln Tyr Thr Ser Ala Leu
            850                 855                 860

Leu Ala Gly Thr Ile Thr Ser Gly Trp Thr Phe Gly Ala Gly Ala Ala
865                 870                 875                 880

Leu Gln Ile Pro Phe Ala Met Gln Met Ala Tyr Arg Phe Asn Gly Ile
            885                 890                 895

Gly Val Thr Gln Asn Val Leu Tyr Glu Asn Gln Lys Leu Ile Ala Asn
            900                 905                 910

Gln Phe Asn Ser Ala Ile Gly Lys Ile Gln Asp Ser Leu Ser Ser Thr
            915                 920                 925

Ala Ser Ala Leu Gly Lys Leu Gln Asp Val Val Asn Gln Asn Ala Gln
            930                 935                 940

Ala Leu Asn Thr Leu Val Lys Gln Leu Ser Ser Asn Phe Gly Ala Ile
945                 950                 955                 960

Ser Ser Val Leu Asn Asp Ile Leu Ser Arg Leu Asp Lys Val Glu Ala
            965                 970                 975

Glu Val Gln Ile Asp Arg Leu Ile Thr Gly Arg Leu Gln Ser Leu Gln
            980                 985                 990

Thr Tyr Val Thr Gln Gln Leu Ile Arg Ala Ala Glu Ile Arg Ala Ser
            995                 1000                1005

Ala Asn Leu Ala Ala Thr Lys Met Ser Glu Cys Val Leu Gly Gln Ser
            1010                1015                1020

Lys Arg Val Asp Phe Cys Gly Lys Gly Tyr His Leu Met Ser Phe Pro
1025                1030                1035                1040

Gln Ser Ala Pro His Gly Val Val Phe Leu His Val Thr Tyr Val Pro
            1045                1050                1055

Ala Gln Glu Lys Asn Phe Thr Thr Ala Pro Ala Ile Cys His Asp Gly
            1060                1065                1070

Lys Ala His Phe Pro Arg Glu Gly Val Phe Val Ser Asn Gly Thr His
            1075                1080                1085

Trp Phe Val Thr Gln Arg Asn Phe Tyr Glu Pro Gln Ile Ile Thr Thr
            1090                1095                1100

Asp Asn Thr Phe Val Ser Gly Asn Cys Asp Val Val Ile Gly Ile Val
1105                1110                1115                1120

Asn Asn Thr Val Tyr Asp Pro Leu Gln Pro Glu Leu Asp Ser Phe Lys
            1125                1130                1135

Glu Glu Leu Asp Lys Tyr Phe Lys Asn His Thr Ser Pro Asp Val Asp
```

```
                    1140              1145              1150

Leu Gly Asp Ile Ser Gly Ile Asn Ala Ser Val Val Asn Ile Gln Lys
        1155              1160              1165

Glu Ile Asp Arg Leu Asn Glu Val Ala Lys Asn Leu Asn Glu Ser Leu
    1170              1175              1180

Ile Asp Leu Gln Glu Leu Gly Lys Tyr Glu Gln Tyr Ile Lys Arg Ser
1185              1190              1195              1200

Asn Gly Leu Pro Gly Pro Ile Gly Pro Pro Gly Pro Arg Gly Arg Thr
            1205              1210              1215

Gly Asp Ala Gly Pro Val Gly Pro Pro Gly Pro Pro Gly Pro Pro Gly
        1220              1225              1230

Pro Pro Gly Pro Pro Ser Ala Gly Phe Asp Phe Ser Phe Leu Pro Gln
        1235              1240              1245

Pro Pro Gln Glu Lys Ala His Asp Gly Gly Arg Tyr Tyr Arg Ala Asn
        1250              1255              1260

Asp Ala Asn Val Val Arg Asp Arg Asp Leu Glu Val Asp Thr Thr Leu
1265              1270              1275              1280

Lys Ser Leu Ser Gln Gln Ile Glu Asn Ile Arg Ser Pro Glu Gly Ser
            1285              1290              1295

Arg Lys Asn Pro Ala Arg Thr Cys Arg Asp Leu Lys Met Cys His Ser
            1300              1305              1310

Asp Trp Lys Ser Gly Glu Tyr Trp Ile Asp Pro Asn Gln Gly Cys Asn
        1315              1320              1325

Leu Asp Ala Ile Lys Val Phe Cys Asn Met Glu Thr Gly Glu Thr Cys
        1330              1335              1340

Val Tyr Pro Thr Gln Pro Ser Val Ala Gln Lys Asn Trp Tyr Ile Ser
1345              1350              1355              1360

Lys Asn Pro Lys Asp Lys Arg His Val Trp Phe Gly Glu Ser Met Thr
            1365              1370              1375

Asp Gly Phe Gln Phe Glu Tyr Gly Gly Gln Gly Ser Asp Pro Ala Asp
            1380              1385              1390

Val Ala Ile Gln Leu Thr Phe Leu Arg Leu Met Ser Thr Glu Ala Ser
        1395              1400              1405

Gln Asn Ile Thr Tyr His Cys Lys Asn Ser Val Ala Tyr Met Asp Gln
    1410              1415              1420

Gln Thr Gly Asn Leu Lys Lys Ala Leu Leu Leu Gln Gly Ser Asn Glu
1425              1430              1435              1440

Ile Glu Ile Arg Ala Glu Gly Asn Ser Arg Phe Thr Tyr Ser Val Thr
            1445              1450              1455

Val Asp Gly Cys Thr Ser His Thr Gly Ala Trp Gly Lys Thr Val Ile
            1460              1465              1470

Glu Tyr Lys Thr Thr Lys Thr Ser Arg Leu Pro Ile Ile Asp Val Ala
        1475              1480              1485

Pro Leu Asp Val Gly Ala Pro Asp Gln Glu Phe Gly Phe Asp Val Gly
        1490              1495              1500

Pro Val Cys Phe Leu
1505

<210> SEQ ID NO 11
<211> LENGTH: 1509
<212> TYPE: PRT
<213> ORGANISM: Artificial Sequence
<220> FEATURE:
<223> OTHER INFORMATION: Synthetic construct
```

<400> SEQUENCE: 11

```
Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205

Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
                245                 250                 255

Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
        275                 280                 285

Thr Leu Lys Ser Phe Thr Val Glu Lys Gly Ile Tyr Gln Thr Ser Asn
    290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
            340                 345                 350

Ser Val Leu Tyr Asn Ser Ala Ser Phe Ser Thr Phe Lys Cys Tyr Gly
        355                 360                 365

Val Ser Pro Thr Lys Leu Asn Asp Leu Cys Phe Thr Asn Val Tyr Ala
    370                 375                 380

Asp Ser Phe Val Ile Arg Gly Asp Glu Val Arg Gln Ile Ala Pro Gly
385                 390                 395                 400

Gln Thr Gly Asn Ile Ala Asp Tyr Asn Tyr Lys Leu Pro Asp Asp Phe
                405                 410                 415
```

-continued

```
Thr Gly Cys Val Ile Ala Trp Asn Ser Asn Leu Asp Ser Lys Val
            420                 425                 430
Gly Gly Asn Tyr Asn Tyr Leu Tyr Arg Leu Phe Arg Lys Ser Asn Leu
        435                 440                 445
Lys Pro Phe Glu Arg Asp Ile Ser Thr Glu Ile Tyr Gln Ala Gly Ser
    450                 455                 460
Thr Pro Cys Asn Gly Val Lys Gly Phe Asn Cys Tyr Phe Pro Leu Gln
465                 470                 475                 480
Ser Tyr Gly Phe Gln Pro Thr Tyr Gly Val Gly Tyr Gln Pro Tyr Arg
                485                 490                 495
Val Val Val Leu Ser Phe Glu Leu Leu His Ala Pro Ala Thr Val Cys
            500                 505                 510
Gly Pro Lys Lys Ser Thr Asn Leu Val Lys Asn Lys Cys Val Asn Phe
        515                 520                 525
Asn Phe Asn Gly Leu Thr Gly Thr Gly Val Leu Thr Glu Ser Asn Lys
    530                 535                 540
Lys Phe Leu Pro Phe Gln Gln Phe Gly Arg Asp Ile Ala Asp Thr Thr
545                 550                 555                 560
Asp Ala Val Arg Asp Pro Gln Thr Leu Glu Ile Leu Asp Ile Thr Pro
                565                 570                 575
Cys Ser Phe Gly Gly Val Ser Val Ile Thr Pro Gly Thr Asn Thr Ser
            580                 585                 590
Asn Gln Val Ala Val Leu Tyr Gln Gly Val Asn Cys Thr Glu Val Pro
        595                 600                 605
Val Ala Ile His Ala Asp Gln Leu Thr Pro Thr Trp Arg Val Tyr Ser
    610                 615                 620
Thr Gly Ser Asn Val Phe Gln Thr Arg Ala Gly Cys Leu Ile Gly Ala
625                 630                 635                 640
Glu His Val Asn Asn Ser Tyr Glu Cys Asp Ile Pro Ile Gly Ala Gly
                645                 650                 655
Ile Cys Ala Ser Tyr Gln Thr Gln Thr Asn Ser Pro Arg Arg Ala Ala
            660                 665                 670
Ser Val Ala Ser Gln Ser Ile Ile Ala Tyr Thr Met Ser Leu Gly Ala
        675                 680                 685
Glu Asn Ser Val Ala Tyr Ser Asn Asn Ser Ile Ala Ile Pro Thr Asn
    690                 695                 700
Phe Thr Ile Ser Val Thr Thr Glu Ile Leu Pro Val Ser Met Thr Lys
705                 710                 715                 720
Thr Ser Val Asp Cys Thr Met Tyr Ile Cys Gly Asp Ser Thr Glu Cys
                725                 730                 735
Ser Asn Leu Leu Leu Gln Tyr Gly Ser Phe Cys Thr Gln Leu Asn Arg
            740                 745                 750
Ala Leu Thr Gly Ile Ala Val Glu Gln Asp Lys Asn Thr Gln Glu Val
        755                 760                 765
Phe Ala Gln Val Lys Gln Ile Tyr Lys Thr Pro Pro Ile Lys Asp Phe
    770                 775                 780
Gly Gly Phe Asn Phe Ser Gln Ile Leu Pro Asp Pro Ser Lys Pro Ser
785                 790                 795                 800
Lys Arg Ser Phe Ile Glu Asp Leu Leu Phe Asn Lys Val Thr Leu Ala
                805                 810                 815
Asp Ala Gly Phe Ile Lys Gln Tyr Gly Asp Cys Leu Gly Asp Ile Ala
            820                 825                 830
```

```
Ala Arg Asp Leu Ile Cys Ala Gln Lys Phe Asn Gly Leu Thr Val Leu
        835                 840                 845

Pro Pro Leu Leu Thr Asp Glu Met Ile Ala Gln Tyr Thr Ser Ala Leu
        850                 855                 860

Leu Ala Gly Thr Ile Thr Ser Gly Trp Thr Phe Gly Ala Gly Ala Ala
865                 870                 875                 880

Leu Gln Ile Pro Phe Ala Met Gln Met Ala Tyr Arg Phe Asn Gly Ile
                885                 890                 895

Gly Val Thr Gln Asn Val Leu Tyr Glu Asn Gln Lys Leu Ile Ala Asn
            900                 905                 910

Gln Phe Asn Ser Ala Ile Gly Lys Ile Gln Asp Ser Leu Ser Ser Thr
        915                 920                 925

Ala Ser Ala Leu Gly Lys Leu Gln Asp Val Val Asn Gln Asn Ala Gln
    930                 935                 940

Ala Leu Asn Thr Leu Val Lys Gln Leu Ser Ser Asn Phe Gly Ala Ile
945                 950                 955                 960

Ser Ser Val Leu Asn Asp Ile Leu Ser Arg Leu Asp Lys Val Glu Ala
                965                 970                 975

Glu Val Gln Ile Asp Arg Leu Ile Thr Gly Arg Leu Gln Ser Leu Gln
            980                 985                 990

Thr Tyr Val Thr Gln Gln Leu Ile Arg Ala Ala Glu Ile Arg Ala Ser
        995                 1000                1005

Ala Asn Leu Ala Ala Thr Lys Met Ser Glu Cys Val Leu Gly Gln Ser
        1010                1015                1020

Lys Arg Val Asp Phe Cys Gly Lys Gly Tyr His Leu Met Ser Phe Pro
1025                1030                1035                1040

Gln Ser Ala Pro His Gly Val Val Phe Leu His Val Thr Tyr Val Pro
            1045                1050                1055

Ala Gln Glu Lys Asn Phe Thr Thr Ala Pro Ala Ile Cys His Asp Gly
        1060                1065                1070

Lys Ala His Phe Pro Arg Glu Gly Val Phe Val Ser Asn Gly Thr His
            1075                1080                1085

Trp Phe Val Thr Gln Arg Asn Phe Tyr Glu Pro Gln Ile Ile Thr Thr
1090                1095                1100

Asp Asn Thr Phe Val Ser Gly Asn Cys Asp Val Val Ile Gly Ile Val
1105                1110                1115                1120

Asn Asn Thr Val Tyr Asp Pro Leu Gln Pro Glu Leu Asp Ser Phe Lys
                1125                1130                1135

Glu Glu Leu Asp Lys Tyr Phe Lys Asn His Thr Ser Pro Asp Val Asp
            1140                1145                1150

Leu Gly Asp Ile Ser Gly Ile Asn Ala Ser Val Val Asn Ile Gln Lys
        1155                1160                1165

Glu Ile Asp Arg Leu Asn Glu Val Ala Lys Asn Leu Asn Glu Ser Leu
    1170                1175                1180

Ile Asp Leu Gln Glu Leu Gly Lys Tyr Glu Gln Tyr Ile Lys Arg Ser
1185                1190                1195                1200

Asn Gly Leu Pro Gly Pro Ile Gly Pro Pro Gly Pro Arg Gly Arg Thr
            1205                1210                1215

Gly Asp Ala Gly Pro Val Gly Pro Pro Gly Pro Pro Gly Pro Pro Gly
        1220                1225                1230

Pro Pro Gly Pro Pro Ser Ala Gly Phe Asp Phe Ser Phe Leu Pro Gln
        1235                1240                1245

Pro Pro Gln Glu Lys Ala His Asp Gly Gly Arg Tyr Tyr Arg Ala Asn
```

```
                1250                1255                1260

Asp Ala Asn Val Val Arg Asp Arg Asp Leu Glu Val Asp Thr Thr Leu
1265                1270                1275                1280

Lys Ser Leu Ser Gln Gln Ile Glu Asn Ile Arg Ser Pro Glu Gly Ser
                1285                1290                1295

Arg Lys Asn Pro Ala Arg Thr Cys Arg Asp Leu Lys Met Cys His Ser
            1300                1305                1310

Asp Trp Lys Ser Gly Glu Tyr Trp Ile Asp Pro Asn Gln Gly Cys Asn
            1315                1320                1325

Leu Asp Ala Ile Lys Val Phe Cys Asn Met Glu Thr Gly Glu Thr Cys
        1330                1335                1340

Val Tyr Pro Thr Gln Pro Ser Val Ala Gln Lys Asn Trp Tyr Ile Ser
1345                1350                1355                1360

Lys Asn Pro Lys Asp Lys Arg His Val Trp Phe Gly Glu Ser Met Thr
            1365                1370                1375

Asp Gly Phe Gln Phe Glu Tyr Gly Gly Gln Gly Ser Asp Pro Ala Asp
        1380                1385                1390

Val Ala Ile Gln Leu Thr Phe Leu Arg Leu Met Ser Thr Glu Ala Ser
            1395                1400                1405

Gln Asn Ile Thr Tyr His Cys Lys Asn Ser Val Ala Tyr Met Asp Gln
        1410                1415                1420

Gln Thr Gly Asn Leu Lys Lys Ala Leu Leu Leu Gln Gly Ser Asn Glu
1425                1430                1435                1440

Ile Glu Ile Arg Ala Glu Gly Asn Ser Arg Phe Thr Tyr Ser Val Thr
            1445                1450                1455

Val Asp Gly Cys Thr Ser His Thr Gly Ala Trp Gly Lys Thr Val Ile
            1460                1465                1470

Glu Tyr Lys Thr Thr Lys Thr Ser Arg Leu Pro Ile Ile Asp Val Ala
            1475                1480                1485

Pro Leu Asp Val Gly Ala Pro Asp Gln Glu Phe Gly Phe Asp Val Gly
            1490                1495                1500

Pro Val Cys Phe Leu
1505

<210> SEQ ID NO 12
<211> LENGTH: 1509
<212> TYPE: PRT
<213> ORGANISM: Artificial Sequence
<220> FEATURE:
<223> OTHER INFORMATION: Synthetic construct

<400> SEQUENCE: 12

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
```

```
            100             105             110
Val Val Ile Lys Val Cys Glu Phe Gln Phe Cys Asn Asp Pro Phe Leu
            115             120             125
Gly Val Tyr Tyr His Lys Asn Asn Lys Ser Trp Met Glu Ser Glu Phe
            130             135             140
Arg Val Tyr Ser Ser Ala Asn Asn Cys Thr Phe Glu Tyr Val Ser Gln
145             150             155             160
Pro Phe Leu Met Asp Leu Glu Gly Lys Gln Gly Asn Phe Lys Asn Leu
            165             170             175
Arg Glu Phe Val Phe Lys Asn Ile Asp Gly Tyr Phe Lys Ile Tyr Ser
            180             185             190
Lys His Thr Pro Ile Asn Leu Val Arg Asp Leu Pro Gln Gly Phe Ser
            195             200             205
Ala Leu Glu Pro Leu Val Asp Leu Pro Ile Gly Ile Asn Ile Thr Arg
            210             215             220
Phe Gln Thr Leu Leu Ala Leu His Arg Ser Tyr Leu Thr Pro Gly Asp
225             230             235             240
Ser Ser Ser Gly Trp Thr Ala Gly Ala Ala Ala Tyr Tyr Val Gly Tyr
                245             250             255
Leu Gln Pro Arg Thr Phe Leu Leu Lys Tyr Asn Glu Asn Gly Thr Ile
            260             265             270
Thr Asp Ala Val Asp Cys Ala Leu Asp Pro Leu Ser Glu Thr Lys Cys
            275             280             285
Thr Leu Lys Ser Phe Thr Val Glu Lys Gly Ile Tyr Gln Thr Ser Asn
            290             295             300
Phe Arg Val Gln Pro Thr Glu Ser Ile Val Arg Phe Pro Asn Ile Thr
305             310             315             320
Asn Leu Cys Pro Phe Gly Glu Val Phe Asn Ala Thr Arg Phe Ala Ser
                325             330             335
Val Tyr Ala Trp Asn Arg Lys Arg Ile Ser Asn Cys Val Ala Asp Tyr
                340             345             350
Ser Val Leu Tyr Asn Ser Ala Ser Phe Ser Thr Phe Lys Cys Tyr Gly
            355             360             365
Val Ser Pro Thr Lys Leu Asn Asp Leu Cys Phe Thr Asn Val Tyr Ala
            370             375             380
Asp Ser Phe Val Ile Arg Gly Asp Glu Val Arg Gln Ile Ala Pro Gly
385             390             395             400
Gln Thr Gly Asn Ile Ala Asp Tyr Asn Tyr Lys Leu Pro Asp Asp Phe
                405             410             415
Thr Gly Cys Val Ile Ala Trp Asn Ser Asn Asn Leu Asp Ser Lys Val
            420             425             430
Gly Gly Asn Tyr Asn Tyr Leu Tyr Arg Leu Phe Arg Lys Ser Asn Leu
            435             440             445
Lys Pro Phe Glu Arg Asp Ile Ser Thr Glu Ile Tyr Gln Ala Gly Ser
            450             455             460
Thr Pro Cys Asn Gly Val Lys Gly Phe Asn Cys Tyr Phe Pro Leu Gln
465             470             475             480
Ser Tyr Gly Phe Gln Pro Thr Tyr Gly Val Gly Tyr Gln Pro Tyr Arg
                485             490             495
Val Val Val Leu Ser Phe Glu Leu Leu His Ala Pro Ala Thr Val Cys
            500             505             510
Gly Pro Lys Lys Ser Thr Asn Leu Val Lys Asn Lys Cys Val Asn Phe
            515             520             525
```

```
Asn Phe Asn Gly Leu Thr Gly Thr Gly Val Leu Thr Glu Ser Asn Lys
    530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
            580                 585                 590

Asn Gln Val Ala Val Leu Tyr Gln Gly Val Asn Cys Thr Glu Val Pro
        595                 600                 605

Val Ala Ile His Ala Asp Gln Leu Thr Pro Thr Trp Arg Val Tyr Ser
    610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Arg Arg Ala Arg
            660                 665                 670

Ser Val Ala Ser Gln Ser Ile Ile Ala Tyr Thr Met Ser Leu Gly Ala
        675                 680                 685

Glu Asn Ser Val Ala Tyr Ser Asn Asn Ser Ile Ala Ile Pro Thr Asn
    690                 695                 700

Phe Thr Ile Ser Val Thr Thr Glu Ile Leu Pro Val Ser Met Thr Lys
705                 710                 715                 720

Thr Ser Val Asp Cys Thr Met Tyr Ile Cys Gly Asp Ser Thr Glu Cys
                725                 730                 735

Ser Asn Leu Leu Leu Gln Tyr Gly Ser Phe Cys Thr Gln Leu Asn Arg
            740                 745                 750

Ala Leu Thr Gly Ile Ala Val Glu Gln Asp Lys Asn Thr Gln Glu Val
        755                 760                 765

Phe Ala Gln Val Lys Gln Ile Tyr Lys Thr Pro Pro Ile Lys Asp Phe
    770                 775                 780

Gly Gly Phe Asn Phe Ser Gln Ile Leu Pro Asp Pro Ser Lys Pro Ser
785                 790                 795                 800

Lys Arg Ser Phe Ile Glu Asp Leu Leu Phe Asn Lys Val Thr Leu Ala
                805                 810                 815

Asp Ala Gly Phe Ile Lys Gln Tyr Gly Asp Cys Leu Gly Asp Ile Ala
            820                 825                 830

Ala Arg Asp Leu Ile Cys Ala Gln Lys Phe Asn Gly Leu Thr Val Leu
        835                 840                 845

Pro Pro Leu Leu Thr Asp Glu Met Ile Ala Gln Tyr Thr Ser Ala Leu
    850                 855                 860

Leu Ala Gly Thr Ile Thr Ser Gly Trp Thr Phe Gly Ala Gly Ala Ala
865                 870                 875                 880

Leu Gln Ile Pro Phe Ala Met Gln Met Ala Tyr Arg Phe Asn Gly Ile
                885                 890                 895

Gly Val Thr Gln Asn Val Leu Tyr Glu Asn Gln Lys Leu Ile Ala Asn
            900                 905                 910

Gln Phe Asn Ser Ala Ile Gly Lys Ile Gln Asp Ser Leu Ser Ser Thr
        915                 920                 925

Ala Ser Ala Leu Gly Lys Leu Gln Asp Val Val Asn Gln Asn Ala Gln
    930                 935                 940
```

-continued

```
Ala Leu Asn Thr Leu Val Lys Gln Leu Ser Ser Asn Phe Gly Ala Ile
945                 950                 955                 960

Ser Ser Val Leu Asn Asp Ile Leu Ser Arg Leu Asp Pro Pro Glu Ala
            965                 970                 975

Glu Val Gln Ile Asp Arg Leu Ile Thr Gly Arg Leu Gln Ser Leu Gln
                980                 985                 990

Thr Tyr Val Thr Gln Gln Leu Ile Arg Ala Ala Glu Ile Arg Ala Ser
        995                1000                1005

Ala Asn Leu Ala Ala Thr Lys Met Ser Glu Cys Val Leu Gly Gln Ser
    1010                1015                1020

Lys Arg Val Asp Phe Cys Gly Lys Gly Tyr His Leu Met Ser Phe Pro
1025                1030                1035                1040

Gln Ser Ala Pro His Gly Val Val Phe Leu His Val Thr Tyr Val Pro
                1045                1050                1055

Ala Gln Glu Lys Asn Phe Thr Thr Ala Pro Ala Ile Cys His Asp Gly
            1060                1065                1070

Lys Ala His Phe Pro Arg Glu Gly Val Phe Val Ser Asn Gly Thr His
    1075                1080                1085

Trp Phe Val Thr Gln Arg Asn Phe Tyr Glu Pro Gln Ile Ile Thr Thr
    1090                1095                1100

Asp Asn Thr Phe Val Ser Gly Asn Cys Asp Val Val Ile Gly Ile Val
1105                1110                1115                1120

Asn Asn Thr Val Tyr Asp Pro Leu Gln Pro Glu Leu Asp Ser Phe Lys
                1125                1130                1135

Glu Glu Leu Asp Lys Tyr Phe Lys Asn His Thr Ser Pro Asp Val Asp
            1140                1145                1150

Leu Gly Asp Ile Ser Gly Ile Asn Ala Ser Val Val Asn Ile Gln Lys
    1155                1160                1165

Glu Ile Asp Arg Leu Asn Glu Val Ala Lys Asn Leu Asn Glu Ser Leu
1170                1175                1180

Ile Asp Leu Gln Glu Leu Gly Lys Tyr Glu Gln Tyr Ile Lys Arg Ser
1185                1190                1195                1200

Asn Gly Leu Pro Gly Pro Ile Gly Pro Pro Gly Pro Arg Gly Arg Thr
                1205                1210                1215

Gly Asp Ala Gly Pro Val Gly Pro Pro Gly Pro Pro Gly Pro Pro Gly
    1220                1225                1230

Pro Pro Gly Pro Pro Ser Ala Gly Phe Asp Phe Ser Phe Leu Pro Gln
        1235                1240                1245

Pro Pro Gln Glu Lys Ala His Asp Gly Gly Arg Tyr Tyr Arg Ala Asn
    1250                1255                1260

Asp Ala Asn Val Val Arg Asp Arg Asp Leu Glu Val Asp Thr Thr Leu
1265                1270                1275                1280

Lys Ser Leu Ser Gln Gln Ile Glu Asn Ile Arg Ser Pro Glu Gly Ser
            1285                1290                1295

Arg Lys Asn Pro Ala Arg Thr Cys Arg Asp Leu Lys Met Cys His Ser
            1300                1305                1310

Asp Trp Lys Ser Gly Glu Tyr Trp Ile Asp Pro Asn Gln Gly Cys Asn
    1315                1320                1325

Leu Asp Ala Ile Lys Val Phe Cys Asn Met Glu Thr Gly Glu Thr Cys
    1330                1335                1340

Val Tyr Pro Thr Gln Pro Ser Val Ala Gln Lys Asn Trp Tyr Ile Ser
1345                1350                1355                1360

Lys Asn Pro Lys Asp Lys Arg His Val Trp Phe Gly Glu Ser Met Thr
```

-continued

```
                1365                1370                1375
Asp Gly Phe Gln Phe Glu Tyr Gly Gly Gln Gly Ser Asp Pro Ala Asp
            1380                1385                1390

Val Ala Ile Gln Leu Thr Phe Leu Arg Leu Met Ser Thr Glu Ala Ser
            1395                1400                1405

Gln Asn Ile Thr Tyr His Cys Lys Asn Ser Val Ala Tyr Met Asp Gln
            1410                1415                1420

Gln Thr Gly Asn Leu Lys Lys Ala Leu Leu Gln Gly Ser Asn Glu
1425                1430                1435                1440

Ile Glu Ile Arg Ala Glu Gly Asn Ser Arg Phe Thr Tyr Ser Val Thr
            1445                1450                1455

Val Asp Gly Cys Thr Ser His Thr Gly Ala Trp Gly Lys Thr Val Ile
            1460                1465                1470

Glu Tyr Lys Thr Thr Lys Thr Ser Arg Leu Pro Ile Ile Asp Val Ala
            1475                1480                1485

Pro Leu Asp Val Gly Ala Pro Asp Gln Glu Phe Gly Phe Asp Val Gly
            1490                1495                1500

Pro Val Cys Phe Leu
1505

<210> SEQ ID NO 13
<211> LENGTH: 1509
<212> TYPE: PRT
<213> ORGANISM: Artificial Sequence
<220> FEATURE:
<223> OTHER INFORMATION: Synthetic construct

<400> SEQUENCE: 13

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
                20                  25                  30

Ser Val Leu His Ser Thr Gln Asp Leu Phe Leu Pro Phe Phe Ser Asn
            35                  40                  45

Val Thr Trp Phe His Ala Ile His Val Ser Gly Thr Asn Gly Thr Lys
        50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205

Ala Leu Glu Pro Leu Val Asp Leu Pro Ile Gly Ile Asn Ile Thr Arg
```

-continued

```
                210                 215                 220
    Phe Gln Thr Leu Leu Ala Leu His Arg Ser Tyr Leu Thr Pro Gly Asp
    225                 230                 235                 240

Ser Ser Ser Gly Trp Thr Ala Gly Ala Ala Tyr Val Gly Tyr
                    245                 250                 255

Leu Gln Pro Arg Thr Phe Leu Leu Lys Tyr Asn Glu Asn Gly Thr Ile
                    260                 265                 270

Thr Asp Ala Val Asp Cys Ala Leu Asp Pro Leu Ser Glu Thr Lys Cys
                275                 280                 285

Thr Leu Lys Ser Phe Thr Val Glu Lys Gly Ile Tyr Gln Thr Ser Asn
                290                 295                 300

Phe Arg Val Gln Pro Thr Glu Ser Ile Val Arg Phe Pro Asn Ile Thr
    305                 310                 315                 320

Asn Leu Cys Pro Phe Gly Glu Val Phe Asn Ala Thr Arg Phe Ala Ser
                    325                 330                 335

Val Tyr Ala Trp Asn Arg Lys Arg Ile Ser Asn Cys Val Ala Asp Tyr
                    340                 345                 350

Ser Val Leu Tyr Asn Ser Ala Ser Phe Ser Thr Phe Lys Cys Tyr Gly
                355                 360                 365

Val Ser Pro Thr Lys Leu Asn Asp Leu Cys Phe Thr Asn Val Tyr Ala
                370                 375                 380

Asp Ser Phe Val Ile Arg Gly Asp Glu Val Arg Gln Ile Ala Pro Gly
    385                 390                 395                 400

Gln Thr Gly Asn Ile Ala Asp Tyr Asn Tyr Lys Leu Pro Asp Asp Phe
                    405                 410                 415

Thr Gly Cys Val Ile Ala Trp Asn Ser Asn Asn Leu Asp Ser Lys Val
                    420                 425                 430

Gly Gly Asn Tyr Asn Tyr Leu Tyr Arg Leu Phe Arg Lys Ser Asn Leu
                435                 440                 445

Lys Pro Phe Glu Arg Asp Ile Ser Thr Glu Ile Tyr Gln Ala Gly Ser
    450                 455                 460

Thr Pro Cys Asn Gly Val Lys Gly Phe Asn Cys Tyr Phe Pro Leu Gln
    465                 470                 475                 480

Ser Tyr Gly Phe Gln Pro Thr Tyr Gly Val Gly Tyr Gln Pro Tyr Arg
                    485                 490                 495

Val Val Val Leu Ser Phe Glu Leu Leu His Ala Pro Ala Thr Val Cys
                500                 505                 510

Gly Pro Lys Lys Ser Thr Asn Leu Val Lys Asn Lys Cys Val Asn Phe
                515                 520                 525

Asn Phe Asn Gly Leu Thr Gly Thr Gly Val Leu Thr Glu Ser Asn Lys
    530                 535                 540

Lys Phe Leu Pro Phe Gln Gln Phe Gly Arg Asp Ile Ala Asp Thr Thr
    545                 550                 555                 560

Asp Ala Val Arg Asp Pro Gln Thr Leu Glu Ile Leu Asp Ile Thr Pro
                    565                 570                 575

Cys Ser Phe Gly Gly Val Ser Val Ile Thr Pro Gly Thr Asn Thr Ser
                    580                 585                 590

Asn Gln Val Ala Val Leu Tyr Gln Gly Val Asn Cys Thr Glu Val Pro
                595                 600                 605

Val Ala Ile His Ala Asp Gln Leu Thr Pro Thr Trp Arg Val Tyr Ser
                610                 615                 620

Thr Gly Ser Asn Val Phe Gln Thr Arg Ala Gly Cys Leu Ile Gly Ala
    625                 630                 635                 640
```

```
Glu His Val Asn Asn Ser Tyr Glu Cys Asp Ile Pro Ile Gly Ala Gly
            645                 650                 655

Ile Cys Ala Ser Tyr Gln Thr Gln Thr Asn Ser Pro Arg Arg Ala Ala
        660                 665                 670

Ser Val Ala Ser Gln Ser Ile Ile Ala Tyr Thr Met Ser Leu Gly Ala
            675                 680                 685

Glu Asn Ser Val Ala Tyr Ser Asn Asn Ser Ile Ala Ile Pro Thr Asn
        690                 695                 700

Phe Thr Ile Ser Val Thr Thr Glu Ile Leu Pro Val Ser Met Thr Lys
705                 710                 715                 720

Thr Ser Val Asp Cys Thr Met Tyr Ile Cys Gly Asp Ser Thr Glu Cys
            725                 730                 735

Ser Asn Leu Leu Leu Gln Tyr Gly Ser Phe Cys Thr Gln Leu Asn Arg
            740                 745                 750

Ala Leu Thr Gly Ile Ala Val Glu Gln Asp Lys Asn Thr Gln Glu Val
            755                 760                 765

Phe Ala Gln Val Lys Gln Ile Tyr Lys Thr Pro Pro Ile Lys Asp Phe
        770                 775                 780

Gly Gly Phe Asn Phe Ser Gln Ile Leu Pro Asp Pro Ser Lys Pro Ser
785                 790                 795                 800

Lys Arg Ser Phe Ile Glu Asp Leu Leu Phe Asn Lys Val Thr Leu Ala
            805                 810                 815

Asp Ala Gly Phe Ile Lys Gln Tyr Gly Asp Cys Leu Gly Asp Ile Ala
            820                 825                 830

Ala Arg Asp Leu Ile Cys Ala Gln Lys Phe Asn Gly Leu Thr Val Leu
        835                 840                 845

Pro Pro Leu Leu Thr Asp Glu Met Ile Ala Gln Tyr Thr Ser Ala Leu
        850                 855                 860

Leu Ala Gly Thr Ile Thr Ser Gly Trp Thr Phe Gly Ala Gly Ala Ala
865                 870                 875                 880

Leu Gln Ile Pro Phe Ala Met Gln Met Ala Tyr Arg Phe Asn Gly Ile
            885                 890                 895

Gly Val Thr Gln Asn Val Leu Tyr Glu Asn Gln Lys Leu Ile Ala Asn
        900                 905                 910

Gln Phe Asn Ser Ala Ile Gly Lys Ile Gln Asp Ser Leu Ser Ser Thr
        915                 920                 925

Ala Ser Ala Leu Gly Lys Leu Gln Asp Val Val Asn Gln Asn Ala Gln
        930                 935                 940

Ala Leu Asn Thr Leu Val Lys Gln Leu Ser Ser Asn Phe Gly Ala Ile
945                 950                 955                 960

Ser Ser Val Leu Asn Asp Ile Leu Ser Arg Leu Asp Pro Pro Glu Ala
            965                 970                 975

Glu Val Gln Ile Asp Arg Leu Ile Thr Gly Arg Leu Gln Ser Leu Gln
            980                 985                 990

Thr Tyr Val Thr Gln Gln Leu Ile Arg Ala Ala Glu Ile Arg Ala Ser
            995                 1000                1005

Ala Asn Leu Ala Ala Thr Lys Met Ser Glu Cys Val Leu Gly Gln Ser
        1010                1015                1020

Lys Arg Val Asp Phe Cys Gly Lys Gly Tyr His Leu Met Ser Phe Pro
1025                1030                1035                1040

Gln Ser Ala Pro His Gly Val Val Phe Leu His Val Thr Tyr Val Pro
            1045                1050                1055
```

```
Ala Gln Glu Lys Asn Phe Thr Thr Ala Pro Ala Ile Cys His Asp Gly
                1060                1065                1070

Lys Ala His Phe Pro Arg Glu Gly Val Phe Val Ser Asn Gly Thr His
    1075                1080                1085

Trp Phe Val Thr Gln Arg Asn Phe Tyr Glu Pro Gln Ile Ile Thr Thr
    1090                1095                1100

Asp Asn Thr Phe Val Ser Gly Asn Cys Asp Val Val Gly Ile Val
1105                1110                1115                1120

Asn Asn Thr Val Tyr Asp Pro Leu Gln Pro Glu Leu Asp Ser Phe Lys
                1125                1130                1135

Glu Glu Leu Asp Lys Tyr Phe Lys Asn His Thr Ser Pro Asp Val Asp
                1140                1145                1150

Leu Gly Asp Ile Ser Gly Ile Asn Ala Ser Val Val Asn Ile Gln Lys
                1155                1160                1165

Glu Ile Asp Arg Leu Asn Glu Val Ala Lys Asn Leu Asn Glu Ser Leu
                1170                1175                1180

Ile Asp Leu Gln Glu Leu Gly Lys Tyr Glu Gln Tyr Ile Lys Arg Ser
1185                1190                1195                1200

Asn Gly Leu Pro Gly Pro Ile Gly Pro Pro Gly Pro Arg Gly Arg Thr
                1205                1210                1215

Gly Asp Ala Gly Pro Val Gly Pro Pro Gly Pro Pro Gly Pro Pro Gly
                1220                1225                1230

Pro Pro Gly Pro Pro Ser Ala Gly Phe Asp Phe Ser Phe Leu Pro Gln
                1235                1240                1245

Pro Pro Gln Glu Lys Ala His Asp Gly Gly Arg Tyr Tyr Arg Ala Asn
                1250                1255                1260

Asp Ala Asn Val Val Arg Asp Arg Asp Leu Glu Val Asp Thr Thr Leu
1265                1270                1275                1280

Lys Ser Leu Ser Gln Gln Ile Glu Asn Ile Arg Ser Pro Glu Gly Ser
                1285                1290                1295

Arg Lys Asn Pro Ala Arg Thr Cys Arg Asp Leu Lys Met Cys His Ser
                1300                1305                1310

Asp Trp Lys Ser Gly Glu Tyr Trp Ile Asp Pro Asn Gln Gly Cys Asn
                1315                1320                1325

Leu Asp Ala Ile Lys Val Phe Cys Asn Met Glu Thr Gly Glu Thr Cys
                1330                1335                1340

Val Tyr Pro Thr Gln Pro Ser Val Ala Gln Lys Asn Trp Tyr Ile Ser
1345                1350                1355                1360

Lys Asn Pro Lys Asp Lys Arg His Val Trp Phe Gly Glu Ser Met Thr
                1365                1370                1375

Asp Gly Phe Gln Phe Glu Tyr Gly Gly Gln Gly Ser Asp Pro Ala Asp
                1380                1385                1390

Val Ala Ile Gln Leu Thr Phe Leu Arg Leu Met Ser Thr Glu Ala Ser
                1395                1400                1405

Gln Asn Ile Thr Tyr His Cys Lys Asn Ser Val Ala Tyr Met Asp Gln
                1410                1415                1420

Gln Thr Gly Asn Leu Lys Lys Ala Leu Leu Leu Gln Gly Ser Asn Glu
1425                1430                1435                1440

Ile Glu Ile Arg Ala Glu Gly Asn Ser Arg Phe Thr Tyr Ser Val Thr
                1445                1450                1455

Val Asp Gly Cys Thr Ser His Thr Gly Ala Trp Gly Lys Thr Val Ile
                1460                1465                1470

Glu Tyr Lys Thr Thr Lys Thr Ser Arg Leu Pro Ile Ile Asp Val Ala
```

-continued

```
                1475                1480                1485

Pro Leu Asp Val Gly Ala Pro Asp Gln Glu Phe Gly Phe Asp Val Gly
            1490                1495                1500

Pro Val Cys Phe Leu
1505

<210> SEQ ID NO 14
<211> LENGTH: 1509
<212> TYPE: PRT
<213> ORGANISM: Artificial Sequence
<220> FEATURE:
<223> OTHER INFORMATION: Synthetic construct

<400> SEQUENCE: 14

Gln Cys Val Asn Phe Thr Asn Arg Thr Gln Leu Pro Ser Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Tyr Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Ser Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205

Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
                245                 250                 255

Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
        275                 280                 285

Thr Leu Lys Ser Phe Thr Val Glu Lys Gly Ile Tyr Gln Thr Ser Asn
    290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
```

-continued

```
                325                 330                 335
Val Tyr Ala Trp Asn Arg Lys Arg Ile Ser Asn Cys Val Ala Asp Tyr
            340                 345                 350
Ser Val Leu Tyr Asn Ser Ala Ser Phe Ser Thr Phe Lys Cys Tyr Gly
            355                 360                 365
Val Ser Pro Thr Lys Leu Asn Asp Leu Cys Phe Thr Asn Val Tyr Ala
        370                 375                 380
Asp Ser Phe Val Ile Arg Gly Asp Glu Val Arg Gln Ile Ala Pro Gly
385                 390                 395                 400
Gln Thr Gly Thr Ile Ala Asp Tyr Asn Tyr Lys Leu Pro Asp Asp Phe
                405                 410                 415
Thr Gly Cys Val Ile Ala Trp Asn Ser Asn Asn Leu Asp Ser Lys Val
            420                 425                 430
Gly Gly Asn Tyr Asn Tyr Leu Tyr Arg Leu Phe Arg Lys Ser Asn Leu
            435                 440                 445
Lys Pro Phe Glu Arg Asp Ile Ser Thr Glu Ile Tyr Gln Ala Gly Ser
        450                 455                 460
Thr Pro Cys Asn Gly Val Lys Gly Phe Asn Cys Tyr Phe Pro Leu Gln
465                 470                 475                 480
Ser Tyr Gly Phe Gln Pro Thr Tyr Gly Val Gly Tyr Gln Pro Tyr Arg
                485                 490                 495
Val Val Val Leu Ser Phe Glu Leu Leu His Ala Pro Ala Thr Val Cys
            500                 505                 510
Gly Pro Lys Lys Ser Thr Asn Leu Val Lys Asn Lys Cys Val Asn Phe
            515                 520                 525
Asn Phe Asn Gly Leu Thr Gly Thr Gly Val Leu Thr Glu Ser Asn Lys
        530                 535                 540
Lys Phe Leu Pro Phe Gln Gln Phe Gly Arg Asp Ile Ala Asp Thr Thr
545                 550                 555                 560
Asp Ala Val Arg Asp Pro Gln Thr Leu Glu Ile Leu Asp Ile Thr Pro
                565                 570                 575
Cys Ser Phe Gly Gly Val Ser Val Ile Thr Pro Gly Thr Asn Thr Ser
            580                 585                 590
Asn Gln Val Ala Val Leu Tyr Gln Gly Val Asn Cys Thr Glu Val Pro
            595                 600                 605
Val Ala Ile His Ala Asp Gln Leu Thr Pro Thr Trp Arg Val Tyr Ser
        610                 615                 620
Thr Gly Ser Asn Val Phe Gln Thr Arg Ala Gly Cys Leu Ile Gly Ala
625                 630                 635                 640
Glu Tyr Val Asn Asn Ser Tyr Glu Cys Asp Ile Pro Ile Gly Ala Gly
                645                 650                 655
Ile Cys Ala Ser Tyr Gln Thr Gln Thr Asn Ser Pro Arg Arg Ala Arg
            660                 665                 670
Ser Val Ala Ser Gln Ser Ile Ile Ala Tyr Thr Met Ser Leu Gly Ala
            675                 680                 685
Glu Asn Ser Val Ala Tyr Ser Asn Asn Ser Ile Ala Ile Pro Thr Asn
        690                 695                 700
Phe Thr Ile Ser Val Thr Thr Glu Ile Leu Pro Val Ser Met Thr Lys
705                 710                 715                 720
Thr Ser Val Asp Cys Thr Met Tyr Ile Cys Gly Asp Ser Thr Glu Cys
                725                 730                 735
Ser Asn Leu Leu Leu Gln Tyr Gly Ser Phe Cys Thr Gln Leu Asn Arg
            740                 745                 750
```

-continued

```
Ala Leu Thr Gly Ile Ala Val Glu Gln Asp Lys Asn Thr Gln Glu Val
            755                 760                 765
Phe Ala Gln Val Lys Gln Ile Tyr Lys Thr Pro Pro Ile Lys Asp Phe
            770                 775                 780
Gly Gly Phe Asn Phe Ser Gln Ile Leu Pro Asp Pro Ser Lys Pro Ser
785                 790                 795                 800
Lys Arg Ser Phe Ile Glu Asp Leu Leu Phe Asn Lys Val Thr Leu Ala
            805                 810                 815
Asp Ala Gly Phe Ile Lys Gln Tyr Gly Asp Cys Leu Gly Asp Ile Ala
            820                 825                 830
Ala Arg Asp Leu Ile Cys Ala Gln Lys Phe Asn Gly Leu Thr Val Leu
            835                 840                 845
Pro Pro Leu Leu Thr Asp Glu Met Ile Ala Gln Tyr Thr Ser Ala Leu
850                 855                 860
Leu Ala Gly Thr Ile Thr Ser Gly Trp Thr Phe Gly Ala Gly Ala Ala
865                 870                 875                 880
Leu Gln Ile Pro Phe Ala Met Gln Met Ala Tyr Arg Phe Asn Gly Ile
            885                 890                 895
Gly Val Thr Gln Asn Val Leu Tyr Glu Asn Gln Lys Leu Ile Ala Asn
            900                 905                 910
Gln Phe Asn Ser Ala Ile Gly Lys Ile Gln Asp Ser Leu Ser Ser Thr
            915                 920                 925
Ala Ser Ala Leu Gly Lys Leu Gln Asp Val Val Asn Gln Asn Ala Gln
930                 935                 940
Ala Leu Asn Thr Leu Val Lys Gln Leu Ser Ser Asn Phe Gly Ala Ile
945                 950                 955                 960
Ser Ser Val Leu Asn Asp Ile Leu Ser Arg Leu Asp Lys Val Glu Ala
            965                 970                 975
Glu Val Gln Ile Asp Arg Leu Ile Thr Gly Arg Leu Gln Ser Leu Gln
            980                 985                 990
Thr Tyr Val Thr Gln Gln Leu Ile Arg Ala Ala Glu Ile Arg Ala Ser
            995                 1000                1005
Ala Asn Leu Ala Ala Ile Lys Met Ser Glu Cys Val Leu Gly Gln Ser
        1010                1015                1020
Lys Arg Val Asp Phe Cys Gly Lys Gly Tyr His Leu Met Ser Phe Pro
1025                1030                1035                1040
Gln Ser Ala Pro His Gly Val Val Phe Leu His Val Thr Tyr Val Pro
            1045                1050                1055
Ala Gln Glu Lys Asn Phe Thr Thr Ala Pro Ala Ile Cys His Asp Gly
            1060                1065                1070
Lys Ala His Phe Pro Arg Glu Gly Val Phe Val Ser Asn Gly Thr His
            1075                1080                1085
Trp Phe Val Thr Gln Arg Asn Phe Tyr Glu Pro Gln Ile Ile Thr Thr
            1090                1095                1100
Asp Asn Thr Phe Val Ser Gly Asn Cys Asp Val Val Ile Gly Ile Val
1105                1110                1115                1120
Asn Asn Thr Val Tyr Asp Pro Leu Gln Pro Glu Leu Asp Ser Phe Lys
            1125                1130                1135
Glu Glu Leu Asp Lys Tyr Phe Lys Asn His Thr Ser Pro Asp Val Asp
            1140                1145                1150
Leu Gly Asp Ile Ser Gly Ile Asn Ala Ser Val Val Asn Ile Gln Lys
            1155                1160                1165
```

```
Glu Ile Asp Arg Leu Asn Glu Val Ala Lys Asn Leu Asn Glu Ser Leu
    1170                1175                1180

Ile Asp Leu Gln Glu Leu Gly Lys Tyr Glu Gln Tyr Ile Lys Arg Ser
1185                1190                1195                1200

Asn Gly Leu Pro Gly Pro Ile Gly Pro Pro Gly Pro Arg Gly Arg Thr
                1205                1210                1215

Gly Asp Ala Gly Pro Val Gly Pro Pro Gly Pro Pro Gly Pro Pro Gly
            1220                1225                1230

Pro Pro Gly Pro Pro Ser Ala Gly Phe Asp Phe Ser Phe Leu Pro Gln
            1235                1240                1245

Pro Pro Gln Glu Lys Ala His Asp Gly Gly Arg Tyr Tyr Arg Ala Asn
        1250                1255                1260

Asp Ala Asn Val Val Arg Asp Arg Asp Leu Glu Val Asp Thr Thr Leu
1265                1270                1275                1280

Lys Ser Leu Ser Gln Gln Ile Glu Asn Ile Arg Ser Pro Glu Gly Ser
                1285                1290                1295

Arg Lys Asn Pro Ala Arg Thr Cys Arg Asp Leu Lys Met Cys His Ser
            1300                1305                1310

Asp Trp Lys Ser Gly Glu Tyr Trp Ile Asp Pro Asn Gln Gly Cys Asn
            1315                1320                1325

Leu Asp Ala Ile Lys Val Phe Cys Asn Met Glu Thr Gly Glu Thr Cys
        1330                1335                1340

Val Tyr Pro Thr Gln Pro Ser Val Ala Gln Lys Asn Trp Tyr Ile Ser
1345                1350                1355                1360

Lys Asn Pro Lys Asp Lys Arg His Val Trp Phe Gly Glu Ser Met Thr
                1365                1370                1375

Asp Gly Phe Gln Phe Glu Tyr Gly Gly Gln Gly Ser Asp Pro Ala Asp
            1380                1385                1390

Val Ala Ile Gln Leu Thr Phe Leu Arg Leu Met Ser Thr Glu Ala Ser
            1395                1400                1405

Gln Asn Ile Thr Tyr His Cys Lys Asn Ser Val Ala Tyr Met Asp Gln
        1410                1415                1420

Gln Thr Gly Asn Leu Lys Lys Ala Leu Leu Leu Gln Gly Ser Asn Glu
1425                1430                1435                1440

Ile Glu Ile Arg Ala Glu Gly Asn Ser Arg Phe Thr Tyr Ser Val Thr
                1445                1450                1455

Val Asp Gly Cys Thr Ser His Thr Gly Ala Trp Gly Lys Thr Val Ile
            1460                1465                1470

Glu Tyr Lys Thr Thr Lys Thr Ser Arg Leu Pro Ile Ile Asp Val Ala
            1475                1480                1485

Pro Leu Asp Val Gly Ala Pro Asp Gln Glu Phe Gly Phe Asp Val Gly
        1490                1495                1500

Pro Val Cys Phe Leu
1505

<210> SEQ ID NO 15
<211> LENGTH: 1509
<212> TYPE: PRT
<213> ORGANISM: Artificial Sequence
<220> FEATURE:
<223> OTHER INFORMATION: Synthetic construct

<400> SEQUENCE: 15

Gln Cys Val Asn Phe Thr Asn Arg Thr Gln Leu Pro Ser Ala Tyr Thr
1               5                   10                  15
```

-continued

```
Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Tyr Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Ser Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205

Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Tyr Tyr Val Gly Tyr
                245                 250                 255

Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
        275                 280                 285

Thr Leu Lys Ser Phe Thr Val Glu Lys Gly Ile Tyr Gln Thr Ser Asn
    290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
            340                 345                 350

Ser Val Leu Tyr Asn Ser Ala Ser Phe Ser Thr Phe Lys Cys Tyr Gly
        355                 360                 365

Val Ser Pro Thr Lys Leu Asn Asp Leu Cys Phe Thr Asn Val Tyr Ala
    370                 375                 380

Asp Ser Phe Val Ile Arg Gly Asp Glu Val Arg Gln Ile Ala Pro Gly
385                 390                 395                 400

Gln Thr Gly Thr Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
            420                 425                 430

Gly Gly Asn Tyr Asn Tyr Leu Tyr Arg Leu Phe Arg Lys Ser Asn Leu
```

```
                435                 440                 445
Lys Pro Phe Glu Arg Asp Ile Ser Thr Glu Ile Tyr Gln Ala Gly Ser
450                 455                 460

Thr Pro Cys Asn Gly Val Lys Gly Phe Asn Cys Tyr Phe Pro Leu Gln
465                 470                 475                 480

Ser Tyr Gly Phe Gln Pro Thr Tyr Gly Val Gly Tyr Gln Pro Tyr Arg
                485                 490                 495

Val Val Val Leu Ser Phe Glu Leu Leu His Ala Pro Ala Thr Val Cys
            500                 505                 510

Gly Pro Lys Lys Ser Thr Asn Leu Val Lys Asn Lys Cys Val Asn Phe
        515                 520                 525

Asn Phe Asn Gly Leu Thr Gly Thr Gly Val Leu Thr Glu Ser Asn Lys
530                 535                 540

Lys Phe Leu Pro Phe Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
            580                 585                 590

Asn Gln Val Ala Val Leu Tyr Gln Gly Val Asn Cys Thr Glu Val Pro
        595                 600                 605

Val Ala Ile His Ala Asp Gln Leu Thr Pro Thr Trp Arg Val Tyr Ser
610                 615                 620

Thr Gly Ser Asn Val Phe Gln Thr Arg Ala Gly Cys Leu Ile Gly Ala
625                 630                 635                 640

Glu Tyr Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Arg Arg Ala Ala
            660                 665                 670

Ser Val Ala Ser Gln Ser Ile Ile Ala Tyr Thr Met Ser Leu Gly Ala
        675                 680                 685

Glu Asn Ser Val Ala Tyr Ser Asn Asn Ser Ile Ala Ile Pro Thr Asn
690                 695                 700

Phe Thr Ile Ser Val Thr Thr Glu Ile Leu Pro Val Ser Met Thr Lys
705                 710                 715                 720

Thr Ser Val Asp Cys Thr Met Tyr Ile Cys Gly Asp Ser Thr Glu Cys
                725                 730                 735

Ser Asn Leu Leu Leu Gln Tyr Gly Ser Phe Cys Thr Gln Leu Asn Arg
            740                 745                 750

Ala Leu Thr Gly Ile Ala Val Glu Gln Asp Lys Asn Thr Gln Glu Val
        755                 760                 765

Phe Ala Gln Val Lys Gln Ile Tyr Lys Thr Pro Pro Ile Lys Asp Phe
770                 775                 780

Gly Gly Phe Asn Phe Ser Gln Ile Leu Pro Asp Pro Ser Lys Pro Ser
785                 790                 795                 800

Lys Arg Ser Phe Ile Glu Asp Leu Leu Phe Asn Lys Val Thr Leu Ala
                805                 810                 815

Asp Ala Gly Phe Ile Lys Gln Tyr Gly Asp Cys Leu Gly Asp Ile Ala
            820                 825                 830

Ala Arg Asp Leu Ile Cys Ala Gln Lys Phe Asn Gly Leu Thr Val Leu
        835                 840                 845

Pro Pro Leu Leu Thr Asp Glu Met Ile Ala Gln Tyr Thr Ser Ala Leu
850                 855                 860
```

```
Leu Ala Gly Thr Ile Thr Ser Gly Trp Thr Phe Gly Ala Ala
865                 870             875             880

Leu Gln Ile Pro Phe Ala Met Gln Met Ala Tyr Arg Phe Asn Gly Ile
                885             890                 895

Gly Val Thr Gln Asn Val Leu Tyr Glu Asn Gln Lys Leu Ile Ala Asn
            900             905             910

Gln Phe Asn Ser Ala Ile Gly Lys Ile Gln Asp Ser Leu Ser Ser Thr
            915             920             925

Ala Ser Ala Leu Gly Lys Leu Gln Asp Val Val Asn Gln Asn Ala Gln
            930             935             940

Ala Leu Asn Thr Leu Val Lys Gln Leu Ser Ser Asn Phe Gly Ala Ile
945             950             955             960

Ser Ser Val Leu Asn Asp Ile Leu Ser Arg Leu Asp Lys Val Glu Ala
            965             970             975

Glu Val Gln Ile Asp Arg Leu Ile Thr Gly Arg Leu Gln Ser Leu Gln
            980             985             990

Thr Tyr Val Thr Gln Gln Leu Ile Arg Ala Ala Glu Ile Arg Ala Ser
            995             1000            1005

Ala Asn Leu Ala Ala Ile Lys Met Ser Glu Cys Val Leu Gly Gln Ser
        1010            1015            1020

Lys Arg Val Asp Phe Cys Gly Lys Gly Tyr His Leu Met Ser Phe Pro
1025            1030            1035            1040

Gln Ser Ala Pro His Gly Val Val Phe Leu His Val Thr Tyr Val Pro
                1045            1050            1055

Ala Gln Glu Lys Asn Phe Thr Thr Ala Pro Ala Ile Cys His Asp Gly
                1060            1065            1070

Lys Ala His Phe Pro Arg Glu Gly Val Phe Val Ser Asn Gly Thr His
                1075            1080            1085

Trp Phe Val Thr Gln Arg Asn Phe Tyr Glu Pro Gln Ile Ile Thr Thr
        1090            1095            1100

Asp Asn Thr Phe Val Ser Gly Asn Cys Asp Val Val Ile Gly Ile Val
1105            1110            1115            1120

Asn Asn Thr Val Tyr Asp Pro Leu Gln Pro Glu Leu Asp Ser Phe Lys
                1125            1130            1135

Glu Glu Leu Asp Lys Tyr Phe Lys Asn His Thr Ser Pro Asp Val Asp
                1140            1145            1150

Leu Gly Asp Ile Ser Gly Ile Asn Ala Ser Val Val Asn Ile Gln Lys
                1155            1160            1165

Glu Ile Asp Arg Leu Asn Glu Val Ala Lys Asn Leu Asn Glu Ser Leu
        1170            1175            1180

Ile Asp Leu Gln Glu Leu Gly Lys Tyr Glu Gln Tyr Ile Lys Arg Ser
1185            1190            1195            1200

Asn Gly Leu Pro Gly Pro Ile Gly Pro Pro Gly Pro Arg Gly Arg Thr
                1205            1210            1215

Gly Asp Ala Gly Pro Val Gly Pro Pro Gly Pro Pro Gly Pro Pro Gly
            1220            1225            1230

Pro Pro Gly Pro Pro Ser Ala Gly Phe Asp Phe Ser Phe Leu Pro Gln
            1235            1240            1245

Pro Pro Gln Glu Lys Ala His Asp Gly Gly Arg Tyr Tyr Arg Ala Asn
            1250            1255            1260

Asp Ala Asn Val Val Arg Asp Arg Asp Leu Glu Val Asp Thr Thr Leu
1265            1270            1275            1280
```

```
Lys Ser Leu Ser Gln Gln Ile Glu Asn Ile Arg Ser Pro Glu Gly Ser
                1285                1290                1295

Arg Lys Asn Pro Ala Arg Thr Cys Arg Asp Leu Lys Met Cys His Ser
            1300                1305                1310

Asp Trp Lys Ser Gly Glu Tyr Trp Ile Asp Pro Asn Gln Gly Cys Asn
            1315                1320                1325

Leu Asp Ala Ile Lys Val Phe Cys Asn Met Glu Thr Gly Glu Thr Cys
            1330                1335                1340

Val Tyr Pro Thr Gln Pro Ser Val Ala Gln Lys Asn Trp Tyr Ile Ser
1345                1350                1355                1360

Lys Asn Pro Lys Asp Lys Arg His Val Trp Phe Gly Glu Ser Met Thr
                1365                1370                1375

Asp Gly Phe Gln Phe Glu Tyr Gly Gly Gln Gly Ser Asp Pro Ala Asp
            1380                1385                1390

Val Ala Ile Gln Leu Thr Phe Leu Arg Leu Met Ser Thr Glu Ala Ser
            1395                1400                1405

Gln Asn Ile Thr Tyr His Cys Lys Asn Ser Val Ala Tyr Met Asp Gln
            1410                1415                1420

Gln Thr Gly Asn Leu Lys Lys Ala Leu Leu Leu Gln Gly Ser Asn Glu
1425                1430                1435                1440

Ile Glu Ile Arg Ala Glu Gly Asn Ser Arg Phe Thr Tyr Ser Val Thr
                1445                1450                1455

Val Asp Gly Cys Thr Ser His Thr Gly Ala Trp Gly Lys Thr Val Ile
            1460                1465                1470

Glu Tyr Lys Thr Thr Lys Thr Ser Arg Leu Pro Ile Ile Asp Val Ala
            1475                1480                1485

Pro Leu Asp Val Gly Ala Pro Asp Gln Glu Phe Gly Phe Asp Val Gly
            1490                1495                1500

Pro Val Cys Phe Leu
1505

<210> SEQ ID NO 16
<211> LENGTH: 1509
<212> TYPE: PRT
<213> ORGANISM: Artificial Sequence
<220> FEATURE:
<223> OTHER INFORMATION: Synthetic construct

<400> SEQUENCE: 16

Gln Cys Val Asn Phe Thr Asn Arg Thr Gln Leu Pro Ser Ala Tyr Thr
1               5                   10                  15

Asn Ser Phe Thr Arg Gly Val Tyr Tyr Pro Asp Lys Val Phe Arg Ser
                20                  25                  30

Ser Val Leu His Ser Thr Gln Asp Leu Phe Leu Pro Phe Phe Ser Asn
            35                  40                  45

Val Thr Trp Phe His Ala Ile His Val Ser Gly Thr Asn Gly Thr Lys
        50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Tyr Pro Phe Leu
        115                 120                 125
```

Gly Val Tyr Tyr His Lys Asn Asn Lys Ser Trp Met Glu Ser Glu Phe
130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Ser Glu Phe Val Phe Lys Asn Ile Asp Gly Tyr Phe Lys Ile Tyr Ser
                180                 185                 190

Lys His Thr Pro Ile Asn Leu Val Arg Asp Leu Pro Gln Gly Phe Ser
                195                 200                 205

Ala Leu Glu Pro Leu Val Asp Leu Pro Ile Gly Ile Asn Ile Thr Arg
210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
                245                 250                 255

Leu Gln Pro Arg Thr Phe Leu Leu Lys Tyr Asn Glu Asn Gly Thr Ile
                260                 265                 270

Thr Asp Ala Val Asp Cys Ala Leu Asp Pro Leu Ser Glu Thr Lys Cys
                275                 280                 285

Thr Leu Lys Ser Phe Thr Val Glu Lys Gly Ile Tyr Gln Thr Ser Asn
290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
                340                 345                 350

Ser Val Leu Tyr Asn Ser Ala Ser Phe Ser Thr Phe Lys Cys Tyr Gly
                355                 360                 365

Val Ser Pro Thr Lys Leu Asn Asp Leu Cys Phe Thr Asn Val Tyr Ala
                370                 375                 380

Asp Ser Phe Val Ile Arg Gly Asp Glu Val Arg Gln Ile Ala Pro Gly
385                 390                 395                 400

Gln Thr Gly Thr Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
                420                 425                 430

Gly Gly Asn Tyr Asn Tyr Leu Tyr Arg Leu Phe Arg Lys Ser Asn Leu
                435                 440                 445

Lys Pro Phe Glu Arg Asp Ile Ser Thr Glu Ile Tyr Gln Ala Gly Ser
450                 455                 460

Thr Pro Cys Asn Gly Val Lys Gly Phe Asn Cys Tyr Phe Pro Leu Gln
465                 470                 475                 480

Ser Tyr Gly Phe Gln Pro Thr Tyr Gly Val Gly Tyr Gln Pro Tyr Arg
                485                 490                 495

Val Val Val Leu Ser Phe Glu Leu Leu His Ala Pro Ala Thr Val Cys
                500                 505                 510

Gly Pro Lys Lys Ser Thr Asn Leu Val Lys Asn Lys Cys Val Asn Phe
                515                 520                 525

Asn Phe Asn Gly Leu Thr Gly Thr Gly Val Leu Thr Glu Ser Asn Lys
530                 535                 540

Lys Phe Leu Pro Phe Gln Gln Phe Gly Arg Asp Ile Ala Asp Thr Thr

```
                    545                 550                 555                 560
Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
                580                 585                 590

Asn Gln Val Ala Val Leu Tyr Gln Gly Val Asn Cys Thr Glu Val Pro
                595                 600                 605

Val Ala Ile His Ala Asp Gln Leu Thr Pro Thr Trp Arg Val Tyr Ser
    610                 615                 620

Thr Gly Ser Asn Val Phe Gln Thr Arg Ala Gly Cys Leu Ile Gly Ala
625                 630                 635                 640

Glu Tyr Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Arg Arg Ala Arg
                660                 665                 670

Ser Val Ala Ser Gln Ser Ile Ile Ala Tyr Thr Met Ser Leu Gly Ala
                675                 680                 685

Glu Asn Ser Val Ala Tyr Ser Asn Asn Ser Ile Ala Ile Pro Thr Asn
    690                 695                 700

Phe Thr Ile Ser Val Thr Thr Glu Ile Leu Pro Val Ser Met Thr Lys
705                 710                 715                 720

Thr Ser Val Asp Cys Thr Met Tyr Ile Cys Gly Asp Ser Thr Glu Cys
                725                 730                 735

Ser Asn Leu Leu Leu Gln Tyr Gly Ser Phe Cys Thr Gln Leu Asn Arg
                740                 745                 750

Ala Leu Thr Gly Ile Ala Val Glu Gln Asp Lys Asn Thr Gln Glu Val
                755                 760                 765

Phe Ala Gln Val Lys Gln Ile Tyr Lys Thr Pro Pro Ile Lys Asp Phe
                770                 775                 780

Gly Gly Phe Asn Phe Ser Gln Ile Leu Pro Asp Pro Ser Lys Pro Ser
785                 790                 795                 800

Lys Arg Ser Phe Ile Glu Asp Leu Leu Phe Asn Lys Val Thr Leu Ala
                805                 810                 815

Asp Ala Gly Phe Ile Lys Gln Tyr Gly Asp Cys Leu Gly Asp Ile Ala
                820                 825                 830

Ala Arg Asp Leu Ile Cys Ala Gln Lys Phe Asn Gly Leu Thr Val Leu
                835                 840                 845

Pro Pro Leu Leu Thr Asp Glu Met Ile Ala Gln Tyr Thr Ser Ala Leu
850                 855                 860

Leu Ala Gly Thr Ile Thr Ser Gly Trp Thr Phe Gly Ala Gly Ala Ala
865                 870                 875                 880

Leu Gln Ile Pro Phe Ala Met Gln Met Ala Tyr Arg Phe Asn Gly Ile
                885                 890                 895

Gly Val Thr Gln Asn Val Leu Tyr Glu Asn Gln Lys Leu Ile Ala Asn
                900                 905                 910

Gln Phe Asn Ser Ala Ile Gly Lys Ile Gln Asp Ser Leu Ser Ser Thr
                915                 920                 925

Ala Ser Ala Leu Gly Lys Leu Gln Asp Val Val Asn Gln Asn Ala Gln
                930                 935                 940

Ala Leu Asn Thr Leu Val Lys Gln Leu Ser Ser Asn Phe Gly Ala Ile
945                 950                 955                 960

Ser Ser Val Leu Asn Asp Ile Leu Ser Arg Leu Asp Pro Pro Glu Ala
                965                 970                 975
```

Glu Val Gln Ile Asp Arg Leu Ile Thr Gly Arg Leu Gln Ser Leu Gln
            980                 985                 990

Thr Tyr Val Thr Gln Gln Leu Ile Arg Ala Ala Glu Ile Arg Ala Ser
            995                1000                1005

Ala Asn Leu Ala Ala Ile Lys Met Ser Glu Cys Val Leu Gly Gln Ser
1010                1015                1020

Lys Arg Val Asp Phe Cys Gly Lys Gly Tyr His Leu Met Ser Phe Pro
1025                1030                1035                1040

Gln Ser Ala Pro His Gly Val Val Phe Leu His Val Thr Tyr Val Pro
                1045                1050                1055

Ala Gln Glu Lys Asn Phe Thr Thr Ala Pro Ala Ile Cys His Asp Gly
            1060                1065                1070

Lys Ala His Phe Pro Arg Glu Gly Val Phe Val Ser Asn Gly Thr His
                1075                1080                1085

Trp Phe Val Thr Gln Arg Asn Phe Tyr Glu Pro Gln Ile Ile Thr Thr
            1090                1095                1100

Asp Asn Thr Phe Val Ser Gly Asn Cys Asp Val Val Ile Gly Ile Val
1105                1110                1115                1120

Asn Asn Thr Val Tyr Asp Pro Leu Gln Pro Glu Leu Asp Ser Phe Lys
                1125                1130                1135

Glu Glu Leu Asp Lys Tyr Phe Lys Asn His Thr Ser Pro Asp Val Asp
            1140                1145                1150

Leu Gly Asp Ile Ser Gly Ile Asn Ala Ser Val Val Asn Ile Gln Lys
                1155                1160                1165

Glu Ile Asp Arg Leu Asn Glu Val Ala Lys Asn Leu Asn Glu Ser Leu
            1170                1175                1180

Ile Asp Leu Gln Glu Leu Gly Lys Tyr Glu Gln Tyr Ile Lys Arg Ser
1185                1190                1195                1200

Asn Gly Leu Pro Gly Pro Ile Gly Pro Pro Gly Pro Arg Gly Arg Thr
                1205                1210                1215

Gly Asp Ala Gly Pro Val Gly Pro Pro Gly Pro Pro Gly Pro Pro Gly
            1220                1225                1230

Pro Pro Gly Pro Pro Ser Ala Gly Phe Asp Phe Ser Phe Leu Pro Gln
            1235                1240                1245

Pro Pro Gln Glu Lys Ala His Asp Gly Gly Arg Tyr Tyr Arg Ala Asn
            1250                1255                1260

Asp Ala Asn Val Val Arg Asp Arg Asp Leu Glu Val Asp Thr Thr Leu
1265                1270                1275                1280

Lys Ser Leu Ser Gln Gln Ile Glu Asn Ile Arg Ser Pro Glu Gly Ser
                1285                1290                1295

Arg Lys Asn Pro Ala Arg Thr Cys Arg Asp Leu Lys Met Cys His Ser
            1300                1305                1310

Asp Trp Lys Ser Gly Glu Tyr Trp Ile Asp Pro Asn Gln Gly Cys Asn
            1315                1320                1325

Leu Asp Ala Ile Lys Val Phe Cys Asn Met Glu Thr Gly Glu Thr Cys
            1330                1335                1340

Val Tyr Pro Thr Gln Pro Ser Val Ala Gln Lys Asn Trp Tyr Ile Ser
1345                1350                1355                1360

Lys Asn Pro Lys Asp Lys Arg His Val Trp Phe Gly Glu Ser Met Thr
                1365                1370                1375

Asp Gly Phe Gln Phe Glu Tyr Gly Gly Gln Gly Ser Asp Pro Ala Asp
            1380                1385                1390

```
Val Ala Ile Gln Leu Thr Phe Leu Arg Leu Met Ser Thr Glu Ala Ser
         1395                1400                1405

Gln Asn Ile Thr Tyr His Cys Lys Asn Ser Val Ala Tyr Met Asp Gln
         1410                1415                1420

Gln Thr Gly Asn Leu Lys Lys Ala Leu Leu Leu Gln Gly Ser Asn Glu
1425                1430                1435                1440

Ile Glu Ile Arg Ala Glu Gly Asn Ser Arg Phe Thr Tyr Ser Val Thr
                1445                1450                1455

Val Asp Gly Cys Thr Ser His Thr Gly Ala Trp Gly Lys Thr Val Ile
                1460                1465                1470

Glu Tyr Lys Thr Thr Lys Thr Ser Arg Leu Pro Ile Ile Asp Val Ala
                1475                1480                1485

Pro Leu Asp Val Gly Ala Pro Asp Gln Glu Phe Gly Phe Asp Val Gly
         1490                1495                1500

Pro Val Cys Phe Leu
1505

<210> SEQ ID NO 17
<211> LENGTH: 1509
<212> TYPE: PRT
<213> ORGANISM: Artificial Sequence
<220> FEATURE:
<223> OTHER INFORMATION: Synthetic construct

<400> SEQUENCE: 17

Gln Cys Val Asn Phe Thr Asn Arg Thr Gln Leu Pro Ser Ala Tyr Thr
1               5                   10                  15

Asn Ser Phe Thr Arg Gly Val Tyr Tyr Pro Asp Lys Val Phe Arg Ser
                20                  25                  30

Ser Val Leu His Ser Thr Gln Asp Leu Phe Leu Pro Phe Phe Ser Asn
            35                  40                  45

Val Thr Trp Phe His Ala Ile His Val Ser Gly Thr Asn Gly Thr Lys
        50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Tyr Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Ser Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205

Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240
```

```
Ser Ser Ser Gly Trp Thr Ala Gly Ala Ala Tyr Val Gly Tyr
            245                 250                 255

Leu Gln Pro Arg Thr Phe Leu Lys Tyr Asn Glu Asn Gly Thr Ile
        260                 265                 270

Thr Asp Ala Val Asp Cys Ala Leu Asp Pro Leu Ser Glu Thr Lys Cys
        275                 280                 285

Thr Leu Lys Ser Phe Thr Val Glu Lys Gly Ile Tyr Gln Thr Ser Asn
    290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
                340                 345                 350

Ser Val Leu Tyr Asn Ser Ala Ser Phe Ser Thr Phe Lys Cys Tyr Gly
                355                 360                 365

Val Ser Pro Thr Lys Leu Asn Asp Leu Cys Phe Thr Asn Val Tyr Ala
    370                 375                 380

Asp Ser Phe Val Ile Arg Gly Asp Glu Val Arg Gln Ile Ala Pro Gly
385                 390                 395                 400

Gln Thr Gly Thr Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
                420                 425                 430

Gly Gly Asn Tyr Asn Tyr Leu Tyr Arg Leu Phe Arg Lys Ser Asn Leu
                435                 440                 445

Lys Pro Phe Glu Arg Asp Ile Ser Thr Glu Ile Tyr Gln Ala Gly Ser
    450                 455                 460

Thr Pro Cys Asn Gly Val Lys Gly Phe Asn Cys Tyr Phe Pro Leu Gln
465                 470                 475                 480

Ser Tyr Gly Phe Gln Pro Thr Tyr Gly Val Gly Tyr Gln Pro Tyr Arg
                485                 490                 495

Val Val Val Leu Ser Phe Glu Leu Leu His Ala Pro Ala Thr Val Cys
                500                 505                 510

Gly Pro Lys Lys Ser Thr Asn Leu Val Lys Asn Lys Cys Val Asn Phe
                515                 520                 525

Asn Phe Asn Gly Leu Thr Gly Thr Gly Val Leu Thr Glu Ser Asn Lys
    530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
                580                 585                 590

Asn Gln Val Ala Val Leu Tyr Gln Gly Val Asn Cys Thr Glu Val Pro
                595                 600                 605

Val Ala Ile His Ala Asp Gln Leu Thr Pro Thr Trp Arg Val Tyr Ser
                610                 615                 620

Thr Gly Ser Asn Val Phe Gln Thr Arg Ala Gly Cys Leu Ile Gly Ala
625                 630                 635                 640

Glu Tyr Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Arg Arg Ala Ala
```

```
                660             665             670
Ser Val Ala Ser Gln Ser Ile Ile Ala Tyr Thr Met Ser Leu Gly Ala
            675             680             685
Glu Asn Ser Val Ala Tyr Ser Asn Asn Ser Ile Ala Ile Pro Thr Asn
            690             695             700
Phe Thr Ile Ser Val Thr Thr Glu Ile Leu Pro Val Ser Met Thr Lys
705             710             715             720
Thr Ser Val Asp Cys Thr Met Tyr Ile Cys Gly Asp Ser Thr Glu Cys
                725             730             735
Ser Asn Leu Leu Leu Gln Tyr Gly Ser Phe Cys Thr Gln Leu Asn Arg
            740             745             750
Ala Leu Thr Gly Ile Ala Val Glu Gln Asp Lys Asn Thr Gln Glu Val
            755             760             765
Phe Ala Gln Val Lys Gln Ile Tyr Lys Thr Pro Pro Ile Lys Asp Phe
            770             775             780
Gly Gly Phe Asn Phe Ser Gln Ile Leu Pro Asp Pro Ser Lys Pro Ser
785             790             795             800
Lys Arg Ser Phe Ile Glu Asp Leu Leu Phe Asn Lys Val Thr Leu Ala
                805             810             815
Asp Ala Gly Phe Ile Lys Gln Tyr Gly Asp Cys Leu Gly Asp Ile Ala
                820             825             830
Ala Arg Asp Leu Ile Cys Ala Gln Lys Phe Asn Gly Leu Thr Val Leu
            835             840             845
Pro Pro Leu Leu Thr Asp Glu Met Ile Ala Gln Tyr Thr Ser Ala Leu
            850             855             860
Leu Ala Gly Thr Ile Thr Ser Gly Trp Thr Phe Gly Ala Gly Ala Ala
865             870             875             880
Leu Gln Ile Pro Phe Ala Met Gln Met Ala Tyr Arg Phe Asn Gly Ile
                885             890             895
Gly Val Thr Gln Asn Val Leu Tyr Glu Asn Gln Lys Leu Ile Ala Asn
                900             905             910
Gln Phe Asn Ser Ala Ile Gly Lys Ile Gln Asp Ser Leu Ser Ser Thr
            915             920             925
Ala Ser Ala Leu Gly Lys Leu Gln Asp Val Val Asn Gln Asn Ala Gln
            930             935             940
Ala Leu Asn Thr Leu Val Lys Gln Leu Ser Ser Asn Phe Gly Ala Ile
945             950             955             960
Ser Ser Val Leu Asn Asp Ile Leu Ser Arg Leu Asp Pro Pro Glu Ala
                965             970             975
Glu Val Gln Ile Asp Arg Leu Ile Thr Gly Arg Leu Gln Ser Leu Gln
                980             985             990
Thr Tyr Val Thr Gln Gln Leu Ile Arg Ala Ala Glu Ile Arg Ala Ser
            995             1000            1005
Ala Asn Leu Ala Ala Ile Lys Met Ser Glu Cys Val Leu Gly Gln Ser
            1010            1015            1020
Lys Arg Val Asp Phe Cys Gly Lys Gly Tyr His Leu Met Ser Phe Pro
1025            1030            1035            1040
Gln Ser Ala Pro His Gly Val Val Phe Leu His Val Thr Tyr Val Pro
                1045            1050            1055
Ala Gln Glu Lys Asn Phe Thr Thr Ala Pro Ala Ile Cys His Asp Gly
            1060            1065            1070
Lys Ala His Phe Pro Arg Glu Gly Val Phe Val Ser Asn Gly Thr His
            1075            1080            1085
```

```
Trp Phe Val Thr Gln Arg Asn Phe Tyr Glu Pro Gln Ile Ile Thr Thr
    1090                1095                1100

Asp Asn Thr Phe Val Ser Gly Asn Cys Asp Val Val Gly Ile Val
1105                1110                1115                1120

Asn Asn Thr Val Tyr Asp Pro Leu Gln Pro Glu Leu Asp Ser Phe Lys
            1125                1130                1135

Glu Glu Leu Asp Lys Tyr Phe Lys Asn His Thr Ser Pro Asp Val Asp
            1140                1145                1150

Leu Gly Asp Ile Ser Gly Ile Asn Ala Ser Val Val Asn Ile Gln Lys
            1155                1160                1165

Glu Ile Asp Arg Leu Asn Glu Val Ala Lys Asn Leu Asn Glu Ser Leu
    1170                1175                1180

Ile Asp Leu Gln Glu Leu Gly Lys Tyr Glu Gln Tyr Ile Lys Arg Ser
1185                1190                1195                1200

Asn Gly Leu Pro Gly Pro Ile Gly Pro Pro Gly Pro Arg Gly Arg Thr
            1205                1210                1215

Gly Asp Ala Gly Pro Val Gly Pro Pro Gly Pro Pro Gly Pro Pro Gly
            1220                1225                1230

Pro Pro Gly Pro Pro Ser Ala Gly Phe Asp Phe Ser Phe Leu Pro Gln
            1235                1240                1245

Pro Pro Gln Glu Lys Ala His Asp Gly Gly Arg Tyr Tyr Arg Ala Asn
            1250                1255                1260

Asp Ala Asn Val Val Arg Asp Arg Asp Leu Glu Val Asp Thr Thr Leu
1265                1270                1275                1280

Lys Ser Leu Ser Gln Gln Ile Glu Asn Ile Arg Ser Pro Glu Gly Ser
            1285                1290                1295

Arg Lys Asn Pro Ala Arg Thr Cys Arg Asp Leu Lys Met Cys His Ser
            1300                1305                1310

Asp Trp Lys Ser Gly Glu Tyr Trp Ile Asp Pro Asn Gln Gly Cys Asn
            1315                1320                1325

Leu Asp Ala Ile Lys Val Phe Cys Asn Met Glu Thr Gly Glu Thr Cys
            1330                1335                1340

Val Tyr Pro Thr Gln Pro Ser Val Ala Gln Lys Asn Trp Tyr Ile Ser
1345                1350                1355                1360

Lys Asn Pro Lys Asp Lys Arg His Val Trp Phe Gly Glu Ser Met Thr
            1365                1370                1375

Asp Gly Phe Gln Phe Glu Tyr Gly Gly Gln Gly Ser Asp Pro Ala Asp
            1380                1385                1390

Val Ala Ile Gln Leu Thr Phe Leu Arg Leu Met Ser Thr Glu Ala Ser
            1395                1400                1405

Gln Asn Ile Thr Tyr His Cys Lys Asn Ser Val Ala Tyr Met Asp Gln
            1410                1415                1420

Gln Thr Gly Asn Leu Lys Lys Ala Leu Leu Leu Gln Gly Ser Asn Glu
1425                1430                1435                1440

Ile Glu Ile Arg Ala Glu Gly Asn Ser Arg Phe Thr Tyr Ser Val Thr
            1445                1450                1455

Val Asp Gly Cys Thr Ser His Thr Gly Ala Trp Gly Lys Thr Val Ile
            1460                1465                1470

Glu Tyr Lys Thr Thr Lys Thr Ser Arg Leu Pro Ile Ile Asp Val Ala
            1475                1480                1485

Pro Leu Asp Val Gly Ala Pro Asp Gln Glu Phe Gly Phe Asp Val Gly
            1490                1495                1500
```

-continued

Pro Val Cys Phe Leu
1505

<210> SEQ ID NO 18
<211> LENGTH: 1507
<212> TYPE: PRT
<213> ORGANISM: Artificial Sequence
<220> FEATURE:
<223> OTHER INFORMATION: Synthetic construct

<400> SEQUENCE: 18

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile Ser Gly Thr Asn Gly Thr Lys Arg Phe
    50                  55                  60

Asp Asn Pro Val Leu Pro Phe Asn Asp Gly Val Tyr Phe Ala Ser Thr
65                  70                  75                  80

Glu Lys Ser Asn Ile Ile Arg Gly Trp Ile Phe Gly Thr Thr Leu Asp
                85                  90                  95

Ser Lys Thr Gln Ser Leu Leu Ile Val Asn Asn Ala Thr Asn Val Val
            100                 105                 110

Ile Lys Val Cys Glu Phe Gln Phe Cys Asn Asp Pro Phe Leu Gly Val
        115                 120                 125

Tyr Tyr His Lys Asn Asn Lys Ser Trp Met Glu Ser Glu Phe Arg Val
    130                 135                 140

Tyr Ser Ser Ala Asn Asn Cys Thr Phe Glu Tyr Val Ser Gln Pro Phe
145                 150                 155                 160

Leu Met Asp Leu Glu Gly Lys Gln Gly Asn Phe Lys Asn Leu Arg Glu
                165                 170                 175

Phe Val Phe Lys Asn Ile Asp Gly Tyr Phe Lys Ile Tyr Ser Lys His
            180                 185                 190

Thr Pro Ile Asn Leu Val Arg Asp Leu Pro Gln Gly Phe Ser Ala Leu
        195                 200                 205

Glu Pro Leu Val Asp Leu Pro Ile Gly Ile Asn Ile Thr Arg Phe Gln
    210                 215                 220

Thr Leu Leu Ala Leu His Arg Ser Tyr Leu Thr Pro Gly Asp Ser Ser
225                 230                 235                 240

Ser Gly Trp Thr Ala Gly Ala Ala Ala Tyr Tyr Val Gly Tyr Leu Gln
                245                 250                 255

Pro Arg Thr Phe Leu Leu Lys Tyr Asn Glu Asn Gly Thr Ile Thr Asp
            260                 265                 270

Ala Val Asp Cys Ala Leu Asp Pro Leu Ser Glu Thr Lys Cys Thr Leu
        275                 280                 285

Lys Ser Phe Thr Val Glu Lys Gly Ile Tyr Gln Thr Ser Asn Phe Arg
    290                 295                 300

Val Gln Pro Thr Glu Ser Ile Val Arg Phe Pro Asn Ile Thr Asn Leu
305                 310                 315                 320

Cys Pro Phe Gly Glu Val Phe Asn Ala Thr Arg Phe Ala Ser Val Tyr
                325                 330                 335

Ala Trp Asn Arg Lys Arg Ile Ser Asn Cys Val Ala Asp Tyr Ser Val
            340                 345                 350

```
Leu Tyr Asn Ser Ala Ser Phe Ser Thr Phe Lys Cys Tyr Gly Val Ser
            355                 360                 365

Pro Thr Lys Leu Asn Asp Leu Cys Phe Thr Asn Val Tyr Ala Asp Ser
370                 375                 380

Phe Val Ile Arg Gly Asp Glu Val Arg Gln Ile Ala Pro Gly Gln Thr
385                 390                 395                 400

Gly Lys Ile Ala Asp Tyr Asn Tyr Lys Leu Pro Asp Asp Phe Thr Gly
            405                 410                 415

Cys Val Ile Ala Trp Asn Ser Asn Leu Asp Ser Lys Val Gly Gly
            420                 425                 430

Asn Tyr Asn Tyr Leu Tyr Arg Leu Phe Arg Lys Ser Asn Leu Lys Pro
            435                 440                 445

Phe Glu Arg Asp Ile Ser Thr Glu Ile Tyr Gln Ala Gly Ser Thr Pro
450                 455                 460

Cys Asn Gly Val Glu Gly Phe Asn Cys Tyr Phe Pro Leu Gln Ser Tyr
465                 470                 475                 480

Gly Phe Gln Pro Thr Tyr Gly Val Gly Tyr Gln Pro Tyr Arg Val Val
            485                 490                 495

Val Leu Ser Phe Glu Leu Leu His Ala Pro Ala Thr Val Cys Gly Pro
            500                 505                 510

Lys Lys Ser Thr Asn Leu Val Lys Asn Lys Cys Val Asn Phe Asn Phe
            515                 520                 525

Asn Gly Leu Thr Gly Thr Gly Val Leu Thr Glu Ser Asn Lys Lys Phe
            530                 535                 540

Leu Pro Phe Gln Gln Phe Gly Arg Asp Ile Ala Asp Thr Thr Asp Ala
545                 550                 555                 560

Val Arg Asp Pro Gln Thr Leu Glu Ile Leu Asp Ile Thr Pro Cys Ser
            565                 570                 575

Phe Gly Gly Val Ser Val Ile Thr Pro Gly Thr Asn Thr Ser Asn Gln
            580                 585                 590

Val Ala Val Leu Tyr Gln Gly Val Asn Cys Thr Glu Val Pro Val Ala
            595                 600                 605

Ile His Ala Asp Gln Leu Thr Pro Thr Trp Arg Val Tyr Ser Thr Gly
610                 615                 620

Ser Asn Val Phe Gln Thr Arg Ala Gly Cys Leu Ile Gly Ala Glu His
625                 630                 635                 640

Val Asn Asn Ser Tyr Glu Cys Asp Ile Pro Ile Gly Ala Gly Ile Cys
            645                 650                 655

Ala Ser Tyr Gln Thr Gln Thr Asn Ser His Arg Arg Ala Arg Ser Val
            660                 665                 670

Ala Ser Gln Ser Ile Ile Ala Tyr Thr Met Ser Leu Gly Ala Glu Asn
            675                 680                 685

Ser Val Ala Tyr Ser Asn Asn Ser Ile Ala Ile Pro Thr Asn Phe Thr
            690                 695                 700

Ile Ser Val Thr Thr Glu Ile Leu Pro Val Ser Met Thr Lys Thr Ser
705                 710                 715                 720

Val Asp Cys Thr Met Tyr Ile Cys Gly Asp Ser Thr Glu Cys Ser Asn
            725                 730                 735

Leu Leu Leu Gln Tyr Gly Ser Phe Cys Thr Gln Leu Asn Arg Ala Leu
            740                 745                 750

Thr Gly Ile Ala Val Glu Gln Asp Lys Asn Thr Gln Glu Val Phe Ala
            755                 760                 765

Gln Val Lys Gln Ile Tyr Lys Thr Pro Pro Ile Lys Asp Phe Gly Gly
```

```
            770             775             780
Phe Asn Phe Ser Gln Ile Leu Pro Asp Pro Ser Lys Pro Ser Lys Arg
785             790             795             800

Ser Phe Ile Glu Asp Leu Leu Phe Asn Lys Val Thr Leu Ala Asp Ala
                805             810             815

Gly Phe Ile Lys Gln Tyr Gly Asp Cys Leu Gly Asp Ile Ala Ala Arg
                820             825             830

Asp Leu Ile Cys Ala Gln Lys Phe Asn Gly Leu Thr Val Leu Pro Pro
                835             840             845

Leu Leu Thr Asp Glu Met Ile Ala Gln Tyr Thr Ser Ala Leu Leu Ala
            850             855             860

Gly Thr Ile Thr Ser Gly Trp Thr Phe Gly Ala Gly Ala Ala Leu Gln
865             870             875             880

Ile Pro Phe Ala Met Gln Met Ala Tyr Arg Phe Asn Gly Ile Gly Val
                885             890             895

Thr Gln Asn Val Leu Tyr Glu Asn Gln Lys Leu Ile Ala Asn Gln Phe
                900             905             910

Asn Ser Ala Ile Gly Lys Ile Gln Asp Ser Leu Ser Ser Thr Ala Ser
                915             920             925

Ala Leu Gly Lys Leu Gln Asp Val Val Asn Gln Asn Ala Gln Ala Leu
                930             935             940

Asn Thr Leu Val Lys Gln Leu Ser Ser Asn Phe Gly Ala Ile Ser Ser
945             950             955             960

Val Leu Asn Asp Ile Leu Ser Arg Leu Asp Lys Val Glu Ala Glu Val
                965             970             975

Gln Ile Asp Arg Leu Ile Thr Gly Arg Leu Gln Ser Leu Gln Thr Tyr
                980             985             990

Val Thr Gln Gln Leu Ile Arg Ala Ala Glu Ile Arg Ala Ser Ala Asn
                995             1000            1005

Leu Ala Ala Thr Lys Met Ser Glu Cys Val Leu Gly Gln Ser Lys Arg
            1010            1015            1020

Val Asp Phe Cys Gly Lys Gly Tyr His Leu Met Ser Phe Pro Gln Ser
1025            1030            1035            1040

Ala Pro His Gly Val Val Phe Leu His Val Thr Tyr Val Pro Ala Gln
                1045            1050            1055

Glu Lys Asn Phe Thr Thr Ala Pro Ala Ile Cys His Asp Gly Lys Ala
                1060            1065            1070

His Phe Pro Arg Glu Gly Val Phe Val Ser Asn Gly Thr His Trp Phe
                1075            1080            1085

Val Thr Gln Arg Asn Phe Tyr Glu Pro Gln Ile Ile Thr Thr Asp Asn
                1090            1095            1100

Thr Phe Val Ser Gly Asn Cys Asp Val Val Ile Gly Ile Val Asn Asn
1105            1110            1115            1120

Thr Val Tyr Asp Pro Leu Gln Pro Glu Leu Asp Ser Phe Lys Glu Glu
                1125            1130            1135

Leu Asp Lys Tyr Phe Lys Asn His Thr Ser Pro Asp Val Asp Leu Gly
                1140            1145            1150

Asp Ile Ser Gly Ile Asn Ala Ser Val Val Asn Ile Gln Lys Glu Ile
                1155            1160            1165

Asp Arg Leu Asn Glu Val Ala Lys Asn Leu Asn Glu Ser Leu Ile Asp
            1170            1175            1180

Leu Gln Glu Leu Gly Lys Tyr Glu Gln Tyr Ile Lys Arg Ser Asn Gly
1185            1190            1195            1200
```

```
Leu Pro Gly Pro Ile Gly Pro Pro Gly Pro Arg Gly Arg Thr Gly Asp
        1205                1210                1215

Ala Gly Pro Val Gly Pro Pro Gly Pro Pro Gly Pro Pro Gly Pro Pro
    1220                1225                1230

Gly Pro Pro Ser Ala Gly Phe Asp Phe Ser Phe Leu Pro Gln Pro Pro
    1235                1240                1245

Gln Glu Lys Ala His Asp Gly Gly Arg Tyr Tyr Arg Ala Asn Asp Ala
1250                1255                1260

Asn Val Val Arg Asp Arg Asp Leu Glu Val Asp Thr Thr Leu Lys Ser
1265                1270                1275                1280

Leu Ser Gln Gln Ile Glu Asn Ile Arg Ser Pro Glu Gly Ser Arg Lys
            1285                1290                1295

Asn Pro Ala Arg Thr Cys Arg Asp Leu Lys Met Cys His Ser Asp Trp
            1300                1305                1310

Lys Ser Gly Glu Tyr Trp Ile Asp Pro Asn Gln Gly Cys Asn Leu Asp
            1315                1320                1325

Ala Ile Lys Val Phe Cys Asn Met Glu Thr Gly Glu Thr Cys Val Tyr
            1330                1335                1340

Pro Thr Gln Pro Ser Val Ala Gln Lys Asn Trp Tyr Ile Ser Lys Asn
1345                1350                1355                1360

Pro Lys Asp Lys Arg His Val Trp Phe Gly Glu Ser Met Thr Asp Gly
            1365                1370                1375

Phe Gln Phe Glu Tyr Gly Gly Gln Gly Ser Asp Pro Ala Asp Val Ala
            1380                1385                1390

Ile Gln Leu Thr Phe Leu Arg Leu Met Ser Thr Glu Ala Ser Gln Asn
            1395                1400                1405

Ile Thr Tyr His Cys Lys Asn Ser Val Ala Tyr Met Asp Gln Gln Thr
            1410                1415                1420

Gly Asn Leu Lys Lys Ala Leu Leu Leu Gln Gly Ser Asn Glu Ile Glu
1425                1430                1435                1440

Ile Arg Ala Glu Gly Asn Ser Arg Phe Thr Tyr Ser Val Thr Val Asp
            1445                1450                1455

Gly Cys Thr Ser His Thr Gly Ala Trp Gly Lys Thr Val Ile Glu Tyr
            1460                1465                1470

Lys Thr Thr Lys Thr Ser Arg Leu Pro Ile Ile Asp Val Ala Pro Leu
            1475                1480                1485

Asp Val Gly Ala Pro Asp Gln Glu Phe Gly Phe Asp Val Gly Pro Val
            1490                1495                1500

Cys Phe Leu
1505

<210> SEQ ID NO 19
<211> LENGTH: 1507
<212> TYPE: PRT
<213> ORGANISM: Artificial Sequence
<220> FEATURE:
<223> OTHER INFORMATION: Synthetic construct

<400> SEQUENCE: 19

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45
```

```
Val Thr Trp Phe His Ala Ile Ser Gly Thr Asn Gly Thr Lys Arg Phe
 50                  55                  60

Asp Asn Pro Val Leu Pro Phe Asn Asp Gly Val Tyr Phe Ala Ser Thr
 65                  70                  75                  80

Glu Lys Ser Asn Ile Ile Arg Gly Trp Ile Phe Gly Thr Thr Leu Asp
                     85                  90                  95

Ser Lys Thr Gln Ser Leu Leu Ile Val Asn Asn Ala Thr Asn Val Val
                100                 105                 110

Ile Lys Val Cys Glu Phe Gln Phe Cys Asn Asp Pro Phe Leu Gly Val
            115                 120                 125

Tyr Tyr His Lys Asn Asn Lys Ser Trp Met Glu Ser Glu Phe Arg Val
130                 135                 140

Tyr Ser Ser Ala Asn Asn Cys Thr Phe Glu Tyr Val Ser Gln Pro Phe
145                 150                 155                 160

Leu Met Asp Leu Glu Gly Lys Gln Gly Asn Phe Lys Asn Leu Arg Glu
                165                 170                 175

Phe Val Phe Lys Asn Ile Asp Gly Tyr Phe Lys Ile Tyr Ser Lys His
            180                 185                 190

Thr Pro Ile Asn Leu Val Arg Asp Leu Pro Gln Gly Phe Ser Ala Leu
195                 200                 205

Glu Pro Leu Val Asp Leu Pro Ile Gly Ile Asn Ile Thr Arg Phe Gln
210                 215                 220

Thr Leu Leu Ala Leu His Arg Ser Tyr Leu Thr Pro Gly Asp Ser Ser
225                 230                 235                 240

Ser Gly Trp Thr Ala Gly Ala Ala Ala Tyr Tyr Val Gly Tyr Leu Gln
                245                 250                 255

Pro Arg Thr Phe Leu Leu Lys Tyr Asn Glu Asn Gly Thr Ile Thr Asp
                260                 265                 270

Ala Val Asp Cys Ala Leu Asp Pro Leu Ser Glu Thr Lys Cys Thr Leu
            275                 280                 285

Lys Ser Phe Thr Val Glu Lys Gly Ile Tyr Gln Thr Ser Asn Phe Arg
290                 295                 300

Val Gln Pro Thr Glu Ser Ile Val Arg Phe Pro Asn Ile Thr Asn Leu
305                 310                 315                 320

Cys Pro Phe Gly Glu Val Phe Asn Ala Thr Arg Phe Ala Ser Val Tyr
                325                 330                 335

Ala Trp Asn Arg Lys Arg Ile Ser Asn Cys Val Ala Asp Tyr Ser Val
                340                 345                 350

Leu Tyr Asn Ser Ala Ser Phe Ser Thr Phe Lys Cys Tyr Gly Val Ser
            355                 360                 365

Pro Thr Lys Leu Asn Asp Leu Cys Phe Thr Asn Val Tyr Ala Asp Ser
370                 375                 380

Phe Val Ile Arg Gly Asp Glu Val Arg Gln Ile Ala Pro Gly Gln Thr
385                 390                 395                 400

Gly Lys Ile Ala Asp Tyr Asn Tyr Lys Leu Pro Asp Asp Phe Thr Gly
                405                 410                 415

Cys Val Ile Ala Trp Asn Ser Asn Asn Leu Asp Ser Lys Val Gly Gly
            420                 425                 430

Asn Tyr Asn Tyr Leu Tyr Arg Leu Phe Arg Lys Ser Asn Leu Lys Pro
            435                 440                 445

Phe Glu Arg Asp Ile Ser Thr Glu Ile Tyr Gln Ala Gly Ser Thr Pro
450                 455                 460
```

Cys Asn Gly Val Glu Gly Phe Asn Cys Tyr Phe Pro Leu Gln Ser Tyr
465                 470                 475                 480

Gly Phe Gln Pro Thr Tyr Gly Val Gly Tyr Gln Pro Tyr Arg Val Val
            485                 490                 495

Val Leu Ser Phe Glu Leu Leu His Ala Pro Ala Thr Val Cys Gly Pro
            500                 505                 510

Lys Lys Ser Thr Asn Leu Val Lys Asn Lys Cys Val Asn Phe Asn Phe
            515                 520                 525

Asn Gly Leu Thr Gly Thr Gly Val Leu Thr Glu Ser Asn Lys Lys Phe
            530                 535                 540

Leu Pro Phe Gln Gln Phe Gly Arg Asp Ile Ala Asp Thr Thr Asp Ala
545                 550                 555                 560

Val Arg Asp Pro Gln Thr Leu Glu Ile Leu Asp Ile Thr Pro Cys Ser
            565                 570                 575

Phe Gly Gly Val Ser Val Ile Thr Pro Gly Thr Asn Thr Ser Asn Gln
            580                 585                 590

Val Ala Val Leu Tyr Gln Gly Val Asn Cys Thr Glu Val Pro Val Ala
            595                 600                 605

Ile His Ala Asp Gln Leu Thr Pro Thr Trp Arg Val Tyr Ser Thr Gly
610                 615                 620

Ser Asn Val Phe Gln Thr Arg Ala Gly Cys Leu Ile Gly Ala Glu His
625                 630                 635                 640

Val Asn Asn Ser Tyr Glu Cys Asp Ile Pro Ile Gly Ala Gly Ile Cys
            645                 650                 655

Ala Ser Tyr Gln Thr Gln Thr Asn Ser His Arg Arg Ala Ala Ser Val
            660                 665                 670

Ala Ser Gln Ser Ile Ile Ala Tyr Thr Met Ser Leu Gly Ala Glu Asn
            675                 680                 685

Ser Val Ala Tyr Ser Asn Asn Ser Ile Ala Ile Pro Thr Asn Phe Thr
            690                 695                 700

Ile Ser Val Thr Thr Glu Ile Leu Pro Val Ser Met Thr Lys Thr Ser
705                 710                 715                 720

Val Asp Cys Thr Met Tyr Ile Cys Gly Asp Ser Thr Glu Cys Ser Asn
            725                 730                 735

Leu Leu Leu Gln Tyr Gly Ser Phe Cys Thr Gln Leu Asn Arg Ala Leu
            740                 745                 750

Thr Gly Ile Ala Val Glu Gln Asp Lys Asn Thr Gln Glu Val Phe Ala
            755                 760                 765

Gln Val Lys Gln Ile Tyr Lys Thr Pro Pro Ile Lys Asp Phe Gly Gly
            770                 775                 780

Phe Asn Phe Ser Gln Ile Leu Pro Asp Pro Ser Lys Pro Ser Lys Arg
785                 790                 795                 800

Ser Phe Ile Glu Asp Leu Leu Phe Asn Lys Val Thr Leu Ala Asp Ala
            805                 810                 815

Gly Phe Ile Lys Gln Tyr Gly Asp Cys Leu Gly Asp Ile Ala Ala Arg
            820                 825                 830

Asp Leu Ile Cys Ala Gln Lys Phe Asn Gly Leu Thr Val Leu Pro Pro
            835                 840                 845

Leu Leu Thr Asp Glu Met Ile Ala Gln Tyr Thr Ser Ala Leu Leu Ala
            850                 855                 860

Gly Thr Ile Thr Ser Gly Trp Thr Phe Gly Ala Gly Ala Ala Leu Gln
865                 870                 875                 880

Ile Pro Phe Ala Met Gln Met Ala Tyr Arg Phe Asn Gly Ile Gly Val

```
            885                 890                 895
Thr Gln Asn Val Leu Tyr Glu Asn Gln Lys Leu Ile Ala Asn Gln Phe
            900                 905                 910

Asn Ser Ala Ile Gly Lys Ile Gln Asp Ser Leu Ser Ser Thr Ala Ser
            915                 920                 925

Ala Leu Gly Lys Leu Gln Asp Val Val Asn Gln Asn Ala Gln Ala Leu
            930                 935                 940

Asn Thr Leu Val Lys Gln Leu Ser Ser Asn Phe Gly Ala Ile Ser Ser
945                 950                 955                 960

Val Leu Asn Asp Ile Leu Ser Arg Leu Asp Lys Val Glu Ala Glu Val
                965                 970                 975

Gln Ile Asp Arg Leu Ile Thr Gly Arg Leu Gln Ser Leu Gln Thr Tyr
            980                 985                 990

Val Thr Gln Gln Leu Ile Arg Ala Ala Glu Ile Arg Ala Ser Ala Asn
            995                 1000                1005

Leu Ala Ala Thr Lys Met Ser Glu Cys Val Leu Gly Gln Ser Lys Arg
            1010                1015                1020

Val Asp Phe Cys Gly Lys Gly Tyr His Leu Met Ser Phe Pro Gln Ser
1025                1030                1035                1040

Ala Pro His Gly Val Val Phe Leu His Val Thr Tyr Val Pro Ala Gln
                1045                1050                1055

Glu Lys Asn Phe Thr Thr Ala Pro Ala Ile Cys His Asp Gly Lys Ala
            1060                1065                1070

His Phe Pro Arg Glu Gly Val Phe Val Ser Asn Gly Thr His Trp Phe
            1075                1080                1085

Val Thr Gln Arg Asn Phe Tyr Glu Pro Gln Ile Ile Thr Thr Asp Asn
            1090                1095                1100

Thr Phe Val Ser Gly Asn Cys Asp Val Val Ile Gly Ile Val Asn Asn
1105                1110                1115                1120

Thr Val Tyr Asp Pro Leu Gln Pro Glu Leu Asp Ser Phe Lys Glu Glu
                1125                1130                1135

Leu Asp Lys Tyr Phe Lys Asn His Thr Ser Pro Asp Val Asp Leu Gly
            1140                1145                1150

Asp Ile Ser Gly Ile Asn Ala Ser Val Val Asn Ile Gln Lys Glu Ile
            1155                1160                1165

Asp Arg Leu Asn Glu Val Ala Lys Asn Leu Asn Glu Ser Leu Ile Asp
            1170                1175                1180

Leu Gln Glu Leu Gly Lys Tyr Glu Gln Tyr Ile Lys Arg Ser Asn Gly
1185                1190                1195                1200

Leu Pro Gly Pro Ile Gly Pro Pro Gly Pro Arg Gly Arg Thr Gly Asp
            1205                1210                1215

Ala Gly Pro Val Gly Pro Pro Gly Pro Pro Gly Pro Gly Pro Pro
            1220                1225                1230

Gly Pro Pro Ser Ala Gly Phe Asp Phe Ser Phe Leu Pro Gln Pro Pro
            1235                1240                1245

Gln Glu Lys Ala His Asp Gly Gly Arg Tyr Tyr Arg Ala Asn Asp Ala
            1250                1255                1260

Asn Val Val Arg Asp Arg Asp Leu Glu Val Asp Thr Thr Leu Lys Ser
1265                1270                1275                1280

Leu Ser Gln Gln Ile Glu Asn Ile Arg Ser Pro Glu Gly Ser Arg Lys
                1285                1290                1295

Asn Pro Ala Arg Thr Cys Arg Asp Leu Lys Met Cys His Ser Asp Trp
            1300                1305                1310
```

```
Lys Ser Gly Glu Tyr Trp Ile Asp Pro Asn Gln Gly Cys Asn Leu Asp
        1315                1320                1325

Ala Ile Lys Val Phe Cys Asn Met Glu Thr Gly Glu Thr Cys Val Tyr
    1330                1335                1340

Pro Thr Gln Pro Ser Val Ala Gln Lys Asn Trp Tyr Ile Ser Lys Asn
1345                1350                1355                1360

Pro Lys Asp Lys Arg His Val Trp Phe Gly Glu Ser Met Thr Asp Gly
                1365                1370                1375

Phe Gln Phe Glu Tyr Gly Gly Gln Gly Ser Asp Pro Ala Asp Val Ala
                1380                1385                1390

Ile Gln Leu Thr Phe Leu Arg Leu Met Ser Thr Glu Ala Ser Gln Asn
                1395                1400                1405

Ile Thr Tyr His Cys Lys Asn Ser Val Ala Tyr Met Asp Gln Gln Thr
                1410                1415                1420

Gly Asn Leu Lys Lys Ala Leu Leu Leu Gln Gly Ser Asn Glu Ile Glu
1425                1430                1435                1440

Ile Arg Ala Glu Gly Asn Ser Arg Phe Thr Tyr Ser Val Thr Val Asp
                1445                1450                1455

Gly Cys Thr Ser His Thr Gly Ala Trp Gly Lys Thr Val Ile Glu Tyr
                1460                1465                1470

Lys Thr Thr Lys Thr Ser Arg Leu Pro Ile Ile Asp Val Ala Pro Leu
                1475                1480                1485

Asp Val Gly Ala Pro Asp Gln Glu Phe Gly Phe Asp Val Gly Pro Val
                1490                1495                1500

Cys Phe Leu
1505

<210> SEQ ID NO 20
<211> LENGTH: 1507
<212> TYPE: PRT
<213> ORGANISM: Artificial Sequence
<220> FEATURE:
<223> OTHER INFORMATION: Synthetic construct

<400> SEQUENCE: 20

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
                20                  25                  30

Ser Val Leu His Ser Thr Gln Asp Leu Phe Leu Pro Phe Phe Ser Asn
            35                  40                  45

Val Thr Trp Phe His Ala Ile Ser Gly Thr Asn Gly Thr Lys Arg Phe
    50                  55                  60

Asp Asn Pro Val Leu Pro Phe Asn Asp Gly Val Tyr Phe Ala Ser Thr
65                  70                  75                  80

Glu Lys Ser Asn Ile Ile Arg Gly Trp Ile Phe Gly Thr Thr Leu Asp
                85                  90                  95

Ser Lys Thr Gln Ser Leu Leu Ile Val Asn Asn Ala Thr Asn Val Val
                100                 105                 110

Ile Lys Val Cys Glu Phe Gln Phe Cys Asn Asp Pro Phe Leu Gly Val
            115                 120                 125

Tyr Tyr His Lys Asn Asn Lys Ser Trp Met Glu Ser Glu Phe Arg Val
    130                 135                 140

Tyr Ser Ser Ala Asn Asn Cys Thr Phe Glu Tyr Val Ser Gln Pro Phe
145                 150                 155                 160
```

```
Leu Met Asp Leu Glu Gly Lys Gln Gly Asn Phe Lys Asn Leu Arg Glu
             165                 170                 175
Phe Val Phe Lys Asn Ile Asp Gly Tyr Phe Lys Ile Tyr Ser Lys His
             180                 185                 190
Thr Pro Ile Asn Leu Val Arg Asp Leu Pro Gln Gly Phe Ser Ala Leu
             195                 200                 205
Glu Pro Leu Val Asp Leu Pro Ile Gly Ile Asn Ile Thr Arg Phe Gln
             210                 215                 220
Thr Leu Leu Ala Leu His Arg Ser Tyr Leu Thr Pro Gly Asp Ser Ser
225                  230                 235                 240
Ser Gly Trp Thr Ala Gly Ala Ala Ala Tyr Tyr Val Gly Tyr Leu Gln
             245                 250                 255
Pro Arg Thr Phe Leu Leu Lys Tyr Asn Glu Asn Gly Thr Ile Thr Asp
             260                 265                 270
Ala Val Asp Cys Ala Leu Asp Pro Leu Ser Glu Thr Lys Cys Thr Leu
             275                 280                 285
Lys Ser Phe Thr Val Glu Lys Gly Ile Tyr Gln Thr Ser Asn Phe Arg
             290                 295                 300
Val Gln Pro Thr Glu Ser Ile Val Arg Phe Pro Asn Ile Thr Asn Leu
305                  310                 315                 320
Cys Pro Phe Gly Glu Val Phe Asn Ala Thr Arg Phe Ala Ser Val Tyr
             325                 330                 335
Ala Trp Asn Arg Lys Arg Ile Ser Asn Cys Val Ala Asp Tyr Ser Val
             340                 345                 350
Leu Tyr Asn Ser Ala Ser Phe Ser Thr Phe Lys Cys Tyr Gly Val Ser
             355                 360                 365
Pro Thr Lys Leu Asn Asp Leu Cys Phe Thr Asn Val Tyr Ala Asp Ser
             370                 375                 380
Phe Val Ile Arg Gly Asp Glu Val Arg Gln Ile Ala Pro Gly Gln Thr
385                  390                 395                 400
Gly Lys Ile Ala Asp Tyr Asn Tyr Lys Leu Pro Asp Asp Phe Thr Gly
             405                 410                 415
Cys Val Ile Ala Trp Asn Ser Asn Asn Leu Asp Ser Lys Val Gly Gly
             420                 425                 430
Asn Tyr Asn Tyr Leu Tyr Arg Leu Phe Arg Lys Ser Asn Leu Lys Pro
             435                 440                 445
Phe Glu Arg Asp Ile Ser Thr Glu Ile Tyr Gln Ala Gly Ser Thr Pro
             450                 455                 460
Cys Asn Gly Val Glu Gly Phe Asn Cys Tyr Phe Pro Leu Gln Ser Tyr
465                  470                 475                 480
Gly Phe Gln Pro Thr Tyr Gly Val Gly Tyr Gln Pro Tyr Arg Val Val
             485                 490                 495
Val Leu Ser Phe Glu Leu Leu His Ala Pro Ala Thr Val Cys Gly Pro
             500                 505                 510
Lys Lys Ser Thr Asn Leu Val Lys Asn Lys Cys Val Asn Phe Asn Phe
             515                 520                 525
Asn Gly Leu Thr Gly Thr Gly Val Leu Thr Glu Ser Asn Lys Lys Phe
             530                 535                 540
Leu Pro Phe Gln Gln Phe Gly Arg Asp Ile Ala Asp Thr Thr Asp Ala
545                  550                 555                 560
Val Arg Asp Pro Gln Thr Leu Glu Ile Leu Asp Ile Thr Pro Cys Ser
             565                 570                 575
```

```
Phe Gly Gly Val Ser Val Ile Thr Pro Gly Thr Asn Thr Ser Asn Gln
                580                 585                 590

Val Ala Val Leu Tyr Gln Gly Val Asn Cys Thr Glu Val Pro Val Ala
            595                 600                 605

Ile His Ala Asp Gln Leu Thr Pro Thr Trp Arg Val Tyr Ser Thr Gly
        610                 615                 620

Ser Asn Val Phe Gln Thr Arg Ala Gly Cys Leu Ile Gly Ala Glu His
625                 630                 635                 640

Val Asn Asn Ser Tyr Glu Cys Asp Ile Pro Ile Gly Ala Gly Ile Cys
            645                 650                 655

Ala Ser Tyr Gln Thr Gln Thr Asn Ser His Arg Arg Ala Arg Ser Val
        660                 665                 670

Ala Ser Gln Ser Ile Ile Ala Tyr Thr Met Ser Leu Gly Ala Glu Asn
    675                 680                 685

Ser Val Ala Tyr Ser Asn Asn Ser Ile Ala Ile Pro Thr Asn Phe Thr
690                 695                 700

Ile Ser Val Thr Thr Glu Ile Leu Pro Val Ser Met Thr Lys Thr Ser
705                 710                 715                 720

Val Asp Cys Thr Met Tyr Ile Cys Gly Asp Ser Thr Glu Cys Ser Asn
            725                 730                 735

Leu Leu Leu Gln Tyr Gly Ser Phe Cys Thr Gln Leu Asn Arg Ala Leu
        740                 745                 750

Thr Gly Ile Ala Val Glu Gln Asp Lys Asn Thr Gln Glu Val Phe Ala
    755                 760                 765

Gln Val Lys Gln Ile Tyr Lys Thr Pro Pro Ile Lys Asp Phe Gly Gly
770                 775                 780

Phe Asn Phe Ser Gln Ile Leu Pro Asp Pro Ser Lys Pro Ser Lys Arg
785                 790                 795                 800

Ser Phe Ile Glu Asp Leu Leu Phe Asn Lys Val Thr Leu Ala Asp Ala
            805                 810                 815

Gly Phe Ile Lys Gln Tyr Gly Asp Cys Leu Gly Asp Ile Ala Ala Arg
        820                 825                 830

Asp Leu Ile Cys Ala Gln Lys Phe Asn Gly Leu Thr Val Leu Pro Pro
    835                 840                 845

Leu Leu Thr Asp Glu Met Ile Ala Gln Tyr Thr Ser Ala Leu Leu Ala
850                 855                 860

Gly Thr Ile Thr Ser Gly Trp Thr Phe Gly Ala Gly Ala Ala Leu Gln
865                 870                 875                 880

Ile Pro Phe Ala Met Gln Met Ala Tyr Arg Phe Asn Gly Ile Gly Val
            885                 890                 895

Thr Gln Asn Val Leu Tyr Glu Asn Gln Lys Leu Ile Ala Asn Gln Phe
        900                 905                 910

Asn Ser Ala Ile Gly Lys Ile Gln Asp Ser Leu Ser Ser Thr Ala Ser
    915                 920                 925

Ala Leu Gly Lys Leu Gln Asp Val Val Asn Gln Asn Ala Gln Ala Leu
930                 935                 940

Asn Thr Leu Val Lys Gln Leu Ser Ser Asn Phe Gly Ala Ile Ser Ser
945                 950                 955                 960

Val Leu Asn Asp Ile Leu Ser Arg Leu Asp Pro Pro Glu Ala Glu Val
            965                 970                 975

Gln Ile Asp Arg Leu Ile Thr Gly Arg Leu Gln Ser Leu Gln Thr Tyr
        980                 985                 990

Val Thr Gln Gln Leu Ile Arg Ala Ala Glu Ile Arg Ala Ser Ala Asn
```

-continued

```
              995                 1000                1005
Leu Ala Ala Thr Lys Met Ser Glu Cys Val Leu Gly Gln Ser Lys Arg
         1010                1015                1020
Val Asp Phe Cys Gly Lys Gly Tyr His Leu Met Ser Phe Pro Gln Ser
1025                1030                1035                1040
Ala Pro His Gly Val Val Phe Leu His Val Thr Tyr Val Pro Ala Gln
                1045                1050                1055
Glu Lys Asn Phe Thr Thr Ala Pro Ala Ile Cys His Asp Gly Lys Ala
            1060                1065                1070
His Phe Pro Arg Glu Gly Val Phe Val Ser Asn Gly Thr His Trp Phe
        1075                1080                1085
Val Thr Gln Arg Asn Phe Tyr Glu Pro Gln Ile Ile Thr Thr Asp Asn
    1090                1095                1100
Thr Phe Val Ser Gly Asn Cys Asp Val Val Ile Gly Ile Val Asn Asn
1105                1110                1115                1120
Thr Val Tyr Asp Pro Leu Gln Pro Glu Leu Asp Ser Phe Lys Glu Glu
                1125                1130                1135
Leu Asp Lys Tyr Phe Lys Asn His Thr Ser Pro Asp Val Asp Leu Gly
            1140                1145                1150
Asp Ile Ser Gly Ile Asn Ala Ser Val Val Asn Ile Gln Lys Glu Ile
        1155                1160                1165
Asp Arg Leu Asn Glu Val Ala Lys Asn Leu Asn Glu Ser Leu Ile Asp
    1170                1175                1180
Leu Gln Glu Leu Gly Lys Tyr Glu Gln Tyr Ile Lys Arg Ser Asn Gly
1185                1190                1195                1200
Leu Pro Gly Pro Ile Gly Pro Pro Gly Pro Arg Gly Arg Thr Gly Asp
                1205                1210                1215
Ala Gly Pro Val Gly Pro Pro Gly Pro Pro Gly Pro Pro Gly Pro Pro
            1220                1225                1230
Gly Pro Pro Ser Ala Gly Phe Asp Phe Ser Phe Leu Pro Gln Pro Pro
        1235                1240                1245
Gln Glu Lys Ala His Asp Gly Gly Arg Tyr Tyr Arg Ala Asn Asp Ala
    1250                1255                1260
Asn Val Val Arg Asp Arg Asp Leu Glu Val Asp Thr Thr Leu Lys Ser
1265                1270                1275                1280
Leu Ser Gln Gln Ile Glu Asn Ile Arg Ser Pro Glu Gly Ser Arg Lys
                1285                1290                1295
Asn Pro Ala Arg Thr Cys Arg Asp Leu Lys Met Cys His Ser Asp Trp
            1300                1305                1310
Lys Ser Gly Glu Tyr Trp Ile Asp Pro Asn Gln Gly Cys Asn Leu Asp
        1315                1320                1325
Ala Ile Lys Val Phe Cys Asn Met Glu Thr Gly Glu Thr Cys Val Tyr
    1330                1335                1340
Pro Thr Gln Pro Ser Val Ala Gln Lys Asn Trp Tyr Ile Ser Lys Asn
1345                1350                1355                1360
Pro Lys Asp Lys Arg His Val Trp Phe Gly Glu Ser Met Thr Asp Gly
                1365                1370                1375
Phe Gln Phe Glu Tyr Gly Gly Gln Gly Ser Asp Pro Ala Asp Val Ala
            1380                1385                1390
Ile Gln Leu Thr Phe Leu Arg Leu Met Ser Thr Glu Ala Ser Gln Asn
        1395                1400                1405
Ile Thr Tyr His Cys Lys Asn Ser Val Ala Tyr Met Asp Gln Gln Thr
    1410                1415                1420
```

-continued

Gly Asn Leu Lys Lys Ala Leu Leu Gln Gly Ser Asn Glu Ile Glu
1425                1430                1435                1440

Ile Arg Ala Glu Gly Asn Ser Arg Phe Thr Tyr Ser Val Thr Val Asp
            1445                1450                1455

Gly Cys Thr Ser His Thr Gly Ala Trp Gly Lys Thr Val Ile Glu Tyr
            1460                1465                1470

Lys Thr Thr Lys Thr Ser Arg Leu Pro Ile Ile Asp Val Ala Pro Leu
        1475                1480                1485

Asp Val Gly Ala Pro Asp Gln Glu Phe Gly Phe Asp Val Gly Pro Val
        1490                1495                1500

Cys Phe Leu
1505

<210> SEQ ID NO 21
<211> LENGTH: 1507
<212> TYPE: PRT
<213> ORGANISM: Artificial Sequence
<220> FEATURE:
<223> OTHER INFORMATION: Synthetic construct

<400> SEQUENCE: 21

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile Ser Gly Thr Asn Gly Thr Lys Arg Phe
    50                  55                  60

Asp Asn Pro Val Leu Pro Phe Asn Asp Gly Val Tyr Phe Ala Ser Thr
65                  70                  75                  80

Glu Lys Ser Asn Ile Ile Arg Gly Trp Ile Phe Gly Thr Thr Leu Asp
                85                  90                  95

Ser Lys Thr Gln Ser Leu Leu Ile Val Asn Asn Ala Thr Asn Val Val
            100                 105                 110

Ile Lys Val Cys Glu Phe Gln Phe Cys Asn Asp Pro Phe Leu Gly Val
        115                 120                 125

Tyr Tyr His Lys Asn Asn Lys Ser Trp Met Glu Ser Glu Phe Arg Val
    130                 135                 140

Tyr Ser Ser Ala Asn Asn Cys Thr Phe Glu Tyr Val Ser Gln Pro Phe
145                 150                 155                 160

Leu Met Asp Leu Glu Gly Lys Gln Gly Asn Phe Lys Asn Leu Arg Glu
                165                 170                 175

Phe Val Phe Lys Asn Ile Asp Gly Tyr Phe Lys Ile Tyr Ser Lys His
            180                 185                 190

Thr Pro Ile Asn Leu Val Arg Asp Leu Pro Gln Gly Phe Ser Ala Leu
        195                 200                 205

Glu Pro Leu Val Asp Leu Pro Ile Gly Ile Asn Ile Thr Arg Phe Gln
    210                 215                 220

Thr Leu Leu Ala Leu His Arg Ser Tyr Leu Thr Pro Gly Asp Ser Ser
225                 230                 235                 240

Ser Gly Trp Thr Ala Gly Ala Ala Ala Tyr Tyr Val Gly Tyr Leu Gln
                245                 250                 255

Pro Arg Thr Phe Leu Leu Lys Tyr Asn Glu Asn Gly Thr Ile Thr Asp
            260                 265                 270

```
Ala Val Asp Cys Ala Leu Asp Pro Leu Ser Glu Thr Lys Cys Thr Leu
            275                 280                 285

Lys Ser Phe Thr Val Glu Lys Gly Ile Tyr Gln Thr Ser Asn Phe Arg
        290                 295                 300

Val Gln Pro Thr Glu Ser Ile Val Arg Phe Pro Asn Ile Thr Asn Leu
305                 310                 315                 320

Cys Pro Phe Gly Glu Val Phe Asn Ala Thr Arg Phe Ala Ser Val Tyr
                325                 330                 335

Ala Trp Asn Arg Lys Arg Ile Ser Asn Cys Val Ala Asp Tyr Ser Val
            340                 345                 350

Leu Tyr Asn Ser Ala Ser Phe Ser Thr Phe Lys Cys Tyr Gly Val Ser
        355                 360                 365

Pro Thr Lys Leu Asn Asp Leu Cys Phe Thr Asn Val Tyr Ala Asp Ser
370                 375                 380

Phe Val Ile Arg Gly Asp Glu Val Arg Gln Ile Ala Pro Gly Gln Thr
385                 390                 395                 400

Gly Lys Ile Ala Asp Tyr Asn Tyr Lys Leu Pro Asp Asp Phe Thr Gly
                405                 410                 415

Cys Val Ile Ala Trp Asn Ser Asn Asn Leu Asp Ser Lys Val Gly Gly
            420                 425                 430

Asn Tyr Asn Tyr Leu Tyr Arg Leu Phe Arg Lys Ser Asn Leu Lys Pro
        435                 440                 445

Phe Glu Arg Asp Ile Ser Thr Glu Ile Tyr Gln Ala Gly Ser Thr Pro
    450                 455                 460

Cys Asn Gly Val Glu Gly Phe Asn Cys Tyr Phe Pro Leu Gln Ser Tyr
465                 470                 475                 480

Gly Phe Gln Pro Thr Tyr Gly Val Gly Tyr Gln Pro Tyr Arg Val Val
                485                 490                 495

Val Leu Ser Phe Glu Leu Leu His Ala Pro Ala Thr Val Cys Gly Pro
            500                 505                 510

Lys Lys Ser Thr Asn Leu Val Lys Asn Lys Cys Val Asn Phe Asn Phe
        515                 520                 525

Asn Gly Leu Thr Gly Thr Gly Val Leu Thr Glu Ser Asn Lys Lys Phe
    530                 535                 540

Leu Pro Phe Gln Gln Phe Gly Arg Asp Ile Ala Asp Thr Thr Asp Ala
545                 550                 555                 560

Val Arg Asp Pro Gln Thr Leu Glu Ile Leu Asp Ile Thr Pro Cys Ser
                565                 570                 575

Phe Gly Gly Val Ser Val Ile Thr Pro Gly Thr Asn Thr Ser Asn Gln
            580                 585                 590

Val Ala Val Leu Tyr Gln Gly Val Asn Cys Thr Glu Val Pro Val Ala
        595                 600                 605

Ile His Ala Asp Gln Leu Thr Pro Thr Trp Arg Val Tyr Ser Thr Gly
    610                 615                 620

Ser Asn Val Phe Gln Thr Arg Ala Gly Cys Leu Ile Gly Ala Glu His
625                 630                 635                 640

Val Asn Asn Ser Tyr Glu Cys Asp Ile Pro Ile Gly Ala Gly Ile Cys
                645                 650                 655

Ala Ser Tyr Gln Thr Gln Thr Asn Ser His Arg Arg Ala Ala Ser Val
            660                 665                 670

Ala Ser Gln Ser Ile Ile Ala Tyr Thr Met Ser Leu Gly Ala Glu Asn
        675                 680                 685
```

```
Ser Val Ala Tyr Ser Asn Asn Ser Ile Ala Ile Pro Thr Asn Phe Thr
690             695                 700
Ile Ser Val Thr Thr Glu Ile Leu Pro Val Ser Met Thr Lys Thr Ser
705             710                 715                 720
Val Asp Cys Thr Met Tyr Ile Cys Gly Asp Ser Thr Glu Cys Ser Asn
                725                 730                 735
Leu Leu Leu Gln Tyr Gly Ser Phe Cys Thr Gln Leu Asn Arg Ala Leu
                740                 745                 750
Thr Gly Ile Ala Val Glu Gln Asp Lys Asn Thr Gln Glu Val Phe Ala
            755                 760                 765
Gln Val Lys Gln Ile Tyr Lys Thr Pro Pro Ile Lys Asp Phe Gly Gly
770             775                 780
Phe Asn Phe Ser Gln Ile Leu Pro Asp Pro Ser Lys Pro Ser Lys Arg
785             790                 795                 800
Ser Phe Ile Glu Asp Leu Leu Phe Asn Lys Val Thr Leu Ala Asp Ala
                805                 810                 815
Gly Phe Ile Lys Gln Tyr Gly Asp Cys Leu Gly Asp Ile Ala Ala Arg
                820                 825                 830
Asp Leu Ile Cys Ala Gln Lys Phe Asn Gly Leu Thr Val Leu Pro Pro
                835                 840                 845
Leu Leu Thr Asp Glu Met Ile Ala Gln Tyr Thr Ser Ala Leu Leu Ala
850             855                 860
Gly Thr Ile Thr Ser Gly Trp Thr Phe Gly Ala Gly Ala Ala Leu Gln
865             870                 875                 880
Ile Pro Phe Ala Met Gln Met Ala Tyr Arg Phe Asn Gly Ile Gly Val
                885                 890                 895
Thr Gln Asn Val Leu Tyr Glu Asn Gln Lys Leu Ile Ala Asn Gln Phe
            900                 905                 910
Asn Ser Ala Ile Gly Lys Ile Gln Asp Ser Leu Ser Ser Thr Ala Ser
            915                 920                 925
Ala Leu Gly Lys Leu Gln Asp Val Val Asn Gln Asn Ala Gln Ala Leu
            930                 935                 940
Asn Thr Leu Val Lys Gln Leu Ser Ser Asn Phe Gly Ala Ile Ser Ser
945             950                 955                 960
Val Leu Asn Asp Ile Leu Ser Arg Leu Asp Pro Pro Glu Ala Glu Val
                965                 970                 975
Gln Ile Asp Arg Leu Ile Thr Gly Arg Leu Gln Ser Leu Gln Thr Tyr
                980                 985                 990
Val Thr Gln Gln Leu Ile Arg Ala Ala Glu Ile Arg Ala Ser Ala Asn
            995                 1000                1005
Leu Ala Ala Thr Lys Met Ser Glu Cys Val Leu Gly Gln Ser Lys Arg
            1010                1015                1020
Val Asp Phe Cys Gly Lys Gly Tyr His Leu Met Ser Phe Pro Gln Ser
1025            1030                1035                1040
Ala Pro His Gly Val Val Phe Leu His Val Thr Tyr Val Pro Ala Gln
                1045                1050                1055
Glu Lys Asn Phe Thr Thr Ala Pro Ala Ile Cys His Asp Gly Lys Ala
                1060                1065                1070
His Phe Pro Arg Glu Gly Val Phe Val Ser Asn Gly Thr His Trp Phe
                1075                1080                1085
Val Thr Gln Arg Asn Phe Tyr Glu Pro Gln Ile Ile Thr Thr Asp Asn
            1090                1095                1100
Thr Phe Val Ser Gly Asn Cys Asp Val Val Ile Gly Ile Val Asn Asn
```

```
               1105                1110                1115                1120
          Thr Val Tyr Asp Pro Leu Gln Pro Glu Leu Asp Ser Phe Lys Glu Glu
                            1125                1130                1135
          Leu Asp Lys Tyr Phe Lys Asn His Thr Ser Pro Asp Val Asp Leu Gly
                       1140                1145                1150
          Asp Ile Ser Gly Ile Asn Ala Ser Val Val Asn Ile Gln Lys Glu Ile
                  1155                1160                1165
          Asp Arg Leu Asn Glu Val Ala Lys Asn Leu Asn Glu Ser Leu Ile Asp
              1170                1175                1180
          Leu Gln Glu Leu Gly Lys Tyr Glu Gln Tyr Ile Lys Arg Ser Asn Gly
          1185                1190                1195                1200
          Leu Pro Gly Pro Ile Gly Pro Pro Gly Pro Arg Gly Arg Thr Gly Asp
                       1205                1210                1215
          Ala Gly Pro Val Gly Pro Pro Gly Pro Pro Gly Pro Pro Gly Pro Pro
                  1220                1225                1230
          Gly Pro Pro Ser Ala Gly Phe Asp Phe Ser Phe Leu Pro Gln Pro Pro
              1235                1240                1245
          Gln Glu Lys Ala His Asp Gly Gly Arg Tyr Tyr Arg Ala Asn Asp Ala
              1250                1255                1260
          Asn Val Val Arg Asp Arg Asp Leu Glu Val Asp Thr Thr Leu Lys Ser
          1265                1270                1275                1280
          Leu Ser Gln Gln Ile Glu Asn Ile Arg Ser Pro Glu Gly Ser Arg Lys
                       1285                1290                1295
          Asn Pro Ala Arg Thr Cys Arg Asp Leu Lys Met Cys His Ser Asp Trp
                            1300                1305                1310
          Lys Ser Gly Glu Tyr Trp Ile Asp Pro Asn Gln Gly Cys Asn Leu Asp
                       1315                1320                1325
          Ala Ile Lys Val Phe Cys Asn Met Glu Thr Gly Glu Thr Cys Val Tyr
                       1330                1335                1340
          Pro Thr Gln Pro Ser Val Ala Gln Lys Asn Trp Tyr Ile Ser Lys Asn
          1345                1350                1355                1360
          Pro Lys Asp Lys Arg His Val Trp Phe Gly Glu Ser Met Thr Asp Gly
                       1365                1370                1375
          Phe Gln Phe Glu Tyr Gly Gly Gln Gly Ser Asp Pro Ala Asp Val Ala
                       1380                1385                1390
          Ile Gln Leu Thr Phe Leu Arg Leu Met Ser Thr Glu Ala Ser Gln Asn
                  1395                1400                1405
          Ile Thr Tyr His Cys Lys Asn Ser Val Ala Tyr Met Asp Gln Gln Thr
              1410                1415                1420
          Gly Asn Leu Lys Lys Ala Leu Leu Leu Gln Gly Ser Asn Glu Ile Glu
          1425                1430                1435                1440
          Ile Arg Ala Glu Gly Asn Ser Arg Phe Thr Tyr Ser Val Thr Val Asp
                            1445                1450                1455
          Gly Cys Thr Ser His Thr Gly Ala Trp Gly Lys Thr Val Ile Glu Tyr
                       1460                1465                1470
          Lys Thr Thr Lys Thr Ser Arg Leu Pro Ile Ile Asp Val Ala Pro Leu
                  1475                1480                1485
          Asp Val Gly Ala Pro Asp Gln Glu Phe Gly Phe Asp Val Gly Pro Val
              1490                1495                1500

Cys Phe Leu
          1505

<210> SEQ ID NO 22
```

<211> LENGTH: 1509
<212> TYPE: PRT
<213> ORGANISM: Artificial Sequence
<220> FEATURE:
<223> OTHER INFORMATION: Synthetic construct

<400> SEQUENCE: 22

```
Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205

Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Tyr Tyr Val Gly Tyr
                245                 250                 255

Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
        275                 280                 285

Thr Leu Lys Ser Phe Thr Val Glu Lys Gly Ile Tyr Gln Thr Ser Asn
    290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
            340                 345                 350

Ser Val Leu Tyr Asn Ser Ala Ser Phe Ser Thr Phe Lys Cys Tyr Gly
        355                 360                 365

Val Ser Pro Thr Lys Leu Asn Asp Leu Cys Phe Thr Asn Val Tyr Ala
    370                 375                 380
```

```
Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
            405                 410                 415

Thr Gly Cys Val Ile Ala Trp Asn Ser Asn Asn Leu Asp Ser Lys Val
            420                 425                 430

Gly Gly Asn Tyr Asn Tyr Leu Tyr Arg Leu Phe Arg Lys Ser Asn Leu
            435                 440                 445

Lys Pro Phe Glu Arg Asp Ile Ser Thr Glu Ile Tyr Gln Ala Gly Ser
            450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
            485                 490                 495

Val Val Val Leu Ser Phe Glu Leu Leu His Ala Pro Ala Thr Val Cys
            500                 505                 510

Gly Pro Lys Lys Ser Thr Asn Leu Val Lys Asn Lys Cys Val Asn Phe
            515                 520                 525

Asn Phe Asn Gly Leu Thr Gly Thr Gly Val Leu Thr Glu Ser Asn Lys
530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
            565                 570                 575

Cys Ser Phe Gly Gly Val Ser Val Ile Thr Pro Gly Thr Asn Thr Ser
            580                 585                 590

Asn Gln Val Ala Val Leu Tyr Gln Gly Val Asn Cys Thr Glu Val Pro
            595                 600                 605

Val Ala Ile His Ala Asp Gln Leu Thr Pro Thr Trp Arg Val Tyr Ser
            610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
            645                 650                 655

Ile Cys Ala Ser Tyr Gln Thr Gln Thr Asn Ser Pro Arg Arg Ala Arg
            660                 665                 670

Ser Val Ala Ser Gln Ser Ile Ile Ala Tyr Thr Met Ser Leu Gly Ala
            675                 680                 685

Glu Asn Ser Val Ala Tyr Ser Asn Asn Ser Ile Ala Ile Pro Thr Asn
            690                 695                 700

Phe Thr Ile Ser Val Thr Thr Glu Ile Leu Pro Val Ser Met Thr Lys
705                 710                 715                 720

Thr Ser Val Asp Cys Thr Met Tyr Ile Cys Gly Asp Ser Thr Glu Cys
            725                 730                 735

Ser Asn Leu Leu Leu Gln Tyr Gly Ser Phe Cys Thr Gln Leu Asn Arg
            740                 745                 750

Ala Leu Thr Gly Ile Ala Val Glu Gln Asp Lys Asn Thr Gln Glu Val
            755                 760                 765

Phe Ala Gln Val Lys Gln Ile Tyr Lys Thr Pro Pro Ile Lys Asp Phe
            770                 775                 780

Gly Gly Phe Asn Phe Ser Gln Ile Leu Pro Asp Pro Ser Lys Pro Ser
785                 790                 795                 800
```

-continued

```
Lys Arg Ser Phe Ile Glu Asp Leu Leu Phe Asn Lys Val Thr Leu Ala
            805                 810                 815
Asp Ala Gly Phe Ile Lys Gln Tyr Gly Asp Cys Leu Gly Asp Ile Ala
            820                 825                 830
Ala Arg Asp Leu Ile Cys Ala Gln Lys Phe Asn Gly Leu Thr Val Leu
            835                 840                 845
Pro Pro Leu Leu Thr Asp Glu Met Ile Ala Gln Tyr Thr Ser Ala Leu
850                 855                 860
Leu Ala Gly Thr Ile Thr Ser Gly Trp Thr Phe Gly Ala Gly Ala Ala
865                 870                 875                 880
Leu Gln Ile Pro Phe Ala Met Gln Met Ala Tyr Arg Phe Asn Gly Ile
            885                 890                 895
Gly Val Thr Gln Asn Val Leu Tyr Glu Asn Gln Lys Leu Ile Ala Asn
            900                 905                 910
Gln Phe Asn Ser Ala Ile Gly Lys Ile Gln Asp Ser Leu Ser Ser Thr
            915                 920                 925
Ala Ser Ala Leu Gly Lys Leu Gln Asp Val Val Asn Gln Asn Ala Gln
            930                 935                 940
Ala Leu Asn Thr Leu Val Lys Gln Leu Ser Ser Asn Phe Gly Ala Ile
945                 950                 955                 960
Ser Ser Val Leu Asn Asp Ile Leu Ser Arg Leu Asp Lys Val Glu Ala
            965                 970                 975
Glu Val Gln Ile Asp Arg Leu Ile Thr Gly Arg Leu Gln Ser Leu Gln
            980                 985                 990
Thr Tyr Val Thr Gln Gln Leu Ile Arg Ala Ala Glu Ile Arg Ala Ser
            995                 1000                1005
Ala Asn Leu Ala Ala Thr Lys Met Ser Glu Cys Val Leu Gly Gln Ser
        1010                1015                1020
Lys Arg Val Asp Phe Cys Gly Lys Gly Tyr His Leu Met Ser Phe Pro
1025                1030                1035                1040
Gln Ser Ala Pro His Gly Val Val Phe Leu His Val Thr Tyr Val Pro
                1045                1050                1055
Ala Gln Glu Lys Asn Phe Thr Thr Ala Pro Ala Ile Cys His Asp Gly
            1060                1065                1070
Lys Ala His Phe Pro Arg Glu Gly Val Phe Val Ser Asn Gly Thr His
        1075                1080                1085
Trp Phe Val Thr Gln Arg Asn Phe Tyr Glu Pro Gln Ile Ile Thr Thr
        1090                1095                1100
Asp Asn Thr Phe Val Ser Gly Asn Cys Asp Val Val Ile Gly Ile Val
1105                1110                1115                1120
Asn Asn Thr Val Tyr Asp Pro Leu Gln Pro Glu Leu Asp Ser Phe Lys
            1125                1130                1135
Glu Glu Leu Asp Lys Tyr Phe Lys Asn His Thr Ser Pro Asp Val Asp
            1140                1145                1150
Leu Gly Asp Ile Ser Gly Ile Asn Ala Ser Val Val Asn Ile Gln Lys
        1155                1160                1165
Glu Ile Asp Arg Leu Asn Glu Val Ala Lys Asn Leu Asn Glu Ser Leu
        1170                1175                1180
Ile Asp Leu Gln Glu Leu Gly Lys Tyr Glu Gln Tyr Ile Lys Arg Ser
1185                1190                1195                1200
Asn Gly Leu Pro Gly Pro Ile Gly Pro Pro Gly Arg Gly Arg Thr
        1205                1210                1215
Gly Asp Ala Gly Pro Val Gly Pro Pro Gly Pro Pro Gly Pro Pro Gly
```

```
            1220                1225                1230
Pro Pro Gly Pro Pro Ser Ala Gly Phe Asp Phe Ser Phe Leu Pro Gln
            1235                1240                1245

Pro Pro Gln Glu Lys Ala His Asp Gly Gly Arg Tyr Tyr Arg Ala Asn
        1250                1255                1260

Asp Ala Asn Val Val Arg Asp Arg Asp Leu Glu Val Asp Thr Thr Leu
1265                1270                1275                1280

Lys Ser Leu Ser Gln Gln Ile Glu Asn Ile Arg Ser Pro Glu Gly Ser
            1285                1290                1295

Arg Lys Asn Pro Ala Arg Thr Cys Arg Asp Leu Lys Met Cys His Ser
        1300                1305                1310

Asp Trp Lys Ser Gly Glu Tyr Trp Ile Asp Pro Asn Gln Gly Cys Asn
        1315                1320                1325

Leu Asp Ala Ile Lys Val Phe Cys Asn Met Glu Thr Gly Glu Thr Cys
        1330                1335                1340

Val Tyr Pro Thr Gln Pro Ser Val Ala Gln Lys Asn Trp Tyr Ile Ser
1345                1350                1355                1360

Lys Asn Pro Lys Asp Lys Arg His Val Trp Phe Gly Glu Ser Met Thr
            1365                1370                1375

Asp Gly Phe Gln Phe Glu Tyr Gly Gly Gln Gly Ser Asp Pro Ala Asp
        1380                1385                1390

Val Ala Ile Gln Leu Thr Phe Leu Arg Leu Met Ser Thr Glu Ala Ser
        1395                1400                1405

Gln Asn Ile Thr Tyr His Cys Lys Asn Ser Val Ala Tyr Met Asp Gln
        1410                1415                1420

Gln Thr Gly Asn Leu Lys Lys Ala Leu Leu Leu Gln Gly Ser Asn Glu
1425                1430                1435                1440

Ile Glu Ile Arg Ala Glu Gly Asn Ser Arg Phe Thr Tyr Ser Val Thr
            1445                1450                1455

Val Asp Gly Cys Thr Ser His Thr Gly Ala Trp Gly Lys Thr Val Ile
        1460                1465                1470

Glu Tyr Lys Thr Thr Lys Thr Ser Arg Leu Pro Ile Ile Asp Val Ala
        1475                1480                1485

Pro Leu Asp Val Gly Ala Pro Asp Gln Glu Phe Gly Phe Asp Val Gly
        1490                1495                1500

Pro Val Cys Phe Leu
1505

<210> SEQ ID NO 23
<211> LENGTH: 1509
<212> TYPE: PRT
<213> ORGANISM: Artificial Sequence
<220> FEATURE:
<223> OTHER INFORMATION: Synthetic construct

<400> SEQUENCE: 23

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
```

```
                65                  70                  75                  80
        Ser Thr Glu Lys Ser Asn Ile Ile Arg Gly Trp Ile Phe Gly Thr Thr
                        85                  90                  95
        Leu Asp Ser Lys Thr Gln Ser Leu Leu Ile Val Asn Asn Ala Thr Asn
                       100                 105                 110
        Val Val Ile Lys Val Cys Glu Phe Gln Phe Cys Asn Asp Pro Phe Leu
                       115                 120                 125
        Gly Val Tyr Tyr His Lys Asn Asn Lys Ser Trp Met Glu Ser Glu Phe
                       130                 135                 140
        Arg Val Tyr Ser Ser Ala Asn Asn Cys Thr Phe Glu Tyr Val Ser Gln
        145                 150                 155                 160
        Pro Phe Leu Met Asp Leu Glu Gly Lys Gln Gly Asn Phe Lys Asn Leu
                            165                 170                 175
        Arg Glu Phe Val Phe Lys Asn Ile Asp Gly Tyr Phe Lys Ile Tyr Ser
                        180                 185                 190
        Lys His Thr Pro Ile Asn Leu Val Arg Asp Leu Pro Gln Gly Phe Ser
                        195                 200                 205
        Ala Leu Glu Pro Leu Val Asp Leu Pro Ile Gly Ile Asn Ile Thr Arg
        210                 215                 220
        Phe Gln Thr Leu Leu Ala Leu His Arg Ser Tyr Leu Thr Pro Gly Asp
        225                 230                 235                 240
        Ser Ser Ser Gly Trp Thr Ala Gly Ala Ala Tyr Tyr Val Gly Tyr
                        245                 250                 255
        Leu Gln Pro Arg Thr Phe Leu Leu Lys Tyr Asn Glu Asn Gly Thr Ile
                        260                 265                 270
        Thr Asp Ala Val Asp Cys Ala Leu Asp Pro Leu Ser Glu Thr Lys Cys
                    275                 280                 285
        Thr Leu Lys Ser Phe Thr Val Glu Lys Gly Ile Tyr Gln Thr Ser Asn
                    290                 295                 300
        Phe Arg Val Gln Pro Thr Glu Ser Ile Val Arg Phe Pro Asn Ile Thr
        305                 310                 315                 320
        Asn Leu Cys Pro Phe Gly Glu Val Phe Asn Ala Thr Arg Phe Ala Ser
                            325                 330                 335
        Val Tyr Ala Trp Asn Arg Lys Arg Ile Ser Asn Cys Val Ala Asp Tyr
                        340                 345                 350
        Ser Val Leu Tyr Asn Ser Ala Ser Phe Ser Thr Phe Lys Cys Tyr Gly
                    355                 360                 365
        Val Ser Pro Thr Lys Leu Asn Asp Leu Cys Phe Thr Asn Val Tyr Ala
                    370                 375                 380
        Asp Ser Phe Val Ile Arg Gly Asp Glu Val Arg Gln Ile Ala Pro Gly
        385                 390                 395                 400
        Gln Thr Gly Lys Ile Ala Asp Tyr Asn Tyr Lys Leu Pro Asp Asp Phe
                            405                 410                 415
        Thr Gly Cys Val Ile Ala Trp Asn Ser Asn Asn Leu Asp Ser Lys Val
                        420                 425                 430
        Gly Gly Asn Tyr Asn Tyr Leu Tyr Arg Leu Phe Arg Lys Ser Asn Leu
                    435                 440                 445
        Lys Pro Phe Glu Arg Asp Ile Ser Thr Glu Ile Tyr Gln Ala Gly Ser
                    450                 455                 460
        Thr Pro Cys Asn Gly Val Glu Gly Phe Asn Cys Tyr Phe Pro Leu Gln
        465                 470                 475                 480
        Ser Tyr Gly Phe Gln Pro Thr Asn Gly Val Gly Tyr Gln Pro Tyr Arg
                            485                 490                 495
```

```
Val Val Val Leu Ser Phe Glu Leu Leu His Ala Pro Ala Thr Val Cys
            500                 505                 510

Gly Pro Lys Ser Thr Asn Leu Val Lys Asn Lys Cys Val Asn Phe
            515                 520                 525

Asn Phe Asn Gly Leu Thr Gly Thr Gly Val Leu Thr Glu Ser Asn Lys
            530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
                580                 585                 590

Asn Gln Val Ala Val Leu Tyr Gln Gly Val Asn Cys Thr Glu Val Pro
            595                 600                 605

Val Ala Ile His Ala Asp Gln Leu Thr Pro Thr Trp Arg Val Tyr Ser
            610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Arg Arg Ala Ala
            660                 665                 670

Ser Val Ala Ser Gln Ser Ile Ile Ala Tyr Thr Met Ser Leu Gly Ala
            675                 680                 685

Glu Asn Ser Val Ala Tyr Ser Asn Asn Ser Ile Ala Ile Pro Thr Asn
            690                 695                 700

Phe Thr Ile Ser Val Thr Thr Glu Ile Leu Pro Val Ser Met Thr Lys
705                 710                 715                 720

Thr Ser Val Asp Cys Thr Met Tyr Ile Cys Gly Asp Ser Thr Glu Cys
                725                 730                 735

Ser Asn Leu Leu Leu Gln Tyr Gly Ser Phe Cys Thr Gln Leu Asn Arg
            740                 745                 750

Ala Leu Thr Gly Ile Ala Val Glu Gln Asp Lys Asn Thr Gln Glu Val
            755                 760                 765

Phe Ala Gln Val Lys Gln Ile Tyr Lys Thr Pro Pro Ile Lys Asp Phe
            770                 775                 780

Gly Gly Phe Asn Phe Ser Gln Ile Leu Pro Asp Pro Ser Lys Pro Ser
785                 790                 795                 800

Lys Arg Ser Phe Ile Glu Asp Leu Leu Phe Asn Lys Val Thr Leu Ala
                805                 810                 815

Asp Ala Gly Phe Ile Lys Gln Tyr Gly Asp Cys Leu Gly Asp Ile Ala
                820                 825                 830

Ala Arg Asp Leu Ile Cys Ala Gln Lys Phe Asn Gly Leu Thr Val Leu
            835                 840                 845

Pro Pro Leu Leu Thr Asp Glu Met Ile Ala Gln Tyr Thr Ser Ala Leu
            850                 855                 860

Leu Ala Gly Thr Ile Thr Ser Gly Trp Thr Phe Gly Ala Gly Ala Ala
865                 870                 875                 880

Leu Gln Ile Pro Phe Ala Met Gln Met Ala Tyr Arg Phe Asn Gly Ile
                885                 890                 895

Gly Val Thr Gln Asn Val Leu Tyr Glu Asn Gln Lys Leu Ile Ala Asn
                900                 905                 910
```

```
Gln Phe Asn Ser Ala Ile Gly Lys Ile Gln Asp Ser Leu Ser Ser Thr
            915                 920                 925

Ala Ser Ala Leu Gly Lys Leu Gln Asp Val Val Asn Gln Asn Ala Gln
        930                 935                 940

Ala Leu Asn Thr Leu Val Lys Gln Leu Ser Ser Asn Phe Gly Ala Ile
945                 950                 955                 960

Ser Ser Val Leu Asn Asp Ile Leu Ser Arg Leu Asp Lys Val Glu Ala
            965                 970                 975

Glu Val Gln Ile Asp Arg Leu Ile Thr Gly Arg Leu Gln Ser Leu Gln
                980                 985                 990

Thr Tyr Val Thr Gln Gln Leu Ile Arg Ala Ala Glu Ile Arg Ala Ser
        995                 1000                1005

Ala Asn Leu Ala Ala Thr Lys Met Ser Glu Cys Val Leu Gly Gln Ser
        1010                1015                1020

Lys Arg Val Asp Phe Cys Gly Lys Gly Tyr His Leu Met Ser Phe Pro
1025                1030                1035                1040

Gln Ser Ala Pro His Gly Val Val Phe Leu His Val Thr Tyr Val Pro
            1045                1050                1055

Ala Gln Glu Lys Asn Phe Thr Thr Ala Pro Ala Ile Cys His Asp Gly
        1060                1065                1070

Lys Ala His Phe Pro Arg Glu Gly Val Phe Val Ser Asn Gly Thr His
1075                1080                1085

Trp Phe Val Thr Gln Arg Asn Phe Tyr Glu Pro Gln Ile Ile Thr Thr
        1090                1095                1100

Asp Asn Thr Phe Val Ser Gly Asn Cys Asp Val Val Ile Gly Ile Val
1105                1110                1115                1120

Asn Asn Thr Val Tyr Asp Pro Leu Gln Pro Glu Leu Asp Ser Phe Lys
            1125                1130                1135

Glu Glu Leu Asp Lys Tyr Phe Lys Asn His Thr Ser Pro Asp Val Asp
                1140                1145                1150

Leu Gly Asp Ile Ser Gly Ile Asn Ala Ser Val Val Asn Ile Gln Lys
        1155                1160                1165

Glu Ile Asp Arg Leu Asn Glu Val Ala Lys Asn Leu Asn Glu Ser Leu
        1170                1175                1180

Ile Asp Leu Gln Glu Leu Gly Lys Tyr Glu Gln Tyr Ile Lys Arg Ser
1185                1190                1195                1200

Asn Gly Leu Pro Gly Pro Ile Gly Pro Pro Gly Pro Arg Gly Arg Thr
            1205                1210                1215

Gly Asp Ala Gly Pro Val Gly Pro Pro Gly Pro Pro Gly Pro Pro Gly
        1220                1225                1230

Pro Pro Gly Pro Pro Ser Ala Gly Phe Asp Phe Ser Phe Leu Pro Gln
        1235                1240                1245

Pro Pro Gln Glu Lys Ala His Asp Gly Gly Arg Tyr Tyr Arg Ala Asn
        1250                1255                1260

Asp Ala Asn Val Val Arg Asp Arg Asp Leu Glu Val Asp Thr Thr Leu
1265                1270                1275                1280

Lys Ser Leu Ser Gln Gln Ile Glu Asn Ile Arg Ser Pro Glu Gly Ser
            1285                1290                1295

Arg Lys Asn Pro Ala Arg Thr Cys Arg Asp Leu Lys Met Cys His Ser
            1300                1305                1310

Asp Trp Lys Ser Gly Glu Tyr Trp Ile Asp Pro Asn Gln Gly Cys Asn
        1315                1320                1325

Leu Asp Ala Ile Lys Val Phe Cys Asn Met Glu Thr Gly Glu Thr Cys
```

```
                1330                1335                1340
Val Tyr Pro Thr Gln Pro Ser Val Ala Gln Lys Asn Trp Tyr Ile Ser
1345                1350                1355                1360

Lys Asn Pro Lys Asp Lys Arg His Val Trp Phe Gly Glu Ser Met Thr
                1365                1370                1375

Asp Gly Phe Gln Phe Glu Tyr Gly Gly Gln Gly Ser Asp Pro Ala Asp
                1380                1385                1390

Val Ala Ile Gln Leu Thr Phe Leu Arg Leu Met Ser Thr Glu Ala Ser
                1395                1400                1405

Gln Asn Ile Thr Tyr His Cys Lys Asn Ser Val Ala Tyr Met Asp Gln
                1410                1415                1420

Gln Thr Gly Asn Leu Lys Lys Ala Leu Leu Leu Gln Gly Ser Asn Glu
1425                1430                1435                1440

Ile Glu Ile Arg Ala Glu Gly Asn Ser Arg Phe Thr Tyr Ser Val Thr
                1445                1450                1455

Val Asp Gly Cys Thr Ser His Thr Gly Ala Trp Gly Lys Thr Val Ile
                1460                1465                1470

Glu Tyr Lys Thr Thr Lys Thr Ser Arg Leu Pro Ile Ile Asp Val Ala
                1475                1480                1485

Pro Leu Asp Val Gly Ala Pro Asp Gln Glu Phe Gly Phe Asp Val Gly
                1490                1495                1500

Pro Val Cys Phe Leu
1505

<210> SEQ ID NO 24
<211> LENGTH: 1509
<212> TYPE: PRT
<213> ORGANISM: Artificial Sequence
<220> FEATURE:
<223> OTHER INFORMATION: Synthetic construct

<400> SEQUENCE: 24

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
                20                  25                  30

Ser Val Leu His Ser Thr Gln Asp Leu Phe Leu Pro Phe Phe Ser Asn
                35                  40                  45

Val Thr Trp Phe His Ala Ile His Val Ser Gly Thr Asn Gly Thr Lys
                50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
                100                 105                 110

Val Val Ile Lys Val Cys Glu Phe Gln Phe Cys Asn Asp Pro Phe Leu
                115                 120                 125

Gly Val Tyr Tyr His Lys Asn Asn Lys Ser Trp Met Glu Ser Glu Phe
                130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
```

```
                180             185             190
Lys His Thr Pro Ile Asn Leu Val Arg Asp Leu Pro Gln Gly Phe Ser
                195             200             205
Ala Leu Glu Pro Leu Val Asp Leu Pro Ile Gly Ile Asn Ile Thr Arg
    210             215             220
Phe Gln Thr Leu Leu Ala Leu His Arg Ser Tyr Leu Thr Pro Gly Asp
225             230             235             240
Ser Ser Ser Gly Trp Thr Ala Gly Ala Ala Tyr Tyr Val Gly Tyr
                245             250             255
Leu Gln Pro Arg Thr Phe Leu Leu Lys Tyr Asn Glu Asn Gly Thr Ile
            260             265             270
Thr Asp Ala Val Asp Cys Ala Leu Asp Pro Leu Ser Glu Thr Lys Cys
            275             280             285
Thr Leu Lys Ser Phe Thr Val Glu Lys Gly Ile Tyr Gln Thr Ser Asn
        290             295             300
Phe Arg Val Gln Pro Thr Glu Ser Ile Val Arg Phe Pro Asn Ile Thr
305             310             315             320
Asn Leu Cys Pro Phe Gly Glu Val Phe Asn Ala Thr Arg Phe Ala Ser
                325             330             335
Val Tyr Ala Trp Asn Arg Lys Arg Ile Ser Asn Cys Val Ala Asp Tyr
                340             345             350
Ser Val Leu Tyr Asn Ser Ala Ser Phe Ser Thr Phe Lys Cys Tyr Gly
            355             360             365
Val Ser Pro Thr Lys Leu Asn Asp Leu Cys Phe Thr Asn Val Tyr Ala
        370             375             380
Asp Ser Phe Val Ile Arg Gly Asp Glu Val Arg Gln Ile Ala Pro Gly
385             390             395             400
Gln Thr Gly Lys Ile Ala Asp Tyr Asn Tyr Lys Leu Pro Asp Asp Phe
                405             410             415
Thr Gly Cys Val Ile Ala Trp Asn Ser Asn Asn Leu Asp Ser Lys Val
                420             425             430
Gly Gly Asn Tyr Asn Tyr Leu Tyr Arg Leu Phe Arg Lys Ser Asn Leu
            435             440             445
Lys Pro Phe Glu Arg Asp Ile Ser Thr Glu Ile Tyr Gln Ala Gly Ser
        450             455             460
Thr Pro Cys Asn Gly Val Glu Gly Phe Asn Cys Tyr Phe Pro Leu Gln
465             470             475             480
Ser Tyr Gly Phe Gln Pro Thr Asn Gly Val Gly Tyr Gln Pro Tyr Arg
                485             490             495
Val Val Val Leu Ser Phe Glu Leu Leu His Ala Pro Ala Thr Val Cys
            500             505             510
Gly Pro Lys Lys Ser Thr Asn Leu Val Lys Asn Lys Cys Val Asn Phe
        515             520             525
Asn Phe Asn Gly Leu Thr Gly Thr Gly Val Leu Thr Glu Ser Asn Lys
    530             535             540
Lys Phe Leu Pro Phe Gln Gln Phe Gly Arg Asp Ile Ala Asp Thr Thr
545             550             555             560
Asp Ala Val Arg Asp Pro Gln Thr Leu Glu Ile Leu Asp Ile Thr Pro
                565             570             575
Cys Ser Phe Gly Gly Val Ser Val Ile Thr Pro Gly Thr Asn Thr Ser
            580             585             590
Asn Gln Val Ala Val Leu Tyr Gln Gly Val Asn Cys Thr Glu Val Pro
        595             600             605
```

Val Ala Ile His Ala Asp Gln Leu Thr Pro Thr Trp Arg Val Tyr Ser
610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Arg Arg Ala Arg
                660                 665                 670

Ser Val Ala Ser Gln Ser Ile Ile Ala Tyr Thr Met Ser Leu Gly Ala
                675                 680                 685

Glu Asn Ser Val Ala Tyr Ser Asn Asn Ser Ile Ala Ile Pro Thr Asn
690                 695                 700

Phe Thr Ile Ser Val Thr Thr Glu Ile Leu Pro Val Ser Met Thr Lys
705                 710                 715                 720

Thr Ser Val Asp Cys Thr Met Tyr Ile Cys Gly Asp Ser Thr Glu Cys
                725                 730                 735

Ser Asn Leu Leu Leu Gln Tyr Gly Ser Phe Cys Thr Gln Leu Asn Arg
                740                 745                 750

Ala Leu Thr Gly Ile Ala Val Glu Gln Asp Lys Asn Thr Gln Glu Val
                755                 760                 765

Phe Ala Gln Val Lys Gln Ile Tyr Lys Thr Pro Pro Ile Lys Asp Phe
770                 775                 780

Gly Gly Phe Asn Phe Ser Gln Ile Leu Pro Asp Pro Ser Lys Pro Ser
785                 790                 795                 800

Lys Arg Ser Phe Ile Glu Asp Leu Leu Phe Asn Lys Val Thr Leu Ala
                805                 810                 815

Asp Ala Gly Phe Ile Lys Gln Tyr Gly Asp Cys Leu Gly Asp Ile Ala
                820                 825                 830

Ala Arg Asp Leu Ile Cys Ala Gln Lys Phe Asn Gly Leu Thr Val Leu
                835                 840                 845

Pro Pro Leu Leu Thr Asp Glu Met Ile Ala Gln Tyr Thr Ser Ala Leu
850                 855                 860

Leu Ala Gly Thr Ile Thr Ser Gly Trp Thr Phe Gly Ala Gly Ala Ala
865                 870                 875                 880

Leu Gln Ile Pro Phe Ala Met Gln Met Ala Tyr Arg Phe Asn Gly Ile
                885                 890                 895

Gly Val Thr Gln Asn Val Leu Tyr Glu Asn Gln Lys Leu Ile Ala Asn
                900                 905                 910

Gln Phe Asn Ser Ala Ile Gly Lys Ile Gln Asp Ser Leu Ser Ser Thr
                915                 920                 925

Ala Ser Ala Leu Gly Lys Leu Gln Asp Val Val Asn Gln Asn Ala Gln
930                 935                 940

Ala Leu Asn Thr Leu Val Lys Gln Leu Ser Ser Asn Phe Gly Ala Ile
945                 950                 955                 960

Ser Ser Val Leu Asn Asp Ile Leu Ser Arg Leu Asp Pro Pro Glu Ala
                965                 970                 975

Glu Val Gln Ile Asp Arg Leu Ile Thr Gly Arg Leu Gln Ser Leu Gln
                980                 985                 990

Thr Tyr Val Thr Gln Gln Leu Ile Arg Ala Ala Glu Ile Arg Ala Ser
                995                 1000                1005

Ala Asn Leu Ala Ala Thr Lys Met Ser Glu Cys Val Leu Gly Gln Ser
1010                1015                1020

-continued

```
Lys Arg Val Asp Phe Cys Gly Lys Gly Tyr His Leu Met Ser Phe Pro
1025                1030                1035                1040

Gln Ser Ala Pro His Gly Val Val Phe Leu His Val Thr Tyr Val Pro
            1045                1050                1055

Ala Gln Glu Lys Asn Phe Thr Thr Ala Pro Ala Ile Cys His Asp Gly
        1060                1065                1070

Lys Ala His Phe Pro Arg Glu Gly Val Phe Val Ser Asn Gly Thr His
    1075                1080                1085

Trp Phe Val Thr Gln Arg Asn Phe Tyr Glu Pro Gln Ile Ile Thr Thr
1090                1095                1100

Asp Asn Thr Phe Val Ser Gly Asn Cys Asp Val Val Ile Gly Ile Val
1105                1110                1115                1120

Asn Asn Thr Val Tyr Asp Pro Leu Gln Pro Glu Leu Asp Ser Phe Lys
            1125                1130                1135

Glu Glu Leu Asp Lys Tyr Phe Lys Asn His Thr Ser Pro Asp Val Asp
        1140                1145                1150

Leu Gly Asp Ile Ser Gly Ile Asn Ala Ser Val Val Asn Ile Gln Lys
    1155                1160                1165

Glu Ile Asp Arg Leu Asn Glu Val Ala Lys Asn Leu Asn Glu Ser Leu
1170                1175                1180

Ile Asp Leu Gln Glu Leu Gly Lys Tyr Glu Gln Tyr Ile Lys Arg Ser
1185                1190                1195                1200

Asn Gly Leu Pro Gly Pro Ile Gly Pro Pro Gly Pro Arg Gly Arg Thr
            1205                1210                1215

Gly Asp Ala Gly Pro Val Gly Pro Pro Gly Pro Pro Gly Pro Pro Gly
        1220                1225                1230

Pro Pro Gly Pro Pro Ser Ala Gly Phe Asp Phe Ser Phe Leu Pro Gln
    1235                1240                1245

Pro Pro Gln Glu Lys Ala His Asp Gly Gly Arg Tyr Tyr Arg Ala Asn
1250                1255                1260

Asp Ala Asn Val Val Arg Asp Arg Asp Leu Glu Val Asp Thr Thr Leu
1265                1270                1275                1280

Lys Ser Leu Ser Gln Gln Ile Glu Asn Ile Arg Ser Pro Glu Gly Ser
            1285                1290                1295

Arg Lys Asn Pro Ala Arg Thr Cys Arg Asp Leu Lys Met Cys His Ser
        1300                1305                1310

Asp Trp Lys Ser Gly Glu Tyr Trp Ile Asp Pro Asn Gln Gly Cys Asn
    1315                1320                1325

Leu Asp Ala Ile Lys Val Phe Cys Asn Met Glu Thr Gly Glu Thr Cys
1330                1335                1340

Val Tyr Pro Thr Gln Pro Ser Val Ala Gln Lys Asn Trp Tyr Ile Ser
1345                1350                1355                1360

Lys Asn Pro Lys Asp Lys Arg His Val Trp Phe Gly Glu Ser Met Thr
            1365                1370                1375

Asp Gly Phe Gln Phe Glu Tyr Gly Gly Gln Gly Ser Asp Pro Ala Asp
        1380                1385                1390

Val Ala Ile Gln Leu Thr Phe Leu Arg Leu Met Ser Thr Glu Ala Ser
    1395                1400                1405

Gln Asn Ile Thr Tyr His Cys Lys Asn Ser Val Ala Tyr Met Asp Gln
1410                1415                1420

Gln Thr Gly Asn Leu Lys Lys Ala Leu Leu Leu Gln Gly Ser Asn Glu
1425                1430                1435                1440

Ile Glu Ile Arg Ala Glu Gly Asn Ser Arg Phe Thr Tyr Ser Val Thr
```

1445                1450                1455

Val Asp Gly Cys Thr Ser His Thr Gly Ala Trp Gly Lys Thr Val Ile
            1460                1465                1470

Glu Tyr Lys Thr Thr Lys Thr Ser Arg Leu Pro Ile Ile Asp Val Ala
        1475                1480                1485

Pro Leu Asp Val Gly Ala Pro Asp Gln Glu Phe Gly Phe Asp Val Gly
    1490                1495                1500

Pro Val Cys Phe Leu
1505

<210> SEQ ID NO 25
<211> LENGTH: 1509
<212> TYPE: PRT
<213> ORGANISM: Artificial Sequence
<220> FEATURE:
<223> OTHER INFORMATION: Synthetic construct

<400> SEQUENCE: 25

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205

Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
                245                 250                 255

Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
        275                 280                 285

Thr Leu Lys Ser Phe Thr Val Glu Lys Gly Ile Tyr Gln Thr Ser Asn

```
            290                 295                 300
Phe Arg Val Gln Pro Thr Glu Ser Ile Val Arg Phe Pro Asn Ile Thr
305                 310                 315                 320
Asn Leu Cys Pro Phe Gly Glu Val Phe Asn Ala Thr Arg Phe Ala Ser
                    325                 330                 335
Val Tyr Ala Trp Asn Arg Lys Arg Ile Ser Asn Cys Val Ala Asp Tyr
                340                 345                 350
Ser Val Leu Tyr Asn Ser Ala Ser Phe Ser Thr Phe Lys Cys Tyr Gly
            355                 360                 365
Val Ser Pro Thr Lys Leu Asn Asp Leu Cys Phe Thr Asn Val Tyr Ala
            370                 375                 380
Asp Ser Phe Val Ile Arg Gly Asp Glu Val Arg Gln Ile Ala Pro Gly
385                 390                 395                 400
Gln Thr Gly Lys Ile Ala Asp Tyr Asn Tyr Lys Leu Pro Asp Asp Phe
                    405                 410                 415
Thr Gly Cys Val Ile Ala Trp Asn Ser Asn Asn Leu Asp Ser Lys Val
                420                 425                 430
Gly Gly Asn Tyr Asn Tyr Leu Tyr Arg Leu Phe Arg Lys Ser Asn Leu
            435                 440                 445
Lys Pro Phe Glu Arg Asp Ile Ser Thr Glu Ile Tyr Gln Ala Gly Ser
            450                 455                 460
Thr Pro Cys Asn Gly Val Glu Gly Phe Asn Cys Tyr Phe Pro Leu Gln
465                 470                 475                 480
Ser Tyr Gly Phe Gln Pro Thr Asn Gly Val Gly Tyr Gln Pro Tyr Arg
                    485                 490                 495
Val Val Val Leu Ser Phe Glu Leu Leu His Ala Pro Ala Thr Val Cys
                500                 505                 510
Gly Pro Lys Lys Ser Thr Asn Leu Val Lys Asn Lys Cys Val Asn Phe
            515                 520                 525
Asn Phe Asn Gly Leu Thr Gly Thr Gly Val Leu Thr Glu Ser Asn Lys
            530                 535                 540
Lys Phe Leu Pro Phe Gln Gln Phe Gly Arg Asp Ile Ala Asp Thr Thr
545                 550                 555                 560
Asp Ala Val Arg Asp Pro Gln Thr Leu Glu Ile Leu Asp Ile Thr Pro
                    565                 570                 575
Cys Ser Phe Gly Gly Val Ser Val Ile Thr Pro Gly Thr Asn Thr Ser
                580                 585                 590
Asn Gln Val Ala Val Leu Tyr Gln Gly Val Asn Cys Thr Glu Val Pro
            595                 600                 605
Val Ala Ile His Ala Asp Gln Leu Thr Pro Thr Trp Arg Val Tyr Ser
            610                 615                 620
Thr Gly Ser Asn Val Phe Gln Thr Arg Ala Gly Cys Leu Ile Gly Ala
625                 630                 635                 640
Glu His Val Asn Asn Ser Tyr Glu Cys Asp Ile Pro Ile Gly Ala Gly
                    645                 650                 655
Ile Cys Ala Ser Tyr Gln Thr Gln Thr Asn Ser Pro Arg Arg Ala Ala
                660                 665                 670
Ser Val Ala Ser Gln Ser Ile Ile Ala Tyr Thr Met Ser Leu Gly Ala
            675                 680                 685
Glu Asn Ser Val Ala Tyr Ser Asn Asn Ser Ile Ala Ile Pro Thr Asn
            690                 695                 700
Phe Thr Ile Ser Val Thr Thr Glu Ile Leu Pro Val Ser Met Thr Lys
705                 710                 715                 720
```

-continued

```
Thr Ser Val Asp Cys Thr Met Tyr Ile Cys Gly Asp Ser Thr Glu Cys
                725                 730                 735

Ser Asn Leu Leu Leu Gln Tyr Gly Ser Phe Cys Thr Gln Leu Asn Arg
            740                 745                 750

Ala Leu Thr Gly Ile Ala Val Glu Gln Asp Lys Asn Thr Gln Glu Val
            755                 760                 765

Phe Ala Gln Val Lys Gln Ile Tyr Lys Thr Pro Pro Ile Lys Asp Phe
        770                 775                 780

Gly Gly Phe Asn Phe Ser Gln Ile Leu Pro Asp Pro Ser Lys Pro Ser
785                 790                 795                 800

Lys Arg Ser Phe Ile Glu Asp Leu Leu Phe Asn Lys Val Thr Leu Ala
                805                 810                 815

Asp Ala Gly Phe Ile Lys Gln Tyr Gly Asp Cys Leu Gly Asp Ile Ala
            820                 825                 830

Ala Arg Asp Leu Ile Cys Ala Gln Lys Phe Asn Gly Leu Thr Val Leu
            835                 840                 845

Pro Pro Leu Leu Thr Asp Glu Met Ile Ala Gln Tyr Thr Ser Ala Leu
        850                 855                 860

Leu Ala Gly Thr Ile Thr Ser Gly Trp Thr Phe Gly Ala Gly Ala Ala
865                 870                 875                 880

Leu Gln Ile Pro Phe Ala Met Gln Met Ala Tyr Arg Phe Asn Gly Ile
                885                 890                 895

Gly Val Thr Gln Asn Val Leu Tyr Glu Asn Gln Lys Leu Ile Ala Asn
            900                 905                 910

Gln Phe Asn Ser Ala Ile Gly Lys Ile Gln Asp Ser Leu Ser Ser Thr
        915                 920                 925

Ala Ser Ala Leu Gly Lys Leu Gln Asp Val Val Asn Gln Asn Ala Gln
        930                 935                 940

Ala Leu Asn Thr Leu Val Lys Gln Leu Ser Ser Asn Phe Gly Ala Ile
945                 950                 955                 960

Ser Ser Val Leu Asn Asp Ile Leu Ser Arg Leu Asp Pro Pro Glu Ala
                965                 970                 975

Glu Val Gln Ile Asp Arg Leu Ile Thr Gly Arg Leu Gln Ser Leu Gln
            980                 985                 990

Thr Tyr Val Thr Gln Gln Leu Ile Arg Ala Ala Glu Ile Arg Ala Ser
        995                 1000                1005

Ala Asn Leu Ala Ala Thr Lys Met Ser Glu Cys Val Leu Gly Gln Ser
    1010                1015                1020

Lys Arg Val Asp Phe Cys Gly Lys Gly Tyr His Leu Met Ser Phe Pro
1025                1030                1035                1040

Gln Ser Ala Pro His Gly Val Val Phe Leu His Val Thr Tyr Val Pro
                1045                1050                1055

Ala Gln Glu Lys Asn Phe Thr Thr Ala Pro Ala Ile Cys His Asp Gly
            1060                1065                1070

Lys Ala His Phe Pro Arg Glu Gly Val Phe Val Ser Asn Gly Thr His
        1075                1080                1085

Trp Phe Val Thr Gln Arg Asn Phe Tyr Glu Pro Gln Ile Ile Thr Thr
        1090                1095                1100

Asp Asn Thr Phe Val Ser Gly Asn Cys Asp Val Val Ile Gly Ile Val
1105                1110                1115                1120

Asn Asn Thr Val Tyr Asp Pro Leu Gln Pro Glu Leu Asp Ser Phe Lys
                1125                1130                1135
```

```
Glu Glu Leu Asp Lys Tyr Phe Lys Asn His Thr Ser Pro Asp Val Asp
            1140                1145                1150

Leu Gly Asp Ile Ser Gly Ile Asn Ala Ser Val Val Asn Ile Gln Lys
        1155                1160                1165

Glu Ile Asp Arg Leu Asn Glu Val Ala Lys Asn Leu Asn Glu Ser Leu
    1170                1175                1180

Ile Asp Leu Gln Glu Leu Gly Lys Tyr Glu Gln Tyr Ile Lys Arg Ser
1185                1190                1195                1200

Asn Gly Leu Pro Gly Pro Ile Gly Pro Gly Pro Arg Gly Arg Thr
            1205                1210                1215

Gly Asp Ala Gly Pro Val Gly Pro Pro Gly Pro Pro Gly Pro Pro Gly
        1220                1225                1230

Pro Pro Gly Pro Pro Ser Ala Gly Phe Asp Phe Ser Phe Leu Pro Gln
        1235                1240                1245

Pro Pro Gln Glu Lys Ala His Asp Gly Gly Arg Tyr Tyr Arg Ala Asn
        1250                1255                1260

Asp Ala Asn Val Val Arg Asp Arg Asp Leu Glu Val Asp Thr Thr Leu
1265                1270                1275                1280

Lys Ser Leu Ser Gln Gln Ile Glu Asn Ile Arg Ser Pro Glu Gly Ser
            1285                1290                1295

Arg Lys Asn Pro Ala Arg Thr Cys Arg Asp Leu Lys Met Cys His Ser
        1300                1305                1310

Asp Trp Lys Ser Gly Glu Tyr Trp Ile Asp Pro Asn Gln Gly Cys Asn
        1315                1320                1325

Leu Asp Ala Ile Lys Val Phe Cys Asn Met Glu Thr Gly Glu Thr Cys
        1330                1335                1340

Val Tyr Pro Thr Gln Pro Ser Val Ala Gln Lys Asn Trp Tyr Ile Ser
1345                1350                1355                1360

Lys Asn Pro Lys Asp Lys Arg His Val Trp Phe Gly Glu Ser Met Thr
            1365                1370                1375

Asp Gly Phe Gln Phe Glu Tyr Gly Gly Gln Gly Ser Asp Pro Ala Asp
        1380                1385                1390

Val Ala Ile Gln Leu Thr Phe Leu Arg Leu Met Ser Thr Glu Ala Ser
        1395                1400                1405

Gln Asn Ile Thr Tyr His Cys Lys Asn Ser Val Ala Tyr Met Asp Gln
        1410                1415                1420

Gln Thr Gly Asn Leu Lys Lys Ala Leu Leu Leu Gln Gly Ser Asn Glu
1425                1430                1435                1440

Ile Glu Ile Arg Ala Glu Gly Asn Ser Arg Phe Thr Tyr Ser Val Thr
            1445                1450                1455

Val Asp Gly Cys Thr Ser His Thr Gly Ala Trp Gly Lys Thr Val Ile
        1460                1465                1470

Glu Tyr Lys Thr Thr Lys Thr Ser Arg Leu Pro Ile Ile Asp Val Ala
        1475                1480                1485

Pro Leu Asp Val Gly Ala Pro Asp Gln Glu Phe Gly Phe Asp Val Gly
        1490                1495                1500

Pro Val Cys Phe Leu
1505

<210> SEQ ID NO 26
<211> LENGTH: 1491
<212> TYPE: PRT
<213> ORGANISM: Artificial Sequence
<220> FEATURE:
<223> OTHER INFORMATION: Synthetic construct
```

```
<400> SEQUENCE: 26

Ser Asp Leu Asp Arg Cys Thr Thr Phe Asp Val Gln Ala Pro Asn
1               5                   10                  15

Tyr Thr Gln His Thr Ser Ser Met Arg Gly Val Tyr Tyr Pro Asp Glu
            20                  25                  30

Ile Phe Arg Ser Asp Thr Leu Tyr Leu Thr Gln Asp Leu Phe Leu Pro
                35                  40                  45

Phe Tyr Ser Asn Val Thr Gly Phe His Thr Ile Asn His Thr Phe Asp
    50                  55                  60

Asn Pro Val Ile Pro Phe Lys Asp Gly Ile Tyr Phe Ala Ala Thr Glu
65                  70                  75                  80

Lys Ser Asn Val Val Arg Gly Trp Val Phe Gly Ser Thr Met Asn Asn
                85                  90                  95

Lys Ser Gln Ser Val Ile Ile Ile Asn Asn Ser Thr Asn Val Val Ile
                100                 105                 110

Arg Ala Cys Asn Phe Glu Leu Cys Asp Asn Pro Phe Phe Ala Val Ser
            115                 120                 125

Lys Pro Met Gly Thr Gln Thr His Thr Met Ile Phe Asp Asn Ala Phe
130                 135                 140

Asn Cys Thr Phe Glu Tyr Ile Ser Asp Ala Phe Ser Leu Asp Val Ser
145                 150                 155                 160

Glu Lys Ser Gly Asn Phe Lys His Leu Arg Glu Phe Val Phe Lys Asn
                165                 170                 175

Lys Asp Gly Phe Leu Tyr Val Tyr Lys Gly Tyr Gln Pro Ile Asp Val
            180                 185                 190

Val Arg Asp Leu Pro Ser Gly Phe Asn Thr Leu Lys Pro Ile Phe Lys
    195                 200                 205

Leu Pro Leu Gly Ile Asn Ile Thr Asn Phe Arg Ala Ile Leu Thr Ala
210                 215                 220

Phe Leu Pro Ala Gln Asp Thr Trp Gly Thr Ser Ala Ala Ala Tyr Phe
225                 230                 235                 240

Val Gly Tyr Leu Lys Pro Thr Thr Phe Met Leu Lys Tyr Asp Glu Asn
                245                 250                 255

Gly Thr Ile Thr Asp Ala Val Asp Cys Ser Gln Asn Pro Leu Ala Glu
            260                 265                 270

Leu Lys Cys Ser Val Lys Ser Phe Glu Ile Asp Lys Gly Ile Tyr Gln
            275                 280                 285

Thr Ser Asn Phe Arg Val Val Pro Ser Arg Asp Val Val Arg Phe Pro
290                 295                 300

Asn Ile Thr Asn Leu Cys Pro Phe Gly Glu Val Phe Asn Ala Thr Lys
305                 310                 315                 320

Phe Pro Ser Val Tyr Ala Trp Glu Arg Lys Arg Ile Ser Asn Cys Val
                325                 330                 335

Ala Asp Tyr Ser Val Leu Tyr Asn Ser Thr Phe Phe Ser Thr Phe Lys
            340                 345                 350

Cys Tyr Gly Val Ser Ala Thr Lys Leu Asn Asp Leu Cys Phe Ser Asn
            355                 360                 365

Val Tyr Ala Asp Ser Phe Val Val Lys Gly Asp Asp Val Arg Gln Ile
            370                 375                 380

Ala Pro Gly Gln Thr Gly Val Ile Ala Asp Tyr Asn Tyr Lys Leu Pro
385                 390                 395                 400

Asp Asp Phe Met Gly Cys Val Leu Ala Trp Asn Thr Arg Asn Ile Asp
```

```
                        405                 410                 415
Ala Thr Ser Thr Gly Asn Tyr Asn Tyr Lys Tyr Arg Tyr Leu Arg His
            420                 425                 430
Gly Lys Leu Arg Pro Phe Glu Arg Asp Ile Ser Asn Val Pro Phe Ser
            435                 440                 445
Pro Asp Gly Lys Pro Cys Thr Pro Ala Leu Asn Cys Tyr Trp Pro
450                 455                 460
Leu Asn Asp Tyr Gly Phe Tyr Thr Thr Gly Ile Gly Tyr Gln Pro
465                 470                 475                 480
Tyr Arg Val Val Val Leu Ser Phe Glu Leu Leu Asn Ala Pro Ala Thr
            485                 490                 495
Val Cys Gly Pro Lys Leu Ser Thr Asp Leu Ile Lys Asn Gln Cys Val
            500                 505                 510
Asn Phe Asn Phe Asn Gly Leu Thr Gly Thr Gly Val Leu Thr Pro Ser
            515                 520                 525
Ser Lys Arg Phe Gln Pro Phe Gln Gln Phe Gly Arg Asp Val Ser Asp
            530                 535                 540
Phe Thr Asp Ser Val Arg Asp Pro Lys Thr Ser Glu Ile Leu Asp Ile
545                 550                 555                 560
Ser Pro Cys Ser Phe Gly Gly Val Ser Val Ile Thr Pro Gly Thr Asn
                565                 570                 575
Ala Ser Ser Glu Val Ala Val Leu Tyr Gln Asp Val Asn Cys Thr Asp
            580                 585                 590
Val Ser Thr Ala Ile His Ala Asp Gln Leu Thr Pro Ala Trp Arg Ile
            595                 600                 605
Tyr Ser Thr Gly Asn Asn Val Phe Gln Thr Gln Ala Gly Cys Leu Ile
            610                 615                 620
Gly Ala Glu His Val Asp Thr Ser Tyr Glu Cys Asp Ile Pro Ile Gly
625                 630                 635                 640
Ala Gly Ile Cys Ala Ser Tyr His Thr Val Ser Leu Leu Arg Ser Thr
                645                 650                 655
Ser Gln Lys Ser Ile Val Ala Tyr Thr Met Ser Leu Gly Ala Asp Ser
            660                 665                 670
Ser Ile Ala Tyr Ser Asn Asn Thr Ile Ala Ile Pro Thr Asn Phe Ser
            675                 680                 685
Ile Ser Ile Thr Thr Glu Val Met Pro Val Ser Met Ala Lys Thr Ser
            690                 695                 700
Val Asp Cys Asn Met Tyr Ile Cys Gly Asp Ser Thr Glu Cys Ala Asn
705                 710                 715                 720
Leu Leu Leu Gln Tyr Gly Ser Phe Cys Thr Gln Leu Asn Arg Ala Leu
                725                 730                 735
Ser Gly Ile Ala Ala Glu Gln Asp Arg Asn Thr Arg Glu Val Phe Ala
            740                 745                 750
Gln Val Lys Gln Met Tyr Lys Thr Pro Thr Leu Lys Asp Phe Gly Gly
            755                 760                 765
Phe Asn Phe Ser Gln Ile Leu Pro Asp Pro Leu Lys Pro Thr Lys Arg
            770                 775                 780
Ser Phe Ile Glu Asp Leu Leu Phe Asn Lys Val Thr Leu Ala Asp Ala
785                 790                 795                 800
Gly Phe Met Lys Gln Tyr Gly Glu Cys Leu Gly Asp Ile Asn Ala Arg
                805                 810                 815
Asp Leu Ile Cys Ala Gln Lys Phe Asn Gly Leu Thr Val Leu Pro Pro
            820                 825                 830
```

```
Leu Leu Thr Asp Asp Met Ile Ala Ala Tyr Thr Ala Ala Leu Val Ser
        835                 840                 845

Gly Thr Ala Thr Ala Gly Trp Thr Phe Gly Ala Gly Ala Ala Leu Gln
    850                 855                 860

Ile Pro Phe Ala Met Gln Met Ala Tyr Arg Phe Asn Gly Ile Gly Val
865                 870                 875                 880

Thr Gln Asn Val Leu Tyr Glu Asn Gln Lys Gln Ile Ala Asn Gln Phe
                885                 890                 895

Asn Lys Ala Ile Ser Gln Ile Gln Glu Ser Leu Thr Thr Thr Ser Thr
            900                 905                 910

Ala Leu Gly Lys Leu Gln Asp Val Val Asn Gln Asn Ala Gln Ala Leu
            915                 920                 925

Asn Thr Leu Val Lys Gln Leu Ser Ser Asn Phe Gly Ala Ile Ser Ser
        930                 935                 940

Val Leu Asn Asp Ile Leu Ser Arg Leu Asp Lys Val Glu Ala Glu Val
945                 950                 955                 960

Gln Ile Asp Arg Leu Ile Thr Gly Arg Leu Gln Ser Leu Gln Thr Tyr
                965                 970                 975

Val Thr Gln Gln Leu Ile Arg Ala Ala Glu Ile Arg Ala Ser Ala Asn
            980                 985                 990

Leu Ala Ala Thr Lys Met Ser Glu Cys Val Leu Gly Gln Ser Lys Arg
        995                 1000                1005

Val Asp Phe Cys Gly Lys Gly Tyr His Leu Met Ser Phe Pro Gln Ala
    1010                1015                1020

Ala Pro His Gly Val Val Phe Leu His Val Thr Tyr Val Pro Ser Gln
1025                1030                1035                1040

Glu Arg Asn Phe Thr Thr Ala Pro Ala Ile Cys His Glu Gly Lys Ala
                1045                1050                1055

Tyr Phe Pro Arg Glu Gly Val Phe Val Phe Asn Gly Thr Ser Trp Phe
            1060                1065                1070

Ile Thr Gln Arg Asn Phe Phe Ser Pro Gln Ile Ile Thr Thr Asp Asn
        1075                1080                1085

Thr Phe Val Ser Gly Asn Cys Asp Val Val Ile Gly Ile Ile Asn Asn
    1090                1095                1100

Thr Val Tyr Asp Pro Leu Gln Pro Glu Leu Asp Ser Phe Lys Glu Glu
1105                1110                1115                1120

Leu Asp Lys Tyr Phe Lys Asn His Thr Ser Pro Asp Val Asp Leu Gly
                1125                1130                1135

Asp Ile Ser Gly Ile Asn Ala Ser Val Val Asn Ile Gln Glu Glu Ile
            1140                1145                1150

Asp Arg Leu Asn Glu Val Ala Lys Asn Leu Asn Glu Ser Leu Ile Asp
        1155                1160                1165

Leu Gln Glu Leu Gly Lys Tyr Glu Gln Tyr Ile Lys Arg Ser Asn Gly
    1170                1175                1180

Leu Pro Gly Pro Ile Gly Pro Pro Gly Pro Arg Gly Arg Thr Gly Asp
1185                1190                1195                1200

Ala Gly Pro Val Gly Pro Pro Gly Pro Pro Gly Pro Gly Pro Pro
                1205                1210                1215

Gly Pro Pro Ser Ala Gly Phe Asp Phe Ser Phe Leu Pro Gln Pro Pro
            1220                1225                1230

Gln Glu Lys Ala His Asp Gly Gly Arg Tyr Tyr Arg Ala Asn Asp Ala
        1235                1240                1245
```

Asn Val Val Arg Asp Arg Asp Leu Glu Val Asp Thr Thr Leu Lys Ser
    1250                1255                1260

Leu Ser Gln Gln Ile Glu Asn Ile Arg Ser Pro Glu Gly Ser Arg Lys
1265                1270                1275                1280

Asn Pro Ala Arg Thr Cys Arg Asp Leu Lys Met Cys His Ser Asp Trp
            1285                1290                1295

Lys Ser Gly Glu Tyr Trp Ile Asp Pro Asn Gln Gly Cys Asn Leu Asp
        1300                1305                1310

Ala Ile Lys Val Phe Cys Asn Met Glu Thr Gly Glu Thr Cys Val Tyr
    1315                1320                1325

Pro Thr Gln Pro Ser Val Ala Gln Lys Asn Trp Tyr Ile Ser Lys Asn
1330                1335                1340

Pro Lys Asp Lys Arg His Val Trp Phe Gly Glu Ser Met Thr Asp Gly
1345                1350                1355                1360

Phe Gln Phe Glu Tyr Gly Gly Gln Gly Ser Asp Pro Ala Asp Val Ala
            1365                1370                1375

Ile Gln Leu Thr Phe Leu Arg Leu Met Ser Thr Glu Ala Ser Gln Asn
        1380                1385                1390

Ile Thr Tyr His Cys Lys Asn Ser Val Ala Tyr Met Asp Gln Gln Thr
    1395                1400                1405

Gly Asn Leu Lys Lys Ala Leu Leu Leu Gln Gly Ser Asn Glu Ile Glu
    1410                1415                1420

Ile Arg Ala Glu Gly Asn Ser Arg Phe Thr Tyr Ser Val Thr Val Asp
1425                1430                1435                1440

Gly Cys Thr Ser His Thr Gly Ala Trp Gly Lys Thr Val Ile Glu Tyr
            1445                1450                1455

Lys Thr Thr Lys Thr Ser Arg Leu Pro Ile Ile Asp Val Ala Pro Leu
        1460                1465                1470

Asp Val Gly Ala Pro Asp Gln Glu Phe Gly Phe Asp Val Gly Pro Val
    1475                1480                1485

Cys Phe Leu
    1490

<210> SEQ ID NO 27
<211> LENGTH: 1195
<212> TYPE: PRT
<213> ORGANISM: Artificial Sequence
<220> FEATURE:
<223> OTHER INFORMATION: Synthetic construct

<400> SEQUENCE: 27

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

```
Val Val Ile Lys Val Cys Glu Phe Gln Phe Cys Asn Asp Pro Phe Leu
            115                 120                 125

Gly Val Tyr Tyr His Lys Asn Asn Lys Ser Trp Met Glu Ser Glu Phe
130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
                180                 185                 190

Lys His Thr Pro Ile Asn Leu Val Arg Asp Leu Pro Gln Gly Phe Ser
            195                 200                 205

Ala Leu Glu Pro Leu Val Asp Leu Pro Ile Gly Ile Asn Ile Thr Arg
210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Tyr Tyr Val Gly Tyr
                245                 250                 255

Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
            275                 280                 285

Thr Leu Lys Ser Phe Thr Val Glu Lys Gly Ile Tyr Gln Thr Ser Asn
            290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
                340                 345                 350

Ser Val Leu Tyr Asn Ser Ala Ser Phe Ser Thr Phe Lys Cys Tyr Gly
            355                 360                 365

Val Ser Pro Thr Lys Leu Asn Asp Leu Cys Phe Thr Asn Val Tyr Ala
370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
                420                 425                 430

Gly Gly Asn Tyr Asn Tyr Leu Tyr Arg Leu Phe Arg Lys Ser Asn Leu
            435                 440                 445

Lys Pro Phe Glu Arg Asp Ile Ser Thr Glu Ile Tyr Gln Ala Gly Ser
450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
                485                 490                 495

Val Val Val Leu Ser Phe Glu Leu Leu His Ala Pro Ala Thr Val Cys
                500                 505                 510

Gly Pro Lys Lys Ser Thr Asn Leu Val Lys Asn Lys Cys Val Asn Phe
            515                 520                 525

Asn Phe Asn Gly Leu Thr Gly Thr Gly Val Leu Thr Glu Ser Asn Lys
```

-continued

```
                530                 535                 540
Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
                580                 585                 590

Asn Gln Val Ala Val Leu Tyr Gln Asp Val Asn Cys Thr Glu Val Pro
                595                 600                 605

Val Ala Ile His Ala Asp Gln Leu Thr Pro Thr Trp Arg Val Tyr Ser
                610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Arg Arg Ala Arg
                660                 665                 670

Ser Val Ala Ser Gln Ser Ile Ile Ala Tyr Thr Met Ser Leu Gly Ala
                675                 680                 685

Glu Asn Ser Val Ala Tyr Ser Asn Asn Ser Ile Ala Ile Pro Thr Asn
690                 695                 700

Phe Thr Ile Ser Val Thr Thr Glu Ile Leu Pro Val Ser Met Thr Lys
705                 710                 715                 720

Thr Ser Val Asp Cys Thr Met Tyr Ile Cys Gly Asp Ser Thr Glu Cys
                725                 730                 735

Ser Asn Leu Leu Leu Gln Tyr Gly Ser Phe Cys Thr Gln Leu Asn Arg
                740                 745                 750

Ala Leu Thr Gly Ile Ala Val Glu Gln Asp Lys Asn Thr Gln Glu Val
                755                 760                 765

Phe Ala Gln Val Lys Gln Ile Tyr Lys Thr Pro Pro Ile Lys Asp Phe
770                 775                 780

Gly Gly Phe Asn Phe Ser Gln Ile Leu Pro Asp Pro Ser Lys Pro Ser
785                 790                 795                 800

Lys Arg Ser Phe Ile Glu Asp Leu Leu Phe Asn Lys Val Thr Leu Ala
                805                 810                 815

Asp Ala Gly Phe Ile Lys Gln Tyr Gly Asp Cys Leu Gly Asp Ile Ala
                820                 825                 830

Ala Arg Asp Leu Ile Cys Ala Gln Lys Phe Asn Gly Leu Thr Val Leu
                835                 840                 845

Pro Pro Leu Leu Thr Asp Glu Met Ile Ala Gln Tyr Thr Ser Ala Leu
850                 855                 860

Leu Ala Gly Thr Ile Thr Ser Gly Trp Thr Phe Gly Ala Gly Ala Ala
865                 870                 875                 880

Leu Gln Ile Pro Phe Ala Met Gln Met Ala Tyr Arg Phe Asn Gly Ile
                885                 890                 895

Gly Val Thr Gln Asn Val Leu Tyr Glu Asn Gln Lys Leu Ile Ala Asn
                900                 905                 910

Gln Phe Asn Ser Ala Ile Gly Lys Ile Gln Asp Ser Leu Ser Ser Thr
                915                 920                 925

Ala Ser Ala Leu Gly Lys Leu Gln Asp Val Val Asn Gln Asn Ala Gln
                930                 935                 940

Ala Leu Asn Thr Leu Val Lys Gln Leu Ser Ser Asn Phe Gly Ala Ile
945                 950                 955                 960
```

```
Ser Ser Val Leu Asn Asp Ile Leu Ser Arg Leu Asp Lys Val Glu Ala
            965                 970                 975

Glu Val Gln Ile Asp Arg Leu Ile Thr Gly Arg Leu Gln Ser Leu Gln
            980                 985                 990

Thr Tyr Val Thr Gln Gln Leu Ile Arg Ala Ala Glu Ile Arg Ala Ser
            995                1000                1005

Ala Asn Leu Ala Ala Thr Lys Met Ser Glu Cys Val Leu Gly Gln Ser
       1010                1015                1020

Lys Arg Val Asp Phe Cys Gly Lys Gly Tyr His Leu Met Ser Phe Pro
1025                1030                1035                1040

Gln Ser Ala Pro His Gly Val Val Phe Leu His Val Thr Tyr Val Pro
            1045                1050                1055

Ala Gln Glu Lys Asn Phe Thr Thr Ala Pro Ala Ile Cys His Asp Gly
            1060                1065                1070

Lys Ala His Phe Pro Arg Glu Gly Val Phe Val Ser Asn Gly Thr His
       1075                1080                1085

Trp Phe Val Thr Gln Arg Asn Phe Tyr Glu Pro Gln Ile Ile Thr Thr
       1090                1095                1100

Asp Asn Thr Phe Val Ser Gly Asn Cys Asp Val Val Ile Gly Ile Val
1105                1110                1115                1120

Asn Asn Thr Val Tyr Asp Pro Leu Gln Pro Glu Leu Asp Ser Phe Lys
            1125                1130                1135

Glu Glu Leu Asp Lys Tyr Phe Lys Asn His Thr Ser Pro Asp Val Asp
            1140                1145                1150

Leu Gly Asp Ile Ser Gly Ile Asn Ala Ser Val Val Asn Ile Gln Lys
            1155                1160                1165

Glu Ile Asp Arg Leu Asn Glu Val Ala Lys Asn Leu Asn Glu Ser Leu
            1170                1175                1180

Ile Asp Leu Gln Glu Leu Gly Lys Tyr Glu Gln
1185                1190                1195

<210> SEQ ID NO 28
<211> LENGTH: 1195
<212> TYPE: PRT
<213> ORGANISM: Artificial Sequence
<220> FEATURE:
<223> OTHER INFORMATION: Synthetic construct

<400> SEQUENCE: 28

Gln Cys Val Asn Leu Thr Thr Arg Thr Gln Leu Pro Pro Ala Tyr Thr
1               5                  10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125
```

-continued

Gly Val Tyr Tyr His Lys Asn Asn Lys Ser Trp Met Glu Ser Glu Phe
          130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
              165                 170                 175

Arg Glu Phe Val Phe Lys Asn Ile Asp Gly Tyr Phe Lys Ile Tyr Ser
              180                 185                 190

Lys His Thr Pro Ile Asn Leu Val Arg Asp Leu Pro Gln Gly Phe Ser
              195                 200                 205

Ala Leu Glu Pro Leu Val Asp Leu Pro Ile Gly Ile Asn Ile Thr Arg
          210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
              245                 250                 255

Leu Gln Pro Arg Thr Phe Leu Leu Lys Tyr Asn Glu Asn Gly Thr Ile
              260                 265                 270

Thr Asp Ala Val Asp Cys Ala Leu Asp Pro Leu Ser Glu Thr Lys Cys
          275                 280                 285

Thr Leu Lys Ser Phe Thr Val Glu Lys Gly Ile Tyr Gln Thr Ser Asn
290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
              325                 330                 335

Val Tyr Ala Trp Asn Arg Lys Arg Ile Ser Asn Cys Val Ala Asp Tyr
              340                 345                 350

Ser Val Leu Tyr Asn Ser Ala Ser Phe Ser Thr Phe Lys Cys Tyr Gly
              355                 360                 365

Val Ser Pro Thr Lys Leu Asn Asp Leu Cys Phe Thr Asn Val Tyr Ala
          370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
              405                 410                 415

Thr Gly Cys Val Ile Ala Trp Asn Ser Asn Asn Leu Asp Ser Lys Val
              420                 425                 430

Gly Gly Asn Tyr Asn Tyr Leu Tyr Arg Leu Phe Arg Lys Ser Asn Leu
              435                 440                 445

Lys Pro Phe Glu Arg Asp Ile Ser Thr Glu Ile Tyr Gln Ala Gly Ser
          450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
              485                 490                 495

Val Val Val Leu Ser Phe Glu Leu Leu His Ala Pro Ala Thr Val Cys
              500                 505                 510

Gly Pro Lys Lys Ser Thr Asn Leu Val Lys Asn Lys Cys Val Asn Phe
          515                 520                 525

Asn Phe Asn Gly Leu Thr Gly Thr Gly Val Leu Thr Glu Ser Asn Lys
530                 535                 540

```
Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
            580                 585                 590

Asn Gln Val Ala Val Leu Tyr Gln Asp Val Asn Cys Thr Glu Val Pro
        595                 600                 605

Val Ala Ile His Ala Asp Gln Leu Thr Pro Thr Trp Arg Val Tyr Ser
    610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Arg Arg Ala Ala
            660                 665                 670

Ser Val Ala Ser Gln Ser Ile Ile Ala Tyr Thr Met Ser Leu Gly Ala
        675                 680                 685

Glu Asn Ser Val Ala Tyr Ser Asn Asn Ser Ile Ala Ile Pro Thr Asn
690                 695                 700

Phe Thr Ile Ser Val Thr Thr Glu Ile Leu Pro Val Ser Met Thr Lys
705                 710                 715                 720

Thr Ser Val Asp Cys Thr Met Tyr Ile Cys Gly Asp Ser Thr Glu Cys
                725                 730                 735

Ser Asn Leu Leu Leu Gln Tyr Gly Ser Phe Cys Thr Gln Leu Asn Arg
            740                 745                 750

Ala Leu Thr Gly Ile Ala Val Glu Gln Asp Lys Asn Thr Gln Glu Val
        755                 760                 765

Phe Ala Gln Val Lys Gln Ile Tyr Lys Thr Pro Pro Ile Lys Asp Phe
    770                 775                 780

Gly Gly Phe Asn Phe Ser Gln Ile Leu Pro Asp Pro Ser Lys Pro Ser
785                 790                 795                 800

Lys Arg Ser Phe Ile Glu Asp Leu Leu Phe Asn Lys Val Thr Leu Ala
                805                 810                 815

Asp Ala Gly Phe Ile Lys Gln Tyr Gly Asp Cys Leu Gly Asp Ile Ala
            820                 825                 830

Ala Arg Asp Leu Ile Cys Ala Gln Lys Phe Asn Gly Leu Thr Val Leu
        835                 840                 845

Pro Pro Leu Leu Thr Asp Glu Met Ile Ala Gln Tyr Thr Ser Ala Leu
850                 855                 860

Leu Ala Gly Thr Ile Thr Ser Gly Trp Thr Phe Gly Ala Gly Ala Ala
865                 870                 875                 880

Leu Gln Ile Pro Phe Ala Met Gln Met Ala Tyr Arg Phe Asn Gly Ile
                885                 890                 895

Gly Val Thr Gln Asn Val Leu Tyr Glu Asn Gln Lys Leu Ile Ala Asn
            900                 905                 910

Gln Phe Asn Ser Ala Ile Gly Lys Ile Gln Asp Ser Leu Ser Ser Thr
        915                 920                 925

Ala Ser Ala Leu Gly Lys Leu Gln Asp Val Val Asn Gln Asn Ala Gln
930                 935                 940

Ala Leu Asn Thr Leu Val Lys Gln Leu Ser Ser Asn Phe Gly Ala Ile
945                 950                 955                 960

Ser Ser Val Leu Asn Asp Ile Leu Ser Arg Leu Asp Lys Val Glu Ala
```

```
                     965                 970                 975
Glu Val Gln Ile Asp Arg Leu Ile Thr Gly Arg Leu Gln Ser Leu Gln
                980                 985                 990

Thr Tyr Val Thr Gln Gln Leu Ile Arg Ala Ala Glu Ile Arg Ala Ser
            995                1000                1005

Ala Asn Leu Ala Ala Thr Lys Met Ser Glu Cys Val Leu Gly Gln Ser
       1010                1015                1020

Lys Arg Val Asp Phe Cys Gly Lys Gly Tyr His Leu Met Ser Phe Pro
1025                1030                1035                1040

Gln Ser Ala Pro His Gly Val Val Phe Leu His Val Thr Tyr Val Pro
            1045                1050                1055

Ala Gln Glu Lys Asn Phe Thr Thr Ala Pro Ala Ile Cys His Asp Gly
       1060                1065                1070

Lys Ala His Phe Pro Arg Glu Gly Val Phe Val Ser Asn Gly Thr His
       1075                1080                1085

Trp Phe Val Thr Gln Arg Asn Phe Tyr Glu Pro Gln Ile Ile Thr Thr
       1090                1095                1100

Asp Asn Thr Phe Val Ser Gly Asn Cys Asp Val Val Ile Gly Ile Val
1105                1110                1115                1120

Asn Asn Thr Val Tyr Asp Pro Leu Gln Pro Glu Leu Asp Ser Phe Lys
            1125                1130                1135

Glu Glu Leu Asp Lys Tyr Phe Lys Asn His Thr Ser Pro Asp Val Asp
       1140                1145                1150

Leu Gly Asp Ile Ser Gly Ile Asn Ala Ser Val Val Asn Ile Gln Lys
            1155                1160                1165

Glu Ile Asp Arg Leu Asn Glu Val Ala Lys Asn Leu Asn Glu Ser Leu
       1170                1175                1180

Ile Asp Leu Gln Glu Leu Gly Lys Tyr Glu Gln
1185                1190                1195

<210> SEQ ID NO 29
<211> LENGTH: 1195
<212> TYPE: PRT
<213> ORGANISM: Artificial Sequence
<220> FEATURE:
<223> OTHER INFORMATION: Synthetic construct

<400> SEQUENCE: 29

Gln Cys Val Asn Leu Thr Thr Arg Thr Gln Leu Pro Pro Ala Tyr Thr
1               5                  10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
```

```
            130                 135                 140
Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
                180                 185                 190

Lys His Thr Pro Ile Asn Leu Val Arg Asp Leu Pro Gln Gly Phe Ser
                195                 200                 205

Ala Leu Glu Pro Leu Val Asp Leu Pro Ile Gly Ile Asn Ile Thr Arg
210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Tyr Tyr Val Gly Tyr
                245                 250                 255

Leu Gln Pro Arg Thr Phe Leu Leu Lys Tyr Asn Glu Asn Gly Thr Ile
                260                 265                 270

Thr Asp Ala Val Asp Cys Ala Leu Asp Pro Leu Ser Glu Thr Lys Cys
                275                 280                 285

Thr Leu Lys Ser Phe Thr Val Glu Lys Gly Ile Tyr Gln Thr Ser Asn
290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
                340                 345                 350

Ser Val Leu Tyr Asn Ser Ala Ser Phe Ser Thr Phe Lys Cys Tyr Gly
                355                 360                 365

Val Ser Pro Thr Lys Leu Asn Asp Leu Cys Phe Thr Asn Val Tyr Ala
                370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                405                 410                 415

Thr Gly Cys Val Ile Ala Trp Asn Ser Asn Leu Asp Ser Lys Val
                420                 425                 430

Gly Gly Asn Tyr Asn Tyr Leu Tyr Arg Leu Phe Arg Lys Ser Asn Leu
                435                 440                 445

Lys Pro Phe Glu Arg Asp Ile Ser Thr Glu Ile Tyr Gln Ala Gly Ser
450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
                485                 490                 495

Val Val Val Leu Ser Phe Glu Leu Leu His Ala Pro Ala Thr Val Cys
                500                 505                 510

Gly Pro Lys Lys Ser Thr Asn Leu Val Lys Asn Lys Cys Val Asn Phe
                515                 520                 525

Asn Phe Asn Gly Leu Thr Gly Thr Gly Val Leu Thr Glu Ser Asn Lys
                530                 535                 540

Lys Phe Leu Pro Phe Gln Gln Phe Gly Arg Asp Ile Ala Asp Thr Thr
545                 550                 555                 560
```

```
Asp Ala Val Arg Asp Pro Gln Thr Leu Glu Ile Leu Asp Ile Thr Pro
            565                 570                 575

Cys Ser Phe Gly Gly Val Ser Val Ile Thr Pro Gly Thr Asn Thr Ser
            580                 585                 590

Asn Gln Val Ala Val Leu Tyr Gln Asp Val Asn Cys Thr Glu Val Pro
            595                 600                 605

Val Ala Ile His Ala Asp Gln Leu Thr Pro Thr Trp Arg Val Tyr Ser
            610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
            645                 650                 655

Ile Cys Ala Ser Tyr Gln Thr Gln Thr Asn Ser Pro Arg Arg Ala Arg
            660                 665                 670

Ser Val Ala Ser Gln Ser Ile Ile Ala Tyr Thr Met Ser Leu Gly Ala
            675                 680                 685

Glu Asn Ser Val Ala Tyr Ser Asn Asn Ser Ile Ala Ile Pro Thr Asn
            690                 695                 700

Phe Thr Ile Ser Val Thr Thr Glu Ile Leu Pro Val Ser Met Thr Lys
705                 710                 715                 720

Thr Ser Val Asp Cys Thr Met Tyr Ile Cys Gly Asp Ser Thr Glu Cys
            725                 730                 735

Ser Asn Leu Leu Leu Gln Tyr Gly Ser Phe Cys Thr Gln Leu Asn Arg
            740                 745                 750

Ala Leu Thr Gly Ile Ala Val Glu Gln Asp Lys Asn Thr Gln Glu Val
            755                 760                 765

Phe Ala Gln Val Lys Gln Ile Tyr Lys Thr Pro Pro Ile Lys Asp Phe
            770                 775                 780

Gly Gly Phe Asn Phe Ser Gln Ile Leu Pro Asp Pro Ser Lys Pro Ser
785                 790                 795                 800

Lys Arg Ser Phe Ile Glu Asp Leu Leu Phe Asn Lys Val Thr Leu Ala
            805                 810                 815

Asp Ala Gly Phe Ile Lys Gln Tyr Gly Asp Cys Leu Gly Asp Ile Ala
            820                 825                 830

Ala Arg Asp Leu Ile Cys Ala Gln Lys Phe Asn Gly Leu Thr Val Leu
            835                 840                 845

Pro Pro Leu Leu Thr Asp Glu Met Ile Ala Gln Tyr Thr Ser Ala Leu
850                 855                 860

Leu Ala Gly Thr Ile Thr Ser Gly Trp Thr Phe Gly Ala Gly Ala Ala
865                 870                 875                 880

Leu Gln Ile Pro Phe Ala Met Gln Met Ala Tyr Arg Phe Asn Gly Ile
            885                 890                 895

Gly Val Thr Gln Asn Val Leu Tyr Glu Asn Gln Lys Leu Ile Ala Asn
            900                 905                 910

Gln Phe Asn Ser Ala Ile Gly Lys Ile Gln Asp Ser Leu Ser Ser Thr
            915                 920                 925

Ala Ser Ala Leu Gly Lys Leu Gln Asp Val Val Asn Gln Asn Ala Gln
            930                 935                 940

Ala Leu Asn Thr Leu Val Lys Gln Leu Ser Ser Asn Phe Gly Ala Ile
945                 950                 955                 960

Ser Ser Val Leu Asn Asp Ile Leu Ser Arg Leu Asp Pro Pro Glu Ala
            965                 970                 975
```

```
Glu Val Gln Ile Asp Arg Leu Ile Thr Gly Arg Leu Gln Ser Leu Gln
                980                 985                 990

Thr Tyr Val Thr Gln Gln Leu Ile Arg Ala Ala Glu Ile Arg Ala Ser
            995                 1000                1005

Ala Asn Leu Ala Ala Thr Lys Met Ser Glu Cys Val Leu Gly Gln Ser
        1010                1015                1020

Lys Arg Val Asp Phe Cys Gly Lys Gly Tyr His Leu Met Ser Phe Pro
1025                1030                1035                1040

Gln Ser Ala Pro His Gly Val Val Phe Leu His Val Thr Tyr Val Pro
                1045                1050                1055

Ala Gln Glu Lys Asn Phe Thr Thr Ala Pro Ala Ile Cys His Asp Gly
            1060                1065                1070

Lys Ala His Phe Pro Arg Glu Gly Val Phe Val Ser Asn Gly Thr His
        1075                1080                1085

Trp Phe Val Thr Gln Arg Asn Phe Tyr Glu Pro Gln Ile Ile Thr Thr
    1090                1095                1100

Asp Asn Thr Phe Val Ser Gly Asn Cys Asp Val Val Ile Gly Ile Val
1105                1110                1115                1120

Asn Asn Thr Val Tyr Asp Pro Leu Gln Pro Glu Leu Asp Ser Phe Lys
                1125                1130                1135

Glu Glu Leu Asp Lys Tyr Phe Lys Asn His Thr Ser Pro Asp Val Asp
            1140                1145                1150

Leu Gly Asp Ile Ser Gly Ile Asn Ala Ser Val Val Asn Ile Gln Lys
        1155                1160                1165

Glu Ile Asp Arg Leu Asn Glu Val Ala Lys Asn Leu Asn Glu Ser Leu
    1170                1175                1180

Ile Asp Leu Gln Glu Leu Gly Lys Tyr Glu Gln
1185                1190                1195

<210> SEQ ID NO 30
<211> LENGTH: 1195
<212> TYPE: PRT
<213> ORGANISM: Artificial Sequence
<220> FEATURE:
<223> OTHER INFORMATION: Synthetic construct

<400> SEQUENCE: 30

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140
```

```
Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
            165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
            195                 200                 205

Ala Leu Glu Pro Leu Val Asp Leu Pro Ile Gly Ile Asn Ile Thr Arg
            210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Tyr Tyr Val Gly Tyr
                245                 250                 255

Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
            275                 280                 285

Thr Leu Lys Ser Phe Thr Val Glu Lys Gly Ile Tyr Gln Thr Ser Asn
290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
            325                 330                 335

Val Tyr Ala Trp Asn Arg Lys Arg Ile Ser Asn Cys Val Ala Asp Tyr
            340                 345                 350

Ser Val Leu Tyr Asn Ser Ala Ser Phe Ser Thr Phe Lys Cys Tyr Gly
            355                 360                 365

Val Ser Pro Thr Lys Leu Asn Asp Leu Cys Phe Thr Asn Val Tyr Ala
            370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
            405                 410                 415

Thr Gly Cys Val Ile Ala Trp Asn Ser Asn Asn Leu Asp Ser Lys Val
            420                 425                 430

Gly Gly Asn Tyr Asn Tyr Leu Tyr Arg Leu Phe Arg Lys Ser Asn Leu
            435                 440                 445

Lys Pro Phe Glu Arg Asp Ile Ser Thr Glu Ile Tyr Gln Ala Gly Ser
            450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
            485                 490                 495

Val Val Val Leu Ser Phe Glu Leu Leu His Ala Pro Ala Thr Val Cys
            500                 505                 510

Gly Pro Lys Lys Ser Thr Asn Leu Val Lys Asn Lys Cys Val Asn Phe
            515                 520                 525

Asn Phe Asn Gly Leu Thr Gly Thr Gly Val Leu Thr Glu Ser Asn Lys
            530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
```

-continued

```
            565                 570                 575
Cys Ser Phe Gly Gly Val Ser Val Ile Thr Pro Gly Thr Asn Thr Ser
            580                 585                 590

Asn Gln Val Ala Val Leu Tyr Gln Asp Val Asn Cys Thr Glu Val Pro
            595                 600                 605

Val Ala Ile His Ala Asp Gln Leu Thr Pro Thr Trp Arg Val Tyr Ser
            610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
            645                 650                 655

Ile Cys Ala Ser Tyr Gln Thr Gln Thr Asn Ser Pro Arg Arg Ala Ala
            660                 665                 670

Ser Val Ala Ser Gln Ser Ile Ile Ala Tyr Thr Met Ser Leu Gly Ala
            675                 680                 685

Glu Asn Ser Val Ala Tyr Ser Asn Asn Ser Ile Ala Ile Pro Thr Asn
            690                 695                 700

Phe Thr Ile Ser Val Thr Thr Glu Ile Leu Pro Val Ser Met Thr Lys
705                 710                 715                 720

Thr Ser Val Asp Cys Thr Met Tyr Ile Cys Gly Asp Ser Thr Glu Cys
            725                 730                 735

Ser Asn Leu Leu Leu Gln Tyr Gly Ser Phe Cys Thr Gln Leu Asn Arg
            740                 745                 750

Ala Leu Thr Gly Ile Ala Val Glu Gln Asp Lys Asn Thr Gln Glu Val
            755                 760                 765

Phe Ala Gln Val Lys Gln Ile Tyr Lys Thr Pro Pro Ile Lys Asp Phe
            770                 775                 780

Gly Gly Phe Asn Phe Ser Gln Ile Leu Pro Asp Pro Ser Lys Pro Ser
785                 790                 795                 800

Lys Arg Ser Phe Ile Glu Asp Leu Leu Phe Asn Lys Val Thr Leu Ala
            805                 810                 815

Asp Ala Gly Phe Ile Lys Gln Tyr Gly Asp Cys Leu Gly Asp Ile Ala
            820                 825                 830

Ala Arg Asp Leu Ile Cys Ala Gln Lys Phe Asn Gly Leu Thr Val Leu
            835                 840                 845

Pro Pro Leu Leu Thr Asp Glu Met Ile Ala Gln Tyr Thr Ser Ala Leu
850                 855                 860

Leu Ala Gly Thr Ile Thr Ser Gly Trp Thr Phe Gly Ala Gly Ala Ala
865                 870                 875                 880

Leu Gln Ile Pro Phe Ala Met Gln Met Ala Tyr Arg Phe Asn Gly Ile
            885                 890                 895

Gly Val Thr Gln Asn Val Leu Tyr Glu Asn Gln Lys Leu Ile Ala Asn
            900                 905                 910

Gln Phe Asn Ser Ala Ile Gly Lys Ile Gln Asp Ser Leu Ser Ser Thr
            915                 920                 925

Ala Ser Ala Leu Gly Lys Leu Gln Asp Val Val Asn Gln Asn Ala Gln
            930                 935                 940

Ala Leu Asn Thr Leu Val Lys Gln Leu Ser Ser Asn Phe Gly Ala Ile
945                 950                 955                 960

Ser Ser Val Leu Asn Asp Ile Leu Ser Arg Leu Asp Pro Pro Glu Ala
            965                 970                 975

Glu Val Gln Ile Asp Arg Leu Ile Thr Gly Arg Leu Gln Ser Leu Gln
            980                 985                 990
```

-continued

```
Thr Tyr Val Thr Gln Gln Leu Ile Arg Ala Ala Glu Ile Arg Ala Ser
        995                 1000                1005

Ala Asn Leu Ala Ala Thr Lys Met Ser Glu Cys Val Leu Gly Gln Ser
    1010                1015                1020

Lys Arg Val Asp Phe Cys Gly Lys Gly Tyr His Leu Met Ser Phe Pro
1025                1030                1035                1040

Gln Ser Ala Pro His Gly Val Val Phe Leu His Val Thr Tyr Val Pro
        1045                1050                1055

Ala Gln Glu Lys Asn Phe Thr Thr Ala Pro Ala Ile Cys His Asp Gly
        1060                1065                1070

Lys Ala His Phe Pro Arg Glu Gly Val Phe Val Ser Asn Gly Thr His
        1075                1080                1085

Trp Phe Val Thr Gln Arg Asn Phe Tyr Glu Pro Gln Ile Ile Thr Thr
        1090                1095                1100

Asp Asn Thr Phe Val Ser Gly Asn Cys Asp Val Val Ile Gly Ile Val
1105                1110                1115                1120

Asn Asn Thr Val Tyr Asp Pro Leu Gln Pro Glu Leu Asp Ser Phe Lys
        1125                1130                1135

Glu Glu Leu Asp Lys Tyr Phe Lys Asn His Thr Ser Pro Asp Val Asp
        1140                1145                1150

Leu Gly Asp Ile Ser Gly Ile Asn Ala Ser Val Val Asn Ile Gln Lys
        1155                1160                1165

Glu Ile Asp Arg Leu Asn Glu Val Ala Lys Asn Leu Asn Glu Ser Leu
        1170                1175                1180

Ile Asp Leu Gln Glu Leu Gly Lys Tyr Glu Gln
1185                1190                1195

<210> SEQ ID NO 31
<211> LENGTH: 525
<212> TYPE: PRT
<213> ORGANISM: Artificial Sequence
<220> FEATURE:
<223> OTHER INFORMATION: Synthetic construct

<400> SEQUENCE: 31

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160
```

```
Pro Phe Leu Met Asp Leu Glu Gly Lys Gln Gly Asn Phe Lys Asn Leu
            165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
            195                 200                 205

Ala Leu Glu Pro Leu Val Asp Leu Pro Ile Gly Ile Asn Ile Thr Arg
            210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
            245                 250                 255

Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
            275                 280                 285

Thr Leu Lys Ser Phe Thr Val Glu Lys Gly Ile Tyr Gln Thr Ser Asn
            290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
            325                 330                 335

Val Tyr Ala Trp Asn Arg Lys Arg Ile Ser Asn Cys Val Ala Asp Tyr
            340                 345                 350

Ser Val Leu Tyr Asn Ser Ala Ser Phe Ser Thr Phe Lys Cys Tyr Gly
            355                 360                 365

Val Ser Pro Thr Lys Leu Asn Asp Leu Cys Phe Thr Asn Val Tyr Ala
            370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
            405                 410                 415

Thr Gly Cys Val Ile Ala Trp Asn Ser Asn Asn Leu Asp Ser Lys Val
            420                 425                 430

Gly Gly Asn Tyr Asn Tyr Leu Tyr Arg Leu Phe Arg Lys Ser Asn Leu
            435                 440                 445

Lys Pro Phe Glu Arg Asp Ile Ser Thr Glu Ile Tyr Gln Ala Gly Ser
450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
            485                 490                 495

Val Val Val Leu Ser Phe Glu Leu Leu His Ala Pro Ala Thr Val Cys
            500                 505                 510

Gly Pro Lys Lys Ser Thr Asn Leu Val Lys Asn Lys Cys
            515                 520                 525
```

<210> SEQ ID NO 32
<211> LENGTH: 668
<212> TYPE: PRT
<213> ORGANISM: Artificial Sequence
<220> FEATURE:
<223> OTHER INFORMATION: Synthetic construct

<400> SEQUENCE: 32

-continued

```
Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205

Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
                245                 250                 255

Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
        275                 280                 285

Thr Leu Lys Ser Phe Thr Val Glu Lys Gly Ile Tyr Gln Thr Ser Asn
    290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
            340                 345                 350

Ser Val Leu Tyr Asn Ser Ala Ser Phe Ser Thr Phe Lys Cys Tyr Gly
        355                 360                 365

Val Ser Pro Thr Lys Leu Asn Asp Leu Cys Phe Thr Asn Val Tyr Ala
    370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                405                 410                 415
```

```
Thr Gly Cys Val Ile Ala Trp Asn Ser Asn Asn Leu Asp Ser Lys Val
            420                 425                 430

Gly Gly Asn Tyr Asn Tyr Leu Tyr Arg Leu Phe Arg Lys Ser Asn Leu
                435                 440                 445

Lys Pro Phe Glu Arg Asp Ile Ser Thr Glu Ile Tyr Gln Ala Gly Ser
450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
                485                 490                 495

Val Val Val Leu Ser Phe Glu Leu Leu His Ala Pro Ala Thr Val Cys
            500                 505                 510

Gly Pro Lys Lys Ser Thr Asn Leu Val Lys Asn Lys Cys Val Asn Phe
            515                 520                 525

Asn Phe Asn Gly Leu Thr Gly Thr Gly Val Leu Thr Glu Ser Asn Lys
            530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
                580                 585                 590

Asn Gln Val Ala Val Leu Tyr Gln Asp Val Asn Cys Thr Glu Val Pro
            595                 600                 605

Val Ala Ile His Ala Asp Gln Leu Thr Pro Thr Trp Arg Val Tyr Ser
610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
                645                 650                 655

Ile Cys Ala Ser Tyr Gln Thr Gln Thr Asn Ser Pro
            660                 665

<210> SEQ ID NO 33
<211> LENGTH: 523
<212> TYPE: PRT
<213> ORGANISM: Artificial Sequence
<220> FEATURE:
<223> OTHER INFORMATION: Synthetic construct

<400> SEQUENCE: 33

Ser Val Ala Ser Gln Ser Ile Ile Ala Tyr Thr Met Ser Leu Gly Ala
1               5                   10                  15

Glu Asn Ser Val Ala Tyr Ser Asn Asn Ser Ile Ala Ile Pro Thr Asn
                20                  25                  30

Phe Thr Ile Ser Val Thr Thr Glu Ile Leu Pro Val Ser Met Thr Lys
            35                  40                  45

Thr Ser Val Asp Cys Thr Met Tyr Ile Cys Gly Asp Ser Thr Glu Cys
        50                  55                  60

Ser Asn Leu Leu Leu Gln Tyr Gly Ser Phe Cys Thr Gln Leu Asn Arg
65                  70                  75                  80

Ala Leu Thr Gly Ile Ala Val Glu Gln Asp Lys Asn Thr Gln Glu Val
                85                  90                  95

Phe Ala Gln Val Lys Gln Ile Tyr Lys Thr Pro Pro Ile Lys Asp Phe
            100                 105                 110
```

```
Gly Gly Phe Asn Phe Ser Gln Ile Leu Pro Asp Pro Ser Lys Pro Ser
            115                 120                 125

Lys Arg Ser Phe Ile Glu Asp Leu Leu Phe Asn Lys Val Thr Leu Ala
130                 135                 140

Asp Ala Gly Phe Ile Lys Gln Tyr Gly Asp Cys Leu Gly Asp Ile Ala
145                 150                 155                 160

Ala Arg Asp Leu Ile Cys Ala Gln Lys Phe Asn Gly Leu Thr Val Leu
                165                 170                 175

Pro Pro Leu Leu Thr Asp Glu Met Ile Ala Gln Tyr Thr Ser Ala Leu
            180                 185                 190

Leu Ala Gly Thr Ile Thr Ser Gly Trp Thr Phe Gly Ala Gly Ala Ala
            195                 200                 205

Leu Gln Ile Pro Phe Ala Met Gln Met Ala Tyr Arg Phe Asn Gly Ile
            210                 215                 220

Gly Val Thr Gln Asn Val Leu Tyr Glu Asn Gln Lys Leu Ile Ala Asn
225                 230                 235                 240

Gln Phe Asn Ser Ala Ile Gly Lys Ile Gln Asp Ser Leu Ser Ser Thr
                245                 250                 255

Ala Ser Ala Leu Gly Lys Leu Gln Asp Val Val Asn Gln Asn Ala Gln
            260                 265                 270

Ala Leu Asn Thr Leu Val Lys Gln Leu Ser Ser Asn Phe Gly Ala Ile
            275                 280                 285

Ser Ser Val Leu Asn Asp Ile Leu Ser Arg Leu Asp Lys Val Glu Ala
290                 295                 300

Glu Val Gln Ile Asp Arg Leu Ile Thr Gly Arg Leu Gln Ser Leu Gln
305                 310                 315                 320

Thr Tyr Val Thr Gln Gln Leu Ile Arg Ala Ala Glu Ile Arg Ala Ser
                325                 330                 335

Ala Asn Leu Ala Ala Thr Lys Met Ser Glu Cys Val Leu Gly Gln Ser
            340                 345                 350

Lys Arg Val Asp Phe Cys Gly Lys Gly Tyr His Leu Met Ser Phe Pro
            355                 360                 365

Gln Ser Ala Pro His Gly Val Val Phe Leu His Val Thr Tyr Val Pro
370                 375                 380

Ala Gln Glu Lys Asn Phe Thr Thr Ala Pro Ala Ile Cys His Asp Gly
385                 390                 395                 400

Lys Ala His Phe Pro Arg Glu Gly Val Phe Val Ser Asn Gly Thr His
                405                 410                 415

Trp Phe Val Thr Gln Arg Asn Phe Tyr Glu Pro Gln Ile Ile Thr Thr
            420                 425                 430

Asp Asn Thr Phe Val Ser Gly Asn Cys Asp Val Val Ile Gly Ile Val
            435                 440                 445

Asn Asn Thr Val Tyr Asp Pro Leu Gln Pro Glu Leu Asp Ser Phe Lys
450                 455                 460

Glu Glu Leu Asp Lys Tyr Phe Lys Asn His Thr Ser Pro Asp Val Asp
465                 470                 475                 480

Leu Gly Asp Ile Ser Gly Ile Asn Ala Ser Val Val Asn Ile Gln Lys
                485                 490                 495

Glu Ile Asp Arg Leu Asn Glu Val Ala Lys Asn Leu Asn Glu Ser Leu
            500                 505                 510

Ile Asp Leu Gln Glu Leu Gly Lys Tyr Glu Gln
            515                 520
```

<210> SEQ ID NO 34
<211> LENGTH: 513
<212> TYPE: PRT
<213> ORGANISM: Artificial Sequence
<220> FEATURE:
<223> OTHER INFORMATION: Synthetic construct

<400> SEQUENCE: 34

```
Thr Met Ser Leu Gly Ala Glu Asn Ser Val Ala Tyr Ser Asn Asn Ser
1               5                   10                  15

Ile Ala Ile Pro Thr Asn Phe Thr Ile Ser Val Thr Thr Glu Ile Leu
            20                  25                  30

Pro Val Ser Met Thr Lys Thr Ser Val Asp Cys Thr Met Tyr Ile Cys
        35                  40                  45

Gly Asp Ser Thr Glu Cys Ser Asn Leu Leu Leu Gln Tyr Gly Ser Phe
    50                  55                  60

Cys Thr Gln Leu Asn Arg Ala Leu Thr Gly Ile Ala Val Glu Gln Asp
65                  70                  75                  80

Lys Asn Thr Gln Glu Val Phe Ala Gln Val Lys Gln Ile Tyr Lys Thr
                85                  90                  95

Pro Pro Ile Lys Asp Phe Gly Gly Phe Asn Phe Ser Gln Ile Leu Pro
            100                 105                 110

Asp Pro Ser Lys Pro Ser Lys Arg Ser Phe Ile Glu Asp Leu Leu Phe
        115                 120                 125

Asn Lys Val Thr Leu Ala Asp Ala Gly Phe Ile Lys Gln Tyr Gly Asp
    130                 135                 140

Cys Leu Gly Asp Ile Ala Ala Arg Asp Leu Ile Cys Ala Gln Lys Phe
145                 150                 155                 160

Asn Gly Leu Thr Val Leu Pro Pro Leu Leu Thr Asp Glu Met Ile Ala
                165                 170                 175

Gln Tyr Thr Ser Ala Leu Leu Ala Gly Thr Ile Thr Ser Gly Trp Thr
            180                 185                 190

Phe Gly Ala Gly Ala Ala Leu Gln Ile Pro Phe Ala Met Gln Met Ala
        195                 200                 205

Tyr Arg Phe Asn Gly Ile Gly Val Thr Gln Asn Val Leu Tyr Glu Asn
    210                 215                 220

Gln Lys Leu Ile Ala Asn Gln Phe Asn Ser Ala Ile Gly Lys Ile Gln
225                 230                 235                 240

Asp Ser Leu Ser Ser Thr Ala Ser Ala Leu Gly Lys Leu Gln Asp Val
                245                 250                 255

Val Asn Gln Asn Ala Gln Ala Leu Asn Thr Leu Val Lys Gln Leu Ser
            260                 265                 270

Ser Asn Phe Gly Ala Ile Ser Ser Val Leu Asn Asp Ile Leu Ser Arg
        275                 280                 285

Leu Asp Lys Val Glu Ala Glu Val Gln Ile Asp Arg Leu Ile Thr Gly
    290                 295                 300

Arg Leu Gln Ser Leu Gln Thr Tyr Val Thr Gln Gln Leu Ile Arg Ala
305                 310                 315                 320

Ala Glu Ile Arg Ala Ser Ala Asn Leu Ala Ala Thr Lys Met Ser Glu
                325                 330                 335

Cys Val Leu Gly Gln Ser Lys Arg Val Asp Phe Cys Gly Lys Gly Tyr
            340                 345                 350

His Leu Met Ser Phe Pro Gln Ser Ala Pro His Gly Val Val Phe Leu
        355                 360                 365

His Val Thr Tyr Val Pro Ala Gln Glu Lys Asn Phe Thr Thr Ala Pro
```

```
                370                 375                 380
Ala Ile Cys His Asp Gly Lys Ala His Phe Pro Arg Glu Gly Val Phe
385                 390                 395                 400

Val Ser Asn Gly Thr His Trp Phe Val Thr Gln Arg Asn Phe Tyr Glu
                405                 410                 415

Pro Gln Ile Ile Thr Thr Asp Asn Thr Phe Val Ser Gly Asn Cys Asp
                420                 425                 430

Val Val Ile Gly Ile Val Asn Asn Thr Val Tyr Asp Pro Leu Gln Pro
                435                 440                 445

Glu Leu Asp Ser Phe Lys Glu Glu Leu Asp Lys Tyr Phe Lys Asn His
                450                 455                 460

Thr Ser Pro Asp Val Asp Leu Gly Asp Ile Ser Gly Ile Asn Ala Ser
465                 470                 475                 480

Val Val Asn Ile Gln Lys Glu Ile Asp Arg Leu Asn Glu Val Ala Lys
                485                 490                 495

Asn Leu Asn Glu Ser Leu Ile Asp Leu Gln Glu Leu Gly Lys Tyr Glu
                500                 505                 510

Gln

<210> SEQ ID NO 35
<211> LENGTH: 393
<212> TYPE: PRT
<213> ORGANISM: Artificial Sequence
<220> FEATURE:
<223> OTHER INFORMATION: Synthetic construct

<400> SEQUENCE: 35

Ser Phe Ile Glu Asp Leu Leu Phe Asn Lys Val Thr Leu Ala Asp Ala
1               5                   10                  15

Gly Phe Ile Lys Gln Tyr Gly Asp Cys Leu Gly Asp Ile Ala Ala Arg
                20                  25                  30

Asp Leu Ile Cys Ala Gln Lys Phe Asn Gly Leu Thr Val Leu Pro Pro
                35                  40                  45

Leu Leu Thr Asp Glu Met Ile Ala Gln Tyr Thr Ser Ala Leu Leu Ala
            50                  55                  60

Gly Thr Ile Thr Ser Gly Trp Thr Phe Gly Ala Gly Ala Ala Leu Gln
65                  70                  75                  80

Ile Pro Phe Ala Met Gln Met Ala Tyr Arg Phe Asn Gly Ile Gly Val
                85                  90                  95

Thr Gln Asn Val Leu Tyr Glu Asn Gln Lys Leu Ile Ala Asn Gln Phe
                100                 105                 110

Asn Ser Ala Ile Gly Lys Ile Gln Asp Ser Leu Ser Ser Thr Ala Ser
            115                 120                 125

Ala Leu Gly Lys Leu Gln Asp Val Val Asn Gln Asn Ala Gln Ala Leu
130                 135                 140

Asn Thr Leu Val Lys Gln Leu Ser Ser Asn Phe Gly Ala Ile Ser Ser
145                 150                 155                 160

Val Leu Asn Asp Ile Leu Ser Arg Leu Asp Lys Val Glu Ala Glu Val
                165                 170                 175

Gln Ile Asp Arg Leu Ile Thr Gly Arg Leu Gln Ser Leu Gln Thr Tyr
                180                 185                 190

Val Thr Gln Gln Leu Ile Arg Ala Ala Glu Ile Arg Ala Ser Ala Asn
            195                 200                 205

Leu Ala Ala Thr Lys Met Ser Glu Cys Val Leu Gly Gln Ser Lys Arg
210                 215                 220
```

```
Val Asp Phe Cys Gly Lys Gly Tyr His Leu Met Ser Phe Pro Gln Ser
225                 230                 235                 240

Ala Pro His Gly Val Val Phe Leu His Val Thr Tyr Val Pro Ala Gln
                245                 250                 255

Glu Lys Asn Phe Thr Thr Ala Pro Ala Ile Cys His Asp Gly Lys Ala
            260                 265                 270

His Phe Pro Arg Glu Gly Val Phe Val Ser Asn Gly Thr His Trp Phe
        275                 280                 285

Val Thr Gln Arg Asn Phe Tyr Glu Pro Gln Ile Ile Thr Thr Asp Asn
    290                 295                 300

Thr Phe Val Ser Gly Asn Cys Asp Val Val Ile Gly Ile Val Asn Asn
305                 310                 315                 320

Thr Val Tyr Asp Pro Leu Gln Pro Glu Leu Asp Ser Phe Lys Glu Glu
                325                 330                 335

Leu Asp Lys Tyr Phe Lys Asn His Thr Ser Pro Asp Val Asp Leu Gly
            340                 345                 350

Asp Ile Ser Gly Ile Asn Ala Ser Val Val Asn Ile Gln Lys Glu Ile
        355                 360                 365

Asp Arg Leu Asn Glu Val Ala Lys Asn Leu Asn Glu Ser Leu Ile Asp
    370                 375                 380

Leu Gln Glu Leu Gly Lys Tyr Glu Gln
385                 390

<210> SEQ ID NO 36
<211> LENGTH: 1195
<212> TYPE: PRT
<213> ORGANISM: Artificial Sequence
<220> FEATURE:
<223> OTHER INFORMATION: Synthetic construct

<400> SEQUENCE: 36

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190
```

```
Lys His Thr Pro Ile Asn Leu Val Arg Asp Leu Pro Gln Gly Phe Ser
        195                 200                 205

Ala Leu Glu Pro Leu Val Asp Leu Pro Ile Gly Ile Asn Ile Thr Arg
210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Tyr Tyr Val Gly Tyr
                245                 250                 255

Leu Gln Pro Arg Thr Phe Leu Leu Lys Tyr Asn Glu Asn Gly Thr Ile
                260                 265                 270

Thr Asp Ala Val Asp Cys Ala Leu Asp Pro Leu Ser Glu Thr Lys Cys
                275                 280                 285

Thr Leu Lys Ser Phe Thr Val Glu Lys Gly Ile Tyr Gln Thr Ser Asn
            290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
                340                 345                 350

Ser Val Leu Tyr Asn Ser Ala Ser Phe Ser Thr Phe Lys Cys Tyr Gly
                355                 360                 365

Val Ser Pro Thr Lys Leu Asn Asp Leu Cys Phe Thr Asn Val Tyr Ala
            370                 375                 380

Asp Ser Phe Val Ile Arg Gly Asp Glu Val Arg Gln Ile Ala Pro Gly
385                 390                 395                 400

Gln Thr Gly Asn Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
                420                 425                 430

Gly Gly Asn Tyr Asn Tyr Leu Tyr Arg Leu Phe Arg Lys Ser Asn Leu
            435                 440                 445

Lys Pro Phe Glu Arg Asp Ile Ser Thr Glu Ile Tyr Gln Ala Gly Ser
            450                 455                 460

Thr Pro Cys Asn Gly Val Lys Gly Phe Asn Cys Tyr Phe Pro Leu Gln
465                 470                 475                 480

Ser Tyr Gly Phe Gln Pro Thr Tyr Gly Val Gly Tyr Gln Pro Tyr Arg
                485                 490                 495

Val Val Val Leu Ser Phe Glu Leu Leu His Ala Pro Ala Thr Val Cys
                500                 505                 510

Gly Pro Lys Lys Ser Thr Asn Leu Val Lys Asn Lys Cys Val Asn Phe
            515                 520                 525

Asn Phe Asn Gly Leu Thr Gly Thr Gly Val Leu Thr Glu Ser Asn Lys
            530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
                580                 585                 590

Asn Gln Val Ala Val Leu Tyr Gln Gly Val Asn Cys Thr Glu Val Pro
            595                 600                 605
```

```
Val Ala Ile His Ala Asp Gln Leu Thr Pro Thr Trp Arg Val Tyr Ser
    610             615                 620
Thr Gly Ser Asn Val Phe Gln Thr Arg Ala Gly Cys Leu Ile Gly Ala
625             630                 635                 640
Glu His Val Asn Ser Tyr Glu Cys Asp Ile Pro Ile Gly Ala Gly
                645                 650                 655
Ile Cys Ala Ser Tyr Gln Thr Gln Thr Asn Ser Pro Arg Arg Ala Arg
                660                 665                 670
Ser Val Ala Ser Gln Ser Ile Ala Tyr Thr Met Ser Leu Gly Ala
            675                 680                 685
Glu Asn Ser Val Ala Tyr Ser Asn Asn Ser Ile Ala Ile Pro Thr Asn
690                 695                 700
Phe Thr Ile Ser Val Thr Thr Glu Ile Leu Pro Val Ser Met Thr Lys
705             710                 715                 720
Thr Ser Val Asp Cys Thr Met Tyr Ile Cys Gly Asp Ser Thr Glu Cys
                725                 730                 735
Ser Asn Leu Leu Leu Gln Tyr Gly Ser Phe Cys Thr Gln Leu Asn Arg
            740                 745                 750
Ala Leu Thr Gly Ile Ala Val Glu Gln Asp Lys Asn Thr Gln Glu Val
            755                 760                 765
Phe Ala Gln Val Lys Gln Ile Tyr Lys Thr Pro Pro Ile Lys Asp Phe
770                 775                 780
Gly Gly Phe Asn Phe Ser Gln Ile Leu Pro Asp Pro Ser Lys Pro Ser
785             790                 795                 800
Lys Arg Ser Phe Ile Glu Asp Leu Leu Phe Asn Lys Val Thr Leu Ala
                805                 810                 815
Asp Ala Gly Phe Ile Lys Gln Tyr Gly Asp Cys Leu Gly Asp Ile Ala
            820                 825                 830
Ala Arg Asp Leu Ile Cys Ala Gln Lys Phe Asn Gly Leu Thr Val Leu
            835                 840                 845
Pro Pro Leu Leu Thr Asp Glu Met Ile Ala Gln Tyr Thr Ser Ala Leu
850                 855                 860
Leu Ala Gly Thr Ile Thr Ser Gly Trp Thr Phe Gly Ala Gly Ala Ala
865                 870                 875                 880
Leu Gln Ile Pro Phe Ala Met Gln Met Ala Tyr Arg Phe Asn Gly Ile
                885                 890                 895
Gly Val Thr Gln Asn Val Leu Tyr Glu Asn Gln Lys Leu Ile Ala Asn
                900                 905                 910
Gln Phe Asn Ser Ala Ile Gly Lys Ile Gln Asp Ser Leu Ser Ser Thr
            915                 920                 925
Ala Ser Ala Leu Gly Lys Leu Gln Asp Val Val Asn Gln Asn Ala Gln
930                 935                 940
Ala Leu Asn Thr Leu Val Lys Gln Leu Ser Ser Asn Phe Gly Ala Ile
945                 950                 955                 960
Ser Ser Val Leu Asn Asp Ile Leu Ser Arg Leu Asp Lys Val Glu Ala
                965                 970                 975
Glu Val Gln Ile Asp Arg Leu Ile Thr Gly Arg Leu Gln Ser Leu Gln
                980                 985                 990
Thr Tyr Val Thr Gln Gln Leu Ile Arg Ala Ala Glu Ile Arg Ala Ser
            995                 1000                1005
Ala Asn Leu Ala Ala Thr Lys Met Ser Glu Cys Val Leu Gly Gln Ser
            1010                1015                1020
Lys Arg Val Asp Phe Cys Gly Lys Gly Tyr His Leu Met Ser Phe Pro
```

```
                1025                1030                1035                1040
Gln Ser Ala Pro His Gly Val Phe Leu His Val Thr Tyr Val Pro
                        1045                1050                1055

Ala Gln Glu Lys Asn Phe Thr Thr Ala Pro Ala Ile Cys His Asp Gly
                1060                1065                1070

Lys Ala His Phe Pro Arg Glu Gly Val Phe Val Ser Asn Gly Thr His
            1075                1080                1085

Trp Phe Val Thr Gln Arg Asn Phe Tyr Glu Pro Gln Ile Ile Thr Thr
        1090                1095                1100

Asp Asn Thr Phe Val Ser Gly Asn Cys Asp Val Val Ile Gly Ile Val
1105                1110                1115                1120

Asn Asn Thr Val Tyr Asp Pro Leu Gln Pro Glu Leu Asp Ser Phe Lys
                1125                1130                1135

Glu Glu Leu Asp Lys Tyr Phe Lys Asn His Thr Ser Pro Asp Val Asp
                    1140                1145                1150

Leu Gly Asp Ile Ser Gly Ile Asn Ala Ser Val Val Asn Ile Gln Lys
            1155                1160                1165

Glu Ile Asp Arg Leu Asn Glu Val Ala Lys Asn Leu Asn Glu Ser Leu
    1170                1175                1180

Ile Asp Leu Gln Glu Leu Gly Lys Tyr Glu Gln
1185                1190                1195

<210> SEQ ID NO 37
<211> LENGTH: 1195
<212> TYPE: PRT
<213> ORGANISM: Artificial Sequence
<220> FEATURE:
<223> OTHER INFORMATION: Synthetic construct

<400> SEQUENCE: 37

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
                20                  25                  30

Ser Val Leu His Ser Thr Gln Asp Leu Phe Leu Pro Phe Phe Ser Asn
            35                  40                  45

Val Thr Trp Phe His Ala Ile His Val Ser Gly Thr Asn Gly Thr Lys
        50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
```

```
            195                 200                 205
Ala Leu Glu Pro Leu Val Asp Leu Pro Ile Gly Ile Asn Ile Thr Arg
210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Tyr Tyr Val Gly Tyr
                245                 250                 255

Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
            275                 280                 285

Thr Leu Lys Ser Phe Thr Val Glu Lys Gly Ile Tyr Gln Thr Ser Asn
            290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
            340                 345                 350

Ser Val Leu Tyr Asn Ser Ala Ser Phe Ser Thr Phe Lys Cys Tyr Gly
            355                 360                 365

Val Ser Pro Thr Lys Leu Asn Asp Leu Cys Phe Thr Asn Val Tyr Ala
370                 375                 380

Asp Ser Phe Val Ile Arg Gly Asp Glu Val Arg Gln Ile Ala Pro Gly
385                 390                 395                 400

Gln Thr Gly Asn Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
            420                 425                 430

Gly Gly Asn Tyr Asn Tyr Leu Tyr Arg Leu Phe Arg Lys Ser Asn Leu
            435                 440                 445

Lys Pro Phe Glu Arg Asp Ile Ser Thr Glu Ile Tyr Gln Ala Gly Ser
450                 455                 460

Thr Pro Cys Asn Gly Val Lys Gly Phe Asn Cys Tyr Phe Pro Leu Gln
465                 470                 475                 480

Ser Tyr Gly Phe Gln Pro Thr Tyr Gly Val Gly Tyr Gln Pro Tyr Arg
                485                 490                 495

Val Val Val Leu Ser Phe Glu Leu Leu His Ala Pro Ala Thr Val Cys
            500                 505                 510

Gly Pro Lys Lys Ser Thr Asn Leu Val Lys Asn Lys Cys Val Asn Phe
            515                 520                 525

Asn Phe Asn Gly Leu Thr Gly Thr Gly Val Leu Thr Glu Ser Asn Lys
            530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
            580                 585                 590

Asn Gln Val Ala Val Leu Tyr Gln Gly Val Asn Cys Thr Glu Val Pro
            595                 600                 605

Val Ala Ile His Ala Asp Gln Leu Thr Pro Thr Trp Arg Val Tyr Ser
610                 615                 620
```

```
Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
            645                 650                 655

Ile Cys Ala Ser Tyr Gln Thr Gln Thr Asn Ser Pro Arg Arg Ala Ala
            660                 665                 670

Ser Val Ala Ser Gln Ser Ile Ile Ala Tyr Thr Met Ser Leu Gly Ala
            675                 680                 685

Glu Asn Ser Val Ala Tyr Ser Asn Asn Ser Ile Ala Ile Pro Thr Asn
            690                 695                 700

Phe Thr Ile Ser Val Thr Thr Glu Ile Leu Pro Val Ser Met Thr Lys
705                 710                 715                 720

Thr Ser Val Asp Cys Thr Met Tyr Ile Cys Gly Asp Ser Thr Glu Cys
            725                 730                 735

Ser Asn Leu Leu Leu Gln Tyr Gly Ser Phe Cys Thr Gln Leu Asn Arg
            740                 745                 750

Ala Leu Thr Gly Ile Ala Val Glu Gln Asp Lys Asn Thr Gln Glu Val
            755                 760                 765

Phe Ala Gln Val Lys Gln Ile Tyr Lys Thr Pro Pro Ile Lys Asp Phe
770                 775                 780

Gly Gly Phe Asn Phe Ser Gln Ile Leu Pro Asp Pro Ser Lys Pro Ser
785                 790                 795                 800

Lys Arg Ser Phe Ile Glu Asp Leu Leu Phe Asn Lys Val Thr Leu Ala
            805                 810                 815

Asp Ala Gly Phe Ile Lys Gln Tyr Gly Asp Cys Leu Gly Asp Ile Ala
            820                 825                 830

Ala Arg Asp Leu Ile Cys Ala Gln Lys Phe Asn Gly Leu Thr Val Leu
            835                 840                 845

Pro Pro Leu Leu Thr Asp Glu Met Ile Ala Gln Tyr Thr Ser Ala Leu
850                 855                 860

Leu Ala Gly Thr Ile Thr Ser Gly Trp Thr Phe Gly Ala Gly Ala Ala
865                 870                 875                 880

Leu Gln Ile Pro Phe Ala Met Gln Met Ala Tyr Arg Phe Asn Gly Ile
            885                 890                 895

Gly Val Thr Gln Asn Val Leu Tyr Glu Asn Gln Lys Leu Ile Ala Asn
            900                 905                 910

Gln Phe Asn Ser Ala Ile Gly Lys Ile Gln Asp Ser Leu Ser Ser Thr
            915                 920                 925

Ala Ser Ala Leu Gly Lys Leu Gln Asp Val Val Asn Gln Asn Ala Gln
            930                 935                 940

Ala Leu Asn Thr Leu Val Lys Gln Leu Ser Ser Asn Phe Gly Ala Ile
945                 950                 955                 960

Ser Ser Val Leu Asn Asp Ile Leu Ser Arg Leu Asp Lys Val Glu Ala
            965                 970                 975

Glu Val Gln Ile Asp Arg Leu Ile Thr Gly Arg Leu Gln Ser Leu Gln
            980                 985                 990

Thr Tyr Val Thr Gln Gln Leu Ile Arg Ala Ala Glu Ile Arg Ala Ser
            995                 1000                1005

Ala Asn Leu Ala Ala Thr Lys Met Ser Glu Cys Val Leu Gly Gln Ser
            1010                1015                1020

Lys Arg Val Asp Phe Cys Gly Lys Gly Tyr His Leu Met Ser Phe Pro
1025                1030                1035                1040
```

```
Gln Ser Ala Pro His Gly Val Val Phe Leu His Val Thr Tyr Val Pro
            1045                1050                1055

Ala Gln Glu Lys Asn Phe Thr Thr Ala Pro Ala Ile Cys His Asp Gly
        1060                1065                1070

Lys Ala His Phe Pro Arg Glu Gly Val Phe Val Ser Asn Gly Thr His
    1075                1080                1085

Trp Phe Val Thr Gln Arg Asn Phe Tyr Glu Pro Gln Ile Ile Thr Thr
1090                1095                1100

Asp Asn Thr Phe Val Ser Gly Asn Cys Asp Val Val Ile Gly Ile Val
1105                1110                1115                1120

Asn Asn Thr Val Tyr Asp Pro Leu Gln Pro Glu Leu Asp Ser Phe Lys
            1125                1130                1135

Glu Glu Leu Asp Lys Tyr Phe Lys Asn His Thr Ser Pro Asp Val Asp
        1140                1145                1150

Leu Gly Asp Ile Ser Gly Ile Asn Ala Ser Val Val Asn Ile Gln Lys
    1155                1160                1165

Glu Ile Asp Arg Leu Asn Glu Val Ala Lys Asn Leu Asn Glu Ser Leu
    1170                1175                1180

Ile Asp Leu Gln Glu Leu Gly Lys Tyr Glu Gln
1185                1190                1195

<210> SEQ ID NO 38
<211> LENGTH: 1195
<212> TYPE: PRT
<213> ORGANISM: Artificial Sequence
<220> FEATURE:
<223> OTHER INFORMATION: Synthetic construct

<400> SEQUENCE: 38

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205
```

```
Ala Leu Glu Pro Leu Val Asp Leu Pro Ile Gly Ile Asn Ile Thr Arg
210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Tyr Tyr Val Gly Tyr
                245                 250                 255

Leu Gln Pro Arg Thr Phe Leu Leu Lys Tyr Asn Glu Asn Gly Thr Ile
                260                 265                 270

Thr Asp Ala Val Asp Cys Ala Leu Asp Pro Leu Ser Glu Thr Lys Cys
                275                 280                 285

Thr Leu Lys Ser Phe Thr Val Glu Lys Gly Ile Tyr Gln Thr Ser Asn
290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
                340                 345                 350

Ser Val Leu Tyr Asn Ser Ala Ser Phe Ser Thr Phe Lys Cys Tyr Gly
                355                 360                 365

Val Ser Pro Thr Lys Leu Asn Asp Leu Cys Phe Thr Asn Val Tyr Ala
370                 375                 380

Asp Ser Phe Val Ile Arg Gly Asp Glu Val Arg Gln Ile Ala Pro Gly
385                 390                 395                 400

Gln Thr Gly Asn Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
                420                 425                 430

Gly Gly Asn Tyr Asn Tyr Leu Tyr Arg Leu Phe Arg Lys Ser Asn Leu
                435                 440                 445

Lys Pro Phe Glu Arg Asp Ile Ser Thr Glu Ile Tyr Gln Ala Gly Ser
450                 455                 460

Thr Pro Cys Asn Gly Val Lys Gly Phe Asn Cys Tyr Phe Pro Leu Gln
465                 470                 475                 480

Ser Tyr Gly Phe Gln Pro Thr Tyr Gly Val Gly Tyr Gln Pro Tyr Arg
                485                 490                 495

Val Val Val Leu Ser Phe Glu Leu Leu His Ala Pro Ala Thr Val Cys
                500                 505                 510

Gly Pro Lys Lys Ser Thr Asn Leu Val Lys Asn Lys Cys Val Asn Phe
                515                 520                 525

Asn Phe Asn Gly Leu Thr Gly Thr Gly Val Leu Thr Glu Ser Asn Lys
530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
                580                 585                 590

Asn Gln Val Ala Val Leu Tyr Gln Gly Val Asn Cys Thr Glu Val Pro
                595                 600                 605

Val Ala Ile His Ala Asp Gln Leu Thr Pro Thr Trp Arg Val Tyr Ser
610                 615                 620

Thr Gly Ser Asn Val Phe Gln Thr Arg Ala Gly Cys Leu Ile Gly Ala
```

-continued

```
            625                 630                 635                 640
Glu His Val Asn Asn Ser Tyr Glu Cys Asp Ile Pro Ile Gly Ala Gly
                645                 650                 655
Ile Cys Ala Ser Tyr Gln Thr Gln Thr Asn Ser Pro Arg Arg Ala Arg
                660                 665                 670
Ser Val Ala Ser Gln Ser Ile Ile Ala Tyr Thr Met Ser Leu Gly Ala
                675                 680                 685
Glu Asn Ser Val Ala Tyr Ser Asn Asn Ser Ile Ala Ile Pro Thr Asn
                690                 695                 700
Phe Thr Ile Ser Val Thr Thr Glu Ile Leu Pro Val Ser Met Thr Lys
705                 710                 715                 720
Thr Ser Val Asp Cys Thr Met Tyr Ile Cys Gly Asp Ser Thr Glu Cys
                725                 730                 735
Ser Asn Leu Leu Leu Gln Tyr Gly Ser Phe Cys Thr Gln Leu Asn Arg
                740                 745                 750
Ala Leu Thr Gly Ile Ala Val Glu Gln Asp Lys Asn Thr Gln Glu Val
                755                 760                 765
Phe Ala Gln Val Lys Gln Ile Tyr Lys Thr Pro Pro Ile Lys Asp Phe
                770                 775                 780
Gly Gly Phe Asn Phe Ser Gln Ile Leu Pro Asp Pro Ser Lys Pro Ser
785                 790                 795                 800
Lys Arg Ser Phe Ile Glu Asp Leu Leu Phe Asn Lys Val Thr Leu Ala
                805                 810                 815
Asp Ala Gly Phe Ile Lys Gln Tyr Gly Asp Cys Leu Gly Asp Ile Ala
                820                 825                 830
Ala Arg Asp Leu Ile Cys Ala Gln Lys Phe Asn Gly Leu Thr Val Leu
                835                 840                 845
Pro Pro Leu Leu Thr Asp Glu Met Ile Ala Gln Tyr Thr Ser Ala Leu
                850                 855                 860
Leu Ala Gly Thr Ile Thr Ser Gly Trp Thr Phe Gly Ala Gly Ala Ala
865                 870                 875                 880
Leu Gln Ile Pro Phe Ala Met Gln Met Ala Tyr Arg Phe Asn Gly Ile
                885                 890                 895
Gly Val Thr Gln Asn Val Leu Tyr Glu Asn Gln Lys Leu Ile Ala Asn
                900                 905                 910
Gln Phe Asn Ser Ala Ile Gly Lys Ile Gln Asp Ser Leu Ser Ser Thr
                915                 920                 925
Ala Ser Ala Leu Gly Lys Leu Gln Asp Val Val Asn Gln Asn Ala Gln
930                 935                 940
Ala Leu Asn Thr Leu Val Lys Gln Leu Ser Ser Asn Phe Gly Ala Ile
945                 950                 955                 960
Ser Ser Val Leu Asn Asp Ile Leu Ser Arg Leu Asp Pro Pro Glu Ala
                965                 970                 975
Glu Val Gln Ile Asp Arg Leu Ile Thr Gly Arg Leu Gln Ser Leu Gln
                980                 985                 990
Thr Tyr Val Thr Gln Gln Leu Ile Arg Ala Ala Glu Ile Arg Ala Ser
                995                 1000                1005
Ala Asn Leu Ala Ala Thr Lys Met Ser Glu Cys Val Leu Gly Gln Ser
                1010                1015                1020
Lys Arg Val Asp Phe Cys Gly Lys Gly Tyr His Leu Met Ser Phe Pro
1025                1030                1035                1040
Gln Ser Ala Pro His Gly Val Val Phe Leu His Val Thr Tyr Val Pro
                1045                1050                1055
```

```
Ala Gln Glu Lys Asn Phe Thr Thr Ala Pro Ala Ile Cys His Asp Gly
            1060                1065                1070

Lys Ala His Phe Pro Arg Glu Gly Val Phe Val Ser Asn Gly Thr His
        1075                1080                1085

Trp Phe Val Thr Gln Arg Asn Phe Tyr Glu Pro Gln Ile Ile Thr Thr
1090                1095                1100

Asp Asn Thr Phe Val Ser Gly Asn Cys Asp Val Val Ile Gly Ile Val
1105                1110                1115                1120

Asn Asn Thr Val Tyr Asp Pro Leu Gln Pro Glu Leu Asp Ser Phe Lys
                1125                1130                1135

Glu Glu Leu Asp Lys Tyr Phe Lys Asn His Thr Ser Pro Asp Val Asp
            1140                1145                1150

Leu Gly Asp Ile Ser Gly Ile Asn Ala Ser Val Val Asn Ile Gln Lys
        1155                1160                1165

Glu Ile Asp Arg Leu Asn Glu Val Ala Lys Asn Leu Asn Glu Ser Leu
    1170                1175                1180

Ile Asp Leu Gln Glu Leu Gly Lys Tyr Glu Gln
1185                1190                1195

<210> SEQ ID NO 39
<211> LENGTH: 1195
<212> TYPE: PRT
<213> ORGANISM: Artificial Sequence
<220> FEATURE:
<223> OTHER INFORMATION: Synthetic construct

<400> SEQUENCE: 39

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205

Ala Leu Glu Pro Leu Val Asp Leu Pro Ile Gly Ile Asn Ile Thr Arg
    210                 215                 220
```

```
Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Tyr Tyr Val Gly Tyr
            245                 250                 255

Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
                275                 280                 285

Thr Leu Lys Ser Phe Thr Val Glu Lys Gly Ile Tyr Gln Thr Ser Asn
            290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
            340                 345                 350

Ser Val Leu Tyr Asn Ser Ala Ser Phe Ser Thr Phe Lys Cys Tyr Gly
            355                 360                 365

Val Ser Pro Thr Lys Leu Asn Asp Leu Cys Phe Thr Asn Val Tyr Ala
            370                 375                 380

Asp Ser Phe Val Ile Arg Gly Asp Glu Val Arg Gln Ile Ala Pro Gly
385                 390                 395                 400

Gln Thr Gly Asn Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
                420                 425                 430

Gly Gly Asn Tyr Asn Tyr Leu Tyr Arg Leu Phe Arg Lys Ser Asn Leu
            435                 440                 445

Lys Pro Phe Glu Arg Asp Ile Ser Thr Glu Ile Tyr Gln Ala Gly Ser
            450                 455                 460

Thr Pro Cys Asn Gly Val Lys Gly Phe Asn Cys Tyr Phe Pro Leu Gln
465                 470                 475                 480

Ser Tyr Gly Phe Gln Pro Thr Tyr Gly Val Gly Tyr Gln Pro Tyr Arg
                485                 490                 495

Val Val Val Leu Ser Phe Glu Leu Leu His Ala Pro Ala Thr Val Cys
            500                 505                 510

Gly Pro Lys Lys Ser Thr Asn Leu Val Lys Asn Lys Cys Val Asn Phe
            515                 520                 525

Asn Phe Asn Gly Leu Thr Gly Thr Gly Val Leu Thr Glu Ser Asn Lys
            530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
                580                 585                 590

Asn Gln Val Ala Val Leu Tyr Gln Gly Val Asn Cys Thr Glu Val Pro
            595                 600                 605

Val Ala Ile His Ala Asp Gln Leu Thr Pro Thr Trp Arg Val Tyr Ser
            610                 615                 620

Thr Gly Ser Asn Val Phe Gln Thr Arg Ala Gly Cys Leu Ile Gly Ala
625                 630                 635                 640
```

```
Glu His Val Asn Asn Ser Tyr Glu Cys Asp Ile Pro Ile Gly Ala Gly
                    645                 650                 655

Ile Cys Ala Ser Tyr Gln Thr Gln Thr Asn Ser Pro Arg Arg Ala Ala
            660                 665                 670

Ser Val Ala Ser Gln Ser Ile Ile Ala Tyr Thr Met Ser Leu Gly Ala
            675                 680                 685

Glu Asn Ser Val Ala Tyr Ser Asn Asn Ser Ile Ala Ile Pro Thr Asn
690                 695                 700

Phe Thr Ile Ser Val Thr Thr Glu Ile Leu Pro Val Ser Met Thr Lys
705                 710                 715                 720

Thr Ser Val Asp Cys Thr Met Tyr Ile Cys Gly Asp Ser Thr Glu Cys
                725                 730                 735

Ser Asn Leu Leu Leu Gln Tyr Gly Ser Phe Cys Thr Gln Leu Asn Arg
            740                 745                 750

Ala Leu Thr Gly Ile Ala Val Glu Gln Asp Lys Asn Thr Gln Glu Val
            755                 760                 765

Phe Ala Gln Val Lys Gln Ile Tyr Lys Thr Pro Pro Ile Lys Asp Phe
770                 775                 780

Gly Gly Phe Asn Phe Ser Gln Ile Leu Pro Asp Pro Ser Lys Pro Ser
785                 790                 795                 800

Lys Arg Ser Phe Ile Glu Asp Leu Leu Phe Asn Lys Val Thr Leu Ala
                805                 810                 815

Asp Ala Gly Phe Ile Lys Gln Tyr Gly Asp Cys Leu Gly Asp Ile Ala
            820                 825                 830

Ala Arg Asp Leu Ile Cys Ala Gln Lys Phe Asn Gly Leu Thr Val Leu
            835                 840                 845

Pro Pro Leu Leu Thr Asp Glu Met Ile Ala Gln Tyr Thr Ser Ala Leu
850                 855                 860

Leu Ala Gly Thr Ile Thr Ser Gly Trp Thr Phe Gly Ala Gly Ala Ala
865                 870                 875                 880

Leu Gln Ile Pro Phe Ala Met Gln Met Ala Tyr Arg Phe Asn Gly Ile
                885                 890                 895

Gly Val Thr Gln Asn Val Leu Tyr Glu Asn Gln Lys Leu Ile Ala Asn
            900                 905                 910

Gln Phe Asn Ser Ala Ile Gly Lys Ile Gln Asp Ser Leu Ser Ser Thr
            915                 920                 925

Ala Ser Ala Leu Gly Lys Leu Gln Asp Val Val Asn Gln Asn Ala Gln
930                 935                 940

Ala Leu Asn Thr Leu Val Lys Gln Leu Ser Ser Asn Phe Gly Ala Ile
945                 950                 955                 960

Ser Ser Val Leu Asn Asp Ile Leu Ser Arg Leu Asp Pro Pro Glu Ala
                965                 970                 975

Glu Val Gln Ile Asp Arg Leu Ile Thr Gly Arg Leu Gln Ser Leu Gln
            980                 985                 990

Thr Tyr Val Thr Gln Gln Leu Ile Arg Ala Ala Glu Ile Arg Ala Ser
            995                 1000                1005

Ala Asn Leu Ala Ala Thr Lys Met Ser Glu Cys Val Leu Gly Gln Ser
    1010                1015                1020

Lys Arg Val Asp Phe Cys Gly Lys Gly Tyr His Leu Met Ser Phe Pro
1025                1030                1035                1040

Gln Ser Ala Pro His Gly Val Val Phe Leu His Val Thr Tyr Val Pro
                1045                1050                1055

Ala Gln Glu Lys Asn Phe Thr Thr Ala Pro Ala Ile Cys His Asp Gly
```

```
                    1060                1065                1070
Lys Ala His Phe Pro Arg Glu Gly Val Phe Val Ser Asn Gly Thr His
        1075                1080                1085

Trp Phe Val Thr Gln Arg Asn Phe Tyr Glu Pro Gln Ile Ile Thr Thr
        1090                1095                1100

Asp Asn Thr Phe Val Ser Gly Asn Cys Asp Val Val Ile Gly Ile Val
1105                1110                1115                1120

Asn Asn Thr Val Tyr Asp Pro Leu Gln Pro Glu Leu Asp Ser Phe Lys
                1125                1130                1135

Glu Glu Leu Asp Lys Tyr Phe Lys Asn His Thr Ser Pro Asp Val Asp
                1140                1145                1150

Leu Gly Asp Ile Ser Gly Ile Asn Ala Ser Val Val Asn Ile Gln Lys
        1155                1160                1165

Glu Ile Asp Arg Leu Asn Glu Val Ala Lys Asn Leu Asn Glu Ser Leu
        1170                1175                1180

Ile Asp Leu Gln Glu Leu Gly Lys Tyr Glu Gln
1185                1190                1195
```

<210> SEQ ID NO 40
<211> LENGTH: 1195
<212> TYPE: PRT
<213> ORGANISM: Artificial Sequence
<220> FEATURE:
<223> OTHER INFORMATION: Synthetic construct

<400> SEQUENCE: 40

```
Gln Cys Val Asn Phe Thr Asn Arg Thr Gln Leu Pro Ser Ala Tyr Thr
1               5                   10                  15

Asn Ser Phe Thr Arg Gly Val Tyr Tyr Pro Asp Lys Val Phe Arg Ser
                20                  25                  30

Ser Val Leu His Ser Thr Gln Asp Leu Phe Leu Pro Phe Phe Ser Asn
            35                  40                  45

Val Thr Trp Phe His Ala Ile His Val Ser Gly Thr Asn Gly Thr Lys
        50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
                100                 105                 110

Val Val Ile Lys Val Cys Glu Phe Gln Phe Cys Asn Tyr Pro Phe Leu
            115                 120                 125

Gly Val Tyr Tyr His Lys Asn Asn Lys Ser Trp Met Glu Ser Glu Phe
        130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Ser Glu Phe Val Phe Lys Asn Ile Asp Gly Tyr Phe Lys Ile Tyr Ser
                180                 185                 190

Lys His Thr Pro Ile Asn Leu Val Arg Asp Leu Pro Gln Gly Phe Ser
            195                 200                 205

Ala Leu Glu Pro Leu Val Asp Leu Pro Ile Gly Ile Asn Ile Thr Arg
        210                 215                 220

Phe Gln Thr Leu Leu Ala Leu His Arg Ser Tyr Leu Thr Pro Gly Asp
```

```
             225                 230                 235                 240
Ser Ser Ser Gly Trp Thr Ala Gly Ala Ala Tyr Tyr Val Gly Tyr
                245                 250                 255

Leu Gln Pro Arg Thr Phe Leu Leu Lys Tyr Asn Glu Asn Gly Thr Ile
                260                 265                 270

Thr Asp Ala Val Asp Cys Ala Leu Asp Pro Leu Ser Glu Thr Lys Cys
                275                 280                 285

Thr Leu Lys Ser Phe Thr Val Glu Lys Gly Ile Tyr Gln Thr Ser Asn
            290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
                340                 345                 350

Ser Val Leu Tyr Asn Ser Ala Ser Phe Ser Thr Phe Lys Cys Tyr Gly
                355                 360                 365

Val Ser Pro Thr Lys Leu Asn Asp Leu Cys Phe Thr Asn Val Tyr Ala
            370                 375                 380

Asp Ser Phe Val Ile Arg Gly Asp Glu Val Arg Gln Ile Ala Pro Gly
385                 390                 395                 400

Gln Thr Gly Thr Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
                420                 425                 430

Gly Gly Asn Tyr Asn Tyr Leu Tyr Arg Leu Phe Arg Lys Ser Asn Leu
            435                 440                 445

Lys Pro Phe Glu Arg Asp Ile Ser Thr Glu Ile Tyr Gln Ala Gly Ser
            450                 455                 460

Thr Pro Cys Asn Gly Val Lys Gly Phe Asn Cys Tyr Phe Pro Leu Gln
465                 470                 475                 480

Ser Tyr Gly Phe Gln Pro Thr Tyr Gly Val Gly Tyr Gln Pro Tyr Arg
                485                 490                 495

Val Val Val Leu Ser Phe Glu Leu Leu His Ala Pro Ala Thr Val Cys
                500                 505                 510

Gly Pro Lys Lys Ser Thr Asn Leu Val Lys Asn Lys Cys Val Asn Phe
            515                 520                 525

Asn Phe Asn Gly Leu Thr Gly Thr Gly Val Leu Thr Glu Ser Asn Lys
            530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
                580                 585                 590

Asn Gln Val Ala Val Leu Tyr Gln Gly Val Asn Cys Thr Glu Val Pro
            595                 600                 605

Val Ala Ile His Ala Asp Gln Leu Thr Pro Thr Trp Arg Val Tyr Ser
            610                 615                 620

Thr Gly Ser Asn Val Phe Gln Thr Arg Ala Gly Cys Leu Ile Gly Ala
625                 630                 635                 640

Glu Tyr Val Asn Asn Ser Tyr Glu Cys Asp Ile Pro Ile Gly Ala Gly
                645                 650                 655
```

-continued

```
Ile Cys Ala Ser Tyr Gln Thr Gln Thr Asn Ser Pro Arg Ala Arg
            660                 665                 670

Ser Val Ala Ser Gln Ser Ile Ile Ala Tyr Thr Met Ser Leu Gly Ala
            675                 680                 685

Glu Asn Ser Val Ala Tyr Ser Asn Asn Ser Ile Ala Ile Pro Thr Asn
690                 695                 700

Phe Thr Ile Ser Val Thr Thr Glu Ile Leu Pro Val Ser Met Thr Lys
705                 710                 715                 720

Thr Ser Val Asp Cys Thr Met Tyr Ile Cys Gly Asp Ser Thr Glu Cys
                725                 730                 735

Ser Asn Leu Leu Leu Gln Tyr Gly Ser Phe Cys Thr Gln Leu Asn Arg
            740                 745                 750

Ala Leu Thr Gly Ile Ala Val Glu Gln Asp Lys Asn Thr Gln Glu Val
            755                 760                 765

Phe Ala Gln Val Lys Gln Ile Tyr Lys Thr Pro Pro Ile Lys Asp Phe
            770                 775                 780

Gly Gly Phe Asn Phe Ser Gln Ile Leu Pro Asp Pro Ser Lys Pro Ser
785                 790                 795                 800

Lys Arg Ser Phe Ile Glu Asp Leu Leu Phe Asn Lys Val Thr Leu Ala
                805                 810                 815

Asp Ala Gly Phe Ile Lys Gln Tyr Gly Asp Cys Leu Gly Asp Ile Ala
            820                 825                 830

Ala Arg Asp Leu Ile Cys Ala Gln Lys Phe Asn Gly Leu Thr Val Leu
            835                 840                 845

Pro Pro Leu Leu Thr Asp Glu Met Ile Ala Gln Tyr Thr Ser Ala Leu
850                 855                 860

Leu Ala Gly Thr Ile Thr Ser Gly Trp Thr Phe Gly Ala Gly Ala Ala
865                 870                 875                 880

Leu Gln Ile Pro Phe Ala Met Gln Met Ala Tyr Arg Phe Asn Gly Ile
                885                 890                 895

Gly Val Thr Gln Asn Val Leu Tyr Glu Asn Gln Lys Leu Ile Ala Asn
            900                 905                 910

Gln Phe Asn Ser Ala Ile Gly Lys Ile Gln Asp Ser Leu Ser Ser Thr
            915                 920                 925

Ala Ser Ala Leu Gly Lys Leu Gln Asp Val Val Asn Gln Asn Ala Gln
930                 935                 940

Ala Leu Asn Thr Leu Val Lys Gln Leu Ser Ser Asn Phe Gly Ala Ile
945                 950                 955                 960

Ser Ser Val Leu Asn Asp Ile Leu Ser Arg Leu Asp Lys Val Glu Ala
                965                 970                 975

Glu Val Gln Ile Asp Arg Leu Ile Thr Gly Arg Leu Gln Ser Leu Gln
            980                 985                 990

Thr Tyr Val Thr Gln Gln Leu Ile Arg Ala Ala Glu Ile Arg Ala Ser
            995                 1000                1005

Ala Asn Leu Ala Ala Ile Lys Met Ser Glu Cys Val Leu Gly Gln Ser
            1010                1015                1020

Lys Arg Val Asp Phe Cys Gly Lys Gly Tyr His Leu Met Ser Phe Pro
1025                1030                1035                1040

Gln Ser Ala Pro His Gly Val Val Phe Leu His Val Thr Tyr Val Pro
                1045                1050                1055

Ala Gln Glu Lys Asn Phe Thr Thr Ala Pro Ala Ile Cys His Asp Gly
            1060                1065                1070
```

-continued

```
Lys Ala His Phe Pro Arg Glu Gly Val Phe Val Ser Asn Gly Thr His
        1075                1080                1085

Trp Phe Val Thr Gln Arg Asn Phe Tyr Glu Pro Gln Ile Ile Thr Thr
    1090                1095                1100

Asp Asn Thr Phe Val Ser Gly Asn Cys Asp Val Val Ile Gly Ile Val
1105                1110                1115                1120

Asn Asn Thr Val Tyr Asp Pro Leu Gln Pro Glu Leu Asp Ser Phe Lys
            1125                1130                1135

Glu Glu Leu Asp Lys Tyr Phe Lys Asn His Thr Ser Pro Asp Val Asp
            1140                1145                1150

Leu Gly Asp Ile Ser Gly Ile Asn Ala Ser Val Val Asn Ile Gln Lys
        1155                1160                1165

Glu Ile Asp Arg Leu Asn Glu Val Ala Lys Asn Leu Asn Glu Ser Leu
    1170                1175                1180

Ile Asp Leu Gln Glu Leu Gly Lys Tyr Glu Gln
1185                1190                1195

<210> SEQ ID NO 41
<211> LENGTH: 1195
<212> TYPE: PRT
<213> ORGANISM: Artificial Sequence
<220> FEATURE:
<223> OTHER INFORMATION: Synthetic construct

<400> SEQUENCE: 41

Gln Cys Val Asn Phe Thr Asn Arg Thr Gln Leu Pro Ser Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Tyr Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Ser Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205

Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240
```

-continued

```
Ser Ser Ser Gly Trp Thr Ala Gly Ala Ala Tyr Val Gly Tyr
            245             250             255
Leu Gln Pro Arg Thr Phe Leu Leu Lys Tyr Asn Glu Asn Gly Thr Ile
        260             265             270
Thr Asp Ala Val Asp Cys Ala Leu Asp Pro Leu Ser Glu Thr Lys Cys
        275             280             285
Thr Leu Lys Ser Phe Thr Val Glu Lys Gly Ile Tyr Gln Thr Ser Asn
        290             295             300
Phe Arg Val Gln Pro Thr Glu Ser Ile Val Arg Phe Pro Asn Ile Thr
305             310             315             320
Asn Leu Cys Pro Phe Gly Glu Val Phe Asn Ala Thr Arg Phe Ala Ser
            325             330             335
Val Tyr Ala Trp Asn Arg Lys Arg Ile Ser Asn Cys Val Ala Asp Tyr
            340             345             350
Ser Val Leu Tyr Asn Ser Ala Ser Phe Ser Thr Phe Lys Cys Tyr Gly
            355             360             365
Val Ser Pro Thr Lys Leu Asn Asp Leu Cys Phe Thr Asn Val Tyr Ala
            370             375             380
Asp Ser Phe Val Ile Arg Gly Asp Glu Val Arg Gln Ile Ala Pro Gly
385             390             395             400
Gln Thr Gly Thr Ile Ala Asp Tyr Asn Tyr Lys Leu Pro Asp Asp Phe
            405             410             415
Thr Gly Cys Val Ile Ala Trp Asn Ser Asn Asn Leu Asp Ser Lys Val
            420             425             430
Gly Gly Asn Tyr Asn Tyr Leu Tyr Arg Leu Phe Arg Lys Ser Asn Leu
            435             440             445
Lys Pro Phe Glu Arg Asp Ile Ser Thr Glu Ile Tyr Gln Ala Gly Ser
        450             455             460
Thr Pro Cys Asn Gly Val Lys Gly Phe Asn Cys Tyr Phe Pro Leu Gln
465             470             475             480
Ser Tyr Gly Phe Gln Pro Thr Tyr Gly Val Gly Tyr Gln Pro Tyr Arg
            485             490             495
Val Val Val Leu Ser Phe Glu Leu Leu His Ala Pro Ala Thr Val Cys
            500             505             510
Gly Pro Lys Lys Ser Thr Asn Leu Val Lys Asn Lys Cys Val Asn Phe
        515             520             525
Asn Phe Asn Gly Leu Thr Gly Thr Gly Val Leu Thr Glu Ser Asn Lys
        530             535             540
Lys Phe Leu Pro Phe Gln Gln Phe Gly Arg Asp Ile Ala Asp Thr Thr
545             550             555             560
Asp Ala Val Arg Asp Pro Gln Thr Leu Glu Ile Leu Asp Ile Thr Pro
            565             570             575
Cys Ser Phe Gly Gly Val Ser Val Ile Thr Pro Gly Thr Asn Thr Ser
            580             585             590
Asn Gln Val Ala Val Leu Tyr Gln Gly Val Asn Cys Thr Glu Val Pro
            595             600             605
Val Ala Ile His Ala Asp Gln Leu Thr Pro Thr Trp Arg Val Tyr Ser
            610             615             620
Thr Gly Ser Asn Val Phe Gln Thr Arg Ala Gly Cys Leu Ile Gly Ala
625             630             635             640
Glu Tyr Val Asn Asn Ser Tyr Glu Cys Asp Ile Pro Ile Gly Ala Gly
            645             650             655
Ile Cys Ala Ser Tyr Gln Thr Gln Thr Asn Ser Pro Arg Arg Ala Ala
```

```
                660             665             670
Ser Val Ala Ser Gln Ser Ile Ile Ala Tyr Thr Met Ser Leu Gly Ala
            675             680             685

Glu Asn Ser Val Ala Tyr Ser Asn Asn Ser Ile Ala Ile Pro Thr Asn
            690             695             700

Phe Thr Ile Ser Val Thr Thr Glu Ile Leu Pro Val Ser Met Thr Lys
705             710             715             720

Thr Ser Val Asp Cys Thr Met Tyr Ile Cys Gly Asp Ser Thr Glu Cys
                725             730             735

Ser Asn Leu Leu Leu Gln Tyr Gly Ser Phe Cys Thr Gln Leu Asn Arg
            740             745             750

Ala Leu Thr Gly Ile Ala Val Glu Gln Asp Lys Asn Thr Gln Glu Val
            755             760             765

Phe Ala Gln Val Lys Gln Ile Tyr Lys Thr Pro Pro Ile Lys Asp Phe
            770             775             780

Gly Gly Phe Asn Phe Ser Gln Ile Leu Pro Asp Pro Ser Lys Pro Ser
785             790             795             800

Lys Arg Ser Phe Ile Glu Asp Leu Leu Phe Asn Lys Val Thr Leu Ala
                805             810             815

Asp Ala Gly Phe Ile Lys Gln Tyr Gly Asp Cys Leu Gly Asp Ile Ala
                820             825             830

Ala Arg Asp Leu Ile Cys Ala Gln Lys Phe Asn Gly Leu Thr Val Leu
            835             840             845

Pro Pro Leu Leu Thr Asp Glu Met Ile Ala Gln Tyr Thr Ser Ala Leu
            850             855             860

Leu Ala Gly Thr Ile Thr Ser Gly Trp Thr Phe Gly Ala Gly Ala Ala
865             870             875             880

Leu Gln Ile Pro Phe Ala Met Gln Met Ala Tyr Arg Phe Asn Gly Ile
                885             890             895

Gly Val Thr Gln Asn Val Leu Tyr Glu Asn Gln Lys Leu Ile Ala Asn
            900             905             910

Gln Phe Asn Ser Ala Ile Gly Lys Ile Gln Asp Ser Leu Ser Ser Thr
            915             920             925

Ala Ser Ala Leu Gly Lys Leu Gln Asp Val Val Asn Gln Asn Ala Gln
            930             935             940

Ala Leu Asn Thr Leu Val Lys Gln Leu Ser Ser Asn Phe Gly Ala Ile
945             950             955             960

Ser Ser Val Leu Asn Asp Ile Leu Ser Arg Leu Asp Lys Val Glu Ala
                965             970             975

Glu Val Gln Ile Asp Arg Leu Ile Thr Gly Arg Leu Gln Ser Leu Gln
            980             985             990

Thr Tyr Val Thr Gln Gln Leu Ile Arg Ala Ala Glu Ile Arg Ala Ser
            995             1000            1005

Ala Asn Leu Ala Ala Ile Lys Met Ser Glu Cys Val Leu Gly Gln Ser
            1010            1015            1020

Lys Arg Val Asp Phe Cys Gly Lys Gly Tyr His Leu Met Ser Phe Pro
1025            1030            1035            1040

Gln Ser Ala Pro His Gly Val Val Phe Leu His Val Thr Tyr Val Pro
                1045            1050            1055

Ala Gln Glu Lys Asn Phe Thr Thr Ala Pro Ala Ile Cys His Asp Gly
            1060            1065            1070

Lys Ala His Phe Pro Arg Glu Gly Val Phe Val Ser Asn Gly Thr His
            1075            1080            1085
```

-continued

```
Trp Phe Val Thr Gln Arg Asn Phe Tyr Glu Pro Gln Ile Ile Thr Thr
    1090                1095                1100
Asp Asn Thr Phe Val Ser Gly Asn Cys Asp Val Val Gly Ile Val
1105                1110                1115                1120
Asn Asn Thr Val Tyr Asp Pro Leu Gln Pro Glu Leu Asp Ser Phe Lys
                1125                1130                1135
Glu Glu Leu Asp Lys Tyr Phe Lys Asn His Thr Ser Pro Asp Val Asp
                1140                1145                1150
Leu Gly Asp Ile Ser Gly Ile Asn Ala Ser Val Val Asn Ile Gln Lys
                1155                1160                1165
Glu Ile Asp Arg Leu Asn Glu Val Ala Lys Asn Leu Asn Glu Ser Leu
                1170                1175                1180
Ile Asp Leu Gln Glu Leu Gly Lys Tyr Glu Gln
1185                1190                1195

<210> SEQ ID NO 42
<211> LENGTH: 1195
<212> TYPE: PRT
<213> ORGANISM: Artificial Sequence
<220> FEATURE:
<223> OTHER INFORMATION: Synthetic construct

<400> SEQUENCE: 42

Gln Cys Val Asn Phe Thr Asn Arg Thr Gln Leu Pro Ser Ala Tyr Thr
1               5                   10                  15
Asn Ser Phe Thr Arg Gly Val Tyr Tyr Pro Asp Lys Val Phe Arg Ser
                20                  25                  30
Ser Val Leu His Ser Thr Gln Asp Leu Phe Leu Pro Phe Phe Ser Asn
                35                  40                  45
Val Thr Trp Phe His Ala Ile His Val Ser Gly Thr Asn Gly Thr Lys
            50                  55                  60
Arg Phe Asp Asn Pro Val Leu Pro Phe Asn Asp Gly Val Tyr Phe Ala
65              70                  75                  80
Ser Thr Glu Lys Ser Asn Ile Ile Arg Gly Trp Ile Phe Gly Thr Thr
                85                  90                  95
Leu Asp Ser Lys Thr Gln Ser Leu Leu Ile Val Asn Asn Ala Thr Asn
                100                 105                 110
Val Val Ile Lys Val Cys Glu Phe Gln Phe Cys Asn Tyr Pro Phe Leu
            115                 120                 125
Gly Val Tyr Tyr His Lys Asn Asn Lys Ser Trp Met Glu Ser Glu Phe
            130                 135                 140
Arg Val Tyr Ser Ser Ala Asn Asn Cys Thr Phe Glu Tyr Val Ser Gln
145             150                 155                 160
Pro Phe Leu Met Asp Leu Glu Gly Lys Gln Gly Asn Phe Lys Asn Leu
                165                 170                 175
Ser Glu Phe Val Phe Lys Asn Ile Asp Gly Tyr Phe Lys Ile Tyr Ser
                180                 185                 190
Lys His Thr Pro Ile Asn Leu Val Arg Asp Leu Pro Gln Gly Phe Ser
            195                 200                 205
Ala Leu Glu Pro Leu Val Asp Leu Pro Ile Gly Ile Asn Ile Thr Arg
        210                 215                 220
Phe Gln Thr Leu Leu Ala Leu His Arg Ser Tyr Leu Thr Pro Gly Asp
225             230                 235                 240
Ser Ser Ser Gly Trp Thr Ala Gly Ala Ala Ala Tyr Tyr Val Gly Tyr
                245                 250                 255
```

```
Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
            275                 280                 285

Thr Leu Lys Ser Phe Thr Val Glu Lys Gly Ile Tyr Gln Thr Ser Asn
            290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
            325                 330                 335

Val Tyr Ala Trp Asn Arg Lys Arg Ile Ser Asn Cys Val Ala Asp Tyr
            340                 345                 350

Ser Val Leu Tyr Asn Ser Ala Ser Phe Ser Thr Phe Lys Cys Tyr Gly
            355                 360                 365

Val Ser Pro Thr Lys Leu Asn Asp Leu Cys Phe Thr Asn Val Tyr Ala
            370                 375                 380

Asp Ser Phe Val Ile Arg Gly Asp Glu Val Arg Gln Ile Ala Pro Gly
385                 390                 395                 400

Gln Thr Gly Thr Ile Ala Asp Tyr Asn Tyr Lys Leu Pro Asp Asp Phe
            405                 410                 415

Thr Gly Cys Val Ile Ala Trp Asn Ser Asn Asn Leu Asp Ser Lys Val
            420                 425                 430

Gly Gly Asn Tyr Asn Tyr Leu Tyr Arg Leu Phe Arg Lys Ser Asn Leu
            435                 440                 445

Lys Pro Phe Glu Arg Asp Ile Ser Thr Glu Ile Tyr Gln Ala Gly Ser
            450                 455                 460

Thr Pro Cys Asn Gly Val Lys Gly Phe Asn Cys Tyr Phe Pro Leu Gln
465                 470                 475                 480

Ser Tyr Gly Phe Gln Pro Thr Tyr Gly Val Gly Tyr Gln Pro Tyr Arg
            485                 490                 495

Val Val Val Leu Ser Phe Glu Leu Leu His Ala Pro Ala Thr Val Cys
            500                 505                 510

Gly Pro Lys Lys Ser Thr Asn Leu Val Lys Asn Lys Cys Val Asn Phe
            515                 520                 525

Asn Phe Asn Gly Leu Thr Gly Thr Gly Val Leu Thr Glu Ser Asn Lys
            530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
            565                 570                 575

Cys Ser Phe Gly Gly Val Ser Val Ile Thr Pro Gly Thr Asn Thr Ser
            580                 585                 590

Asn Gln Val Ala Val Leu Tyr Gln Gly Val Asn Cys Thr Glu Val Pro
            595                 600                 605

Val Ala Ile His Ala Asp Gln Leu Thr Pro Thr Trp Arg Val Tyr Ser
            610                 615                 620

Thr Gly Ser Asn Val Phe Gln Thr Arg Ala Gly Cys Leu Ile Gly Ala
625                 630                 635                 640

Glu Tyr Val Asn Asn Ser Tyr Glu Cys Asp Ile Pro Ile Gly Ala Gly
            645                 650                 655

Ile Cys Ala Ser Tyr Gln Thr Gln Thr Asn Ser Pro Arg Arg Ala Arg
            660                 665                 670
```

```
Ser Val Ala Ser Gln Ser Ile Ile Ala Tyr Thr Met Ser Leu Gly Ala
            675                 680                 685

Glu Asn Ser Val Ala Tyr Ser Asn Asn Ser Ile Ala Ile Pro Thr Asn
        690                 695                 700

Phe Thr Ile Ser Val Thr Thr Glu Ile Leu Pro Val Ser Met Thr Lys
705                 710                 715                 720

Thr Ser Val Asp Cys Thr Met Tyr Ile Cys Gly Asp Ser Thr Glu Cys
                725                 730                 735

Ser Asn Leu Leu Leu Gln Tyr Gly Ser Phe Cys Thr Gln Leu Asn Arg
            740                 745                 750

Ala Leu Thr Gly Ile Ala Val Glu Gln Asp Lys Asn Thr Gln Glu Val
        755                 760                 765

Phe Ala Gln Val Lys Gln Ile Tyr Lys Thr Pro Pro Ile Lys Asp Phe
770                 775                 780

Gly Gly Phe Asn Phe Ser Gln Ile Leu Pro Asp Pro Ser Lys Pro Ser
785                 790                 795                 800

Lys Arg Ser Phe Ile Glu Asp Leu Leu Phe Asn Lys Val Thr Leu Ala
                805                 810                 815

Asp Ala Gly Phe Ile Lys Gln Tyr Gly Asp Cys Leu Gly Asp Ile Ala
            820                 825                 830

Ala Arg Asp Leu Ile Cys Ala Gln Lys Phe Asn Gly Leu Thr Val Leu
        835                 840                 845

Pro Pro Leu Leu Thr Asp Glu Met Ile Ala Gln Tyr Thr Ser Ala Leu
850                 855                 860

Leu Ala Gly Thr Ile Thr Ser Gly Trp Thr Phe Gly Ala Gly Ala Ala
865                 870                 875                 880

Leu Gln Ile Pro Phe Ala Met Gln Met Ala Tyr Arg Phe Asn Gly Ile
                885                 890                 895

Gly Val Thr Gln Asn Val Leu Tyr Glu Asn Gln Lys Leu Ile Ala Asn
            900                 905                 910

Gln Phe Asn Ser Ala Ile Gly Lys Ile Gln Asp Ser Leu Ser Ser Thr
        915                 920                 925

Ala Ser Ala Leu Gly Lys Leu Gln Asp Val Val Asn Gln Asn Ala Gln
930                 935                 940

Ala Leu Asn Thr Leu Val Lys Gln Leu Ser Ser Asn Phe Gly Ala Ile
945                 950                 955                 960

Ser Ser Val Leu Asn Asp Ile Leu Ser Arg Leu Asp Pro Pro Glu Ala
                965                 970                 975

Glu Val Gln Ile Asp Arg Leu Ile Thr Gly Arg Leu Gln Ser Leu Gln
            980                 985                 990

Thr Tyr Val Thr Gln Gln Leu Ile Arg Ala Ala Glu Ile Arg Ala Ser
        995                 1000                1005

Ala Asn Leu Ala Ala Ile Lys Met Ser Glu Cys Val Leu Gly Gln Ser
1010                1015                1020

Lys Arg Val Asp Phe Cys Gly Lys Gly Tyr His Leu Met Ser Phe Pro
1025                1030                1035                1040

Gln Ser Ala Pro His Gly Val Val Phe Leu His Val Thr Tyr Val Pro
                1045                1050                1055

Ala Gln Glu Lys Asn Phe Thr Thr Ala Pro Ala Ile Cys His Asp Gly
            1060                1065                1070

Lys Ala His Phe Pro Arg Glu Gly Val Phe Val Ser Asn Gly Thr His
        1075                1080                1085

Trp Phe Val Thr Gln Arg Asn Phe Tyr Glu Pro Gln Ile Ile Thr Thr
```

```
                1090                1095                1100

Asp Asn Thr Phe Val Ser Gly Asn Cys Asp Val Val Ile Gly Ile Val
1105                1110                1115                1120

Asn Asn Thr Val Tyr Asp Pro Leu Gln Pro Glu Leu Asp Ser Phe Lys
                1125                1130                1135

Glu Glu Leu Asp Lys Tyr Phe Lys Asn His Thr Ser Pro Asp Val Asp
                1140                1145                1150

Leu Gly Asp Ile Ser Gly Ile Asn Ala Ser Val Val Asn Ile Gln Lys
            1155                1160                1165

Glu Ile Asp Arg Leu Asn Glu Val Ala Lys Asn Leu Asn Glu Ser Leu
1170                1175                1180

Ile Asp Leu Gln Glu Leu Gly Lys Tyr Glu Gln
1185                1190                1195

<210> SEQ ID NO 43
<211> LENGTH: 1195
<212> TYPE: PRT
<213> ORGANISM: Artificial Sequence
<220> FEATURE:
<223> OTHER INFORMATION: Synthetic construct

<400> SEQUENCE: 43

Gln Cys Val Asn Phe Thr Asn Arg Thr Gln Leu Pro Ser Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Tyr Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Ser Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205

Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
                245                 250                 255

Leu Gln Pro Arg Thr Phe Leu Leu Lys Tyr Asn Glu Asn Gly Thr Ile
```

```
                260                 265                 270
Thr Asp Ala Val Asp Cys Ala Leu Asp Pro Leu Ser Glu Thr Lys Cys
            275                 280                 285

Thr Leu Lys Ser Phe Thr Val Glu Lys Gly Ile Tyr Gln Thr Ser Asn
        290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
            340                 345                 350

Ser Val Leu Tyr Asn Ser Ala Ser Phe Ser Thr Phe Lys Cys Tyr Gly
        355                 360                 365

Val Ser Pro Thr Lys Leu Asn Asp Leu Cys Phe Thr Asn Val Tyr Ala
    370                 375                 380

Asp Ser Phe Val Ile Arg Gly Asp Glu Val Arg Gln Ile Ala Pro Gly
385                 390                 395                 400

Gln Thr Gly Thr Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
            420                 425                 430

Gly Gly Asn Tyr Asn Tyr Leu Tyr Arg Leu Phe Arg Lys Ser Asn Leu
        435                 440                 445

Lys Pro Phe Glu Arg Asp Ile Ser Thr Glu Ile Tyr Gln Ala Gly Ser
    450                 455                 460

Thr Pro Cys Asn Gly Val Lys Gly Phe Asn Cys Tyr Phe Pro Leu Gln
465                 470                 475                 480

Ser Tyr Gly Phe Gln Pro Thr Tyr Gly Val Gly Tyr Gln Pro Tyr Arg
                485                 490                 495

Val Val Val Leu Ser Phe Glu Leu Leu His Ala Pro Ala Thr Val Cys
            500                 505                 510

Gly Pro Lys Lys Ser Thr Asn Leu Val Lys Asn Lys Cys Val Asn Phe
        515                 520                 525

Asn Phe Asn Gly Leu Thr Gly Thr Gly Val Leu Thr Glu Ser Asn Lys
    530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
            580                 585                 590

Asn Gln Val Ala Val Leu Tyr Gln Gly Val Asn Cys Thr Glu Val Pro
        595                 600                 605

Val Ala Ile His Ala Asp Gln Leu Thr Pro Thr Trp Arg Val Tyr Ser
    610                 615                 620

Thr Gly Ser Asn Val Phe Gln Thr Arg Ala Gly Cys Leu Ile Gly Ala
625                 630                 635                 640

Glu Tyr Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Arg Arg Ala Ala
            660                 665                 670

Ser Val Ala Ser Gln Ser Ile Ile Ala Tyr Thr Met Ser Leu Gly Ala
        675                 680                 685
```

-continued

```
Glu Asn Ser Val Ala Tyr Ser Asn Asn Ser Ile Ala Ile Pro Thr Asn
    690                 695                 700
Phe Thr Ile Ser Val Thr Thr Glu Ile Leu Pro Val Ser Met Thr Lys
705                 710                 715                 720
Thr Ser Val Asp Cys Thr Met Tyr Ile Cys Gly Asp Ser Thr Glu Cys
                725                 730                 735
Ser Asn Leu Leu Leu Gln Tyr Gly Ser Phe Cys Thr Gln Leu Asn Arg
            740                 745                 750
Ala Leu Thr Gly Ile Ala Val Glu Gln Asp Lys Asn Thr Gln Glu Val
        755                 760                 765
Phe Ala Gln Val Lys Gln Ile Tyr Lys Thr Pro Pro Ile Lys Asp Phe
    770                 775                 780
Gly Gly Phe Asn Phe Ser Gln Ile Leu Pro Asp Pro Ser Lys Pro Ser
785                 790                 795                 800
Lys Arg Ser Phe Ile Glu Asp Leu Leu Phe Asn Lys Val Thr Leu Ala
                805                 810                 815
Asp Ala Gly Phe Ile Lys Gln Tyr Gly Asp Cys Leu Gly Asp Ile Ala
            820                 825                 830
Ala Arg Asp Leu Ile Cys Ala Gln Lys Phe Asn Gly Leu Thr Val Leu
        835                 840                 845
Pro Pro Leu Leu Thr Asp Glu Met Ile Ala Gln Tyr Thr Ser Ala Leu
    850                 855                 860
Leu Ala Gly Thr Ile Thr Ser Gly Trp Thr Phe Gly Ala Gly Ala Ala
865                 870                 875                 880
Leu Gln Ile Pro Phe Ala Met Gln Met Ala Tyr Arg Phe Asn Gly Ile
                885                 890                 895
Gly Val Thr Gln Asn Val Leu Tyr Glu Asn Gln Lys Leu Ile Ala Asn
            900                 905                 910
Gln Phe Asn Ser Ala Ile Gly Lys Ile Gln Asp Ser Leu Ser Ser Thr
        915                 920                 925
Ala Ser Ala Leu Gly Lys Leu Gln Asp Val Val Asn Gln Asn Ala Gln
    930                 935                 940
Ala Leu Asn Thr Leu Val Lys Gln Leu Ser Ser Asn Phe Gly Ala Ile
945                 950                 955                 960
Ser Ser Val Leu Asn Asp Ile Leu Ser Arg Leu Asp Pro Pro Glu Ala
                965                 970                 975
Glu Val Gln Ile Asp Arg Leu Ile Thr Gly Arg Leu Gln Ser Leu Gln
            980                 985                 990
Thr Tyr Val Thr Gln Gln Leu Ile Arg Ala Ala Glu Ile Arg Ala Ser
        995                 1000                1005
Ala Asn Leu Ala Ala Ile Lys Met Ser Glu Cys Val Leu Gly Gln Ser
    1010                1015                1020
Lys Arg Val Asp Phe Cys Gly Lys Gly Tyr His Leu Met Ser Phe Pro
1025                1030                1035                1040
Gln Ser Ala Pro His Gly Val Val Phe Leu His Val Thr Tyr Val Pro
                1045                1050                1055
Ala Gln Glu Lys Asn Phe Thr Thr Ala Pro Ala Ile Cys His Asp Gly
            1060                1065                1070
Lys Ala His Phe Pro Arg Glu Gly Val Phe Val Ser Asn Gly Thr His
        1075                1080                1085
Trp Phe Val Thr Gln Arg Asn Phe Tyr Glu Pro Gln Ile Ile Thr Thr
    1090                1095                1100
```

```
Asp Asn Thr Phe Val Ser Gly Asn Cys Asp Val Val Ile Gly Ile Val
1105                1110                1115                1120

Asn Asn Thr Val Tyr Asp Pro Leu Gln Pro Glu Leu Asp Ser Phe Lys
            1125                1130                1135

Glu Glu Leu Asp Lys Tyr Phe Lys Asn His Thr Ser Pro Asp Val Asp
        1140                1145                1150

Leu Gly Asp Ile Ser Gly Ile Asn Ala Ser Val Val Asn Ile Gln Lys
    1155                1160                1165

Glu Ile Asp Arg Leu Asn Glu Val Ala Lys Asn Leu Asn Glu Ser Leu
1170                1175                1180

Ile Asp Leu Gln Glu Leu Gly Lys Tyr Glu Gln
1185                1190                1195
```

<210> SEQ ID NO 44
<211> LENGTH: 1193
<212> TYPE: PRT
<213> ORGANISM: Artificial Sequence
<220> FEATURE:
<223> OTHER INFORMATION: Synthetic construct

<400> SEQUENCE: 44

```
Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile Ser Gly Thr Asn Gly Thr Lys Arg Phe
50                  55                  60

Asp Asn Pro Val Leu Pro Phe Asn Asp Gly Val Tyr Phe Ala Ser Thr
65                  70                  75                  80

Glu Lys Ser Asn Ile Ile Arg Gly Trp Ile Phe Gly Thr Thr Leu Asp
                85                  90                  95

Ser Lys Thr Gln Ser Leu Leu Ile Val Asn Asn Ala Thr Asn Val Val
            100                 105                 110

Ile Lys Val Cys Glu Phe Gln Phe Cys Asn Asp Pro Phe Leu Gly Val
        115                 120                 125

Tyr Tyr His Lys Asn Asn Lys Ser Trp Met Glu Ser Glu Phe Arg Val
130                 135                 140

Tyr Ser Ser Ala Asn Asn Cys Thr Phe Glu Tyr Val Ser Gln Pro Phe
145                 150                 155                 160

Leu Met Asp Leu Glu Gly Lys Gln Gly Asn Phe Lys Asn Leu Arg Glu
                165                 170                 175

Phe Val Phe Lys Asn Ile Asp Gly Tyr Phe Lys Ile Tyr Ser Lys His
            180                 185                 190

Thr Pro Ile Asn Leu Val Arg Asp Leu Pro Gln Gly Phe Ser Ala Leu
        195                 200                 205

Glu Pro Leu Val Asp Leu Pro Ile Gly Ile Asn Ile Thr Arg Phe Gln
    210                 215                 220

Thr Leu Leu Ala Leu His Arg Ser Tyr Leu Thr Pro Gly Asp Ser Ser
225                 230                 235                 240

Ser Gly Trp Thr Ala Gly Ala Ala Ala Tyr Tyr Val Gly Tyr Leu Gln
                245                 250                 255

Pro Arg Thr Phe Leu Leu Lys Tyr Asn Glu Asn Gly Thr Ile Thr Asp
            260                 265                 270
```

-continued

```
Ala Val Asp Cys Ala Leu Asp Pro Leu Ser Glu Thr Lys Cys Thr Leu
            275                 280                 285

Lys Ser Phe Thr Val Glu Lys Gly Ile Tyr Gln Thr Ser Asn Phe Arg
290                 295                 300

Val Gln Pro Thr Glu Ser Ile Val Arg Phe Pro Asn Ile Thr Asn Leu
305                 310                 315                 320

Cys Pro Phe Gly Glu Val Phe Asn Ala Thr Arg Phe Ala Ser Val Tyr
                325                 330                 335

Ala Trp Asn Arg Lys Arg Ile Ser Asn Cys Val Ala Asp Tyr Ser Val
            340                 345                 350

Leu Tyr Asn Ser Ala Ser Phe Ser Thr Phe Lys Cys Tyr Gly Val Ser
        355                 360                 365

Pro Thr Lys Leu Asn Asp Leu Cys Phe Thr Asn Val Tyr Ala Asp Ser
370                 375                 380

Phe Val Ile Arg Gly Asp Glu Val Arg Gln Ile Ala Pro Gly Gln Thr
385                 390                 395                 400

Gly Lys Ile Ala Asp Tyr Asn Tyr Lys Leu Pro Asp Asp Phe Thr Gly
                405                 410                 415

Cys Val Ile Ala Trp Asn Ser Asn Asn Leu Asp Ser Lys Val Gly Gly
            420                 425                 430

Asn Tyr Asn Tyr Leu Tyr Arg Leu Phe Arg Lys Ser Asn Leu Lys Pro
        435                 440                 445

Phe Glu Arg Asp Ile Ser Thr Glu Ile Tyr Gln Ala Gly Ser Thr Pro
    450                 455                 460

Cys Asn Gly Val Glu Gly Phe Asn Cys Tyr Phe Pro Leu Gln Ser Tyr
465                 470                 475                 480

Gly Phe Gln Pro Thr Tyr Gly Val Gly Tyr Gln Pro Tyr Arg Val Val
                485                 490                 495

Val Leu Ser Phe Glu Leu Leu His Ala Pro Ala Thr Val Cys Gly Pro
            500                 505                 510

Lys Lys Ser Thr Asn Leu Val Lys Asn Lys Cys Val Asn Phe Asn Phe
        515                 520                 525

Asn Gly Leu Thr Gly Thr Gly Val Leu Thr Glu Ser Asn Lys Lys Phe
    530                 535                 540

Leu Pro Phe Gln Gln Phe Gly Arg Asp Ile Ala Asp Thr Thr Asp Ala
545                 550                 555                 560

Val Arg Asp Pro Gln Thr Leu Glu Ile Leu Asp Ile Thr Pro Cys Ser
                565                 570                 575

Phe Gly Gly Val Ser Val Ile Thr Pro Gly Thr Asn Thr Ser Asn Gln
            580                 585                 590

Val Ala Val Leu Tyr Gln Gly Val Asn Cys Thr Glu Val Pro Val Ala
        595                 600                 605

Ile His Ala Asp Gln Leu Thr Pro Thr Trp Arg Val Tyr Ser Thr Gly
610                 615                 620

Ser Asn Val Phe Gln Thr Arg Ala Gly Cys Leu Ile Gly Ala Glu His
625                 630                 635                 640

Val Asn Asn Ser Tyr Glu Cys Asp Ile Pro Ile Gly Ala Gly Ile Cys
                645                 650                 655

Ala Ser Tyr Gln Thr Gln Thr Asn Ser His Arg Arg Ala Arg Ser Val
            660                 665                 670

Ala Ser Gln Ser Ile Ile Ala Tyr Thr Met Ser Leu Gly Ala Glu Asn
        675                 680                 685

Ser Val Ala Tyr Ser Asn Asn Ser Ile Ala Ile Pro Thr Asn Phe Thr
```

```
            690                 695                 700
Ile Ser Val Thr Thr Glu Ile Leu Pro Val Ser Met Thr Lys Thr Ser
705                 710                 715                 720
Val Asp Cys Thr Met Tyr Ile Cys Gly Asp Ser Thr Glu Cys Ser Asn
                    725                 730                 735
Leu Leu Leu Gln Tyr Gly Ser Phe Cys Thr Gln Leu Asn Arg Ala Leu
                740                 745                 750
Thr Gly Ile Ala Val Glu Gln Asp Lys Asn Thr Gln Glu Val Phe Ala
            755                 760                 765
Gln Val Lys Gln Ile Tyr Lys Thr Pro Pro Ile Lys Asp Phe Gly Gly
        770                 775                 780
Phe Asn Phe Ser Gln Ile Leu Pro Asp Pro Ser Lys Pro Ser Lys Arg
785                 790                 795                 800
Ser Phe Ile Glu Asp Leu Leu Phe Asn Lys Val Thr Leu Ala Asp Ala
                    805                 810                 815
Gly Phe Ile Lys Gln Tyr Gly Asp Cys Leu Gly Asp Ile Ala Ala Arg
                820                 825                 830
Asp Leu Ile Cys Ala Gln Lys Phe Asn Gly Leu Thr Val Leu Pro Pro
            835                 840                 845
Leu Leu Thr Asp Glu Met Ile Ala Gln Tyr Thr Ser Ala Leu Leu Ala
        850                 855                 860
Gly Thr Ile Thr Ser Gly Trp Thr Phe Gly Ala Gly Ala Ala Leu Gln
865                 870                 875                 880
Ile Pro Phe Ala Met Gln Met Ala Tyr Arg Phe Asn Gly Ile Gly Val
                    885                 890                 895
Thr Gln Asn Val Leu Tyr Glu Asn Gln Lys Leu Ile Ala Asn Gln Phe
                900                 905                 910
Asn Ser Ala Ile Gly Lys Ile Gln Asp Ser Leu Ser Ser Thr Ala Ser
            915                 920                 925
Ala Leu Gly Lys Leu Gln Asp Val Val Asn Gln Asn Ala Gln Ala Leu
        930                 935                 940
Asn Thr Leu Val Lys Gln Leu Ser Ser Asn Phe Gly Ala Ile Ser Ser
945                 950                 955                 960
Val Leu Asn Asp Ile Leu Ser Arg Leu Asp Lys Val Glu Ala Glu Val
                    965                 970                 975
Gln Ile Asp Arg Leu Ile Thr Gly Arg Leu Gln Ser Leu Gln Thr Tyr
                980                 985                 990
Val Thr Gln Gln Leu Ile Arg Ala Ala Glu Ile Arg Ala Ser Ala Asn
            995                 1000                1005
Leu Ala Ala Thr Lys Met Ser Glu Cys Val Leu Gly Gln Ser Lys Arg
        1010                1015                1020
Val Asp Phe Cys Gly Lys Gly Tyr His Leu Met Ser Phe Pro Gln Ser
1025                1030                1035                1040
Ala Pro His Gly Val Val Phe Leu His Val Thr Tyr Val Pro Ala Gln
                    1045                1050                1055
Glu Lys Asn Phe Thr Thr Ala Pro Ala Ile Cys His Asp Gly Lys Ala
                1060                1065                1070
His Phe Pro Arg Glu Gly Val Phe Val Ser Asn Gly Thr His Trp Phe
            1075                1080                1085
Val Thr Gln Arg Asn Phe Tyr Glu Pro Gln Ile Ile Thr Thr Asp Asn
        1090                1095                1100
Thr Phe Val Ser Gly Asn Cys Asp Val Val Ile Gly Ile Val Asn Asn
1105                1110                1115                1120
```

-continued

```
Thr Val Tyr Asp Pro Leu Gln Pro Glu Leu Asp Ser Phe Lys Glu Glu
            1125                1130                1135

Leu Asp Lys Tyr Phe Lys Asn His Thr Ser Pro Asp Val Asp Leu Gly
            1140                1145                1150

Asp Ile Ser Gly Ile Asn Ala Ser Val Val Asn Ile Gln Lys Glu Ile
            1155                1160                1165

Asp Arg Leu Asn Glu Val Ala Lys Asn Leu Asn Glu Ser Leu Ile Asp
1170                1175                1180

Leu Gln Glu Leu Gly Lys Tyr Glu Gln
1185                1190

<210> SEQ ID NO 45
<211> LENGTH: 1193
<212> TYPE: PRT
<213> ORGANISM: Artificial Sequence
<220> FEATURE:
<223> OTHER INFORMATION: Synthetic construct

<400> SEQUENCE: 45

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile Ser Gly Thr Asn Gly Thr Lys Arg Phe
    50                  55                  60

Asp Asn Pro Val Leu Pro Phe Asn Asp Gly Val Tyr Phe Ala Ser Thr
65                  70                  75                  80

Glu Lys Ser Asn Ile Ile Arg Gly Trp Ile Phe Gly Thr Thr Leu Asp
                85                  90                  95

Ser Lys Thr Gln Ser Leu Leu Ile Val Asn Asn Ala Thr Asn Val Val
            100                 105                 110

Ile Lys Val Cys Glu Phe Gln Phe Cys Asn Asp Pro Phe Leu Gly Val
        115                 120                 125

Tyr Tyr His Lys Asn Asn Lys Ser Trp Met Glu Ser Glu Phe Arg Val
    130                 135                 140

Tyr Ser Ser Ala Asn Asn Cys Thr Phe Glu Tyr Val Ser Gln Pro Phe
145                 150                 155                 160

Leu Met Asp Leu Glu Gly Lys Gln Gly Asn Phe Lys Asn Leu Arg Glu
                165                 170                 175

Phe Val Phe Lys Asn Ile Asp Gly Tyr Phe Lys Ile Tyr Ser Lys His
            180                 185                 190

Thr Pro Ile Asn Leu Val Arg Asp Leu Pro Gln Gly Phe Ser Ala Leu
        195                 200                 205

Glu Pro Leu Val Asp Leu Pro Ile Gly Ile Asn Ile Thr Arg Phe Gln
    210                 215                 220

Thr Leu Leu Ala Leu His Arg Ser Tyr Leu Thr Pro Gly Asp Ser Ser
225                 230                 235                 240

Ser Gly Trp Thr Ala Gly Ala Ala Ala Tyr Tyr Val Gly Tyr Leu Gln
                245                 250                 255

Pro Arg Thr Phe Leu Leu Lys Tyr Asn Glu Asn Gly Thr Ile Thr Asp
            260                 265                 270

Ala Val Asp Cys Ala Leu Asp Pro Leu Ser Glu Thr Lys Cys Thr Leu
        275                 280                 285
```

-continued

```
Lys Ser Phe Thr Val Glu Lys Gly Ile Tyr Gln Thr Ser Asn Phe Arg
    290                 295                 300

Val Gln Pro Thr Glu Ser Ile Val Arg Phe Pro Asn Ile Thr Asn Leu
305                 310                 315                 320

Cys Pro Phe Gly Glu Val Phe Asn Ala Thr Arg Phe Ala Ser Val Tyr
                325                 330                 335

Ala Trp Asn Arg Lys Arg Ile Ser Asn Cys Val Ala Asp Tyr Ser Val
            340                 345                 350

Leu Tyr Asn Ser Ala Ser Phe Ser Thr Phe Lys Cys Tyr Gly Val Ser
        355                 360                 365

Pro Thr Lys Leu Asn Asp Leu Cys Phe Thr Asn Val Tyr Ala Asp Ser
370                 375                 380

Phe Val Ile Arg Gly Asp Glu Val Arg Gln Ile Ala Pro Gly Gln Thr
385                 390                 395                 400

Gly Lys Ile Ala Asp Tyr Asn Tyr Lys Leu Pro Asp Asp Phe Thr Gly
                405                 410                 415

Cys Val Ile Ala Trp Asn Ser Asn Leu Asp Ser Lys Val Gly Gly
            420                 425                 430

Asn Tyr Asn Tyr Leu Tyr Arg Leu Phe Arg Lys Ser Asn Leu Lys Pro
        435                 440                 445

Phe Glu Arg Asp Ile Ser Thr Glu Ile Tyr Gln Ala Gly Ser Thr Pro
    450                 455                 460

Cys Asn Gly Val Glu Gly Phe Asn Cys Tyr Phe Pro Leu Gln Ser Tyr
465                 470                 475                 480

Gly Phe Gln Pro Thr Tyr Gly Val Gly Tyr Gln Pro Tyr Arg Val Val
                485                 490                 495

Val Leu Ser Phe Glu Leu Leu His Ala Pro Ala Thr Val Cys Gly Pro
            500                 505                 510

Lys Lys Ser Thr Asn Leu Val Lys Asn Lys Cys Val Asn Phe Asn Phe
        515                 520                 525

Asn Gly Leu Thr Gly Thr Gly Val Leu Thr Glu Ser Asn Lys Lys Phe
    530                 535                 540

Leu Pro Phe Gln Gln Phe Gly Arg Asp Ile Ala Asp Thr Thr Asp Ala
545                 550                 555                 560

Val Arg Asp Pro Gln Thr Leu Glu Ile Leu Asp Ile Thr Pro Cys Ser
                565                 570                 575

Phe Gly Gly Val Ser Val Ile Thr Pro Gly Thr Asn Thr Ser Asn Gln
            580                 585                 590

Val Ala Val Leu Tyr Gln Gly Val Asn Cys Thr Glu Val Pro Val Ala
        595                 600                 605

Ile His Ala Asp Gln Leu Thr Pro Thr Trp Arg Val Tyr Ser Thr Gly
    610                 615                 620

Ser Asn Val Phe Gln Thr Arg Ala Gly Cys Leu Ile Gly Ala Glu His
625                 630                 635                 640

Val Asn Asn Ser Tyr Glu Cys Asp Ile Pro Ile Gly Ala Gly Ile Cys
                645                 650                 655

Ala Ser Tyr Gln Thr Gln Thr Asn Ser His Arg Arg Ala Ala Ser Val
            660                 665                 670

Ala Ser Gln Ser Ile Ile Ala Tyr Thr Met Ser Leu Gly Ala Glu Asn
        675                 680                 685

Ser Val Ala Tyr Ser Asn Asn Ser Ile Ala Ile Pro Thr Asn Phe Thr
    690                 695                 700
```

```
Ile Ser Val Thr Thr Glu Ile Leu Pro Val Ser Met Thr Lys Thr Ser
705                 710                 715                 720

Val Asp Cys Thr Met Tyr Ile Cys Gly Asp Ser Thr Glu Cys Ser Asn
                725                 730                 735

Leu Leu Leu Gln Tyr Gly Ser Phe Cys Thr Gln Leu Asn Arg Ala Leu
            740                 745                 750

Thr Gly Ile Ala Val Glu Gln Asp Lys Asn Thr Gln Glu Val Phe Ala
        755                 760                 765

Gln Val Lys Gln Ile Tyr Lys Thr Pro Pro Ile Lys Asp Phe Gly Gly
    770                 775                 780

Phe Asn Phe Ser Gln Ile Leu Pro Asp Pro Ser Lys Pro Ser Lys Arg
785                 790                 795                 800

Ser Phe Ile Glu Asp Leu Leu Phe Asn Lys Val Thr Leu Ala Asp Ala
                805                 810                 815

Gly Phe Ile Lys Gln Tyr Gly Asp Cys Leu Gly Asp Ile Ala Ala Arg
            820                 825                 830

Asp Leu Ile Cys Ala Gln Lys Phe Asn Gly Leu Thr Val Leu Pro Pro
        835                 840                 845

Leu Leu Thr Asp Glu Met Ile Ala Gln Tyr Thr Ser Ala Leu Leu Ala
    850                 855                 860

Gly Thr Ile Thr Ser Gly Trp Thr Phe Gly Ala Gly Ala Ala Leu Gln
865                 870                 875                 880

Ile Pro Phe Ala Met Gln Met Ala Tyr Arg Phe Asn Gly Ile Gly Val
                885                 890                 895

Thr Gln Asn Val Leu Tyr Glu Asn Gln Lys Leu Ile Ala Asn Gln Phe
            900                 905                 910

Asn Ser Ala Ile Gly Lys Ile Gln Asp Ser Leu Ser Ser Thr Ala Ser
        915                 920                 925

Ala Leu Gly Lys Leu Gln Asp Val Val Asn Gln Asn Ala Gln Ala Leu
    930                 935                 940

Asn Thr Leu Val Lys Gln Leu Ser Ser Asn Phe Gly Ala Ile Ser Ser
945                 950                 955                 960

Val Leu Asn Asp Ile Leu Ser Arg Leu Asp Lys Val Glu Ala Glu Val
                965                 970                 975

Gln Ile Asp Arg Leu Ile Thr Gly Arg Leu Gln Ser Leu Gln Thr Tyr
            980                 985                 990

Val Thr Gln Gln Leu Ile Arg Ala Ala Glu Ile Arg Ala Ser Ala Asn
        995                 1000                1005

Leu Ala Ala Thr Lys Met Ser Glu Cys Val Leu Gly Gln Ser Lys Arg
    1010                1015                1020

Val Asp Phe Cys Gly Lys Gly Tyr His Leu Met Ser Phe Pro Gln Ser
1025                1030                1035                1040

Ala Pro His Gly Val Val Phe Leu His Val Thr Tyr Val Pro Ala Gln
                1045                1050                1055

Glu Lys Asn Phe Thr Thr Ala Pro Ala Ile Cys His Asp Gly Lys Ala
            1060                1065                1070

His Phe Pro Arg Glu Gly Val Phe Val Ser Asn Gly Thr His Trp Phe
        1075                1080                1085

Val Thr Gln Arg Asn Phe Tyr Glu Pro Gln Ile Ile Thr Thr Asp Asn
    1090                1095                1100

Thr Phe Val Ser Gly Asn Cys Asp Val Val Ile Gly Ile Val Asn Asn
1105                1110                1115                1120

Thr Val Tyr Asp Pro Leu Gln Pro Glu Leu Asp Ser Phe Lys Glu Glu
```

```
                        1125                 1130                 1135
Leu Asp Lys Tyr Phe Lys Asn His Thr Ser Pro Asp Val Asp Leu Gly
            1140                 1145                 1150

Asp Ile Ser Gly Ile Asn Ala Ser Val Val Asn Ile Gln Lys Glu Ile
            1155                 1160                 1165

Asp Arg Leu Asn Glu Val Ala Lys Asn Leu Asn Glu Ser Leu Ile Asp
    1170                 1175                 1180

Leu Gln Glu Leu Gly Lys Tyr Glu Gln
1185                 1190

<210> SEQ ID NO 46
<211> LENGTH: 1193
<212> TYPE: PRT
<213> ORGANISM: Artificial Sequence
<220> FEATURE:
<223> OTHER INFORMATION: Synthetic construct

<400> SEQUENCE: 46

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile Ser Gly Thr Asn Gly Thr Lys Arg Phe
    50                  55                  60

Asp Asn Pro Val Leu Pro Phe Asn Asp Gly Val Tyr Phe Ala Ser Thr
65                  70                  75                  80

Glu Lys Ser Asn Ile Ile Arg Gly Trp Ile Phe Gly Thr Thr Leu Asp
                85                  90                  95

Ser Lys Thr Gln Ser Leu Leu Ile Val Asn Asn Ala Thr Asn Val Val
            100                 105                 110

Ile Lys Val Cys Glu Phe Gln Phe Cys Asn Asp Pro Phe Leu Gly Val
        115                 120                 125

Tyr Tyr His Lys Asn Asn Lys Ser Trp Met Glu Ser Glu Phe Arg Val
    130                 135                 140

Tyr Ser Ser Ala Asn Asn Cys Thr Phe Glu Tyr Val Ser Gln Pro Phe
145                 150                 155                 160

Leu Met Asp Leu Glu Gly Lys Gln Gly Asn Phe Lys Asn Leu Arg Glu
                165                 170                 175

Phe Val Phe Lys Asn Ile Asp Gly Tyr Phe Lys Ile Tyr Ser Lys His
            180                 185                 190

Thr Pro Ile Asn Leu Val Arg Asp Leu Pro Gln Gly Phe Ser Ala Leu
        195                 200                 205

Glu Pro Leu Val Asp Leu Pro Ile Gly Ile Asn Ile Thr Arg Phe Gln
    210                 215                 220

Thr Leu Leu Ala Leu His Arg Ser Tyr Leu Thr Pro Gly Asp Ser Ser
225                 230                 235                 240

Ser Gly Trp Thr Ala Gly Ala Ala Ala Tyr Tyr Val Gly Tyr Leu Gln
                245                 250                 255

Pro Arg Thr Phe Leu Leu Lys Tyr Asn Glu Asn Gly Thr Ile Thr Asp
            260                 265                 270

Ala Val Asp Cys Ala Leu Asp Pro Leu Ser Glu Thr Lys Cys Thr Leu
        275                 280                 285

Lys Ser Phe Thr Val Glu Lys Gly Ile Tyr Gln Thr Ser Asn Phe Arg
```

```
                290             295             300
Val Gln Pro Thr Glu Ser Ile Val Arg Phe Pro Asn Ile Thr Asn Leu
305             310             315             320

Cys Pro Phe Gly Glu Val Phe Asn Ala Thr Arg Phe Ala Ser Val Tyr
            325             330             335

Ala Trp Asn Arg Lys Arg Ile Ser Asn Cys Val Ala Asp Tyr Ser Val
            340             345             350

Leu Tyr Asn Ser Ala Ser Phe Ser Thr Phe Lys Cys Tyr Gly Val Ser
            355             360             365

Pro Thr Lys Leu Asn Asp Leu Cys Phe Thr Asn Val Tyr Ala Asp Ser
    370             375             380

Phe Val Ile Arg Gly Asp Glu Val Arg Gln Ile Ala Pro Gly Gln Thr
385             390             395             400

Gly Lys Ile Ala Asp Tyr Asn Tyr Lys Leu Pro Asp Asp Phe Thr Gly
            405             410             415

Cys Val Ile Ala Trp Asn Ser Asn Asn Leu Asp Ser Lys Val Gly Gly
            420             425             430

Asn Tyr Asn Tyr Leu Tyr Arg Leu Phe Arg Lys Ser Asn Leu Lys Pro
            435             440             445

Phe Glu Arg Asp Ile Ser Thr Glu Ile Tyr Gln Ala Gly Ser Thr Pro
    450             455             460

Cys Asn Gly Val Glu Gly Phe Asn Cys Tyr Phe Pro Leu Gln Ser Tyr
465             470             475             480

Gly Phe Gln Pro Thr Tyr Gly Val Gly Tyr Gln Pro Tyr Arg Val Val
            485             490             495

Val Leu Ser Phe Glu Leu Leu His Ala Pro Ala Thr Val Cys Gly Pro
            500             505             510

Lys Lys Ser Thr Asn Leu Val Lys Asn Lys Cys Val Asn Phe Asn Phe
            515             520             525

Asn Gly Leu Thr Gly Thr Gly Val Leu Thr Glu Ser Asn Lys Lys Phe
            530             535             540

Leu Pro Phe Gln Gln Phe Gly Arg Asp Ile Ala Asp Thr Thr Asp Ala
545             550             555             560

Val Arg Asp Pro Gln Thr Leu Glu Ile Leu Asp Ile Thr Pro Cys Ser
            565             570             575

Phe Gly Gly Val Ser Val Ile Thr Pro Gly Thr Asn Thr Ser Asn Gln
            580             585             590

Val Ala Val Leu Tyr Gln Gly Val Asn Cys Thr Glu Val Pro Val Ala
            595             600             605

Ile His Ala Asp Gln Leu Thr Pro Thr Trp Arg Val Tyr Ser Thr Gly
            610             615             620

Ser Asn Val Phe Gln Thr Arg Ala Gly Cys Leu Ile Gly Ala Glu His
625             630             635             640

Val Asn Asn Ser Tyr Glu Cys Asp Ile Pro Ile Gly Ala Gly Ile Cys
            645             650             655

Ala Ser Tyr Gln Thr Gln Thr Asn Ser His Arg Arg Ala Arg Ser Val
            660             665             670

Ala Ser Gln Ser Ile Ile Ala Tyr Thr Met Ser Leu Gly Ala Glu Asn
            675             680             685

Ser Val Ala Tyr Ser Asn Asn Ser Ile Ala Ile Pro Thr Asn Phe Thr
            690             695             700

Ile Ser Val Thr Thr Glu Ile Leu Pro Val Ser Met Thr Lys Thr Ser
705             710             715             720
```

```
Val Asp Cys Thr Met Tyr Ile Cys Gly Asp Ser Thr Glu Cys Ser Asn
            725                 730                 735

Leu Leu Leu Gln Tyr Gly Ser Phe Cys Thr Gln Leu Asn Arg Ala Leu
            740                 745                 750

Thr Gly Ile Ala Val Glu Gln Asp Lys Asn Thr Gln Glu Val Phe Ala
            755                 760                 765

Gln Val Lys Gln Ile Tyr Lys Thr Pro Pro Ile Lys Asp Phe Gly Gly
770                 775                 780

Phe Asn Phe Ser Gln Ile Leu Pro Asp Pro Ser Lys Pro Ser Lys Arg
785                 790                 795                 800

Ser Phe Ile Glu Asp Leu Leu Phe Asn Lys Val Thr Leu Ala Asp Ala
                805                 810                 815

Gly Phe Ile Lys Gln Tyr Gly Asp Cys Leu Gly Asp Ile Ala Ala Arg
            820                 825                 830

Asp Leu Ile Cys Ala Gln Lys Phe Asn Gly Leu Thr Val Leu Pro Pro
            835                 840                 845

Leu Leu Thr Asp Glu Met Ile Ala Gln Tyr Thr Ser Ala Leu Leu Ala
850                 855                 860

Gly Thr Ile Thr Ser Gly Trp Thr Phe Gly Ala Gly Ala Ala Leu Gln
865                 870                 875                 880

Ile Pro Phe Ala Met Gln Met Ala Tyr Arg Phe Asn Gly Ile Gly Val
                885                 890                 895

Thr Gln Asn Val Leu Tyr Glu Asn Gln Lys Leu Ile Ala Asn Gln Phe
            900                 905                 910

Asn Ser Ala Ile Gly Lys Ile Gln Asp Ser Leu Ser Ser Thr Ala Ser
            915                 920                 925

Ala Leu Gly Lys Leu Gln Asp Val Val Asn Gln Asn Ala Gln Ala Leu
            930                 935                 940

Asn Thr Leu Val Lys Gln Leu Ser Ser Asn Phe Gly Ala Ile Ser Ser
945                 950                 955                 960

Val Leu Asn Asp Ile Leu Ser Arg Leu Asp Pro Pro Glu Ala Glu Val
                965                 970                 975

Gln Ile Asp Arg Leu Ile Thr Gly Arg Leu Gln Ser Leu Gln Thr Tyr
            980                 985                 990

Val Thr Gln Gln Leu Ile Arg Ala Ala Glu Ile Arg Ala Ser Ala Asn
            995                 1000                1005

Leu Ala Ala Thr Lys Met Ser Glu Cys Val Leu Gly Gln Ser Lys Arg
            1010                1015                1020

Val Asp Phe Cys Gly Lys Gly Tyr His Leu Met Ser Phe Pro Gln Ser
1025                1030                1035                1040

Ala Pro His Gly Val Val Phe Leu His Val Thr Tyr Val Pro Ala Gln
                1045                1050                1055

Glu Lys Asn Phe Thr Thr Ala Pro Ala Ile Cys His Asp Gly Lys Ala
            1060                1065                1070

His Phe Pro Arg Glu Gly Val Phe Val Ser Asn Gly Thr His Trp Phe
            1075                1080                1085

Val Thr Gln Arg Asn Phe Tyr Glu Pro Gln Ile Ile Thr Thr Asp Asn
            1090                1095                1100

Thr Phe Val Ser Gly Asn Cys Asp Val Val Ile Gly Ile Val Asn Asn
1105                1110                1115                1120

Thr Val Tyr Asp Pro Leu Gln Pro Glu Leu Asp Ser Phe Lys Glu Glu
                1125                1130                1135
```

-continued

```
Leu Asp Lys Tyr Phe Lys Asn His Thr Ser Pro Asp Val Asp Leu Gly
            1140                1145                1150

Asp Ile Ser Gly Ile Asn Ala Ser Val Val Asn Ile Gln Lys Glu Ile
        1155                1160                1165

Asp Arg Leu Asn Glu Val Ala Lys Asn Leu Asn Glu Ser Leu Ile Asp
    1170                1175                1180

Leu Gln Glu Leu Gly Lys Tyr Glu Gln
1185                1190

<210> SEQ ID NO 47
<211> LENGTH: 1193
<212> TYPE: PRT
<213> ORGANISM: Artificial Sequence
<220> FEATURE:
<223> OTHER INFORMATION: Synthetic construct

<400> SEQUENCE: 47

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile Ser Gly Thr Asn Gly Thr Lys Arg Phe
    50                  55                  60

Asp Asn Pro Val Leu Pro Phe Asn Asp Gly Val Tyr Phe Ala Ser Thr
65                  70                  75                  80

Glu Lys Ser Asn Ile Ile Arg Gly Trp Ile Phe Gly Thr Thr Leu Asp
                85                  90                  95

Ser Lys Thr Gln Ser Leu Leu Ile Val Asn Asn Ala Thr Asn Val Val
            100                 105                 110

Ile Lys Val Cys Glu Phe Gln Phe Cys Asn Asp Pro Phe Leu Gly Val
        115                 120                 125

Tyr Tyr His Lys Asn Asn Lys Ser Trp Met Glu Ser Glu Phe Arg Val
    130                 135                 140

Tyr Ser Ser Ala Asn Asn Cys Thr Phe Glu Tyr Val Ser Gln Pro Phe
145                 150                 155                 160

Leu Met Asp Leu Glu Gly Lys Gln Gly Asn Phe Lys Asn Leu Arg Glu
                165                 170                 175

Phe Val Phe Lys Asn Ile Asp Gly Tyr Phe Lys Ile Tyr Ser Lys His
            180                 185                 190

Thr Pro Ile Asn Leu Val Arg Asp Leu Pro Gln Gly Phe Ser Ala Leu
        195                 200                 205

Glu Pro Leu Val Asp Leu Pro Ile Gly Ile Asn Ile Thr Arg Phe Gln
    210                 215                 220

Thr Leu Leu Ala Leu His Arg Ser Tyr Leu Thr Pro Gly Asp Ser Ser
225                 230                 235                 240

Ser Gly Trp Thr Ala Gly Ala Ala Ala Tyr Tyr Val Gly Tyr Leu Gln
                245                 250                 255

Pro Arg Thr Phe Leu Leu Lys Tyr Asn Glu Asn Gly Thr Ile Thr Asp
            260                 265                 270

Ala Val Asp Cys Ala Leu Asp Pro Leu Ser Glu Thr Lys Cys Thr Leu
        275                 280                 285

Lys Ser Phe Thr Val Glu Lys Gly Ile Tyr Gln Thr Ser Asn Phe Arg
    290                 295                 300
```

```
Val Gln Pro Thr Glu Ser Ile Val Arg Phe Pro Asn Ile Thr Asn Leu
305                 310                 315                 320

Cys Pro Phe Gly Glu Val Phe Asn Ala Thr Arg Phe Ala Ser Val Tyr
            325                 330                 335

Ala Trp Asn Arg Lys Arg Ile Ser Asn Cys Val Ala Asp Tyr Ser Val
            340                 345                 350

Leu Tyr Asn Ser Ala Ser Phe Ser Thr Phe Lys Cys Tyr Gly Val Ser
        355                 360                 365

Pro Thr Lys Leu Asn Asp Leu Cys Phe Thr Asn Val Tyr Ala Asp Ser
    370                 375                 380

Phe Val Ile Arg Gly Asp Glu Val Arg Gln Ile Ala Pro Gly Gln Thr
385                 390                 395                 400

Gly Lys Ile Ala Asp Tyr Asn Tyr Lys Leu Pro Asp Asp Phe Thr Gly
            405                 410                 415

Cys Val Ile Ala Trp Asn Ser Asn Leu Asp Ser Lys Val Gly Gly
            420                 425                 430

Asn Tyr Asn Tyr Leu Tyr Arg Leu Phe Arg Lys Ser Asn Leu Lys Pro
        435                 440                 445

Phe Glu Arg Asp Ile Ser Thr Glu Ile Tyr Gln Ala Gly Ser Thr Pro
    450                 455                 460

Cys Asn Gly Val Glu Gly Phe Asn Cys Tyr Phe Pro Leu Gln Ser Tyr
465                 470                 475                 480

Gly Phe Gln Pro Thr Tyr Gly Val Gly Tyr Gln Pro Tyr Arg Val Val
            485                 490                 495

Val Leu Ser Phe Glu Leu Leu His Ala Pro Ala Thr Val Cys Gly Pro
        500                 505                 510

Lys Lys Ser Thr Asn Leu Val Lys Asn Lys Cys Val Asn Phe Asn Phe
    515                 520                 525

Asn Gly Leu Thr Gly Thr Gly Val Leu Thr Glu Ser Asn Lys Lys Phe
530                 535                 540

Leu Pro Phe Gln Gln Phe Gly Arg Asp Ile Ala Asp Thr Thr Asp Ala
545                 550                 555                 560

Val Arg Asp Pro Gln Thr Leu Glu Ile Leu Asp Ile Thr Pro Cys Ser
            565                 570                 575

Phe Gly Gly Val Ser Val Ile Thr Pro Gly Thr Asn Thr Ser Asn Gln
            580                 585                 590

Val Ala Val Leu Tyr Gln Gly Val Asn Cys Thr Glu Val Pro Val Ala
        595                 600                 605

Ile His Ala Asp Gln Leu Thr Pro Thr Trp Arg Val Tyr Ser Thr Gly
610                 615                 620

Ser Asn Val Phe Gln Thr Arg Ala Gly Cys Leu Ile Gly Ala Glu His
625                 630                 635                 640

Val Asn Asn Ser Tyr Glu Cys Asp Ile Pro Ile Gly Ala Gly Ile Cys
            645                 650                 655

Ala Ser Tyr Gln Thr Gln Thr Asn Ser His Arg Arg Ala Ala Ser Val
        660                 665                 670

Ala Ser Gln Ser Ile Ile Ala Tyr Thr Met Ser Leu Gly Ala Glu Asn
    675                 680                 685

Ser Val Ala Tyr Ser Asn Asn Ser Ile Ala Ile Pro Thr Asn Phe Thr
        690                 695                 700

Ile Ser Val Thr Thr Glu Ile Leu Pro Val Ser Met Thr Lys Thr Ser
705                 710                 715                 720

Val Asp Cys Thr Met Tyr Ile Cys Gly Asp Ser Thr Glu Cys Ser Asn
```

```
                    725                 730                 735
Leu Leu Leu Gln Tyr Gly Ser Phe Cys Thr Gln Leu Asn Arg Ala Leu
                740                 745                 750

Thr Gly Ile Ala Val Glu Gln Asp Lys Asn Thr Gln Glu Val Phe Ala
                755                 760                 765

Gln Val Lys Gln Ile Tyr Lys Thr Pro Pro Ile Lys Asp Phe Gly Gly
            770                 775                 780

Phe Asn Phe Ser Gln Ile Leu Pro Asp Pro Ser Lys Pro Ser Lys Arg
785                 790                 795                 800

Ser Phe Ile Glu Asp Leu Leu Phe Asn Lys Val Thr Leu Ala Asp Ala
                805                 810                 815

Gly Phe Ile Lys Gln Tyr Gly Asp Cys Leu Gly Asp Ile Ala Ala Arg
                820                 825                 830

Asp Leu Ile Cys Ala Gln Lys Phe Asn Gly Leu Thr Val Leu Pro Pro
                835                 840                 845

Leu Leu Thr Asp Glu Met Ile Ala Gln Tyr Thr Ser Ala Leu Leu Ala
                850                 855                 860

Gly Thr Ile Thr Ser Gly Trp Thr Phe Gly Ala Gly Ala Ala Leu Gln
865                 870                 875                 880

Ile Pro Phe Ala Met Gln Met Ala Tyr Arg Phe Asn Gly Ile Gly Val
                885                 890                 895

Thr Gln Asn Val Leu Tyr Glu Asn Gln Lys Leu Ile Ala Asn Gln Phe
                900                 905                 910

Asn Ser Ala Ile Gly Lys Ile Gln Asp Ser Leu Ser Ser Thr Ala Ser
                915                 920                 925

Ala Leu Gly Lys Leu Gln Asp Val Val Asn Gln Asn Ala Gln Ala Leu
                930                 935                 940

Asn Thr Leu Val Lys Gln Leu Ser Ser Asn Phe Gly Ala Ile Ser Ser
945                 950                 955                 960

Val Leu Asn Asp Ile Leu Ser Arg Leu Asp Pro Pro Glu Ala Glu Val
                965                 970                 975

Gln Ile Asp Arg Leu Ile Thr Gly Arg Leu Gln Ser Leu Gln Thr Tyr
                980                 985                 990

Val Thr Gln Gln Leu Ile Arg Ala Ala Glu Ile Arg Ala Ser Ala Asn
                995                 1000                1005

Leu Ala Ala Thr Lys Met Ser Glu Cys Val Leu Gly Gln Ser Lys Arg
                1010                1015                1020

Val Asp Phe Cys Gly Lys Gly Tyr His Leu Met Ser Phe Pro Gln Ser
1025                1030                1035                1040

Ala Pro His Gly Val Val Phe Leu His Val Thr Tyr Val Pro Ala Gln
                1045                1050                1055

Glu Lys Asn Phe Thr Thr Ala Pro Ala Ile Cys His Asp Gly Lys Ala
                1060                1065                1070

His Phe Pro Arg Glu Gly Val Phe Val Ser Asn Gly Thr His Trp Phe
                1075                1080                1085

Val Thr Gln Arg Asn Phe Tyr Glu Pro Gln Ile Ile Thr Thr Asp Asn
                1090                1095                1100

Thr Phe Val Ser Gly Asn Cys Asp Val Val Ile Gly Ile Val Asn Asn
1105                1110                1115                1120

Thr Val Tyr Asp Pro Leu Gln Pro Glu Leu Asp Ser Phe Lys Glu Glu
                1125                1130                1135

Leu Asp Lys Tyr Phe Lys Asn His Thr Ser Pro Asp Val Asp Leu Gly
                1140                1145                1150
```

-continued

```
Asp Ile Ser Gly Ile Asn Ala Ser Val Val Asn Ile Gln Lys Glu Ile
        1155                1160                1165

Asp Arg Leu Asn Glu Val Ala Lys Asn Leu Asn Glu Ser Leu Ile Asp
        1170                1175                1180

Leu Gln Glu Leu Gly Lys Tyr Glu Gln
1185                1190

<210> SEQ ID NO 48
<211> LENGTH: 1195
<212> TYPE: PRT
<213> ORGANISM: Artificial Sequence
<220> FEATURE:
<223> OTHER INFORMATION: Synthetic construct

<400> SEQUENCE: 48

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205

Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
                245                 250                 255

Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
        275                 280                 285

Thr Leu Lys Ser Phe Thr Val Glu Lys Gly Ile Tyr Gln Thr Ser Asn
    290                 295                 300

Phe Arg Val Gln Pro Thr Glu Ser Ile Val Arg Phe Pro Asn Ile Thr
305                 310                 315                 320
```

```
Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
                340                 345                 350

Ser Val Leu Tyr Asn Ser Ala Ser Phe Ser Thr Phe Lys Cys Tyr Gly
                355                 360                 365

Val Ser Pro Thr Lys Leu Asn Asp Leu Cys Phe Thr Asn Val Tyr Ala
            370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
                420                 425                 430

Gly Gly Asn Tyr Asn Tyr Leu Tyr Arg Leu Phe Arg Lys Ser Asn Leu
                435                 440                 445

Lys Pro Phe Glu Arg Asp Ile Ser Thr Glu Ile Tyr Gln Ala Gly Ser
            450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
                485                 490                 495

Val Val Val Leu Ser Phe Glu Leu Leu His Ala Pro Ala Thr Val Cys
                500                 505                 510

Gly Pro Lys Lys Ser Thr Asn Leu Val Lys Asn Lys Cys Val Asn Phe
            515                 520                 525

Asn Phe Asn Gly Leu Thr Gly Thr Gly Val Leu Thr Glu Ser Asn Lys
            530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
                580                 585                 590

Asn Gln Val Ala Val Leu Tyr Gln Gly Val Asn Cys Thr Glu Val Pro
            595                 600                 605

Val Ala Ile His Ala Asp Gln Leu Thr Pro Thr Trp Arg Val Tyr Ser
610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Arg Arg Ala Arg
            660                 665                 670

Ser Val Ala Ser Gln Ser Ile Ile Ala Tyr Thr Met Ser Leu Gly Ala
            675                 680                 685

Glu Asn Ser Val Ala Tyr Ser Asn Asn Ser Ile Ala Ile Pro Thr Asn
690                 695                 700

Phe Thr Ile Ser Val Thr Thr Glu Ile Leu Pro Val Ser Met Thr Lys
705                 710                 715                 720

Thr Ser Val Asp Cys Thr Met Tyr Ile Cys Gly Asp Ser Thr Glu Cys
                725                 730                 735
```

```
Ser Asn Leu Leu Leu Gln Tyr Gly Ser Phe Cys Thr Gln Leu Asn Arg
            740                 745                 750

Ala Leu Thr Gly Ile Ala Val Glu Gln Asp Lys Asn Thr Gln Glu Val
        755                 760                 765

Phe Ala Gln Val Lys Gln Ile Tyr Lys Thr Pro Pro Ile Lys Asp Phe
    770                 775                 780

Gly Gly Phe Asn Phe Ser Gln Ile Leu Pro Asp Pro Ser Lys Pro Ser
785                 790                 795                 800

Lys Arg Ser Phe Ile Glu Asp Leu Leu Phe Asn Lys Val Thr Leu Ala
                805                 810                 815

Asp Ala Gly Phe Ile Lys Gln Tyr Gly Asp Cys Leu Gly Asp Ile Ala
            820                 825                 830

Ala Arg Asp Leu Ile Cys Ala Gln Lys Phe Asn Gly Leu Thr Val Leu
        835                 840                 845

Pro Pro Leu Leu Thr Asp Glu Met Ile Ala Gln Tyr Thr Ser Ala Leu
    850                 855                 860

Leu Ala Gly Thr Ile Thr Ser Gly Trp Thr Phe Gly Ala Gly Ala Ala
865                 870                 875                 880

Leu Gln Ile Pro Phe Ala Met Gln Met Ala Tyr Arg Phe Asn Gly Ile
                885                 890                 895

Gly Val Thr Gln Asn Val Leu Tyr Glu Asn Gln Lys Leu Ile Ala Asn
            900                 905                 910

Gln Phe Asn Ser Ala Ile Gly Lys Ile Gln Asp Ser Leu Ser Ser Thr
        915                 920                 925

Ala Ser Ala Leu Gly Lys Leu Gln Asp Val Val Asn Gln Asn Ala Gln
    930                 935                 940

Ala Leu Asn Thr Leu Val Lys Gln Leu Ser Ser Asn Phe Gly Ala Ile
945                 950                 955                 960

Ser Ser Val Leu Asn Asp Ile Leu Ser Arg Leu Asp Lys Val Glu Ala
                965                 970                 975

Glu Val Gln Ile Asp Arg Leu Ile Thr Gly Arg Leu Gln Ser Leu Gln
            980                 985                 990

Thr Tyr Val Thr Gln Gln Leu Ile Arg Ala Ala Glu Ile Arg Ala Ser
        995                 1000                1005

Ala Asn Leu Ala Ala Thr Lys Met Ser Glu Cys Val Leu Gly Gln Ser
    1010                1015                1020

Lys Arg Val Asp Phe Cys Gly Lys Gly Tyr His Leu Met Ser Phe Pro
1025                1030                1035                1040

Gln Ser Ala Pro His Gly Val Val Phe Leu His Val Thr Tyr Val Pro
                1045                1050                1055

Ala Gln Glu Lys Asn Phe Thr Thr Ala Pro Ala Ile Cys His Asp Gly
            1060                1065                1070

Lys Ala His Phe Pro Arg Glu Gly Val Phe Val Ser Asn Gly Thr His
        1075                1080                1085

Trp Phe Val Thr Gln Arg Asn Phe Tyr Glu Pro Gln Ile Ile Thr Thr
    1090                1095                1100

Asp Asn Thr Phe Val Ser Gly Asn Cys Asp Val Val Ile Gly Ile Val
1105                1110                1115                1120

Asn Asn Thr Val Tyr Asp Pro Leu Gln Pro Glu Leu Asp Ser Phe Lys
                1125                1130                1135

Glu Glu Leu Asp Lys Tyr Phe Lys Asn His Thr Ser Pro Asp Val Asp
            1140                1145                1150

Leu Gly Asp Ile Ser Gly Ile Asn Ala Ser Val Val Asn Ile Gln Lys
```

```
              1155                1160                1165
Glu Ile Asp Arg Leu Asn Glu Val Ala Lys Asn Leu Asn Glu Ser Leu
            1170                1175                1180

Ile Asp Leu Gln Glu Leu Gly Lys Tyr Glu Gln
1185                1190                1195

<210> SEQ ID NO 49
<211> LENGTH: 1195
<212> TYPE: PRT
<213> ORGANISM: Artificial Sequence
<220> FEATURE:
<223> OTHER INFORMATION: Synthetic construct

<400> SEQUENCE: 49

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205

Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
                245                 250                 255

Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
        275                 280                 285

Thr Leu Lys Ser Phe Thr Val Glu Lys Gly Ile Tyr Gln Thr Ser Asn
    290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
```

-continued

```
                325                 330                 335
Val Tyr Ala Trp Asn Arg Lys Arg Ile Ser Asn Cys Val Ala Asp Tyr
            340                 345                 350
Ser Val Leu Tyr Asn Ser Ala Ser Phe Ser Thr Phe Lys Cys Tyr Gly
            355                 360                 365
Val Ser Pro Thr Lys Leu Asn Asp Leu Cys Phe Thr Asn Val Tyr Ala
            370                 375                 380
Asp Ser Phe Val Ile Arg Gly Asp Glu Val Arg Gln Ile Ala Pro Gly
385                 390                 395                 400
Gln Thr Gly Lys Ile Ala Asp Tyr Asn Tyr Lys Leu Pro Asp Asp Phe
            405                 410                 415
Thr Gly Cys Val Ile Ala Trp Asn Ser Asn Asn Leu Asp Ser Lys Val
            420                 425                 430
Gly Gly Asn Tyr Asn Tyr Leu Tyr Arg Leu Phe Arg Lys Ser Asn Leu
            435                 440                 445
Lys Pro Phe Glu Arg Asp Ile Ser Thr Glu Ile Tyr Gln Ala Gly Ser
            450                 455                 460
Thr Pro Cys Asn Gly Val Glu Gly Phe Asn Cys Tyr Phe Pro Leu Gln
465                 470                 475                 480
Ser Tyr Gly Phe Gln Pro Thr Asn Gly Val Gly Tyr Gln Pro Tyr Arg
            485                 490                 495
Val Val Val Leu Ser Phe Glu Leu Leu His Ala Pro Ala Thr Val Cys
            500                 505                 510
Gly Pro Lys Lys Ser Thr Asn Leu Val Lys Asn Lys Cys Val Asn Phe
            515                 520                 525
Asn Phe Asn Gly Leu Thr Gly Thr Gly Val Leu Thr Glu Ser Asn Lys
            530                 535                 540
Lys Phe Leu Pro Phe Gln Phe Gly Arg Asp Ile Ala Asp Thr Thr
545                 550                 555                 560
Asp Ala Val Arg Asp Pro Gln Thr Leu Glu Ile Leu Asp Ile Thr Pro
            565                 570                 575
Cys Ser Phe Gly Gly Val Ser Val Ile Thr Pro Gly Thr Asn Thr Ser
            580                 585                 590
Asn Gln Val Ala Val Leu Tyr Gln Gly Val Asn Cys Thr Glu Val Pro
            595                 600                 605
Val Ala Ile His Ala Asp Gln Leu Thr Pro Thr Trp Arg Val Tyr Ser
            610                 615                 620
Thr Gly Ser Asn Val Phe Gln Thr Arg Ala Gly Cys Leu Ile Gly Ala
625                 630                 635                 640
Glu His Val Asn Asn Ser Tyr Glu Cys Asp Ile Pro Ile Gly Ala Gly
            645                 650                 655
Ile Cys Ala Ser Tyr Gln Thr Gln Thr Asn Ser Pro Arg Arg Ala Ala
            660                 665                 670
Ser Val Ala Ser Gln Ser Ile Ile Ala Tyr Thr Met Ser Leu Gly Ala
            675                 680                 685
Glu Asn Ser Val Ala Tyr Ser Asn Asn Ser Ile Ala Ile Pro Thr Asn
            690                 695                 700
Phe Thr Ile Ser Val Thr Thr Glu Ile Leu Pro Val Ser Met Thr Lys
705                 710                 715                 720
Thr Ser Val Asp Cys Thr Met Tyr Ile Cys Gly Asp Ser Thr Glu Cys
            725                 730                 735
Ser Asn Leu Leu Leu Gln Tyr Gly Ser Phe Cys Thr Gln Leu Asn Arg
            740                 745                 750
```

```
Ala Leu Thr Gly Ile Ala Val Glu Gln Asp Lys Asn Thr Gln Glu Val
            755                 760                 765

Phe Ala Gln Val Lys Gln Ile Tyr Lys Thr Pro Pro Ile Lys Asp Phe
        770                 775                 780

Gly Gly Phe Asn Phe Ser Gln Ile Leu Pro Asp Pro Ser Lys Pro Ser
785                 790                 795                 800

Lys Arg Ser Phe Ile Glu Asp Leu Leu Phe Asn Lys Val Thr Leu Ala
                805                 810                 815

Asp Ala Gly Phe Ile Lys Gln Tyr Gly Asp Cys Leu Gly Asp Ile Ala
                820                 825                 830

Ala Arg Asp Leu Ile Cys Ala Gln Lys Phe Asn Gly Leu Thr Val Leu
                835                 840                 845

Pro Pro Leu Leu Thr Asp Glu Met Ile Ala Gln Tyr Thr Ser Ala Leu
        850                 855                 860

Leu Ala Gly Thr Ile Thr Ser Gly Trp Thr Phe Gly Ala Gly Ala Ala
865                 870                 875                 880

Leu Gln Ile Pro Phe Ala Met Gln Met Ala Tyr Arg Phe Asn Gly Ile
                885                 890                 895

Gly Val Thr Gln Asn Val Leu Tyr Glu Asn Gln Lys Leu Ile Ala Asn
                900                 905                 910

Gln Phe Asn Ser Ala Ile Gly Lys Ile Gln Asp Ser Leu Ser Ser Thr
        915                 920                 925

Ala Ser Ala Leu Gly Lys Leu Gln Asp Val Val Asn Gln Asn Ala Gln
930                 935                 940

Ala Leu Asn Thr Leu Val Lys Gln Leu Ser Ser Asn Phe Gly Ala Ile
945                 950                 955                 960

Ser Ser Val Leu Asn Asp Ile Leu Ser Arg Leu Asp Lys Val Glu Ala
                965                 970                 975

Glu Val Gln Ile Asp Arg Leu Ile Thr Gly Arg Leu Gln Ser Leu Gln
                980                 985                 990

Thr Tyr Val Thr Gln Gln Leu Ile Arg Ala Ala Glu Ile Arg Ala Ser
        995                 1000                1005

Ala Asn Leu Ala Ala Thr Lys Met Ser Glu Cys Val Leu Gly Gln Ser
    1010                1015                1020

Lys Arg Val Asp Phe Cys Gly Lys Gly Tyr His Leu Met Ser Phe Pro
1025                1030                1035                1040

Gln Ser Ala Pro His Gly Val Val Phe Leu His Val Thr Tyr Val Pro
                1045                1050                1055

Ala Gln Glu Lys Asn Phe Thr Thr Ala Pro Ala Ile Cys His Asp Gly
                1060                1065                1070

Lys Ala His Phe Pro Arg Glu Gly Val Phe Val Ser Asn Gly Thr His
                1075                1080                1085

Trp Phe Val Thr Gln Arg Asn Phe Tyr Glu Pro Gln Ile Ile Thr Thr
    1090                1095                1100

Asp Asn Thr Phe Val Ser Gly Asn Cys Asp Val Val Ile Gly Ile Val
1105                1110                1115                1120

Asn Asn Thr Val Tyr Asp Pro Leu Gln Pro Glu Leu Asp Ser Phe Lys
                1125                1130                1135

Glu Glu Leu Asp Lys Tyr Phe Lys Asn His Thr Ser Pro Asp Val Asp
                1140                1145                1150

Leu Gly Asp Ile Ser Gly Ile Asn Ala Ser Val Val Asn Ile Gln Lys
                1155                1160                1165
```

Glu Ile Asp Arg Leu Asn Glu Val Ala Lys Asn Leu Asn Glu Ser Leu
        1170                1175                1180

Ile Asp Leu Gln Glu Leu Gly Lys Tyr Glu Gln
1185                1190                1195

<210> SEQ ID NO 50
<211> LENGTH: 1195
<212> TYPE: PRT
<213> ORGANISM: Artificial Sequence
<220> FEATURE:
<223> OTHER INFORMATION: Synthetic construct

<400> SEQUENCE: 50

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205

Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Tyr Tyr Val Gly Tyr
                245                 250                 255

Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
        275                 280                 285

Thr Leu Lys Ser Phe Thr Val Glu Lys Gly Ile Tyr Gln Thr Ser Asn
    290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

```
Val Tyr Ala Trp Asn Arg Lys Arg Ile Ser Asn Cys Val Ala Asp Tyr
                340                 345                 350

Ser Val Leu Tyr Asn Ser Ala Ser Phe Ser Thr Phe Lys Cys Tyr Gly
            355                 360                 365

Val Ser Pro Thr Lys Leu Asn Asp Leu Cys Phe Thr Asn Val Tyr Ala
        370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
            420                 425                 430

Gly Gly Asn Tyr Asn Tyr Leu Tyr Arg Leu Phe Arg Lys Ser Asn Leu
        435                 440                 445

Lys Pro Phe Glu Arg Asp Ile Ser Thr Glu Ile Tyr Gln Ala Gly Ser
450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
                485                 490                 495

Val Val Val Leu Ser Phe Glu Leu Leu His Ala Pro Ala Thr Val Cys
            500                 505                 510

Gly Pro Lys Lys Ser Thr Asn Leu Val Lys Asn Lys Cys Val Asn Phe
        515                 520                 525

Asn Phe Asn Gly Leu Thr Gly Thr Gly Val Leu Thr Glu Ser Asn Lys
530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
            580                 585                 590

Asn Gln Val Ala Val Leu Tyr Gln Gly Val Asn Cys Thr Glu Val Pro
        595                 600                 605

Val Ala Ile His Ala Asp Gln Leu Thr Pro Thr Trp Arg Val Tyr Ser
610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Arg Arg Ala Arg
            660                 665                 670

Ser Val Ala Ser Gln Ser Ile Ile Ala Tyr Thr Met Ser Leu Gly Ala
        675                 680                 685

Glu Asn Ser Val Ala Tyr Ser Asn Asn Ser Ile Ala Ile Pro Thr Asn
690                 695                 700

Phe Thr Ile Ser Val Thr Thr Glu Ile Leu Pro Val Ser Met Thr Lys
705                 710                 715                 720

Thr Ser Val Asp Cys Thr Met Tyr Ile Cys Gly Asp Ser Thr Glu Cys
                725                 730                 735

Ser Asn Leu Leu Leu Gln Tyr Gly Ser Phe Cys Thr Gln Leu Asn Arg
            740                 745                 750

Ala Leu Thr Gly Ile Ala Val Glu Gln Asp Lys Asn Thr Gln Glu Val
```

-continued

```
            755                 760                 765
Phe Ala Gln Val Lys Gln Ile Tyr Lys Thr Pro Pro Ile Lys Asp Phe
            770                 775                 780
Gly Gly Phe Asn Phe Ser Gln Ile Leu Pro Asp Pro Ser Lys Pro Ser
785                 790                 795                 800
Lys Arg Ser Phe Ile Glu Asp Leu Leu Phe Asn Lys Val Thr Leu Ala
                    805                 810                 815
Asp Ala Gly Phe Ile Lys Gln Tyr Gly Asp Cys Leu Gly Asp Ile Ala
                    820                 825                 830
Ala Arg Asp Leu Ile Cys Ala Gln Lys Phe Asn Gly Leu Thr Val Leu
                    835                 840                 845
Pro Pro Leu Leu Thr Asp Glu Met Ile Ala Gln Tyr Thr Ser Ala Leu
            850                 855                 860
Leu Ala Gly Thr Ile Thr Ser Gly Trp Thr Phe Gly Ala Gly Ala Ala
865                 870                 875                 880
Leu Gln Ile Pro Phe Ala Met Gln Met Ala Tyr Arg Phe Asn Gly Ile
                    885                 890                 895
Gly Val Thr Gln Asn Val Leu Tyr Glu Asn Gln Lys Leu Ile Ala Asn
                    900                 905                 910
Gln Phe Asn Ser Ala Ile Gly Lys Ile Gln Asp Ser Leu Ser Ser Thr
                    915                 920                 925
Ala Ser Ala Leu Gly Lys Leu Gln Asp Val Val Asn Gln Asn Ala Gln
            930                 935                 940
Ala Leu Asn Thr Leu Val Lys Gln Leu Ser Ser Asn Phe Gly Ala Ile
945                 950                 955                 960
Ser Ser Val Leu Asn Asp Ile Leu Ser Arg Leu Asp Pro Pro Glu Ala
                    965                 970                 975
Glu Val Gln Ile Asp Arg Leu Ile Thr Gly Arg Leu Gln Ser Leu Gln
                    980                 985                 990
Thr Tyr Val Thr Gln Gln Leu Ile Arg Ala Ala Glu Ile Arg Ala Ser
                    995                 1000                1005
Ala Asn Leu Ala Ala Thr Lys Met Ser Glu Cys Val Leu Gly Gln Ser
            1010                1015                1020
Lys Arg Val Asp Phe Cys Gly Lys Gly Tyr His Leu Met Ser Phe Pro
1025                1030                1035                1040
Gln Ser Ala Pro His Gly Val Val Phe Leu His Val Thr Tyr Val Pro
                    1045                1050                1055
Ala Gln Glu Lys Asn Phe Thr Thr Ala Pro Ala Ile Cys His Asp Gly
                    1060                1065                1070
Lys Ala His Phe Pro Arg Glu Gly Val Phe Val Ser Asn Gly Thr His
            1075                1080                1085
Trp Phe Val Thr Gln Arg Asn Phe Tyr Glu Pro Gln Ile Ile Thr Thr
            1090                1095                1100
Asp Asn Thr Phe Val Ser Gly Asn Cys Asp Val Val Ile Gly Ile Val
1105                1110                1115                1120
Asn Asn Thr Val Tyr Asp Pro Leu Gln Pro Glu Leu Asp Ser Phe Lys
                    1125                1130                1135
Glu Glu Leu Asp Lys Tyr Phe Lys Asn His Thr Ser Pro Asp Val Asp
                    1140                1145                1150
Leu Gly Asp Ile Ser Gly Ile Asn Ala Ser Val Val Asn Ile Gln Lys
                    1155                1160                1165
Glu Ile Asp Arg Leu Asn Glu Val Ala Lys Asn Leu Asn Glu Ser Leu
                    1170                1175                1180
```

```
Ile Asp Leu Gln Glu Leu Gly Lys Tyr Glu Gln
1185                1190                1195

<210> SEQ ID NO 51
<211> LENGTH: 1195
<212> TYPE: PRT
<213> ORGANISM: Artificial Sequence
<220> FEATURE:
<223> OTHER INFORMATION: Synthetic construct

<400> SEQUENCE: 51

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205

Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
                245                 250                 255

Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
        275                 280                 285

Thr Leu Lys Ser Phe Thr Val Glu Lys Gly Ile Tyr Gln Thr Ser Asn
    290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
            340                 345                 350
```

-continued

```
Ser Val Leu Tyr Asn Ser Ala Ser Phe Ser Thr Phe Lys Cys Tyr Gly
        355                 360                 365

Val Ser Pro Thr Lys Leu Asn Asp Leu Cys Phe Thr Asn Val Tyr Ala
370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
                420                 425                 430

Gly Gly Asn Tyr Asn Tyr Leu Tyr Arg Leu Phe Arg Lys Ser Asn Leu
            435                 440                 445

Lys Pro Phe Glu Arg Asp Ile Ser Thr Glu Ile Tyr Gln Ala Gly Ser
        450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
                485                 490                 495

Val Val Val Leu Ser Phe Glu Leu Leu His Ala Pro Ala Thr Val Cys
                500                 505                 510

Gly Pro Lys Lys Ser Thr Asn Leu Val Lys Asn Lys Cys Val Asn Phe
            515                 520                 525

Asn Phe Asn Gly Leu Thr Gly Thr Gly Val Leu Thr Glu Ser Asn Lys
        530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
                580                 585                 590

Asn Gln Val Ala Val Leu Tyr Gln Gly Val Asn Cys Thr Glu Val Pro
        595                 600                 605

Val Ala Ile His Ala Asp Gln Leu Thr Pro Thr Trp Arg Val Tyr Ser
        610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Arg Arg Ala Ala
                660                 665                 670

Ser Val Ala Ser Gln Ser Ile Ile Ala Tyr Thr Met Ser Leu Gly Ala
            675                 680                 685

Glu Asn Ser Val Ala Tyr Ser Asn Asn Ser Ile Ala Ile Pro Thr Asn
        690                 695                 700

Phe Thr Ile Ser Val Thr Thr Glu Ile Leu Pro Val Ser Met Thr Lys
705                 710                 715                 720

Thr Ser Val Asp Cys Thr Met Tyr Ile Cys Gly Asp Ser Thr Glu Cys
                725                 730                 735

Ser Asn Leu Leu Leu Gln Tyr Gly Ser Phe Cys Thr Gln Leu Asn Arg
                740                 745                 750

Ala Leu Thr Gly Ile Ala Val Glu Gln Asp Lys Asn Thr Gln Glu Val
            755                 760                 765
```

-continued

Phe Ala Gln Val Lys Gln Ile Tyr Lys Thr Pro Pro Ile Lys Asp Phe
    770                 775                 780
Gly Gly Phe Asn Phe Ser Gln Ile Leu Pro Asp Pro Ser Lys Pro Ser
785                 790                 795                 800
Lys Arg Ser Phe Ile Glu Asp Leu Leu Phe Asn Lys Val Thr Leu Ala
                805                 810                 815
Asp Ala Gly Phe Ile Lys Gln Tyr Gly Asp Cys Leu Gly Asp Ile Ala
                820                 825                 830
Ala Arg Asp Leu Ile Cys Ala Gln Lys Phe Asn Gly Leu Thr Val Leu
                835                 840                 845
Pro Pro Leu Leu Thr Asp Glu Met Ile Ala Gln Tyr Thr Ser Ala Leu
850                 855                 860
Leu Ala Gly Thr Ile Thr Ser Gly Trp Thr Phe Gly Ala Gly Ala Ala
865                 870                 875                 880
Leu Gln Ile Pro Phe Ala Met Gln Met Ala Tyr Arg Phe Asn Gly Ile
                885                 890                 895
Gly Val Thr Gln Asn Val Leu Tyr Glu Asn Gln Lys Leu Ile Ala Asn
                900                 905                 910
Gln Phe Asn Ser Ala Ile Gly Lys Ile Gln Asp Ser Leu Ser Ser Thr
                915                 920                 925
Ala Ser Ala Leu Gly Lys Leu Gln Asp Val Val Asn Gln Asn Ala Gln
930                 935                 940
Ala Leu Asn Thr Leu Val Lys Gln Leu Ser Ser Asn Phe Gly Ala Ile
945                 950                 955                 960
Ser Ser Val Leu Asn Asp Ile Leu Ser Arg Leu Asp Pro Pro Glu Ala
                965                 970                 975
Glu Val Gln Ile Asp Arg Leu Ile Thr Gly Arg Leu Gln Ser Leu Gln
                980                 985                 990
Thr Tyr Val Thr Gln Gln Leu Ile Arg Ala Ala Glu Ile Arg Ala Ser
                995                 1000                1005
Ala Asn Leu Ala Ala Thr Lys Met Ser Glu Cys Val Leu Gly Gln Ser
    1010                1015                1020
Lys Arg Val Asp Phe Cys Gly Lys Gly Tyr His Leu Met Ser Phe Pro
1025                1030                1035                1040
Gln Ser Ala Pro His Gly Val Val Phe Leu His Val Thr Tyr Val Pro
                1045                1050                1055
Ala Gln Glu Lys Asn Phe Thr Thr Ala Pro Ala Ile Cys His Asp Gly
                1060                1065                1070
Lys Ala His Phe Pro Arg Glu Gly Val Phe Val Ser Asn Gly Thr His
                1075                1080                1085
Trp Phe Val Thr Gln Arg Asn Phe Tyr Glu Pro Gln Ile Ile Thr Thr
    1090                1095                1100
Asp Asn Thr Phe Val Ser Gly Asn Cys Asp Val Val Ile Gly Ile Val
1105                1110                1115                1120
Asn Asn Thr Val Tyr Asp Pro Leu Gln Pro Glu Leu Asp Ser Phe Lys
                1125                1130                1135
Glu Glu Leu Asp Lys Tyr Phe Lys Asn His Thr Ser Pro Asp Val Asp
                1140                1145                1150
Leu Gly Asp Ile Ser Gly Ile Asn Ala Ser Val Val Asn Ile Gln Lys
                1155                1160                1165
Glu Ile Asp Arg Leu Asn Glu Val Ala Lys Asn Leu Asn Glu Ser Leu
                1170                1175                1180
Ile Asp Leu Gln Glu Leu Gly Lys Tyr Glu Gln 1185          1190          1195

<210> SEQ ID NO 52
<211> LENGTH: 1177
<212> TYPE: PRT
<213> ORGANISM: Artificial Sequence
<220> FEATURE:
<223> OTHER INFORMATION: Synthetic construct

<400> SEQUENCE: 52

Ser Asp Leu Asp Arg Cys Thr Thr Phe Asp Asp Val Gln Ala Pro Asn
1               5                   10                  15

Tyr Thr Gln His Thr Ser Ser Met Arg Gly Val Tyr Tyr Pro Asp Glu
            20                  25                  30

Ile Phe Arg Ser Asp Thr Leu Tyr Leu Thr Gln Asp Leu Phe Leu Pro
        35                  40                  45

Phe Tyr Ser Asn Val Thr Gly Phe His Thr Ile Asn His Thr Phe Asp
    50                  55                  60

Asn Pro Val Ile Pro Phe Lys Asp Gly Ile Tyr Phe Ala Ala Thr Glu
65                  70                  75                  80

Lys Ser Asn Val Val Arg Gly Trp Val Phe Gly Ser Thr Met Asn Asn
                85                  90                  95

Lys Ser Gln Ser Val Ile Ile Ile Asn Asn Ser Thr Asn Val Val Ile
            100                 105                 110

Arg Ala Cys Asn Phe Glu Leu Cys Asp Asn Pro Phe Phe Ala Val Ser
        115                 120                 125

Lys Pro Met Gly Thr Gln Thr His Thr Met Ile Phe Asp Asn Ala Phe
    130                 135                 140

Asn Cys Thr Phe Glu Tyr Ile Ser Asp Ala Phe Ser Leu Asp Val Ser
145                 150                 155                 160

Glu Lys Ser Gly Asn Phe Lys His Leu Arg Glu Phe Val Phe Lys Asn
                165                 170                 175

Lys Asp Gly Phe Leu Tyr Val Tyr Lys Gly Tyr Gln Pro Ile Asp Val
            180                 185                 190

Val Arg Asp Leu Pro Ser Gly Phe Asn Thr Leu Lys Pro Ile Phe Lys
        195                 200                 205

Leu Pro Leu Gly Ile Asn Ile Thr Asn Phe Arg Ala Ile Leu Thr Ala
    210                 215                 220

Phe Leu Pro Ala Gln Asp Thr Trp Gly Thr Ser Ala Ala Ala Tyr Phe
225                 230                 235                 240

Val Gly Tyr Leu Lys Pro Thr Thr Phe Met Leu Lys Tyr Asp Glu Asn
                245                 250                 255

Gly Thr Ile Thr Asp Ala Val Asp Cys Ser Gln Asn Pro Leu Ala Glu
            260                 265                 270

Leu Lys Cys Ser Val Lys Ser Phe Glu Ile Asp Lys Gly Ile Tyr Gln
        275                 280                 285

Thr Ser Asn Phe Arg Val Val Pro Ser Arg Asp Val Val Arg Phe Pro
    290                 295                 300

Asn Ile Thr Asn Leu Cys Pro Phe Gly Glu Val Phe Asn Ala Thr Lys
305                 310                 315                 320

Phe Pro Ser Val Tyr Ala Trp Glu Arg Lys Arg Ile Ser Asn Cys Val
                325                 330                 335

Ala Asp Tyr Ser Val Leu Tyr Asn Ser Thr Phe Phe Ser Thr Phe Lys
            340                 345                 350

Cys Tyr Gly Val Ser Ala Thr Lys Leu Asn Asp Leu Cys Phe Ser Asn

```
                355                 360                 365
Val Tyr Ala Asp Ser Phe Val Lys Gly Asp Val Arg Gln Ile
370                 375                 380

Ala Pro Gly Gln Thr Gly Val Ile Ala Asp Tyr Asn Tyr Lys Leu Pro
385                 390                 395                 400

Asp Asp Phe Met Gly Cys Val Leu Ala Trp Asn Thr Arg Asn Ile Asp
                405                 410                 415

Ala Thr Ser Thr Gly Asn Tyr Asn Tyr Lys Tyr Arg Tyr Leu Arg His
                420                 425                 430

Gly Lys Leu Arg Pro Phe Glu Arg Asp Ile Ser Asn Val Pro Phe Ser
                435                 440                 445

Pro Asp Gly Lys Pro Cys Thr Pro Pro Ala Leu Asn Cys Tyr Trp Pro
450                 455                 460

Leu Asn Asp Tyr Gly Phe Tyr Thr Thr Thr Gly Ile Gly Tyr Gln Pro
465                 470                 475                 480

Tyr Arg Val Val Val Leu Ser Phe Glu Leu Leu Asn Ala Pro Ala Thr
                485                 490                 495

Val Cys Gly Pro Lys Leu Ser Thr Asp Leu Ile Lys Asn Gln Cys Val
                500                 505                 510

Asn Phe Asn Phe Asn Gly Leu Thr Gly Thr Gly Val Leu Thr Pro Ser
                515                 520                 525

Ser Lys Arg Phe Gln Pro Phe Gln Gln Phe Gly Arg Asp Val Ser Asp
                530                 535                 540

Phe Thr Asp Ser Val Arg Asp Pro Lys Thr Ser Glu Ile Leu Asp Ile
545                 550                 555                 560

Ser Pro Cys Ser Phe Gly Gly Val Ser Val Ile Thr Pro Gly Thr Asn
                565                 570                 575

Ala Ser Ser Glu Val Ala Val Leu Tyr Gln Asp Val Asn Cys Thr Asp
                580                 585                 590

Val Ser Thr Ala Ile His Ala Asp Gln Leu Thr Pro Ala Trp Arg Ile
                595                 600                 605

Tyr Ser Thr Gly Asn Asn Val Phe Gln Thr Gln Ala Gly Cys Leu Ile
                610                 615                 620

Gly Ala Glu His Val Asp Thr Ser Tyr Glu Cys Asp Ile Pro Ile Gly
625                 630                 635                 640

Ala Gly Ile Cys Ala Ser Tyr His Thr Val Ser Leu Leu Arg Ser Thr
                645                 650                 655

Ser Gln Lys Ser Ile Val Ala Tyr Thr Met Ser Leu Gly Ala Asp Ser
                660                 665                 670

Ser Ile Ala Tyr Ser Asn Asn Thr Ile Ala Ile Pro Thr Asn Phe Ser
                675                 680                 685

Ile Ser Ile Thr Thr Glu Val Met Pro Val Ser Met Ala Lys Thr Ser
                690                 695                 700

Val Asp Cys Asn Met Tyr Ile Cys Gly Asp Ser Thr Glu Cys Ala Asn
705                 710                 715                 720

Leu Leu Leu Gln Tyr Gly Ser Phe Cys Thr Gln Leu Asn Arg Ala Leu
                725                 730                 735

Ser Gly Ile Ala Ala Glu Gln Asp Arg Asn Thr Arg Glu Val Phe Ala
                740                 745                 750

Gln Val Lys Gln Met Tyr Lys Thr Pro Thr Leu Lys Asp Phe Gly Gly
                755                 760                 765

Phe Asn Phe Ser Gln Ile Leu Pro Asp Pro Leu Lys Pro Thr Lys Arg
770                 775                 780
```

Ser Phe Ile Glu Asp Leu Leu Phe Asn Lys Val Thr Leu Ala Asp Ala
785                 790                 795                 800

Gly Phe Met Lys Gln Tyr Gly Glu Cys Leu Gly Asp Ile Asn Ala Arg
                805                 810                 815

Asp Leu Ile Cys Ala Gln Lys Phe Asn Gly Leu Thr Val Leu Pro Pro
                820                 825                 830

Leu Leu Thr Asp Asp Met Ile Ala Ala Tyr Thr Ala Ala Leu Val Ser
                835                 840                 845

Gly Thr Ala Thr Ala Gly Trp Thr Phe Gly Ala Gly Ala Ala Leu Gln
850                 855                 860

Ile Pro Phe Ala Met Gln Met Ala Tyr Arg Phe Asn Gly Ile Gly Val
865                 870                 875                 880

Thr Gln Asn Val Leu Tyr Glu Asn Gln Lys Gln Ile Ala Asn Gln Phe
                885                 890                 895

Asn Lys Ala Ile Ser Gln Ile Gln Glu Ser Leu Thr Thr Thr Ser Thr
                900                 905                 910

Ala Leu Gly Lys Leu Gln Asp Val Val Asn Gln Asn Ala Gln Ala Leu
                915                 920                 925

Asn Thr Leu Val Lys Gln Leu Ser Ser Asn Phe Gly Ala Ile Ser Ser
930                 935                 940

Val Leu Asn Asp Ile Leu Ser Arg Leu Asp Lys Val Glu Ala Glu Val
945                 950                 955                 960

Gln Ile Asp Arg Leu Ile Thr Gly Arg Leu Gln Ser Leu Gln Thr Tyr
                965                 970                 975

Val Thr Gln Gln Leu Ile Arg Ala Ala Glu Ile Arg Ala Ser Ala Asn
                980                 985                 990

Leu Ala Ala Thr Lys Met Ser Glu Cys Val Leu Gly Gln Ser Lys Arg
                995                 1000                1005

Val Asp Phe Cys Gly Lys Gly Tyr His Leu Met Ser Phe Pro Gln Ala
    1010                1015                1020

Ala Pro His Gly Val Val Phe Leu His Val Thr Tyr Val Pro Ser Gln
1025                1030                1035                1040

Glu Arg Asn Phe Thr Thr Ala Pro Ala Ile Cys His Glu Gly Lys Ala
                1045                1050                1055

Tyr Phe Pro Arg Glu Gly Val Phe Val Phe Asn Gly Thr Ser Trp Phe
                1060                1065                1070

Ile Thr Gln Arg Asn Phe Phe Ser Pro Gln Ile Ile Thr Thr Asp Asn
                1075                1080                1085

Thr Phe Val Ser Gly Asn Cys Asp Val Val Ile Gly Ile Ile Asn Asn
                1090                1095                1100

Thr Val Tyr Asp Pro Leu Gln Pro Glu Leu Asp Ser Phe Lys Glu Glu
1105                1110                1115                1120

Leu Asp Lys Tyr Phe Lys Asn His Thr Ser Pro Asp Val Asp Leu Gly
                1125                1130                1135

Asp Ile Ser Gly Ile Asn Ala Ser Val Val Asn Ile Gln Glu Glu Ile
                1140                1145                1150

Asp Arg Leu Asn Glu Val Ala Lys Asn Leu Asn Glu Ser Leu Ile Asp
                1155                1160                1165

Leu Gln Glu Leu Gly Lys Tyr Glu Gln
1170                1175

<210> SEQ ID NO 53
<211> LENGTH: 13

```
<212> TYPE: PRT
<213> ORGANISM: Artificial Sequence
<220> FEATURE:
<223> OTHER INFORMATION: Synthetic construct

<400> SEQUENCE: 53

Met Phe Ile Phe Leu Leu Phe Leu Thr Leu Thr Ser Gly
1               5                   10

<210> SEQ ID NO 54
<211> LENGTH: 13
<212> TYPE: PRT
<213> ORGANISM: Artificial Sequence
<220> FEATURE:
<223> OTHER INFORMATION: Synthetic construct

<400> SEQUENCE: 54

Met Phe Val Phe Leu Val Leu Leu Pro Leu Val Ser Ser
1               5                   10

<210> SEQ ID NO 55
<211> LENGTH: 1273
<212> TYPE: PRT
<213> ORGANISM: Artificial Sequence
<220> FEATURE:
<223> OTHER INFORMATION: Synthetic construct

<400> SEQUENCE: 55

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
```

-continued

```
                245                 250                 255
Gly Trp Thr Ala Gly Ala Ala Tyr Tyr Val Gly Tyr Leu Gln Pro
            260                 265                 270
Arg Thr Phe Leu Leu Lys Tyr Asn Glu Asn Gly Thr Ile Thr Asp Ala
        275                 280                 285
Val Asp Cys Ala Leu Asp Pro Leu Ser Glu Thr Lys Cys Thr Leu Lys
    290                 295                 300
Ser Phe Thr Val Glu Lys Gly Ile Tyr Gln Thr Ser Asn Phe Arg Val
305                 310                 315                 320
Gln Pro Thr Glu Ser Ile Val Arg Phe Pro Asn Ile Thr Asn Leu Cys
            325                 330                 335
Pro Phe Gly Glu Val Phe Asn Ala Thr Arg Phe Ala Ser Val Tyr Ala
            340                 345                 350
Trp Asn Arg Lys Arg Ile Ser Asn Cys Val Ala Asp Tyr Ser Val Leu
            355                 360                 365
Tyr Asn Ser Ala Ser Phe Ser Thr Phe Lys Cys Tyr Gly Val Ser Pro
        370                 375                 380
Thr Lys Leu Asn Asp Leu Cys Phe Thr Asn Val Tyr Ala Asp Ser Phe
385                 390                 395                 400
Val Ile Arg Gly Asp Glu Val Arg Gln Ile Ala Pro Gly Gln Thr Gly
                405                 410                 415
Lys Ile Ala Asp Tyr Asn Tyr Lys Leu Pro Asp Asp Phe Thr Gly Cys
            420                 425                 430
Val Ile Ala Trp Asn Ser Asn Asn Leu Asp Ser Lys Val Gly Gly Asn
            435                 440                 445
Tyr Asn Tyr Leu Tyr Arg Leu Phe Arg Lys Ser Asn Leu Lys Pro Phe
    450                 455                 460
Glu Arg Asp Ile Ser Thr Glu Ile Tyr Gln Ala Gly Ser Thr Pro Cys
465                 470                 475                 480
Asn Gly Val Glu Gly Phe Asn Cys Tyr Phe Pro Leu Gln Ser Tyr Gly
                485                 490                 495
Phe Gln Pro Thr Asn Gly Val Gly Tyr Gln Pro Tyr Arg Val Val Val
            500                 505                 510
Leu Ser Phe Glu Leu Leu His Ala Pro Ala Thr Val Cys Gly Pro Lys
        515                 520                 525
Lys Ser Thr Asn Leu Val Lys Asn Lys Cys Val Asn Phe Asn Phe Asn
    530                 535                 540
Gly Leu Thr Gly Thr Gly Val Leu Thr Glu Ser Asn Lys Lys Phe Leu
545                 550                 555                 560
Pro Phe Gln Gln Phe Gly Arg Asp Ile Ala Asp Thr Thr Asp Ala Val
                565                 570                 575
Arg Asp Pro Gln Thr Leu Glu Ile Leu Asp Ile Thr Pro Cys Ser Phe
            580                 585                 590
Gly Gly Val Ser Val Ile Thr Pro Gly Thr Asn Thr Ser Asn Gln Val
            595                 600                 605
Ala Val Leu Tyr Gln Asp Val Asn Cys Thr Glu Val Pro Val Ala Ile
        610                 615                 620
His Ala Asp Gln Leu Thr Pro Thr Trp Arg Val Tyr Ser Thr Gly Ser
625                 630                 635                 640
Asn Val Phe Gln Thr Arg Ala Gly Cys Leu Ile Gly Ala Glu His Val
                645                 650                 655
Asn Asn Ser Tyr Glu Cys Asp Ile Pro Ile Gly Ala Gly Ile Cys Ala
            660                 665                 670
```

```
Ser Tyr Gln Thr Gln Thr Asn Ser Pro Arg Ala Arg Ser Val Ala
        675                 680                 685

Ser Gln Ser Ile Ile Ala Tyr Thr Met Ser Leu Gly Ala Glu Asn Ser
690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
                740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
                820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
                900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
                980                 985                 990

Ile Asp Arg Leu Ile Thr Gly Arg Leu Gln Ser Leu Gln Thr Tyr Val
        995                 1000                1005

Thr Gln Gln Leu Ile Arg Ala Ala Glu Ile Arg Ala Ser Ala Asn Leu
1010                1015                1020

Ala Ala Thr Lys Met Ser Glu Cys Val Leu Gly Gln Ser Lys Arg Val
1025                1030                1035                1040

Asp Phe Cys Gly Lys Gly Tyr His Leu Met Ser Phe Pro Gln Ser Ala
                1045                1050                1055

Pro His Gly Val Val Phe Leu His Val Thr Tyr Val Pro Ala Gln Glu
                1060                1065                1070

Lys Asn Phe Thr Thr Ala Pro Ala Ile Cys His Asp Gly Lys Ala His
                1075                1080                1085
```

```
Phe Pro Arg Glu Gly Val Phe Val Ser Asn Gly Thr His Trp Phe Val
    1090                1095                1100

Thr Gln Arg Asn Phe Tyr Glu Pro Gln Ile Ile Thr Thr Asp Asn Thr
1105                1110                1115                1120

Phe Val Ser Gly Asn Cys Asp Val Val Ile Gly Ile Val Asn Asn Thr
                1125                1130                1135

Val Tyr Asp Pro Leu Gln Pro Glu Leu Asp Ser Phe Lys Glu Glu Leu
            1140                1145                1150

Asp Lys Tyr Phe Lys Asn His Thr Ser Pro Asp Val Asp Leu Gly Asp
            1155                1160                1165

Ile Ser Gly Ile Asn Ala Ser Val Val Asn Ile Gln Lys Glu Ile Asp
        1170                1175                1180

Arg Leu Asn Glu Val Ala Lys Asn Leu Asn Glu Ser Leu Ile Asp Leu
1185                1190                1195                1200

Gln Glu Leu Gly Lys Tyr Glu Gln Tyr Ile Lys Trp Pro Trp Tyr Ile
                1205                1210                1215

Trp Leu Gly Phe Ile Ala Gly Leu Ile Ala Ile Val Met Val Thr Ile
                1220                1225                1230

Met Leu Cys Cys Met Thr Ser Cys Cys Ser Cys Leu Lys Gly Cys Cys
                1235                1240                1245

Ser Cys Gly Ser Cys Cys Lys Phe Asp Glu Asp Asp Ser Glu Pro Val
    1250                1255                1260

Leu Lys Gly Val Lys Leu His Tyr Thr
1265                1270

<210> SEQ ID NO 56
<211> LENGTH: 1208
<212> TYPE: PRT
<213> ORGANISM: Artificial Sequence
<220> FEATURE:
<223> OTHER INFORMATION: Synthetic construct

<400> SEQUENCE: 56

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175
```

-continued

Met Asp Leu Glu Gly Lys Gln Gly Asn Phe Lys Asn Leu Arg Glu Phe
                180                 185                 190

Val Phe Lys Asn Ile Asp Gly Tyr Phe Lys Ile Tyr Ser Lys His Thr
            195                 200                 205

Pro Ile Asn Leu Val Arg Asp Leu Pro Gln Gly Phe Ser Ala Leu Glu
        210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val

-continued

```
            595                 600                 605
Ala Val Leu Tyr Gln Asp Val Asn Cys Thr Glu Val Pro Val Ala Ile
610                     615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                    645                 650                 655

Asn Asn Ser Tyr Glu Cys Asp Ile Pro Ile Gly Ala Gly Ile Cys Ala
                660                 665                 670

Ser Tyr Gln Thr Gln Thr Asn Ser Pro Arg Arg Ala Arg Ser Val Ala
                675                 680                 685

Ser Gln Ser Ile Ile Ala Tyr Thr Met Ser Leu Gly Ala Glu Asn Ser
690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
                740                 745                 750

Leu Leu Gln Tyr Gly Ser Phe Cys Thr Gln Leu Asn Arg Ala Leu Thr
                755                 760                 765

Gly Ile Ala Val Glu Gln Asp Lys Asn Thr Gln Glu Val Phe Ala Gln
770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
                820                 825                 830

Phe Ile Lys Gln Tyr Gly Asp Cys Leu Gly Asp Ile Ala Ala Arg Asp
                835                 840                 845

Leu Ile Cys Ala Gln Lys Phe Asn Gly Leu Thr Val Leu Pro Pro Leu
850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
                900                 905                 910

Gln Asn Val Leu Tyr Glu Asn Gln Lys Leu Ile Ala Asn Gln Phe Asn
                915                 920                 925

Ser Ala Ile Gly Lys Ile Gln Asp Ser Leu Ser Ser Thr Ala Ser Ala
                930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
                980                 985                 990

Ile Asp Arg Leu Ile Thr Gly Arg Leu Gln Ser Leu Gln Thr Tyr Val
                995                 1000                1005

Thr Gln Gln Leu Ile Arg Ala Ala Glu Ile Arg Ala Ser Ala Asn Leu
                1010                1015                1020
```

```
Ala Ala Thr Lys Met Ser Glu Cys Val Leu Gly Gln Ser Lys Arg Val
1025                1030                1035                1040

Asp Phe Cys Gly Lys Gly Tyr His Leu Met Ser Phe Pro Gln Ser Ala
                1045                1050                1055

Pro His Gly Val Val Phe Leu His Val Thr Tyr Val Pro Ala Gln Glu
            1060                1065                1070

Lys Asn Phe Thr Thr Ala Pro Ala Ile Cys His Asp Gly Lys Ala His
        1075                1080                1085

Phe Pro Arg Glu Gly Val Phe Val Ser Asn Gly Thr His Trp Phe Val
    1090                1095                1100

Thr Gln Arg Asn Phe Tyr Glu Pro Gln Ile Ile Thr Thr Asp Asn Thr
1105                1110                1115                1120

Phe Val Ser Gly Asn Cys Asp Val Val Ile Gly Ile Val Asn Asn Thr
                1125                1130                1135

Val Tyr Asp Pro Leu Gln Pro Glu Leu Asp Ser Phe Lys Glu Glu Leu
            1140                1145                1150

Asp Lys Tyr Phe Lys Asn His Thr Ser Pro Asp Val Asp Leu Gly Asp
        1155                1160                1165

Ile Ser Gly Ile Asn Ala Ser Val Val Asn Ile Gln Lys Glu Ile Asp
    1170                1175                1180

Arg Leu Asn Glu Val Ala Lys Asn Leu Asn Glu Ser Leu Ile Asp Leu
1185                1190                1195                1200

Gln Glu Leu Gly Lys Tyr Glu Gln
                1205

<210> SEQ ID NO 57
<211> LENGTH: 290
<212> TYPE: PRT
<213> ORGANISM: Artificial Sequence
<220> FEATURE:
<223> OTHER INFORMATION: Synthetic construct

<400> SEQUENCE: 57

Val Asn Leu Thr Thr Arg Thr Gln Leu Pro Pro Ala Tyr Thr Asn Ser
1               5                   10                  15

Phe Thr Arg Gly Val Tyr Tyr Pro Asp Lys Val Phe Arg Ser Ser Val
                20                  25                  30

Leu His Ser Thr Gln Asp Leu Phe Leu Pro Phe Phe Ser Asn Val Thr
            35                  40                  45

Trp Phe His Ala Ile His Val Ser Gly Thr Asn Gly Thr Lys Arg Phe
        50                  55                  60

Asp Asn Pro Val Leu Pro Phe Asn Asp Gly Val Tyr Phe Ala Ser Thr
65                  70                  75                  80

Glu Lys Ser Asn Ile Ile Arg Gly Trp Ile Phe Gly Thr Thr Leu Asp
                85                  90                  95

Ser Lys Thr Gln Ser Leu Leu Ile Val Asn Asn Ala Thr Asn Val Val
            100                 105                 110

Ile Lys Val Cys Glu Phe Gln Phe Cys Asn Asp Pro Phe Leu Gly Val
        115                 120                 125

Tyr Tyr His Lys Asn Asn Lys Ser Trp Met Glu Ser Glu Phe Arg Val
    130                 135                 140

Tyr Ser Ser Ala Asn Asn Cys Thr Phe Glu Tyr Val Ser Gln Pro Phe
145                 150                 155                 160

Leu Met Asp Leu Glu Gly Lys Gln Gly Asn Phe Lys Asn Leu Arg Glu
                165                 170                 175
```

```
Phe Val Phe Lys Asn Ile Asp Gly Tyr Phe Lys Ile Tyr Ser Lys His
            180                 185                 190

Thr Pro Ile Asn Leu Val Arg Asp Leu Pro Gln Gly Phe Ser Ala Leu
        195                 200                 205

Glu Pro Leu Val Asp Leu Pro Ile Gly Ile Asn Ile Thr Arg Phe Gln
210                 215                 220

Thr Leu Leu Ala Leu His Arg Ser Tyr Leu Thr Pro Gly Asp Ser Ser
225                 230                 235                 240

Ser Gly Trp Thr Ala Gly Ala Ala Tyr Tyr Val Gly Tyr Leu Gln
                245                 250                 255

Pro Arg Thr Phe Leu Leu Lys Tyr Asn Glu Asn Gly Thr Ile Thr Asp
            260                 265                 270

Ala Val Asp Cys Ala Leu Asp Pro Leu Ser Glu Thr Lys Cys Thr Leu
            275                 280                 285

Lys Ser
    290

<210> SEQ ID NO 58
<211> LENGTH: 192
<212> TYPE: PRT
<213> ORGANISM: Artificial Sequence
<220> FEATURE:
<223> OTHER INFORMATION: Synthetic construct

<400> SEQUENCE: 58

Pro Asn Ile Thr Asn Leu Cys Pro Phe Gly Glu Val Phe Asn Ala Thr
1               5                   10                  15

Arg Phe Ala Ser Val Tyr Ala Trp Asn Arg Lys Arg Ile Ser Asn Cys
            20                  25                  30

Val Ala Asp Tyr Ser Val Leu Tyr Asn Ser Ala Ser Phe Ser Thr Phe
        35                  40                  45

Lys Cys Tyr Gly Val Ser Pro Thr Lys Leu Asn Asp Leu Cys Phe Thr
    50                  55                  60

Asn Val Tyr Ala Asp Ser Phe Val Ile Arg Gly Asp Glu Val Arg Gln
65                  70                  75                  80

Ile Ala Pro Gly Gln Thr Gly Lys Ile Ala Asp Tyr Asn Tyr Lys Leu
                85                  90                  95

Pro Asp Asp Phe Thr Gly Cys Val Ile Ala Trp Asn Ser Asn Asn Leu
            100                 105                 110

Asp Ser Lys Val Gly Gly Asn Tyr Asn Tyr Leu Tyr Arg Leu Phe Arg
        115                 120                 125

Lys Ser Asn Leu Lys Pro Phe Glu Arg Asp Ile Ser Thr Glu Ile Tyr
    130                 135                 140

Gln Ala Gly Ser Thr Pro Cys Asn Gly Val Glu Gly Phe Asn Cys Tyr
145                 150                 155                 160

Phe Pro Leu Gln Ser Tyr Gly Phe Gln Pro Thr Asn Gly Val Gly Tyr
                165                 170                 175

Gln Pro Tyr Arg Val Val Val Leu Ser Phe Glu Leu Leu His Ala Pro
            180                 185                 190

<210> SEQ ID NO 59
<211> LENGTH: 4
<212> TYPE: PRT
<213> ORGANISM: Artificial Sequence
<220> FEATURE:
<223> OTHER INFORMATION: Synthetic construct
```

```
<400> SEQUENCE: 59

Arg Arg Ala Arg
1

<210> SEQ ID NO 60
<211> LENGTH: 4
<212> TYPE: PRT
<213> ORGANISM: Artificial Sequence
<220> FEATURE:
<223> OTHER INFORMATION: Synthetic construct

<400> SEQUENCE: 60

Gly Ser Ala Gly
1

<210> SEQ ID NO 61
<211> LENGTH: 18
<212> TYPE: PRT
<213> ORGANISM: Artificial Sequence
<220> FEATURE:
<223> OTHER INFORMATION: Synthetic construct

<400> SEQUENCE: 61

Ser Phe Ile Glu Asp Leu Leu Phe Asn Lys Val Thr Leu Ala Asp Ala
1               5                   10                  15

Gly Phe

<210> SEQ ID NO 62
<211> LENGTH: 78
<212> TYPE: PRT
<213> ORGANISM: Artificial Sequence
<220> FEATURE:
<223> OTHER INFORMATION: Synthetic construct

<400> SEQUENCE: 62

Gly Ile Gly Val Thr Gln Asn Val Leu Tyr Glu Asn Gln Lys Leu Ile
1               5                   10                  15

Ala Asn Gln Phe Asn Ser Ala Ile Gly Lys Ile Gln Asp Ser Leu Ser
                20                  25                  30

Ser Thr Ala Ser Ala Leu Gly Lys Leu Gln Asp Val Val Asn Gln Asn
        35                  40                  45

Ala Gln Ala Leu Asn Thr Leu Val Lys Gln Leu Ser Ser Asn Phe Gly
    50                  55                  60

Ala Ile Ser Ser Val Leu Asn Asp Ile Leu Ser Arg Leu Asp
65                  70                  75

<210> SEQ ID NO 63
<211> LENGTH: 50
<212> TYPE: PRT
<213> ORGANISM: Artificial Sequence
<220> FEATURE:
<223> OTHER INFORMATION: Synthetic construct

<400> SEQUENCE: 63

Lys Val Glu Ala Glu Val Gln Ile Asp Arg Leu Ile Thr Gly Arg Leu
1               5                   10                  15

Gln Ser Leu Gln Thr Tyr Val Thr Gln Gln Leu Ile Arg Ala Ala Glu
                20                  25                  30

Ile Arg Ala Ser Ala Asn Leu Ala Ala Thr Lys Met Ser Glu Cys Val
        35                  40                  45

Leu Gly
    50
```

-continued

<210> SEQ ID NO 64
<211> LENGTH: 66
<212> TYPE: PRT
<213> ORGANISM: Artificial Sequence
<220> FEATURE:
<223> OTHER INFORMATION: Synthetic construct

<400> SEQUENCE: 64

Thr Thr Ala Pro Ala Ile Cys His Asp Gly Lys Ala His Phe Pro Arg
1               5                   10                  15

Glu Gly Val Phe Val Ser Asn Gly Thr His Trp Phe Val Thr Gln Arg
            20                  25                  30

Asn Phe Tyr Glu Pro Gln Ile Ile Thr Thr Asp Asn Thr Phe Val Ser
        35                  40                  45

Gly Asn Cys Asp Val Val Ile Gly Ile Val Asn Asn Thr Val Tyr Asp
    50                  55                  60

Pro Leu
65

<210> SEQ ID NO 65
<211> LENGTH: 59
<212> TYPE: PRT
<213> ORGANISM: Artificial Sequence
<220> FEATURE:
<223> OTHER INFORMATION: Synthetic construct

<400> SEQUENCE: 65

Glu Glu Leu Asp Lys Tyr Phe Lys Asn His Thr Ser Pro Asp Val Asp
1               5                   10                  15

Leu Gly Asp Ile Ser Gly Ile Asn Ala Ser Val Val Asn Ile Gln Lys
            20                  25                  30

Glu Ile Asp Arg Leu Asn Glu Val Ala Lys Asn Leu Asn Glu Ser Leu
        35                  40                  45

Ile Asp Leu Gln Glu Leu Gly Lys Tyr Glu Gln
    50                  55

<210> SEQ ID NO 66
<211> LENGTH: 23
<212> TYPE: PRT
<213> ORGANISM: Artificial Sequence
<220> FEATURE:
<223> OTHER INFORMATION: Synthetic construct

<400> SEQUENCE: 66

Trp Pro Trp Tyr Ile Trp Leu Gly Phe Ile Ala Gly Leu Ile Ala Ile
1               5                   10                  15

Val Met Val Thr Ile Met Leu
            20

<210> SEQ ID NO 67
<211> LENGTH: 244
<212> TYPE: PRT
<213> ORGANISM: Artificial Sequence
<220> FEATURE:
<223> OTHER INFORMATION: Synthetic construct

<400> SEQUENCE: 67

Ala Asn Val Val Arg Asp Arg Asp Leu Glu Val Asp Thr Thr Leu Lys
1               5                   10                  15

Ser Leu Ser Gln Gln Ile Glu Asn Ile Arg Ser Pro Glu Gly Ser Arg
            20                  25                  30

```
Lys Asn Pro Ala Arg Thr Cys Arg Asp Leu Lys Met Cys His Ser Asp
            35                  40                  45

Trp Lys Ser Gly Glu Tyr Trp Ile Asp Pro Asn Gln Gly Cys Asn Leu
    50                  55                  60

Asp Ala Ile Lys Val Phe Cys Asn Met Glu Thr Gly Glu Thr Cys Val
65                  70                  75                  80

Tyr Pro Thr Gln Pro Ser Val Ala Gln Lys Asn Trp Tyr Ile Ser Lys
                85                  90                  95

Asn Pro Lys Asp Lys Arg His Val Trp Phe Gly Ser Met Thr Asp
            100                 105                 110

Gly Phe Gln Phe Glu Tyr Gly Gly Gln Gly Ser Asp Pro Ala Asp Val
                115                 120                 125

Ala Ile Gln Leu Thr Phe Leu Arg Leu Met Ser Thr Glu Ala Ser Gln
130                 135                 140

Asn Ile Thr Tyr His Cys Lys Asn Ser Val Ala Tyr Met Asp Gln Gln
145                 150                 155                 160

Thr Gly Asn Leu Lys Lys Ala Leu Leu Leu Gln Gly Ser Asn Glu Ile
                165                 170                 175

Glu Ile Arg Ala Glu Gly Asn Ser Arg Phe Thr Tyr Ser Val Thr Val
            180                 185                 190

Asp Gly Cys Thr Ser His Thr Gly Ala Trp Gly Lys Thr Val Ile Glu
            195                 200                 205

Tyr Lys Thr Thr Lys Thr Ser Arg Leu Pro Ile Ile Asp Val Ala Pro
    210                 215                 220

Leu Asp Val Gly Ala Pro Asp Gln Glu Phe Gly Phe Asp Val Gly Pro
225                 230                 235                 240

Val Cys Phe Leu

<210> SEQ ID NO 68
<211> LENGTH: 309
<212> TYPE: PRT
<213> ORGANISM: Artificial Sequence
<220> FEATURE:
<223> OTHER INFORMATION: Synthetic construct

<400> SEQUENCE: 68

Asn Gly Leu Pro Gly Pro Ile Gly Pro Pro Gly Pro Arg Gly Arg Thr
1               5                   10                  15

Gly Asp Ala Gly Pro Val Gly Pro Pro Gly Pro Pro Gly Pro Pro Gly
            20                  25                  30

Pro Pro Gly Pro Pro Ser Ala Gly Phe Asp Phe Ser Phe Leu Pro Gln
                35                  40                  45

Pro Pro Gln Glu Lys Ala His Asp Gly Gly Arg Tyr Tyr Arg Ala Asn
    50                  55                  60

Asp Ala Asn Val Val Arg Asp Arg Asp Leu Glu Val Asp Thr Thr Leu
65                  70                  75                  80

Lys Ser Leu Ser Gln Gln Ile Glu Asn Ile Arg Ser Pro Glu Gly Ser
                85                  90                  95

Arg Lys Asn Pro Ala Arg Thr Cys Arg Asp Leu Lys Met Cys His Ser
            100                 105                 110

Asp Trp Lys Ser Gly Glu Tyr Trp Ile Asp Pro Asn Gln Gly Cys Asn
        115                 120                 125

Leu Asp Ala Ile Lys Val Phe Cys Asn Met Glu Thr Gly Glu Thr Cys
    130                 135                 140
```

```
Val Tyr Pro Thr Gln Pro Ser Val Ala Gln Lys Asn Trp Tyr Ile Ser
145                 150                 155                 160

Lys Asn Pro Lys Asp Lys Arg His Val Trp Phe Gly Glu Ser Met Thr
                165                 170                 175

Asp Gly Phe Gln Phe Glu Tyr Gly Gly Gln Gly Ser Asp Pro Ala Asp
            180                 185                 190

Val Ala Ile Gln Leu Thr Phe Leu Arg Leu Met Ser Thr Glu Ala Ser
        195                 200                 205

Gln Asn Ile Thr Tyr His Cys Lys Asn Ser Val Ala Tyr Met Asp Gln
    210                 215                 220

Gln Thr Gly Asn Leu Lys Lys Ala Leu Leu Leu Gln Gly Ser Asn Glu
225                 230                 235                 240

Ile Glu Ile Arg Ala Glu Gly Asn Ser Arg Phe Thr Tyr Ser Val Thr
                245                 250                 255

Val Asp Gly Cys Thr Ser His Thr Gly Ala Trp Gly Lys Thr Val Ile
            260                 265                 270

Glu Tyr Lys Thr Thr Lys Thr Ser Arg Leu Pro Ile Ile Asp Val Ala
        275                 280                 285

Pro Leu Asp Val Gly Ala Pro Asp Gln Glu Phe Gly Phe Asp Val Gly
    290                 295                 300

Pro Val Cys Phe Leu
305

<210> SEQ ID NO 69
<211> LENGTH: 309
<212> TYPE: PRT
<213> ORGANISM: Artificial Sequence
<220> FEATURE:
<223> OTHER INFORMATION: Synthetic construct

<400> SEQUENCE: 69

Asn Gly Leu Pro Gly Pro Ile Gly Pro Pro Gly Pro Arg Gly Arg Thr
1               5                   10                  15

Gly Asp Ala Gly Pro Val Gly Pro Pro Gly Pro Pro Gly Pro Pro Gly
            20                  25                  30

Pro Pro Gly Pro Pro Ser Ala Gly Phe Asp Phe Ser Phe Leu Pro Gln
        35                  40                  45

Pro Pro Gln Glu Lys Ala His Asp Gly Gly Arg Tyr Tyr Arg Asn Asp
    50                  55                  60

Asp Ala Asn Val Val Arg Asp Arg Asp Leu Glu Val Asp Thr Thr Leu
65                  70                  75                  80

Lys Ser Leu Ser Gln Gln Ile Glu Asn Ile Arg Ser Pro Glu Gly Ser
                85                  90                  95

Arg Lys Asn Pro Ala Arg Thr Cys Arg Asp Leu Lys Met Cys His Ser
            100                 105                 110

Asp Trp Lys Ser Gly Glu Tyr Trp Ile Asp Pro Asn Gln Gly Cys Asn
        115                 120                 125

Leu Asp Ala Ile Lys Val Phe Cys Asn Met Glu Thr Gly Glu Thr Cys
    130                 135                 140

Val Tyr Pro Thr Gln Pro Ser Val Ala Gln Lys Asn Trp Tyr Ile Ser
145                 150                 155                 160

Lys Asn Pro Lys Asp Lys Arg His Val Trp Phe Gly Glu Ser Met Thr
                165                 170                 175

Asp Gly Phe Gln Phe Glu Tyr Gly Gly Gln Gly Ser Asp Pro Ala Asp
            180                 185                 190
```

```
Val Ala Ile Gln Leu Thr Phe Leu Arg Leu Met Ser Thr Glu Ala Ser
            195                 200                 205

Gln Asn Ile Thr Tyr His Cys Lys Asn Ser Val Ala Tyr Met Asp Gln
        210                 215                 220

Gln Thr Gly Asn Leu Lys Lys Ala Leu Leu Leu Gln Gly Ser Asn Glu
225                 230                 235                 240

Ile Glu Ile Arg Ala Glu Gly Asn Ser Arg Phe Thr Tyr Ser Val Thr
                245                 250                 255

Val Asp Gly Cys Thr Ser His Thr Gly Ala Trp Gly Lys Thr Val Ile
                260                 265                 270

Glu Tyr Lys Thr Thr Lys Thr Ser Arg Leu Pro Ile Ile Asp Val Ala
            275                 280                 285

Pro Leu Asp Val Gly Ala Pro Asp Gln Glu Phe Gly Phe Asp Val Gly
            290                 295                 300

Pro Val Cys Phe Leu
305

<210> SEQ ID NO 70
<211> LENGTH: 311
<212> TYPE: PRT
<213> ORGANISM: Artificial Sequence
<220> FEATURE:
<223> OTHER INFORMATION: Synthetic construct

<400> SEQUENCE: 70

Arg Ser Asn Gly Leu Pro Gly Pro Ile Gly Pro Pro Gly Pro Arg Gly
1               5                   10                  15

Arg Thr Gly Asp Ala Gly Pro Val Gly Pro Pro Gly Pro Pro Gly Pro
                20                  25                  30

Pro Gly Pro Gly Pro Pro Ser Ala Gly Phe Asp Phe Ser Phe Leu
            35                  40                  45

Pro Gln Pro Pro Gln Glu Lys Ala His Asp Gly Gly Arg Tyr Tyr Arg
    50                  55                  60

Ala Asn Asp Ala Asn Val Val Arg Asp Arg Asp Leu Glu Val Asp Thr
65                  70                  75                  80

Thr Leu Lys Ser Leu Ser Gln Gln Ile Glu Asn Ile Arg Ser Pro Glu
                85                  90                  95

Gly Ser Arg Lys Asn Pro Ala Arg Thr Cys Arg Asp Leu Lys Met Cys
            100                 105                 110

His Ser Asp Trp Lys Ser Gly Glu Tyr Trp Ile Asp Pro Asn Gln Gly
        115                 120                 125

Cys Asn Leu Asp Ala Ile Lys Val Phe Cys Asn Met Glu Thr Gly Glu
    130                 135                 140

Thr Cys Val Tyr Pro Thr Gln Pro Ser Val Ala Gln Lys Asn Trp Tyr
145                 150                 155                 160

Ile Ser Lys Asn Pro Lys Asp Lys Arg His Val Trp Phe Gly Glu Ser
                165                 170                 175

Met Thr Asp Gly Phe Gln Phe Glu Tyr Gly Gly Gln Gly Ser Asp Pro
            180                 185                 190

Ala Asp Val Ala Ile Gln Leu Thr Phe Leu Arg Leu Met Ser Thr Glu
        195                 200                 205

Ala Ser Gln Asn Ile Thr Tyr His Cys Lys Asn Ser Val Ala Tyr Met
    210                 215                 220

Asp Gln Gln Thr Gly Asn Leu Lys Lys Ala Leu Leu Leu Gln Gly Ser
225                 230                 235                 240
```

Asn Glu Ile Glu Ile Arg Ala Glu Gly Asn Ser Arg Phe Thr Tyr Ser
            245                 250                 255

Val Thr Val Asp Gly Cys Thr Ser His Thr Gly Ala Trp Gly Lys Thr
        260                 265                 270

Val Ile Glu Tyr Lys Thr Thr Lys Thr Ser Arg Leu Pro Ile Ile Asp
        275                 280                 285

Val Ala Pro Leu Asp Val Gly Ala Pro Asp Gln Glu Phe Gly Phe Asp
        290                 295                 300

Val Gly Pro Val Cys Phe Leu
305                 310

<210> SEQ ID NO 71
<211> LENGTH: 311
<212> TYPE: PRT
<213> ORGANISM: Artificial Sequence
<220> FEATURE:
<223> OTHER INFORMATION: Synthetic construct

<400> SEQUENCE: 71

Gly Ser Asn Gly Leu Pro Gly Pro Ile Gly Pro Pro Gly Pro Arg Gly
1               5                   10                  15

Arg Thr Gly Asp Ala Gly Pro Val Gly Pro Pro Gly Pro Pro Gly Pro
            20                  25                  30

Pro Gly Pro Pro Gly Pro Pro Ser Ala Gly Phe Asp Phe Ser Phe Leu
        35                  40                  45

Pro Gln Pro Pro Gln Glu Lys Ala His Asp Gly Gly Arg Tyr Tyr Arg
    50                  55                  60

Ala Asn Asp Ala Asn Val Val Arg Asp Arg Asp Leu Glu Val Asp Thr
65                  70                  75                  80

Thr Leu Lys Ser Leu Ser Gln Gln Ile Glu Asn Ile Arg Ser Pro Glu
                85                  90                  95

Gly Ser Arg Lys Asn Pro Ala Arg Thr Cys Arg Asp Leu Lys Met Cys
            100                 105                 110

His Ser Asp Trp Lys Ser Gly Glu Tyr Trp Ile Asp Pro Asn Gln Gly
        115                 120                 125

Cys Asn Leu Asp Ala Ile Lys Val Phe Cys Asn Met Glu Thr Gly Glu
    130                 135                 140

Thr Cys Val Tyr Pro Thr Gln Pro Ser Val Ala Gln Lys Asn Trp Tyr
145                 150                 155                 160

Ile Ser Lys Asn Pro Lys Asp Lys Arg His Val Trp Phe Gly Glu Ser
                165                 170                 175

Met Thr Asp Gly Phe Gln Phe Glu Tyr Gly Gly Gln Gly Ser Asp Pro
            180                 185                 190

Ala Asp Val Ala Ile Gln Leu Thr Phe Leu Arg Leu Met Ser Thr Glu
        195                 200                 205

Ala Ser Gln Asn Ile Thr Tyr His Cys Lys Asn Ser Val Ala Tyr Met
    210                 215                 220

Asp Gln Gln Thr Gly Asn Leu Lys Lys Ala Leu Leu Leu Gln Gly Ser
225                 230                 235                 240

Asn Glu Ile Glu Ile Arg Ala Glu Gly Asn Ser Arg Phe Thr Tyr Ser
                245                 250                 255

Val Thr Val Asp Gly Cys Thr Ser His Thr Gly Ala Trp Gly Lys Thr
            260                 265                 270

Val Ile Glu Tyr Lys Thr Thr Lys Thr Ser Arg Leu Pro Ile Ile Asp
        275                 280                 285

```
Val Ala Pro Leu Asp Val Gly Ala Pro Asp Gln Glu Phe Gly Phe Asp
        290                 295                 300

Val Gly Pro Val Cys Phe Leu
305                 310

<210> SEQ ID NO 72
<211> LENGTH: 244
<212> TYPE: PRT
<213> ORGANISM: Artificial Sequence
<220> FEATURE:
<223> OTHER INFORMATION: Synthetic construct

<400> SEQUENCE: 72

Ala Asn Val Val Arg Asp Arg Asp Leu Glu Val Asp Thr Thr Leu Lys
1               5                   10                  15

Ser Leu Ser Gln Gln Ile Glu Asn Ile Arg Ser Pro Glu Gly Ser Arg
            20                  25                  30

Lys Asn Pro Ala Arg Thr Cys Arg Asp Leu Lys Met Cys His Ser Asp
        35                  40                  45

Trp Lys Ser Gly Glu Tyr Trp Ile Asp Pro Asn Gln Gly Cys Asn Leu
    50                  55                  60

Asp Ala Ile Lys Val Phe Cys Asn Met Glu Thr Gly Gly Thr Cys Val
65                  70                  75                  80

Tyr Pro Thr Gln Pro Ser Val Ala Gln Lys Asn Trp Tyr Ile Ser Lys
                85                  90                  95

Asn Pro Lys Asp Lys Arg His Val Trp Phe Gly Glu Ser Met Thr Asp
            100                 105                 110

Gly Phe Gln Phe Glu Tyr Gly Gly Gln Gly Ser Asp Pro Ala Asp Val
        115                 120                 125

Ala Ile Gln Leu Thr Phe Leu Arg Leu Met Ser Thr Glu Ala Ser Gln
    130                 135                 140

Asn Ile Thr Tyr His Cys Lys Asn Ser Val Ala Tyr Met Asp Gln Gln
145                 150                 155                 160

Thr Gly Asn Leu Lys Lys Ala Leu Leu Leu Lys Gly Ser Asn Glu Ile
                165                 170                 175

Glu Ile Arg Ala Glu Gly Asn Ser Arg Phe Thr Tyr Ser Val Thr Val
            180                 185                 190

Asp Gly Cys Thr Ser His Thr Gly Ala Trp Gly Lys Thr Val Ile Glu
        195                 200                 205

Tyr Lys Thr Thr Lys Ser Ser Arg Leu Pro Ile Ile Asp Val Ala Pro
    210                 215                 220

Leu Asp Val Gly Ala Pro Asp Gln Glu Phe Gly Phe Asp Val Gly Pro
225                 230                 235                 240

Val Cys Phe Leu

<210> SEQ ID NO 73
<211> LENGTH: 309
<212> TYPE: PRT
<213> ORGANISM: Artificial Sequence
<220> FEATURE:
<223> OTHER INFORMATION: Synthetic construct

<400> SEQUENCE: 73

Asn Gly Leu Pro Gly Pro Ile Gly Pro Pro Gly Pro Arg Gly Arg Thr
1               5                   10                  15

Gly Asp Ala Gly Pro Val Gly Pro Pro Gly Pro Pro Gly Pro Pro Gly
            20                  25                  30
```

Pro Pro Gly Pro Pro Ser Ala Gly Phe Asp Phe Ser Phe Leu Pro Gln
            35                  40                  45

Pro Pro Gln Glu Lys Ala His Asp Gly Gly Arg Tyr Tyr Arg Ala Asn
    50                  55                  60

Asp Ala Asn Val Val Arg Asp Arg Asp Leu Glu Val Asp Thr Thr Leu
65                  70                  75                  80

Lys Ser Leu Ser Gln Gln Ile Glu Asn Ile Arg Ser Pro Glu Gly Ser
                85                  90                  95

Arg Lys Asn Pro Ala Arg Thr Cys Arg Asp Leu Lys Met Cys His Ser
            100                 105                 110

Asp Trp Lys Ser Gly Glu Tyr Trp Ile Asp Pro Asn Gln Gly Cys Asn
    115                 120                 125

Leu Asp Ala Ile Lys Val Phe Cys Asn Met Glu Thr Gly Glu Thr Cys
130                 135                 140

Val Tyr Pro Thr Gln Pro Ser Val Ala Gln Lys Asn Trp Tyr Ile Ser
145                 150                 155                 160

Lys Asn Pro Lys Asp Lys Arg His Val Trp Phe Gly Glu Ser Met Thr
                165                 170                 175

Asp Gly Phe Gln Phe Glu Tyr Gly Gly Gln Gly Ser Asp Pro Ala Asp
            180                 185                 190

Val Ala Ile Gln Leu Thr Phe Leu Arg Leu Met Ser Thr Glu Ala Ser
    195                 200                 205

Gln Asn Ile Thr Tyr His Cys Lys Asn Ser Val Ala Tyr Met Asp Gln
            210                 215                 220

Gln Thr Gly Asn Leu Lys Lys Ala Leu Leu Leu Lys Gly Ser Asn Glu
225                 230                 235                 240

Ile Glu Ile Arg Ala Glu Gly Asn Ser Arg Phe Thr Tyr Ser Val Thr
                245                 250                 255

Val Asp Gly Cys Thr Ser His Thr Gly Ala Trp Gly Lys Thr Val Ile
            260                 265                 270

Glu Tyr Lys Thr Thr Lys Ser Ser Arg Leu Pro Ile Ile Asp Val Ala
    275                 280                 285

Pro Leu Asp Val Gly Ala Pro Asp Gln Glu Phe Gly Phe Asp Val Gly
290                 295                 300

Pro Val Cys Phe Leu
305

<210> SEQ ID NO 74
<211> LENGTH: 309
<212> TYPE: PRT
<213> ORGANISM: Artificial Sequence
<220> FEATURE:
<223> OTHER INFORMATION: Synthetic construct

<400> SEQUENCE: 74

Asn Gly Leu Pro Gly Pro Ile Gly Pro Pro Gly Pro Arg Gly Arg Thr
1               5                   10                  15

Gly Asp Ala Gly Pro Val Gly Pro Pro Gly Pro Pro Gly Pro Pro Gly
            20                  25                  30

Pro Pro Gly Pro Pro Ser Ala Gly Phe Asp Phe Ser Phe Leu Pro Gln
            35                  40                  45

Pro Pro Gln Glu Lys Ala His Asp Gly Gly Arg Tyr Tyr Arg Asn Asp
    50                  55                  60

Asp Ala Asn Val Val Arg Asp Arg Asp Leu Glu Val Asp Thr Thr Leu
65                  70                  75                  80

```
Lys Ser Leu Ser Gln Gln Ile Glu Asn Ile Arg Ser Pro Glu Gly Ser
                85                  90                  95

Arg Lys Asn Pro Ala Arg Thr Cys Arg Asp Leu Lys Met Cys His Ser
            100                 105                 110

Asp Trp Lys Ser Gly Glu Tyr Trp Ile Asp Pro Asn Gln Gly Cys Asn
        115                 120                 125

Leu Asp Ala Ile Lys Val Phe Cys Asn Met Glu Thr Gly Glu Thr Cys
    130                 135                 140

Val Tyr Pro Thr Gln Pro Ser Val Ala Gln Lys Asn Trp Tyr Ile Ser
145                 150                 155                 160

Lys Asn Pro Lys Asp Lys Arg His Val Trp Phe Gly Glu Ser Met Thr
                165                 170                 175

Asp Gly Phe Gln Phe Glu Tyr Gly Gly Gln Gly Ser Asp Pro Ala Asp
            180                 185                 190

Val Ala Ile Gln Leu Thr Phe Leu Arg Leu Met Ser Thr Glu Ala Ser
        195                 200                 205

Gln Asn Ile Thr Tyr His Cys Lys Asn Ser Val Ala Tyr Met Asp Gln
    210                 215                 220

Gln Thr Gly Asn Leu Lys Lys Ala Leu Leu Leu Lys Gly Ser Asn Glu
225                 230                 235                 240

Ile Glu Ile Arg Ala Glu Gly Asn Ser Arg Phe Thr Tyr Ser Val Thr
                245                 250                 255

Val Asp Gly Cys Thr Ser His Thr Gly Ala Trp Gly Lys Thr Val Ile
            260                 265                 270

Glu Tyr Lys Thr Thr Lys Ser Ser Arg Leu Pro Ile Ile Asp Val Ala
        275                 280                 285

Pro Leu Asp Val Gly Ala Pro Asp Gln Glu Phe Gly Phe Asp Val Gly
    290                 295                 300

Pro Val Cys Phe Leu
305

<210> SEQ ID NO 75
<211> LENGTH: 311
<212> TYPE: PRT
<213> ORGANISM: Artificial Sequence
<220> FEATURE:
<223> OTHER INFORMATION: Synthetic construct

<400> SEQUENCE: 75

Arg Ser Asn Gly Leu Pro Gly Pro Ile Gly Pro Pro Gly Pro Arg Gly
1               5                   10                  15

Arg Thr Gly Asp Ala Gly Pro Val Gly Pro Pro Gly Pro Pro Gly Pro
            20                  25                  30

Pro Gly Pro Gly Pro Pro Ser Ala Gly Phe Asp Phe Ser Phe Leu
        35                  40                  45

Pro Gln Pro Pro Gln Glu Lys Ala His Asp Gly Gly Arg Tyr Tyr Arg
    50                  55                  60

Ala Asn Asp Ala Asn Val Val Arg Asp Arg Asp Leu Glu Val Asp Thr
65                  70                  75                  80

Thr Leu Lys Ser Leu Ser Gln Gln Ile Glu Asn Ile Arg Ser Pro Glu
                85                  90                  95

Gly Ser Arg Lys Asn Pro Ala Arg Thr Cys Arg Asp Leu Lys Met Cys
            100                 105                 110

His Ser Asp Trp Lys Ser Gly Glu Tyr Trp Ile Asp Pro Asn Gln Gly
        115                 120                 125
```

```
Cys Asn Leu Asp Ala Ile Lys Val Phe Cys Asn Met Glu Thr Gly Glu
    130                 135                 140

Thr Cys Val Tyr Pro Thr Gln Pro Ser Val Ala Gln Lys Asn Trp Tyr
145                 150                 155                 160

Ile Ser Lys Asn Pro Lys Asp Lys Arg His Val Trp Phe Gly Glu Ser
                165                 170                 175

Met Thr Asp Gly Phe Gln Phe Glu Tyr Gly Gln Gly Ser Asp Pro
            180                 185                 190

Ala Asp Val Ala Ile Gln Leu Thr Phe Leu Arg Leu Met Ser Thr Glu
                195                 200                 205

Ala Ser Gln Asn Ile Thr Tyr His Cys Lys Asn Ser Val Ala Tyr Met
    210                 215                 220

Asp Gln Gln Thr Gly Asn Leu Lys Lys Ala Leu Leu Leu Lys Gly Ser
225                 230                 235                 240

Asn Glu Ile Glu Ile Arg Ala Glu Gly Asn Ser Arg Phe Thr Tyr Ser
                245                 250                 255

Val Thr Val Asp Gly Cys Thr Ser His Thr Gly Ala Trp Gly Lys Thr
                260                 265                 270

Val Ile Glu Tyr Lys Thr Thr Lys Ser Ser Arg Leu Pro Ile Ile Asp
    275                 280                 285

Val Ala Pro Leu Asp Val Gly Ala Pro Asp Gln Glu Phe Gly Phe Asp
290                 295                 300

Val Gly Pro Val Cys Phe Leu
305                 310

<210> SEQ ID NO 76
<211> LENGTH: 311
<212> TYPE: PRT
<213> ORGANISM: Artificial Sequence
<220> FEATURE:
<223> OTHER INFORMATION: Synthetic construct

<400> SEQUENCE: 76

Gly Ser Asn Gly Leu Pro Gly Pro Ile Gly Pro Pro Gly Pro Arg Gly
1               5                   10                  15

Arg Thr Gly Asp Ala Gly Pro Val Gly Pro Pro Gly Pro Pro Gly Pro
                20                  25                  30

Pro Gly Pro Pro Gly Pro Pro Ser Ala Gly Phe Asp Phe Ser Phe Leu
            35                  40                  45

Pro Gln Pro Pro Gln Glu Lys Ala His Asp Gly Gly Arg Tyr Tyr Arg
    50                  55                  60

Ala Asn Asp Ala Asn Val Arg Asp Arg Asp Leu Glu Val Asp Thr
65                  70                  75                  80

Thr Leu Lys Ser Leu Ser Gln Gln Ile Glu Asn Ile Arg Ser Pro Glu
                85                  90                  95

Gly Ser Arg Lys Asn Pro Ala Arg Thr Cys Arg Asp Leu Lys Met Cys
                100                 105                 110

His Ser Asp Trp Lys Ser Gly Glu Tyr Trp Ile Asp Pro Asn Gln Gly
            115                 120                 125

Cys Asn Leu Asp Ala Ile Lys Val Phe Cys Asn Met Glu Thr Gly Glu
    130                 135                 140

Thr Cys Val Tyr Pro Thr Gln Pro Ser Val Ala Gln Lys Asn Trp Tyr
145                 150                 155                 160

Ile Ser Lys Asn Pro Lys Asp Lys Arg His Val Trp Phe Gly Glu Ser
                165                 170                 175
```

Met Thr Asp Gly Phe Gln Phe Glu Tyr Gly Gln Gly Ser Asp Pro
                180                 185                 190

Ala Asp Val Ala Ile Gln Leu Thr Phe Leu Arg Leu Met Ser Thr Glu
195                 200                 205

Ala Ser Gln Asn Ile Thr Tyr His Cys Lys Asn Ser Val Ala Tyr Met
210                 215                 220

Asp Gln Gln Thr Gly Asn Leu Lys Lys Ala Leu Leu Lys Gly Ser
225                 230                 235                 240

Asn Glu Ile Glu Ile Arg Ala Glu Gly Asn Ser Arg Phe Thr Tyr Ser
                245                 250                 255

Val Thr Val Asp Gly Cys Thr Ser His Thr Gly Ala Trp Gly Lys Thr
                260                 265                 270

Val Ile Glu Tyr Lys Thr Thr Lys Ser Ser Arg Leu Pro Ile Ile Asp
                275                 280                 285

Val Ala Pro Leu Asp Val Gly Ala Pro Asp Gln Glu Phe Gly Phe Asp
                290                 295                 300

Val Gly Pro Val Cys Phe Leu
305                 310

<210> SEQ ID NO 77
<211> LENGTH: 234
<212> TYPE: PRT
<213> ORGANISM: Artificial Sequence
<220> FEATURE:
<223> OTHER INFORMATION: Synthetic construct

<400> SEQUENCE: 77

Asp Glu Ile Met Thr Ser Leu Lys Ser Val Asn Gly Gln Ile Glu Ser
1               5                   10                  15

Leu Ile Ser Pro Asp Gly Ser Arg Lys Asn Pro Ala Arg Asn Cys Arg
                20                  25                  30

Asp Leu Lys Phe Cys His Pro Glu Leu Lys Ser Gly Glu Tyr Trp Val
                35                  40                  45

Asp Pro Asn Gln Gly Cys Lys Leu Asp Ala Ile Lys Val Phe Cys Asn
                50                  55                  60

Met Glu Thr Gly Glu Thr Cys Ile Ser Ala Asn Pro Leu Asn Val Pro
65                  70                  75                  80

Arg Lys His Trp Trp Thr Asp Ser Ser Ala Glu Lys Lys His Val Trp
                85                  90                  95

Phe Gly Glu Ser Met Asp Gly Gly Phe Gln Phe Ser Tyr Gly Asn Pro
                100                 105                 110

Glu Leu Pro Glu Asp Val Leu Asp Val Gln Leu Ala Phe Leu Arg Leu
                115                 120                 125

Leu Ser Ser Arg Ala Ser Gln Asn Ile Thr Tyr His Cys Lys Asn Ser
                130                 135                 140

Ile Ala Tyr Met Asp Gln Ala Ser Gly Asn Val Lys Lys Ala Leu Lys
145                 150                 155                 160

Leu Met Gly Ser Asn Glu Gly Glu Phe Lys Ala Glu Gly Asn Ser Lys
                165                 170                 175

Phe Thr Tyr Thr Val Leu Glu Asp Gly Cys Thr Lys His Thr Gly Glu
                180                 185                 190

Trp Ser Lys Thr Val Phe Glu Tyr Arg Thr Arg Lys Ala Val Arg Leu
                195                 200                 205

Pro Ile Val Asp Ile Ala Pro Tyr Asp Ile Gly Gly Pro Asp Gln Glu
                210                 215                 220

Phe Gly Val Asp Val Gly Pro Val Cys Phe
225                 230

<210> SEQ ID NO 78
<211> LENGTH: 244
<212> TYPE: PRT
<213> ORGANISM: Artificial Sequence
<220> FEATURE:
<223> OTHER INFORMATION: Synthetic construct

<400> SEQUENCE: 78

Glu Pro Met Asp Phe Lys Ile Asn Thr Asp Glu Ile Met Thr Ser Leu
1               5                   10                  15

Lys Ser Val Asn Gly Gln Ile Glu Ser Leu Ile Ser Pro Asp Gly Ser
            20                  25                  30

Arg Lys Asn Pro Ala Arg Asn Cys Arg Asp Leu Lys Phe Cys His Pro
        35                  40                  45

Glu Leu Lys Ser Gly Glu Tyr Trp Val Asp Pro Asn Gln Gly Cys Lys
    50                  55                  60

Leu Asp Ala Ile Lys Val Phe Cys Asn Met Glu Thr Gly Glu Thr Cys
65                  70                  75                  80

Ile Ser Ala Asn Pro Leu Asn Val Pro Arg Lys His Trp Trp Thr Asp
                85                  90                  95

Ser Ser Ala Glu Lys Lys His Val Trp Phe Gly Glu Ser Met Asp Gly
            100                 105                 110

Gly Phe Gln Phe Ser Tyr Gly Asn Pro Glu Leu Pro Glu Asp Val Leu
        115                 120                 125

Asp Val Gln Leu Ala Phe Leu Arg Leu Leu Ser Ser Arg Ala Ser Gln
    130                 135                 140

Asn Ile Thr Tyr His Cys Lys Asn Ser Ile Ala Tyr Met Asp Gln Ala
145                 150                 155                 160

Ser Gly Asn Val Lys Lys Ala Leu Lys Leu Met Gly Ser Asn Glu Gly
                165                 170                 175

Glu Phe Lys Ala Glu Gly Asn Ser Lys Phe Thr Tyr Thr Val Leu Glu
            180                 185                 190

Asp Gly Cys Thr Lys His Thr Gly Glu Trp Ser Lys Thr Val Phe Glu
        195                 200                 205

Tyr Arg Thr Arg Lys Ala Val Arg Leu Pro Ile Val Asp Ile Ala Pro
    210                 215                 220

Tyr Asp Ile Gly Gly Pro Asp Gln Glu Phe Gly Val Asp Val Gly Pro
225                 230                 235                 240

Val Cys Phe Leu

<210> SEQ ID NO 79
<211> LENGTH: 245
<212> TYPE: PRT
<213> ORGANISM: Artificial Sequence
<220> FEATURE:
<223> OTHER INFORMATION: Synthetic construct

<400> SEQUENCE: 79

Ser Glu Pro Met Asp Phe Lys Ile Asn Thr Asp Glu Ile Met Thr Ser
1               5                   10                  15

Leu Lys Ser Val Asn Gly Gln Ile Glu Ser Leu Ile Ser Pro Asp Gly
            20                  25                  30

Ser Arg Lys Asn Pro Ala Arg Asn Cys Arg Asp Leu Lys Phe Cys His
        35                  40                  45

```
Pro Glu Leu Lys Ser Gly Glu Tyr Trp Val Asp Pro Asn Gln Gly Cys
 50                  55                  60

Lys Leu Asp Ala Ile Lys Val Phe Cys Asn Met Glu Thr Gly Glu Thr
 65                  70                  75                  80

Cys Ile Ser Ala Asn Pro Leu Asn Val Pro Arg Lys His Trp Trp Thr
                 85                  90                  95

Asp Ser Ser Ala Glu Lys Lys His Val Trp Phe Gly Glu Ser Met Asp
                100                 105                 110

Gly Gly Phe Gln Phe Ser Tyr Gly Asn Pro Glu Leu Pro Glu Asp Val
            115                 120                 125

Leu Asp Val Gln Leu Ala Phe Leu Arg Leu Leu Ser Ser Arg Ala Ser
130                 135                 140

Gln Asn Ile Thr Tyr His Cys Lys Asn Ser Ile Ala Tyr Met Asp Gln
145                 150                 155                 160

Ala Ser Gly Asn Val Lys Lys Ala Leu Lys Leu Met Gly Ser Asn Glu
                165                 170                 175

Gly Glu Phe Lys Ala Glu Gly Asn Ser Lys Phe Thr Tyr Thr Val Leu
            180                 185                 190

Glu Asp Gly Cys Thr Lys His Thr Gly Glu Trp Ser Lys Thr Val Phe
            195                 200                 205

Glu Tyr Arg Thr Arg Lys Ala Val Arg Leu Pro Ile Val Asp Ile Ala
210                 215                 220

Pro Tyr Asp Ile Gly Gly Pro Asp Gln Glu Phe Gly Val Asp Val Gly
225                 230                 235                 240

Pro Val Cys Phe Leu
                245

<210> SEQ ID NO 80
<211> LENGTH: 246
<212> TYPE: PRT
<213> ORGANISM: Artificial Sequence
<220> FEATURE:
<223> OTHER INFORMATION: Synthetic construct

<400> SEQUENCE: 80

Arg Ser Glu Pro Met Asp Phe Lys Ile Asn Thr Asp Glu Ile Met Thr
 1               5                  10                  15

Ser Leu Lys Ser Val Asn Gly Gln Ile Glu Ser Leu Ile Ser Pro Asp
                20                  25                  30

Gly Ser Arg Lys Asn Pro Ala Arg Asn Cys Arg Asp Leu Lys Phe Cys
            35                  40                  45

His Pro Glu Leu Lys Ser Gly Glu Tyr Trp Val Asp Pro Asn Gln Gly
 50                  55                  60

Cys Lys Leu Asp Ala Ile Lys Val Phe Cys Asn Met Glu Thr Gly Glu
 65                  70                  75                  80

Thr Cys Ile Ser Ala Asn Pro Leu Asn Val Pro Arg Lys His Trp Trp
                 85                  90                  95

Thr Asp Ser Ser Ala Glu Lys Lys His Val Trp Phe Gly Glu Ser Met
                100                 105                 110

Asp Gly Gly Phe Gln Phe Ser Tyr Gly Asn Pro Glu Leu Pro Glu Asp
            115                 120                 125

Val Leu Asp Val Gln Leu Ala Phe Leu Arg Leu Leu Ser Ser Arg Ala
130                 135                 140

Ser Gln Asn Ile Thr Tyr His Cys Lys Asn Ser Ile Ala Tyr Met Asp
145                 150                 155                 160
```

```
                                        -continued
Gln Ala Ser Gly Asn Val Lys Lys Ala Leu Lys Leu Met Gly Ser Asn
                165                 170                 175

Glu Gly Glu Phe Lys Ala Glu Gly Asn Ser Lys Phe Thr Tyr Thr Val
            180                 185                 190

Leu Glu Asp Gly Cys Thr Lys His Thr Gly Glu Trp Ser Lys Thr Val
        195                 200                 205

Phe Glu Tyr Arg Thr Arg Lys Ala Val Arg Leu Pro Ile Val Asp Ile
    210                 215                 220

Ala Pro Tyr Asp Ile Gly Gly Pro Asp Gln Glu Phe Gly Val Asp Val
225                 230                 235                 240

Gly Pro Val Cys Phe Leu
                245
```

CORONAVIRUS VACCINE COMPOSITIONS, METHODS, AND USES THEREOF

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is CHNG005_003C2_SL2.txt, the date of creation of the ASCII text file is Oct. 29, 2024, and the size of the ASCII text file is 575.3 KB.

CROSS-REFERENCE TO RELATED APPLICATIONS

This application claims priority to and the benefit of application Ser. No. 17/489,572, filed on Sep. 29, 2021, which claims priority to and the benefit of International Patent Application Nos. PCT/CN2020/095269, filed Jun. 10, 2020; PCT/CN2021/087066, filed Apr. 13, 2021; PCT/CN2021/093895, filed May 14, 2021; 17/489,572, filed on Sep. 29, 2021, and the disclosures of those applications are incorporated herein by reference in their entireties for all purposes.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 165762000143SEQLIST.TXT, date recorded: Sep. 28, 2021, size: 575 KB).

FIELD

The present disclosure relates in some aspects to immunogenic compositions including recombinant peptides and proteins comprising coronavirus viral antigens and immunogens, e.g., coronavirus S protein peptides, for treating and/or preventing a coronavirus infection.

BACKGROUND

Coronaviruses infect a wide range of avian and mammalian species, including humans. Coronaviruses may circulate annually in humans and generally cause mild respiratory diseases, although severity can be greater in infants, elderly, and the immunocompromised. However, certain coronaviruses, including the Middle East respiratory syndrome coronavirus (MERS-CoV), the severe acute respiratory syndrome coronavirus (SARS-CoV-1), and severe acute respiratory syndrome coronavirus 2 (SARS-CoV-2), are highly pathogenic. The high pathogenicity, airborne transmissibility, high case-fatality rate, and vaguely defined epidemiology against coronaviruses have created an urgent need for an effective vaccine and related therapeutic agents. In particular, vaccines that are able to rapidly induce effective immune responses against SARS-CoV-2 is urgently needed. Provided are methods, uses and articles of manufacture that meet such and other needs.

SUMMARY

In some embodiments, disclosed herein is a protein comprising a plurality of recombinant polypeptides, each recombinant polypeptide comprising a surface antigen of a coronavirus linked to a C-terminal propeptide of collagen, wherein the C-terminal propeptides of the recombinant polypeptides form inter-polypeptide disulfide bonds.

In some embodiments, disclosed herein are recombinant subunit vaccines that comprise an ecto-domain (e.g., without transmembrane and cytoplasmic domains) of an S protein or its fragments from a coronavirus, such as SARS-CoV-2, which is fused in-frame to a C-propeptide of a collagen that is capable of forming disulfide bond-linked homo-trimer. The resulting recombinant subunit vaccines, such as an S-Trimer, can be expressed and purified from transfected cells, and are expected to be in native-like conformation in trimeric form. This solves the problems of mis-folding of a viral antigen often encountered when it is expressed as a recombinant peptide or protein in soluble forms without the transmembrane and/or cytoplasmic domains. Such mis-folded viral antigens do not faithfully preserve the native viral antigen conformation, and often fail to evoke neutralizing antibodies.

In some embodiments, the coronavirus is a Severe Acute Respiratory Syndrome (SARS)-coronavirus (SARS-CoV-1), a SARS-coronavirus 2 (SARS-CoV-2), a SARS-like coronavirus, a Middle East Respiratory Syndrome (MERS)-coronavirus (MERS-CoV), a MERS-like coronavirus, NL63-CoV, 229E-CoV, OC43-CoV, HKU1-CoV, WIV1-CoV, MHV, HKU9-CoV, PEDV-CoV, or SDCV.

In any of the preceding embodiments, the surface antigen can comprise a coronavirus spike (S) protein or a fragment or epitope thereof, wherein the epitope is optionally a linear epitope or a conformational epitope, and wherein the protein comprises three recombinant polypeptides.

In any of the preceding embodiments, the surface antigen can comprise a signal peptide, an S1 subunit peptide, an S2 subunit peptide, or any combination thereof.

In any of the preceding embodiments, the surface antigen can comprise a signal peptide, a receptor binding domain (RBD) peptide, a receptor binding motif (RBM) peptide, a fusion peptide (FP), a heptad repeat 1 (HR1) peptide, or a heptad repeat 2 (HR2) peptide, or any combination thereof.

In any of the preceding embodiments, the surface antigen can comprises a receptor binding domain (RBD) of the S protein.

In any of the preceding embodiments, the surface antigen can comprise an S1 subunit and an S2 subunit of the S protein.

In any of the preceding embodiments, the surface antigen can be free of a transmembrane (TM) domain peptide and/or a cytoplasm (CP) domain peptide.

In any of the preceding embodiments, the surface antigen can comprise a protease cleavage site, wherein the protease is optionally furin, trypsin, factor Xa, thrombin, or cathepsin L.

In any of the preceding embodiments, the surface antigen can be free of a protease cleavage site, wherein the protease is optionally furin, trypsin, factor Xa, thrombin, or cathepsin L, or can contain a mutated protease cleavage site that is not cleavable by the protease.

In any of the preceding embodiments, the surface antigen can be soluble or do not directly bind to a lipid bilayer, e.g., a membrane or viral envelope.

In any of the preceding embodiments, the surface antigens can be the same or different among the recombinant polypeptides of the protein.

In any of the preceding embodiments, the surface antigen can be directly fused to the C-terminal propeptide, or can be linked to the C-terminal propeptide via a linker, such as a linker comprising glycine-X-Y repeats, wherein X and Y and independently any amino acid and optionally proline or hydroxyproline.

In any of the preceding embodiments, the protein can be soluble or do not directly bind to a lipid bilayer, e.g., a membrane or viral envelope.

In any of the preceding embodiments, the protein can bind to a cell surface receptor of a subject, optionally wherein the subject is a mammal such as a primate, e.g., human.

In any of the preceding embodiments, the cell surface receptor can be angiotensin converting enzyme 2 (ACE2), dipeptidyl peptidase 4 (DPP4), dendritic cell-specific intercellular adhesion molecule-3-grabbing non integrin (DC-SIGN), or liver/lymph node-SIGN (L-SIGN).

In any of the preceding embodiments, the C-terminal propeptide can be of human collagen.

In any of the preceding embodiments, the C-terminal propeptide can comprise a C-terminal polypeptide of proα1 (I), proα1(II), proα1(III), proα1(V), proα1(XI), proα2(I), proα2(V), proα2(XI), or proα3(XI), or a fragment thereof.

In any of the preceding embodiments, the C-terminal propeptides can be the same or different among the recombinant polypeptides.

In any of the preceding embodiments, the C-terminal propeptide can comprise any of SEQ ID NOs: 67-80, or an amino acid sequence having at least 90%, 91%, 92%, 93%, 94%, 95%, 96%, 97%, 98%, 99%, or 99.5% sequence homology to any of SEQ ID NOs: 67-80, capable of forming inter-polypeptide disulfide bonds and trimerizing the recombinant polypeptides.

In any of the preceding embodiments, the C-terminal propeptide can comprise SEQ ID NO: 67 or an amino acid sequence at least 95% identical thereto capable of forming inter-polypeptide disulfide bonds and trimerizing the recombinant polypeptides.

In any of the preceding embodiments, the C-terminal propeptide can comprise SEQ ID NO: 68 or an amino acid sequence at least 95% identical thereto capable of forming inter-polypeptide disulfide bonds and trimerizing the recombinant polypeptides.

In any of the preceding embodiments, the C-terminal propeptide can comprise SEQ ID NO: 69 or an amino acid sequence at least 95% identical thereto capable of forming inter-polypeptide disulfide bonds and trimerizing the recombinant polypeptides.

In any of the preceding embodiments, the C-terminal propeptide can comprise SEQ ID NO: 70 or an amino acid sequence at least 95% identical thereto capable of forming inter-polypeptide disulfide bonds and trimerizing the recombinant polypeptides.

In any of the preceding embodiments, the C-terminal propeptide can comprise SEQ ID NO: 71 or an amino acid sequence at least 95% identical thereto capable of forming inter-polypeptide disulfide bonds and trimerizing the recombinant polypeptides.

In any of the preceding embodiments, the C-terminal propeptide can comprise SEQ ID NO: 72 or an amino acid sequence at least 95% identical thereto capable of forming inter-polypeptide disulfide bonds and trimerizing the recombinant polypeptides.

In any of the preceding embodiments, the C-terminal propeptide can comprise SEQ ID NO: 73 or an amino acid sequence at least 95% identical thereto capable of forming inter-polypeptide disulfide bonds and trimerizing the recombinant polypeptides.

In any of the preceding embodiments, the C-terminal propeptide can comprise SEQ ID NO: 74 or an amino acid sequence at least 95% identical thereto capable of forming inter-polypeptide disulfide bonds and trimerizing the recombinant polypeptides.

In any of the preceding embodiments, the C-terminal propeptide can comprise SEQ ID NO: 75 or an amino acid sequence at least 95% identical thereto capable of forming inter-polypeptide disulfide bonds and trimerizing the recombinant polypeptides.

In any of the preceding embodiments, the C-terminal propeptide can comprise SEQ ID NO: 76 or an amino acid sequence at least 95% identical thereto capable of forming inter-polypeptide disulfide bonds and trimerizing the recombinant polypeptides.

In any of the preceding embodiments, the C-terminal propeptide can comprise SEQ ID NO: 77 or an amino acid sequence at least 95% identical thereto capable of forming inter-polypeptide disulfide bonds and trimerizing the recombinant polypeptides.

In any of the preceding embodiments, the C-terminal propeptide can comprise SEQ ID NO: 78 or an amino acid sequence at least 95% identical thereto capable of forming inter-polypeptide disulfide bonds and trimerizing the recombinant polypeptides.

In any of the preceding embodiments, the C-terminal propeptide can comprise SEQ ID NO: 79 or an amino acid sequence at least 95% identical thereto capable of forming inter-polypeptide disulfide bonds and trimerizing the recombinant polypeptides.

In any of the preceding embodiments, the C-terminal propeptide can comprise SEQ ID NO: 80 or an amino acid sequence at least 95% identical thereto capable of forming inter-polypeptide disulfide bonds and trimerizing the recombinant polypeptides.

In any of the preceding embodiments, the C-terminal propeptide can comprise a sequence comprising glycine-X-Y repeats linked to the N-terminus of any of SEQ ID NOs: 67-80, wherein X and Y and independently any amino acid and optionally proline or hydroxyproline, or an amino acid sequence at least 90% identical thereto capable of forming inter-polypeptide disulfide bonds and trimerizing the recombinant polypeptides.

In any of the preceding embodiments, the surface antigen in each recombinant polypeptide can be in a prefusion conformation.

In any of the preceding embodiments, the surface antigen in each recombinant polypeptide can be in a postfusion conformation.

In any of the preceding embodiments, the surface antigen in each recombinant polypeptide can comprise any of SEQ ID NOs: 27-66 or an amino acid sequence at least 80% identical thereto.

In any of the preceding embodiments, the recombinant polypeptide can comprise any of SEQ ID NOs: 1-26 or an amino acid sequence at least 80% identical thereto.

Also provided herein is an immunogen comprising a protein provided herein. Provided herein is a protein nanoparticle comprising protein provided herein directly or indirectly linked to a nanoparticle. Provided herein is a virus-like particle (VLP) comprising a protein provided herein.

Also provided herein is an isolated nucleic acid encoding one, two, three or more of the recombinant polypeptides of the protein provided herein. In some embodiments, a polypeptide encoding the S protein peptide is fused in-frame to a polypeptide encoding the C-terminal propeptide of collagen. In some embodiments, the isolated nucleic acid provided herein is operably linked to a promoter.

In some embodiments, the isolated nucleic acid provided herein is a DNA molecule. In some embodiments, the isolated nucleic acid provided herein is an RNA molecule, optionally an mRNA molecule such as a nucleoside-modified mRNA, a non-amplifying mRNA, a self-amplifying mRNA, or a trans-amplifying mRNA.

Also provided herein is a vector comprising an isolated nucleic acid provided herein. In some embodiments, the vector is a viral vector.

In some aspects, provided herein is a virus, a pseudovirus, or a cell comprising vector provided herein, optionally wherein the virus or cell has a recombinant genome. In some aspects, provided herein is an immunogenic composition comprising the protein, immunogen, protein nanoparticle, VLP, isolated nucleic acid, vector, virus, pseudovirus, or cell provided herein, and a pharmaceutically acceptable carrier.

Also provided herein is a vaccine comprising an immunogenic composition provided herein and optionally an adjuvant, wherein the vaccine is optionally a subunit vaccine. In some embodiments, the vaccine is a prophylactic and/or therapeutic vaccine.

In some aspects, provided herein is a method of producing a protein, comprising: expressing the isolated nucleic acid or vector provided herein in a host cell to produce the protein as provided herein; and purifying the protein. Provided herein is a protein produced by a method provided herein.

Provided herein are methods for generating an immune response to an S protein peptide or fragment or epitope thereof of a coronavirus in a subject, comprising administering to the subject an effective amount of the protein, immunogen, protein nanoparticle, VLP, isolated nucleic acid, vector, virus, pseudovirus, cell, immunogenic composition, or vaccine as provided herein to generate the immune response. In some embodiments, the method provided herein is for treating or preventing infection with the coronavirus. In some embodiments, generating the immune response inhibits or reduces replication of the coronavirus in the subject. In some embodiments, the immune response comprises a cell-mediated response and/or a humoral response, optionally comprising production of one or more neutralizing antibody, such as a polyclonal antibody or a monoclonal antibody. In some embodiments, the immune response is against the S protein peptide or fragment or epitope thereof of the coronavirus but not against the C-terminal propeptide. In some embodiments, the administering to the subject does not lead to antibody dependent enhancement (ADE) in the subject due to prior exposure to one or more coronavirus. In some embodiments, the administering does not lead to antibody dependent enhancement (ADE) in the subject when subsequently exposed to one or more coronavirus. In some embodiments, the method further comprises a priming step and/or a boosting step. In some embodiments, the administering step is performed via topical, transdermal, subcutaneous, intradermal, oral, intranasal (e.g., intranasal spray), intratracheal, sublingual, buccal, rectal, vaginal, inhaled, intravenous (e.g., intravenous injection), intraarterial, intramuscular (e.g., intramuscular injection), intracardiac, intraosseous, intraperitoneal, transmucosal, intravitreal, subretinal, intraarticular, peri-articular, local, or epicutaneous administration. In some embodiments, the effective amount is administered in a single dose or a series of doses separated by one or more interval. In some embodiments, the effective amount is administered without an adjuvant. In some embodiments, the effective amount is administered with an adjuvant.

Provided herein are methods comprising administering to a subject an effective amount of a protein provided herein to generate in the subject a neutralizing antibody or neutralizing antisera to the coronavirus. In some embodiments, the subject is a mammal, optionally a human or a non-human primate. In some embodiments, the method further comprises isolating the neutralizing antibody or neutralizing antisera from the subject. In some embodiments, the method further comprises administering an effective amount of the isolated neutralizing antibody or neutralizing antisera to a human subject via passive immunization to prevent or treat an infection by the coronavirus. In some embodiments, the neutralizing antibody or neutralizing antisera to the coronavirus comprises polyclonal antibodies to the coronavirus S protein peptide or fragment or epitope thereof, optionally wherein the neutralizing antibody or neutralizing antisera is free or substantially free of antibodies to the C-terminal propeptide of collagen. In some embodiments, the neutralizing antibody comprises a monoclonal antibody to the coronavirus S protein peptide or fragment or epitope thereof, optionally wherein the neutralizing antibody is free or substantially free of antibodies to the C-terminal propeptide of collagen.

In some aspects, the protein, immunogen, protein nanoparticle, VLP, isolated nucleic acid, vector, virus, pseudovirus, cell, immunogenic composition, or vaccine provided herein, is for use in inducing an immune response to a coronavirus in a subject, and/or in treating or preventing an infection by the coronavirus.

In some aspects, provided herein is use of the protein, immunogen, protein nanoparticle, VLP, isolated nucleic acid, vector, virus, pseudovirus, cell, immunogenic composition, or vaccine provided herein, for inducing an immune response to a coronavirus in a subject, and/or for treating or preventing an infection by the coronavirus. In some aspects, provided herein is use of the protein, immunogen, protein nanoparticle, VLP, isolated nucleic acid, vector, virus, pseudovirus, cell, immunogenic composition, or vaccine provided herein, for the manufacture of a medicament or a prophylactic for inducing an immune response to a coronavirus in a subject, and/or for treating or preventing an infection by the coronavirus.

Also provided herein are methods for analyzing a sample, comprising: contacting a sample with the protein provided herein, and detecting a binding between the protein and an analyte capable of specific binding to the S protein peptide or fragment or epitope thereof of the coronavirus. In some embodiments, the analyte is an antibody, a receptor, or a cell recognizing the S protein peptide or fragment or epitope thereof. In some embodiments, the binding indicates the presence of the analyte in the sample, and/or an infection by the coronavirus in a subject from which the sample is derived.

Provided herein are kits comprising the protein provided herein and a substrate, pad, or vial containing or immobilizing the protein, optionally wherein the kit is an ELISA or lateral flow assay kit.

DETAILED DESCRIPTION

Figure 2:
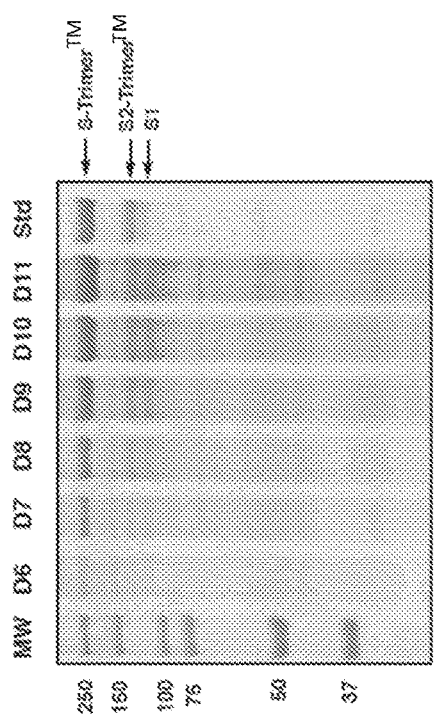
FIG. 2 shows high-level expression of an exemplary S-Trimer. The full-length S-Trimer and partially cleaved forms at S1/S2 furin site, namely the S2-Trimer and the cleaved S1 fragment, are indicated.

Provided herein are immunogenic compositions, methods, and uses of fusion peptides and proteins comprising coronavirus viral antigens or immunogens for the treatment, e.g., prophylactic, therapeutic, of coronavirus infections. In some embodiments, compositions and methods of use of recombinant soluble surface antigens from RNA viruses in covalently linked trimeric forms are disclosed. In some embodiments, the resulting fusion proteins are secreted as disulfide bond-linked homo-trimers, which are more stable in structure, while preserving the conformations of native-like trimeric viral antigens, thereby can be used as more effective vaccines against these dangerous pathogens.

In some embodiments, disclosed herein are methods for using viral antigen trimers as a vaccine or as part of a multivalent vaccine to prevent viral infections, without or with adjuvant, or with more than one adjuvant, optionally via either intra-muscular injections or intra-nasal administrations.

In some embodiments, disclosed herein are methods for using viral antigen trimers as an antigen for diagnosis of viral infections through detection of antibodies, e.g., IgM or IgG, that recognize the viral antigen, such as neutralizing antibodies.

In some embodiments, disclosed herein are methods for using viral antigen trimers as an antigen to generate polyclonal or monoclonal antibodies which can be used for passive immunization, e.g., neutralizing mAb for treating a coronavirus infection.

In some embodiments, disclosed herein is a viral antigen trimer as a vaccine or as part of a multivalent vaccine, wherein the vaccine comprises a plurality of trimeric subunit vaccines comprising viral antigens of the same protein of a virus or comprising viral antigens of two or more different proteins of one or more viruses or one or more strains of the same virus.

In some embodiments, disclosed herein is a monovalent vaccine comprising a viral antigen trimer disclosed herein. In some embodiments, disclosed herein is a bi-valent vaccine comprising a viral antigen trimer disclosed herein. In some embodiments, disclosed herein is a tri-valent vaccine comprising a viral antigen trimer disclosed herein. In some embodiments, disclosed herein is a quadrivalent vaccine comprising a viral antigen trimer disclosed herein.

In some embodiments, disclosed herein is a monovalent vaccine comprising an S-Trimer disclosed herein. In some embodiments, disclosed herein is a bi-valent vaccine comprising an S-Trimer disclosed herein. In some embodiments, disclosed herein is a bi-valent vaccine comprising at least one S-Trimer comprising a first S protein antigen and at least one S-Trimer comprising a second S protein antigen. In some embodiments, the first and second S protein antigens are from the same S protein of one or more virus species or strains/subtypes, or from two or more different S proteins of one or more virus species or one or more strains/subtypes of the same virus species. In some embodiments, disclosed herein is a tri-valent vaccine comprising an S-Trimer disclosed herein. In some embodiments, disclosed herein is a tri-valent vaccine comprising at least one S-Trimer comprising a first S protein antigen, at least one S-Trimer comprising a second S protein antigen, and at least one S-Trimer comprising a third S protein antigen. In some embodiments, the first, second and third S protein antigens are from the same S protein of one or more virus species or strains/subtypes, or from two, three, or more different S proteins of one or more virus species or one or more strains/subtypes of the same virus species. In some embodiments, disclosed herein is a quadrivalent vaccine comprising an S-Trimer disclosed herein. In some embodiments, disclosed herein is quadrivalent vaccine comprising at least one S-Trimer comprising a first S protein antigen, at least one S-Trimer comprising a second S protein antigen, at least one S-Trimer comprising a third S protein antigen, and at least one S-Trimer comprising a fourth S protein antigen. In some embodiments, the first, second, third, and fourth S protein antigens are from the same S protein of one or more virus species or strains/subtypes, or from two, three, four, or more different S proteins of one or more virus species or one or more strains/subtypes of the same virus species.

The proteins, including recombinant polypeptides and fusion proteins, comprising coronavirus viral antigens and immunogens provided herein are useful for effectively and safely treating (e.g., therapeutically, prophylactically) coronavirus infection. For example, the proteins comprising coronavirus viral antigens and immunogens provided herein treat coronavirus infection without meditated vaccine-induced disease enhancement (VED) and/or antibody dependent enhancement (ADE). In addition, the proteins comprising coronavirus viral antigens and immunogens provided herein are easily produced, and demonstrate stability under high stress conditions such as, e.g., high temperature, extreme pH, and high and low osmolality. Thus, the proteins and immunogenic compositions provided herein circumvent and satisfy the issues of production, stability, safety, and efficacy that have hindered coronavirus vaccine development.

In some aspects, the coronavirus viral antigens and immunogens provided herein include the coronavirus Spike (S) protein or peptide, particularly SARS-CoV or SARS-CoV-2 S proteins. The spikes of SARS-CoV and SARS-CoV-2 are composed of trimers of S protein, which belongs to a group of class I viral fusion glycoproteins that also includes HIV glycoprotein 160 (Env), influenza haemagglutinin (HA), paramyxovirus F and Ebola virus glycoprotein. The SARS-CoV and SARS-CoV-2 S proteins each encodes a surface glycoprotein precursor, and the amino terminus and most of the protein is predicted to be on the outside of the cell surface or the virus particles. The S protein comprises a signal peptide located at the N terminus, an extracellular domain, a transmembrane domain and an intracellular domain. Similarly to other coronaviruses, the S protein of SARS-CoV and SARS-CoV-2 can be cleaved into the S1 and S2 subunits by proteases. In particular, SARS-CoV-2 contains a furin-like cleavage site that is lacking in the other SARS-like CoVs.

In some embodiments, provided herein are recombinant S ectodomain trimers. In some embodiments, the recombinant S ectodomain trimer comprises recombinant S ectodomain protomers from an alphacoronavirus, such as NL63-CoV or 229E-CoV. In some embodiments, the recombinant S ectodomain trimers comprise S ectodomain protomers from a betacoronavirus, such as OC43-CoV, SARS-CoV, SARS-CoV-2, MERS-CoV, HKU1-CoV, WIV1-CoV, mouse hepatitis virus (MHV), or HKU9-CoV.

Similar to other enveloped RNA viruses such as HIV, RSV and Influenza, coronaviruses including SARS-CoV-2, all each has a trimeric surface antigen on its viral envelopes to gain entry into different host cells via specific cell surface receptors during infections. Like SARS-CoV-1, SARS-CoV-2 uses its trimeric viral surface antigen S protein to enter host cells of respiratory systems in mammals upon binding to its specific cell surface receptor ACE2. The prerequisite for generating an effective recombinant subunit vaccine is to be able to create a viral S antigen that is native-like, and in particular, to maintain its trimeric conformation in order to evoke sufficient amount of antibodies that could bind to the receptor binding domain (RBD) of the viral S protein, thereby preventing the virus from binding to ACE2 receptor, thus abolishing viral infections.

In some embodiments, the protein comprising a coronavirus viral antigen or immunogen, e.g., SARS-CoV or SARS-CoV-2 S protein peptide, is capable of generating an immune response, e.g., an immune response to the SARS-CoV or SARS-CoV-2 S protein peptide. In some embodiments, the immune response inhibits or reduces replication of a coronavirus in a subject, e.g., a patient. In some embodiments, the immune response includes production of one or more neutralizing antibodies, such as polyclonal and/or monoclonal antibodies. In some embodiments, the neutralizing antibodies inhibit or reduce replication of a coronavirus in a subject, e.g., a patient. In some embodiments, administration of the protein, for example as an immunogenic composition, to the subject does not lead to antibody dependent enhancement (ADE) in the subject due to prior exposure to a coronavirus. In some aspects, the protein comprising a coronavirus viral antigen and immunogen is used as a vaccine.

In some embodiments, the coronavirus viral antigen and immunogen, e.g., SARS-CoV or SARS-CoV-2 S protein peptide, is linked to a protein or peptide to form a fusion protein or recombinant polypeptide. In some embodiments, the protein or peptide to which the coronavirus viral antigen or immunogen is linked is capable of associating, e.g., covalently or non-covalently linking, with proteins or peptides, such as proteins or peptides of fusion proteins or recombinant polypeptides. Thus, in some cases, the protein or peptide to which the coronavirus viral antigen or immunogen is linked is a multimerization domain.

In some embodiments, the coronavirus viral antigen and immunogen, e.g., coronavirus S protein peptide, is linked to a propeptide of collagen, e.g., at the C-terminal of propeptide of collagen, to form a fusion peptide or recombinant polypeptide. Thus, in some embodiments, the protein provided herein comprises recombinant polypeptides containing coronavirus viral antigens and immunogens, e.g., coronavirus S protein peptides or a fragment or epitope thereof, linked to a C-terminal propeptide of collagen. In some embodiments, the propeptide of collagen is derived from the human C-propeptide of al collagen and is capable self-trimerization upon expression.

In some embodiments, linking the coronavirus viral antigen and immunogen, e.g., coronavirus S protein peptide, to a propeptide of collagen, e.g., at the C-terminal of propeptide of collagen, aids in the ability of the protein to generate an immune response. For example, the creation of the recombinant protein may preserve the tertiary and quaternary structures of the coronavirus S protein peptide, which may be important for the stability of the native conformation of the coronavirus S protein peptide, and in turn the availability of antigenic sites on the surface of the protein capable of eliciting an immune response, e.g., neutralizing antibodies. Additionally, linking of the coronavirus S protein peptide to a protein or peptide capable of self-trimerization allows the aggregation of the recombinant proteins, thus mimicking the native homotrimeric structure of the coronavirus S protein peptides on the viral envelope.

In some embodiments, linking the coronavirus S protein peptide to a C-terminal propeptide of collagen results in self-trimerized recombinant polypeptides. In some embodiments, the protein provided herein comprises a plurality of self-trimerized coronavirus S protein peptide and propeptide of collagen recombinant polypeptides. In some embodiments, the trimeric nature of the recombinant proteins aids in the stability of the protein. In some embodiments, the trimeric nature of the recombinant proteins aids in the ability of the protein to generate an immune response. In some embodiments, the trimeric nature of the recombinant proteins and/or a macrostructure of a plurality of self-trimerized recombinant proteins aids in the ability of the protein to generate an immune response.

Also provided herein are immunogenic compositions comprising the proteins provided herein, methods of producing proteins provided herein, methods of treating subjects with proteins and compositions provided herein, and kits.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference. The section headings used herein are for organizational purposes only and are not to be construed as limiting the subject matter described.

I. Viral Antigens and Immunogens

The proteins provided herein comprise coronavirus viral antigens and immunogens. The coronavirus viral antigens and immunogens contemplated herein are capable of promoting or stimulating a cell-mediated response and/or a humoral response. In some embodiments, the response, e.g., cell-mediated or humoral response, comprises the production of antibodies, e.g., neutralizing antibodies. In some embodiments, the coronavirus viral antigen or immunogen is an coronavirus spike (S) protein peptide.

Coronavirus is a family of positive-sense, single-stranded RNA viruses that are known to cause severe respiratory illness. They have the largest genomes (26-32 kb) among known RNA viruses, and are phylogenetically divided into four genera (α, β, γ, δ), with betacoronaviruses further subdivided into four lineages (A, B, C, D). Viruses currently known to infect human from the coronavirus family are from the alphacoronavirus and betacoronavirus genera. Additionally, it is believed that the gammacoronavirus and deltacoronavirus genera may infect humans in the future. Non-limiting examples of betacoronaviruses include Middle East respiratory syndrome coronavirus (MERS-CoV), Severe Acute Respiratory Syndrome coronavirus (SARS-CoV), Human coronavirus HKU1 (HKU1-CoV), Human coronavirus OC43 (OC43-CoV), Murine Hepatitis Virus (MHV-CoV), Bat SARS-like coronavirus WIV1 (WIV1-CoV), and Human coronavirus HKU9 (HKU9-CoV). Non-limiting examples of alphacoronaviruses include human coronavirus 229E (229E-CoV), human coronavirus NL63 (NL63-CoV), porcine epidemic diarrhea virus (PEDV), and Transmissible gastroenteritis coronavirus (TGEV). A non-limiting example of a deltacoronaviruses is the Swine Delta Coronavirus (SDCV).

A list of Severe acute respiratory syndrome-related coronavirus is disclosed herein:
Bat coronavirus Cp/Yunnan2011
Bat coronavirus RaTG13
Bat coronavirus Rp/Shaanxi2011
Bat SARS coronavirus HKU3
   Bat SARS coronavirus HKU3-1
   Bat SARS coronavirus HKU3-10
   Bat SARS coronavirus HKU3-11
   Bat SARS coronavirus HKU3-12
   Bat SARS coronavirus HKU3-13
   Bat SARS coronavirus HKU3-2
   Bat SARS coronavirus HKU3-3
   Bat SARS coronavirus HKU3-4
   Bat SARS coronavirus HKU3-5
   Bat SARS coronavirus HKU3-6
   Bat SARS coronavirus HKU3-7
   Bat SARS coronavirus HKU3-8
   Bat SARS coronavirus HKU3-9
Bat SARS coronavirus Rp1
Bat SARS coronavirus Rp2
Bat SARS CoV Rf1/2004
   Bat CoV 273/2005
Bat SARS CoV Rm1/2004
   Bat CoV 279/2005
Bat SARS CoV Rp3/2004
Bat SARS-like coronavirus
Bat SARS-like coronavirus Rs3367
Bat SARS-like coronavirus RsSHC014
Bat SARS-like coronavirus WIV1
Bat SARS-like coronavirus YNLF_31C
Bat SARS-like coronavirus YNLF_34C
BtRf-BetaCoV/HeB2013
BtRf-BetaCoV/JL2012
BtRf-BetaCoV/SX2013
BtRs-BetaCoV/GX2013
BtRs-BetaCoV/HuB2013
BtRs-BetaCoV/YN2013
Civet SARS CoV 007/2004
Civet SARS CoV SZ16/2003
Civet SARS CoV SZ3/2003
recombinant SARSr-CoV
   SARS coronavirus ExoN1
   SARS coronavirus MA15
   SARS coronavirus MA15 ExoN1
   SARS coronavirus wtic-MB
Rhinolophus affinis coronavirus
SARS bat coronavirus
SARS coronavirus A001
SARS coronavirus A013
SARS coronavirus A021
SARS coronavirus A022
SARS coronavirus A030
SARS coronavirus A031
SARS coronavirus AS
SARS coronavirus B012
SARS coronavirus B024
SARS coronavirus B029
SARS coronavirus B033
SARS coronavirus B039
SARS coronavirus B040
SARS coronavirus BJ01
SARS coronavirus BJ02
SARS coronavirus BJ03
SARS coronavirus BJ04
SARS coronavirus BJ162
SARS coronavirus BJ182-12

SARS coronavirus BJ182-4
SARS coronavirus BJ182-8
SARS coronavirus BJ182a
SARS coronavirus BJ182b
SARS coronavirus BJ202
SARS coronavirus BJ2232
SARS coronavirus BJ302
SARS coronavirus C013
SARS coronavirus C014
SARS coronavirus C017
SARS coronavirus C018
SARS coronavirus C019
SARS coronavirus C025
SARS coronavirus C028
SARS coronavirus C029
SARS Coronavirus CDC#200301157
SARS coronavirus civet010
SARS coronavirus civet014
SARS coronavirus civet019
SARS coronavirus civet020
SARS coronavirus CS21
SARS coronavirus CS24
SARS coronavirus CUHK-AG01
SARS coronavirus CUHK-AG02
SARS coronavirus CUHK-AG03
SARS coronavirus CUHK-L2
SARS coronavirus CUHK-Su10
SARS coronavirus CUHK-W1
SARS coronavirus cw037
SARS coronavirus cw049
SARS coronavirus ES191
SARS coronavirus ES260
SARS coronavirus FRA
SARS coronavirus Frankfurt 1
    SARS coronavirus Frankfurt1-v01
SARS coronavirus GD01
SARS coronavirus GD03T0013
SARS coronavirus GD322
SARS coronavirus GD69
SARS coronavirus GDH-BJH01
SARS coronavirus GZ-A
SARS coronavirus GZ-B
SARS coronavirus GZ-C
SARS coronavirus GZ-D
SARS coronavirus GZ02
SARS coronavirus GZ0401
SARS coronavirus GZ0402
SARS coronavirus GZ0403
SARS coronavirus GZ43
SARS coronavirus GZ50
SARS coronavirus GZ60
SARS coronavirus HB
SARS coronavirus HC/SZ/61/03
SARS coronavirus HGZ8L1-A
SARS coronavirus HGZ8L1-B
SARS coronavirus HGZ8L2
SARS coronavirus HHS-2004
SARS coronavirus HKU-36871
SARS coronavirus HKU-39849
SARS coronavirus HKU-65806
SARS coronavirus HKU-66078
SARS coronavirus Hong Kong/03/2003
SARS coronavirus HPZ-2003
SARS coronavirus HSR 1
SARS coronavirus HSZ-A
SARS coronavirus HSZ-Bb
SARS coronavirus HSZ-Bc
SARS coronavirus HSZ-Cb
SARS coronavirus HSZ-Cc
SARS coronavirus HSZ2-A
SARS coronavirus HZS2-Bb
SARS coronavirus HZS2-C
SARS coronavirus HZS2-D
SARS coronavirus HZS2-E
SARS coronavirus HZS2-Fb
SARS coronavirus HZS2-Fc
SARS coronavirus JMD
SARS coronavirus LC1
SARS coronavirus LC2
SARS coronavirus LC3
SARS coronavirus LC4
SARS coronavirus LC5
SARS coronavirus LLJ-2004
SARS coronavirus NS-1
SARS coronavirus P2
SARS coronavirus PC4-115
SARS coronavirus PC4-127
SARS coronavirus PC4-13
SARS coronavirus PC4-136
SARS coronavirus PC4-137
SARS coronavirus PC4-145
SARS coronavirus PC4-199
SARS coronavirus PC4-205
SARS coronavirus PC4-227
SARS coronavirus PC4-241
SARS coronavirus PUMC01
SARS coronavirus PUMC02
SARS coronavirus PUMC03
SARS coronavirus Rs_672/2006
SARS coronavirus sf098
SARS coronavirus sf099
SARS coronavirus ShanghaiQXC1
SARS coronavirus ShanghaiQXC2
SARS coronavirus Shanhgai LY
SARS coronavirus Sin0409
SARS coronavirus Sin2500
SARS coronavirus Sin2677
SARS coronavirus Sin2679
SARS coronavirus Sin2748
SARS coronavirus Sin2774
SARS coronavirus Sin3408
SARS coronavirus Sin3408L
SARS coronavirus Sin3725V
SARS coronavirus Sin3765V
SARS coronavirus Sin842
SARS coronavirus Sin845
SARS coronavirus Sin846
SARS coronavirus Sin847
SARS coronavirus Sin848
SARS coronavirus Sin849
SARS coronavirus Sin850
SARS coronavirus Sin852
SARS coronavirus Sin_WNV
SARS coronavirus Sino1-11
SARS coronavirus Sino3-11
SARS coronavirus SinP1
SARS coronavirus SinP2
SARS coronavirus SinP3
SARS coronavirus SinP4
SARS coronavirus SinP5
SARS coronavirus SoD
SARS coronavirus SZ1
SARS coronavirus SZ13
SARS coronavirus Taiwan SARS coronavirus Taiwan JC-2003
SARS coronavirus Taiwan TC1
SARS coronavirus Taiwan TC2
SARS coronavirus Taiwan TC3
SARS coronavirus TJ01
SARS coronavirus TJF
SARS coronavirus Tor2
SARS coronavirus TW
  SARS coronavirus TW-GD1
  SARS coronavirus TW-GD2
  SARS coronavirus TW-GD3
  SARS coronavirus TW-GD4
  SARS coronavirus TW-GD5
  SARS coronavirus TW-HP1
  SARS coronavirus TW-HP2
  SARS coronavirus TW-HP3
SARS coronavirus Vietnam
SARS coronavirus WF188
SARS coronavirus WH20
SARS coronavirus WHU
SARS coronavirus xw002
SARS coronavirus ZJ01
SARS coronavirus ZJ02
SARS coronavirus ZJ0301
SARS coronavirus ZMY 1
SARS coronavirus ZS-A
SARS coronavirus ZS-B
SARS coronavirus ZS-C
SARS-related bat coronavirus RsSHC014
SARS-related betacoronavirus Rp3/2004
Severe acute respiratory syndrome coronavirus 2

Exemplary SARS CoV-2 strains are shown in the table below.

| Name/Designation | Distribution | | Notable Mutation(s) | Impact | Sequence |
|---|---|---|---|---|---|
| D614G | | Worldwide | D614G | Increased infectivity, Dominant circulating since June 2020 | P0DTC2 |
| B.1.1.7 | 501Y.V1 | UK/Worldwide (nearly dominant in US) | D614G, N501Y, P681H | Increased infectivity | B.1.1.7 Lineages |
| B.1.351 | 501.V2, or N501Y.V2 | South Africa | N501Y, E484K*, K417N | Increased infectivity, *escape mutation* | B.1.351 Lineages |
| B.1.1.248 | P1 | Brazil | N501Y, E484K*, K417T | Increased infectivity, *escape mutation* | P1 Lineages |

SARS coronavirus TW-HP4
SARS coronavirus TW-JC2
SARS coronavirus TW-KC1
SARS coronavirus TW-KC3
SARS coronavirus TW-PH1
SARS coronavirus TW-PH2
SARS coronavirus TW-YM1
SARS coronavirus TW-YM2
SARS coronavirus TW-YM3
SARS coronavirus TW-YM4
SARS coronavirus TW1
SARS coronavirus TW10
SARS coronavirus TW11
SARS coronavirus TW2
SARS coronavirus TW3
SARS coronavirus TW4
SARS coronavirus TW5
SARS coronavirus TW6
SARS coronavirus TW7
SARS coronavirus TW8
SARS coronavirus TW9
SARS coronavirus TWC
SARS coronavirus TWC2
SARS coronavirus TWC3
SARS coronavirus TWH
SARS coronavirus TWJ
SARS coronavirus TWK
SARS coronavirus TWS
SARS coronavirus TWY
SARS coronavirus Urbani The coronavirus viral genome is capped, polyadenylated, and covered with nucleocapsid proteins. The coronavirus virion includes a viral envelope containing type I fusion glycoproteins referred to as the spike (S) protein. Most coronaviruses have a common genome organization with the replicase gene included in the 5'-portion of the genome, and structural genes included in the 3'-portion of the genome.

Coronavirus Spike (S) protein is class I fusion glycoprotein initially synthesized as a precursor protein. Individual precursor S polypeptides form a homotrimer and undergo glycosylation within the Golgi apparatus as well as processing to remove the signal peptide, and cleavage by a cellular protease to generate separate S1 and S2 polypeptide chains, which remain associated as S1/S2 protomers within the homotrimer and is therefore a trimer of heterodimers. The S1 subunit is distal to the virus membrane and contains the receptor-binding domain (RBD) that mediates virus attachment to its host receptor. The S2 subunit contains fusion protein machinery, such as the fusion peptide, two heptad-repeat sequences (HR1 and HR2) and a central helix typical of fusion glycoproteins, a transmembrane domain, and the cytosolic tail domain.

In some cases, the coronavirus viral antigen or immunogen is a coronavirus S protein peptide in a prefusion conformation, which is a structural conformation adopted by the ectodomain of the coronavirus S protein following processing into a mature coronavirus S protein in the secretory system, and prior to triggering of the fusogenic event that leads to transition of coronavirus S to the postfusion conformation. The three-dimensional structure of an exemplary coronavirus S protein (HKU1-CoV) in a prefusion conformation is provided in Kirchdoerfer et al., "Pre-fusion structure of a human coronavirus spike protein," Nature, 531: 118-121, 2016.

In some cases, the coronavirus viral antigen or immunogen comprises one or more amino acid substitutions, deletions, or insertions compared to a native coronavirus S sequence that provide for increased retention of the prefusion conformation compared to coronavirus S ectodomain trimers formed from a corresponding native coronavirus S sequence. The "stabilization" of the prefusion conformation by the one or more amino acid substitutions, deletions, or insertions can be, for example, energetic stabilization (for example, reducing the energy of the prefusion conformation relative to the post-fusion open conformation) and/or kinetic stabilization (for example, reducing the rate of transition from the prefusion conformation to the postfusion conformation). Additionally, stabilization of the coronavirus S ectodomain trimer in the prefusion conformation can include an increase in resistance to denaturation compared to a corresponding native coronavirus S sequence. Methods of determining if a coronavirus S ectodomain trimer is in the prefusion conformation are provided herein, and include (but are not limited to) negative-stain electron microscopy and antibody binding assays using a prefusion-conformation-specific antibody.

In some cases, the coronavirus viral antigen or immunogen is a fragment of an S protein peptide. In some embodiments, the antigen or immunogen is an epitope of an S protein peptide. Epitopes include antigenic determinant chemical groups or peptide sequences on a molecule that are antigenic, such that they elicit a specific immune response, for example, an epitope is the region of an antigen to which B and/or T cells respond. An antibody can bind to a particular antigenic epitope, such as an epitope on coronavirus S ectodomain. Epitopes can be formed both from contiguous amino acids or noncontiguous amino acids juxtaposed by tertiary folding of a protein. In some embodiments, the coronavirus epitope is a linear epitope. In some embodiments, the coronavirus epitope is a conformational epitope. In some embodiments, the coronavirus epitope is a neutralizing epitope site. In some embodiments, all neutralizing epitopes of the coronavirus S protein peptide or fragment thereof are present as the antigen or immunogen.

In some cases, for example when the viral antigen or immunogen is a fragment of an S protein peptide, only a single subunit of the S protein peptide is present, and that single subunit of the S protein peptide is trimerized. In some embodiments, the viral antigen or immunogen comprises a signal peptide, an S1 subunit peptide, an S2 subunit peptide, or any combination thereof. In some embodiments, the viral antigen or immunogen comprises a signal peptide, a receptor binding domain (RBD) peptide, a receptor binding motif (RBM) peptide, a fusion peptide (FP), a heptad repeat 1 (HR1) peptide, or a heptad repeat 2 (HR2) peptide, or any combination thereof. In some embodiments, the viral antigen or immunogen comprises a receptor binding domain (RBD) of the S protein. In some embodiments, the viral antigen or immunogen comprises an S1 subunit and an S2 subunit of the S protein. In some embodiments, the viral antigen or immunogen comprises an S1 subunit of the S protein but not an S2 subunit. In some embodiments, the viral antigen or immunogen comprises an S2 subunit of the S protein but not an S1 subunit. In some embodiments, the viral antigen or immunogen is free of a transmembrane (TM) domain peptide and/or a cytoplasm (CP) domain peptide.

In some embodiments, the viral antigen or immunogen comprises a protease cleavage site, wherein the protease is optionally furin, trypsin, factor Xa, or cathepsin L.

In some embodiments, the viral antigen or immunogen is free of a protease cleavage site, wherein the protease is optionally furin, trypsin, factor Xa, or cathepsin L, or contains a mutated protease cleavage site that is not cleavable by the protease.

In some embodiments, the viral antigen or immunogen is a SARS-CoV-2 antigen comprising at least one SARS-CoV-2 protein or fragment thereof. In some embodiments, the SARS-CoV-2 antigen is recognized by SARS-CoV-2 reactive antibodies and/or T cells. In some embodiments, the SARS-CoV-2 antigen is an inactivated whole virus (COVID-19 virus). In some embodiments, the SARS-CoV-2 antigen comprises is a subunit of the virus. In some embodiments, the SARS-CoV-2 antigen comprises a structural protein of SARS-CoV-2 or a fragment thereof. In some embodiments, the structural protein of SARS-CoV-2 comprises one or more of the group consisting of the spike (S) protein, the membrane (M) protein, nucleocapsid (N) protein, and envelope (E) protein. In some embodiments, the SARS-CoV-2 antigen comprises or further comprises a non-structural protein of SARS-CoV-2 or a fragment thereof. The nucleotide sequence of a representative SARS-CoV-2 isolate (Wuhan-Hu-1) is set forth as GenBank No. MN908947.3 (Wu et al., Nature, 579:265-269, 2020).

In some embodiments, the viral antigen or immunogen comprises the sequence set forth in SEQ ID NO: 55. In some embodiments, the viral antigen or immunogen comprises an amino acid sequence having at least or about 80%, 85%, 90%, 92%, 95%, or 97% sequence identity to sequence of SEQ ID NO: 55 shown below (underlined sequence indicating the receptor-binding motif (RBM) within the receptor binding domain (RBD)).

```
         10        20        30        40        50        60
MFVFLVLLPLVSSQCVNLTTRTQLPPAYTNSFTRGVYYPDKVFRSSVLHSTQDLFLPFFS 70        80        90       100       110       120
NVTWFHAIHVSGTNGTKRFDNPVLPFNDGVYFASTEKSNIIRGWIFGTTLDSKTQSLLIV 130       140       150       160       170       180
NNATNVVIKVCEFQFCNDPFLGVYYHKNNKSWMESEFRVYSSANNCTFEYVSQPFLMDLE 190       200       210       220       230       240
GKQGNFKNLREFVFKNIDGYFKIYSKHTPINLVRDLPQGFSALEPLVDLPIGINITRFQT 250       260       270       280       290       300
LLALHRSYLTPGDSSSGWTAGAAAYYVGYLQPRTFLLKYNENGTITDAVDCALDPLSETK
```

```
            310        320        330        340        350        360
CTLKSFTVEKGIYQTSNFRVQPTESIVRFPNITNLCPFGEVFNATRFASVYAWNRKRISN 370        380        390        400        410        420
CVADYSVLYNSASFSTFKCYGVSPTKLNDLCFTNVYADSFVIRGDEVRQIAPGQTGKIAD 430        440        450        460        470        480
YNYKLPDDFTGCVIAWNSNNLDSKVGGNYNYLYRLFRKSNLKPFERDISTEIYQAGSTPC 490        500        510        520        530        540
NGVEGFNCYFPLQSYGFQPTNGVGYQPYRVVVLSFELLHAPATVCGPKKSTNLVKNKCVN 550        560        570        580        590        600
FNFNGLTGTGVLTESNKKFLPFQQFGRDIADTTDAVRDPQTLEILDITPCSFGGVSVITP 610        620        630        640        650        660
GTNTSNQVAVLYQDVNCTEVPVAIHADQLTPTWRVYSTGSNVFQTRAGCLIGAEHVNNSY 670        680        690        700        710        720
ECDIPIGAGICASYQTQTNSPRRARSVASQSIIAYTMSLGAENSVAYSNNSIAIPTNFTI 730        740        750        760        770        780
SVTTEILPVSMTKTSVDCTMYICGDSTECSNLLLQYGSFCTQLNRALTGIAVEQDKNTQE 790        800        810        820        830        840
VFAQVKQIYKTPPIKDFGGFNFSQILPDPSKPSKRSFIEDLLFNKVTLADAGFIKQYGDC 850        860        870        880        890        900
LGDIAARDLICAQKFNGLTVLPPLLTDEMIAQYTSALLAGTITSGWTFGAGAALQIPFAM 910        920        930        940        950        960
QMAYRFNGIGVTQNVLYENQKLIANQFNSAIGKIQDSLSSTASALGKLQDVVNQNAQALN 970        980        990       1000       1010       1020
TLVKQLSSNFGAISSVLNDILSRLDKVEAEVQIDRLITGRLQSLQTYVTQQLIRAAEIRA 1030       1040       1050       1060       1070       1080
SANLAATKMSECVLGQSKRVDFCGKGYHLMSFPQSAPHGVVFLHVTYVPAQEKNFTTAPA 1090       1100       1110       1120       1130       1140
ICHDGKAHFPREGVFVSNGTHWFVTQRNFYEPQIITTDNTFVSGNCDVVIGIVNNTVYDP 1150       1160       1170       1180       1190       1200
LQPELDSFKEELDKYFKNHTSPDVDLGDISGINASVVNIQKEIDRLNEVAKNLNESLIDL 1210       1220       1230       1240       1250       1260
QELGKYEQYIKWPWYIWLGFIAGLIAIVMVTIMLCCMTSCCSCLKGCCSCGSCCKFDEDD

1270
SEPVLKGVKLHYT
```

In some embodiments, the viral antigen or immunogen comprises a sequence of the spike glycoprotein of the original Wuhan-Hu-1 coronavirus (e.g., NC_045512). In some embodiments, the viral antigen or immunogen comprises a sequence of the spike glycoprotein of a virus in the B.1.526 lineage. In some embodiments, the viral antigen or immunogen comprises a sequence of the spike glycoprotein of a Cluster 5 (ΔFVI-spike) virus. In some embodiments, the viral antigen or immunogen comprises a sequence of the spike glycoprotein of a virus in the B.1.1.7 lineage. In some embodiments, the viral antigen or immunogen comprises a sequence of the spike glycoprotein of a virus in the B.1.1.207 lineage. In some embodiments, the viral antigen or immunogen comprises a sequence of the spike glycoprotein of a virus in the B.1.1.317 lineage. In some embodiments, the viral antigen or immunogen comprises a sequence of the spike glycoprotein of a virus in the B.1.1.318 lineage. In some embodiments, the viral antigen or immunogen comprises a sequence of the spike glycoprotein of a virus in the P.1 lineage. In some embodiments, the viral antigen or immunogen comprises a sequence of the spike glycoprotein of a virus in the B.1.351 lineage. In some embodiments, the viral antigen or immunogen comprises a sequence of the spike glycoprotein of a virus in the B.1.429/CAL.20C lineage. In some embodiments, the viral antigen or immunogen comprises a sequence of the spike glycoprotein of a virus in the B.1.525 lineage. In some embodiments, the viral antigen or immunogen comprises a sequence of the spike glycoprotein of a virus in the B.1.526 lineage. In some embodiments, the viral antigen or immunogen comprises a sequence of the spike glycoprotein of a virus in the B.1.617 lineage. In some embodiments, the viral antigen or immunogen comprises a sequence of the spike glycoprotein of a virus in the B.1.617.2 lineage. In some embodiments, the viral antigen or immunogen comprises a sequence of the spike glycoprotein of a virus in the B.1.618 lineage. In some embodiments, the viral antigen or immunogen comprises a sequence of the spike glycoprotein of a virus in the B.1.620 lineage. In some embodiments, the viral antigen or immunogen comprises a sequence of the spike glycoprotein of a virus in the P.2 lineage. In some embodiments, the viral antigen or immunogen comprises a sequence of the spike glycoprotein of a virus in the P.3 lineage. In some embodiments, the viral antigen or immunogen comprises a sequence of the spike glycoprotein of a virus in the B.1.1.143 lineage. In some embodiments, the viral antigen or immunogen comprises a sequence of the spike glycoprotein of a virus in the A.23.1 lineage. In some embodiments, the viral antigen or immunogen comprises a sequence of the spike glycoprotein of a virus in the B.1.617 lineage. In some embodiments, the viral antigen or immunogen comprises sequences derived from the spike glycoproteins of any two or more viruses, in any suitable combination, selected from the group consisting of Wuhan-Hu-1, a virus in the B.1.526 lineage, a virus in the B.1.1.7 lineage, a virus in the P.1 lineage, a virus in the B.1.351 lineage, a virus in the P.2 lineage, a virus in the B.1.1.143 lineage, a virus in the A.23.1 lineage, and a virus in the B.1.617 lineage.

In some embodiments, the viral antigen or immunogen comprises E484K and/or S477N, e.g., as in a B.1.526 variant. In some embodiments, the viral antigen or immunogen comprises Δ400-402 (ΔFVI), e.g., as in a Cluster 5 (ΔFVI-spike) variant. In some embodiments, the viral antigen or immunogen comprises Δ69-70 (ΔHV), Δ144 (ΔY), N501Y, A570D, D614G, P681H, T716I, S982A, and/or D1118H, e.g., as in a B.1.1.7 variant. In some embodiments, the viral antigen or immunogen comprises P681H, e.g., as in a B.1.1.207 variant. In some embodiments, the viral antigen or immunogen comprises L18F, T20N, P26S, D138Y, R190S, K417T, E484K, N501Y, D614G, H655Y, T1027I, and/or V1176F, e.g., as in a P.1 variant. In some embodiments, the viral antigen or immunogen comprises E484K, e.g., as in a P.2 variant. In some embodiments, the viral antigen or immunogen comprises E484K and/or N501Y, e.g., as in a P.3 variant. In some embodiments, the viral antigen or immunogen comprises L18F, D80A, D215G, Δ242-244 (ΔLAL), R246I, K417N, E484K, N501Y, D614G, and/or A701V, e.g., as in a B.1.351 variant. In some embodiments, the viral antigen or immunogen comprises S13I, W152C, and/or L452R, e.g., as in a B.1.429/CAL.20C variant. In some embodiments, the viral antigen or immunogen comprises Δ69-70 (ΔHV), E484K, and/or F888L, e.g., as in a B.1.525 variant. In some embodiments, the viral antigen or immunogen comprises G142D, L452R, E484Q, and/or P681R, e.g., as in a B.1.617 variant. In some embodiments, the viral antigen or immunogen comprises G142D, L452R, and/or P681R, e.g., as in a B.1.617.2 variant. In some embodiments, the viral antigen or immunogen comprises E484K, e.g., as in a B.1.618 variant. In some embodiments, the viral antigen or immunogen may comprise a fusion polypeptide (protomer) comprising any one or more of the aforementioned mutations in any suitable combination. In some embodiments, the viral antigen or immunogen may comprise a trimer of three fusion polypeptides, and any of the three protomer fusion polypeptides may comprise any one or more of the aforementioned mutations in any suitable combination. In some embodiments, two or all three of the three protomer fusion polypeptides forming a trimer may comprise different mutations and/or different combinations of mutations in each protomer. In some embodiments, the viral antigen or immunogen may comprise a mixture of trimers, and each trimer may comprise different mutations and/or different combinations of mutations.

In some embodiments, the viral antigen or immunogen comprises any one, two, three, four, five or more of the mutations selected from the group consisting of mutations (e.g., substitution(s), deletion(s) and/or insertion(s)) at amino acid positions 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and 1176 of SEQ ID NO: 55. In some embodiments, the viral antigen or immunogen comprises any one, two, three, four, five, six, seven, eight, or all of the mutations selected from the group consisting of mutations (e.g., substitution(s), deletion(s) and/or insertion(s)) at amino acid positions 440, 452, 477, 484, 501, 614, 655, 681, and 701. In some embodiments, the viral antigen or immunogen comprises a chimeric polypeptide comprising sequences from different viruses, such as one or more mutations from a first variant of a coronavirus and one or more mutations from a second variant of the coronavirus that is different from the first variant. In some embodiments, such a chimeric viral antigen or immunogen (or a combination of chimeric viral antigens or immunogens) may be used to elicit a broad immune response against both the first and second variants of the coronavirus.

In some embodiments, the viral antigen or immunogen comprises any one, two, three, four, five or more of the mutations selected from the group consisting of S13I, L18F, T20N, P26S, Δ69-70 (ΔHV), D80A, D138Y, G142D, Δ144 (ΔY), W152C, R190S, D215G, Δ242-244 (ΔLAL), R246I, Δ400-402 (ΔFVI), K417T, K417N, N440K, L452R, S477N, S477G, E484K, E484Q, N501Y, A570D, D614G, H655Y, P681H, P681R, R682G, R683S, R685G, A701V, T716I, F888L, S982A, T1027I, D1118H, and V1176F. In some embodiments, the viral antigen or immunogen comprises any one, two, three, four, five or more of the mutations selected from the group consisting of N440K, L452R, S477G, S477N, E484K, E484Q, N501Y, D614G, H655Y, P681H, P681R, and A701V.

In some embodiments, the SARS-CoV-2 antigen comprises a truncated, S protein devoid of signal peptide, transmembrane and cytoplasmic domains of a full length S protein. In some embodiments, the SARS-CoV-2 antigen is a recombinant protein, while in other embodiments, the SARS-CoV-2 antigen is purified from virions. In some preferred embodiments, the SARS-CoV-2 antigen is an isolated antigen.

In some embodiments, the viral antigen or immunogen comprises the sequence set forth in SEQ ID NO: 27. In some embodiments, the viral antigen or immunogen comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 27, including a sequence comprising substitution, deletion, and/or insertion at one or more amino acid positions selected from the group consisting of 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and 1176 (amino acid positions with respect to SEQ ID NO: 55). In some embodiments, the viral antigen or immunogen comprises a variant of SEQ ID NO: 27 and the variant comprises any one, two, three, four, five or more of the mutations selected from the group consisting of S13I, L18F, T20N, P26S, Δ69-70 (ΔHV), D80A, D138Y, G142D, Δ144 (ΔY), W152C, R190S, D215G, Δ242-244 (ΔLAL), R246I, 66 400-402 (ΔFVI), K417T, K417N, N440K, L452R, S477N, S477G, E484K, E484Q, N501Y, A570D, D614G, H655Y, P681H, P681R, R682G, R683S, R685G, A701V, T716I, F888L, S982A, T1027I, D1118H, and V1176F.

In some embodiments, the viral antigen or immunogen comprises the sequence set forth in SEQ ID NO: 28. In some embodiments, the viral antigen or immunogen comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 28, including a sequence comprising substitution, deletion, and/or insertion at one or more amino acid positions selected from the group consisting of 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and 1176 (amino acid positions with respect to SEQ ID NO: 55). In some embodiments, the viral antigen or immunogen comprises a variant of SEQ ID NO: 28 and the variant comprises any one, two, three, four, five or more of the mutations selected from the group consisting of S13I, L18F, T20N, P26S, Δ69-70 (ΔHV), D80A, D138Y, G142D, Δ144 (ΔY), W152C, R190S, D215G, Δ242-244 (ΔLAL), R246I, Δ400-402 (ΔFVI), K417T, K417N, N440K, L452R, S477N, S477G, E484K, E484Q, N501Y, A570D, D614G, H655Y, P681H, P681R, R682G, R683S, R685G, A701V, T716I, F888L, S982A, T1027I, D1118H, and V1176F.

In some embodiments, the viral antigen or immunogen comprises the sequence set forth in SEQ ID NO: 29. In some embodiments, the viral antigen or immunogen comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 29, including a sequence comprising substitution, deletion, and/or insertion at one or more amino acid positions selected from the group consisting of 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and 1176 (amino acid positions with respect to SEQ ID NO: 55). In some embodiments, the viral antigen or immunogen comprises a variant of SEQ ID NO: 29 and the variant comprises any one, two, three, four, five or more of the mutations selected from the group consisting of S13I, L18F, T20N, P26S, Δ69-70 (ΔHV), D80A, D138Y, G142D, Δ144 (ΔY), W152C, R190S, D215G, Δ242-244 (ΔLAL), R246I, Δ400-402 (ΔFVI), K417T, K417N, N440K, L452R, S477N, S477G, E484K, E484Q, N501Y, A570D, D614G, H655Y, P681H, P681R, R682G, R683S, R685G, A701V, T716I, F888L, S982A, T1027I, D1118H, and V1176F.

In some embodiments, the viral antigen or immunogen comprises the sequence set forth in SEQ ID NO: 30. In some embodiments, the viral antigen or immunogen comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 30, including a sequence comprising substitution, deletion, and/or insertion at one or more amino acid positions selected from the group consisting of 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and 1176 (amino acid positions with respect to SEQ ID NO: 55). In some embodiments, the viral antigen or immunogen comprises a variant of SEQ ID NO: 30 and the variant comprises any one, two, three, four, five or more of the mutations selected from the group consisting of S13I, L18F, T20N, P26S, Δ69-70 (ΔHV), D80A, D138Y, G142D, Δ144 (ΔY), W152C, R190S, D215G, Δ242-244 (ΔLAL), R246I, Δ400-402 (ΔFVI), K417T, K417N, N440K, L452R, S477N, S477G, E484K, E484Q, N501Y, A570D, D614G, H655Y, P681H, P681R, R682G, R683S, R685G, A701V, T716I, F888L, S982A, T1027I, D1118H, and V1176F.

In some embodiments, the viral antigen or immunogen comprises the sequence set forth in SEQ ID NO: 31. In some embodiments, the viral antigen or immunogen comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 31, including a sequence comprising substitution, deletion, and/or insertion at one or more amino acid positions selected from the group consisting of 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and 1176 (amino acid positions with respect to SEQ ID NO: 55). In some embodiments, the viral antigen or immunogen comprises a variant of SEQ ID NO: 31 and the variant comprises any one, two, three, four, five or more of the mutations selected from the group consisting of S13I, L18F, T20N, P26S, Δ69-70 (ΔHV), D80A, D138Y, G142D, Δ144 (ΔY), W152C, R190S, D215G, Δ242-244 (ΔLAL), R246I, Δ400-402 (ΔFVI), K417T, K417N, N440K, L452R, S477N, S477G, E484K, E484Q, N501Y, A570D, D614G, H655Y, P681H, P681R, R682G, R683S, R685G, A701V, T716I, F888L, S982A, T1027I, D1118H, and V1176F.

In some embodiments, the viral antigen or immunogen comprises the sequence set forth in SEQ ID NO: 32. In some embodiments, the viral antigen or immunogen comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 32, including a sequence comprising substitution, deletion, and/or insertion at one or more amino acid positions selected from the group consisting of 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and 1176 (amino acid positions with respect to SEQ ID NO: 55). In some embodiments, the viral antigen or immunogen comprises a variant of SEQ ID NO: 32 and the variant comprises any one, two, three, four, five or more of the mutations selected from the group consisting of S13I, L18F, T20N, P26S, Δ69-70 (ΔHV), D80A, D138Y, G142D, Δ144 (ΔY), W152C, R190S, D215G, Δ242-244 (ΔLAL), R246I, Δ400-402 (ΔFVI), K417T, K417N, N440K, L452R, S477N, S477G, E484K, E484Q, N501Y, A570D, D614G, H655Y, P681H, P681R, R682G, R683S, R685G, A701V, T716I, F888L, S982A, T1027I, D1118H, and V1176F.

In some embodiments, the viral antigen or immunogen comprises the sequence set forth in SEQ ID NO: 33. In some embodiments, the viral antigen or immunogen comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 33, including a sequence comprising substitution, deletion, and/or insertion at one or more amino acid positions selected from the group consisting of 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and 1176 (amino acid positions with respect to SEQ ID NO: 55). In some embodiments, the viral antigen or immunogen comprises a variant of SEQ ID NO: 33 and the variant comprises any one, two, three, four, five or more of the mutations selected from the group consisting of S13I, L18F, T20N, P26S, Δ69-70 (ΔHV), D80A, D138Y, G142D, Δ144 (ΔY), W152C, R190S, D215G, Δ242-244 (ΔLAL), R246I, Δ400-402 (ΔFVI), K417T, K417N, N440K, L452R, S477N, S477G, E484K, E484Q, N501Y, A570D, D614G, H655Y, P681H, P681R, R682G, R683S, R685G, A701V, T716I, F888L, S982A, T1027I, D1118H, and V1176F.

In some embodiments, the viral antigen or immunogen comprises the sequence set forth in SEQ ID NO: 34. In some embodiments, the viral antigen or immunogen comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 34, including a sequence comprising substitution, deletion, and/or insertion at one or more amino acid positions selected from the group consisting of 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and 1176 (amino acid positions with respect to SEQ ID NO: 55). In some embodiments, the viral antigen or immunogen comprises a variant of SEQ ID NO: 34 and the variant comprises any one, two, three, four, five or more of the mutations selected from the group consisting of S13I, L18F, T20N, P26S, Δ69-70 (ΔHV), D80A, D138Y, G142D, Δ144 (ΔY), W152C, R190S, D215G, Δ242-244 (ΔLAL), R246I, Δ400-402 (ΔFVI), K417T, K417N, N440K, L452R, S477N, S477G, E484K, E484Q, N501Y, A570D, D614G, H655Y, P681H, P681R, R682G, R683S, R685G, A701V, T716I, F888L, S982A, T1027I, D1118H, and V1176F.

In some embodiments, the viral antigen or immunogen comprises the sequence set forth in SEQ ID NO: 35. In some embodiments, the viral antigen or immunogen comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 35, including a sequence comprising substitution, deletion, and/or insertion at one or more amino acid positions selected from the group consisting of 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and 1176 (amino acid positions with respect to SEQ ID NO: 55). In some embodiments, the viral antigen or immunogen comprises a variant of SEQ ID NO: 35 and the variant comprises any one, two, three, four, five or more of the mutations selected from the group consisting of S13I, L18F, T20N, P26S, Δ69-70 (ΔHV), D80A, D138Y, G142D, Δ144 (ΔY), W152C, R190S, D215G, Δ242-244 (ΔLAL), R246I, Δ400-402 (ΔFVI), K417T, K417N, N440K, L452R, S477N, S477G, E484K, E484Q, N501Y, A570D, D614G, H655Y, P681H, P681R, R682G, R683S, R685G, A701V, T716I, F888L, S982A, T1027I, D1118H, and V1176F.

In some embodiments, the viral antigen or immunogen comprises the sequence set forth in SEQ ID NO: 36. In some embodiments, the viral antigen or immunogen comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 36, including a sequence comprising substitution, deletion, and/or insertion at one or more amino acid positions selected from the group consisting of 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and 1176 (amino acid positions with respect to SEQ ID NO: 55). In some embodiments, the viral antigen or immunogen comprises a variant of SEQ ID NO: 36 and the variant comprises any one, two, three, four, five or more of the mutations selected from the group consisting of S13I, L18F, T20N, P26S, Δ69-70 (ΔHV), D80A, D138Y, G142D, Δ144 (ΔY), W152C, R190S, D215G, Δ242-244 (ΔLAL), R246I, Δ400-402 (ΔFVI), K417T, K417N, N440K, L452R, S477N, S477G, E484K, E484Q, N501Y, A570D, D614G, H655Y, P681H, P681R, R682G, R683S, R685G, A701V, T716I, F888L, S982A, T1027I, D1118H, and V1176F.

In some embodiments, the viral antigen or immunogen comprises the sequence set forth in SEQ ID NO: 37. In some embodiments, the viral antigen or immunogen comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 37, including a sequence comprising substitution, deletion, and/or insertion at one or more amino acid positions selected from the group consisting of 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and 1176 (amino acid positions with respect to SEQ ID NO: 55). In some embodiments, the viral antigen or immunogen comprises a variant of SEQ ID NO: 37 and the variant comprises any one, two, three, four, five or more of the mutations selected from the group consisting of S13I, L18F, T20N, P26S, Δ69-70 (ΔHV), D80A, D138Y, G142D, Δ144 (ΔY), W152C, R190S, D215G, Δ242-244 (ΔLAL), R246I, Δ400-402 (ΔFVI), K417T, K417N, N440K, L452R, S477N, S477G, E484K, E484Q, N501Y, A570D, D614G, H655Y, P681H, P681R, R682G, R683S, R685G, A701V, T716I, F888L, S982A, T1027I, D1118H, and V1176F.

In some embodiments, the viral antigen or immunogen comprises the sequence set forth in SEQ ID NO: 38. In some embodiments, the viral antigen or immunogen comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 38, including a sequence comprising substitution, deletion, and/or insertion at one or more amino acid positions selected from the group consisting of 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and 1176 (amino acid positions with respect to SEQ ID NO: 55). In some embodiments, the viral antigen or immunogen comprises a variant of SEQ ID NO: 38 and the variant comprises any one, two, three, four, five or more of the mutations selected from the group consisting of S13I, L18F, T20N, P26S, Δ69-70 (ΔHV), D80A, D138Y, G142D, Δ144 (ΔY), W152C, R190S, D215G, Δ242-244 (ΔLAL), R246I, Δ400-402 (ΔFVI), K417T, K417N, N440K, L452R, S477N, S477G, E484K, E484Q, N501Y, A570D, D614G, H655Y, P681H, P681R, R682G, R683S, R685G, A701V, T716I, F888L, S982A, T1027I, D1118H, and V1176F.

In some embodiments, the viral antigen or immunogen comprises the sequence set forth in SEQ ID NO: 39. In some embodiments, the viral antigen or immunogen comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 39, including a sequence comprising substitution, deletion, and/or insertion at one or more amino acid positions selected from the group consisting of 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and 1176 (amino acid positions with respect to SEQ ID NO: 55). In some embodiments, the viral antigen or immunogen comprises a variant of SEQ ID NO: 39 and the variant comprises any one, two, three, four, five or more of the mutations selected from the group consisting of S13I, L18F, T20N, P26S, Δ69-70 (ΔHV), D80A, D138Y, G142D, Δ144 (ΔY), W152C, R190S, D215G, Δ242-244 (ΔLAL), R246I, Δ400-402 (ΔFVI), K417T, K417N, N440K, L452R, S477N, S477G, E484K, E484Q, N501Y, A570D, D614G, H655Y, P681H, P681R, R682G, R683S, R685G, A701V, T716I, F888L, S982A, T1027I, D1118H, and V1176F.

In some embodiments, the viral antigen or immunogen comprises the sequence set forth in SEQ ID NO: 40. In some embodiments, the viral antigen or immunogen comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 40, including a sequence comprising substitution, deletion, and/or insertion at one or more amino acid positions selected from the group consisting of 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and 1176 (amino acid positions with respect to SEQ ID NO: 55). In some embodiments, the viral antigen or immunogen comprises a variant of SEQ ID NO: 40 and the variant comprises any one, two, three, four, five or more of the mutations selected from the group consisting of S13I, L18F, T20N, P26S, Δ69-70 (ΔHV), D80A, D138Y, G142D, Δ144 (ΔY), W152C, R190S, D215G, Δ242-244 (ΔLAL), R246I, Δ400-402 (ΔFVI), K417T, K417N, N440K, L452R, S477N, S477G, E484K, E484Q, N501Y, A570D, D614G, H655Y, P681H, P681R, R682G, R683S, R685G, A701V, T716I, F888L, S982A, T1027I, D1118H, and V1176F.

In some embodiments, the viral antigen or immunogen comprises the sequence set forth in SEQ ID NO: 41. In some embodiments, the viral antigen or immunogen comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 41, including a sequence comprising substitution, deletion, and/or insertion at one or more amino acid positions selected from the group consisting of 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and 1176 (amino acid positions with respect to SEQ ID NO: 55). In some embodiments, the viral antigen or immunogen comprises a variant of SEQ ID NO: 41 and the variant comprises any one, two, three, four, five or more of the mutations selected from the group consisting of S13I, L18F, T20N, P26S, Δ69-70 (ΔHV), D80A, D138Y, G142D, Δ144 (ΔY), W152C, R190S, D215G, Δ242-244 (ΔLAL), R246I, Δ400-402 (ΔFVI), K417T, K417N, N440K, L452R, S477N, S477G, E484K, E484Q, N501Y, A570D, D614G, H655Y, P681H, P681R, R682G, R683S, R685G, A701V, T716I, F888L, S982A, T1027I, D1118H, and V1176F.

In some embodiments, the viral antigen or immunogen comprises the sequence set forth in SEQ ID NO: 42. In some embodiments, the viral antigen or immunogen comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 42, including a sequence comprising substitution, deletion, and/or insertion at one or more amino acid positions selected from the group consisting of 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and 1176 (amino acid positions with respect to SEQ ID NO: 55). In some embodiments, the viral antigen or immunogen comprises a variant of SEQ ID NO: 42 and the variant comprises any one, two, three, four, five or more of the mutations selected from the group consisting of S13I, L18F, T20N, P26S, Δ69-70 (ΔHV), D80A, D138Y, G142D, Δ144 (ΔY), W152C, R190S, D215G, Δ242-244 (ΔLAL), R246I, Δ400-402 (ΔFVI), K417T, K417N, N440K, L452R, S477N, S477G, E484K, E484Q, N501Y, A570D, D614G, H655Y, P681H, P681R, R682G, R683S, R685G, A701V, T716I, F888L, S982A, T1027I, D1118H, and V1176F.

In some embodiments, the viral antigen or immunogen comprises the sequence set forth in SEQ ID NO: 43. In some embodiments, the viral antigen or immunogen comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 43, including a sequence comprising substitution, deletion, and/or insertion at one or more amino acid positions selected from the group consisting of 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and 1176 (amino acid positions with respect to SEQ ID NO: 55). In some embodiments, the viral antigen or immunogen comprises a variant of SEQ ID NO: 43 and the variant comprises any one, two, three, four, five or more of the mutations selected from the group consisting of S13I, L18F, T20N, P26S, Δ69-70 (ΔHV), D80A, D138Y, G142D, Δ144 (ΔY), W152C, R190S, D215G, Δ242-244 (ΔLAL), R246I, Δ400-402 (ΔFVI), K417T, K417N, N440K, L452R, S477N, S477G, E484K, E484Q, N501Y, A570D, D614G, H655Y, P681H, P681R, R682G, R683S, R685G, A701V, T716I, F888L, S982A, T1027I, D1118H, and V1176F.

In some embodiments, the viral antigen or immunogen comprises the sequence set forth in SEQ ID NO: 44. In some embodiments, the viral antigen or immunogen comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 44, including a sequence comprising substitution, deletion, and/or insertion at one or more amino acid positions selected from the group consisting of 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and 1176 (amino acid positions with respect to SEQ ID NO: 55). In some embodiments, the viral antigen or immunogen comprises a variant of SEQ ID NO: 44 and the variant comprises any one, two, three, four, five or more of the mutations selected from the group consisting of 5131, L18F, T20N, P26S, Δ69-70 (ΔHV), D80A, D138Y, G142D, Δ144 (ΔY), W152C, R190S, D215G, Δ242-244 (ΔLAL), R246I, Δ400-402 (ΔFVI), K417T, K417N, N440K, L452R, S477N, S477G, E484K, E484Q, N501Y, A570D, D614G, H655Y, P681H, P681R, R682G, R683S, R685G, A701V, T716I, F888L, S982A, T1027I, D1118H, and V1176F.

In some embodiments, the viral antigen or immunogen comprises the sequence set forth in SEQ ID NO: 45. In some embodiments, the viral antigen or immunogen comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 45, including a sequence comprising substitution, deletion, and/or insertion at one or more amino acid positions selected from the group consisting of 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and 1176 (amino acid positions with respect to SEQ ID NO: 55). In some embodiments, the viral antigen or immunogen comprises a variant of SEQ ID NO: 45 and the variant comprises any one, two, three, four, five or more of the mutations selected from the group consisting of S13I, L18F, T20N, P26S, Δ69-70 (ΔHV), D80A, D138Y, G142D, Δ144 (ΔY), W152C, R190S, D215G, Δ242-244 (ΔLAL), R246I, Δ400-402 (ΔFVI), K417T, K417N, N440K, L452R, S477N, S477G, E484K, E484Q, N501Y, A570D, D614G, H655Y, P681H, P681R, R682G, R683S, R685G, A701V, T716I, F888L, S982A, T1027I, D1118H, and V1176F.

In some embodiments, the viral antigen or immunogen comprises the sequence set forth in SEQ ID NO: 46. In some embodiments, the viral antigen or immunogen comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 46, including a sequence comprising substitution, deletion, and/or insertion at one or more amino acid positions selected from the group consisting of 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and 1176 (amino acid positions with respect to SEQ ID NO: 55). In some embodiments, the viral antigen or immunogen comprises a variant of SEQ ID NO: 46 and the variant comprises any one, two, three, four, five or more of the mutations selected from the group consisting of S13I, L18F, T20N, P26S, Δ69-70 (ΔHV), D80A, D138Y, G142D, Δ144 (ΔY), W152C, R190S, D215G, Δ242-244 (ΔLAL), R246I, Δ400-402 (ΔFVI), K417T, K417N, N440K, L452R, S477N, S477G, E484K, E484Q, N501Y, A570D, D614G, H655Y, P681H, P681R, R682G, R683S, R685G, A701V, T716I, F888L, S982A, T1027I, D1118H, and V1176F.

In some embodiments, the viral antigen or immunogen comprises the sequence set forth in SEQ ID NO: 47. In some embodiments, the viral antigen or immunogen comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 47, including a sequence comprising substitution, deletion, and/or insertion at one or more amino acid positions selected from the group consisting of 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and 1176 (amino acid positions with respect to SEQ ID NO: 55). In some embodiments, the viral antigen or immunogen comprises a variant of SEQ ID NO: 47 and the variant comprises any one, two, three, four, five or more of the mutations selected from the group consisting of S13I, L18F, T20N, P26S, Δ69-70 (ΔHV), D80A, D138Y, G142D, Δ144 (ΔY), W152C, R190S, D215G, Δ242-244 (ΔLAL), R246I, Δ400-402 (ΔFVI), K417T, K417N, N440K, L452R, S477N, S477G, E484K, E484Q, N501Y, A570D, D614G, H655Y, P681H, P681R, R682G, R683S, R685G, A701V, T716I, F888L, S982A, T1027I, D1118H, and V1176F.

In some embodiments, the viral antigen or immunogen comprises the sequence set forth in SEQ ID NO: 48. In some embodiments, the viral antigen or immunogen comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 48, including a sequence comprising substitution, deletion, and/or insertion at one or more amino acid positions selected from the group consisting of 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and 1176 (amino acid positions with respect to SEQ ID NO: 55). In some embodiments, the viral antigen or immunogen comprises a variant of SEQ ID NO: 48 and the variant comprises any one, two, three, four, five or more of the mutations selected from the group consisting of S13I, L18F, T20N, P26S, Δ69-70 (ΔHV), D80A, D138Y, G142D, Δ144 (ΔY), W152C, R190S, D215G, Δ242-244 (ΔLAL), R246I, Δ400-402 (ΔFVI), K417T, K417N, N440K, L452R, S477N, S477G, E484K, E484Q, N501Y, A570D, D614G, H655Y, P681H, P681R, R682G, R683S, R685G, A701V, T716I, F888L, S982A, T1027I, D1118H, and V1176F.

In some embodiments, the viral antigen or immunogen comprises the sequence set forth in SEQ ID NO: 49. In some embodiments, the viral antigen or immunogen comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 49, including a sequence comprising substitution, deletion, and/or insertion at one or more amino acid positions selected from the group consisting of 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and 1176 (amino acid positions with respect to SEQ ID NO: 55). In some embodiments, the viral antigen or immunogen comprises a variant of SEQ ID NO: 49 and the variant comprises any one, two, three, four, five or more of the mutations selected from the group consisting of S13I, L18F, T20N, P26S, Δ69-70 (ΔHV), D80A, D138Y, G142D, Δ144 (ΔY), W152C, R190S, D215G, Δ242-244 (ΔLAL), R246I, Δ400-402 (ΔFVI), K417T, K417N, N440K, L452R, S477N, S477G, E484K, E484Q, N501Y, A570D, D614G, H655Y, P681H, P681R, R682G, R683S, R685G, A701V, T716I, F888L, S982A, T1027I, D1118H, and V1176F.

In some embodiments, the viral antigen or immunogen comprises the sequence set forth in SEQ ID NO: 50. In some embodiments, the viral antigen or immunogen comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 50, including a sequence comprising substitution, deletion, and/or insertion at one or more amino acid positions selected from the group consisting of 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and 1176 (amino acid positions with respect to SEQ ID NO: 55). In some embodiments, the viral antigen or immunogen comprises a variant of SEQ ID NO: 50 and the variant comprises any one, two, three, four, five or more of the mutations selected from the group consisting of S13I, L18F, T20N, P26S, Δ69-70 (ΔHV), D80A, D138Y, G142D, Δ144 (ΔY), W152C, R190S, D215G, Δ242-244 (ΔLAL), R246I, Δ400-402 (ΔFVI), K417T, K417N, N440K, L452R, S477N, S477G, E484K, E484Q, N501Y, A570D, D614G, H655Y, P681H, P681R, R682G, R683S, R685G, A701V, T716I, F888L, S982A, T1027I, D1118H, and V1176F.

In some embodiments, the viral antigen or immunogen comprises the sequence set forth in SEQ ID NO: 51. In some embodiments, the viral antigen or immunogen comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 51, including a sequence comprising substitution, deletion, and/or insertion at one or more amino acid positions selected from the group consisting of 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and 1176 (amino acid positions with respect to SEQ ID NO: 55). In some embodiments, the viral antigen or immunogen comprises a variant of SEQ ID NO: 51 and the variant comprises any one, two, three, four, five or more of the mutations selected from the group consisting of S13I, L18F, T20N, P26S, Δ69-70 (ΔHV), D80A, D138Y, G142D, Δ144 (ΔY), W152C, R190S, D215G, Δ242-244 (ΔLAL), R246I, Δ400-402 (ΔFVI), K417T, K417N, N440K, L452R, S477N, S477G, E484K, E484Q, N501Y, A570D, D614G, H655Y, P681H, P681R, R682G, R683S, R685G, A701V, T716I, F888L, S982A, T1027I, D1118H, and V1176F.

In some embodiments, the viral antigen or immunogen comprises the sequence set forth in SEQ ID NO: 52. In some embodiments, the viral antigen or immunogen comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 52.

In some embodiments, the viral antigen or immunogen comprises a signal peptide. In some embodiments, the viral antigen or immunogen comprises the sequence set forth in SEQ ID NO: 53. In some embodiments, the viral antigen or immunogen comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 53. In some embodiments, the viral antigen or immunogen comprises the sequence set forth in SEQ ID NO: 54. In some embodiments, the viral antigen or immunogen comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 54.

In some embodiments, the viral antigen or immunogen comprises the sequence set forth in SEQ ID NO: 55. In some embodiments, the viral antigen or immunogen comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 55, including a sequence comprising substitution, deletion, and/or insertion at one or more amino acid positions selected from the group consisting of 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and 1176. In some embodiments, the viral antigen or immunogen comprises a variant of SEQ ID NO: 55 and the variant comprises any one, two, three, four, five or more of the mutations selected from the group consisting of 5131, L18F, T20N, P26S, Δ69-70 (ΔHV), D80A, D138Y, G142D, Δ144 (ΔY), W152C, R190S, D215G, Δ242-244 (ΔLAL), R246I, Δ400-402 (ΔFVI), K417T, K417N, N440K, L452R, S477N, S477G, E484K, E484Q, N501Y, A570D, D614G, H655Y, P681H, P681R, R682G, R683S, R685G, A701V, T716I, F888L, S982A, T1027I, D1118H, and V1176F.

In some embodiments, the viral antigen or immunogen comprises the sequence set forth in SEQ ID NO: 56. In some embodiments, the viral antigen or immunogen comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 56, including a sequence comprising substitution, deletion, and/or insertion at one or more amino acid positions selected from the group consisting of 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and 1176 (amino acid positions with respect to SEQ ID NO: 55). In some embodiments, the viral antigen or immunogen comprises a variant of SEQ ID NO: 56 and the variant comprises any one, two, three, four, five or more of the mutations selected from the group consisting of S13I, L18F, T20N, P26S, Δ69-70 (ΔHV), D80A, D138Y, G142D, Δ144 (ΔY), W152C, R190S, D215G, Δ242-244 (ΔLAL), R246I, Δ400-402 (ΔFVI), K417T, K417N, N440K, L452R, S477N, S477G, E484K, E484Q, N501Y, A570D, D614G, H655Y, P681H, P681R, R682G, R683S, R685G, A701V, T716I, F888L, S982A, T1027I, D1118H, and V1176F.

In some embodiments, the viral antigen or immunogen comprises the sequence set forth in SEQ ID NO: 57. In some embodiments, the viral antigen or immunogen comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 57, including a sequence comprising substitution, deletion, and/or insertion at one or more amino acid positions of SEQ ID NO: 57.

In some embodiments, the viral antigen or immunogen comprises the sequence set forth in SEQ ID NO: 58. In some embodiments, the viral antigen or immunogen comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 58, including a sequence comprising substitution, deletion, and/or insertion at one or more amino acid positions of SEQ ID NO: 58.

In some embodiments, the viral antigen or immunogen comprises the sequence set forth in SEQ ID NO: 59. In some embodiments, the viral antigen or immunogen comprises an amino acid sequence comprising substitution, deletion, and/or insertion at one or more amino acid positions of SEQ ID NO: 59. In some embodiments, the viral antigen or immunogen comprises the sequence set forth in SEQ ID NO: 60. In some embodiments, the viral antigen or immunogen comprises an amino acid sequence comprising substitution, deletion, and/or insertion at one or more amino acid positions of SEQ ID NO: 60.

In some embodiments, the viral antigen or immunogen comprises the sequence set forth in SEQ ID NO: 61. In some embodiments, the viral antigen or immunogen comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 61, including a sequence comprising substitution, deletion, and/or insertion at one or more amino acid positions of SEQ ID NO: 61.

In some embodiments, the viral antigen or immunogen comprises the sequence set forth in SEQ ID NO: 62. In some embodiments, the viral antigen or immunogen comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 62, including a sequence comprising substitution, deletion, and/or insertion at one or more amino acid positions of SEQ ID NO: 62.

In some embodiments, the viral antigen or immunogen comprises the sequence set forth in SEQ ID NO: 63. In some embodiments, the viral antigen or immunogen comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 63, including a sequence comprising substitution, deletion, and/or insertion at one or more amino acid positions of SEQ ID NO: 63.

In some embodiments, the viral antigen or immunogen comprises the sequence set forth in SEQ ID NO: 64. In some embodiments, the viral antigen or immunogen comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 64, including a sequence comprising substitution, deletion, and/or insertion at one or more amino acid positions of SEQ ID NO: 64.

In some embodiments, the viral antigen or immunogen comprises the sequence set forth in SEQ ID NO: 65. In some embodiments, the viral antigen or immunogen comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 65, including a sequence comprising substitution, deletion, and/or insertion at one or more amino acid positions of SEQ ID NO: 65.

In some embodiments, the viral antigen or immunogen does not comprise a transmembrane domain such as SEQ ID NO: 66 or a portion thereof. In some embodiments, the coronavirus viral antigen or immunogen comprises an S protein peptide that is soluble. In some embodiments, the soluble S protein peptide lacks a TM domain peptide and a CP domain peptide. In some embodiments, the soluble S protein peptide does not bind to a lipid bilayer, such as a membrane or viral envelope.

In some embodiments, the S protein peptide is produced from a nucleic acid sequence that has been codon optimized. In some embodiments, the S protein peptide is produced from a nucleic acid sequence that has not been codon optimized.

In some embodiments, the viral antigen or immunogen as referred to herein can include recombinant polypeptides or fusion peptides comprising said viral antigen or immunogen. The terms viral antigen or immunogen may be used to refer to proteins comprising a coronavirus viral antigen or immunogen. In certain cases, the coronavirus viral antigen or immunogen is a coronavirus protein peptide as provided herein.

II. Recombinant Peptides and Proteins

It is contemplated that the coronavirus viral antigens and immunogens provided herein, e.g., S protein peptides (see, Section I), can be combined, e.g., linked, to other proteins or peptides to form recombinant polypeptides, including fusion peptides. In some embodiments, individual recombinant polypeptides (e.g., monomers) provided herein associate to form multimers, e.g., trimers, of recombinant polypeptides. In some embodiments, association of the individual recombinant polypeptide monomers occurs via covalent interactions. In some embodiments, association of the individual recombinant polypeptide monomers occurs via non-covalent interactions. In some embodiments, the interaction, e.g., covalent or non-covalent, is effected by the protein or peptide to which the coronavirus viral antigen or immunogen, e.g., S protein peptide, is linked. In some embodiments, for example when the coronavirus viral antigen or immunogen is an S protein peptide as described herein, the protein or peptide to which it will be linked can be selected such that the native homotrimeric structure of the glycoprotein is preserved. This can be advantageous for evoking a strong and effective immunogenic response to the S protein peptide. For example, preservation and/or maintenance of the native conformation of the coronavirus viral antigens or immunogens (e.g., S protein peptide) may improve or allow access to antigenic sites capable to generating an immune response. In some cases, the recombinant polypeptide comprising an S protein peptide described herein, e.g., see Section I, is referred to herein alternatively as a recombinant S antigen, recombinant S immunogen, or a recombinant S protein.

It is further contemplated that in some cases, the recombinant polypeptides or multimerized recombinant polypeptides thereof aggregate or can be aggregated to form a protein or a complex comprising a plurality of coronavirus viral antigen and/or immunogen recombinant polypeptides. Formation of such proteins may be advantageous for generating a strong and effective immunogenic response to the coronavirus viral antigens and/or immunogens. For instance, formation of a protein comprising a plurality of recombinant polypeptides, and thus a plurality of coronavirus viral antigens, e.g., coronavirus S protein peptides, may preserve the tertiary and/or quaternary structures of the viral antigen, allowing an immune response to be mounted against the native structure. In some cases, the aggregation may confer structural stability of the coronavirus viral antigen or immunogen, which in turn can afford access to potentially antigenic sites capable of promoting an immune response.

1. Fusion Peptides and Recombinant Polypeptides

In some embodiments, the coronavirus viral antigen or immunogen can be linked at their C-terminus (C-terminal linkage) to a trimerization domain to promote trimerization of the monomers. In some embodiments, the trimerization stabilizes the membrane proximal aspect of the coronavirus viral antigen or immunogen, e.g., coronavirus S protein peptide, in a trimeric configuration.

Non-limiting examples of exogenous multimerization domains that promote stable trimers of soluble recombinant proteins include: the GCN4 leucine zipper (Harbury et al. 1993 Science 262:1401-1407), the trimerization motif from the lung surfactant protein (Hoppe et al. 1994 FEBS Lett 344:191-195), collagen (McAlinden et al. 2003 J Biol Chem 278:42200-42207), and the phage T4 fibritin Foldon (Miroshnikov et al. 1998 Protein Eng 11:329-414), any of which can be linked to a coronavirus viral antigen or immunogen described herein (e.g., by linkage to the C-terminus of an S peptide) to promote trimerization of the recombinant viral antigen or immunogen. See also U.S. Pat. Nos. 7,268,116, 7,666,837, 7,691,815, 10,618,949, 10,906,944, and 10,960,070, and US2020/0009244, which are incorporated herein by reference in their entireties for all purposes.

In some embodiments, one or more peptide linkers (such as a gly-ser linker, for example, a 10 amino acid glycine-serine peptide linker) can be used to link the recombinant viral antigen or immunogen to the multimerization domain. The trimer can include any of the stabilizing mutations provided herein (or combinations thereof) as long as the recombinant viral antigen or immunogen trimer retains the desired properties (e.g., the prefusion conformation). In some embodiments, the recombinant polypeptide or the fusion protein comprises a first sequence set forth in any of SEQ ID NOs: 27-66 linked to a second sequence set forth in any of SEQ ID NOs: 67-80, wherein the C terminus of the first sequence is directly linked to the N terminus of the second sequence. In some embodiments, the recombinant polypeptide or the fusion protein comprises a first sequence set forth in any of SEQ ID NOs: 27-66 linked to a second sequence set forth in any of SEQ ID NOs: 67-80, wherein the C terminus of the first sequence is indirectly linked to the N terminus of the second sequence, e.g. through a linker. In some embodiments, the linker comprises a sequence comprising glycine-X-Y repeats.

To be therapeutically feasible, a desired trimerizing protein moiety for biologic drug designs should satisfy the following criteria. Ideally it should be part of a naturally secreted protein, like immunoglobulin Fc, that is also abundant (non-toxic) in the circulation, human in origin (lack of immunogenicity), relatively stable (long half-life) and capable of efficient self-trimerization which is strengthened by inter-chain covalent disulfide bonds so the trimerized coronavirus viral antigens or immunogens are structurally stable.

Collagen is a family of fibrous proteins that are the major components of the extracellular matrix. It is the most abundant protein in mammals, constituting nearly 25% of the total protein in the body. Collagen plays a major structural role in the formation of bone, tendon, skin, cornea, cartilage, blood vessels, and teeth. The fibrillar types of collagen I, II, III, IV, V, and XI are all synthesized as larger trimeric precursors, called procollagens, in which the central uninterrupted triple-helical domain consisting of hundreds of "G-X-Y" repeats (or glycine repeats) is flanked by non-collagenous domains (NC), the N-propeptide and the C-propeptide. Both the C- and N-terminal extensions are processed proteolytically upon secretion of the procollagen, an event that triggers the assembly of the mature protein into collagen fibrils which forms an insoluble cell matrix. BMP-1 is a protease that recognizes a specific peptide sequence of procollagen near the junction between the glycine repeats and the C-prodomain of collagens and is responsible for the removal of the propeptide. The shed trimeric C-propeptide of type I collagen is found in human sera of normal adults at a concentration in the range of 50-300 ng/mL, with children having a much higher level which is indicative of active bone formation. In people with familial high serum concentration of C-propeptide of type I collagen, the level could reach as high as 1-6 μg/mL with no apparent abnormality, suggesting the C-propeptide is not toxic. Structural study of the trimeric C-propeptide of collagen suggested that it is a tri-lobed structure with all three subunits coming together in a junction region near their N-termini to connect to the rest of the procollagen molecule. Such geometry in projecting proteins to be fused in one direction is similar to that of Fc dimer.

Type I, IV, V and XI collagens are mainly assembled into heterotrimeric forms consisting of either two α-1 chains and one α-2 chain (for Type I, IV, V), or three different a chains (for Type XI), which are highly homologous in sequence. The type II and III collagens are both homotrimers of α-1 chain. For type I collagen, the most abundant form of collagen, stable α(I) homotrimer is also formed and is present at variable levels in different tissues. Most of these collagen C-propeptide chains can self-assemble into homotrimers, when over-expressed alone in a cell. Although the N-propeptide domains are synthesized first, molecular assembly into trimeric collagen begins with the in-register association of the C-propeptides. It is believed the C-propeptide complex is stabilized by the formation of interchain disulfide bonds, but the necessity of disulfide bond formation for proper chain registration is not clear. The triple helix of the glycine repeats and is then propagated from the associated C-termini to the N-termini in a zipper-like manner. This knowledge has led to the creation of non-natural types of collagen matrix by swapping the C-propeptides of different collagen chains using recombinant DNA technology. Non-collagenous proteins, such as cytokines and growth factors, also have been fused to the N-termini of either pro-collagens or mature collagens to allow new collagen matrix formation, which is intended to allow slow release of the noncollagenous proteins from the cell matrix. However, under both circumstances, the C-propeptides are required to be cleaved before recombinant collagen fibril assembly into an insoluble cell matrix.

Although other protein trimerization domains, such as those from GCN4 from yeast fibritin from bacteria phage T4 and aspartate transcarbamoylase of Escherichia coli, have been described previously to allow trimerization of heterologous proteins, none of these trimerizing proteins are human in nature, nor are they naturally secreted proteins. As such, any trimeric fusion proteins would have to be made intracellularly, which not only may fold incorrectly for naturally secreted proteins such as soluble receptors, but also make purification of such fusion proteins from thousands of other intracellular proteins difficult. Moreover, the fatal drawback of using such non-human protein trimerization domains (e.g. from yeast, bacteria phage and bacteria) for trimeric biologic drug design is their presumed immunogenicity in the human body, rendering such fusion proteins ineffective shortly after injecting them into the human body.

The use of collagen in a recombinant polypeptide as described herein thus has many advantages, including: (1) collagen is the most abundant protein secreted in the body of a mammal, constituting nearly 25% of the total proteins in the body; (2) the major forms of collagen naturally occur as trimeric helixes, with their globular C-propeptides being responsible for the initiating of trimerization; (3) the trimeric C-propeptide of collagen proteolytically released from the mature collagen is found naturally at sub microgram/mL level in the blood of mammals and is not known to be toxic to the body; (4) the linear triple helical region of collagen can be included as a linker with predicted 2.9 A spacing per residue, or excluded as part of the fusion protein so the distance between a protein to be trimerized and the C-propeptide of collagen can be precisely adjusted to achieve an optimal biological activity; (5) the recognition site of BMP1 which cleaves the C-propeptide off the pro-collagen can be mutated or deleted to prevent the disruption of a trimeric fusion protein; (6) the C-propeptide domain self-trimerizes via disulfide bonds and it provides a universal affinity tag, which can be used for purification of any secreted fusion proteins created. In some embodiments, the C-propeptide of collagen to which the coronavirus viral antigen and immunogen, e.g., S protein peptide, enables the recombinant production of soluble, covalently-linked homotrimeric fusion proteins.

In some embodiments, the coronavirus viral antigen or immunogen is linked to a C-terminal propeptide of collagen to form a recombinant polypeptide. In some embodiments, the C-terminal propeptides of the recombinant polypeptides form inter-polypeptide disulfide bonds. In some embodiments, the recombinant proteins form trimers. In some embodiments, the coronavirus viral antigen or immunogen is an S protein peptide as described in Section I.

For example, a fusion polypeptide comprising a signal peptide MFVFLVLLPLVSS (SEQ ID NO: 54) on the N-terminus of the fusion polypeptide in SEQ ID NO: 1 may be produced and trimerized via inter-polypeptide disulfide bonds (Cys residues that may form inter-polypeptide disulfide bonds are bolded).

```
          10        20        30        40        50        60
MFVFLVLLPLVSSQCVNLTTRTQLPPAYTNSFTRGVYYPDKVFRSSVLHSTQDLFLPFFS 70        80        90       100       110       120
NVTWFHAIHVSGTNGTKRFDNPVLPFNDGVYFASTEKSNIIRGWIFGTTLDSKTQSLLIV 130       140       150       160       170       180
NNATNVVIKVCEFQFCNDPFLGVYYHKNNKSWMESEFRVYSSANNCTFEYVSQPFLMDLE 190       200       210       220       230       240
GKQGNFKNLREFVFKNIDGYFKIYSKHTPINLVRDLPQGFSALEPLVDLPIGINITRFQT 250       260       270       280       290       300
LLALHRSYLTPGDSSSGWTAGAAAYYVGYLQPRTFLLKYNENGTITDAVDCALDPLSETK 310       320       330       340       350       360
CTLKSFTVEKGIYQTSNFRVQPTESIVRFPNITNLCPFGEVFNATRFASVYAWNRKRISN 370       380       390       400       410       420
CVADYSVLYNSASFSTFKCYGVSPTKLNDLCFTNVYADSFVIRGDEVRQIAPGQTGKIAD 430       440       450       460       470       480
YNYKLPDDFTGCVIAWNSNNLDSKVGGNYNYLYRLFRKSNLKPFERDISTEIYQAGSTPC 490       500       510       520       530       540
NGVEGFNCYFPLQSYGFQPTNGVGYQPYRVVVLSFELLHAPATVCGPKKSTNLVKNKCVN 550       560       570       580       590       600
FNFNGLTGTGVLTESNKKFLPFQQFGRDIADTTDAVRDPQTLEILDITPCSFGGVSVITP 610       620       630       640       650       660
GTNTSNQVAVLYQDVNCTEVPVAIHADQLTPTWRVYSTGSNVFQTRAGCLIGAEHVNNSY 670       680       690       700       710       720
ECDIPIGAGICASYQTQTNSPRRARSVASQSIIAYTMSLGAENSVAYSNNSIAIPTNFTI 730       740       750       760       770       780
SVTTEILPVSMTKTSVDCTMYICGDSTECSNLLLQYGSFCTQLNRALTGIAVEQDKNTQE 790       800       810       820       830       840
VFAQVKQIYKTPPIKDFGGFNFSQILPDPSKPSKRSFIEDLLFNKVTLADAGFIKQYGDC 850       860       870       880       890       900
LGDIAARDLICAQKFNGLTVLPPLLTDEMIAQYTSALLAGTITSGWTFGAGAALQIPFAM 910       920       930       940       950       960
QMAYRFNGIGVTQNVLYENQKLIANQFNSAIGKIQDSLSSTASALGKLQDVVNQNAQALN 970       980       990      1000      1010      1020
TLVKQLSSNFGAISSVLNDILSRLDKVEAEVQIDRLITGRLQSLQTYVTQQLIRAAEIRA 1030      1040      1050      1060      1070      1080
SANLAATKMSECVLGQSKRVDFCGKGYHLMSFPQSAPHGVVFLHVTYVPAQEKNFTTAPA 1090      1100      1110      1120      1130      1140
ICHDGKAHFPREGVFVSNGTHWFVTQRNFYEPQIITTDNTFVSGNCDVVIGIVNNTVYDP 1150      1160      1170      1180      1190      1200
LQPELDSFKEELDKYFKNHTSPDVDLGDISGINASVVNIQKEIDRLNEVAKNLNESLIDL 1210      1220      1230      1240      1250      1260
QELGKYEQYIKRSNGLPGPIGPPGPRGRTGDAGPVGPPGPPGPPGPPGPPSAGFDFSFLP 1270      1280      1290      1300      1310      1320
QPPQEKAHDGGRYYRANDANVVRDRDLEVDTTLKSLSQQIENIRSPEGSRKNPARTCRDL 1330      1340      1350      1360      1370      1380
KMCHSDWKSGEYWIDPNQGCNLDAIKVFCNMETGETCVYPTQPSVAQKNWYISKNPKDKR
```

```
      1390       1400       1410       1420       1430       1440
HVWFGESMTDGFQFEYGGQGSDPADVAIQLTFLRLMSTEASQNITYHCKNSVAYMDQQTG 1450       1460       1470       1480       1490       1500
NLKKALLLQGSNEIEIRAEGNSRFTYSVTVDGCTSHTGAWGKTVIEYKTTKTSRLPIIDV 1510       1520
APLDVGAPDQEFGFDVGPVCFL
```

In some embodiments, the inter-polypeptide disulfide bonds may comprise one or more or all of Cys15-136, Cys131-166, Cys291-301, Cys379-432, Cys336-361, Cys391-525, Cys480-488, Cys538-590, Cys617-649, Cys662-671, Cys743-749, Cys738-760, Cys840-851, Cys1032-1043, and Cys1082-1126, in any suitable combination. In some embodiments, the fusion polypeptide in the trimer may comprise one or more glycosylation sites (e.g., Asn-linked), for example, at one or more or all of Asn residues at 17, 61, 122, 149, 165, 234, 282, 331, 343, 603, 616, 657, 709, 717, 801, 1074, 1098, and 1134, in any suitable combination.

In some embodiments, the C-terminal propeptide is of human collagen. In some embodiments, the C-terminal propeptide comprises a C-terminal polypeptide of proα1(I), proα1(II), proα1(III), proα1(V), proα1(XI), proα2(I), proα2(V), proα2(XI), or proα3(XI), or a fragment thereof. In some embodiments, the C-terminal propeptide is or comprises a C-terminal polypeptide of proα1(I).

In some embodiments, the C-terminal propeptide is or comprises the amino acid sequence set forth by SEQ ID NO: 67. In some embodiments, the C-terminal propeptide is an amino acid sequence having at least or about 85%, 90%, 92%, 95%, or 97% sequence identity to sequence of SEQ ID NO: 67. In some embodiments, the C-terminal propeptide is or comprises the amino acid sequence set forth by SEQ ID NO: 68. In some embodiments, the C-terminal propeptide is an amino acid sequence having at least or about 85%, 90%, 92%, 95%, or 97% sequence identity to sequence of SEQ ID NO: 68. In some embodiments, the C-terminal propeptide is or is the amino acid sequence set forth by SEQ ID NO: 69. In some embodiments, the C-terminal propeptide exhibits an amino acid sequence having at least or about 85%, 90%, 92%, 95%, or 97% sequence identity to sequence of SEQ ID NO: 69. In some embodiments, the C-terminal propeptide is or comprises the amino acid sequence set forth by SEQ ID NO: 70. In some embodiments, the C-terminal propeptide is an amino acid sequence having at least or about 85%, 90%, 92%, 95%, or 97% sequence identity to sequence of SEQ ID NO: 70. In some embodiments, the C-terminal propeptide is or comprises the amino acid sequence set forth by SEQ ID NO: 71. In some embodiments, the C-terminal propeptide is an amino acid sequence having at least or about 85%, 90%, 92%, 95%, or 97% sequence identity to sequence of SEQ ID NO: 71.

In some embodiments, the C-terminal propeptide is or comprises the amino acid sequence set forth by SEQ ID NO: 72. In some embodiments, the C-terminal propeptide is an amino acid sequence having at least or about 85%, 90%, 92%, 95%, or 97% sequence identity to sequence of SEQ ID NO: 72. In some embodiments, the C-terminal propeptide is or comprises the amino acid sequence set forth by SEQ ID NO: 73. In some embodiments, the C-terminal propeptide is an amino acid sequence having at least or about 85%, 90%, 92%, 95%, or 97% sequence identity to sequence of SEQ ID NO: 73. In some embodiments, the C-terminal propeptide is or is the amino acid sequence set forth by SEQ ID NO: 74. In some embodiments, the C-terminal propeptide exhibits an amino acid sequence having at least or about 85%, 90%, 92%, 95%, or 97% sequence identity to sequence of SEQ ID NO: 74. In some embodiments, the C-terminal propeptide is or comprises the amino acid sequence set forth by SEQ ID NO: 75. In some embodiments, the C-terminal propeptide is an amino acid sequence having at least or about 85%, 90%, 92%, 95%, or 97% sequence identity to sequence of SEQ ID NO: 75. In some embodiments, the C-terminal propeptide is or comprises the amino acid sequence set forth by SEQ ID NO: 76. In some embodiments, the C-terminal propeptide is an amino acid sequence having at least or about 85%, 90%, 92%, 95%, or 97% sequence identity to sequence of SEQ ID NO: 76.

In some embodiments, the C-terminal propeptide is or comprises the amino acid sequence set forth by SEQ ID NO: 77. In some embodiments, the C-terminal propeptide is an amino acid sequence having at least or about 85%, 90%, 92%, 95%, or 97% sequence identity to sequence of SEQ ID NO: 77. In some embodiments, the C-terminal propeptide is or comprises the amino acid sequence set forth by SEQ ID NO: 78. In some embodiments, the C-terminal propeptide is an amino acid sequence having at least or about 85%, 90%, 92%, 95%, or 97% sequence identity to sequence of SEQ ID NO: 78. In some embodiments, the C-terminal propeptide is or is the amino acid sequence set forth by SEQ ID NO: 79. In some embodiments, the C-terminal propeptide exhibits an amino acid sequence having at least or about 85%, 90%, 92%, 95%, or 97% sequence identity to sequence of SEQ ID NO: 79. In some embodiments, the C-terminal propeptide is or comprises the amino acid sequence set forth by SEQ ID NO: 80. In some embodiments, the C-terminal propeptide is an amino acid sequence having at least or about 85%, 90%, 92%, 95%, or 97% sequence identity to sequence of SEQ ID NO: 80.

In some embodiments, the C-terminal propeptide is or comprises the amino acid sequence of a collagen trimerization domain (e.g., C-propeptide of human α1(I) collagen) with an aspartic acid (D) to asparagine (N) substitution in the BMP-1 site, for instance, as shown in SEQ ID NO: 68 where RAD is mutated to RAN. In some embodiments, the C-terminal propeptide is or comprises the amino acid sequence of a collagen trimerization domain (e.g., C-propeptide of human al(I) collagen) with an alanine (A) to asparagine (N) substitution in the BMP-1 site, for instance, as shown in SEQ ID NO: 69 where RAD is mutated to RND. In some embodiments, the C-terminal propeptide herein may comprise a mutated BMP-1 site, e.g., RSAN instead of DDAN. In some embodiments, the C-terminal propeptide herein may comprise a BMP-1 site, e.g., a sequence (such as SEQ ID NO: 68 or 69) comprising the RAD (e.g., RADDAN) sequence instead of RAN (e.g., RANDAN) or RND (e.g., RNDDAN) may be used in a fusion polypeptide disclosed herein. For instance, SEQ ID NO: 27 (underlined) or a fragment, variant or mutant thereof may be directly or indirectly linked to SEQ ID NO: 67 (italicized) or a fragment, variant or mutant there, e.g., to form the following fusion protein:

QCVNLTTRTQLPPAYTNSFTRGVYYPDKVFRSSVLHSTQDLFLPFFSNVT

WFHAIHVSGTNGTKRFDNPVLPFNDGVYFASTEKSNIIRGWIFGTTLDSK

TQSLLIVNNATNVVIKVCEFQFCNDPFLGVYYHKNNKSWMESEFRVYSSA

NNCTFEYVSQPFLMDLEGKQGNFKNLREFVFKNIDGYFKIYSKHTPINLV

RDLPQGFSALEPLVDLPIGINITRFQTLLALHRSYLTPGDSSSGWTAGAA

AYYVGYLQPRTFLLKYNENGTITDAVDCALDPLSETKCTLKSFTVEKGIY

QTSNFRVQPTESIVRFPNITNLCPFGEVFNATRFASVYAWNRKRISNCVA

DYSVLYNSASFSTFKCYGVSPTKLNDLCFTNVYADSFVIRGDEVRQIAPG

QTGKIADYNYKLPDDFTGCVIAWNSNNLDSKVGGNYNYLYRLFRKSNLKP

FERDISTEIYQAGSTPCNGVEGFNCYFPLQSYGFQPTNGVGYQPYRVVVL

SPELLHAPATVCGPKKSTNLVKNKCVNFNFNGLTGTGVLTESNKKFLPFQ

QFGRDIADTTDAVRDPQTLEILDITPCSFGGVSVITPGTNTSNQVAVLYQ

DVNCTEVPVAIHADQLTPTWRVYSTGSNVFQTRAGCLIGAEHVNNSYECD

IPIGAGICASYQTQTNSPRRARSVASQSIIAYTMSLGAENSVAYSNNSIA

IPTNFTISVTTEILPVSMTKTSVDCTMYICGDSTECSNLLLQYGSFCTQL

NRALTGIAVEQDKNTQEVFAQVKQIYKTPPIKDFGGFNFSQILPDPSKPS

KRSFIEDLLFNKVTLADAGFIKQYGDCLGDIAARDLICAQKFNGLTVLPP

LLTDEMIAQYTSALLAGTITSGWTFGAGAALQIPFAMQMAYRFNGIGVTQ

NVLYENQKLIANQFNSAIGKIQDSLSSTASALGKLQDVVNQNAQALNTLV

KQLSSNFGAISSVLNDILSRLDKVEAEVQIDRLITGRLQSLQTYVTQQLI

RAAEIRASANLAATKMSECVLGQSKRVDFCGKGYHLMSFPQSAPHGVVFL

HVTYVPAQEKNFTTAPAICHDGKAHFPREGVFVSNGTHWFVTQRNFYEPQ

IITTDNTFVSGNCDVVIGIVNNTVYDPLQPELDSFKEELDKYFKNHTSPD

VDLGDISGINASVVNIQKEIDRLNEVAKNLNESLIDLQELGKYEQYIKRS

*ANVVRDRDLEVDTTLKSLSQQIENIRSPEGSRKNPARTCRDLKMCHSDWK*

*SGEYWIDPNQGCNLDAIKVFCNMETGETCVYPTQPSVAQKNWYISKNPKD*

*KRHVWFGESMTDGFQFEYGGQGSDPADVAIQLTFLRLMSTEASQNITYHC*

*KNSVAYMDQQTGNLKKALLLQGSNEIEIRAEGNSRFTYSVTVDGCTSHTG*

*AWGKTVIEYKTTKTSRLPIIDVAPLDVGAPDQEFGFDVGPVCFL*

In some embodiments, the C-terminal propeptide is or comprises an amino acid sequence that is a fragment of any of SEQ ID NOs: 67-80.

In some embodiments, the C-terminal propeptide can comprise a sequence comprising glycine-X-Y repeats, wherein X and Y are independently any amino acid, or an amino acid sequence at least 85%, 90%, 92%, 95%, or 97% identical thereto capable of forming inter-polypeptide disulfide bonds and trimerizing the recombinant polypeptides. In some embodiments, X and Y are independently proline or hydroxyproline.

In some cases where an S protein peptide is linked to the C-terminal propeptide to form the recombinant polypeptide, the recombinant polypeptides form a trimer resulting in a homotrimer of S protein peptides. In some embodiments, the S protein peptides of the trimerized recombinant polypeptides are in a prefusion conformation. In some embodiments, the S protein peptides of the trimerized recombinant polypeptides are in a postfusion conformation. In some embodiments, the confirmation state allows for access to different antigenic sites on the S protein peptides. In some embodiments, the antigenic sites are epitopes, such as linear epitopes or conformational epitopes. An advantage of having a trimerized recombinant polypeptides as described is that an immune response can be mounted against a variety of potential and diverse antigenic sites.

In some embodiments, trimerized recombinant polypeptides include individual recombinant polypeptides comprising the same viral antigen or immunogen. In some embodiments, trimerized recombinant polypeptides include individual recombinant polypeptides each comprising a different viral antigen or immunogen from the other recombinant polypeptides. In some embodiments, trimerized recombinant polypeptides include individual recombinant polypeptides wherein one of the individual recombinant polypeptides comprises a viral antigen or immunogen different from the other recombinant polypeptides. In some embodiments, trimerized recombinant polypeptides include individual recombinant polypeptides wherein two of the individual recombinant polypeptides comprise the same viral antigen or immunogen, and the viral antigen or immunogen is different from the viral antigen or immunogen comprised in the remaining recombinant polypeptide.

In some embodiments, the recombinant polypeptide comprises any coronavirus viral antigen or immunogen described in Section I. In some embodiments, the recombinant polypeptide comprises any coronavirus viral antigen or immunogen described in Section I linked, as described herein, to the C-terminal propeptide of collagen as described herein.

In some embodiments, the immunogen comprises a recombinant SARS-CoV or SARS-CoV-2 S ectodomain trimer comprising protomers comprising one or more (such as two, for example two consecutive) proline substitutions at or near the boundary between a HR1 domain and a central helix domain that stabilize the S ectodomain trimer in the prefusion conformation. In some such embodiments, the one or more (such as two, for example two consecutive) proline substitutions that stabilize the S ectodomain in the prefusion conformation are located between a position 15 amino acids N-terminal of a C-terminal residue of the HR1 and a position 5 amino acids C-terminal of a N-terminal residue of the central helix.

In some embodiments, the one or more (such as two, for example two consecutive) proline substitutions stabilize the coronavirus (e.g., SARS-CoV or SARS-CoV-2) S ectodomain trimer in the prefusion conformation. In some embodiments, the SARS-CoV-2 S protein peptide comprises 986K/987V to 986P/987P mutations.

In some embodiments, the recombinant coronavirus (e.g., SARS-CoV or SARS-CoV-2) S ectodomain trimer stabilized in the prefusion conformation comprises single-chain S ectodomain protomers comprising mutations to the S1/S2 and/or S2' protease cleavage sites to prevent protease cleavage at these sites. In some embodiments, the SARS-CoV-2 S protein peptide comprises a 685R to 685A mutation. Exemplary protease cleavage sites for various viruses are shown below:

| Coronavirus | S1/S2, site 1 | S1/S2, site 2 | S2' |
|---|---|---|---|
| 2019-nCoV | SPRRAR↓SVAS | IAY↓TMS | SKPSKR↓SF |
| CoV-ZX21 | TASILR↓STGQ | IAY↓TMS | SKPSKR↓SF |

-continued

| Coronovirus | S1/S2, site 1 | S1/S2, site 2 | S2' |
|---|---|---|---|
| Bat-AC45 | TASILR↓STGQ | IAY↓TMS | SKPSKR↓SF |
| SARS-CoV | TVSLLR↓STGQ | IAY↓TMS | LFPTKR↓SF |
| BM48-31 | SSTLVR↓SGGM | LAY↓TMS | LKPTKR↓SF |
| HKU9-1 | ADSLPR↓LQLV | VNY↓DPL | GATTYR↓SA |
| MERS-CoV | TFRSCR↓SVPG | | GSRSAR↓SA |
| HKU1 | SRRKFR↓SISA | | CGSSSR↓SF |
| HCoV-OC43 | KNRRER↓GAITT | | SKASSR↓SA |
| HCoV-229E | IAVQPR↓RVSYD | | SRVAGR↓GA |
| HCoV-NL63 | IFVRPR↓NSSDN | | SRIAGR↓SA |

In some embodiments, the protomers of the recombinant coronavirus (e.g., SARS-CoV or SARS-CoV-2) S ectodomain trimer stabilized in the prefusion conformation by the one or more proline substitutions (such as 986P/987P substitutions) comprises additional modifications for stabilization in the prefusion conformation, such as a mutation at a protease cleavage site to prevent protease cleavage.

With reference to the SARS-CoV-2 S protein sequence provided as SEQ ID NO: 55, the ectodomain comprises a signal peptide (SP), which is removed during cellular processing; an N-terminal domain (NTD); a receptor binding domain (RBD); one or more S1/S2 cleavage sites; a fusion peptide (FP); internal fusion peptide (IFP); heptad repeat ½ (HR½), and the transmembrane domain (TM). Exemplary sources of the sequence can be found at https://www.ncbi.nlm.nih.gov/nuccore/1VIN908947.3, https://www.ncbi.nlm.nih.gov/nuccore/MN908947, ncbi.nlm.nih.gov/nuccore/MN908947.2. Additoinal sequences can be found at ncbi.nlm.nih.gov/genbank/sars-cov-2-seqs/, including the pneumonia virus isolate Wuhan-Hu-1, complete genome.

In some embodiments, the protomers of the prefusion-stabilized SARS-CoV-2 S ectodomain trimer can have a C-terminal residue (which can be linked to a trimerization domain, or a transmembrane domain, for example) of the C-terminal residue of the NTD, the RBD, S1 (at either the S1/S2 site 1, or S1/S2 site 2), FP, IFP, HR1, HR2, or the ectodomain. The position numbering of the S protein may vary between SARS-CoV stains, but the sequences can be aligned to determine relevant structural domains and cleavage sites. It will be appreciated that a few residues (such as up to 10) on the N and C-terminal ends of any of the ectodomain fragment can be removed or modified in the disclosed immunogens without decreasing the utility of the S ectodomain trimer as an immunogen.

In some embodiments, the recombinant polypeptide is or comprises an NTD peptide of SARS-CoV or SARS-CoV-2 S protein. In some embodiments, the recombinant polypeptide is or comprises an RBD peptide of SARS-CoV or SARS-CoV-2 S protein. In some embodiments, the recombinant polypeptide is or comprises an NTD peptide and an RBD peptide of SARS-CoV or SARS-CoV-2 S protein. In some embodiments, the recombinant polypeptide is or comprises an S1 domain peptide of SARS-CoV or SARS-CoV-2 S protein. In some embodiments, the recombinant polypeptide is or comprises an S2 domain peptide of SARS-CoV or SARS-CoV-2 S protein.

An exemplary SARS-CoV-1 S recombinant polypeptide without a signal peptide is provided in SEQ ID NO: 26 (1491 aa):

```
                10         20         30         40         50         60
        SDLDRCTTFD DVQAPNYTQH TSSMRGVYYP DEIFRSDTLY LTQDLFLPFY SNVTGFHTIN 70         80         90        100        110        120
        HTFDNPVIPF KDGIYFAATE KSNVVRGWVF GSTMNNKSQS VIIINNSTNV VIRACNFELC 130        140        150        160        170        180
        DNPFFAVSKP MGTQTHTMIF DNAFNCTFEY ISDAFSLDVS EKSGNFKHLR EFVFKNKDGF 190        200        210        220        230        240
        LYVYKGYQPI DVVRDLPSGF NTLKPIFKLP LGINITNFRA ILTAFLPAQD TWGTSAAAYF 250        260        270        280        290        300
        VGYLKPTTFM LKYDENGTIT DAVDCSQNPL AELKCSVKSF EIDKGIYQTS NFRVVPSRDV 310        320        330        340        350        360
        VRFPNITNLC PFGEVFNATK FPSVYAWERK RISNCVADYS VLYNSTFFST FKCYGVSATK 370        380        390        400        410        420
        LNDLCFSNVY ADSFVVKGDD VRQIAPGQTG VIADYNYKLP DDFMGCVLAW NTRNIDATST 430        440        450        460        470        480
        GNYNYKYRYL RHGKLRPFER DISNVPFSPD GKPCTPPALN CYWPLNDYGF YTTTGIGYQP 490        500        510        520        530        540
        YRVVVLSFEL LNAPATVCGP KLSTDLIKNQ CVNFNFNGLT GTGVLTPSSK RFQPFQQFGR 550        560        570        580        590        600
        DVSDFTDSVR DPKTSEILDI SPCSFGGVSV ITPGTNASSE VAVLYQDVNC TDVSTAIHAD 610        620        630        640        650        660
        QLTPAWRIYS TGNNVFQTQA GCLIGAEHVD TSYECDIPIG AGICASYHTV SLLRSTSQKS 670        680        690        700        710        720
        IVAYTMSLGA DSSIAYSNNT IAIPTNFSIS ITTEVMPVSM AKTSVDCNMY ICGDSTECAN
```

-continued

```
         730        740        750        760        770        780
  LLLQYGSFCT QLNRALSGIA AEQDRNTREV FAQVKQMYKT PTLKDFGGFN FSQILPDPLK 790        800        810        820        830        840
  PTKRSFIEDL LFNKVTLADA GFMKQYGECL GDINARDLIC AQKFNGLTVL PPLLTDDMIA 850        860        870        880        890        900
  AYTAALVSGT ATAGWTFGAG AALQIPFAMQ MAYRFNGIGV TQNVLYENQK QIANQFNKAI 910        920        930        940        950        960
  SQIQESLTTT STALGKLQDV VNQNAQALNT LVKQLSSNFG AISSVLNDIL SRLDKVEAEV 970        980        990       1000       1010       1020
  QIDRLITGRL QSLQTYVTQQ LIRAAEIRAS ANLAATKMSE CVLGQSKRVD FCGKGYHLMS 1030       1040       1050       1060       1070       1080
  FPQAAPHGVV FLHVTYVPSQ ERNFTTAPAI CHEGKAYFPR EGVFVFNGTS WFITQRNFFS 1090       1100       1110       1120       1130       1140
  PQIITTDNTF VSGNCDVVIG IINNTVYDPL QPELDSFKEE LDKYFKNHTS PDVDLGDISG 1150       1160       1170       1180       1190       1200
  INASVVNIQE EIDRLNEVAK NLNESLIDLQ ELGKYEQYIK RSNGLPGPIG PPGPRGRTGD 1210       1220       1230       1240       1250       1260
  AGPVGPPGPP GPPGPPGPPS AGFDFSFLPQ PPQEKAHDGG RYYRANDANV VRDRDLEVDT 1270       1280       1290       1300       1310       1320
  TLKSLSQQIE NIRSPEGSRK NPARTCRDLK MCHSDWKSGE YWIDPNQGCN LDAIKVFCNM 1330       1340       1350       1360       1370       1380
  ETGETCVYPT QPSVAQKNWY ISKNPKDKRH VWFGESMTDG FQFEYGGQGS DPADVAIQLT 1390       1400       1410       1420       1430       1440
  FLRLMSTEAS QNITYHCKNS VAYMDQQTGN LKKALLLQGS NEIEIRAEGN SRFTYSVTVD 1450       1460       1470       1480       1490
  GCTSHTGAWG KTVIEYKTTK TSRLPIIDVA PLDVGAPDQE FGFDVGPVCF L
```

The above SARS-CoV-1 S recombinant polypeptide may comprise an N-terminal signal peptide provided in SEQ ID NO: 53.

An exemplary SARS-CoV-2 S recombinant polypeptide without a signal peptide is provided in SEQ ID NO: 1 (1509 aa):

```
          10         20         30         40         50         60
  QCVNLTTRTQ LPPAYTNSFT RGVYYPDKVF RSSVLHSTQD LFLPFFSNVT WFHAIHVSGT 70         80         90        100        110        120
  NGTKRFDNPV LPFNDGVYFA STEKSNIIRG WIFGTTLDSK TQSLLIVNNA TNVVIKVCEF 130        140        150        160        170        180
  QFCNDPFLGV YYHKNNKSWM ESEFRVYSSA NNCTFEYVSQ PFLMDLEGKQ GNFKNLREFV 190        200        210        220        230        240
  FKNIDGYFKI YSKHTPINLV RDLPQGFSAL EPLVDLPIGI NITRFQTLLA LHRSYLTPGD 250        260        270        280        290        300
  SSSGWTAGAA AYYVGYLQPR TFLLKYNENG TITDAVDCAL DPLSETKCTL KSFTVEKGIY 310        320        330        340        350        360
  QTSNFRVQPT ESIVRFPNIT NLCPFGEVFN ATRFASVYAW NRKRISNCVA DYSVLYNSAS 370        380        390        400        410        420
  FSTFKCYGVS PTKLNDLCFT NVYADSFVIR GDEVRQIAPG QTGKIADYNY KLPDDFTGCV 430        440        450        460        470        480
  IAWNSNNLDS KVGGNYNYLY RLFRKSNLKP FERDISTEIY QAGSTPCNGV EGFNCYFPLQ 490        500        510        520        530        540
  SYGFQPTNGV GYQPYRVVVL SFELLHAPAT VCGPKKSTNL VKNKCVNFNF NGLTGTGVLT 550        560        570        580        590        600
  ESNKKFLPFQ QFGRDIADTT DAVRDPQTLE ILDITPCSFG GVSVITPGTN TSNQVAVLYQ 610        620        630        640        650        660
  DVNCTEVPVA IHADQLTPTW RVYSTGSNVF QTRAGCLIGA EHVNNSYECD IPIGAGICAS 670        680        690        700        710        720
  YQTQTNSPRR ARSVASQSII AYTMSLGAEN SVAYSNNSIA IPTNFTISVT TEILPVSMTK
```

-continued

```
       730        740        750        760        770        780
TSVDCTMYIC GDSTECSNLL LQYGSFCTQL NRALTGIAVE QDKNTQEVFA QVKQIYKTPP 790        800        810        820        830        840
IKDFGGFNFS QILPDPSKPS KRSFIEDLLF NKVTLADAGF IKQYGDCLGD IAARDLICAQ 850        860        870        880        890        900
KFNGLTVLPP LLTDEMIAQY TSALLAGTIT SGWTFGAGAA LQIPFAMQMA YRFNGIGVTQ 910        920        930        940        950        960
NVLYENQKLI ANQFNSAIGK IQDSLSSTAS ALGKLQDVVN QNAQALNTLV KQLSSNFGAI 970        980        990       1000       1010       1020
SSVLNDILSR LDKVEAEVQI DRLITGRLQS LQTYVTQQLI RAAEIRASAN LAATKMSECV 1030       1040       1050       1060       1070       1080
LGQSKRVDFC GKGYHLMSFP QSAPHGVVFL HVTYVPAQEK NFTTAPAICH DGKAHFPREG 1090       1100       1110       1120       1130       1140
VFVSNGTHWF VTQRNFYEPQ IITTDNTFVS GNCDVVIGIV NNTVYDPLQP ELDSFKEELD 1150       1160       1170       1180       1190       1200
KYFKNHTSPD VDLGDISGIN ASVVNIQKEI DRLNEVAKNL NESLIDLQEL GKYEQYIKRS 1210       1220       1230       1240       1250       1260
NGLPGPIGPP GPRGRTGDAG PVGPPGPPGP PGPPGPPSAG FDFSFLPQPP QEKAHDGGRY 1270       1280       1290       1300       1310       1320
YRANDANVVR DRDLEVDTTL KSLSQQIENI RSPEGSRKNP ARTCRDLKMC HSDWKSGEYW 1330       1340       1350       1360       1370       1380
IDPNQGCNLD AIKVFCNMET GETCVYPTQP SVAQKNWYIS KNPKDKRHVW FGESMTDGFQ 1390       1400       1410       1420       1430       1440
FEYGGQGSDP ADVAIQLTFL RLMSTEASQN ITYHCKNSVA YMDQQTGNLK KALLLQGSNE 1450       1460       1470       1480       1490       1500
IEIRAEGNSR FTYSVTVDGC TSHTGAWGKT VIEYKTTKTS RLPIIDVAPL DVGAPDQEFG

1509
FDVGPVCFL
```

The above SARS-CoV-2 S recombinant polypeptide may comprise an N-terminal signal peptide provided in SEQ ID NO: 54.

In some embodiments, the recombinant polypeptide is or comprises the sequence set forth in SEQ ID NO: 1. In some embodiments, the recombinant polypeptide is or comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 1, including a sequence comprising substitution, deletion, and/or insertion at one or more amino acid positions, such as 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and/or 1176 (amino acid positions with respect to SEQ ID NO: 55), or any combination thereof. In some embodiments, the recombinant polypeptide is or comprises a variant of SEQ ID NO: 1 and the variant comprises any one, two, three, four, five or more of the mutations selected from the group consisting of S13I, L18F, T20N, P26S, Δ69-70 (ΔHV), D80A, D138Y, G142D, Δ144 (ΔY), W152C, R190S, D215G, Δ242-244 (ΔLAL), R246I, Δ400-402 (ΔFVI), K417T, K417N, N440K, L452R, S477N, S477G, E484K, E484Q, N501Y, A570D, D614G, H655Y, P681H, P681R, R682G, R683S, R685G, A701V, T716I, F888L, S982A, T1027I, D1118H, and V1176F, or any combination thereof.

In some embodiments, the recombinant polypeptide is or comprises the sequence set forth in SEQ ID NO: 2. In some embodiments, the recombinant polypeptide is or comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 2, including a sequence comprising substitution, deletion, and/or insertion at one or more amino acid positions, such as 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and/or 1176 (amino acid positions with respect to SEQ ID NO: 55), or any combination thereof. In some embodiments, the recombinant polypeptide is or comprises a variant of SEQ ID NO: 2 and the variant comprises any one, two, three, four, five or more of the mutations selected from the group consisting of S13I, L18F, T20N, P26S, Δ69-70 (ΔHV), D80A, D138Y, G142D, Δ144 (ΔY), W152C, R190S, D215G, Δ242-244 (ΔLAL), R246I, Δ400-402 (ΔFVI), K417T, K417N, N440K, L452R, S477N, S477G, E484K, E484Q, N501Y, A570D, D614G, H655Y, P681H, P681R, R682G, R683S, R685G, A701V, T716I, F888L, S982A, T1027I, D1118H, and V1176F, or any combination thereof.

In some embodiments, the recombinant polypeptide is or comprises the sequence set forth in SEQ ID NO: 3. In some embodiments, the recombinant polypeptide is or comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 3, including a sequence comprising substitution, deletion, and/or insertion at one or more amino acid positions, such as 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and/or 1176 (amino acid positions with respect to SEQ ID NO: 55), or any combination thereof. In some embodiments, the recombinant polypeptide is or comprises a variant of SEQ ID NO: 3 and the variant comprises any one, two, three, four, five or more of the mutations selected from the group consisting of S13I, L18F, T20N, P26S, Δ69-70 (ΔHV), D80A, D138Y, G142D, Δ144 (ΔY), W152C, R190S, D215G, Δ242-244 (ΔLAL), R246I, Δ400-402 (ΔFVI), K417T, K417N, N440K, L452R, S477N, S477G, E484K, E484Q, N501Y, A570D, D614G, H655Y, P681H, P681R, R682G, R683S, R685G, A701V, T716I, F888L, S982A, T1027I, D1118H, and V1176F, or any combination thereof.

In some embodiments, the recombinant polypeptide is or comprises the sequence set forth in SEQ ID NO: 4. In some embodiments, the recombinant polypeptide is or comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 4, including a sequence comprising substitution, deletion, and/or insertion at one or more amino acid positions, such as 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and/or 1176 (amino acid positions with respect to SEQ ID NO: 55), or any combination thereof. In some embodiments, the recombinant polypeptide is or comprises a variant of SEQ ID NO: 4 and the variant comprises any one, two, three, four, five or more of the mutations selected from the group consisting of S13I, L18F, T20N, P26S, Δ69-70 (ΔHV), D80A, D138Y, G142D, Δ144 (ΔY), W152C, R190S, D215G, Δ242-244 (ΔLAL), R246I, Δ400-402 (ΔFVI), K417T, K417N, N440K, L452R, S477N, S477G, E484K, E484Q, N501Y, A570D, D614G, H655Y, P681H, P681R, R682G, R683S, R685G, A701V, T716I, F888L, S982A, T1027I, D1118H, and V1176F, or any combination thereof.

In some embodiments, the recombinant polypeptide is or comprises the sequence set forth in SEQ ID NO: 5. In some embodiments, the recombinant polypeptide is or comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 5, including a sequence comprising substitution, deletion, and/or insertion at one or more amino acid positions, such as 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and/or 1176 (amino acid positions with respect to SEQ ID NO: 55), or any combination thereof. In some embodiments, the recombinant polypeptide is or comprises a variant of SEQ ID NO: 5 and the variant comprises any one, two, three, four, five or more of the mutations selected from the group consisting of S13I, L18F, T20N, P26S, Δ69-70 (ΔHV), D80A, D138Y, G142D, Δ144 (ΔY), W152C, R190S, D215G, Δ242-244 (ΔLAL), R246I, Δ400-402 (ΔFVI), K417T, K417N, N440K, L452R, S477N, S477G, E484K, E484Q, N501Y, A570D, D614G, H655Y, P681H, P681R, R682G, R683S, R685G, A701V, T716I, F888L, S982A, T1027I, D1118H, and V1176F, or any combination thereof.

In some embodiments, the recombinant polypeptide is or comprises the sequence set forth in SEQ ID NO: 6. In some embodiments, the recombinant polypeptide is or comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 6, including a sequence comprising substitution, deletion, and/or insertion at one or more amino acid positions, such as 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and/or 1176 (amino acid positions with respect to SEQ ID NO: 55), or any combination thereof. In some embodiments, the recombinant polypeptide is or comprises a variant of SEQ ID NO: 6 and the variant comprises any one, two, three, four, five or more of the mutations selected from the group consisting of S13I, L18F, T20N, P26S, Δ69-70 (ΔHV), D80A, D138Y, G142D, Δ144 (ΔY), W152C, R190S, D215G, Δ242-244 (ΔLAL), R246I, Δ400-402 (ΔFVI), K417T, K417N, N440K, L452R, S477N, S477G, E484K, E484Q, N501Y, A570D, D614G, H655Y, P681H, P681R, R682G, R683S, R685G, A701V, T716I, F888L, S982A, T1027I, D1118H, and V1176F, or any combination thereof.

In some embodiments, the recombinant polypeptide is or comprises the sequence set forth in SEQ ID NO: 7. In some embodiments, the recombinant polypeptide is or comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 7, including a sequence comprising substitution, deletion, and/or insertion at one or more amino acid positions, such as 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and/or 1176 (amino acid positions with respect to SEQ ID NO: 55), or any combination thereof. In some embodiments, the recombinant polypeptide is or comprises a variant of SEQ ID NO: 7 and the variant comprises any one, two, three, four, five or more of the mutations selected from the group consisting of S13I, L18F, T20N, P26S, Δ69-70 (ΔHV), D80A, D138Y, G142D, Δ144 (ΔY), W152C, R190S, D215G, Δ242-244 (ΔLAL), R246I, Δ400-402 (ΔFVI), K417T, K417N, N440K, L452R, S477N, S477G, E484K, E484Q, N501Y, A570D, D614G, H655Y, P681H, P681R, R682G, R683S, R685G, A701V, T716I, F888L, S982A, T1027I, D1118H, and V1176F, or any combination thereof.

In some embodiments, the recombinant polypeptide is or comprises the sequence set forth in SEQ ID NO: 8. In some embodiments, the recombinant polypeptide is or comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 8, including a sequence comprising substitution, deletion, and/or insertion at one or more amino acid positions, such as 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and/or 1176 (amino acid positions with respect to SEQ ID NO: 55), or any combination thereof. In some embodiments, the recombinant polypeptide is or comprises a variant of SEQ ID NO: 8 and the variant comprises any one, two, three, four, five or more of the mutations selected from the group consisting of S13I, L18F, T20N, P26S, Δ69-70 (ΔHV), D80A, D138Y, G142D, Δ144 (ΔY), W152C, R190S, D215G, Δ242-244 (ΔLAL), R246I, Δ400-402 (ΔFVI), K417T, K417N, N440K, L452R, S477N, S477G, E484K, E484Q, N501Y, A570D, D614G, H655Y, P681H, P681R, R682G, R683S, R685G, A701V, T716I, F888L, S982A, T1027I, D1118H, and V1176F, or any combination thereof.

In some embodiments, the recombinant polypeptide is or comprises the sequence set forth in SEQ ID NO: 9. In some embodiments, the recombinant polypeptide is or comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 9, including a sequence comprising substitution, deletion, and/or insertion at one or more amino acid positions, such as 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and/or 1176 (amino acid positions with respect to SEQ ID NO: 55), or any combination thereof. In some embodiments, the recombinant polypeptide is or comprises a variant of SEQ ID NO: 9 and the variant comprises any one, two, three, four, five or more of the mutations selected from the group consisting of S13I, L18F, T20N, P26S, Δ69-70 (ΔHV), D80A, D138Y, G142D, Δ144 (ΔY), W152C, R190S, D215G, Δ242-244 (ΔLAL), R246I, Δ400-402 (ΔFVI), K417T, K417N, N440K, L452R, S477N, S477G, E484K, E484Q, N501Y, A570D, D614G,
H655Y, P681H, P681R, R682G, R683S, R685G, A701V, T716I, F888L, S982A, T1027I, D1118H, and V1176F, or any combination thereof.

In some embodiments, the recombinant polypeptide is or comprises the sequence set forth in SEQ ID NO: 10. In some embodiments, the recombinant polypeptide is or comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 10, including a sequence comprising substitution, deletion, and/or insertion at one or more amino acid positions, such as 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and/or 1176 (amino acid positions with respect to SEQ ID NO: 55), or any combination thereof. In some embodiments, the recombinant polypeptide is or comprises a variant of SEQ ID NO: 10 and the variant comprises any one, two, three, four, five or more of the mutations selected from the group consisting of S13I, L18F, T20N, P26S, Δ69-70 (ΔHV), D80A, D138Y, G142D, Δ144 (ΔY), W152C, R190S, D215G, Δ242-244 (ΔLAL), R246I, Δ400-402 (ΔFVI), K417T, K417N, N440K, L452R, S477N, S477G, E484K, E484Q, N501Y, A570D, D614G, H655Y, P681H, P681R, R682G, R683S, R685G, A701V, T716I, F888L, S982A, T1027I, D1118H, and V1176F, or any combination thereof.

In some embodiments, the recombinant polypeptide is or comprises the sequence set forth in SEQ ID NO: 11. In some embodiments, the recombinant polypeptide is or comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 11, including a sequence comprising substitution, deletion, and/or insertion at one or more amino acid positions, such as 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and/or 1176 (amino acid positions with respect to SEQ ID NO: 55), or any combination thereof. In some embodiments, the recombinant polypeptide is or comprises a variant of SEQ ID NO: 11 and the variant comprises any one, two, three, four, five or more of the mutations selected from the group consisting of S13I, L18F, T20N, P26S, Δ69-70 (ΔHV), D80A, D138Y, G142D, Δ144 (ΔY), W152C, R190S, D215G, Δ242-244 (ΔLAL), R246I, Δ400-402 (ΔFVI), K417T, K417N, N440K, L452R, S477N, S477G, E484K, E484Q, N501Y, A570D, D614G, H655Y, P681H, P681R, R682G, R683S, R685G, A701V, T716I, F888L, S982A, T1027I, D1118H, and V1176F, or any combination thereof.

In some embodiments, the recombinant polypeptide is or comprises the sequence set forth in SEQ ID NO: 12. In some embodiments, the recombinant polypeptide is or comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 12, including a sequence comprising substitution, deletion, and/or insertion at one or more amino acid positions, such as 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and/or 1176 (amino acid positions with respect to SEQ ID NO: 55), or any combination thereof. In some embodiments, the recombinant polypeptide is or comprises a variant of SEQ ID NO: 12 and the variant comprises any one, two, three, four, five or more of the mutations selected from the group consisting of S13I, L18F, T20N, P26S, Δ69-70 (ΔHV), D80A, D138Y, G142D, Δ144 (ΔY), W152C, R190S, D215G, Δ242-244 (ΔLAL), R246I, Δ400-402 (ΔFVI), K417T, K417N, N440K, L452R, S477N, S477G, E484K, E484Q, N501Y, A570D, D614G, H655Y, P681H, P681R, R682G, R683S, R685G, A701V, T716I, F888L, S982A, T1027I, D1118H, and V1176F, or any combination thereof.

In some embodiments, the recombinant polypeptide is or comprises the sequence set forth in SEQ ID NO: 13. In some embodiments, the recombinant polypeptide is or comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 13, including a sequence comprising substitution, deletion, and/or insertion at one or more amino acid positions, such as 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and/or 1176 (amino acid positions with respect to SEQ ID NO: 55), or any combination thereof. In some embodiments, the recombinant polypeptide is or comprises a variant of SEQ ID NO: 13 and the variant comprises any one, two, three, four, five or more of the mutations selected from the group consisting of S13I, L18F, T20N, P26S, Δ69-70 (ΔHV), D80A, D138Y, G142D, Δ144 (ΔY), W152C, R190S, D215G, Δ242-244 (ΔLAL), R246I, Δ400-402 (ΔFVI), K417T, K417N, N440K, L452R, S477N, S477G, E484K, E484Q, N501Y, A570D, D614G, H655Y, P681H, P681R, R682G, R683S, R685G, A701V, T716I, F888L, S982A, T1027I, D1118H, and V1176F, or any combination thereof.

In some embodiments, the recombinant polypeptide is or comprises the sequence set forth in SEQ ID NO: 14. In some embodiments, the recombinant polypeptide is or comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 14, including a sequence comprising substitution, deletion, and/or insertion at one or more amino acid positions, such as 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and/or 1176 (amino acid positions with respect to SEQ ID NO: 55), or any combination thereof. In some embodiments, the recombinant polypeptide is or comprises a variant of SEQ ID NO: 14 and the variant comprises any one, two, three, four, five or more of the mutations selected from the group consisting of S13I, L18F, T20N, P26S, Δ69-70 (ΔHV), D80A, D138Y, G142D, Δ144 (ΔY), W152C, R190S, D215G, Δ242-244 (ΔLAL), R246I, Δ400-402 (ΔFVI), K417T, K417N, N440K, L452R, S477N, S477G, E484K, E484Q, N501Y, A570D, D614G, H655Y, P681H, P681R, R682G, R683S, R685G, A701V, T716I, F888L, S982A, T1027I, D1118H, and V1176F, or any combination thereof.

In some embodiments, the recombinant polypeptide is or comprises the sequence set forth in SEQ ID NO: 15. In some embodiments, the recombinant polypeptide is or comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 15, including a sequence comprising substitution, deletion, and/or insertion at one or more amino acid positions, such as 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and/or 1176 (amino acid positions with respect to SEQ ID NO: 55), or any combination thereof. In some embodiments, the recombinant polypeptide is or comprises a variant of SEQ ID NO: 15 and the variant comprises any one, two, three, four, five or more of the mutations selected from the group consisting of S13I, L18F, T20N, P26S, Δ69-70 (ΔHV), D80A, D138Y, G142D, Δ144 (ΔY), W152C, R190S, D215G, Δ242-244 (ΔLAL), R246I, Δ400-402 (ΔFVI), K417T, K417N, N440K, L452R, S477N, S477G, E484K, E484Q, N501Y, A570D, D614G, H655Y, P681H, P681R, R682G, R683S, R685G, A701V, T716I, F888L, S982A, T1027I, D1118H, and V1176F, or any combination thereof.

In some embodiments, the recombinant polypeptide is or comprises the sequence set forth in SEQ ID NO: 16. In some embodiments, the recombinant polypeptide is or comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 16, including a sequence comprising substitution, deletion, and/or insertion at one or more amino acid positions, such as 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and/or 1176 (amino acid positions with respect to SEQ ID NO: 55), or any combination thereof. In some embodiments, the recombinant polypeptide is or comprises a variant of SEQ ID NO: 16 and the variant comprises any one, two, three, four, five or more of the mutations selected from the group consisting of S13I, L18F, T20N, P26S, Δ69-70 (ΔHV), D80A, D138Y, G142D, Δ144 (ΔY), W152C, R190S, D215G, Δ242-244 (ΔLAL), R246I, Δ400-402 (ΔFVI), K417T, K417N, N440K, L452R, S477N, S477G, E484K, E484Q, N501Y, A570D, D614G, H655Y, P681H, P681R, R682G, R683S, R685G, A701V, T716I, F888L, S982A, T1027I, D1118H, and V1176F, or any combination thereof.

In some embodiments, the recombinant polypeptide is or comprises the sequence set forth in SEQ ID NO: 17. In some embodiments, the recombinant polypeptide is or comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 17, including a sequence comprising substitution, deletion, and/or insertion at one or more amino acid positions, such as 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and/or 1176 (amino acid positions with respect to SEQ ID NO: 55), or any combination thereof. In some embodiments, the recombinant polypeptide is or comprises a variant of SEQ ID NO: 17 and the variant comprises any one, two, three, four, five or more of the mutations selected from the group consisting of S13I, L18F, T20N, P26S, Δ69-70 (ΔHV), D80A, D138Y, G142D, Δ144 (ΔY), W152C, R190S, D215G, Δ242-244 (ΔLAL), R246I, Δ400-402 (ΔFVI), K417T, K417N, N440K, L452R, S477N, S477G, E484K, E484Q, N501Y, A570D, D614G, H655Y, P681H, P681R, R682G, R683S, R685G, A701V, T716I, F888L, S982A, T1027I, D1118H, and V1176F, or any combination thereof.

In some embodiments, the recombinant polypeptide is or comprises the sequence set forth in SEQ ID NO: 18. In some embodiments, the recombinant polypeptide is or comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 18, including a sequence comprising substitution, deletion, and/or insertion at one or more amino acid positions, such as 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and/or 1176 (amino acid positions with respect to SEQ ID NO: 55), or any combination thereof. In some embodiments, the recombinant polypeptide is or comprises a variant of SEQ ID NO: 18 and the variant comprises any one, two, three, four, five or more of the mutations selected from the group consisting of S13I, L18F, T20N, P26S, Δ69-70 (ΔHV), D80A, D138Y, G142D, Δ144 (ΔY), W152C, R190S, D215G, Δ242-244 (ΔLAL), R246I, Δ400-402 (ΔFVI), K417T, K417N, N440K, L452R, S477N, S477G, E484K, E484Q, N501Y, A570D, D614G, H655Y, P681H, P681R, R682G, R683S, R685G, A701V, T716I, F888L, S982A, T1027I, D1118H, and V1176F, or any combination thereof.

In some embodiments, the recombinant polypeptide is or comprises the sequence set forth in SEQ ID NO: 19. In some embodiments, the recombinant polypeptide is or comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 19, including a sequence comprising substitution, deletion, and/or insertion at one or more amino acid positions, such as 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and/or 1176 (amino acid positions with respect to SEQ ID NO: 55), or any combination thereof. In some embodiments, the recombinant polypeptide is or comprises a variant of SEQ ID NO: 19 and the variant comprises any one, two, three, four, five or more of the mutations selected from the group consisting of S13I, L18F, T20N, P26S, Δ69-70 (ΔHV), D80A, D138Y, G142D, Δ144 (ΔY), W152C, R190S, D215G, Δ242-244 (ΔLAL), R246I, Δ400-402 (ΔFVI), K417T, K417N, N440K, L452R, S477N, S477G, E484K, E484Q, N501Y, A570D, D614G, H655Y, P681H, P681R, R682G, R683S, R685G, A701V, T716I, F888L, S982A, T1027I, D1118H, and V1176F, or any combination thereof.

In some embodiments, the recombinant polypeptide is or comprises the sequence set forth in SEQ ID NO: 20. In some embodiments, the recombinant polypeptide is or comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 20, including a sequence comprising substitution, deletion, and/or insertion at one or more amino acid positions, such as 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and/or 1176 (amino acid positions with respect to SEQ ID NO: 55), or any combination thereof. In some embodiments, the recombinant polypeptide is or comprises a variant of SEQ ID NO: 20 and the variant comprises any one, two, three, four, five or more of the mutations selected from the group consisting of S13I, L18F, T20N, P26S, Δ69-70 (ΔHV), D80A, D138Y, G142D, Δ144 (ΔY), W152C, R190S, D215G, Δ242-244 (ΔLAL), R246I, Δ400-402 (ΔFVI), K417T, K417N, N440K, L452R, S477N, S477G, E484K, E484Q, N501Y, A570D, D614G, H655Y, P681H, P681R, R682G, R683S, R685G, A701V, T716I, F888L, S982A, T1027I, D1118H, and V1176F, or any combination thereof.

In some embodiments, the recombinant polypeptide is or comprises the sequence set forth in SEQ ID NO: 21. In some embodiments, the recombinant polypeptide is or comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 21, including a sequence comprising substitution, deletion, and/or insertion at one or more amino acid positions, such as 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and/or 1176 (amino acid positions with respect to SEQ ID NO: 55), or any combination thereof. In some embodiments, the recombinant polypeptide is or comprises a variant of SEQ ID NO: 21 and the variant comprises any one, two, three, four, five or more of the mutations selected from the group consisting of S13I, L18F, T20N, P26S, Δ69-70 (ΔHV), D80A, D138Y, G142D, Δ144 (ΔY), W152C, R190S, D215G, Δ242-244 (ΔLAL), R246I, Δ400-402 (ΔFVI), K417T, K417N, N440K, L452R, S477N, S477G, E484K, E484Q, N501Y, A570D, D614G, H655Y, P681H, P681R, R682G, R683S, R685G, A701V, T716I, F888L, S982A, T1027I, D1118H, and V1176F, or any combination thereof.

In some embodiments, the recombinant polypeptide is or comprises the sequence set forth in SEQ ID NO: 22. In some embodiments, the recombinant polypeptide is or comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 22, including a sequence comprising substitution, deletion, and/or insertion at one or more amino acid positions, such as 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and/or 1176 (amino acid positions with respect to SEQ ID NO: 55), or any combination thereof. In some embodiments, the recombinant polypeptide is or comprises a variant of SEQ ID NO: 22 and the variant comprises any one, two, three, four, five or more of the mutations selected from the group consisting of S13I, L18F, T20N, P26S, Δ69-70 (ΔHV), D80A, D138Y, G142D, Δ144 (ΔY), W152C, R190S, D215G, Δ242-244 (ΔLAL), R246I, Δ400-402 (ΔFVI), K417T, K417N, N440K, L452R, S477N, S477G, E484K, E484Q, N501Y, A570D, D614G, H655Y, P681H, P681R, R682G, R683S, R685G, A701V, T716I, F888L, S982A, T1027I, D1118H, and V1176F, or any combination thereof.

In some embodiments, the recombinant polypeptide is or comprises the sequence set forth in SEQ ID NO: 23. In some embodiments, the recombinant polypeptide is or comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 23, including a sequence comprising substitution, deletion, and/or insertion at one or more amino acid positions, such as 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and/or 1176 (amino acid positions with respect to SEQ ID NO: 55), or any combination thereof. In some embodiments, the recombinant polypeptide is or comprises a variant of SEQ ID NO: 23 and the variant comprises any one, two, three, four, five or more of the mutations selected from the group consisting of S13I, L18F, T20N, P26S, Δ69-70 (ΔHV), D80A, D138Y, G142D, Δ144 (ΔY), W152C, R190S, D215G, Δ242-244 (ΔLAL), R246I, Δ400-402 (ΔFVI), K417T, K417N, N440K, L452R, S477N, S477G, E484K, E484Q, N501Y, A570D, D614G, H655Y, P681H, P681R, R682G, R683S, R685G, A701V, T716I, F888L, S982A, T1027I, D1118H, and V1176F, or any combination thereof.

In some embodiments, the recombinant polypeptide is or comprises the sequence set forth in SEQ ID NO: 24. In some embodiments, the recombinant polypeptide is or comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 24, including a sequence comprising substitution, deletion, and/or insertion at one or more amino acid positions, such as 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and/or 1176 (amino acid positions with respect to SEQ ID NO: 55), or any combination thereof. In some embodiments, the recombinant polypeptide is or comprises a variant of SEQ ID NO: 24 and the variant comprises any one, two, three, four, five or more of the mutations selected from the group consisting of S13I, L18F, T20N, P26S, Δ69-70 (ΔHV), D80A, D138Y, G142D, Δ144 (ΔY), W152C, R190S, D215G, Δ242-244 (ΔLAL), R246I, Δ400-402 (ΔFVI), K417T, K417N, N440K, L452R, S477N, S477G, E484K, E484Q, N501Y, A570D, D614G, H655Y, P681H, P681R, R682G, R683S, R685G, A701V, T716I, F888L, S982A, T1027I, D1118H, and V1176F, or any combination thereof.

In some embodiments, the recombinant polypeptide is or comprises the sequence set forth in SEQ ID NO: 25. In some embodiments, the recombinant polypeptide is or comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 25, including a sequence comprising substitution, deletion, and/or insertion at one or more amino acid positions, such as 13, 18, 20, 26, 69, 70, 80, 138, 142, 144, 152, 190, 215, 242, 243, 244, 246, 400, 401, 402, 417, 440, 452, 477, 484, 501, 570, 614, 655, 681, 682, 683, 684, 685, 701, 716, 888, 982, 1027, 1118, and/or 1176 (amino acid positions with respect to SEQ ID NO: 55), or any combination thereof. In some embodiments, the recombinant polypeptide is or comprises a variant of SEQ ID NO: 25 and the variant comprises any one, two, three, four, five or more of the mutations selected from the group consisting of S13I, L18F, T20N, P26S, Δ69-70 (ΔHV), D80A, D138Y, G142D, Δ144 (ΔY), W152C, R190S, D215G, Δ242-244 (ΔLAL), R246I, Δ400-402 (ΔFVI), K417T, K417N, N440K, L452R, S477N, S477G, E484K, E484Q, N501Y, A570D, D614G, H655Y, P681H, P681R, R682G, R683S, R685G, A701V, T716I, F888L, S982A, T1027I, D1118H, and V1176F, or any combination thereof.

In some embodiments, the recombinant polypeptide is or comprises the sequence set forth in SEQ ID NO: 26. In some embodiments, the recombinant polypeptide is or comprises an amino acid sequence having at least or about 80%, 81%, 82%, 83%, 84%, 85%, 86%, 87%, 88%, 89%, 90%, 91%, 92%, 93%, 94%, 95%, 96%, 97%, 98%, or 99% sequence identity to sequence of SEQ ID NO: 26, including a sequence comprising substitution, deletion, and/or insertion at one or more amino acid positions of SEQ ID NO: 26.

As indicated above, in some embodiments, the recombinant polypeptides provided herein associate not only to form trimers, but can also aggregate or be aggregated to generate proteins comprising a plurality of recombinant polypeptides. In some embodiments, the proteins formed have macrostructures. In some cases, the macrostructure may confer structural stability of the coronavirus viral antigen or immunogen recombinant polypeptides, which in turn can afford access to potentially antigenic sites capable of promoting an immune response.

In some embodiments, the trimerized recombinant polypeptides aggregate to form a protein containing a plurality of trimerized recombinant polypeptides. In some embodiments, the plurality of trimerized recombinant polypeptides forms a protein having a macrostructure.

In some embodiments, the proteins described herein comprising a plurality of recombinant polypeptides are an immunogen. In some embodiments, the proteins described herein comprising a plurality of recombinant polypeptides are comprised in a nanoparticle. For example, in some embodiments, the proteins are linked directly to a nanoparticle, e.g., protein nanoparticle. In some embodiments, the proteins are linked indirectly to a nanoparticle. In some embodiments, the proteins described herein comprising a plurality of recombinant polypeptides are comprised in virus-like particle (VLP).

In some embodiments, provided herein is a complex comprising a recombinant polypeptide selected from the group consisting of SEQ ID NOs: 1-26 or a fragment, variant, or mutant thereof, in any suitable combination. In some embodiments, provided herein is a complex comprising a trimer of a recombinant polypeptide selected from the group consisting of SEQ ID NOs: 1-26 or a fragment, variant, or mutant thereof, wherein the recombinant polypeptides are trimerized via inter-polypeptide disulfide bonds to form the trimer.

In some embodiments, provided herein is a fusion protein comprising a plurality of recombinant polypeptides, each recombinant polypeptide comprising, from amino to carboxy terminus: a) a first region comprising a portion of a coronavirus spike protein ectodomain that precedes a coronavirus spike protein receptor binding domain (RBD) as located in a nonchimeric coronavirus spike protein, of a first coronavirus; b) a second region comprising a coronavirus spike protein receptor binding domain (RBD) of a second coronavirus that is different from said first coronavirus; and c) a C-terminal propeptide of collagen, wherein the C-terminal propeptides of the recombinant polypeptides form inter-polypeptide disulfide bonds. In some embodiments, the fusion protein further comprises a third region between the second region and the C-terminal propeptide of collagen. In some embodiments, the third region comprises an S1 domain of a third coronavirus, wherein the third coronavirus is the same or different from the first coronavirus or second coronavirus. In some embodiments, the third region comprises an S2 domain of a fourth coronavirus, wherein the fourth coronavirus is the same or different from the first, second, or fourth coronavirus. In some embodiments, the first region comprises an N-terminal domain (NTD) of the first coronavirus. In some embodiments, the first region comprises one or more amino acid residues that is/are different from corresponding amino acid residue(s) in the second coronavirus. In some embodiments, the second region comprises one or more amino acid residues that is/are different from corresponding amino acid residue(s) in the first coronavirus. In some embodiments, the first and second coronaviruses are different variants or strains of the same coronavirus. In some embodiments, the the first region comprises the NTD of the first coronavirus, the second region comprises the RBD of the second coronavirus, and the first and second coronaviruses are different variants of SARS-CoV-2. In some embodiments, the first coronavirus and the second coronavirus are independently selected from the group consisting of SARS-CoV-2 viruses of the B.1.526, B.1.1.143, P.2, B.1.351, P.1, B.1.1.7, B.1.617, and A.23.1 lineages.

In some embodiments, provided herein is a trimeric fusion protein comprising three recombinant polypeptides, each recombinant polypeptide comprising, from amino to carboxy terminus: a) a first region comprising a coronavirus spike protein N-terminal domain (NTD) of a SARS-CoV-2 of the B.1.526 lineage; b) a second region comprising a coronavirus spike protein receptor binding domain (RBD) of a SARS-CoV-2 of the B.1.351 lineage; and c) a C-terminal propeptide of collagen, wherein the C-terminal propeptides of the recombinant polypeptides form inter-polypeptide disulfide bonds.

In some embodiments, provided herein is a method for preventing infection by a coronavirus in a mammal, comprising immunizing a mammal with an effective amount of a fusion protein disclosed herein. In some embodiments, neutralizing antibodies against the first and the second coronaviruses are generated in the mammal. In some embodiments, the first and second coronaviruses are different variants of SARS-CoV-2, and neutralizing antibodies generated in the mammal neutralize two or more of SARS-CoV-2 viruses of the B.1.526, B.1.1.143, P.2, B.1.351, P.1, B.1.1.7, B.1.617, and A.23.1 lineages. In some embodiments, neutralizing antibodies generated in the mammal neutralize three or more of SARS-CoV-2 viruses of the B.1.526, B.1.1.143, P.2, B.1.351, P.1, B.1.1.7, B.1.617, and A.23.1 lineages. In some embodiments, the method comprises immunizing the mammal with two or more doses of the fusion protein. In some embodiments, the fusion protein is administered as a booster dose following one or more doses of an immunogen comprising a spike protein peptide comprising NTD and RBD from the same SARS-CoV-2 variant.

In some embodiments, provided herein are engineered fusion polypeptides that are derived or modified from the spike (S) glycoprotein of coronaviruses including SARS-CoV-1 and SARS-CoV-2. In some embodiments, compared to a wildtype S protein sequence of the coronavirus, the fusion polypeptides disclosed herein can be stabilized in a prefusion conformation. In some embodiments, fusion to the trimerization domain may prevent the S protein peptide in the fusion proteins from forming a straight helix (e.g., similar to what occurs during membrane fusion process). For instance, cryo-EM structures of an S-Trimer subunit vaccine candidate shows it predominantly adopts tightly closed pre-fusion state, unlike the full-length wild-type spike protein which forms both pre- and post-fusion states in the presence of detergent. Ma et al., J Virol (2021) doi: 10.1128/JVI.00194-21. In some embodiments, the fusion proteins may comprise an altered soluble S sequence with modification(s) that inactivates the S1/S2 cleavage site; mutation(s) in the turn region between the heptad repeat 1 (HR1) region and the central helix (CH) region that prevents HR1 and CH to form a straight helix; and/or truncation of the heptad repeat 2 region (HR2) in addition to the stabilizing mutations. In some embodiments, the fusion proteins herein may but do not need to comprise one or more mutations such as K986G/V987G, K986P/V987P, K986G/V987P or K986P/V987G which are believed to stabilize the spike protein in a pre-fusion state. In some embodiments, mutations such as K986G/V987G, K986P/V987P, K986G/V987P or K986P/V987G are not necessary for stabilizing a fusion polypeptide disclosed herein comprising the Trimer-Tag® trimerization domain.

In some of these embodiments, the mutation inactivating S1/S2 cleavage site can contain substitution of RRAR (682-685 in SEQ ID NO:55) with GSAG (SEQ ID NO: 60), and the mutation in the turn region can contain double mutation K986G/V987G, K986P/V987P, K986G/V987P or K986P/V987G. In some embodiments, truncation of HR2 entails deletion of one or more of the residues shown in SEQ ID NO: 65 at the C-terminus of the wildtype soluble S sequence. In some embodiments, the immunogen polypeptide can further include in the region of HR1 that interacts with HR2 (a) one or more proline or glycine substitutions, and/or (b) insertion of one or more amino acid residues. In some of these embodiments, the immunogen polypeptide can have one or more substitutions selected from A942P, S943P, A944P, A942G, S943G and A944G. In some of these embodiments, the insertion can be insertion of G or GS between any residues in A942-A944.

2. Polynucleotides and Vectors

Also provided are polynucleotides (nucleic acid molecules) encoding the coronavirus antigens or immunogens and recombinant polypeptides provided herein, and vectors for genetically engineering cells to express such coronavirus antigens or immunogens and recombinant polypeptides.

In some embodiments, provided are polynucleotides that encode recombinant polypeptides provided herein. In some aspects, the polynucleotide contains a single nucleic acid sequence, such as a nucleic acid sequence encoding a recombinant polypeptide. In other instances, the polynucleotide contains a first nucleic acid sequence encoding a recombinant polypeptide a particular coronavirus viral antigen or immunogen and a second nucleic acid sequence encoding a recombinant polypeptide comprising a different coronavirus viral antigen or immunogen.

In some embodiments, the polynucleotide encoding the recombinant polypeptide contains at least one promoter that is operatively linked to control expression of the recombinant polypeptide. In some embodiments, the polynucleotide contains two, three, or more promoters operatively linked to control expression of the recombinant polypeptide.

In some embodiments, for example when the polynucleotide contains two or more nucleic acid coding sequences, such as a sequences encoding recombinant polypeptides comprising different coronavirus viral antigens or immunogens, at least one promoter is operatively linked to control expression of the two or more nucleic acid sequences. In some embodiments, the polynucleotide contains two, three, or more promoters operatively linked to control expression of the recombinant polypeptides.

In some embodiments, expression of the recombinant polypeptide(s) is inducible or conditional. Thus, in some aspects, the polynucleotide encoding the recombinant polypeptide(s) contains a conditional promoter, enhancer, or transactivator. In some such aspects, the conditional promoter, enhancer, or transactivator is an inducible promoter, enhancer, or transactivator or a repressible promoter, enhancer, or transactivator. For example, in some embodiments, an inducible or conditional promoter can be used to restrict expression of the recombinant polypeptides to a specific microenvironment. In some embodiments, expression driven by the inducible or conditional promoter is regulated by exposure to an exogenous agent, such as heat, radiation, or drug.

In cases where the polynucleotide contains more than one nucleic acid sequence encoding a recombinant polypeptide, the polynucleotide may further include a nucleic acid sequence encoding a peptide between the one or more nucleic acid sequences. In some cases, the nucleic acid positioned between the nucleic acid sequences encodes a peptide that separates the translation products of the nucleic acid sequences during or after translation. In some embodiments, the peptide contains an internal ribosome entry site (IRES), a self-cleaving peptide, or a peptide that causes ribosome skipping, such as a T2A peptide.

In some embodiments, the polynucleotide encoding the recombinant polypeptide(s) is introduced into a composition containing cultured cells (e.g., host cells), such as by retroviral transduction, transfection, or transformation. In some embodiments, this can allow for expression (e.g., production) of the recombinant polypeptides. In some embodiments, the expressed recombinant polypeptides are purified.

In some embodiments, the polynucleotide (nucleic acid molecule) provided herein encodes an coronavirus viral antigen or immunogen as described herein. In some embodiments, the polynucleotide (nucleic acid molecule) provided herein encodes a recombinant polypeptide comprising coronavirus viral antigen or immunogen, e.g., coronavirus S protein peptide, as described herein.

Also provided are vectors or constructs containing nucleic acid molecules as described herein. In some embodiments, the vectors or constructs contain one or more promoters operatively linked to the nucleic acid molecule encoding the recombinant polypeptide to drive expression thereof. In some embodiments, the promoter is operatively linked to one or more than one nucleic acid molecule, e.g., nucleic acid molecule encoding recombinant polypeptides containing different coronavirus viral antigens or immunogens.

In some embodiments, the vector is a viral vector. In some embodiments the viral vector is a retroviral vector. In some embodiments, the retroviral vector is a lentiviral vector. In some embodiments, the retroviral vector is a gammaretroviral vector.

In some embodiments, the vector or construct includes a single promoter that drives the expression of one or more nucleic acid molecules of the polynucleotide. In some embodiments, such promoters can be multicistronic (bicistronic or tricistronic, see e.g., U.S. Pat. No. 6,060,273). For example, in some embodiments, transcription units can be engineered as a bicistronic unit containing an IRES (internal ribosome entry site), which allows coexpression of gene products (e.g., encoding different recombinant polypeptides) by a message from a single promoter. In some embodiments, the vectors provided herein are bicistronic, allowing the vector to contain and express two nucleic acid sequences. In some embodiments, the vectors provided herein are tricistronic, allowing the vector to contain and express three nucleic acid sequences.

In some embodiments, a single promoter directs expression of an RNA that contains, in a single open reading frame (ORF), two or three genes (e.g. encoding the chimeric signaling receptor and encoding a recombinant receptor) separated from one another by sequences encoding a self-cleavage peptide (e.g., 2A sequences) or a protease recognition site (e.g., furin). The ORF thus encodes a single polypeptide, which, either during (in the case of 2A) or after translation, is processed into the individual proteins. In some cases, the peptide, such as T2A, can cause the ribosome to skip (ribosome skipping) synthesis of a peptide bond at the C-terminus of a 2A element, leading to separation between the end of the 2A sequence and the next peptide downstream (see, for example, de Felipe. *Genetic Vaccines and Ther.* 2:13 (2004) and deFelipe et al. *Traffic* 5:616-626 (2004)). Many 2A elements are known in the art. Examples of 2A sequences that can be used in the methods and nucleic acids disclosed herein include, without limitation, 2A sequences from the foot-and-mouth disease virus (F2A), equine rhinitis A virus (E2A), Thosea asigna virus (T2A), and porcine teschovirus-1 (P2A) as described in U.S. Patent Publication No. 20070116690.

In some embodiments, the vector is comprised in a virus. In some embodiments, the virus is a pseudovirus. In some embodiments, the virus is a viral-like particle. In some embodiments, the vector is comprised in a cell. In some embodiments, the virus or cell in which the vector is comprised contains a recombinant genome.

III. Immunogenic Compositions and Formulations

In some embodiments, provided herein is an immunogenic composition comprising a trimer of a recombinant polypeptide comprising a sequence selected from the group consisting of SEQ ID NOs: 1-26, or a combination of any two or more of the trimers. In some embodiments, provided herein is an immunogenic composition comprising the trimer of the recombinant polypeptide having the sequence set forth in SEQ ID NO: 1.

In some embodiments, a unit dose of the immunogenic composition may comprise from about 10 μg to about 100 μg of the SARS-CoV-2 antigen, preferably from about 25 μg to about 75 μg of the SARS-CoV-2 antigen, preferably from about 40 μg to about 60 μg of the SARS-CoV-2 antigen, or about 50 μg of the SARS-CoV-2 antigen. In some embodiments, the dose contains 3 μg of the SARS-CoV-2 antigen. In other embodiments, the dose contains 9 μg of the SARS-CoV-2 antigen. In further embodiments, the dose contains 30 μg of the SARS-CoV-2 antigen.

In some instances it may be desirable to combine a disclosed immunogen, with other pharmaceutical products (e.g., vaccines) which induce protective responses to other agents. For example, a composition including a recombinant coronavirus S antigen as described herein, e.g., trimer or protein, can be can be administered simultaneously (typically separately) or sequentially with other vaccines recommended by the Advisory Committee on Immunization Practices (ACIP; cdc.gov/vaccines/acip/index.html) for the targeted age group (e.g., infants from approximately one to six months of age), such as an influenza vaccine or a varicella zoster vaccine. As such, a disclosed immunogen including a recombinant coronavirus S antigen described herein may be administered simultaneously or sequentially with vaccines against, for example, hepatitis B (HepB), diphtheria, tetanus and pertussis (DTaP), pneumococcal bacteria (PCV), Haemophilus influenzae type b (Hib), polio, influenza and rotavirus.

Multivalent or combination vaccines provide protection against multiple pathogens. In some aspects, multivalent vaccines can protect against multiple strains of the same pathogen. In some aspects, multivalent vaccines protect against multiple pathogens, such as the combination vaccine Tdap, which protects against strains of tentus, pertussis, and diphtheria. Multivalent vaccines are highly desirable to minimize the number of immunizations required to confer protection against multiple pathogens or pathogenic strains, to reduce administration costs, and to increase coverage rates. This can be particularly useful, for example, when vaccinating babies or children.

In some embodiments, the vaccine, e.g., comprising an immunogenic composition described herein, is a multivalent vaccine. In some embodiments, the antigenic material for incorporation into the multivalent vaccine compositions is derived from coronavirus strains or types, for examples as described herein (see, e.g., Section I). Antigens for incorporation into the multivalent vaccine compositions may be derived from one strain of coronavirus or multiple strains, for example, between two and five strains, in order to provide a broader spectrum of protection. In one embodiment, antigens for incorporation into the multivalent vaccine compositions are derived from multiple strains of coronavirus. Other useful antigens include live, attenuated and inactivated viruses such as inactivated polio virus (Jiang et al., J. Biol. Stand., (1986) 14:103-9), attenuated strains of Hepatitis A virus (Bradley et al., J. Med. Virol., (1984) 14:373-86), attenuated measles virus (James et al., N. Engl. J. Med., (1995) 332:1262-6), and epitopes of pertussis virus (for example, ACEL-IMUNE acellular DTP, Wyeth-Lederle Vaccines and Pediatrics).

In some aspects, the vaccine provided herein is a universal vaccine. In some embodiments, a universal vaccine is a vaccine which protects against multiple strains of the same virus, such as multiple strains of coronavirus. Development of an effective universal coronavirus vaccine would reduce cost and labor, e.g., with seasonal vaccine formulation, and allow for more robust pandemic preparedness.

In some aspects, a universal vaccine is one comprised of multiple epitopes derived from distinct viral strains. In some aspects, a universal vaccine is comprised of a single epitope that is conserved across distinct viral strains. For example, a universal vaccine can be based on the relatively conserved domain(s) of the S protein.

Immunogenic compositions comprising a disclosed immunogen (e.g., a disclosed recombinant coronavirus S antigen or nucleic acid molecule encoding a protomer of disclosed recombinant coronavirus S antigen) and a pharmaceutically acceptable carrier are also provided. In some embodiments, the immunogenic composition comprises trimerized recombinant polypeptides provided herein, and optionally a pharmaceutically acceptable carrier. In some embodiments, the immunogenic composition comprises a protein comprising a plurality of trimerized recombinant polypeptides provided herein, and optionally a pharmaceutically acceptable carrier. In some embodiments, the immunogenic composition a protein nanoparticle provided herein, and optionally a pharmaceutically acceptable carrier. In some embodiments, the immunogenic composition comprises a VLP as provided herein, and optionally a pharmaceutically acceptable carrier. In some embodiments, the immunogenic composition comprises an isolated nucleic acid provided herein, and optionally a pharmaceutically acceptable carrier. In some embodiments, the immunogenic composition comprises a vector as provided herein, and optionally a pharmaceutically acceptable carrier. In some embodiments, the immunogenic composition comprises a virus as provided herein, and optionally a pharmaceutically acceptable carrier. In some embodiments, the immunogenic composition comprises a pseudovirus provided herein, and optionally a pharmaceutically acceptable carrier. In some embodiments, the immunogenic composition comprises a cell as provided herein, and optionally a pharmaceutically acceptable carrier. In some embodiments, the immunogenic composition, such as described herein, is a vaccine. In some embodiments, the vaccine is a prophylactic vaccine. In some embodiments, the vaccine is a therapeutic vaccine. In some embodiments, the vaccine is a prophylactic vaccine and a therapeutic vaccine. Such pharmaceutical compositions can be administered to subjects by a variety of administration modes known to the person of ordinary skill in the art, for example, intramuscular, intradermal, subcutaneous, intravenous, intra-arterial, intra-articular, intraperitoneal, intranasal, sublingual, tonsillar, oropharyngeal, or other parenteral and mucosal routes. In several embodiments, pharmaceutical compositions including one or more of the disclosed immunogens are immunogenic compositions. Actual methods for preparing administrable compositions will be known or apparent to those skilled in the art and are described in more detail in such publications as Remingtons Pharmaceutical Sciences, 19th Ed., Mack Publishing Company, Easton, Pa., 1995.

Thus, an immunogen, e.g., recombinant coronavirus S antigen, e.g., trimer, protein, described herein can be formulated with pharmaceutically acceptable carriers to help retain biological activity while also promoting increased stability during storage within an acceptable temperature range. Potential carriers include, but are not limited to, physiologically balanced culture medium, phosphate buffer saline solution, water, emulsions (e.g., oil/water or water/oil emulsions), various types of wetting agents, cryoprotective additives or stabilizers such as proteins, peptides or hydrolysates (e.g., albumin, gelatin), sugars (e.g., sucrose, lactose, sorbitol), amino acids (e.g., sodium glutamate), or other protective agents. The resulting aqueous solutions may be packaged for use as is or lyophilized. Lyophilized preparations are combined with a sterile solution prior to administration for either single or multiple dosing.

Formulated compositions, especially liquid formulations, may contain a bacteriostat to prevent or minimize degradation during storage, including but not limited to effective concentrations (usually 1% w/v) of benzyl alcohol, phenol, m-cresol, chlorobutanol, methylparaben, and/or propylparaben. A bacteriostat may be contraindicated for some patients; therefore, a lyophilized formulation may be reconstituted in a solution either containing or not containing such a component.

The immunogenic compositions of the disclosure can contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. The immunogenic composition may optionally include an adjuvant to enhance an immune response of the host. Suitable adjuvants are, for example, toll-like receptor (TLR) agonists, alum, $AlPO_4$, alhydrogel, Lipid-A and derivatives or variants thereof, oil-emulsions, saponins, neutral liposomes, liposomes containing the vaccine and cytokines, non-ionic block copolymers, and chemokines. Non-ionic block polymers containing polyoxyethylene (POE) and polyxylpropylene (POP), such as POE-POP-POE block copolymers, MPL™ (3-O-deacylated monophosphoryl lipid A; Corixa, Hamilton, Ind.) and IL-12 (Genetics Institute, Cambridge, Mass.), among many other suitable adjuvants well known in the art, may be used as an adjuvant (Newman et al., 1998*, Critical Reviews in Therapeutic Drug Carrier Systems* 15:89-142). These adjuvants have the advantage in that they help to stimulate the immune system in a non-specific way, thus enhancing the immune response to a pharmaceutical product. In some embodiments, the immunogenic compositions of the disclosure may include or be administered with more than one adjuvant. In some embodiments, the immunogenic compositions of the disclosure may include or be administered with two adjuvants. In some embodiments, the immunogenic compositions of the disclosure may include or be administered with a plurality of adjuvants. For example, in some cases, a vaccine, e.g., comprising an immunogenic composition provided herein, may include or be administered in combination with a plurality of adjuvants.

For vaccine compositions, examples of suitable adjuvants include, e.g., aluminum hydroxide, lecithin, Freund's adjuvant, MPL™ and IL-12. In some embodiments, the vaccine compositions or nanoparticle immunogens disclosed herein (e.g., SARS-COV-2 vaccine composition) can be formulated as a controlled-release or time-release formulation. This can be achieved in a composition that contains a slow release polymer or via a microencapsulated delivery system or bioadhesive gel. The various pharmaceutical compositions can be prepared in accordance with standard procedures well known in the art.

In some embodiments, the immunogenic compositions of the disclosure can contain an adjuvant formulation comprising a metabolizable oil (e.g., squalene) and alpha tocopherol in the form of an oil-in-water emulsion, and polyoxyethylene sorbitan monooleate (Tween-80). In some embodiments, the adjuvant formulation can comprise from about 2% to about 10% squalene, from about 2 to about 10% alpha tocopherol (e.g., D-alpha-tocopherol) and from about 0.3 to about 3% polyoxyethylene sorbitan monooleate. In some embodiments, the adjuvant formulation can comprise about 5% squalene, about 5% tocopherol, and about 0.4% polyoxyethylene sorbitan monooleate. In some embodiments, the immunogenic compositions of the disclosure can contain 3 de-O-acylated monophosphoryl lipid A (3D-MPL), and an adjuvant in the form of an oil in water emulsion, which adjuvant contains a metabolizable oil, alpha tocopherol, and polyoxyethylene sorbitan monoleate. In some embodiments, the immunogenic compositions of the disclosure can contain QS21 (extract of *Quillaja saponaria Molina*: fraction 21), 3D-MPL and an oil in water emulsion wherein the oil in water emulsion comprises a metabolizable oil, alpha tocopherol and polyoxyethelene sorbitan monooleate. In some embodiments, the immunogenic compositions of the disclosure can contain QS21, 3D-MPL and an oil in water emulsion wherein the oil in water emulsion has the following composition: a metabolisible oil, such as squalene, alpha tocopherol and Tween-80. In some embodiments, the immunogenic compositions of the disclosure can contain an adjuvant in the form of a liposome composition.

In some embodiments, the immunogenic compositions of the disclosure can contain an adjuvant formulation comprising a metabolizable oil (e.g., squalene), polyoxyethylene sorbitan monooleate (Tween-80), and Span 85. In some embodiments, the adjuvant formulation can comprise about 5% (w/v) squalene, about 0.5% (w/v) polyoxyethylene sorbitan monooleate, and about about 0.5% (w/v) Span 85.

In some embodiments, the immunogenic compositions of the disclosure can contain an adjuvant formulation comprising Quillaja saponins, cholesterol, and phosphorlipid, e.g., in the form of a nanoparticle composition. In some embodiments, the immunogenic compositions of the disclosure can contain a mixture of separately purified fractions of Quillaja saponaria Molina where are subsequently formulated with cholesterol and phospholipid.

In some embodiments, the immunogenic compositions of the disclosure can contain an adjuvant selected from the group consisting of MF59™, Matrix-A™, Matrix-C™, Matrix-M™, AS01, AS02, AS03, and AS04.

In some embodiments, the immunogenic compositions of the disclosure can contain a toll-like receptor 9 (TLR9) agonist, wherein the TLR9 agonist is an oligonucleotide of from 8 to 35 nucleotides in length comprising an unmethylated cytidine-phospho-guanosine (also referred to as CpG or cytosine-phosphate-guanosine) motif, and the SARS-CoV-2 antigen and the oligonucleotide are present in the immunogenic composition in amounts effective to stimulate an immune response against the SARS-CoV-2 antigen in a mammalian subject, such as a human subject in need thereof. TLR9 (CD289) recognizes unmethylated cytidine-phospho-guanosine (CpG) motifs found in microbial DNA, which can be mimicked using synthetic CpG-containing oligodeoxynucleotides (CpG-ODNs). CpG-ODNs are known to enhance antibody production and to stimulate T helper 1 (Th1) cell responses (Coffman et al., Immunity, 33:492-503, 2010). Optimal oligonucleotide TLR9 agonists often contain a palindromic sequence following the general formula of: 5'-purine-purine-CG-pyrimidine-pyrimidine-3', or 5'-purine-purine-CG-pyrimidine-pyrimidine-CG-3'. U.S. Pat. No. 6,589,940, which is incorporated herein by reference in its entirety. In some embodiments, the CpG oligonucleotide is linear. In other embodiments, the CpG oligonucleotide is circular or includes hairpin loop(s). The CpG oligonucleotide may be single stranded or double stranded. In some embodiments, the CpG oligonucleotide may contain modifications. Modifications include but are not limited to, modifications of the 3'OH or 5'OH group, modifications of the nucleotide base, modifications of the sugar component, and modifications of the phosphate group. Modified bases may be included in the palindromic sequence of the CpG oligonucleotide as long as the modified base(s) maintains the same specificity for its natural complement through Watson-Crick base pairing (e.g., the palindromic portion is still self-complementary). In some embodiments, the CpG oligonucleotide comprises a non-canonical base. In some embodiments, the CpG oligonucleotide comprises a modified nucleoside. In some embodiments, the modified nucleoside is selected from the group consisting of 2'-deoxy-7-deazaguanosine, 2'-deoxy-6-thioguanosine, arabinoguanosine, 2'-deoxy-2'substituted-arabinoguanosine, and 2'-O-substituted-arabinoguanosine. The CpG oligonucleotide may contain a modification of the phosphate group. For example, in addition to phosphodiester linkages, phosphate modifications include, but are not limited to, methyl phosphonate, phosphorothioate, phosphoramidate (bridging or non-bridging), phosphotriester and phosphorodithioate and may be used in any combination. Other non-phosphate linkages may also be used. In some embodiments, the oligonucleotides comprise only phosphorothioate backbones. In some embodiments, the oligonucleotides comprise only phosphodiester backbones. In some embodiments, the oligonucleotide comprises a combination of phosphate linkages in the phosphate backbone such as a combination of phosphodiester and phosphorothioate linkages. Oligonucleotides with phosphorothioate backbones can be more immunogenic than those with phosphodiester backbones and appear to be more resistant to degradation after injection into the host (Braun et al., J Immunol, 141:2084-2089, 1988; and Latimer et al., Mol Immunol, 32:1057-1064, 1995). The CpG oligonucleotides of the present disclosure include at least one, two or three internucleotide phosphorothioate ester linkages. In some embodiments, when a plurality of CpG oligonucleotide molecules are present in a pharmaceutical composition comprising at least one excipient, both stereoisomers of the phosphorothioate ester linkage are present in the plurality of CpG oligonucleotide molecules. In some embodiments, all of the internucleotide linkages of the CpG oligonucleotide are phosphorothioate linkages, or said another way, the CpG oligonucleotide has a phosphorothioate backbone. Exemplary CpG oligonucleotides, such as 5'-TGACTGTGAACGTTCGAGATGA-3', are disclosed in U.S. Pat. Nos. 7,255,868, 7,479,285, 7,785,610, 8,003,115, 8,114,418, 8,222,398, 8,333,980, 8,597,665, 8,669,237, and 9,028,845, all of which are incorporated herein by reference in their entireties for all purposes.

One or more adjuvants may be used in combination and may include, but are not limited to, alum (aluminum salts), oil-in-water emulsions, water-in-oil emulsions, liposomes, and microparticles, such as poly(lactide-co-glycolide) microparticles (Shah et al., Methods Mol Biol, 1494:1-14, 2017). In some embodiments, the immunogenic compositions further comprises an aluminum salt adjuvant to which the SARS-CoV-2 antigen is adsorbed. In some embodiments, the aluminum salt adjuvant comprises one or more of the group consisting of amorphous aluminum hydroxyphosphate sulfate, aluminum hydroxide, aluminum phosphate, and potassium aluminum sulfate. In some embodiments, the aluminum salt adjuvant comprises one or both of aluminum hydroxide and aluminum phosphate. In some embodiments, the aluminum salt adjuvant comprises aluminum hydroxide. In some embodiments, a unit dose of the immunogenic composition comprises from about 0.25 to about 0.50 mg $Al^{3+}$, or about 0.35 mg $Al^{3+}$. In some embodiments, the immunogenic composition further comprises an additional adjuvant. Other suitable adjuvants include, but are not limited to, squalene-in-water emulsion (e.g., MF59 or AS03), TLR3 agonists (e.g., poly-IC or poly-ICLC), TLR4 agonists (e.g., bacterial lipopolysaccharide derivatives such as monophosphoryl lipid A (MPL), and/or a saponin such as Quil A or QS-21, as in AS01 or AS02), a TLR5 agonist (bacterial flagellin), and TLR7, TLR8 and/or TLR9 agonists (imidazoquinoline derivatives such as imiquimod, and resiquimod) (Coffman et al., Immunity, 33:492-503, 2010). In some embodiments, the additional adjuvant comprises MPL and alum (e.g., AS04). For veterinary use and for production of antibodies in non-human animals, mitogenic components of Freund's adjuvant (both complete and incomplete) can be used.

In some embodiments, the immunogenic compositions comprise pharmaceutically acceptable excipients including for instance, solvents, bulking agents, buffering agents, tonicity adjusting agents, and preservatives (Pramanick et al., Pharma Times, 45:65-77, 2013). In some embodiments the immunogenic compositions may comprise an excipient that functions as one or more of a solvent, a bulking agent, a buffering agent, and a tonicity adjusting agent (e.g., sodium chloride in saline may serve as both an aqueous vehicle and a tonicity adjusting agent).

In some embodiments, the immunogenic compositions comprise an aqueous vehicle as a solvent. Suitable vehicles include for instance sterile water, saline solution, phosphate buffered saline, and Ringer's solution. In some embodiments, the composition is isotonic.

The immunogenic compositions may comprise a buffering agent. Buffering agents control pH to inhibit degradation of the active agent during processing, storage and optionally reconstitution. Suitable buffers include for instance salts comprising acetate, citrate, phosphate or sulfate. Other suitable buffers include for instance amino acids such as arginine, glycine, histidine, and lysine. The buffering agent may further comprise hydrochloric acid or sodium hydroxide. In some embodiments, the buffering agent maintains the pH of the composition within a range of 6 to 9. In some embodiments, the pH is greater than (lower limit) 6, 7 or 8. In some embodiments, the pH is less than (upper limit) 9, 8, or 7. That is, the pH is in the range of from about 6 to 9 in which the lower limit is less than the upper limit.

The immunogenic compositions may comprise a tonicity adjusting agent. Suitable tonicity adjusting agents include for instance dextrose, glycerol, sodium chloride, glycerin and mannitol.

The immunogenic compositions may comprise a bulking agent. Bulking agents are particularly useful when the pharmaceutical composition is to be lyophilized before administration. In some embodiments, the bulking agent is a protectant that aids in the stabilization and prevention of degradation of the active agents during freeze or spray drying and/or during storage. Suitable bulking agents are sugars (mono-, di- and polysaccharides) such as sucrose, lactose, trehalose, mannitol, sorbital, glucose and raffinose.

The immunogenic compositions may comprise a preservative. Suitable preservatives include for instance antioxidants and antimicrobial agents. However, in preferred embodiments, the immunogenic composition is prepared under sterile conditions and is in a single use container, and thus does not necessitate inclusion of a preservative.

In some embodiments, the composition can be provided as a sterile composition. The pharmaceutical composition typically contains an effective amount of a disclosed immunogen and can be prepared by conventional techniques. Typically, the amount of immunogen in each dose of the immunogenic composition is selected as an amount which induces an immune response without significant, adverse side effects. In some embodiments, the composition can be provided in unit dosage form for use to induce an immune response in a subject. A unit dosage form contains a suitable single preselected dosage for administration to a subject, or suitable marked or measured multiples of two or more preselected unit dosages, and/or a metering mechanism for administering the unit dose or multiples thereof. In other embodiments, the composition further includes an adjuvant.

IV. Methods of Inducing an Immune Response

In some embodiments, provided herein is a method for generating an immune response to a surface antigen of a coronavirus in a subject, comprising administering to the subject an effective amount of a complex comprising a recombinant polypeptide selected from the group consisting of SEQ ID NOs: 1-26. In some embodiments, provided herein is a method for generating an immune response to a surface antigen of a coronavirus in a subject, wherein the surface antigen comprises an S protein or antigenic fragment thereof, and the method comprises administering to the subject an effective amount of a complex comprising a recombinant polypeptide selected from the group consisting of SEQ ID NOs: 1-26. In some embodiments, provided herein is a method for generating an immune response to a surface antigen of a coronavirus in a subject, wherein the surface antigen comprises a sequence selected from the group consisting of SEQ ID NOs: 27-66, and the method comprises administering to the subject an effective amount of a complex comprising a recombinant polypeptide selected from the group consisting of SEQ ID NOs: 1-26. In some embodiments, provided herein is a method for generating an immune response to a surface antigen of a coronavirus in a subject, wherein the surface antigen comprises an S protein or antigenic fragment thereof of the coronavirus and optionally the surface antigen comprises the sequence set forth in SEQ ID NO: 55 or antigenic fragment thereof, and the method comprises administering to the subject an effective amount of a complex comprising a recombinant polypeptide comprising the sequence set forth in any one of SEQ ID NOs: 10-25.

In some embodiments, provided herein is a method for generating an immune response to a surface antigen of a coronavirus in a subject, wherein the surface antigen comprises an S protein or antigenic fragment thereof, and the method comprises administering to the subject an effective amount of a complex comprising a recombinant polypeptide comprising the sequence selected from the group consisting of SEQ ID NOs: 1-26, or a combination of any two or more of the complexes. In some embodiments, the method comprises administering to the subject an effective amount of the complex comprising the recombinant polypeptide comprising the sequence set forth in SEQ ID NO: 10, SEQ ID NO: 11, SEQ ID NO: 12, and/or SEQ ID NO: 13.

The disclosed immunogens (e.g., recombinant coronavirus S antigen, e.g., an S-Trimer or an S protein described herein, a nucleic acid molecule (such as an RNA molecule) or vector encoding a protomer of a disclosed recombinant coronavirus S antigen, or a protein nanoparticle or virus like particle comprising a disclosed recombinant coronavirus S antigen) can be administered to a subject to induce an immune response to the corresponding coronavirus S antigen in the subject. In a particular example, the subject is a human. The immune response can be a protective immune response, for example a response that inhibits subsequent infection with the corresponding coronavirus. Elicitation of the immune response can also be used to treat or inhibit infection and illnesses associated with the corresponding coronavirus.

A subject can be selected for treatment that has, or is at risk for developing infection with the coronavirus, for example because of exposure or the possibility of exposure to the coronavirus. Following administration of a disclosed immunogen, the subject can be monitored for infection or symptoms associated with coronavirus, or both.

Typical subjects intended for treatment with the therapeutics and methods of the present disclosure include humans, as well as non-human primates and other animals. To identify subjects for prophylaxis or treatment according to the methods of the disclosure, accepted screening methods are employed to determine risk factors associated with a targeted or suspected disease or condition, or to determine the status of an existing disease or condition in a subject. These screening methods include, for example, conventional work-ups to determine environmental, familial, occupational, and other such risk factors that may be associated with the targeted or suspected disease or condition, as well as diagnostic methods, such as various ELISA and other immunoassay methods to detect and/or characterize coronavirus infection. These and other routine methods allow the clinician to select patients in need of therapy using the methods and pharmaceutical compositions of the disclosure. In accordance with these methods and principles, a composition can be administered according to the teachings herein, or other conventional methods, as an independent prophylaxis or treatment program, or as a follow-up, adjunct or coordinate treatment regimen to other treatments.

The administration of a disclosed immunogen, e.g., coronavirus S antigen, e.g., trimer, protein, can be for prophylactic or therapeutic purpose. When provided prophylactically, the disclosed therapeutic agents are provided in advance of any symptom, for example, in advance of infection. The prophylactic administration of the disclosed therapeutic agents serves to prevent or ameliorate any subsequent infection. When provided therapeutically, the disclosed therapeutic agents are provided at or after the onset of a symptom of disease or infection, for example, after development of a symptom of infection with coronavirus corresponding to the coronavirus S antigen, or after diagnosis with the coronavirus infection. The therapeutic agents can thus be provided prior to the anticipated exposure to coronavirus so as to attenuate the anticipated severity, duration or extent of an infection and/or associated disease symptoms, after exposure or suspected exposure to the virus, or after the actual initiation of an infection.

The immunogens described herein, and immunogenic compositions thereof, are provided to a subject in an amount effective to induce or enhance an immune response against the coronavirus S antigen in the subject, preferably a human. The actual dosage of disclosed immunogen will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the composition for eliciting the desired activity or biological response in the subject. Dosage regimens can be adjusted to provide an optimum prophylactic or therapeutic response.

An immunogenic composition including one or more of the disclosed immunogens can be used in coordinate (or prime-boost) vaccination protocols or combinatorial formulations. In certain embodiments, novel combinatorial immunogenic compositions and coordinate immunization protocols employ separate immunogens or formulations, each directed toward eliciting an anti-viral immune response, such as an immune response to coronavirus S antigen. Separate immunogenic compositions that elicit the anti-viral immune response can be combined in a polyvalent immunogenic composition administered to a subject in a single immunization step, or they can be administered separately (in monovalent immunogenic compositions) in a coordinate (or prime-boost) immunization protocol.

There can be several boosts, and each boost can be a different disclosed immunogen. In some examples that the boost may be the same immunogen as another boost, or the prime. The prime and boost can be administered as a single dose or multiple doses, for example two doses, three doses, four doses, five doses, six doses or more can be administered to a subject over days, weeks or months. Multiple boosts can also be given, such one to five (e.g., 1, 2, 3, 4 or 5 boosts), or more. Different dosages can be used in a series of sequential immunizations. For example a relatively large dose in a primary immunization and then a boost with relatively smaller doses.

In some embodiments, the boost can be administered about two, about three to eight, or about four, weeks following the prime, or about several months after the prime. In some embodiments, the boost can be administered about 5, about 6, about 7, about 8, about 10, about 12, about 18, about 24, months after the prime, or more or less time after the prime. Periodic additional boosts can also be used at appropriate time points to enhance the subject's "immune memory." The adequacy of the vaccination parameters chosen, e.g., formulation, dose, regimen and the like, can be determined by taking aliquots of serum from the subject and assaying antibody titers during the course of the immunization program. In addition, the clinical condition of the subject can be monitored for the desired effect, e.g., prevention of infection or improvement in disease state (e.g., reduction in viral load). If such monitoring indicates that vaccination is sub-optimal, the subject can be boosted with an additional dose of immunogenic composition, and the vaccination parameters can be modified in a fashion expected to potentiate the immune response.

In some embodiments, the prime-boost method can include DNA-primer and protein-boost vaccination protocol to a subject. The method can include two or more administrations of the nucleic acid molecule or the protein.

For protein therapeutics, typically, each human dose will comprise 1-1000 μg of protein, such as from about 1 μg to about 100 for example, from about 1 μg to about 50 such as about 1 about 2 about 5 about 10 about 15 about 20 about 25 about 30 about 40 or about 50 μg.

The amount utilized in an immunogenic composition is selected based on the subject population (e.g., infant or elderly). An optimal amount for a particular composition can be ascertained by standard studies involving observation of antibody titers and other responses in subjects. It is understood that a therapeutically effective amount of a disclosed immunogen, such as a disclosed recombinant coronavirus S antigen, e.g., trimer, protein, viral vector, or nucleic acid molecule in a immunogenic composition, can include an amount that is ineffective at eliciting an immune response by administration of a single dose, but that is effective upon administration of multiple dosages, for example in a prime-boost administration protocol.

Upon administration of a disclosed immunogen of this disclosure, the immune system of the subject typically responds to the immunogenic composition by producing antibodies specific for the coronavirus S protein peptide included in the immunogen. Such a response signifies that an immunologically effective dose was delivered to the subject.

In some embodiments, the antibody response of a subject will be determined in the context of evaluating effective dosages/immunization protocols. In most instances it will be sufficient to assess the antibody titer in serum or plasma obtained from the subject. Decisions as to whether to administer booster inoculations and/or to change the amount of the therapeutic agent administered to the individual can be at least partially based on the antibody titer level. The antibody titer level can be based on, for example, an immunobinding assay which measures the concentration of antibodies in the serum which bind to an antigen including, for example, the recombinant coronavirus S antigen, e.g., an S-Trimer.

The coronavirus infection does not need to be completely eliminated or reduced or prevented for the methods to be effective. For example, elicitation of an immune response to a coronavirus with one or more of the disclosed immunogens can reduce or inhibit infection with the coronavirus by a desired amount, for example, by at least 10%, at least 20%, at least 50%, at least 60%, at least 70%, at least 80%, at least 90%, at least 95%, at least 98%, or even at least 100% (elimination or prevention of detectable infected cells), as compared to infection with the coronavirus in the absence of the immunogen. In additional examples, coronavirus replication can be reduced or inhibited by the disclosed methods. Coronavirus replication does not need to be completely eliminated for the method to be effective. For example, the immune response elicited using one or more of the disclosed immunogens can reduce replication of the corresponding coronavirus by a desired amount, for example, by at least 10%, at least 20%, at least 50%, at least 60%, at least 70%, at least 80%, at least 90%, at least 95%, at least 98%, or even at least 100% (elimination or prevention of detectable replication of the coronavirus), as compared to replication of the coronavirus in the absence of the immune response.

In some embodiments, the disclosed immunogen is administered to the subject simultaneously with the administration of the adjuvant. In other embodiments, the disclosed immunogen is administered to the subject after the administration of the adjuvant and within a sufficient amount of time to induce the immune response.

One approach to administration of nucleic acids is direct immunization with plasmid DNA, such as with a mammalian expression plasmid. Immunization by nucleic acid constructs is well known in the art and taught, for example, in U.S. Pat. No. 5,643,578 (which describes methods of immunizing vertebrates by introducing DNA encoding a desired antigen to elicit a cell-mediated or a humoral response), and U.S. Pat. Nos. 5,593,972 and 5,817,637 (which describe operably linking a nucleic acid sequence encoding an antigen to regulatory sequences enabling expression). U.S. Pat. No. 5,880,103 describes several methods of delivery of nucleic acids encoding immunogenic peptides or other antigens to an organism. The methods include liposomal delivery of the nucleic acids (or of the synthetic peptides themselves), and immune-stimulating constructs, or ISCOMS™, negatively charged cage-like structures of 30-40 nm in size formed spontaneously on mixing cholesterol and Quil ATM (saponin). Protective immunity has been generated in a variety of experimental models of infection, including toxoplasmosis and Epstein-Barr virus-induced tumors, using ISCOMS™ as the delivery vehicle for antigens (Mowat and Donachie, *Immunol. Today* 12:383, 1991). Doses of antigen as low as 1 µg encapsulated in ISCOMS™ have been found to produce Class I mediated CTL responses (Takahashi et al., *Nature* 344:873, 1990).

In some embodiments, a plasmid DNA vaccine is used to express a disclosed immunogen in a subject. For example, a nucleic acid molecule encoding a disclosed immunogen can be administered to a subject to induce an immune response to the coronavirus S antigen. In some embodiments, the nucleic acid molecule can be included on a plasmid vector for DNA immunization, such as the pVRC8400 vector (described in Barouch et al., *J. Virol,* 79, 8828-8834, 2005, which is incorporated by reference herein).

In another approach to using nucleic acids for immunization, a disclosed recombinant coronavirus S antigen, e.g., trimer, protein, can be expressed by attenuated viral hosts or vectors or bacterial vectors. Recombinant vaccinia virus, adeno-associated virus (AAV), herpes virus, retrovirus, cytogmeglo virus or other viral vectors can be used to express the peptide or protein, thereby eliciting a CTL response. For example, vaccinia vectors and methods useful in immunization protocols are described in U.S. Pat. No. 4,722,848. BCG (Bacillus Calmette Guerin) provides another vector for expression of the peptides (see Stover, *Nature* 351:456-460, 1991).

In one embodiment, a nucleic acid encoding a disclosed recombinant coronavirus S antigen is introduced directly into cells. For example, the nucleic acid can be loaded onto gold microspheres by standard methods and introduced into the skin by a device such as Bio-Rad's HELIOS™ Gene Gun. The nucleic acids can be "naked," consisting of plasmids under control of a strong promoter. Typically, the DNA is injected into muscle, although it can also be injected directly into other sites. Dosages for injection are usually around 0.5 µg/kg to about 50 mg/kg, and typically are about 0.005 mg/kg to about 5 mg/kg (see, e.g., U.S. Pat. No. 5,589,466).

For example, the nucleic acid can be loaded onto gold microspheres by standard methods and introduced into the skin by a device such as Bio-Rad's HELIOS™ Gene Gun. The nucleic acids can be "naked," consisting of plasmids under control of a strong promoter. Typically, the DNA is injected into muscle, although it can also be injected directly into other sites. Dosages for injection are usually around 0.5 µg/kg to about 50 mg/kg, and typically are about 0.005 mg/kg to about 5 mg/kg (see, e.g., U.S. Pat. No. 5,589,466).

In another embodiment, an mRNA-based immunization protocol can be used to deliver a nucleic acid encoding a disclosed recombinant coronavirus S antigen directly into cells. In some embodiments, nucleic acid-based vaccines based on mRNA may provide a potent alternative to the previously mentioned approaches. mRNA vaccines preclude safety concerns about DNA integration into the host genome and can be directly translated in the host cell cytoplasm. Moreover, the simple cell-free, in vitro synthesis of RNA avoids the manufacturing complications associated with viral vectors. Two exemplary forms of RNA-based vaccination that can be used to deliver a nucleic acid encoding a disclosed recombinant coronavirus S antigen include conventional non-amplifying mRNA immunization (see, e.g., Petsch et al., "Protective efficacy of in vitro synthesized, specific mRNA vaccines against influenza A virus infection," Nature biotechnology, 30(12):1210-6, 2012) and self-amplifying mRNA immunization (see, e.g., Geall et al., "Nonviral delivery of self-amplifying RNA vaccines," PNAS, 109(36): 14604-14609, 2012; Magini et al., "Self-Amplifying mRNA Vaccines Expressing Multiple Conserved Influenza Antigens Confer Protection against Homologous and Heterosubtypic Viral Challenge," PLoS One, 11(8):e0161193, 2016; and Brito et al., "Self-amplifying mRNA vaccines," Adv Genet., 89:179-233, 2015).

In some embodiments, administration of a therapeutically effective amount of one or more of the disclosed immunogens to a subject induces a neutralizing immune response in the subject. To assess neutralization activity, following immunization of a subject, serum can be collected from the subject at appropriate time points, frozen, and stored for neutralization testing. Methods to assay for neutralization activity are known to the person of ordinary skill in the art and are further described herein, and include, but are not limited to, plaque reduction neutralization (PRNT) assays, microneutralization assays, flow cytometry based assays, single-cycle infection assays. In some embodiments, the serum neutralization activity can be assayed using a panel of coronavirus pseudoviruses.

In some embodiments, administration of a therapeutically effective amount of one or more of the disclosed immunogens to a subject induces a neutralizing immune response in the subject. To assess neutralization activity, following immunization of a subject, serum can be collected from the subject at appropriate time points, frozen, and stored for neutralization testing. Methods to assay for neutralization activity are known to the person of ordinary skill in the art and are further described herein, and include, but are not limited to, plaque reduction neutralization (PRNT) assays, microneutralization assays, flow cytometry based assays, single-cycle infection assays. In some embodiments, the serum neutralization activity can be assayed using a panel of coronavirus pseudoviruses.

In some embodiments, a neutralizing immune response induced by the disclosed immunogens herein generates a neutralizing antibody against a coronavirus such as SARS-CoV-2. In some embodiments, the neutralizing antibody herein binds to a cellular receptor or coreceptor of a coronavirus such as SARS-CoV-2 or component thereof. In some embodiments, the viral receptor or coreceptor is a coronavirus receptor or coreceptor, preferably a pneumonia virus receptor or coreceptor, more preferably a human coronavirus receptor such as SARS-CoV-2 receptor or coreceptor. In some embodiments, the neutralizing antibody herein modulates, decreases, antagonizes, mitigates, blocks, inhibits, abrogates and/or interferes with at least one coronavirus such as SARS-CoV-2 activity or binding, or with a coronavirus such as SARS-CoV-2 receptor activity or binding, in vitro, in situ and/or in vivo, such as SARS-CoV-2 release, SARS-CoV-2 receptor signaling, membrane SARS-CoV-2 cleavage, SARS-CoV-2 activity, SARS-CoV-2 production and/or synthesis. In some embodiments, the disclosed immunogens herein induce neutralizing antibodies against SARS-CoV-2 that modulate, decrease, antagonize, mitigate, block, inhibit, abrogate and/or interfere with SARS-CoV-2 binding to a SARS-CoV-2 receptor or coreceptor, such as angiotensin converting enzyme 2 (ACE2), dipeptidyl peptidase 4 (DPP4), dendritic cell-specific intercellular adhesion molecule-3-grabbing non integrin (DC-SIGN), and/or liver/lymph node-SIGN (L-SIGN).

V. Articles of Manufacture or Kits

Also provided are articles of manufacture or kits containing the provided recombinant polypeptide, proteins, and immunogenic compositions. The articles of manufacture may include a container and a label or package insert on or associated with the container. Suitable containers include, for example, bottles, vials, syringes, test tubes, IV solution bags, etc. The containers may be formed from a variety of materials such as glass or plastic. In some embodiments, the container has a sterile access port. Exemplary containers include an intravenous solution bags, vials, including those with stoppers pierceable by a needle for injection. The article of manufacture or kit may further include a package insert indicating that the compositions can be used to treat a particular condition such as a condition described herein (e.g., coronavirus infection). Alternatively, or additionally, the article of manufacture or kit may further include another or the same container comprising a pharmaceutically-acceptable buffer. It may further include other materials such as other buffers, diluents, filters, needles, and/or syringes.

The label or package insert may indicate that the composition is used for treating an coronavirus infection in an individual. The label or a package insert, which is on or associated with the container, may indicate directions for reconstitution and/or use of the formulation. The label or package insert may further indicate that the formulation is useful or intended for subcutaneous, intravenous, or other modes of administration for treating or preventing a coronavirus infection in an individual.

The container in some embodiments holds a composition which is by itself or combined with another composition effective for treating, preventing and/or diagnosing the condition. The article of manufacture or kit may include (a) a first container with a composition contained therein (i.e., first medicament), wherein the composition includes the immunogenic composition or protein or recombinant polypeptide thereof; and (b) a second container with a composition contained therein (i.e., second medicament), wherein the composition includes a further agent, such as an adjuvant or otherwise therapeutic agent, and which article or kit further comprises instructions on the label or package insert for treating the subject with the second medicament, in an effective amount.

Terminology

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

The terms "polypeptide" and "protein" are used interchangeably to refer to a polymer of amino acid residues, and are not limited to a minimum length. Polypeptides, including the provided receptors and other polypeptides, e.g., linkers or peptides, may include amino acid residues including natural and/or non-natural amino acid residues. The terms also include post-expression modifications of the polypeptide, for example, glycosylation, sialylation, acetylation, and phosphorylation. In some aspects, the polypeptides may contain modifications with respect to a native or natural sequence, as long as the protein maintains the desired activity. These modifications may be deliberate, as through site-directed mutagenesis, or may be accidental, such as through mutations of hosts which produce the proteins or errors due to PCR amplification.

As used herein, a "subject" is a mammal, such as a human or other animal, and typically is human. In some embodiments, the subject, e.g., patient, to whom the agent or agents, cells, cell populations, or compositions are administered, is a mammal, typically a primate, such as a human. In some embodiments, the primate is a monkey or an ape. The subject can be male or female and can be any suitable age, including infant, juvenile, adolescent, adult, and geriatric subjects. In some embodiments, the subject is a non-primate mammal, such as a rodent.

As used herein, "treatment" (and grammatical variations thereof such as "treat" or "treating") refers to complete or partial amelioration or reduction of a disease or condition or disorder, or a symptom, adverse effect or outcome, or phenotype associated therewith. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. The terms do not imply complete curing of a disease or complete elimination of any symptom or effect(s) on all symptoms or outcomes.

As used herein, "delaying development of a disease" means to defer, hinder, slow, retard, stabilize, suppress and/or postpone development of the disease (such as cancer). This delay can be of varying lengths of time, depending on the history of the disease and/or individual being treated. In some embodiments, sufficient or significant delay can, in effect, encompass prevention, in that the individual does not develop the disease. For example, a late stage cancer, such as development of metastasis, may be delayed.

"Preventing," as used herein, includes providing prophylaxis with respect to the occurrence or recurrence of a disease in a subject that may be predisposed to the disease but has not yet been diagnosed with the disease. In some embodiments, the provided cells and compositions are used to delay development of a disease or to slow the progression of a disease.

As used herein, to "suppress" a function or activity is to reduce the function or activity when compared to otherwise same conditions except for a condition or parameter of interest, or alternatively, as compared to another condition. For example, cells that suppress tumor growth reduce the rate of growth of the tumor compared to the rate of growth of the tumor in the absence of the cells.

An "effective amount" of an agent, e.g., a pharmaceutical formulation, cells, or composition, in the context of administration, refers to an amount effective, at dosages/amounts and for periods of time necessary, to achieve a desired result, such as a therapeutic or prophylactic result.

A "therapeutically effective amount" of an agent, e.g., a pharmaceutical formulation or cells, refers to an amount effective, at dosages and for periods of time necessary, to achieve a desired therapeutic result, such as for treatment of a disease, condition, or disorder, and/or pharmacokinetic or pharmacodynamic effect of the treatment. The therapeutically effective amount may vary according to factors such as the disease state, age, sex, and weight of the subject, and the populations of cells administered. In some embodiments, the provided methods involve administering the cells and/or compositions at effective amounts, e.g., therapeutically effective amounts.

A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount. In the context of lower tumor burden, the prophylactically effective amount in some aspects will be higher than the therapeutically effective amount. Effective amount of a vaccine or other agent that is sufficient to generate a desired response, such as reduce or eliminate a sign or symptom of a condition or disease, such as pneumonia. For instance, this can be the amount necessary to inhibit viral replication or to measurably alter outward symptoms of the viral infection. In general, this amount will be sufficient to measurably inhibit virus (for example, SARS-CoV-2) replication or infectivity. When administered to a subject, a dosage will generally be used that will achieve target tissue concentrations that has been shown to achieve in vitro inhibition of viral replication. In some embodiments, an "effective amount" is one that treats (including prophylaxis) one or more symptoms and/or underlying causes of any of a disorder or disease, for example to treat a coronavirus infection. In some embodiments, an effective amount is a therapeutically effective amount. In some embodiments, an effective amount is an amount that prevents one or more signs or symptoms of a particular disease or condition from developing, such as one or more signs or symptoms associated with coronaviral infections.

As used herein, the terms "antigen" or "immunogen" are used interchangeably to refer to a substance, typically a protein, which is capable of inducing an immune response in a subject. The term also refers to proteins that are immunologically active in the sense that once administered to a subject (either directly or by administering to the subject a nucleotide sequence or vector that encodes the protein) is able to evoke an immune response of the humoral and/or cellular type directed against that protein. Unless otherwise noted, the term "vaccine immunogen" is used interchangeably with "protein antigen" or "immunogen polypeptide".

The term "conservatively modified variant" applies to both amino acid and nucleic acid sequences. With respect to particular nucleic acid sequences, conservatively modified variants refer to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For polypeptide sequences, "conservatively modified variants" refer to a variant which has conservative amino acid substitutions, amino acid residues replaced with other amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Epitope refers to an antigenic determinant. These are particular chemical groups or peptide sequences on a molecule that are antigenic, such that they elicit a specific immune response, for example, an epitope is the region of an antigen to which B and/or T cells respond. Epitopes can be formed both from contiguous amino acids or noncontiguous amino acids juxtaposed by tertiary folding of a protein.

Unless otherwise noted, a fusion protein is a recombinant protein containing amino acid sequence from at least two unrelated proteins that have been joined together, via a peptide bond, to make a single protein. Thus, it does not encompass the naturally existing coronaviruses surface antigen that is termed fusion (F) protein as described herein. The unrelated amino acid sequences can be joined directly to each other or they can be joined using a linker sequence. As used herein, proteins are unrelated, if their amino acid sequences are not normally found joined together via a peptide bond in their natural environment (e.g., inside a cell). For example, the amino acid sequences of a viral antigen and the amino acid sequences of a collagen or procollagen are not normally found joined together via a peptide bond.

Immunogen is a protein or a portion thereof that is capable of inducing an immune response in a mammal, such as a mammal infected or at risk of infection with a pathogen.

Administration of an immunogen can lead to protective immunity and/or proactive immunity against a pathogen of interest.

Immunogenic composition refers to a composition comprising an immunogenic polypeptide that induces a measurable CTL response against virus expressing the immunogenic polypeptide, or induces a measurable B cell response (such as production of antibodies) against the immunogenic polypeptide.

Sequence identity or similarity between two or more nucleic acid sequences, or two or more amino acid sequences, is expressed in terms of the identity or similarity between the sequences. Sequence identity can be measured in terms of percentage identity; the higher the percentage, the more identical the sequences are. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

Vaccine refers to a pharmaceutical composition that elicits a prophylactic or therapeutic immune response in a subject. In some cases, the immune response is a protective immune response. Typically, a vaccine elicits an antigen-specific immune response to an antigen of a pathogen, for example a viral pathogen, or to a cellular constituent correlated with a pathological condition. A vaccine may include a polynucleotide (such as a nucleic acid encoding a disclosed antigen), a peptide or polypeptide (such as a disclosed antigen), a virus, a cell or one or more cellular constituents. In some embodiments, vaccines or vaccine immunogens or vaccine compositions are expressed from fusion constructs and self-assemble into nanoparticles displaying an immunogen polypeptide or protein on the surface.

Virus-like particle (VLP) refers to a non-replicating, viral shell, derived from any of several viruses. VLPs are generally composed of one or more viral proteins, such as, but not limited to, those proteins referred to as capsid, coat, shell, surface and/or envelope proteins, or particle-forming polypeptides derived from these proteins. VLPs can form spontaneously upon recombinant expression of the protein in an appropriate expression system. Methods for producing particular VLPs are known in the art. The presence of VLPs following recombinant expression of viral proteins can be detected using conventional techniques known in the art, such as by electron microscopy, biophysical characterization, and the like. See, for example, Baker et al. (1991) Biophys. J. 60:1445-1456; and Hagensee et al. (1994) J. Virol. 68:4503-4505. For example, VLPs can be isolated by density gradient centrifugation and/or identified by characteristic density banding. Alternatively, cryoelectron microscopy can be performed on vitrified aqueous samples of the VLP preparation in question, and images recorded under appropriate exposure conditions.

The term "about" as used herein refers to the usual error range for the respective value readily known to the skilled person in this technical field. Reference to "about" a value or parameter herein includes (and describes) embodiments that are directed to that value or parameter per se.

As used herein, the singular forms "a," "an," and "the" include plural referents unless the context clearly dictates otherwise. For example, "a" or "an" means "at least one" or "one or more."

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

As used herein, a composition refers to any mixture of two or more products, substances, or compounds, including cells. It may be a solution, a suspension, liquid, powder, a paste, aqueous, non-aqueous or any combination thereof.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

EXEMPLARY EMBODIMENTS

Embodiment 1. A protein comprising a plurality of recombinant polypeptides, each recombinant polypeptide comprising a surface antigen of a coronavirus linked to a C-terminal propeptide of collagen, wherein the C-terminal propeptides of the recombinant polypeptides form inter-polypeptide disulfide bonds.

Embodiment 2. The protein of embodiment 1, wherein the coronavirus is a Severe Acute Respiratory Syndrome (SARS)-coronavirus (SARS-CoV), a SARS-coronavirus 2 (SARS-CoV-2), a SARS-like coronavirus, a Middle East Respiratory Syndrome (MERS)-coronavirus (MERS-CoV), a MERS-like coronavirus, NL63-CoV, 229E-CoV, OC43-CoV, HKU1-CoV, WIV1-CoV, MHV, HKU9-CoV, PEDV-CoV, or SDCV.

Embodiment 3. The protein of embodiment 1 or 2, wherein the surface antigen comprises a coronavirus spike (S) protein or a fragment or epitope thereof, wherein the epitope is optionally a linear epitope or a conformational epitope, and wherein the protein comprises three recombinant polypeptides.

Embodiment 4. The protein of embodiment 3, wherein the surface antigen comprises a signal peptide, an S1 subunit peptide, an S2 subunit peptide, or any combination thereof.

Embodiment 5. The protein of embodiment 3, wherein the surface antigen comprises a signal peptide, a receptor binding domain (RBD) peptide, a receptor binding motif (RBM)

peptide, a fusion peptide (FP), a heptad repeat 1 (HR1) peptide, or a heptad repeat 2 (HR2) peptide, or any combination thereof.

Embodiment 6. The protein of any of embodiments 3-5, wherein the surface antigen comprises a receptor binding domain (RBD) of the S protein.

Embodiment 7. The protein of any of embodiments 3-6, wherein the surface antigen comprises an S1 subunit and an S2 subunit of the S protein.

Embodiment 8. The protein of any of embodiments 3-7, wherein the surface antigen does not comprise a transmembrane (TM) domain peptide and/or a cytoplasm (CP) domain peptide.

Embodiment 9. The protein of any of embodiments 3-8, wherein the surface antigen comprises a protease cleavage site, wherein the protease is optionally furin, trypsin, factor Xa, thrombin, or cathepsin L.

Embodiment 10. The protein of any of embodiments 3-8, wherein the surface antigen does not comprise a protease cleavage site, wherein the protease is optionally furin, trypsin, factor Xa, thrombin, or cathepsin L.

Embodiment 11. The protein of any of embodiments 1-10, wherein the surface antigen is soluble or does not directly bind to a lipid bilayer, e.g., a membrane or viral envelope.

Embodiment 12. The protein of any of embodiments 1-11, wherein the surface antigens are the same or different among the recombinant polypeptides of the protein.

Embodiment 13. The protein of any of embodiments 1-12, wherein the surface antigen is directly fused to the C-terminal propeptide, or is linked to the C-terminal propeptide via a linker, such as a linker comprising glycine-X-Y repeats, wherein X and Y and independently any amino acid and optionally proline or hydroxyproline.

Embodiment 14. The protein of any of embodiments 1-13, which is soluble or does not directly bind to a lipid bilayer, e.g., a membrane or viral envelope.

Embodiment 15. The protein of any of embodiments 1-14, wherein the protein is capable of binding to a cell surface receptor of a subject, optionally wherein the subject is a mammal such as a primate, e.g., human.

Embodiment 16. The protein of embodiment 15, wherein the cell surface receptor is angiotensin converting enzyme 2 (ACE2), dipeptidyl peptidase 4 (DPP4), dendritic cell-specific intercellular adhesion molecule-3-grabbing non integrin (DC-SIGN), or liver/lymph node-SIGN (L-SIGN).

Embodiment 17. The protein of any of embodiments 1-16, wherein the C-terminal propeptide is of human collagen.

Embodiment 18. The protein of any of embodiments 1-17, wherein the C-terminal propeptide comprises a C-terminal polypeptide of proα1(I), proα1(II), proα1(III), proα1(V), proα1(XI), proα2(I), proα2(V), proα2(XI), or proα3(XI), or a fragment thereof.

Embodiment 19. The protein of any of embodiments 1-18, wherein the C-terminal propeptides are the same or different among the recombinant polypeptides.

Embodiment 20. The protein of any of embodiments 1-19, wherein the C-terminal propeptide comprises any of SEQ ID NOs: 67-80 or an amino acid sequence at least 90% identical thereto capable of forming inter-polypeptide disulfide bonds and trimerizing the recombinant polypeptides.

Embodiment 21. The protein of any of embodiments 1-20, wherein the C-terminal propeptide comprises SEQ ID NO: 67 or an amino acid sequence at least 90% identical thereto capable of forming inter-polypeptide disulfide bonds and trimerizing the recombinant polypeptides.

Embodiment 22. The protein of any of embodiments 1-20, wherein the C-terminal propeptide comprises SEQ ID NO: 68 or an amino acid sequence at least 90% identical thereto capable of forming inter-polypeptide disulfide bonds and trimerizing the recombinant polypeptides.

Embodiment 23. The protein of any of embodiments 1-20, wherein the C-terminal propeptide comprises SEQ ID NO: 69 or an amino acid sequence at least 90% identical thereto capable of forming inter-polypeptide disulfide bonds and trimerizing the recombinant polypeptides.

Embodiment 24. The protein of any of embodiments 1-20, wherein the C-terminal propeptide comprises SEQ ID NO: 70 or an amino acid sequence at least 90% identical thereto capable of forming inter-polypeptide disulfide bonds and trimerizing the recombinant polypeptides.

Embodiment 25. The protein of any of embodiments 1-20, wherein the C-terminal propeptide comprises SEQ ID NO: 71 or an amino acid sequence at least 90% identical thereto capable of forming inter-polypeptide disulfide bonds and trimerizing the recombinant polypeptides.

Embodiment 26. The protein of any of embodiments 1-20, wherein the C-terminal propeptide comprises SEQ ID NO: 72 or an amino acid sequence at least 90% identical thereto capable of forming inter-polypeptide disulfide bonds and trimerizing the recombinant polypeptides.

Embodiment 27. The protein of any of embodiments 1-20, wherein the C-terminal propeptide comprises SEQ ID NO: 73 or an amino acid sequence at least 90% identical thereto capable of forming inter-polypeptide disulfide bonds and trimerizing the recombinant polypeptides.

Embodiment 28. The protein of any of embodiments 1-20, wherein the C-terminal propeptide comprises SEQ ID NO: 74 or an amino acid sequence at least 90% identical thereto capable of forming inter-polypeptide disulfide bonds and trimerizing the recombinant polypeptides.

Embodiment 29. The protein of any of embodiments 1-20, wherein the C-terminal propeptide comprises SEQ ID NO: 75 or SEQ ID NO: 76 or an amino acid sequence at least 90% identical thereto capable of forming inter-polypeptide disulfide bonds and trimerizing the recombinant polypeptides.

Embodiment 30. The protein of any of embodiments 1-29, wherein the C-terminal propeptide comprises a sequence comprising glycine-X-Y repeats linked to the N-terminus of any of SEQ ID NOs: 67-80, wherein X and Y and independently any amino acid and optionally proline or hydroxyproline, or an amino acid sequence at least 90% identical thereto capable of forming inter-polypeptide disulfide bonds and trimerizing the recombinant polypeptides.

Embodiment 31. The protein of any of embodiments 1-30, wherein the surface antigen in each recombinant polypeptide is in a prefusion conformation or a postfusion conformation.

Embodiment 32. The protein of any of embodiments 1-31, wherein the surface antigen in each recombinant polypeptide comprises any of SEQ ID NOs: 27-66 or an amino acid sequence at least 80% identical thereto.

Embodiment 33. The protein of any of embodiments 1-32, wherein the recombinant polypeptide comprises any of SEQ ID NOs: 1-26 or an amino acid sequence at least 80% identical thereto.

Embodiment 34. An immunogen comprising the protein of any of embodiments 1-33.

Embodiment 35. A protein nanoparticle comprising the protein of any of embodiments 1-33 directly or indirectly linked to a nanoparticle.

Embodiment 36. A virus-like particle (VLP) comprising the protein of any of embodiments 1-33.

Embodiment 37. An isolated nucleic acid encoding one, two, three or more of the recombinant polypeptides of the protein of any of embodiments 1-33.

Embodiment 38. The isolated nucleic acid of embodiment 37, wherein a polypeptide encoding the surface antigen is fused in-frame to a polypeptide encoding the C-terminal propeptide of collagen.

Embodiment 39. The isolated nucleic acid of embodiment 37 or 38, which is operably linked to a promoter.

Embodiment 40. The isolated nucleic acid of any of embodiments 37-39, which is a DNA molecule.

Embodiment 41. The isolated nucleic acid of any of embodiments 37-39, which is an RNA molecule, optionally an mRNA molecule such as a nucleoside-modified mRNA, a non-amplifying mRNA, a self-amplifying mRNA, or a trans-amplifying mRNA.

Embodiment 42. A vector comprising the isolated nucleic acid of any of embodiments 37-41.

Embodiment 43. The vector of embodiment 42, which is a viral vector.

Embodiment 44. A virus, a pseudovirus, or a cell comprising the vector of embodiment 42 or 43, optionally wherein the virus or cell has a recombinant genome.

Embodiment 45. An immunogenic composition comprising the protein, immunogen, protein nanoparticle, VLP, isolated nucleic acid, vector, virus, pseudovirus, or cell of any one of embodiments 1-44, and a pharmaceutically acceptable carrier.

Embodiment 46. A vaccine comprising the immunogenic composition of embodiment 45 and optionally an adjuvant, wherein the vaccine is optionally a subunit vaccine, and/or optionally wherein the vaccines is a prophylactic and/or therapeutic vaccine.

Embodiment 47. The vaccine of embodiment 46, wherein the vaccine comprises a plurality of different adjuvants.

Embodiment 48. A method of producing a protein, comprising: expressing the isolated nucleic acid or vector of any one of embodiments 37-43 in a host cell to produce the protein of any of embodiments 1-33; and purifying the protein.

Embodiment 49. The protein produced by the method of embodiment 48.

Embodiment 50. A method for generating an immune response to a surface antigen of a coronavirus in a subject, comprising administering to the subject an effective amount of the protein, immunogen, protein nanoparticle, VLP, isolated nucleic acid, vector, virus, pseudovirus, cell, immunogenic composition, or vaccine of any one of embodiments 1-47 and 49 to generate the immune response.

Embodiment 51. The method of embodiment 50, for treating or preventing infection with the coronavirus.

Embodiment 52. The method of embodiment 50 or 51, wherein generating the immune response inhibits or reduces replication of the coronavirus in the subject.

Embodiment 53. The method of any of embodiments 50-52, wherein the immune response comprises a cell-mediated response and/or a humoral response, optionally comprising production of one or more neutralizing antibody, such as a polyclonal antibody or a monoclonal antibody.

Embodiment 54. The method of any of embodiments 50-53, wherein the immune response is against the surface antigen of the coronavirus but not against the C-terminal propeptide.

Embodiment 55. The method of any of embodiments 50-54, wherein the administering does not lead to antibody dependent enhancement (ADE) in the subject due to prior exposure to one or more coronavirus.

Embodiment 56. The method of any of embodiments 50-55, wherein the administering does not lead to antibody dependent enhancement (ADE) in the subject when subsequently exposed to one or more coronavirus.

Embodiment 57. The method of any of embodiments 50-56, further comprising a priming step and/or a boosting step.

Embodiment 58. The method of any of embodiments 50-57, wherein the administering step is performed via topical, transdermal, subcutaneous, intradermal, oral, intranasal (e.g., intranasal spray), intratracheal, sublingual, buccal, rectal, vaginal, inhaled, intravenous (e.g., intravenous injection), intraarterial, intramuscular (e.g., intramuscular injection), intracardiac, intraosseous, intraperitoneal, transmucosal, intravitreal, subretinal, intraarticular, peri-articular, local, or epicutaneous administration.

Embodiment 59. The method of any of embodiments 50-58, wherein the effective amount is administered in a single dose or a series of doses separated by one or more interval.

Embodiment 60. The method of any of embodiments 50-59, wherein the effective amount is administered without an adjuvant.

Embodiment 61. The method of any of embodiments 50-59, wherein the effective amount is administered with an adjuvant or a plurality of adjuvants.

Embodiment 62. A method comprising administering to a subject an effective amount of the protein of any one of embodiments 1-33 to generate in the subject a neutralizing antibody or neutralizing antisera to the coronavirus.

Embodiment 63. The method of embodiment 62, wherein the subject is a mammal, optionally a human or a non-human primate.

Embodiment 64. The method of embodiment 62 or 63, further comprising isolating the neutralizing antibody or neutralizing antisera from the subject.

Embodiment 65. The method of embodiment 64, further comprising administering an effective amount of the isolated neutralizing antibody or neutralizing antisera to a human subject via passive immunization to prevent or treat an infection by the coronavirus.

Embodiment 66. The method of any of embodiments 62-65, wherein the neutralizing antibody or neutralizing antisera comprises polyclonal antibodies to the coronavirus surface antigen, optionally wherein the neutralizing antibody or neutralizing antisera is free or substantially free of antibodies to the C-terminal propeptide of collagen.

Embodiment 67. The method of any of embodiments 62-65, wherein the neutralizing antibody comprises a monoclonal antibody to the coronavirus surface antigen, optionally wherein the neutralizing antibody is free or substantially free of antibodies to the C-terminal propeptide of collagen.

Embodiment 68. The protein, immunogen, protein nanoparticle, VLP, isolated nucleic acid, vector, virus, pseudovirus, cell, immunogenic composition, or vaccine of any one of embodiments 1-47 and 49, for use in inducing an immune response to a coronavirus in a subject, and/or in treating or preventing an infection by the coronavirus.

Embodiment 69. Use of the protein, immunogen, protein nanoparticle, VLP, isolated nucleic acid, vector, virus, pseudovirus, cell, immunogenic composition, or vaccine of any one of embodiments 1-47 and 49, for inducing an immune response to a coronavirus in a subject, and/or for treating or preventing an infection by the coronavirus.

Embodiment 70. Use of the protein, immunogen, protein nanoparticle, VLP, isolated nucleic acid, vector, virus, pseudovirus, cell, immunogenic composition, or vaccine of any one of embodiments 1-47 and 49, for the manufacture of a medicament or a prophylactic for inducing an immune response to a coronavirus in a subject, and/or for treating or preventing an infection by the coronavirus.

Embodiment 71. A method for analyzing a sample, comprising: contacting a sample with the protein of any of embodiments 1-33, and detecting a binding between the protein and an analyte capable of specific binding to the surface antigen of the coronavirus.

Embodiment 72. The method of embodiment 71, wherein the analyte is an antibody, a receptor, or a cell recognizing the surface antigen.

Embodiment 73. The method of embodiment 71 or 72, wherein the binding indicates the presence of the analyte in the sample, and/or an infection by the coronavirus in a subject from which the sample is derived.

Embodiment 74. A kit comprising the protein of any of embodiments 1-33 and a substrate, pad, or vial containing or immobilizing the protein, optionally wherein the kit is an ELISA or lateral flow assay kit.

EXAMPLES

Figure 1:
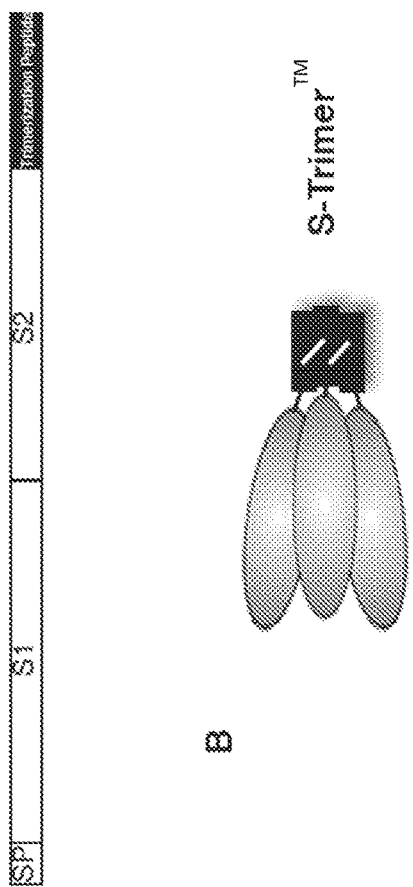
FIG. 1 shows structural features of an exemplary soluble S-Trimer subunit vaccine for COVID-19. (A) Schematic illustration of the structural domains of S-Trimer and (B) its trimeric and covalently-linked three-dimensional conformation.

The following examples are included for illustrative purposes only and are not intended to limit the scope of the present disclosure Example 1: Generation of Recombinant Disulfide-Bond Linked SARS-CoV-2 S-Trimer Fusion Protein as a Subunit Vaccine Secreted forms of recombinant disulfide bond-linked polypeptides comprising SARS-CoV-2 protein peptides fused to a trimerization domain as candidate protein subunit vaccines were generated. In one example, the complete ecto-domain of the native spike protein (S) from SARS-CoV2, including its signal peptide (SP), S1 and S2 domains, was fused in-frame at the C-terminus to a mammalian expression vector that encoded human C-propeptide of al collagen, to enable expression of a secreted and trimeric S-Trimer fusion antigen, e.g., as shown in FIG. 1.

High-level expression of S-Trimer fusion protein was shown in FIG. 2. An 8% SDS-PAGE analysis of S-Trimer expression from a fed-batch serum-free CHO cell culture in a 10 L bioreactor. 10 μL of cell-free conditioned medium from Day 6 to Day 11 were analyzed under reducing condition followed by Coomassie Blue staining. A highly purified S-Trimer was loaded on the gel as a reference standard (Std). The full-length S-Trimer and partially cleaved forms at S1/S2 furin site were as indicated.

Figure 3:
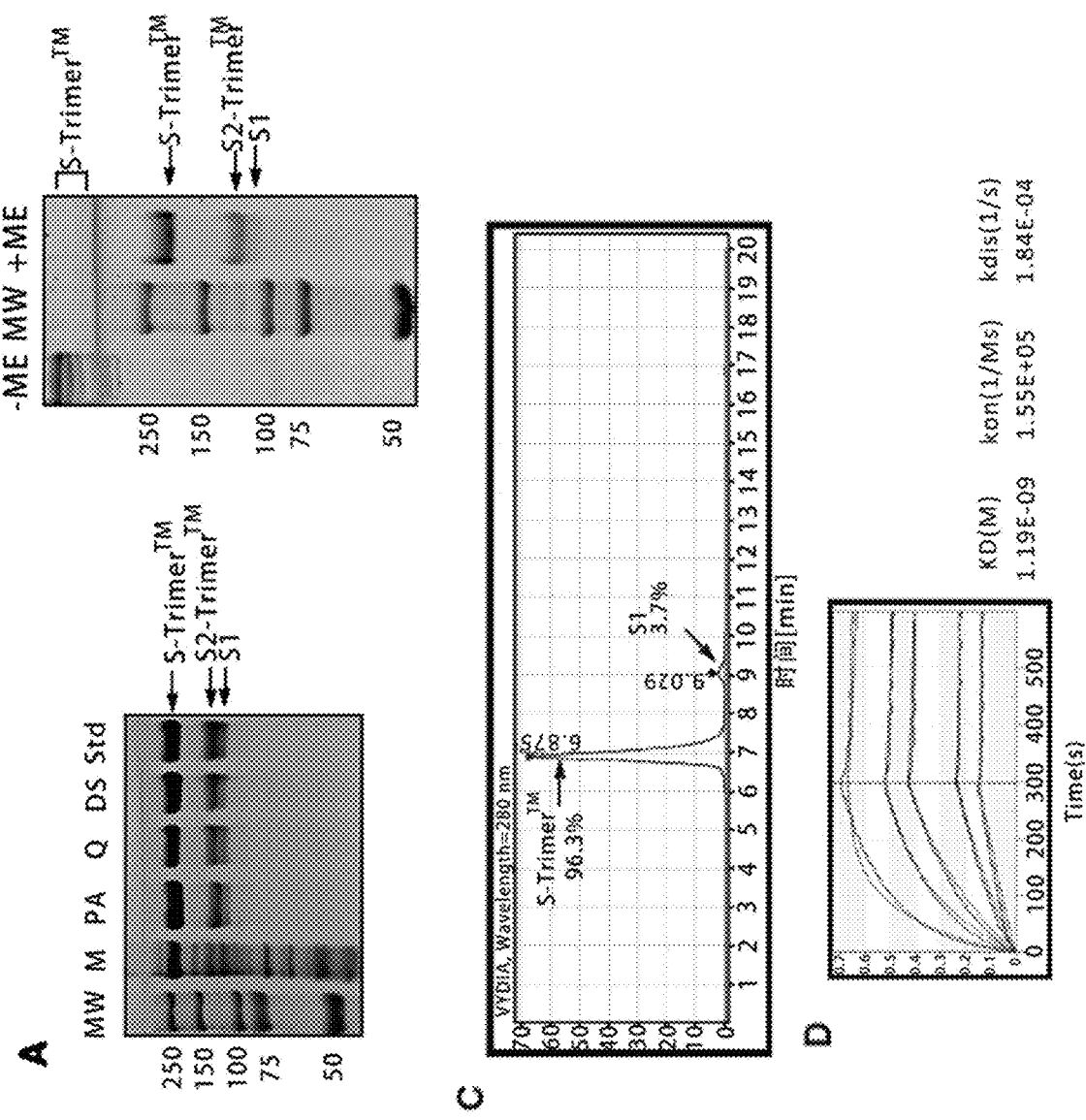
FIG. 3 shows the purification and characterization of an exemplary covalently linked S-Trimer. (A) S-Trimer was purified from the cleared cell cultured medium via a Protein A (PA) affinity chromatography and anion exchange column (Q) followed by ultra-filtration and diafiltration (UF/DF) to obtain the drug substance (DS). (B) S-Trimer is a disulfide bond-linked trimer. (C) The S-Trimer was purified to nearly homogeneity as judged by SEC-HPLC analysis, with some cleaved S1 being separated during the size exclusion chromatography. (D) The receptor binding kinetics of S-Trimer to ACE2-Fc was assessed.

Covalently linked S-Trimers were then purified and characterized. S-Trimer was purified from the cleared cell cultured medium via a Protein A (PA) affinity chromatography and anion exchange column (Q) followed by ultra-filtration and diafiltration (UF/DF) to obtain the drug substance (DS), as shown in FIG. 3A. Four μg of purified protein was analyzed against starting cell culture medium feed by an 8% reducing SDS-PAGE and stained with Coomassie Blue. The 5-Trimer was partially cleaved at the S1/S2 furin cleavage site, but the cleaved S1 subunit appeared to be bound to the S-Trimer since it was co-purified with the S-Trimer. As shown in FIG. 3B, the S-Trimer is a disulfide bond-linked trimer. Four μg of highly purified native-like S-Trimer was analyzed by a 6% SDS-PAGEs under non-reducing and reducing conditions as indicated and stained with Coomassie Blue. The S-Trimer was purified to nearly homogeneity as judged by SEC-HPLC analysis, with some cleaved S1 being separated during the size exclusion chromatography, as shown in FIG. 3C. The molecular weight of S-Trimer was estimated to be 660 Kda. In FIG. 3D, the receptor binding kinetics of S-Trimer to ACE2-Fc was assessed by Fortebio biolayer interferometry measurements using a protein A sensor.

Figure 4:
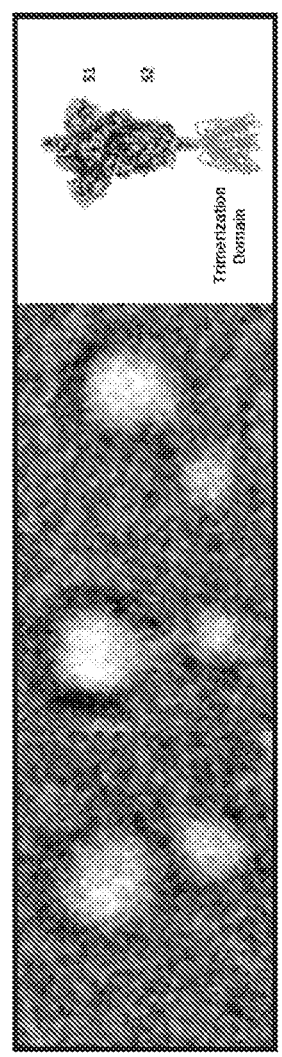
FIG. 4 shows an exemplary S-Trimer is highly glycosylated with N-linked glycans. The full-length S-Trimer, S2-Trimer and cleaved S1 before and after deglycosylation are indicated.
Figure 5:
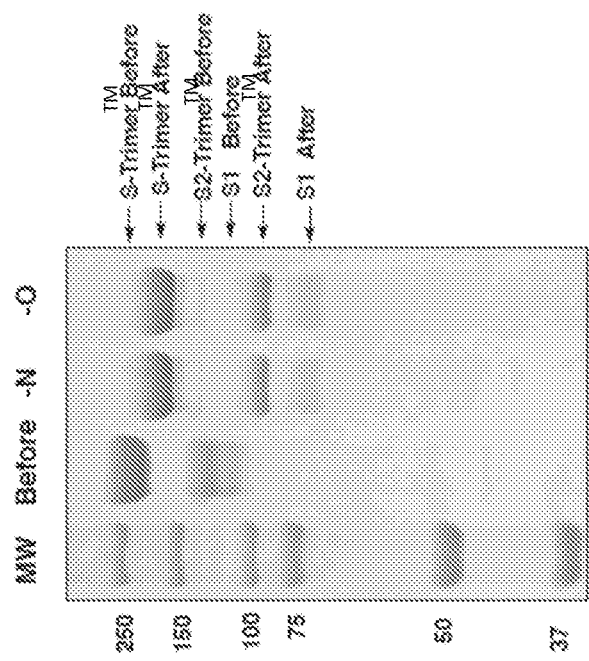
FIG. 5 shows Electron Micrographs (EM) of an exemplary S-Trimer and the predicted conformation of the S-Trimer (right cartoon).

The S-Trimers were highly glycosylated with N-linked glycans. Highly purified S-Trimer before and after digestion with either endoglycanase F (PNGase F) alone or PNGase F plus endo-O-glycosidase to remove N- and O-linked glycans, and analyzed by an 8% reducing SDS-PAGE and stained with Coomassie Blue. The full-length S-Trimer, S2-Trimer and cleaved S1 before and after deglycosylation were as indicated in FIG. 4. Highly purified S-Trimers were visualized by negative EM using FEI Tecnai spirit electron microscopy, with the predicted conformation of S-Trimer shown in FIG. 5.

Figure 6:
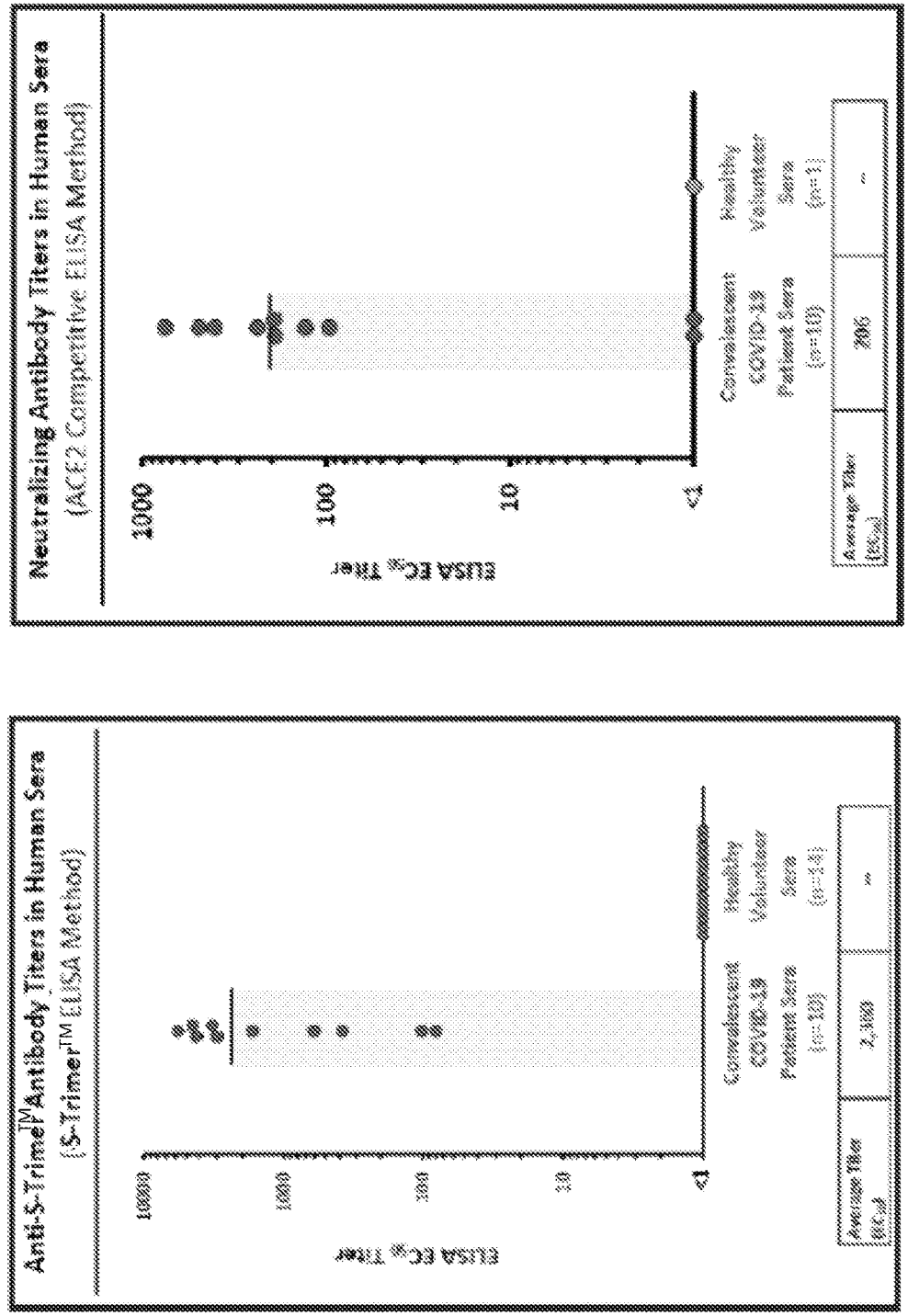
FIG. 6 shows the detection of S-specific antibodies and neutralizing antibodies from convalescent sera using an exemplary S-Trimer as an antigen.

Example 2: Functional Characterization of Recombinant Polypeptides Comprising S-Trimer Protein Peptides Sera from multiple patients who had recently recovered from COVID-19 were analyzed with S-Trimer as an antigen to determine S-specific antibody titers (FIG. 6, Left Panel) and neutralizing antibody levels via inhibition of S-Trimer binding to ACE2 receptor (FIG. 6, Right Panel). The results show that S-specific antibodies and neutralizing antibodies were successfully detected from convalescent sera using S-Trimer as an antigen.

Figure 7A:
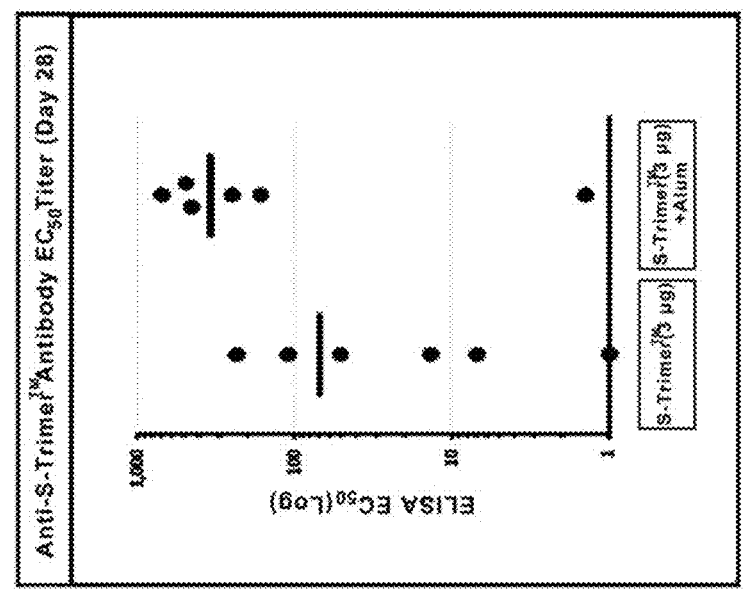
FIG. 7A and FIG. 7B show the induction of antigen-specific antibodies and neutralizing antibodies, respectively, in rats, with an exemplary S-Trimer alone and without any adjuvant.
Figure 7B:
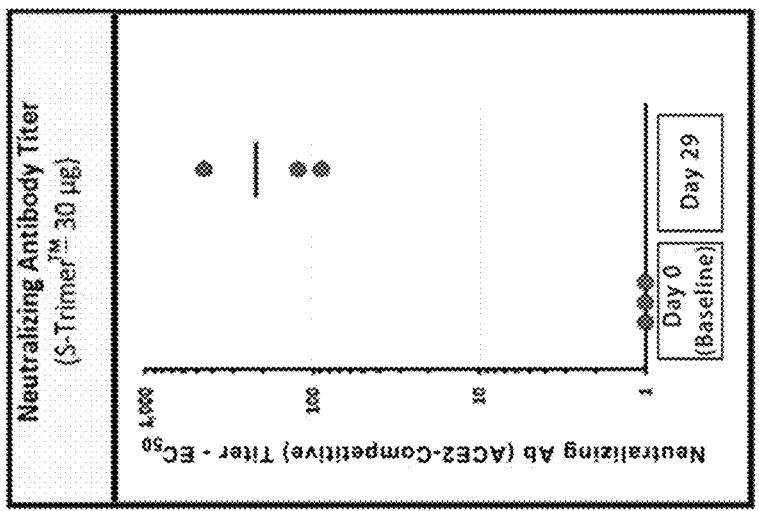
Figure 7C:
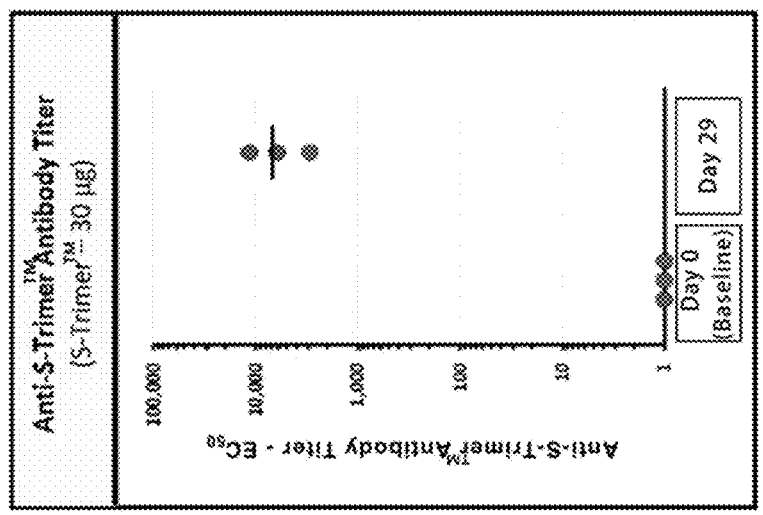
FIG. 7C shows induction of antigen-specific antibodies with an exemplary S-Trimer vaccine in mice, without adjuvant or with Alum (aluminum hydroxide) as the adjuvant.
Figure 7E:
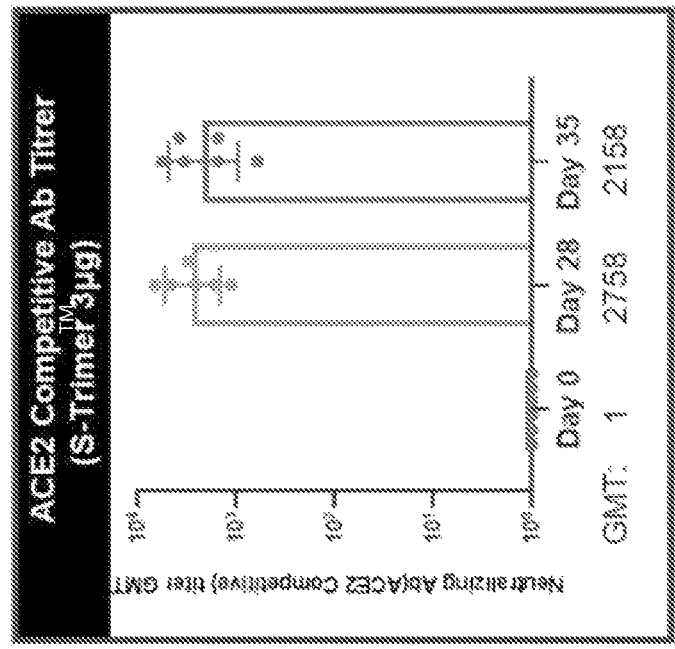
FIG. 7D and FIG. 7E show the induction of antigen-specific antibodies and neutralizing antibodies, respectively, in rats, with an exemplary S-Trimer adjuvanted with a squalene-based adjuvant.
Figure 7D:
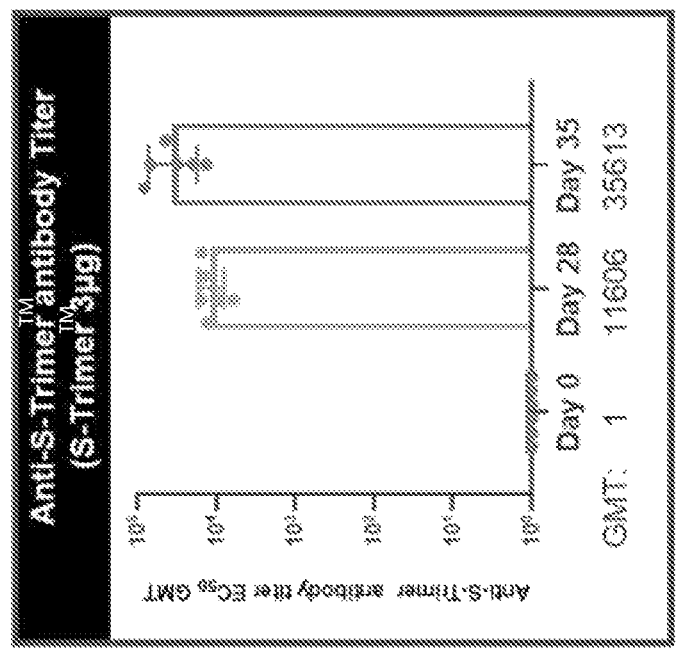
Figure 8:
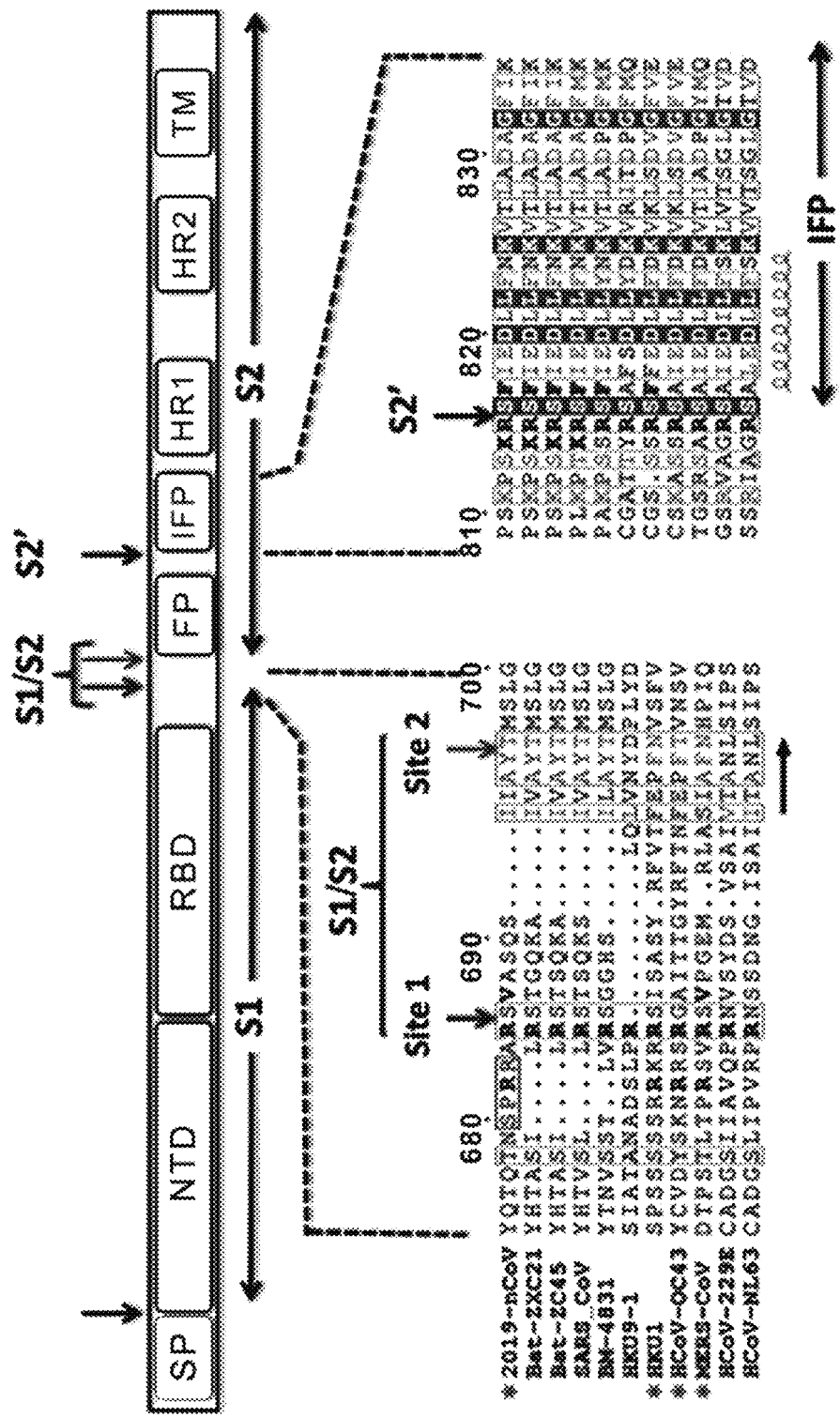
FIG. 8 shows the structure and certain sequences of exemplary coronaviruses.

To further evaluate the immunogenicity and protective efficacy of exemplary recombinant polypeptides generated as described in Example 1, FIG. 7A and FIG. 7B show the induction of antigen-specific antibodies and neutralizing antibodies, respectively, in rats with S-Trimer alone (30 micrograms) and without any adjuvant. Similar to data shown in human in FIG. 6, these results show that antigen-specific antibodies as well as neutralizing antibodies were induced with the S-Trimer vaccine. Similarly, immunogenicity of the S-Trimer was shown in mice. Balb-c mice grouped in 6 were immunized twice at Day 1 and Day 14 with either 3 micrograms of S-Trimer alone or S-Trimer+ Alum (aluminum hydroxide) as an adjuvant. The antisera collected at Day 28 were analyzed with S-Trimer to determine the antibody titers (FIG. 7C). S-Trimer adjuvanted with a squalene-based adjuvant exhibited strong ability to induce antigen-specific antibodies and neutralizing antibodies, as shown in FIG. 7D and FIG. 7E, respectively. GMT stands for geometric mean titer.

Example 3: Broad Neutralization of Viruses Induced by an S-Trimer Vaccine Composition Beginning in late 2020, the emergence and spread of multiple variant SARS-CoV-2 strains harboring mutations which may enable immune escape necessitates the rapid evaluation of second generation vaccines, with the goal of inducing optimized immune responses that are broadly protective. This example demonstrates in a mouse immunogenicity study that two doses of a modified B.1.351 spike (S)-Trimer vaccine candidate (B.1.351 S-Trimer) can induce strong humoral immune responses that can broadly neutralize the original strain (Wuhan-Hu-1), UK variant (B.1.1.7), South African variant (B.1.351) and Brazil variant (P.1) strains of SARS-CoV-2. Furthermore, while immunization with two doses (prime-boost) of a prototype S-Trimer vaccine (based on the original SARS-CoV-2 strain) induced lower levels of cross-reactive neutralization against the B.1.351 variant, a third dose (booster dose) administered with either the prototype S-Trimer or B.1.351 S-Trimer was able to increase neutralizing antibody titers against B.1.351 to levels comparable to neutralizing antibody titers against the original strain elicited by two doses of the prototype S-Trimer.

Despite the tremendous progress and unprecedented speed of development of COVID-19 vaccines, a new record for daily COVID-19 cases was set in April 2021, over 16 months after the SARS-CoV-2 virus outbreak first emerged. Total deaths caused by COVID-19 surpassed 3 million in May 2021, with 1 million deaths having accumulated in the prior 3 months alone.

Most concerning is the emergence of multiple new SARS-CoV-2 variants of concern (VOC) starting in late 2020 that is concurrent with a surge in COVID-19 cases globally. These VOCs appear to be associated with mutations in the spike (S) protein which could potentially increase the rate of viral transmission and/or escape immunity induced by vaccination with first-wave COVID-19 vaccines based on the original strain of SARS-CoV-2 (Wuhan-Hu-1). The emergence and spread of the B.1.1.7 variant in the United Kingdom (UK), B.1.351 variant in South Africa and P.1 variant in Brazil have led to their classification as VOCs. These VOCs all include the N501Y mutation in the receptor-binding domain (RBD) of the S protein that is reported to increase transmission by 40% to 70%. The B.1.351 and P.1 variants have two additional RBD mutations—E484K and K417—that may allow immune escape from antibodies induced by prototype vaccines and natural infection.

Randomized, controlled clinical trials of prototype COVID-19 vaccines suggest decreased vaccine efficacy against VOCs compared to original SARS-CoV-2 strains. NVX-CoV2373, an adjuvanted protein-based COVID-19 vaccine, demonstrated 89% efficacy in the UK (where B.1.1.7 predominates) but only 49% efficacy in South Africa (where B.1.351 predominates). ChAdOx1, an adenovirus-vectored COVID-19 vaccine, demonstrated only 10% efficacy against the B.1.351 variant. Pfizer vaccinees demonstrated 75% effectiveness against the B.1.351 variant whereas 95% efficacy was demonstrated against the original strain. Subjects vaccinated with Coronavac, an inactivated SARS-CoV-2 vaccine based on the original SARS-CoV-2 strain, demonstrated no detectable neutralizing antibody titers against P.1.

While there is some encouraging evidence that the prototype COVID-19 vaccines are likely to protect against severe disease and death caused by the VOCs, lower vaccine efficacy against any COVID-19 disease with increased transmission rates could make achieving herd immunity particularly difficult, a problem that could be further compounded by the shortage of COVID-19 vaccines globally. If not effectively controlled, the rapid global spread of SARS-CoV-2 VOCs could potentially lead to the continued emergence of new variants of interest or VOCs potentially harboring new escape mutations, such as the Indian variant (B.1.617) which emerged concurrent with a massive spike in COVID-19 cases in the spring of 2021 and has now been declared a new VOC by the WHO.

These circumstances necessitate the rapid evaluation of booster dose strategies in order to enhance neutralizing antibody responses to VOCs and the development of second generation COVID-19 vaccines which may confer optimized broadly-protective, cross-neutralizing characteristics. In this study, a modified B.1.351 Spike-Trimer antigen (dubbed "B.1.351 S-Trimer") was generated and compared with a prototype S-Trimer (Liang et al., *Nat. Comms.*, 12:1346, 2021; Richmond et al., *Lancet*, 397: 682-694, 2021) in a mouse immunogenicity study. Heterologous prime-boost and bivalent vaccine approaches were also evaluated, as well as the effect of a third dose (booster dose).

Results

Figure 9:
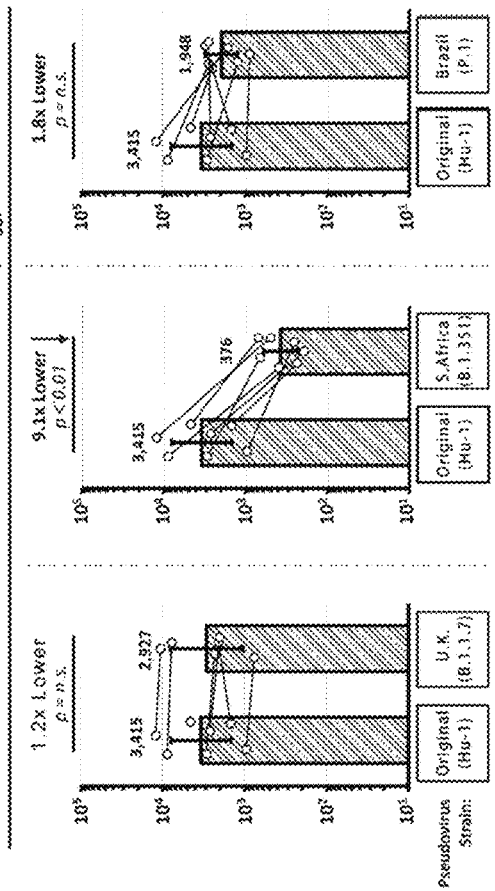
FIG. 9 shows the detection of SARS-CoV-2 neutralizing antibodies and ACE2-competitive titers in human COVID-19 convalescent sera. 8 human convalescent sera (HCS) samples with moderate-to-high antibody titers collected from COVID-19 patients infected with original strain (Wuhan-Hu-1) were analyzed for (a) SARS-CoV-2 pseudovirus neutralization titers and (b) ACE2-competitive ELISA titers based on the original (Wuhan-Hu-1), UK (B.1.1.7), South African (B.1.351) and Brazil (P.1) strains. Data are presented comparing variant strains titers to original strain titers. Dots represent data for individual HCS samples, and bars represent geometric mean titers (GMT) of half maximal effective concentration ($EC_{50}$) values. Error bars represent 95% confidence intervals (95% CI).
Figure 9:
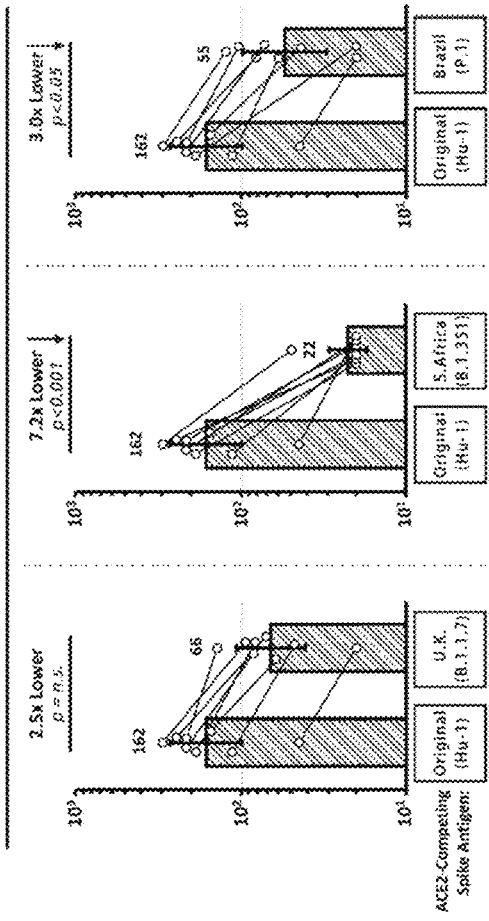

Detection of Cross-Reactive Neutralizing Antibodies in Human COVID-19 Convalescent Sera Eight human convalescent serum (HCS) samples with moderate-to-high antibody titers collected from COVID-19 patients infected with the original strain were analyzed for SARS-CoV-2 pseudovirus neutralization titers (FIG. 9A) and ACE2-competitive ELISA titers (FIG. 9B) against the original strain, UK variant (B.1.1.7), South African variant (B.1.351) and Brazil variant (P.1) strains. Neutralizing antibody titers in HCS against B.1.1.7 appeared to be similar to the original strain, and differences in ACE2-competitive titers were also not statistically significant. However, significantly lower antibody titers in HCS were observed against B.1.351 (7- to 9-fold lower) and P.1 (2- to 3-fold lower) compared to titers against the original strain.

Production and Characterization of Spike Antigens Based on Original and B.1.351 Strains Covalently-trimerized S-protein antigens were produced based on the original SARS-CoV-2 strain (Prototype S-Trimer) and South African variant (B.1.351 S-Trimer) utilizing Trimer-Tag© technology (Liang et al., *Nat. Comms.*, 12:1346, 2021). Prototype S-Trimer is based on the native spike ectodomain sequences of the original SARS-CoV-2 strain (Wuhan-Hu-1), whereas the modified B.1.351 S-Trimer (SEQ ID NO: 10) contains 3 RBD mutations (K417N, E484K, N501Y) and the D614G mutations found in the B.1.351 variant strain, while the N-terminal domain (NTD) and S2 sequences are based on the original strain (FIG. 10A).

Figure 10:
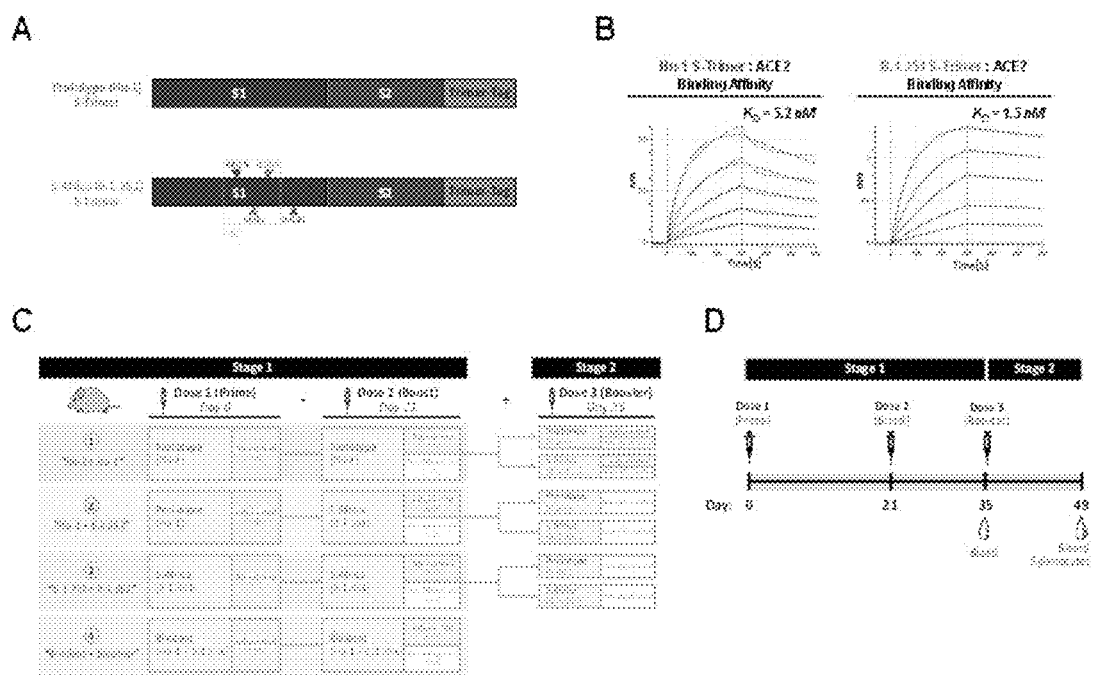
FIG. 10 shows prototype and modified B.1.351 S-Trimer antigens and mouse immunogenicity study design. (a) Schematic representations of Prototype S-Trimer and the modified B.1.351 S-Trimer containing 3 RBD mutations and the D614G mutations in the B.1.351 variant. (b) Determination of the binding affinity ($K_D$) between S-Trimers (Prototype and B.1.351) and human ACE2-Fc by ForteBio BioLayer interferometry. (c) BALB/c mice (n=16-32/group) were immunized in Stage 1 of the study with either two doses of Prototype S-Trimer (3 μg), heterologous prime-boost (dose 1 Prototype S-Trimer; dose 2 B.1.351 S-Trimer; 3 μg of each antigen), two doses B.1.351 S-Trimer (3 μg), or two doses of bivalent vaccine (3 μg Prototype S-Trimer mixed with 3 μg B.1.351 S-Trimer). All animals in Stage 1 received an adjuvanted priming dose (Dose 1) comprising Alum (aluminum hydroxide). For the boost (Dose 2), half of the animals in each group received an adjuvanted boost comprising Alum (aluminum hydroxide), and the other half received non-adjuvanted boost (antigen-only). In Stage 2 of the study, animals in group 1 were randomized to receive a booster dose (Dose 3) with either 3 μg Prototype S-Trimer or 3 μg B.1.351 S-Trimer (half adjuvanted and half non-adjuvanted). Animals in groups 2-3 were randomized to receive a booster (Dose 3) with either 3 μg of non-adjuvanted Prototype or B.1.351 S-Trimer. (d) BALB/c mice were immunized in Stage 1 with priming (Dose 1) on day 0 and boost (Dose 2) on day 21, with primary analysis for humoral immunogenicity was conducted on day 35 blood samples. In Stage 2, a booster dose (Dose 3) was given on day 35 and primary analysis for humoral and cellular immune responses was conducted on day 49 blood samples.

The binding affinity ($K_D$) of purified S-Trimer antigens to the human ACE2 receptor using ForteBio BioLayer interferometry was shown to be approximately 5.2 nM for Prototype S-Trimer and 1.5 nM for B.1.351 S-Trimer (FIG. 10B). The 3- to 4-fold higher ACE2 binding affinity of the B.1.351 S-Trimer compared to Prototype S-Trimer is similar to previously-reported results.

Immunogenicity of Prototype and B.1.351 S-Trimer prime-boost (2 dose) regimens in mice BALB/c mice were immunized in Stage 1 of the study (FIGS. 10C-10D) with either two doses (Day 0 and Day 21) of Prototype S-Trimer, heterologous prime-boost (Dose 1 Prototype S-Trimer+Dose 2 B.1.351 S-Trimer), two doses of B.1.351 S-Trimer, or two doses of bivalent vaccine (Prototype S-Trimer mixed with B.1.351 S-Trimer). All animals in Stage 1 received an adjuvanted priming dose (Dose 1) comprising Alum (aluminum hydroxide). For the second dose (boost), half of the animals in each group received an adjuvanted boost comprising Alum (aluminum hydroxide), and the other half received non-adjuvanted boost (antigen-only). Humoral immunogenicity analysis was conducted on Day 35 blood samples (2 weeks post-dose 2) based on pseudovirus neutralization titers against the original strain and three VOCs (B.1.1.7, B.1.351 and P.1).

Neutralizing antibody titers against B.1.351 and P.1 were highest in the groups receiving two doses of either B.1.351 S-Trimer and bivalent vaccine (FIG. 11A), with the former inducing the numerically-highest titers. Compared to animals receiving two doses of Prototype S-Trimer, animals receiving two doses of B.1.351 S-Trimer observed 13.8-fold higher neutralizing antibody titers against B.1.351 pseudovirus and 2.4-fold higher titers against P.1 pseudovirus. Interestingly, the group receiving heterologous prime boost (Dose 1 Prototype S-Trimer+Dose 2 B.1.351 S-Trimer) did not induce higher antibody titers against B.1.351 and P.1 compared to animals receiving two doses of Prototype S-Trimer.

Neutralizing antibody titers against the original and B.1.1.7 variant pseudoviruses were similar across all vaccine groups (FIG. 11A), demonstrating that two doses of the B.1.351 vaccine were able to elicit antibodies which are capable of fully back-neutralizing against the original strain and can also fully protect against the B.1.1.7 variant.

ACE2-competitive ELISA results were consistent with and further confirmed the pseudovirus neutralization results (FIG. 11B). and ACE2-competitive ELISA titers were found to be correlated with pseudovirus neutralization titers across all four strains tested.

Figure 12:
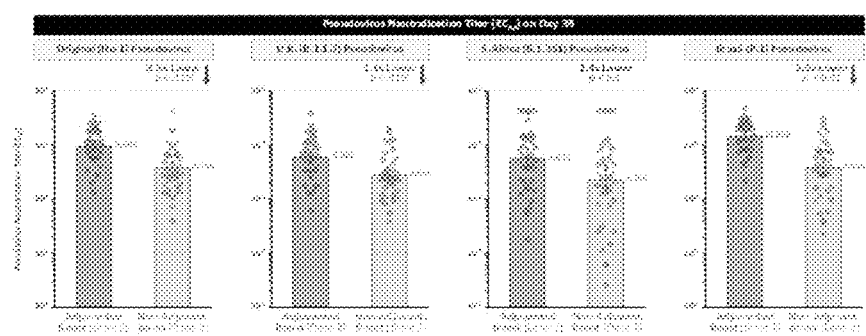
FIG. 12 shows effect of adjuvants on humoral immune response for boost (Dose 2) and booster (Dose 3). Humoral immune responses in the study were evaluated based on SARS-CoV-2 pseudovirus neutralization assays against original strain, UK (B.1.1.7), South African (B.1.351) and Brazil (P.1) strains. Results for pseudovirus neutralization titers based on factorial analyses and are shown here for (a) Stage 1 where all animals received an adjuvanted priming dose (Dose 1) comprising Alum (aluminum hydroxide), whereas half of the animals received an adjuvanted boost (Dose 2) comprising Alum (aluminum hydroxide), and the remaining half of the animals received non-adjuvanted boost (antigen-only), and (b) Stage 2 where half of the animals in Group 1 received an adjuvanted booster Dose 3 comprising Alum (aluminum hydroxide) and the remaining half of the animals received non-adjuvanted booster (antigen-only). Dots represent individual animals; bars represent geometric mean titers (GMT) of $EC_{50}$ values, and error bars represent 95% confidence intervals (95% CI). P values <0.05 were considered significant.
Figure 12:
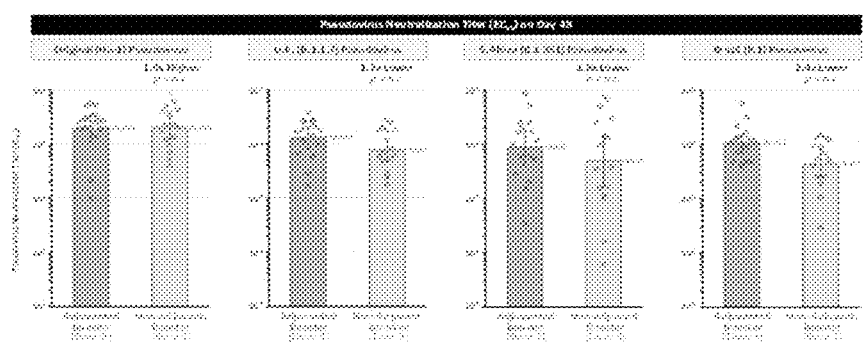

The effect of adjuvanted versus non-adjuvanted second doses (boost) was done via factorial analysis based on pseudovirus neutralization titers (FIG. 12A). Animals receiving an adjuvanted boost appeared to induce approximately 2- to 4-fold higher neutralizing antibody titers compared to animals receiving non-adjuvanted boost (antigen-only), demonstrating the positive impact of adjuvants on immune response when utilized for boost.

Immunogenicity of Prototype or B.1.351 S-Trimer booster doses (dose 3) in mice

In Stage 2 of the study (FIG. 10C), animals in Prototype S-Trimer prime-boost group were randomized to receive a booster dose (Dose 3) on Day 35 with either Prototype S-Trimer or B.1.351 S-Trimer (half adjuvanted and half non-adjuvanted). Animals in the heterologous prime-boost group and B.1.351 S-Trimer prime-boost group were randomized to receive a booster dose (Dose 3) with either non-adjuvanted Prototype or non-adjuvanted B.1.351 S-Trimer. Analyses for humoral and cellular immune responses were conducted on Day 49 samples (2 weeks post-dose 3).

Across all vaccine groups after receiving a booster dose, neutralizing antibody titers against the original strain (FIG. 13A) and B.1.1.7 variant (FIG. 13B) pseudoviruses were similar, and fold-increases in titers after the booster (Dose 3) compared to after Dose 2 were also similar across groups. Neutralizing antibody titers increased by about 1.6- to 3.1-fold against the original strain and 1.8- to 2.8-fold against B.1.1.7 variant on average across the booster group.

In the groups receiving three doses of vaccine which included a Prototype S-Trimer priming dose (Dose 1), neutralizing antibody titers against the B.1.351 variant pseudovirus (FIG. 13C) increased by 1.7- to 4.6-fold on average after the booster dose, achieving levels comparable to neutralization against the original strain elicited by two doses of Prototype S-Trimer. We note that variability in B.1.351 neutralization titers in these groups appeared to be higher than neutralization against the other strains tested. In the group receiving three doses of B.1.351 S-Trimer, neutralizing antibody titers against B.1.351 did not significantly increase after the booster dose, likely because titers were already at high biological levels after the boost (Dose 2).

Interestingly, in the groups perceiving prime-boost with Prototype S-Trimer followed by a booster dose (either Prototype S-Trimer or B.1.351 S-Trimer), P.1 neutralization titers (FIG. 13D) did not appear to increase following the booster dose. Similar to B.1.351 neutralization titers, P.1 neutralization titers were numerically highest in the group receiving three doses of B.1.351 S-Trimer.

Figure 13:
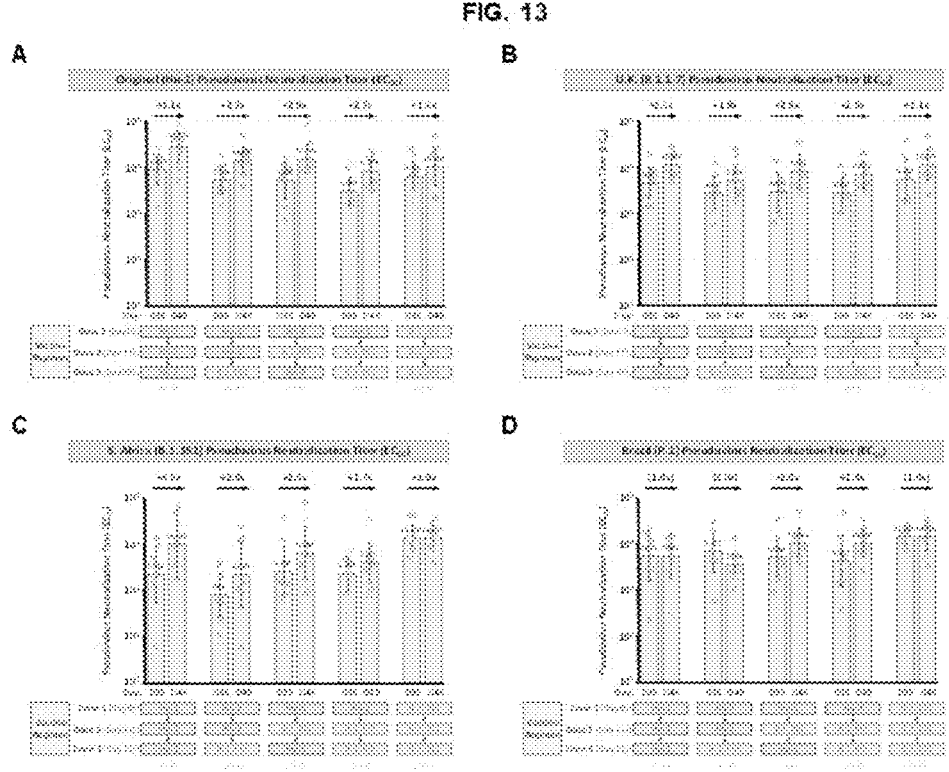
FIG. 13 shows humoral immune response of 3 doses of prototype and/or B.1.351 Spike-Trimer antigens in mice. Humoral immune responses in Stage 2 of the study were evaluated in animals receiving a non-adjuvanted booster (Dose 3) on Day 49 (2 weeks after Dose 3) based on SARS-CoV-2 pseudovirus neutralization assays against (a) Original (Wuhan-Hu-1) strain, (b) UK (B.1.1.7) variant, (c) South African (B.1.351) variant and (d) Brazil (P.1) variant pseudoviruses. Neutralization titers on Day 35 (2 weeks after Dose 2) are also shown. Fold differences in titers (Day 49 versus Day 35) in each booster group are shown. Dots represent individual animals; bars represent geometric mean titers (GMT) of half maximal effective concentration ($EC_{50}$) values, and error bars represent 95% confidence intervals (95% CI).
Figure 14:
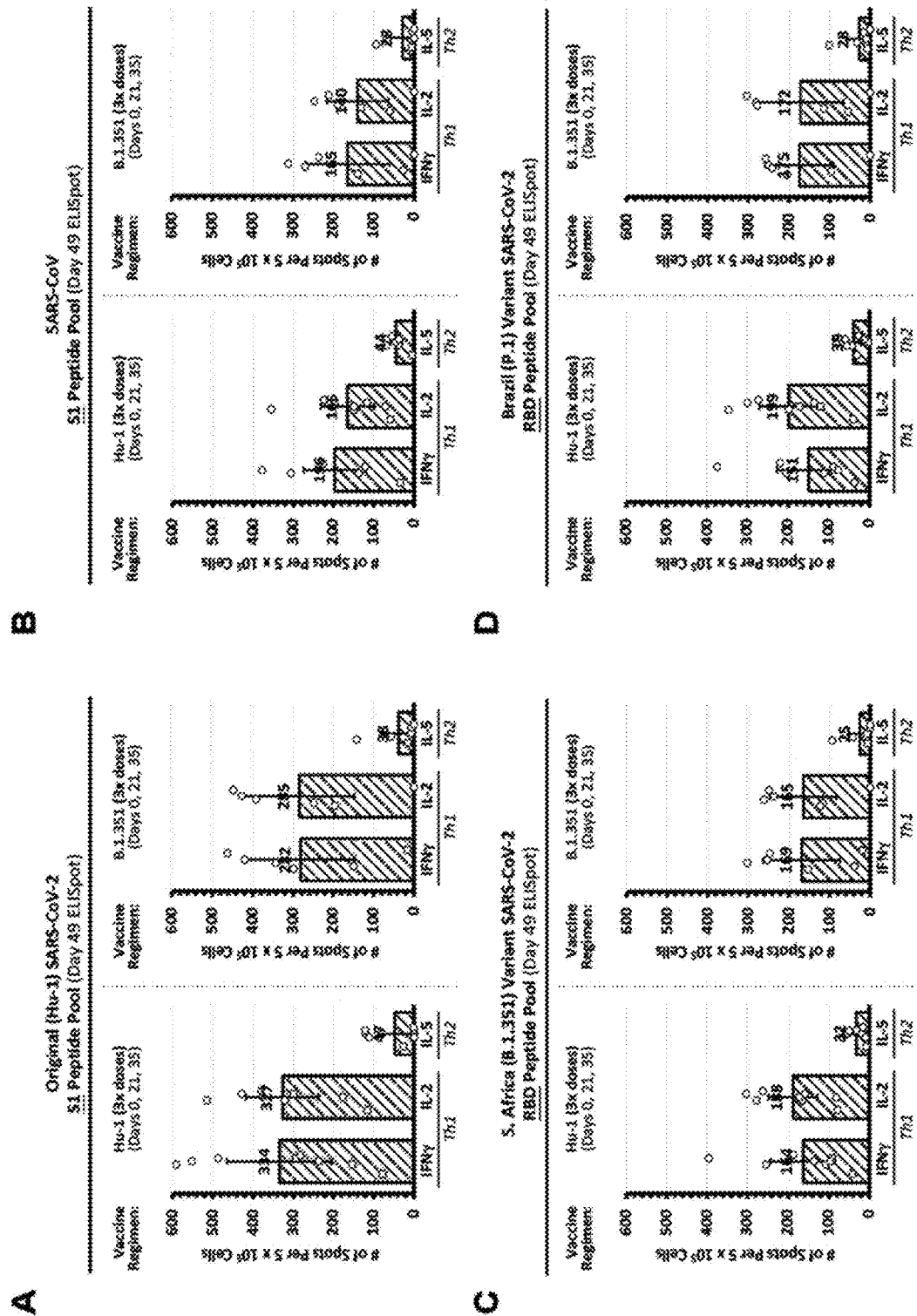
FIG. 14 shows cell-mediated immune responses of 3 doses of prototype or B.1.351 Spike-Trimer antigens in mice. Cell-mediated immune responses in Stage 2 of the study were evaluated on Day 49 (2 weeks after dose 3) based on ELISpot detecting Th1 cytokines (IFNγ and IL-2) or Th2 cytokine (IL-5) in harvested splenocytes stimulated with (a) S1 peptide pool from original (Wuhan-Hu-1) strain, (b) S1 peptide pool from SARS-CoV, (c) RBD peptide pool from B.1.351 variant, or (d) RBD peptide pool from P.1 variant. Dots represent individual animals; bars represent group mean values, and error bars represent 95% confidence intervals (95% CI).
Figure 15:
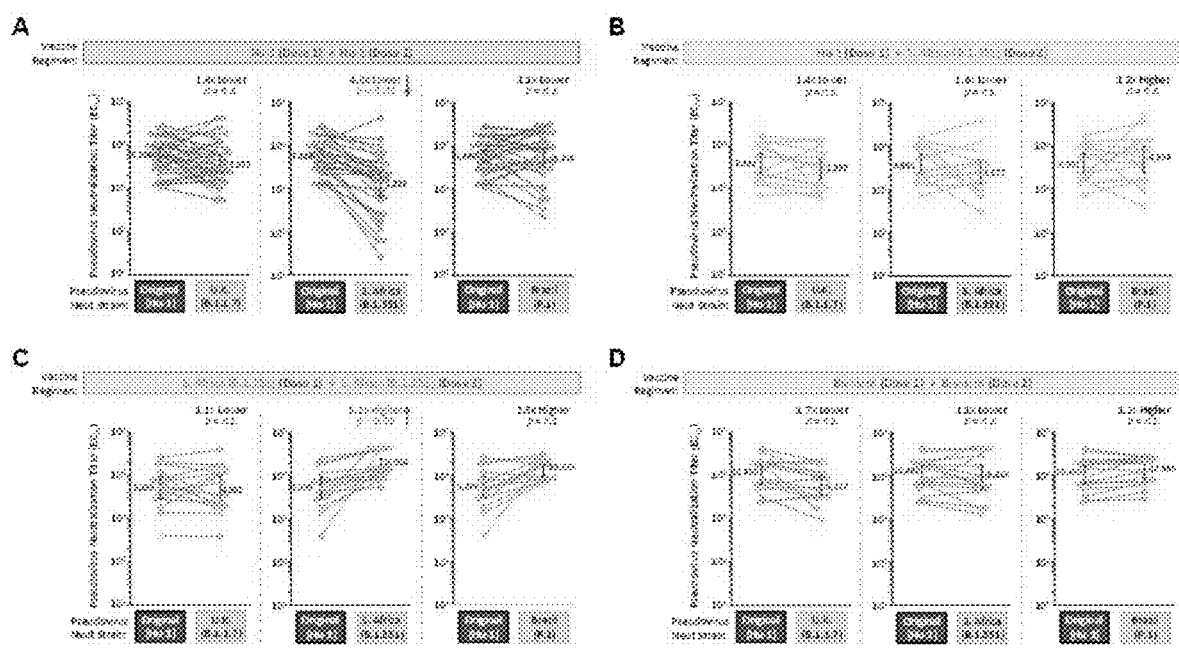
FIG. 15 shows cross-neutralization based on pseudovirus neutralization titers after 2 doses of prototype and/or B.1.351 S-Timer antigens in mice. Humoral immune responses in Stage 1 of the study were evaluated on Day 35 (2 weeks after dose 2) based on SARS-CoV-2 pseudovirus neutralization assays against original strain, UK variant (B.1.1.7), South African variant (B.1.351) and Brazil variant (P.1) strains. Results are shown for (a) Group 1 (two doses of Prototype S-Trimer), (b) Group 2 (heterologous prime-boost), (c) Group 3 (two doses B.1.351 S-Trimer), or (d) two doses of bivalent vaccine. Results from individual animals are represented by dots in each figure, with lines connecting the Original and variant neutralization titers. Geometric mean titers (GMT) of $EC_{50}$ values are shown, and error bars represent 95% confidence intervals (95% CI). P values <0.05 were considered significant (n.s., not significant).
Figure 16:
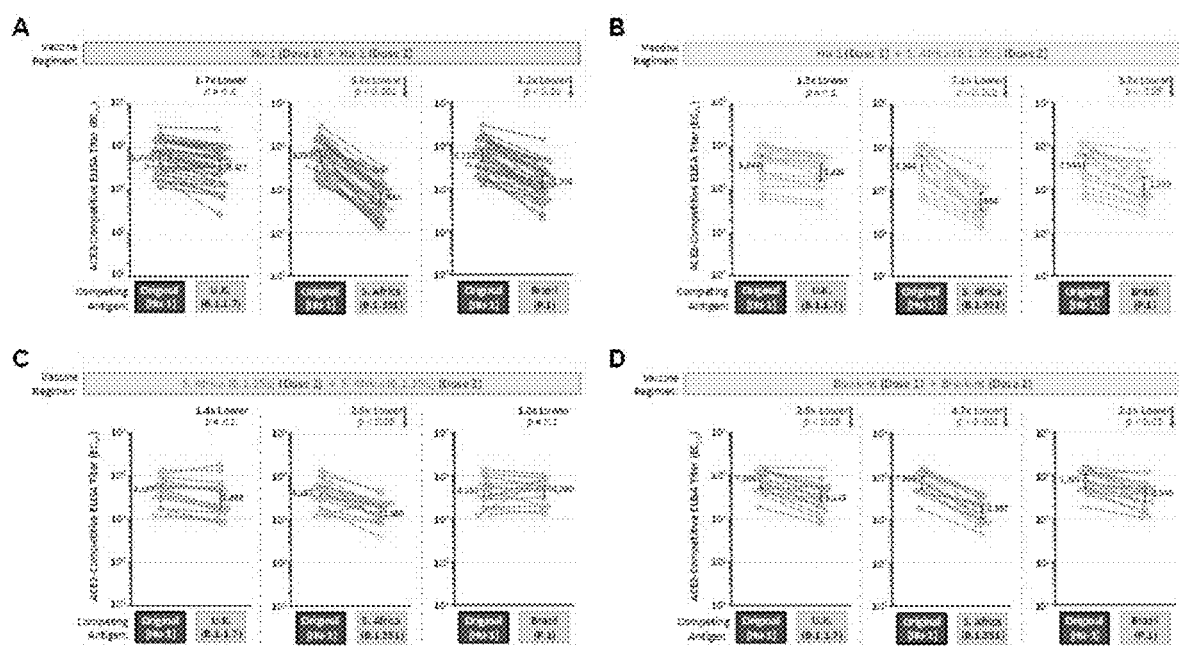
FIG. 16 shows cross-neutralization based on ACE2-competitive titers after 2 doses of prototype and/or B.1.351 S-Timer antigens in mice. Humoral immune responses in Stage 1 of the study were evaluated on Day 35 (2 weeks after dose 2) based on ACE2-competitive ELISA assays against original strain, UK variant (B.1.1.7), South African variant (B.1.351) and Brazil variant (P.1) strains. Results are shown for (a) Group 1 (two doses of Prototype S-Trimer), (b) Group 2 (heterologous prime-boost), (c) Group 3 (two doses B.1.351 S-Trimer), or (d) two doses of bivalent vaccine. Results from individual animals are represented by dots in each figure, with lines connecting the Original and variant neutralization titers. Geometric mean titers (GMT) of $EC_{50}$ values are shown, and error bars represent 95% confidence intervals (95% CI). P values <0.05 were considered significant (n.s., not significant).
Figure 17:
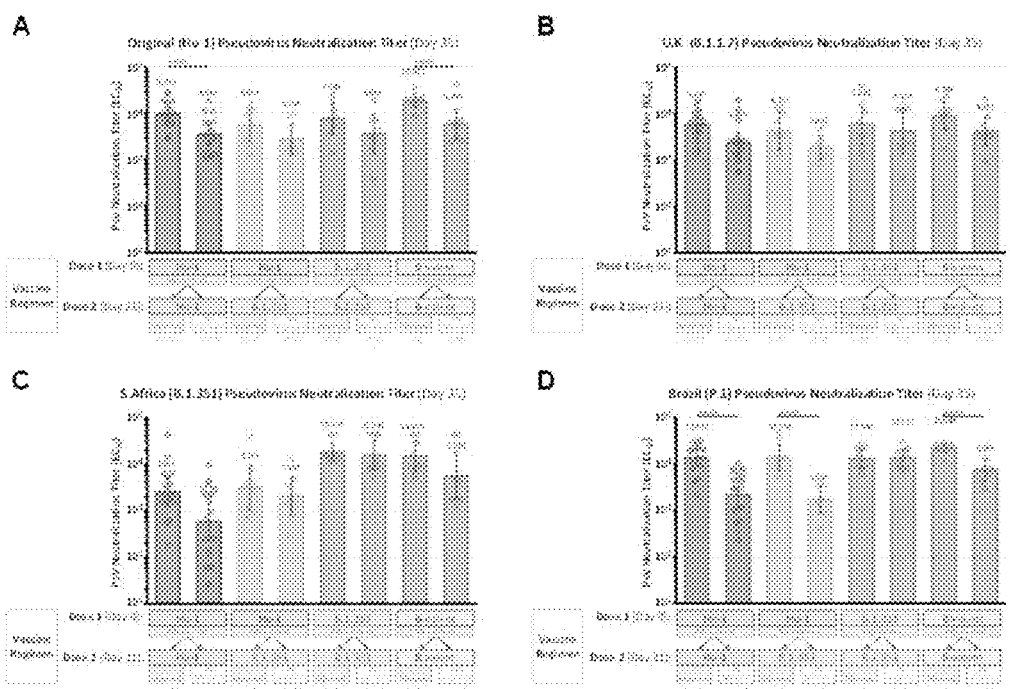
FIG. 17 shows humoral immune response after 2 doses of prototype and/or B.1.351 S-Timer antigens in mice. Humoral immune responses in Stage 1 of the study were evaluated on Day 35 (2 weeks after dose 2) based on SARS-CoV-2 pseudovirus neutralization assays against (a) original strain, (b) UK variant (B.1.1.7), (c) South African variant (B.1.351) and (d) Brazil variant (P.1) strains. All animals in Stage 1 received an adjuvanted priming dose (Dose 1) comprising Alum (aluminum hydroxide), whereas half of the animals in each group received an adjuvanted boost (Dose 2) comprising Alum (aluminum hydroxide), and the other half received non-adjuvanted boost (antigen-only). Results here are shown for subgroups of animals receiving either adjuvanted or non-adjuvanted boost (dose 2). Dots represent individual animals; bars represent geometric mean titers (GMT) of $EC_{50}$ values, and error bars represent 95% confidence intervals (95% CI). P values <0.05 were considered significant.
Figure 18:
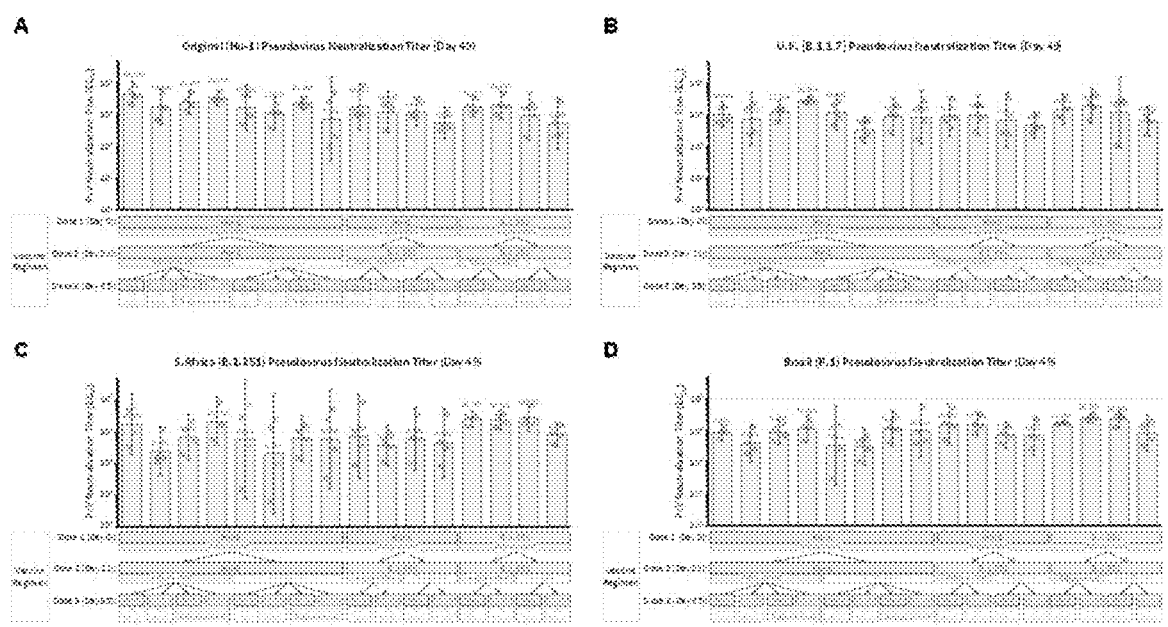
FIG. 18 shows humoral immune response after 3 doses of prototype and/or B.1.351 S-Timer antigens in mice. Humoral immune responses in Stage 2 of the study were evaluated on Day 49 (2 weeks after dose 3) based on SARS-CoV-2 pseudovirus neutralization assays against (a) Original (Wuhan-Hu-1) strain, (b) UK (B.1.1.7) variant, (c) South African (B.1.351) variant and (d) Brazil (P.1) variant pseudoviruses. Results here are shown for all subgroups (representing all vaccination combinations) in the study (n=4/subgroup). Dots represent individual animals; bars represent geometric mean titers (GMT) of $EC_{50}$ values, and error bars represent 95% confidence intervals (95% CI).

In the group of animals receiving two doses of Prototype S-Trimer vaccine (prime-boost), a subsequent booster dose (Dose 3) with B.1.351 S-Trimer did not appear to induce higher neutralizing antibodies against B.1.351 or P.1 compared to animals receiving a booster dose with Prototype S-Trimer (FIGS. 13C-13D).

The effect of adjuvanted versus non-adjuvanted booster doses (Dose 3) on humoral immunogenicity in group 1 was conducted using factorial analysis based on pseudovirus neutralization titers (FIG. 12B). Animals receiving an adjuvanted booster dose did not appear to induce significantly higher neutralizing antibody titers compared to animals receiving non-adjuvanted booster doses (antigen-only).

Cell-Mediated Immune Response Induced by 3 doses of Prototype or B.1.351 S-Trimer in Mice Cell-mediated immune responses were evaluated in animals receiving either three doses of Prototype S-Trimer or three doses of B.1.351 S-Trimer on Day 49 (2 weeks after dose 3). Cell-mediated immunity (CMI) was assessed by ELISpot detecting Th1 cytokines (IFNγ and IL-2) or Th2 cytokine (IL-5) in harvested mouse splenocytes stimulated with either original (Wuhan-Hu-1) strain S1 peptide pool, SARS-CoV S1 peptide pool, B.1.351 variant RBD peptide pool, or P.1 variant RBD peptide pool.

Strong Th1-biased CMI was observed in both vaccine groups across all stimulants tested (FIGS. 14A-14D). The Th1-biased CMI induced by adjuvanted S-Trimer antigen is consistent with results in Liang et al., *Nat. Comms.*, 12:1346, 2021.

Importantly, the magnitude of CMI appeared similar in both vaccine groups across all stimulants, suggesting that broad cross-reactive CMI directed to VOCs (including B.1.1.7, B.1.351 and P.1) can be induced by both the Prototype and B.1.351 S-Trimer vaccines. Cross-reactive CMI against SARS-CoV S1 peptide pool (FIG. 14B) did appear to be at levels which were about 40-50% lower than CMI to original strain of SARS-CoV-2 (FIG. 14A), in-line with the 79% sequence homology of the S1 domains for SARS-CoV and SARS-CoV-2.

Discussion

Figure 11:
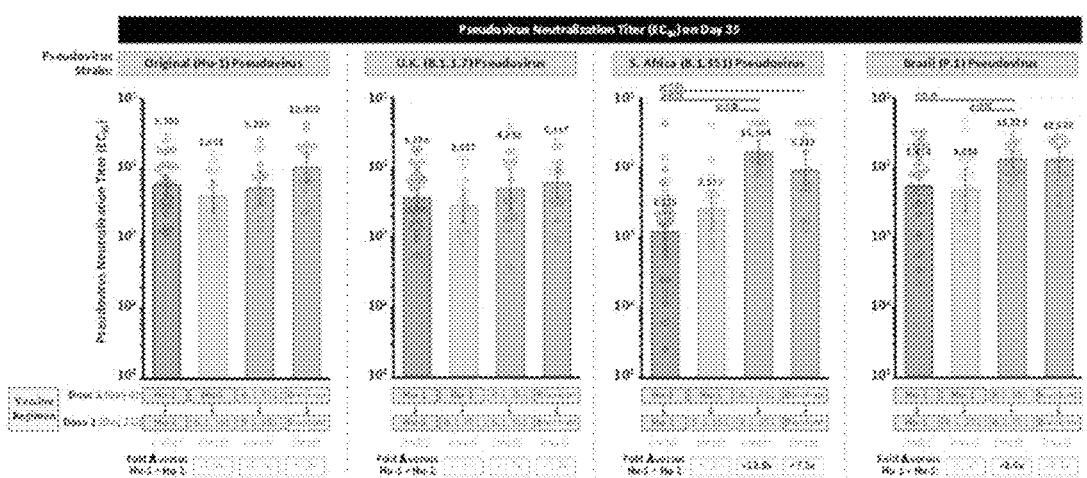
FIG. 11 shows humoral immune response of 2 doses of prototype and/or B.1.351 Spike-Trimer antigens in mice. Humoral immune responses in Stage 1 of the study were evaluated on Day 35 (2 weeks after dose 2) based on (a) SARS-CoV-2 pseudovirus neutralization assays against original strain, UK (B.1.1.7), South African (B.1.351) and Brazil (P.1) strains and (b) ACE2-competitive ELISA detecting competition of vaccine-induced antibodies for binding to ACE2 with S-Trimers based on Original (Wuhan-Hu-1), UK (B.1.1.7), South African (B.1.351) and Brazil (P.1) strains. Dots represent individual animals; bars represent geometric mean titers (GMT) of $EC_{50}$ values, and error bars represent 95% confidence intervals (95% CI). Fold differences (Δ) in GMTs for groups 2-4 compared to group 1 (Prototype S-Trimer) are shown, and statistically-significant differences are shown in black text. P values <0.05 were considered significant.
Figure 11:
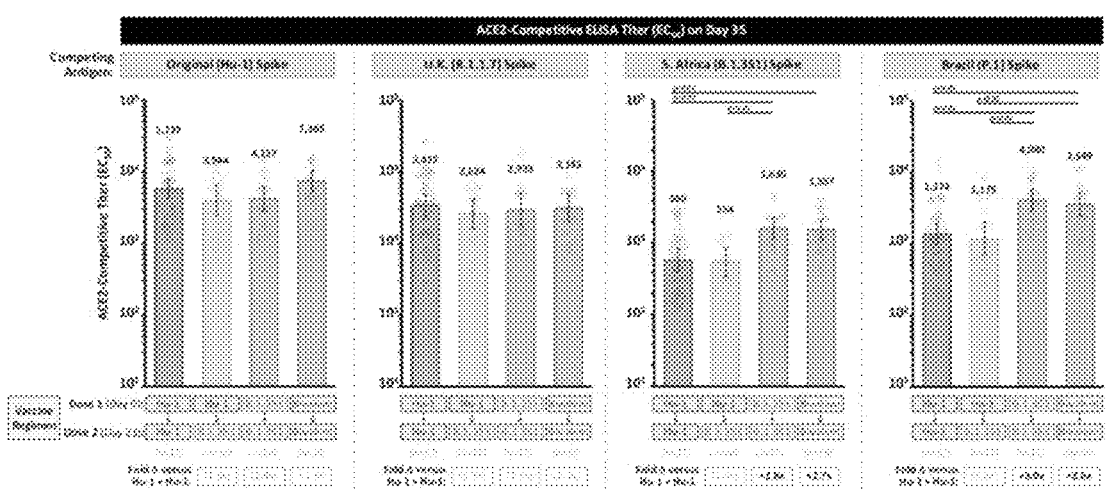

Modified B.1.351 S-Trimer Vaccine Induces Broad Neutralization against Original Strain and Variants of Concern Consistent with results from other studies evaluating prototype COVID-19 vaccines based on the original strain of SARS-CoV-2, in this study Prototype S-Trimer prime-boost vaccination induced lower neutralizing antibody titers against B.1.351 and P.1 variants compared to titers against the homologous original SARS-CoV-2 strain (FIGS. 11A-11B). It is believed that the E484K and K417 mutations in the RBD of both B.1.351 and P.1 variants confer immune escape from antibodies induced by prototype vaccines.

Two doses of modified B.1.351 S-Trimer antigen induced high levels of neutralizing antibodies against the B.1.351 and P.1 variants. Importantly, two doses of B.1.351 S-Trimer was also able to fully back-neutralize against the original SARS-CoV-2 strain, as well as neutralize the B.1.1.7 variant. In contrast, an mRNA COVID-19 vaccine candidate based on the B.1.351 variant spike protein (containing all mutations found in B.1.351) appeared to induce approximately 6-fold lower neutralizing antibody titers against the original SARS-CoV-2 strain compared to the prototype mRNA vaccine in mice (Wu et al., bioRviv 2021.04.13.439482), and results were consistent in a Phase 1 clinical trial for this B.1.351 mRNA vaccine candidate (Wu et al., *N Engl J Med* 2021; 384:1468-1470).

The broad neutralization induced by the modified B.1.351 S-Trimer vaccine candidate could potentially be explained by the chimeric nature of the antigen sequence, which contains 3 RBD mutations (K417N, E484K, N501Y) and the D614G mutations found in the B.1.351 variant strain, while the NTD and S2 sequences are based on the original SARS-CoV-2 strain (Wuhan-Hu-1) (FIG. 10A). Previous studies have identified neutralizing antibodies that target NTD, and emerging evidence suggests that vaccine-induced anti-NTD neutralizing antibodies are co-dominant with anti-RBD neutralizing antibodies, highlighting the importance of NTD. Thus, the data suggests a potential model for inducing broad neutralization whereby a modified B.1.351 S-Trimer antigen could induce (a) anti-RBD antibodies targeting E484K and K417 mutations that can neutralize B.1.351 and P.1 variant strains and (b) anti-NTD antibodies that can neutralize the original strain.

Booster doses following Two Doses of Prototype Vaccine could Strengthen Broad Neutralization Results in this study suggest that a booster dose (with either Prototype S-Trimer or B.1.351 S-Trimer) following two doses of Prototype S-Trimer could increase levels of broad neutralizing antibodies against the original strain and VOCs, including B.1.351. There did not appear to be significant differences in neutralizing antibody titers if the booster dose given was Prototype S-Trimer or B.1.351 S-Trimer. Thus, greater flexibility in effective boosting strategies could be employed based on the supply of prototype and variant vaccines available at a given time.

It should also be noted that heterologous prime-boost (Dose 1 Prototype S-Trimer +Dose 2 B.1.351 S-Trimer) did not induce higher neutralizing antibody titers against B.1.351 and P.1 compared to animals receiving Prototype S-Trimer homologous prime-boost. Furthermore, while a booster dose following Prototype S-Trimer prime-boost increased neutralization titers against the B.1.351 variant by about 2.8- to 4.6-fold (compared to post-dose 2 levels), the titers were still numerically lower but also more variable than animals receiving two doses or three doses of B.1.351 S-Trimer. Additionally, P.1 neutralization titers did not increase in these groups which received Prototype S-Trimer prime-boost followed by a booster and remained 2.7- to 4.1-fold lower than the group receiving three doses of B.1.351 S-Trimer. These results suggest that priming with prototype COVID-19 vaccines may induce some degree of 'original antigenic sin', a phenomenon previously-described for other viruses (such as influenza and dengue) whereby the immune system preferentially responds to the epitopes in the priming immunogen and is less able to respond to the new epitopes in the variant (Vatti et al., $J.$ $Autoimmun.$ 83:12-21, 2017). However, cross-reactive neutralizing antibody titers against VOCs in mice induced by Prototype S-Trimer prime-boost were still relatively high albeit lower than levels induced by the B.1.351 S-Trimer, and neutralization titers could be increased with a booster dose.

The results of booster dose in this example support heterologous prime-boost strategies across different platforms, e.g., utilizing protein-based S-Trimers as booster doses following primary series of adenovirus-vectored, mRNA, and/or inactivated COVID-19 vaccines. Safety concerns have emerged around the safety of multiple doses of mRNA vaccine related to potential PEG sensitization, and anti-vector immunogenicity for adenovirus-vectored vaccines are known to reduce the effectiveness of subsequent homologous doses. Preliminary human clinical data indicates that heterologous prime-boost with adenovirus-vectored and mRNA COVID-19 vaccines (or vice versa) suggest that they induce higher rates of systemic reactogenicity than heir homologous prime-boost counterparts (Shaw et al., $Lancet.$ (2021) doi:10.1016/S0140-6736(21)01115-6).

Broad Cross-Reactive Cell-Mediated Immune Responses Against SARS-CoV-2

While the precise role of cell-mediated immunity (CMI) in the prevention or recovery from COVID-19 remains to be elucidated, there is ample evidence that strong cellular immune responses against the spike (S) protein are induced in COVID-19 patients and that CMI could contribute to the attenuation of symptoms and accelerated clearance of of SARS-CoV-2. Furthermore, it has been reported that up to ~35% of SARS-CoV-2 naïve individuals have some degree of cross-reactive $CD4^+$ T-cell responses to SARS-CoV-2 antigens due to prior infection by other common-cold coronaviruses. In this study, while lower levels of neutralizing antibodies against B.1.351 were induced by Prototype S-Trimer compared with B.1.351 S-Trimer, CMI levels appeared to be similar for both vaccine candidates and were cross-reactive for antigens to SARS-CoV-2 (original strain S1, B.1.351 variant RBD, P.1 variant RBD) and SARS-CoV (S1), suggesting that CMI against coronavirus spike proteins could be more broadly cross-reactive than humoral immune responses. The CMI induced by the S-Trimers in this study appeared to be Th1-biased in nature, which is consistent with previous studies evaluating adjuvanted Prototype S-Trimer (Liang et al., Nat. Comms., 12:1346, 2021; Richmond et al., Lancet, 397: 682-694, 2021).

Use of Adjuvants in Boosting Strategies

Given the high productivity of S-Trimer antigens utilizing Trimer-Tag technology and the potential to rapidly scale-up production to billions of doses, the potential for "adjuvant sparing," should the supply of adjuvants be a limiting factor for the availability of COVID-19 vaccines, were evaluated in this study.

Because the use of adjuvants is believed to establish immunological priming, the administration of adjuvanted versus non-adjuvanted second dose (boost) and third dose (booster) doses were evaluated and compared. Animals receiving an adjuvanted boost induced 2-4 fold higher neutralizing antibody titers compared to animals receiving non-adjuvanted boost (antigen-only) (FIG. 12A), suggesting that adjuvants may still be needed for second doses in the primary vaccination series to achieve an optimal immune response. However, animals receiving an adjuvanted booster (third dose) did not appear to induce significantly higher neutralizing antibody titers compared to animals receiving non-adjuvanted booster doses (antigen-only) (FIG. 12B).

Methods

Protein Expression and Purification

The Prototype S-Trimer and modified B.1.351 S-Trimer antigens were produced and purified as previously described (Liang et al., Nat. Comms., 12:1346, 2021) and used for immunogenicity studies. S-Trimer antigens based on B.1.1.7 variant and P.1 variant were also produced and used for ACE2-competitive ELISA assays. cDNA encoding the ectodomain of the respective SARS-CoV-2 variant strain Spike (S) proteins were subcloned into the pTRIMER mammalian expression vector to allow in-frame fusion to Trimer-Tag, which is capable of self-trimerization via disulfide bonds. After transient transfection in 293F cells, the variant S-Trimer antigens were expressed and secreted at sufficient levels to enable further characterization and mouse immunogenicity studies. To obtain the variant S-Trimer antigens in a highly-purified form for characterization and vaccine studies, an affinity purification scheme as previously described (Liang et al., Nat. Comms., 12:1346, 2021) was utilized to purify the antigens to near homogeneity in a single step.

Receptor binding studies of S-Trimer to human ACE2

The binding affinity of S-Trimer to ACE2 was assessed by Bio-Layer Interferometry measurements on ForteBio Octet QKe (Pall). ACE2-Fc (10 µg/mL) was immobilized on Protein A (ProA) biosensors (Pall). Real-time receptor-binding curves were obtained by applying the sensor in two-fold serial dilutions of S-Trimer (22.5-36 µg/mL in PBS). Kinetic parameters ($K_{on}$ and $K_{off}$) and affinities ($K_D$) were analyzed using Octet software, version 12.0. Dissociation constants ($K_D$) were determined using steady state analysis, assuming a 1:1 binding model for a S-Trimer (Prototype or B.1.351) to ACE2-Fc.

Immunogenicity analysis of Prototype S-Trimer and modified B.1.351 S-Trimer in mice BALB/c mice (n=16-32/group) were immunized in Stage 1 of the study with either two doses (Day 0 and Day 21) of Prototype S-Trimer (3 µg), heterologous prime-boost (dose 1 Prototype S-Trimer; dose 2 B.1.351 S-Trimer; 3 µg of each antigen), two doses B.1.351 S-Trimer (3 µg), or two doses of bivalent vaccine (3 µg Prototype S-Trimer mixed with 3 µg B.1.351 S-Trimer). All animals in Stage 1 received an adjuvanted priming dose (Dose 1), whereas half of the animals in each group received an adjuvanted boost (Dose 2), and the other half received non-adjuvanted boost (antigen-only). In Stage 2 of the study, animals in group 1 were randomized to receive a booster (Dose 3 on Day 35) with either 3 µg Prototype or 3 µg B.1.351 S-Trimer (half adjuvanted and half non-adjuvanted). Animals in groups 2-3 were randomized to receive a booster (Dose 3) with either 3 µg of non-adjuvanted Prototype or B.1.351 S-Trimer. In Stage 1, primary analysis for humoral immunogenicity was conducted on day 35 blood samples. In Stage 2, primary analysis for humoral and cellular immune responses was conducted on day 49 blood samples. Animals were bled from tail veins for humoral immune responses analyses. Spleens were removed after sacrifice for ELISpot assays.

ACE2-Competitive ELISA Assays 96-well plates (Corning) were coated with 1 µg/mL ACE2-Fc (100 µL/well) at 4° C. overnight, blocked with 2% non-fat milk 37° C. for 2 h. After washing 3 times with PBST, the plates were incubated with 100 ng/mL S-Trimer (Prototype, B.1.351, B.1.1.7 or P.1) mixed with serially diluted antisera for 1 h at 37° C. After washing 3 times with PBST, the plates were incubated with 1:5000 dilution of rabbit anti-Trimer-Tag antibody (Clover Biopharmaceuticals) at 37° C. for 1 h, followed by washing 3 times with PBST and then a 1:20000 dilution of goat anti-rabbit IgG-HRP (Southern Biotech). After washing 3 times with PBST, TMB (Thermo Scientific) was added for signal development. The percentage of inhibition was calculated as follows: % inhibition=[(A−Blank)−(P−Blank)]/(A−Blank)×100, where A is the maximum OD signal of S-Trimer binding to ACE2-Fc when no serum was present, and P is the OD signal of S-Trimer binding to ACE2-Fc in presence of serum at a given dilution. The $IC_{50}$ of a given serum sample was defined as the reciprocal of the dilution where the sample shows 50% competition.

Pseudovirus Neutralization Assays

SARS-CoV-2 pseudovirus neutralization assay for the original (Wuhan-Hu-1) strain and variant B.1.1.7, B.1.351 and P.1 strains were conducted. To evaluate the SARS-CoV-2 pseudovirus neutralization activity of antisera, samples were first heat-inactivated for 30 min and serially diluted (3-fold), incubated with an equal volume of 650 $TCID_{50}$ pseudovirus at 37° C. for 1 h, along with virus-alone (positive control) and cell-alone (negative control). Then, freshly-trypsinized ACE2 overexpression-293 cells were added to each well at 20000 cells/well. Following 24 h incubation at 37° C. in a 5% CO2 incubator, the cells were lysed and luciferase activity was determined by a Luciferase Assay System (Beyotime), according to the manufacturer's protocol. The $EC_{50}$ neutralizing antibody titer of a given serum sample was defined as the reciprocal of the dilution where the sample showed the relative light units (RLUs) were reduced by 50% compared to virus alone control wells.

Splenocyte Stimulation and ELISpot Assays

To detect antigen-specific T-cell responses, ELISpot kits (Mabtech) measuring Th1 cytokines (IFN-γ, IL-2) and Th2 cytokine (IL-5) were used per manufacturer's instructions. Splenocytes from immunized mice or PBMC from immunized mice were harvested 2 weeks after the third immunization. 5×10⁵ splenocytes (96-well plate) were stimulated in vitro with 2 µg/mL of either original SARS-CoV-2 51 peptide pool, SARS-CoV S1 peptide pool, B.1.351 RBD peptide pool or P.1 RBD peptide pool. Phorbol 12-myristate 13-acetate (PMA) and ionomycin as the non-specific stimulus were added to the positive control wells, whereas the negative control well received no stimuli. After 24-48 h incubation, biotinylated detection antibodies from the ELISpot kits and SA-ALP/SA-HRP were added. Blots were developed by the addition of BCIP/NBT or AEC substrate solution, which produced colored spots after 5-30 min incubation in the dark. Finally, the IFN-γ, IL-2 and IL-5 spot-forming cells (SFCs) were counted using an automatic ELISpot reader (CTL).

Example 4: Immunogenicity of Adjuvanted SARS-CoV-2 Vaccine

To rapidly express the S-Trimer antigen, Trimer-Tag technology was employed (Liu et al., Scientific Reports, 7(1): 8953, 2017). cDNA encoding the ectodomain of wild-type SARS-CoV-2 Spike (S) protein was subcloned into the pTRIMER mammalian expression vector to allow in-frame fusion to Trimer-Tag, which is capable of self-trimerization via disulfide bonds. After stable transfection into CHO cells, subsequent screening for high-titer production clones, and extensive process optimization, a fed-batch serum free cell culture process in bioreactor was developed leading to high-level expression of S-Trimer as a secreted protein with a titer around 500 mg/L.

To obtain S-Trimer in a highly-purified form for vaccine studies, an affinity purification scheme was developed by taking advantage of the high binding-affinity between Trimer-Tag and Endo180, a collagen receptor capable of binding to the C-terminal region of Type 1 procollagen and to mature collagen. Endo180-Fc fusion protein was loaded onto a Protein A column and captured by the resins via high-affinity binding between Protein A and human IgG1 Fc domain of Endo180-Fc. Then, serum-free cell culture medium containing S-Trimer secreted by CHO cells was loaded onto the Protein A column with pre-captured Endo180-Fc. After washing off any unbound contaminating host cell proteins (HCP) and other impurities, the bound S-Trimer was purified to near homogeneity in a single step using moderate salt elution, conditions that do not dissociate Endo180-Fc from the Protein A column. S-Trimer was further purified through low pH for preventative viral inactivation (VI), anion exchange chromatography to remove host cell DNA and any residual endotoxins, nanofiltration as a preventative viral removal (VR) step and finally UF/DF to concentrate S-Trimer to the desired concentration in formulation buffer to obtain active drug substance (DS) of S-Trimer subunit vaccine candidate was obtained. Stability analysis of purified S-Trimer indicates that S-Trimer is stable in liquid solution formulations at 2-8° C.

SDS-PAGE analysis under both non-reducing and reducing conditions confirmed that the purified S-Trimer was a disulfide bond-linked trimer and partially cleaved at S1/S2 boundary by furin protease, which is produced by CHO cells. Under non-reducing conditions, S-Trimer appeared in multiple high molecular weight forms, likely as a result of partial cleavage of the antigen, with non-covalently linked and cleaved S1 released during sample treatment. The reduced form of uncleaved S-Trimer has a molecular weight of around 245 kDa. Peptide sequencing via Edman degradation confirmed S1/S2 cleavage between 685R-686S and also revealed that the N-terminal amino acid of S-Trimer was blocked after signal peptide cleavage between 13S-14Q, likely via pyroglutamate formation at residual 14Q. This was confirmed by subsequent peptide sequencing after pyroglutamate aminopeptidase removal of 14Q. Protein glycosylation of S-Trimer was analyzed by N- and O-linked deglycosylases, which showed extensive N-linked glycosylation at both S1 and S2 regions, accounting for about 32% mass (79 kDa) to be glycans based on molecular weight changes of S2-Trimer and S1 before (129 kDa and 116 kDa) and after deglycosylation (93 kDa and 72 kDa). The purity of purified S-Trimer was analyzed by size-exclusion SEC-HPLC showing a 96.3% main peak around 700 Kda and a 3.7% minor peak around 180 Kda identified as cleaved S1. The binding affinity ($K_D$) of purified S-Trimer to the human ACE2 receptor using ForteBio BioLayer interferometry was shown to be 1.33 nM. Negative-stain EM visualization confirmed that S-Trimer particles exist predominantly in a metastable, trimeric pre-fusion form resembling the full-length wild-type spike protein, which was further confirmed by cryo-EM structural studies in the accompanying paper (Ma et al., bioRxiv 2020.09.21.306357. doi:10.1101/2020.09.21.306357).

Detection of SARS-CoV-2 specific binding and neutralizing antibodies in convalescent sera with S-Trimer. S-Trimer was used as an antigen to detect the presence of SARS-CoV-2 Spike protein binding antibodies and ACE2-competitive antibodies in human convalescent sera samples collected from recovered COVID-19 patients. High levels of S-Trimer binding antibody and ACE2-competitive titers were detected in the convalescent sera, as well as high neutralizing antibody titers using a pseudovirus neutralization assay. S-Trimer binding antibodies were not detected in the sera of naïve human volunteers, whereas antibodies binding to influenza hemagglutinin (HA)-Trimers were detected in both COVID-19 convalescent sera and naïve sera, implying prior infection by influenza in all subjects tested but only SARS-CoV-2 infection in the COVID-19 convalescent subjects. These results support the specificity of the assay and demonstrate the ability of S-Trimer to detect SARS-CoV-2 Spike protein-specific antibodies in convalescent sera, further confirming the native-like conformation of the Spike antigen in S-Trimer.

Antibody titers were observed to correlate with disease severity, with lower antibody titers observed in patients with mild COVID-19 disease and higher titers in severe cases. Antibody titers also appeared to moderately correlate with patient age, but no differences were observed between genders.

Antibody titers in human convalescent sera were observed to be correlated between the three assays utilized, and these correlations were further confirmed in sera from animals immunized with S-Trimer. Interestingly, several convalescent sera samples with detectable pseudoviral neutralizing antibody titers did not have any detectable ACE2-competitive titers, suggesting that RBD, which binds to ACE2, is not the only target for neutralizing antibodies, and other domains such as NTD and S2 may also be important antigenic epitopes for viral neutralization as previously reported.

The immunogenicity of S-Trimer was evaluated in BALB/c mice. Mice were vaccinated intramuscularly twice in a two-dose prime-boost regimen (Days 0 and 21) with S-Trimer either non-adjuvanted or with various adjuvants. The adjuvant effects on humoral immunogenicity were evident, as S-Trimer binding antibody titers, ACE-2 competitive titers and neutralizing antibody titers in the adjuvanted groups were significantly higher than non-adjuvanted vaccine at corresponding antigen dose levels. S-Trimer adjuvanted with different adjuvants elicited both ACE2-competitve and pseudovirus neutralizing antibody titers similar to or higher than levels observed in human convalescent sera samples. Similar results were observed in rats immunized with S-Trimer.

S-Trimer antigen-specific cell-mediated immunity (CMI) was studied by harvesting splenocytes from immunized mice at sacrifice, followed by stimulation with S-Trimer antigen and detection of Th1 (IL-2 and IFNγ) and Th2 (IL-4 and IL-5) cytokines by ELISpot. The adjuvanted groups appeared to induce a stronger overall CMI response than non-adjuvanted S-Trimer. A Th1-biased cell-mediated immune response was observed across non-adjuvanted and certain adjuvanted S-Trimer groups, while a mixed Th1-Th2 profile was observed in other adjuvanted groups. CMI did not appear to be dependent on the dose of antigen.

The immunogenicity of adjuvanted S-Trimer was further studied in nonhuman primates (rhesus macaques). Animals were vaccinated intramuscularly twice with adjuvanted S-Trimer or a PBS vehicle control. The animals were then challenged on Day 35 with SARS-CoV-2 virus and then evaluated for immune protection by various parameters. High levels of binding and neutralizing antibody titers measured by different methods, including wild-type SARS-CoV-2 virus neutralization assay, were observed in both groups receiving adjuvanted S-Trimer. The boost-effect of the second dose (on Day 21) was evident, with significant increases in neutralizing antibody levels observed at Day 28 and continuing to rise through Day 35 prior to challenge. At Day 35, neutralizing antibody titers in an adjuvanted S-Trimer group were significantly higher than levels in human convalescent sera. Moreover, animals in an adjuvanted S-Trimer group appeared to mount a rapid and more durable lymphocyte response that remained high 7 days after viral challenge. Antibody titers post-viral challenge appeared to modestly decrease following challenge at Day 40 (5 dpi), suggesting that challenge with high doses of SARS-CoV-2 may have led to rapid binding of circulating anti-Spike antibodies to the virus and subsequent clearance; a similar trend was reported in convalescent humans that were re-exposed to the virus (Addetia et al., J Clin Microbiol, 21, JCM.021107-20 (2020)).

Following challenge with SARS-CoV-2, animals in the adjuvanted S-Trimer groups were protected from body weight loss, whereas animals in the vehicle control group observed rapid body weight loss of approximately 8% through 7 dpi, in line with other reported studies (Munster et al., Nature, 585: 268-272, 2020). Similarly, animals receiving adjuvanted S-Trimer appeared to be protected from increases in body temperature following SARS-CoV-2 challenge. Various blood chemistry parameters also suggested that animals in the active vaccine groups may have been protected from organ and tissue damage and other adverse effects of SARS-CoV-2 infection, as animals in the vehicle control group observed increases in blood albumin (ALB), A/G ratio, AST, creatine kinase (CK), glucose (GLU), lactic acid (LAC), and triglycerides (TRIG) through 7 dpi compared to the adjuvanted S-Trimer groups.

Lung tissues were harvested at necropsy from 5 to 7 dpi and tested for SARS-CoV-2 viral loads based on genomic RNA (gRNA). Complete reduction of viral loads in lung tissues was observed in adjuvanted S-Trimer groups, whereas viral loads were detectable in the vehicle group. Similar trends of reduced viral loads in animals receiving active vaccine were observed from throat swabs, anal swabs and tracheal brushes after challenge through 7 dpi. Viral gRNA detected in nasal swabs were expected given the location of viral challenge and is not necessarily indicative of replicating virus. Histopathological analysis conducted in lung tissues and IHC staining with antibody specific to the Spike protein further confirmed the reduced SARS-CoV-2 infection in animals vaccinated with S-Trimer.

D614G mutation in SARS-CoV-2 Spike protein does not alter receptor binding nor escape from neutralizing antibodies elicited by S-Trimer. Since SARS-CoV-2 with D614G mutation in the Spike protein has become the predominant circulating strain in many regions of the world, S-Trimer with the D614G mutation was also produced. The results showed that, compared to the wild-type S-Trimer, no significant differences were observed in ACE2 binding affinity, nor ACE2 competitive binding against anti-Spike neutralizing antibodies produced from animals immunized with wild-type S-Trimer.

In view of the above, immunization of S-Trimer with adjuvants induced high-levels of neutralizing antibodies and Th1-biased cellular immune responses in animal models. Moreover, rhesus macaques immunized with adjuvanted S-Trimer were protected from SARS-CoV-2 challenge compared to vehicle controls, based on clinical observations and reduction of viral loads in lungs.

Unlike other Spike protein ectodomains used for structural studies and vaccine development, the S-Trimer does not include mutations introduced to abolish S1/S2 cleavage by furin protease or to stabilize the protein in a prefusion form. As such, the S-Trimer is partially cleaved at the S1/S2 junction, similar to S proteins isolated from live SARS-CoV-2 virus (Gao et al., Science, 369: 77-81, 2020) and recombinant full-length S protein expressed in HEK293 cells (Cai et al., Science, eabd4251, 2020. doi: 10.1126/science.abd425132). As described herein, the S-Trimer vaccine candidate, with a fully wild-type S protein ectodomain sequence from SARS-CoV-2, is not only expressed at high levels in CHO cells but also is highly glycosylated and adopts a native-like trimeric pre-fusion conformation. N-terminal protein sequence analysis revealed that upon signal peptide removal during its biosynthesis, S-Trimer has N-terminal 14Q modified by pyroglutamate formation to protect itself from exo-protease degradation. Fusion to Trimer-Tag allows the soluble wild-type S protein ectodomain to form a disulfide-linked homotrimer with a partially-cleaved S1 that remains noncovalently bound to S-Trimer. Importantly, the S-Trimer maintains high affinity binding to the ACE2 receptor, indicating that crucial antigenic epitopes necessary for viral neutralization are preserved.

The present disclosure is not intended to be limited in scope to the particular disclosed embodiments, which are provided, for example, to illustrate various aspects of the disclosure. Various modifications to the compositions and methods described will become apparent from the description and teachings herein. Such variations may be practiced without departing from the true scope and spirit of the disclosure and are intended to fall within the scope of the present disclosure.

SEQUENCES

| SEQ ID NO. | SEQUENCE | DESCRIPTION |
|---|---|---|
| 1 | QCVNLTTRTQLPPAYTNSFTRGVYYPDKVFRSSVLHSTQDLFLPFFSNVTWFHAIH VSGTNGTKRFDNPVLPFNDGVYFASTEKSNIIRGWIFGTTLDSKTQSLLIVNNATN VVIKVCEFQFCNDPFLGVYYHKNNKSWMESEFRVYSSANNCTFEYVSQPFLMDLEG KQGNFKNLREFVFKNIDGYFKIYSKHTPINLVRDLPQGFSALEPLVDLPIGINITR FQTLLALHRSYLTPGDSSSGWTAGAAAYYVGYLQPRTFLLKYNENGTITDAVDCAL DPLSETKCTLKSFTVEKGIYQTSNFRVQPTESIVRFPNITNLCPFGEVFNATRFAS VYAWNRKRISNCVADYSVLYNSASFSTFKCYGVSPTKLNDLCFTNVYADSFVIRGD EVRQIAPGQTGKIADYNYKLPDDFTGCVIAWNSNNLDSKVGGNYNYLYRLFRKSNL KPFERDISTEIYQAGSTPCNGVEGFNCYFPLQSYGFQPTNGVGYQPYRVVVLSFEL LHAPATVCGPKKSTNLVKNKCVNFNFNGLTGTGVLTESNKKFLPFQQFGRDIADTT DAVRDPQTLEILDITPCSFGGVSVITPGTNTSNQVAVLYQDVNCTEVPVAIHADQL TPTWRVYSTGSNVFQTRAGCLIGAEHVNNSYECDIPIGAGICASYQTQTNSPRRAR SVASQSIIAYTMSLGAENSVAYSNNSIAIPTNFTISVTTEILPVSMTKTSVDCTMY ICGDSTECSNLLLQYGSFCTQLNRALTGIAVEQDKNTQEVFAQVKQIYKTPPIKDF GGFNFSQILPDPSKPSKRSFIEDLLFNKVTLADAGFIKQYGDCLGDIAARDLICAQ KFNGLTVLPPLLTDEMIAQYTSALLAGTITSGWTFGAGAALQIPFAMQMAYRFNGI GVTQNVLYENQKLIANQFNSAIGKIQDSLSSTASALGKLQDVVNQNAQALNTLVKQ LSSNFGAISSVLNDILSRLDKVEAEVQIDRLITGRLQSLQTYVTQQLIRAAEIRAS ANLAATKMSECVLGQSKRVDFCGKGYHLMSFPQSAPHGVVFLHVTYVPAQEKNFTT APAICHDGKAHFPREGVFVSNGTHWFVTQRNFYEPQIITTDNTFVSGNCDVVIGIV NNTVYDPLQPELDSFKEELDKYFKNHTSPDVDLGDISGINASVVNIQKEIDRLNEV AKNLNESLIDLQELGKYEQYIKRSNGLPGPIGPPGPRGRTGDAGPVGPPGPPGPPG PPGPPSAGFDFSFLPQPPQEKAHDGGRYYRANDANVVRDRDLEVDTTLKSLSQQIE NIRSPEGSRKNPARTCRDLKMCHSDWKSGEYWIDPNQGCNLDAIKVFCNMETGETC VYPTQPSVAQKNWYISKNPKDKRHVWFGESMTDGFQFEYGGQGSDPADVAIQLTFL RLMSTEASQNITYHCKNSVAYMDQQTGNLKKALLLQGSNEIEIRAEGNSRFTYSVT VDGCTSHTGAWGKTVIEYKTTKTSRLPIIDVAPLDVGAPDQEFGFDVGPVCFL | Prototypic SARS-CoV-2 spike S-Trimer fusion polypeptide without signal peptide, 1509 aa |

| SEQ ID NO. | SEQUENCE | DESCRIPTION |
|---|---|---|
| 2 | QCVNLTTRTQLPPAYTNSFTRGVYYPDKVFRSSVLHSTQDLFLPFFSNVTWFHAIH<br>VSGTNGTKRFDNPVLPFNDGVYFASTEKSNIIRGWIFGTTLDSKTQSLLIVNNATN<br>VVIKVCEFQFCNDPFLGVYYHKNNKSWMESEFRVYSSANNCTFEYVSQPFLMDLEG<br>KQGNFKNLREFVFKNIDGYFKIYSKHTPINLVRDLPQGFSALEPLVDLPIGINITR<br>FQTLLALHRSYLTPGDSSSGWTAGAAAYYVGYLQPRTFLLKYNENGTITDAVDCAL<br>DPLSETKCTLKSFTVEKGIYQTSNFRVQPTESIVRFPNITNLCPFGEVFNATRFAS<br>VYAWNRKRISNCVADYSVLYNSASFSTFKCYGVSPTKLNDLCFTNVYADSFVIRGD<br>EVRQIAPGQTGKIADYNYKLPDDFTGCVIAWNSNNLDSKVGGNYNYLYRLFRKSNL<br>KPFERDISTEIYQAGSTPCNGVEGFNCYFPLQSYGFQPTNGVGYQPYRVVVLSFEL<br>LHAPATVCGPKKSTNLVKNKCVNFNFNGLTGTGVLTESNKKFLPFQQFGRDIADTT<br>DAVRDPQTLEILDITPCSFGGVSVITPGTNTSNQVAVLYQDVNCTEVPVAIHADQL<br>TPTWRVYSTGSNVFQTRAGCLIGAEHVNNSYECDIPIGAGICASYQTQTNSPRRAA<br>SVASQSIIAYTMSLGAENSVAYSNNSIAIPTNFTISVTTEILPVSMTKTSVDCTMY<br>ICGDSTECSNLLLQYGSFCTQLNRALTGIAVEQDKNTQEVFAQVKQIYKTPPIKDF<br>GGFNFSQILPDPSKPSKRSFIEDLLFNKVTLADAGFIKQYGDCLGDIAARDLICAQ<br>KFNGLTVLPPLLTDEMIAQYTSALLAGTITSGWTFGAGAALQIPFAMQMAYRFNGI<br>GVTQNVLYENQKLIANQFNSAIGKIQDSLSSTASALGKLQDVVNQNAQALNTLVKQ<br>LSSNFGAISSVLNDILSRLDKVEAEVQIDRLITGRLQSLQTYVTQQLIRAAEIRAS<br>ANLAATKMSECVLGQSKRVDFCGKGYHLMSFPQSAPHGVVFLHVTYVPAQEKNFTT<br>APAICHDGKAHFPREGVFVSNGTHWFVTQRNFYEPQIITTDNTFVSGNCDVVIGIV<br>NNTVYDPLQPELDSFKEELDKYFKNHTSPDVDLGDISGINASVVNIQKEIDRLNEV<br>AKNLNESLIDLQELGKYEQYIKRSNGLPGPIGPPGPRGRTGDAGPVGPPGPPGPPG<br>PPGPPSAGFDFSFLPQPPQEKAHDGGRYYRANDANVVRDRDLEVDTTLKSLSQQIE<br>NIRSPEGSRKNPARTCRDLKMCHSDWKSGEYWIDPNQGCNLDAIKVFCNMETGETC<br>VYPTQPSVAQKNWYISKNPKDKRHVWFGESMTDGFQFEYGGQGSDPADVAIQLTFL<br>RLMSTEASQNITYHCKNSVAYMDQQTGNLKKALLLQGSNEIEIRAEGNSRFTYSVT<br>VDGCTSHTGAWGKTVIEYKTTKTSRLPIIDVAPLDVGAPDQEFGFDVGPVCFL | Prototypic<br>SARS-CoV-2<br>spike S-Trimer<br>fusion<br>polypeptide<br>without signal<br>peptide, 1509<br>aa, S1/S2 furin<br>cleavage site 1<br>mutant<br>(685R→685A) |
| 3 | QCVNLTTRTQLPPAYTNSFTRGVYYPDKVFRSSVLHSTQDLFLPFFSNVTWFHAIH<br>VSGTNGTKRFDNPVLPFNDGVYFASTEKSNIIRGWIFGTTLDSKTQSLLIVNNATN<br>VVIKVCEFQFCNDPFLGVYYHKNNKSWMESEFRVYSSANNCTFEYVSQPFLMDLEG<br>KQGNFKNLREFVFKNIDGYFKIYSKHTPINLVRDLPQGFSALEPLVDLPIGINITR<br>FQTLLALHRSYLTPGDSSSGWTAGAAAYYVGYLQPRTFLLKYNENGTITDAVDCAL<br>DPLSETKCTLKSFTVEKGIYQTSNFRVQPTESIVRFPNITNLCPFGEVFNATRFAS<br>VYAWNRKRISNCVADYSVLYNSASFSTFKCYGVSPTKLNDLCFTNVYADSFVIRGD<br>EVRQIAPGQTGKIADYNYKLPDDFTGCVIAWNSNNLDSKVGGNYNYLYRLFRKSNL<br>KPFERDISTEIYQAGSTPCNGVEGFNCYFPLQSYGFQPTNGVGYQPYRVVVLSFEL<br>LHAPATVCGPKKSTNLVKNKCVNFNFNGLTGTGVLTESNKKFLPFQQFGRDIADTT<br>DAVRDPQTLEILDITPCSFGGVSVITPGTNTSNQVAVLYQDVNCTEVPVAIHADQL<br>TPTWRVYSTGSNVFQTRAGCLIGAEHVNNSYECDIPIGAGICASYQTQTNSPRRAR<br>SVASQSIIAYTMSLGAENSVAYSNNSIAIPTNFTISVTTEILPVSMTKTSVDCTMY<br>ICGDSTECSNLLLQYGSFCTQLNRALTGIAVEQDKNTQEVFAQVKQIYKTPPIKDF<br>GGFNFSQILPDPSKPSKRSFIEDLLFNKVTLADAGFIKQYGDCLGDIAARDLICAQ<br>KFNGLTVLPPLLTDEMIAQYTSALLAGTITSGWTFGAGAALQIPFAMQMAYRFNGI<br>GVTQNVLYENQKLIANQFNSAIGKIQDSLSSTASALGKLQDVVNQNAQALNTLVKQ<br>LSSNFGAISSVLNDILSRLDPPEAEVQIDRLITGRLQSLQTYVTQQLIRAAEIRAS<br>ANLAATKMSECVLGQSKRVDFCGKGYHLMSFPQSAPHGVVFLHVTYVPAQEKNFTT<br>APAICHDGKAHFPREGVFVSNGTHWFVTQRNFYEPQIITTDNTFVSGNCDVVIGIV<br>NNTVYDPLQPELDSFKEELDKYFKNHTSPDVDLGDISGINASVVNIQKEIDRLNEV<br>AKNLNESLIDLQELGKYEQYIKRSNGLPGPIGPPGPRGRTGDAGPVGPPGPPGPPG<br>PPGPPSAGFDFSFLPQPPQEKAHDGGRYYRANDANVVRDRDLEVDTTLKSLSQQIE<br>NIRSPEGSRKNPARTCRDLKMCHSDWKSGEYWIDPNQGCNLDAIKVFCNMETGETC<br>VYPTQPSVAQKNWYISKNPKDKRHVWFGESMTDGFQFEYGGQGSDPADVAIQLTFL<br>RLMSTEASQNITYHCKNSVAYMDQQTGNLKKALLLQGSNEIEIRAEGNSRFTYSVT<br>VDGCTSHTGAWGKTVIEYKTTKTSRLPIIDVAPLDVGAPDQEFGFDVGPVCFL | Prototypic<br>SARS-CoV-2<br>spike S-Trimer<br>fusion<br>polypeptide<br>without signal<br>peptide, 1509<br>aa, proline<br>mutant<br>(986K/987V→986P/<br>987P) |
| 4 | QCVNLTTRTQLPPAYTNSFTRGVYYPDKVFRSSVLHSTQDLFLPFFSNVTWFHAIH<br>VSGTNGTKRFDNPVLPFNDGVYFASTEKSNIIRGWIFGTTLDSKTQSLLIVNNATN<br>VVIKVCEFQFCNDPFLGVYYHKNNKSWMESEFRVYSSANNCTFEYVSQPFLMDLEG<br>KQGNFKNLREFVFKNIDGYFKIYSKHTPINLVRDLPQGFSALEPLVDLPIGINITR<br>FQTLLALHRSYLTPGDSSSGWTAGAAAYYVGYLQPRTFLLKYNENGTITDAVDCAL<br>DPLSETKCTLKSFTVEKGIYQTSNFRVQPTESIVRFPNITNLCPFGEVFNATRFAS<br>VYAWNRKRISNCVADYSVLYNSASFSTFKCYGVSPTKLNDLCFTNVYADSFVIRGD<br>EVRQIAPGQTGKIADYNYKLPDDFTGCVIAWNSNNLDSKVGGNYNYLYRLFRKSNL<br>KPFERDISTEIYQAGSTPCNGVEGFNCYFPLQSYGFQPTNGVGYQPYRVVVLSFEL<br>LHAPATVCGPKKSTNLVKNKCVNFNFNGLTGTGVLTESNKKFLPFQQFGRDIADTT<br>DAVRDPQTLEILDITPCSFGGVSVITPGTNTSNQVAVLYQDVNCTEVPVAIHADQL<br>TPTWRVYSTGSNVFQTRAGCLIGAEHVNNSYECDIPIGAGICASYQTQTNSPRRAA<br>SVASQSIIAYTMSLGAENSVAYSNNSIAIPTNFTISVTTEILPVSMTKTSVDCTMY<br>ICGDSTECSNLLLQYGSFCTQLNRALTGIAVEQDKNTQEVFAQVKQIYKTPPIKDF<br>GGFNFSQILPDPSKPSKRSFIEDLLFNKVTLADAGFIKQYGDCLGDIAARDLICAQ<br>KFNGLTVLPPLLTDEMIAQYTSALLAGTITSGWTFGAGAALQIPFAMQMAYRFNGI<br>GVTQNVLYENQKLIANQFNSAIGKIQDSLSSTASALGKLQDVVNQNAQALNTLVKQ<br>LSSNFGAISSVLNDILSRLDPPEAEVQIDRLITGRLQSLQTYVTQQLIRAAEIRAS<br>ANLAATKMSECVLGQSKRVDFCGKGYHLMSFPQSAPHGVVFLHVTYVPAQEKNFTT<br>APAICHDGKAHFPREGVFVSNGTHWFVTQRNFYEPQIITTDNTFVSGNCDVVIGIV | Prototypic<br>SARS-CoV-2<br>spike S-Trimer<br>fusion<br>polypeptide<br>without signal<br>peptide, 1509<br>aa, S1/S2 furin<br>cleavage site 1<br>and proline<br>mutant<br>(685R→685A,<br>986K/987V→986P/<br>987P) |

| SEQ ID NO. | SEQUENCE | DESCRIPTION |
|---|---|---|
| | NNTVYDPLQPELDSFKEELDKYFKNHTSPDVDLGDISGINASVVNIQKEIDRLNEV<br>AKNLNESLIDLQELGKYEQYIKRSNGLPGPIGPPGPRGRTGDAGPVGPPGPPGPPG<br>PPGPPSAGFDFSFLPQPPQEKAHDGGRYYRANDANVVRDRDLEVDTTLKSLSQQIE<br>NIRSPEGSRKNPARTCRDLKMCHSDWKSGEYWIDPNQGCNLDAIKVFCNMETGETC<br>VYPTQPSVAQKNWYISKNPKDKRHVWFGESMTDGFQFEYGGQGSDPADVAIQLTFL<br>RLMSTEASQNITYHCKNSVAYMDQQTGNLKKALLLQGSNEIEIRAEGNSRFTYSVT<br>VDGCTSHTGAWGKTVIEYKTTKTSRLPIIDVAPLDVGAPDQEFGFDVGPVCFL | |
| 5 | QCVNLTTRTQLPPAYTNSFTRGVYYPDKVFRSSVLHSTQDLFLPFFSNVTWFHAIH<br>VSGTNGTKRFDNPVLPFNDGVYFASTEKSNIIRGWIFGTTLDSKTQSLLIVNNATN<br>VVIKVCEFQFCNDPFLGVYYHKNNKSWMESEFRVYSSANNCTFEYVSQPFLMDLEG<br>KQGNFKNLREFVFKNIDGYFKIYSKHTPINLVRDLPQGFSALEPLVDLPIGINITR<br>FQTLLALHRSYLTPGDSSSGWTAGAAAYYVGYLQPRTFLLKYNENGTITDAVDCAL<br>DPLSETKCTLKSFTVEKGIYQTSNFRVQPTESIVRFPNITNLCPFGEVFNATRFAS<br>VYAWNRKRISNCVADYSVLYNSASFSTFKCYGVSPTKLNDLCFTNVYADSFVIRGD<br>EVRQIAPGQTGKIADYNYKLPDDFTGCVIAWNSNNLDSKVGGNYNYLYRLFRKSNL<br>KPFERDISTEIYQAGSTPCNGVEGFNCYFPLQSYGFQPTNGVGYQPYRVVVLSFEL<br>LHAPATVCGPKKSTNLVKNKCRSNGLPGPIGPPGPRGRTGDAGPVGPPGPPGPPGP<br>PGPPSAGFDFSFLPQPPQEKAHDGGRYYRANDANVVRDRDLEVDTTLKSLSQQIEN<br>IRSPEGSRKNPARTCRDLKMCHSDWKSGEYWIDPNQGCNLDAIKVFCNMETGETCV<br>YPTQPSVAQKNWYISKNPKDKRHVWFGESMTDGFQFEYGGQGSDPADVAIQLTFLR<br>LMSTEASQNITYHCKNSVAYMDQQTGNLKKALLLQGSNEIEIRAEGNSRFTYSVTV<br>DGCTSHTGAWGKTVIEYKTTKTSRLPIIDVAPLDVGAPDQEFGFDVGPVCFL | Prototypic SARS-CoV-2 spike NTD/RBD-Trimer fusion polypeptide without signal peptide, 836 aa |
| 6 | QCVNLTTRT

| SEQ ID NO. | SEQUENCE | DESCRIPTION |
|---|---|---|
|  | NSAIGKIQDSLSSTASALGKLQDVVNQNAQALNTLVKQLSSNFGAISSVLNDILSR<br>LDKVEAEVQIDRLITGRLQSLQTYVTQQLIRAAEIRASANLAATKMSECVLGQSKR<br>VDFCGKGYHLMSFPQSAPHGVVFLHVTYVPAQEKNFTTAPAICHDGKAHFPREGVF<br>VSNGTHWFVTQRNFYEPQIITTDNTFVSGNCDVVIGIVNNTVYDPLQPELDSFKEE<br>LDKYFKNHTSPDVDLGDISGINASVVNIQKEIDRLNEVAKNLNESLIDLQELGKYE<br>QYIKRSNGLPGPIGPPGPRGRTGDAGPVGPPGPPGPPGPPGPPSAGFDFSFLPQPP<br>QEKAHDGGRYYRANDANVVRDRDLEVDTTLKSLSQQIENIRSPEGSRKNPARTCRD<br>LKMCHSDWKSGEYWIDPNQGCNLDAIKVFCNMETGETCVYPTQPSVAQKNWYISKN<br>PKDKRHVWFGESMTDGFQFEYGGQGSDPADVAIQLTFLRLMSTEASQNITYHCKNS<br>VAYMDQQTGNLKKALLLQGSNEIEIRAEGNSRFTYSVTVDGCTSHTGAWGKTVIEY<br>KTTKTSRLPIIDVAPLDVGAPDQEFGFDVGPVCFL | spike S2-Trimer<br>fusion<br>polypeptide,<br>707 aa (cleaved<br>at S2') |
| 10 | QCVNLTTRTQLPPAYTNSFTRGVYYPDKVFRSSVLHSTQDLFLPFFSNVTWFHAIH<br>VSGTNGTKRFDNPVLPFNDGVYFASTEKSNIIRGWIFGTTLDSKTQSLLIVNNATN<br>VVIKVCEFQFCNDPFLGVYYHKNNKSWMESEFRVYSSANNCTFEYVSQPFLMDLEG<br>KQGNFKNLREFVFKNIDGYFKIYSKHTPINLVRDLPQGFSALEPLVDLPIGINITR<br>FQTLLALHRSYLTPGDSSSGWTAGAAAYYVGYLQPRTFLLKYNENGTITDAVDCAL<br>DPLSETKCTLKSFTVEKGIYQTSNFRVQPTESIVRFPNITNLCPFGEVFNATRFAS<br>VYAWNRKRISNCVADYSVLYNSASFSTFKCYGVSPTKLNDLCFTNVYADSFVIRGD<br>EVRQIAPGQTGNIADYNYKLPDDFTGCVIAWNSNNLDSKVGGNYNYLYRLFRKSNL<br>KPFERDISTEIYQAGSTPCNGVKGFNCYFPLQSYGFQPTYGVGYQPYRVVVLSFEL<br>LHAPATVCGPKKSTNLVKNKCVNFNFNGLTGTGVLTESNKKFLPFQQFGRDIADTT<br>DAVRDPQTLEILDITPCSFGGVSVITPGTNTSNQVAVLYQGVNCTEVPVAIHADQL<br>TPTWRVYSTGSNVFQTRAGCLIGAEHVNNSYECDIPIGAGICASYQTQTNSPRRAR<br>SVASQSIIAYTMSLGAENSVAYSNNSIAIPTNFTISVTTEILPVSMTKTSVDCTMY<br>ICGDSTECSNLLLQYGSFCTQLNRALTGIAVEQDKNTQEVFAQVKQIYKTPPIKDF<br>GGFNFSQILPDPSKPSKRSFIEDLLFNKVTLADAGFIKQYGDCLGDIAARDLICAQ<br>KFNGLTVLPPLLTDEMIAQYTSALLAGTITSGWTFGAGAALQIPFAMQMAYRFNGI<br>GVTQNVLYENQKLIANQFNSAIGKIQDSLSSTASALGKLQDVVNQNAQALNTLVKQ<br>LSSNFGAISSVLNDILSRLDKVEAEVQIDRLITGRLQSLQTYVTQQLIRAAEIRAS<br>ANLAATKMSECVLGQSKRVDFCGKGYHLMSFPQSAPHGVVFLHVTYVPAQEKNFTT<br>APAICHDGKAHFPREGVFVSNGTHWFVTQRNFYEPQIITTDNTFVSGNCDVVIGIV<br>NNTVYDPLQPELDSFKEELDKYFKNHTSPDVDLGDISGINASVVNIQKEIDRLNEV<br>AKNLNESLIDLQELGKYEQYIKRSNGLPGPIGPPGPRGRTGDAGPVGPPGPPGPPG<br>PPGPPSAGFDFSFLPQPPQEKAHDGGRYYRANDANVVRDRDLEVDTTLKSLSQQIE<br>NIRSPEGSRKNPARTCRDLKMCHSDWKSGEYWIDPNQGCNLDAIKVFCNMETGETC<br>VYPTQPSVAQKNWYISKNPKDKRHVWFGESMTDGFQFEYGGQGSDPADVAIQLTFL<br>RLMSTEASQNITYHCKNSVAYMDQQTGNLKKALLLQGSNEIEIRAEGNSRFTYSVT<br>VDGCTSHTGAWGKTVIEYKTTKTSRLPIIDVAPLDVGAPDQEFGFDVGPVCFL | B.1.351 South<br>African variant<br>SARS-CoV-2<br>spike S-Trimer<br>fusion<br>polypeptide<br>without signal<br>peptide, 1509<br>aa |
| 11 | QCVNLTTRTQLPPAYTNSFTRGVYYPDKVFRSSVLHSTQDLFLPFFSNVTWFHAIH<br>VSGTNGTKRFDNPVLPFNDGVYFASTEKSNIIRGWIFGTTLDSKTQSLLIVNNATN<br>VVIKVCEFQFCNDPFLGVYYHKNNKSWMESEFRVYSSANNCTFEYVSQPFLMDLEG<br>KQGNFKNLREFVFKNIDGYFKIYSKHTPINLVRDLPQGFSALEPLVDLPIGINITR<br>FQTLLALHRSYLTPGDSSSGWTAGAAAYYVGYLQPRTFLLKYNENGTITDAVDCAL<br>DPLSETKCTLKSFTVEKGIYQTSNFRVQPTESIVRFPNITNLCPFGEVFNATRFAS<br>VYAWNRKRISNCVADYSVLYNSASFSTFKCYGVSPTKLNDLCFTNVYADSFVIRGD<br>EVRQIAPGQTGNIADYNYKLPDDFTGCVIAWNSNNLDSKVGGNYNYLYRLFRKSNL<br>KPFERDISTEIYQAGSTPCNGVKGFNCYFPLQSYGFQPTYGVGYQPYRVVVLSFEL<br>LHAPATVCGPKKSTNLVKNKCVNFNFNGLTGTGVLTESNKKFLPFQQFGRDIADTT<br>DAVRDPQTLEILDITPCSFGGVSVITPGTNTSNQVAVLYQGVNCTEVPVAIHADQL<br>TPTWRVYSTGSNVFQTRAGCLIGAEHVNNSYECDIPIGAGICASYQTQTNSPRRAA<br>SVASQSIIAYTMSLGAENSVAYSNNSIAIPTNFTISVTTEILPVSMTKTSVDCTMY<br>ICGDSTECSNLLLQYGSFCTQLNRALTGIAVEQDKNTQEVFAQVKQIYKTPPIKDF<br>GGFNFSQILPDPSKPSKRSFIEDLLFNKVTLADAGFIKQYGDCLGDIAARDLICAQ<br>KFNGLTVLPPLLTDEMIAQYTSALLAGTITSGWTFGAGAALQIPFAMQMAYRFNGI<br>GVTQNVLYENQKLIANQFNSAIGKIQDSLSSTASALGKLQDVVNQNAQALNTLVKQ<br>LSSNFGAISSVLNDILSRLDKVEAEVQIDRLITGRLQSLQTYVTQQLIRAAEIRAS<br>ANLAATKMSECVLGQSKRVDFCGKGYHLMSFPQSAPHGVVFLHVTYVPAQEKNFTT<br>APAICHDGKAHFPREGVFVSNGTHWFVTQRNFYEPQIITTDNTFVSGNCDVVIGIV<br>NNTVYDPLQPELDSFKEELDKYFKNHTSPDVDLGDISGINASVVNIQKEIDRLNEV<br>AKNLNESLIDLQELGKYEQYIKRSNGLPGPIGPPGPRGRTGDAGPVGPPGPPGPPG<br>PPGPPSAGFDFSFLPQPPQEKAHDGGRYYRANDANVVRDRDLEVDTTLKSLSQQIE<br>NIRSPEGSRKNPARTCRDLKMCHSDWKSGEYWIDPNQGCNLDAIKVFCNMETGETC<br>VYPTQPSVAQKNWYISKNPKDKRHVWFGESMTDGFQFEYGGQGSDPADVAIQLTFL<br>RLMSTEASQNITYHCKNSVAYMDQQTGNLKKALLLQGSNEIEIRAEGNSRFTYSVT<br>VDGCTSHTGAWGKTVIEYKTTKTSRLPIIDVAPLDVGAPDQEFGFDVGPVCFL | B.1.351 South<br>African variant<br>SARS-CoV-2<br>spike S-Trimer<br>fusion<br>polypeptide<br>without signal<br>peptide, 1509<br>aa, S1/S2 furin<br>cleavage site 1<br>mutant<br>(685R→685A) |
| 12 | QCVNLTTRTQLPPAYTNSFTRGVYYPDKVFRSSVLHSTQDLFLPFFSNVTWFHAIH<br>VSGTNGTKRFDNPVLPFNDGVYFASTEKSNIIRGWIFGTTLDSKTQSLLIVNNATN<br>VVIKVCEFQFCNDPFLGVYYHKNNKSWMESEFRVYSSANNCTFEYVSQPFLMDLEG<br>KQGNFKNLREFVFKNIDGYFKIYSKHTPINLVRDLPQGFSALEPLVDLPIGINITR<br>FQTLLALHRSYLTPGDSSSGWTAGAAAYYVGYLQPRTFLLKYNENGTITDAVDCAL<br>DPLSETKCTLKSFTVEKGIYQTSNFRVQPTESIVRFPNITNLCPFGEVFNATRFAS<br>VYAWNRKRISNCVADYSVLYNSASFSTFKCYGVSPTKLNDLCFTNVYADSFVIRGD<br>EVRQIAPGQTGNIADYNYKLPDDFTGCVIAWNSNNLDSKVGGNYNYLYRLFRKSNL<br>KPFERDISTEIYQAGSTPCNGVKGFNCYFPLQSYGFQPTYGVGYQPYRVVVLSFEL | B.1.351 South<br>African variant<br>SARS-CoV-2<br>spike S-Trimer<br>fusion<br>polypeptide<br>without signal<br>peptide, 1509<br>aa, proline |

| SEQ ID NO. | SEQUENCE | DESCRIPTION |
|---|---|---|
| | LHAPATVCGPKKSTNLVKNKCVNFNFNGLTGTGVLTESNKKFLPFQQFGRDIADTT<br>DAVRDPQTLEILDITPCSFGGVSVITPGTNTSNQVAVLYQGVNCTEVPVAIHADQL<br>TPTWRVYSTGSNVFQTRAGCLIGAEHVNNSYECDIPIGAGICASYQTQTNSPRRAR<br>SVASQSIIAYTMSLGAENSVAYSNNSIAIPTNFTISVTTEILPVSMTKTSVDCTMY<br>ICGDSTECSNLLLQYGSFCTQLNRALTGIAVEQDKNTQEVFAQVKQIYKTPPIKDF<br>GGFNFSQILPDPSKPSKRSFIEDLLFNKVTLADAGFIKQYGDCLGDIAARDLICAQ<br>KFNGLTVLPPLLTDEMIAQYTSALLAGTITSGWTFGAGAALQIPFAMQMAYRFNGI<br>GVTQNVLYENQKLIANQFNSAIGKIQDSLSSTASALGKLQDVVNQNAQALNTLVKQ<br>LSSNFGAISSVLNDILSRLDPPEAEVQIDRLITGRLQSLQTYVTQQLIRAAEIRAS<br>ANLAATKMSECVLGQSKRVDFCGKGYHLMSFPQSAPHGVVFLHVTYVPAQEKNFTT<br>APAICHDGKAHFPREGVFVSNGTHWFVTQRNFYEPQIITTDNTFVSGNCDVVIGIV<br>NNTVYDPLQPELDSFKEELDKYFKNHTSPDVDLGDISGINASVVNIQKEIDRLNEV<br>AKNLNESLIDLQELGKYEQYIKRSNGLPGIGPPGPRGRTGDAGPVGPPGPPGPPG<br>PPGPPSAGFDFSFLPQPPQEKAHDGGRYYRANDANVVRDRDLEVDTTLKSLSQQIE<br>NIRSPEGSRKNPARTCRDLKMCHSDWKSGEYWIDPNQGCNLDAIKVFCNMETGETC<br>VYPTQPSVAQKNWYISKNPKDKRHVWFGESMTDGFQFEYGGQGSDPADVAIQLTFL<br>RLMSTEASQNITYHCKNSVAYMDQQTGNLKKALLLQGSNEIEIRAEGNSRFTYSVT<br>VDGCTSHTGAWGKTVIEYKTTKTSRLPIIDVAPLDVGAPDQEFGFDVGPVCFL | mutant (986K/<br>987V→986P/<br>987P) |
| 13 | QCVNLTTRTQLPPAYTNSFTRGVYYPDKVFRSSVLHSTQDLFLPFFSNVTWFHAIH<br>VSGTNGTKRFDNPVLPFNDGVYFASTEKSNIIRGWIFGTTLDSKTQSLLIVNNATN<br>VVIKVCEFQFCNDPFLGVYYHKNNKSWMESEFRVYSSANNCTFEYVSQPFLMDLEG<br>KQGNFKNLREFVFKNIDGYFKIYSKHTPINLVRDLPQGFSALEPLVDLPIGINITR<br>FQTLLALHRSYLTPGDSSSGWTAGAAAYYVGYLQPRTFLLKYNENGTITDAVDCAL<br>DPLSETKCTLKSFTVEKGIYQTSNFRVQPTESIVRFPNITNLCPFGEVFNATRFAS<br>VYAWNRKRISNCVADYSVLYNSASFSTFKCYGVSPTKLNDLCFTNVYADSFVIRGD<br>EVRQIAPGQTGNIADYNYKLPDDFTGCVIAWNSNNLDSKVGGNYNYLYRLFRKSNL<br>KPFERDISTEIYQAGSTPCNGVKGFNCYFPLQSYGFQPTYGVGYQPYRVVVLSFEL<br>LHAPATVCGPKKSTNLVKNKCVNFNFNGLTGTGVLTESNKKFLPFQQFGRDIADTT<br>DAVRDPQTLEILDITPCSFGGVSVITPGTNTSNQVAVLYQGVNCTEVPVAIHADQL<br>TPTWRVYSTGSNVFQTRAGCLIGAEHVNNSYECDIPIGAGICASYQTQTNSPRRAA<br>SVASQSIIAYTMSLGAENSVAYSNNSIAIPTNFTISVTTEILPVSMTKTSVDCTMY<br>ICGDSTECSNLLLQYGSFCTQLNRALTGIAVEQDKNTQEVFAQVKQIYKTPPIKDF<br>GGFNFSQILPDPSKPSKRSFIEDLLFNKVTLADAGFIKQYGDCLGDIAARDLICAQ<br>KFNGLTVLPPLLTDEMIAQYTSALLAGTITSGWTFGAGAALQIPFAMQMAYRFNGI<br>GVTQNVLYENQKLIANQFNSAIGKIQDSLSSTASALGKLQDVVNQNAQALNTLVKQ<br>LSSNFGAISSVLNDILSRLDPPEAEVQIDRLITGRLQSLQTYVTQQLIRAAEIRAS<br>ANLAATKMSECVLGQSKRVDFCGKGYHLMSFPQSAPHGVVFLHVTYVPAQEKNFTT<br>APAICHDGKAHFPREGVFVSNGTHWFVTQRNFYEPQIITTDNTFVSGNCDVVIGIV<br>NNTVYDPLQPELDSFKEELDKYFKNHTSPDVDLGDISGINASVVNIQKEIDRLNEV<br>AKNLNESLIDLQELGKYEQYIKRSNGLPGIGPPGPRGRTGDAGPVGPPGPPGPPG<br>PPGPPSAGFDFSFLPQPPQEKAHDGGRYYRANDANVVRDRDLEVDTTLKSLSQQIE<br>NIRSPEGSRKNPARTCRDLKMCHSDWKSGEYWIDPNQGCNLDAIKVFCNMETGETC<br>VYPTQPSVAQKNWYISKNPKDKRHVWFGESMTDGFQFEYGGQGSDPADVAIQLTFL<br>RLMSTEASQNITYHCKNSVAYMDQQTGNLKKALLLQGSNEIEIRAEGNSRFTYSVT<br>VDGCTSHTGAWGKTVIEYKTTKTSRLPIIDVAPLDVGAPDQEFGFDVGPVCFL | B.1.351 South<br>African variant<br>SARS-CoV-2<br>spike S-Trimer<br>fusion<br>polypeptide<br>without signal<br>peptide, 1509<br>aa, S1/S2 furin<br>cleavage site 1<br>and proline<br>mutant<br>(685R→685A,<br>986K/987V→986P/<br>987P) |
| 14 | QCVNFTNRTQLPSAYTNSFTRGVYYPDKVFRSSVLHSTQDLFLPFFSNVTWFHAIH<br>VSGTNGTKRFDNPVLPFNDGVYFASTEKSNIIRGWIFGTTLDSKTQSLLIVNNATN<br>VVIKVCEFQFCNYPFLGVYYHKNNKSWMESEFRVYSSANNCTFEYVSQPFLMDLEG<br>KQGNFKNLSEFVFKNIDGYFKIYSKHTPINLVRDLPQGFSALEPLVDLPIGINITR<br>FQTLLALHRSYLTPGDSSSGWTAGAAAYYVGYLQPRTFLLKYNENGTITDAVDCAL<br>DPLSETKCTLKSFTVEKGIYQTSNFRVQPTESIVRFPNITNLCPFGEVFNATRFAS<br>VYAWNRKRISNCVADYSVLYNSASFSTFKCYGVSPTKLNDLCFTNVYADSFVIRGD<br>EVRQIAPGQTGTIADYNYKLPDDFTGCVIAWNSNNLDSKVGGNYNYLYRLFRKSNL<br>KPFERDISTEIYQAGSTPCNGVKGFNCYFPLQSYGFQPTYGVGYQPYRVVVLSFEL<br>LHAPATVCGPKKSTNLVKNKCVNFNFNGLTGTGVLTESNKKFLPFQQFGRDIADTT<br>DAVRDPQTLEILDITPCSFGGVSVITPGTNTSNQVAVLYQGVNCTEVPVAIHADQL<br>TPTWRVYSTGSNVFQTRAGCLIGAEYVNNSYECDIPIGAGICASYQTQTNSPRRAR<br>SVASQSIIAYTMSLGAENSVAYSNNSIAIPTNFTISVTTEILPVSMTKTSVDCTMY<br>ICGDSTECSNLLLQYGSFCTQLNRALTGIAVEQDKNTQEVFAQVKQIYKTPPIKDF<br>GGFNFSQILPDPSKPSKRSFIEDLLFNKVTLADAGFIKQYGDCLGDIAARDLICAQ<br>KFNGLTVLPPLLTDEMIAQYTSALLAGTITSGWTFGAGAALQIPFAMQMAYRFNGI<br>GVTQNVLYENQKLIANQFNSAIGKIQDSLSSTASALGKLQDVVNQNAQALNTLVKQ<br>LSSNFGAISSVLNDILSRLDKVEAEVQIDRLITGRLQSLQTYVTQQLIRAAEIRAS<br>ANLAAIKMSECVLGQSKRVDFCGKGYHLMSFPQSAPHGVVFLHVTYVPAQEKNFTT<br>APAICHDGKAHFPREGVFVSNGTHWFVTQRNFYEPQIITTDNTFVSGNCDVVIGIV<br>NNTVYDPLQPELDSFKEELDKYFKNHTSPDVDLGDISGINASVVNIQKEIDRLNEV<br>AKNLNESLIDLQELGKYEQYIKRSNGLPGIGPPGPRGRTGDAGPVGPPGPPGPPG<br>PPGPPSAGFDFSFLPQPPQEKAHDGGRYYRANDANVVRDRDLEVDTTLKSLSQQIE<br>NIRSPEGSRKNPARTCRDLKMCHSDWKSGEYWIDPNQGCNLDAIKVFCNMETGETC<br>VYPTQPSVAQKNWYISKNPKDKRHVWFGESMTDGFQFEYGGQGSDPADVAIQLTFL<br>RLMSTEASQNITYHCKNSVAYMDQQTGNLKKALLLQGSNEIEIRAEGNSRFTYSVT<br>VDGCTSHTGAWGKTVIEYKTTKTSRLPIIDVAPLDVGAPDQEFGFDVGPVCFL | P.1 Brazilian<br>variant SARS-<br>CoV-2 spike S-<br>Trimer fusion<br>polypeptide<br>without signal<br>peptide, 1509<br>aa |
| 15 | QCVNFTNRTQLPSAYTNSFTRGVYYPDKVFRSSVLHSTQDLFLPFFSNVTWFHAIH<br>VSGTNGTKRFDNPVLPFNDGVYFASTEKSNIIRGWIFGTTLDSKTQSLLIVNNATN | P.1 Brazilian<br>variant SARS- |

| SEQ ID NO. | SEQUENCE | DESCRIPTION |
|---|---|---|
| | VVIKVCEFQFCNYPFLGVYYHKNNKSWMESEFRVYSSANNCTFEYVSQPFLMDLEG<br>KQGNFKNLSEFVFKNIDGYFKIYSKHTPINLVRDLPQGFSALEPLVDLPIGINITR<br>FQTLLALHRSYLTPGDSSSGWTAGAAAYYVGYLQPRTFLLKYNENGTITDAVDCAL<br>DPLSETKCTLKSFTVEKGIYQTSNFRVQPTESIVRFPNITNLCPFGEVFNATRFAS<br>VYAWNRKRISNCVADYSVLYNSASFSTFKCYGVSPTKLNDLCFTNVYADSFVIRGD<br>EVRQIAPGQTGTIADYNYKLPDDFTGCVIAWNSNNLDSKVGGNYNYLYRLFRKSNL<br>KPFERDISTEIYQAGSTPCNGVKGFNCYFPPLQSYGFQPTYGVGYQPYRVVVLSFEL<br>LHAPATVCGPKKSTNLVKNKCVNFNFNGLTGTVLTESNKKFLPFQQFGRDIADTT<br>DAVRDPQTLEILDITPCSFGGVSVITPGTNTSNQVAVLYQGVNCTEVPVAIHADQL<br>TPTWRVYSTGSNVFQTRAGCLIGAEYVNNSYECDIPIGAGICASYQTQTNSPRRAA<br>SVASQSIIAYTMSLGAENSVAYSNNSIAIPTNFTISVTTEILPVSMTKTSVDCTMY<br>ICGDSTECSNLLLQYGSFCTQLNRALTGIAVEQDKNTQEVFAQVKQIYKTPPIKDF<br>GGFNFSQILPDPSKPSKRSFIEDLLFNKVTLADAGFIKQYGDCLGDIAARDLICAQ<br>KFNGLTVLPPLLTDEMIAQYTSALLAGTITSGWTFGAGAALQIPFAMQMAYRFNGI<br>GVTQNVLYENQKLIANQFNSAIGKIQDSLSSTASALGKLQDVVNQNAQALNTLVKQ<br>LSSNFGAISSVLNDILSRLDKVEAEVQIDRLITGRLQSLQTYVTQQLIRAAEIRAS<br>ANLAAIKMSECVLGQSKRVDFCGKGYHLMSFPQSAPHGVVFLHVTYVPAQEKNFTT<br>APAICHDGKAHFPREGVFVSNGTHWFVTQRNFYEPQIITTDNTFVSGNCDVVIGIV<br>NNTVYDPLQPELDSFKEELDKYFKNHTSPDVDLGDISGINASVVNIQKEIDRLNEV<br>AKNLNESLIDLQELGKYEQYIKRSNGLPGPIGPPGPRGRTGDAGPVGPPGPPGPPG<br>PPGPPSAGFDFSFLPQPPQEKAHDGGRYYRANDANVVRDRDLEVDTTLKSLSQQIE<br>NIRSPEGSRKNPARTCRDLKMCHSDWKSGEYWIDPNQGCNLDAIKVFCNMETGETC<br>VYPTQPSVAQKNWYISKNPKDKRHVWFGESMTDGFQFEYGGQGSDPADVAIQLTFL<br>RLMSTEASQNITYHCKNSVAYMDQQTGNLKKALLLQGSNEIEIRAEGNSRFTYSVT<br>VDGCTSHTGAWGKTVIEYKTTKTSRLPIIDVAPLDVGAPDQEFGFDVGPVCFL | CoV-2 spike S-<br>Trimer fusion<br>polypeptide<br>without signal<br>peptide, 1509

| SEQ ID NO. | SEQUENCE | DESCRIPTION |
|---|---|---|
| | NIRSPEGSRKNPARTCRDLKMCHSDWKSGEYWIDPNQGCNLDAIKVFCNMETGETC<br>VYPTQPSVAQKNWYISKNPKDKRHVWFGESMTDGFQFEYGGQGSDPADVAIQLTFL<br>RLMSTEASQNITYHCKNSVAYMDQQTGNLKKALLLQGSNEIEIRAEGNSRFTYSVT<br>VDGCTSHTGAWGKTVIEYKTTKTSRLPIIDVAPLDVGAPDQEFGFDVGPVCFL | |
| 18 | QCVNLTTRTQLPPAYTNSFTRGVYYPDKVFRSSVLHSTQDLFLPFFSNVTWFHAIS<br>GTNGTKRFDNPVLPFNDGVYFASTEKSNIIRGWIFGTTLDSKTQSLLIVNNATNVV<br>IKVCEFQFCNDPFLGVYYHKNNKSWMESEFRVYSSANNCTFEYVSQPFLMDLEGKQ<br>GNFKNLREFVFKNIDGYFKIYSKHTPINLVRDLPQGFSALEPLVDLPIGINITRFQ<br>TLLALHRSYLTPGDSSSGWTAGAAAYYVGYLQPRTFLLKYNENGTITDAVDCALDP<br>LSETKCTLKSFTVEKGIYQTSNFRVQPTESIVRFPNITNLCPFGEVFNATRFASVY<br>AWNRKRISNCVADYSVLYNSASFSTFKCYGVSPTKLNDLCFTNVYADSFVIRGDEV<br>RQIAPGQTGKIADYNYKLPDDFTGCVIAWNSNNLDSKVGGNYNYLYRLFRKSNLKP<br>FERDISTEIYQAGSTPCNGVEGFNCYFPLQSYGFQPTYGVGYQPYRVVVLSFELLH<br>APATVCGPKKSTNLVKNKCVNFNFNGLTGTGVLTESNKKFLPFQQFGRDIADTTDA<br>VRDPQTLEILDITPCSFGGVSVITPGTNTSNQVAVLYQGVNCTEVPVAIHADQLTP<br>TWRVYSTGSNVFQTRAGCLIGAEHVNNSYECDIPIGAGICASYQTQTNSHRRARSV<br>ASQSIIAYTMSLGAENSVAYSNNSIAIPTNFTISVTTEILPVSMTKTSVDCTMYIC<br>GDSTECSNLLLQYGSFCTQLNRALTGIAVEQDKNTQEVFAQVKQIYKTPPIKDFGG<br>FNFSQILPDPSKPSKRSFIEDLLFNKVTLADAGFIKQYGDCLGDIAARDLICAQKF<br>NGLTVLPPLLTDEMIAQYTSALLAGTITSGWTFGAGAALQIPFAMQMAYRFNGIGV<br>TQNVLYENQKLIANQFNSAIGKIQDSLSSTASALGKLQDVVNQNAQALNTLVKQLS<br>SNFGAISSVLNDILSRLDKVEAEVQIDRLITGRLQSLQTYVTQQLIRAAEIRASAN<br>LAATKMSECVLGQSKRVDFCGKGYHLMSFPQSAPHGVVFLHVTYVPAQEKNFTTAP<br>AICHDGKAHFPREGVFVSNGTHWFVTQRNFYEPQIITTDNTFVSGNCDVVIGIVNN<br>TVYDPLQPELDSFKEELDKYFKNHTSPDVDLGDISGINASVVNIQKEIDRLNEVAK<br>NLNESLIDLQELGKYEQYIKRSNGLPGPIGPPGPRGRTGDAGPVGPPGPPGPPGPP<br>GPPSAGFDFSFLPQPPQEKAHDGGRYYRANDANVVRDRDLEVDTTLKSLSQQIENI<br>RSPEGSRKNPARTCRDLKMCHSDWKSGEYWIDPNQGCNLDAIKVFCNMETGETCVY<br>PTQPSVAQKNWYISKNPKDKRHVWFGESMTDGFQFEYGGQGSDPADVAIQLTFLRL<br>MSTEASQNITYHCKNSVAYMDQQTGNLKKALLLQGSNEIEIRAEGNSRFTYSVTVD<br>GCTSHTGAWGKTVIEYKTTKTSRLPIIDVAPLDVGAPDQEFGFDVGPVCFL | B.1.1.7 UK variant SARS-CoV-2 spike S-Trimer fusion polypeptide without signal peptide, 1507 aa |
| 19 | QCVNLTTRTQLPPAYTNSFTRGVYYPDKVFRSSVLHSTQDLFLPFFSNVTWFHAIS<br>GTNGTKRFDNPVLPFNDGVYFASTEKSNIIRGWIFGTTLDSKTQSLLIVNNATNVV<br>IKVCEFQFCNDPFLGVYYHKNNKSWMESEFRVYSSANNCTFEYVSQPFLMDLEGKQ<br>GNFKNLREFVFKNIDGYFKIYSKHTPINLVRDLPQGFSALEPLVDLPIGINITRFQ<br>TLLALHRSYLTPGDSSSGWTAGAAAYYVGYLQPRTFLLKYNENGTITDAVDCALDP<br>LSETKCTLKSFTVEKGIYQTSNFRVQPTESIVRFPNITNLCPFGEVFNATRFASVY<br>AWNRKRISNCVADYSVLYNSASFSTFKCYGVSPTKLNDLCFTNVYADSFVIRGDEV<br>RQIAPGQTGKIADYNYKLPDDFTGCVIAWNSNNLDSKVGGNYNYLYRLFRKSNLKP<br>FERDISTEIYQAGSTPCNGVEGFNCYFPLQSYGFQPTYGVGYQPYRVVVLSFELLH<br>APATVCGPKKSTNLVKNKCVNFNFNGLTGTGVLTESNKKFLPFQQFGRDIADTTDA<br>VRDPQTLEILDITPCSFGGVSVITPGTNTSNQVAVLYQGVNCTEVPVAIHADQLTP<br>TWRVYSTGSNVFQTRAGCLIGAEHVNNSYECDIPIGAGICASYQTQTNSHRRAASV<br>ASQSIIAYTMSLGAENSVAYSNNSIAIPTNFTISVTTEILPVSMTKTSVDCTMYIC<br>GDSTECSNLLLQYGSFCTQLNRALTGIAVEQDKNTQEVFAQVKQIYKTPPIKDFGG<br>FNFSQILPDPSKPSKRSFIEDLLFNKVTLADAGFIKQYGDCLGDIAARDLICAQKF<br>NGLTVLPPLLTDEMIAQYTSALLAGTITSGWTFGAGAALQIPFAMQMAYRFNGIGV<br>TQNVLYENQKLIANQFNSAIGKIQDSLSSTASALGKLQDVVNQNAQALNTLVKQLS<br>SNFGAISSVLNDILSRLDKVEAEVQIDRLITGRLQSLQTYVTQQLIRAAEIRASAN<br>LAATKMSECVLGQSKRVDFCGKGYHLMSFPQSAPHGVVFLHVTYVPAQEKNFTTAP<br>AICHDGKAHFPREGVFVSNGTHWFVTQRNFYEPQIITTDNTFVSGNCDVVIGIVNN<br>TVYDPLQPELDSFKEELDKYFKNHTSPDVDLGDISGINASVVNIQKEIDRLNEVAK<br>NLNESLIDLQELGKYEQYIKRSNGLPGPIGPPGPRGRTGDAGPVGPPGPPGPPGPP<br>GPPSAGFDFSFLPQPPQEKAHDGGRYYRANDANVVRDRDLEVDTTLKSLSQQIENI<br>RSPEGSRKNPARTCRDLKMCHSDWKSGEYWIDPNQGCNLDAIKVFCNMETGETCVY<br>PTQPSVAQKNWYISKNPKDKRHVWFGESMTDGFQFEYGGQGSDPADVAIQLTFLRL<br>MSTEASQNITYHCKNSVAYMDQQTGNLKKALLLQGSNEIEIRAEGNSRFTYSVTVD<br>GCTSHTGAWGKTVIEYKTTKTSRLPIIDVAPLDVGAPDQEFGFDVGPVCFL | B.1.1.7 UK variant SARS-CoV-2 spike S-Trimer fusion polypeptide without signal peptide, 1507 aa, S1/S2 furin cleavage site 1 mutant (685R→685A) |
| 20 | QCVNLTTRTQLPPAYTNSFTRGVYYPDKVFRSSVLHSTQDLFLPFFSNVTWFHAIS<br>GTNGTKRFDNPVLPFNDGVYFASTEKSNIIRGWIFGTTLDSKTQSLLIVNNATNVV<br>IKVCEFQFCNDPFLGVYYHKNNKSWMESEFRVYSSANNCTFEYVSQPFLMDLEGKQ<br>GNFKNLREFVFKNIDGYFKIYSKHTPINLVRDLPQGFSALEPLVDLPIGINITRFQ<br>TLLALHRSYLTPGDSSSGWTAGAAAYYVGYLQPRTFLLKYNENGTITDAVDCALDP<br>LSETKCTLKSFTVEKGIYQTSNFRVQPTESIVRFPNITNLCPFGEVFNATRFASVY<br>AWNRKRISNCVADYSVLYNSASFSTFKCYGVSPTKLNDLCFTNVYADSFVIRGDEV<br>RQIAPGQTGKIADYNYKLPDDFTGCVIAWNSNNLDSKVGGNYNYLYRLFRKSNLKP<br>FERDISTEIYQAGSTPCNGVEGFNCYFPLQSYGFQPTYGVGYQPYRVVVLSFELLH<br>APATVCGPKKSTNLVKNKCVNFNFNGLTGTGVLTESNKKFLPFQQFGRDIADTTDA<br>VRDPQTLEILDITPCSFGGVSVITPGTNTSNQVAVLYQGVNCTEVPVAIHADQLTP<br>TWRVYSTGSNVFQTRAGCLIGAEHVNNSYECDIPIGAGICASYQTQTNSHRRARSV<br>ASQSIIAYTMSLGAENSVAYSNNSIAIPTNFTISVTTEILPVSMTKTSVDCTMYIC<br>GDSTECSNLLLQYGSFCTQLNRALTGIAVEQDKNTQEVFAQVKQIYKTPPIKDFGG<br>FNFSQILPDPSKPSKRSFIEDLLFNKVTLADAGFIKQYGDCLGDIAARDLICAQKF<br>NGLTVLPPLLTDEMIAQYTSALLAGTITSGWTFGAGAALQIPFAMQMAYRFNGIGV | B.1.1.7 UK variant SARS-CoV-2 spike S-Trimer fusion polypeptide without signal peptide, 1507 aa, proline mutant (986K/987V→986P/987P) |

| SEQ ID NO. | SEQUENCE | DESCRIPTION |
|---|---|---|
| | TQNVLYENQKLIANQFNSAI

| SEQ ID NO. | SEQUENCE | DESCRIPTION |
|---|---|---|
| | LHAPATVCGPKKSTNLVKNKCVNFNFNGLTGTGVLTESNKKFLPFQQFGRDIADTT<br>DAVRDPQTLEILDITPCSFGGVSVITPGTNTSNQVAVLYQGVNCTEVPVAIHADQL<br>TPTWRVYSTGSNVFQTRAGCLIGAEHVNNSYECDIPIGAGICASYQTQTNSPRRAA<br>SVASQSIIAYTMSLGAENSVAYSNNSIAIPTNFTISVTTEILPVSMTKTSVDCTMY<br>ICGDSTECSNLLLQYGSFCTQLNRALTGIAVEQDKNTQEVFAQVKQIYKTPPIKDF<br>GGFNFSQILPDPSKPSKRSFIEDLLFNKVTLADAGFIKQYGDCLGDIAARDLICAQ<br>KFNGLTVLPPLLTDEMIAQYTSALLAGTITSGWTFGAGAALQIPFAMQMAYRFNGI<br>GVTQNVLYENQKLIANQFNSAIGKIQDSLSSTASALGKLQDVVNQNAQALNTLVKQ<br>LSSNFGAISSVLNDILSRLDKVEAEVQIDRLITGRLQSLQTYVTQQLIRAAEIRAS<br>ANLAATKMSECVLGQSKRVDFCGKGYHLMSFPQSAPHGVVFLHVTYVPAQEKNFTT<br>APAICHDGKAHFPREGVFVSNGTHWFVTQRNFYEPQIITTDNTFVSGNCDVVIGIV<br>NNTVYDPLQPELDSFKEELDKYFKNHTSPDVDLGDISGINASVVNIQKEIDRLNEV<br>AKNLNESLIDLQELGKYEQYIKRSNGLPGPIGPPGPRGRTGDAGPVGPPGPPGPPG<br>PPGPPSAGFDFSFLPQPPQEKAHDGGRYYRANDANVVRDRDLEVDTTLKSLSQQIE<br>NIRSPEGSRKNPARTCRDLKMCHSDWKSGEYWIDPNQGCNLDAIKVFCNMETGETC<br>VYPTQPSVAQKNWYISKNPKDKRHVWFGESMTDGFQFEYGGQGSDPADVAIQLTFL<br>RLMSTEASQNITYHCKNSVAYMDQQTGNLKKALLLQGSNEIEIRAEGNSRFTYSVT<br>VDGCTSHTGAWGKTVIEYKTTKTSRLPIIDVAPLDVGAPDQEFGFDVGPVCFL | mutant<br>(685R→685A) |
| 24 | QCVNLTTRTQLPPAYTNSFTRGVYYPDKVFRSSVLHSTQDLFLPFFSNVTWFHAIH<br>VSGTNGTKRFDNPVLPFNDGVYFASTEKSNIIRGWIFGTTLDSKTQSLLIVNNATN<br>VVIKVCEFQFCNDPFLGVYYHKNNKSWMESEFRVYSSANNCTFEYVSQPFLMDLEG<br>KQGNFKNLREFVFKNIDGYFKIYSKHTPINLVRDLPQGFSALEPLVDLPIGINITR<br>FQTLLALHRSYLTPGDSSSGWTAGAAAYYVGYLQPRTFLLKYNENGTITDAVDCAL<br>DPLSETKCTLKSFTVEKGIYQTSNFRVQPTESIVRFPNITNLCPFGEVFNATRFAS<br>VYAWNRKRISNCVADYSVLYNSASFSTFKCYGVSPTKLNDLCFTNVYADSFVIRGD<br>EVRQIAPGQTGKIADYNYKLPDDFTGCVIAWNSNNLDSKVGGNYNYLYRLFRKSNL<br>KPFERDISTEIYQAGSTPCNGVEGFNCYFPLQSYGFQPTNGVGYQPYRVVVLSFEL<br>LHAPATVCGPKKSTNLVKNKCVNFNFNGLTGTGVLTESNKKFLPFQQFGRDIADTT<br>DAVRDPQTLEILDITPCSFGGVSVITPGTNTSNQVAVLYQGVNCTEVPVAIHADQL<br>TPTWRVYSTGSNVFQTRAGCLIGAEHVNNSYECDIPIGAGICASYQTQTNSPRRAR<br>SVASQSIIAYTMSLGAENSVAYSNNSIAIPTNFTISVTTEILPVSMTKTSVDCTMY<br>ICGDSTECSNLLLQYGSFCTQLNRALTGIAVEQDKNTQEVFAQVKQIYKTPPIKDF<br>GGFNFSQILPDPSKPSKRSFIEDLLFNKVTLADAGFIKQYGDCLGDIAARDLICAQ<br>KFNGLTVLPPLLTDEMIAQYTSALLAGTITSGWTFGAGAALQIPFAMQMAYRFNGI<br>GVTQNVLYENQKLIANQFNSAIGKIQDSLSSTASALGKLQDVVNQNAQALNTLVKQ<br>LSSNFGAISSVLNDILSRLDPPEAEVQIDRLITGRLQSLQTYVTQQLIRAAEIRAS<br>ANLAATKMSECVLGQSKRVDFCGKGYHLMSFPQSAPHGVVFLHVTYVPAQEKNFTT<br>APAICHDGKAHFPREGVFVSNGTHWFVTQRNFYEPQIITTDNTFVSGNCDVVIGIV<br>NNTVYDPLQPELDSFKEELDKYFKNHTSPDVDLGDISGINASVVNIQKEIDRLNEV<br>AKNLNESLIDLQELGKYEQYIKRSNGLPGPIGPPGPRGRTGDAGPVGPPGPPGPPG<br>PPGPPSAGFDFSFLPQPPQEKAHDGGRYYRANDANVVRDRDLEVDTTLKSLSQQIE<br>NIRSPEGSRKNPARTCRDLKMCHSDWKSGEYWIDPNQGCNLDAIKVFCNMETGETC<br>VYPTQPSVAQKNWYISKNPKDKRHVWFGESMTDGFQFEYGGQGSDPADVAIQLTFL<br>RLMSTEASQNITYHCKNSVAYMDQQTGNLKKALLLQGSNEIEIRAEGNSRFTYSVT<br>VDGCTSHTGAWGKTVIEYKTTKTSRLPIIDVAPLDVGAPDQEFGFDVGPVCFL | D614G variant<br>SARS-CoV-2<br>spike S-Trimer<br>fusion<br>polypeptide<br>without signal<br>peptide, 1509<br>aa, proline<br>mutant (

| SEQ ID NO. | SEQUENCE | DESCRIPTION |
|---|---|---|
| | RACNFELCDNPFFAVSKPMGTQTHTMIFDNAFNCTFEYISDAFSLDVSEKSGNFKH<br>LREFVFKNKDGFLYVYKGYQPIDVVRDLPSGFNTLKPIFKLPLGINITNFRAILTA<br>FLPAQDTWGTSAAAYFVGYLKPTTFMLKYDENGTITDAVDCSQNPLAELKCSVKSF<br>EIDKGIYQTSNFRVVPSRDVVRFPNITNLCPFGEVFNATKFPSVYAWERKRISNCV<br>ADYSVLYNSTFFSTFKCYGVSATKLNDLCFSNVYADSFVVKGDDVRQIAPGQTGVI<br>ADYNYKLPDDFMGCVLAWNTRNIDATSTGNYNYKYRLRHGKLRPFERDISNVPFS<br>PDGKPCTPPALNCYWPLNDYGFYTTTGIGYQPYRVVVLSFELLNAPATVCGPKLST<br>DLIKNQCVNFNFNGLTGTGVLTPSSKRFQPFQQFGRDVSDFTDSVRDPKTSEILDI<br>SPCSFGGVSVITPGTNASSEVAVLYQDVNCTDVSTAIHADQLTPAWRIYSTGNNVF<br>QTQAGCLIGAEHVDTSYECDIPIGAGICASYHTVSLLRSTSQKSIVAYTMSLGADS<br>SIAYSNNTIAIPTNFSISITTEVMPVSMAKTSVDCNMYICGDSTECANLLLQYGSF<br>CTQLNRALSGIAAEQDRNTREVFAQVKQMYKTPTLKDFGGFNFSQILPDDPLKPTKR<br>SFIEDLLFNKVTLADAGFMKQYGECLGDINARDLICAQKFNGLTVLPPLLTDDMIA<br>AYTAALVSGTATAGWTFGAGAALQIPFAMQMAYRFNGIGVTQNVLYENQKQIANQF<br>NKAISQIQESLTTTSTALGKLQDVVNQNAQALNTLVKQLSSNFGAISSVLNDILSR<br>LDKVEAEVQIDRLITGRLQSLQTYVTQQLIRAAEIRASANLAATKMSECVLGQSKR<br>VDFCGKGYHLMSFPQAAPHGVVFLHVTYVPSQERNFTTAPAICHEGKAYFPREGVF<br>VFNGTSWFITQRNFFSPQIITTDNTFVSGNCDVVIGIINNTVYDPLQPELDSFKEE<br>LDKYFKNHTSPDVDLGDISGINASVVNIQEEIDRLNEVAKNLNESLIDLQELGKYE<br>QYIKRSNGLPGPIGPPGPRGRTGDAGPVGPPGPPGPPPGPPSAGFDFSFLPQPP<br>QEKAHDGGRYYRANDANVVRDRDLEVDTTLKSLSQQIENIRSPEGSRKNPARTCRD<br>LKMCHSDWKSGEYWIDPNQGCNLDAIKVFCNMETGETCVYPTQPSVAQKNWYISKN<br>PKDKRHVWFGESMTDGFQFEYGGQGSDPADVAIQLTFLRLMSTEASQNITYHCKNS<br>VAYMDQQTGNLKKALLLQGSNEIEIRAEGNSRFTYSVTVDGCTSHTGAWGKTVIEY<br>KTTKTSRLPIIDVAPLDVGAPDQEFGFDVGPVCFL | fusion<br>polypeptide<br>without signal<br>peptide, 1491<br>aa |
| 27 | QCVNLTTRTQLPPAYTNSFTRGVYYPDKVFRSSVLHSTQDLFLPFFSNVTWFHAIH<br>VSGTNGTKRFDNPVLPFNDGVYFASTEKSNIIRGWIFGTTLDSKTQSLLIVNNATN<br>VVIKVCEFQFCNDPFLGVYHKNNKSWMESEFRVYSSANNCTFEYVSQPFLMDLEG<br>KQGNFKNLREFVFKNIDGYFKIYSKHTPINLVRDLPQGFSALEPLVDLPIGINITR<br>FQTLLALHRSYLTPGDSSSGWTAGAAAYYVGYLQPRTFLLKYNENGTITDAVDCAL<br>DPLSETKCTLKSFTVEKGIYQTSNFRVQPTESIVRFPNITNLCPFGEVFNATRFAS<br>VYAWNRKRISNCVADYSVLYNSASFSTFKCYGVSPTKLNDLCFTNVYADSFVIRGD<br>EVRQIAPGQTGKIADYNYKLPDDFTGCVIAWNSNNLDSKVGGNYNYLYRLFRKSNL<br>KPFERDISTEIYQAGSTPCNGVEGFNCYFPLQSYGFQPTNGVGYQPYRVVVLSFEL<br>LHAPATVCGPKKSTNLVKNKCVNFNFNGLTGTGVLTESNKKFLPFQQFGRDIADTT<br>DAVRDPQTLEILDITPCSFGGVSVITPGTNTSNQVAVLYQDVNCTEVPVAIHADQL<br>TPTWRVYSTGSNVFQTRAGCLIGAEHVNNSYECDIPIGAGICASYQTQTNSPRRAR<br>SVASQSIIAYTMSLGAENSVAYSNNSIAIPTNFTISVTTEILPVSMTKTSVDCTMY<br>ICGDSTECSNLLLQYGSFCTQLNRALTGIAVEQDKNTQEVFAQVKQIYKTPPIKDF<br>GGFNFSQILPDPSKPSKRSFIEDLLFNKVTLADAGFIKQYGDCLGDIAARDLICAQ<br>KFNGLTVLPPLLTDEMIAQYTSALLAGTITSGWTFGAGAALQIPFAMQMAYRFNGI<br>GVTQNVLYENQKLIANQFNSAIGKIQDSLSSTASALGKLQDVVNQNAQALNTLVKQ<br>LSSNFGAISSVLNDILSRLDKVEAEVQIDRLITGRLQSLQTYVTQQLIRAAEIRAS<br>ANLAATKMSECVLGQSKRVDFCGKGYHLMSFPQSAPHGVVFLHVTYVPAQEKNFTT<br>APAICHDGKAHFPREGVFVSNGTHWFVTQRNFYEPQIITTDNTFVSGNCDVVIGIV<br>NNTVYDPLQPELDSFKEELDKYFKNHTSPDVDLGDISGINASVVNIQKEIDRLNEV<br>AKNLNESLIDLQELGKYEQ | Prototypic<br>SARS-CoV-2<br>spike protein<br>ectodomain<br>without signal<br>peptide |
| 28 | QCVNLTTRTQLPPAYTNSFTRGVYYPDKVFRSSVLHSTQDLFLPFFSNVTWFHAIH<br>VSGTNGTKRFDNPVLPFNDGVYFASTEKSNIIRGWIFGTTLDSKTQSLLIVNNATN<br>VVIKVCEFQFCNDPFLGVYHKNNKSWMESEFRVYSSANNCTFEYVSQPFLMDLEG<br>KQGNFKNLREFVFKNIDGYFKIYSKHTPINLVRDLPQGFSALEPLVDLPIGINITR<br>FQTLLALHRSYLTPGDSSSGWTAGAAAYYVGYLQPRTFLLKYNENGTITDAVDCAL<br>DPLSETKCTLKSFTVEKGIYQTSNFRVQPTESIVRFPNITNLCPFGEVFNATRFAS<br>VYAWNRKRISNCVADYSVLYNSASFSTFKCYGVSPTKLNDLCFTNVYADSFVIRGD<br>EVRQIAPGQTGKIADYNYKLPDDFTGCVIAWNSNNLDSKVGGNYNYLYRLFRKSNL<br>KPFERDISTEIYQAGSTPCNGVEGFNCYFPLQSYGFQPTNGVGYQPYRVVVLSFEL<br>LHAPATVCGPKKSTNLVKNKCVNFNFNGLTGTGVLTESNKKFLPFQQFGRDIADTT<br>DAVRDPQTLEILDITPCSFGGVSVITPGTNTSNQVAVLYQDVNCTEVPVAIHADQL<br>TPTWRVYSTGSNVFQTRAGCLIGAEHVNNSYECDIPIGAGICASYQTQTNSPRRAA<br>SVASQSIIAYTMSLGAENSVAYSNNSIAIPTNFTISVTTEILPVSMTKTSVDCTMY<br>ICGDSTECSNLLLQYGSFCTQLNRALTGIAVEQDKNTQEVFAQVKQIYKTPPIKDF<br>GGFNFSQILPDPSKPSKRSFIEDLLFNKVTLADAGFIKQYGDCLGDIAARDLICAQ<br>KFNGLTVLPPLLTDEMIAQYTSALLAGTITSGWTFGAGAALQIPFAMQMAYRFNGI<br>GVTQNVLYENQKLIANQFNSAIGKIQDSLSSTASALGKLQDVVNQNAQALNTLVKQ<br>LSSNFGAISSVLNDILSRLDKVEAEVQIDRLITGRLQSLQTYVTQQLIRAAEIRAS<br>ANLAATKMSECVLGQSKRVDFCGKGYHLMSFPQSAPHGVVFLHVTYVPAQEKNFTT<br>APAICHDGKAHFPREGVFVSNGTHWFVTQRNFYEPQIITTDNTFVSGNCDVVIGIV<br>NNTVYDPLQPELDSFKEELDKYFKNHTSPDVDLGDISGINASVVNIQKEIDRLNEV<br>AKNLNESLIDLQELGKYEQ | Prototypic<br>SARS-CoV-2<br>spike protein<br>ectodomain<br>without signal<br>peptide, S1/S2<br>furin cleavage<br>site 1 mutant<br>(685R→685A) |
| 29 | QCVNLTTRTQLPPAYTNSFTRGVYYPDKVFRSSVLHSTQDLFLPFFSNVTWFHAIH<br>VSGTNGTKRFDNPVLPFNDGVYFASTEKSNIIRGWIFGTTLDSKTQSLLIVNNATN<br>VVIKVCEFQFCNDPFLGVYHKNNKSWMESEFRVYSSANNCTFEYVSQPFLMDLEG<br>KQGNFKNLREFVFKNIDGYFKIYSKHTPINLVRDLPQGFSALEPLVDLPIGINITR<br>FQTLLALHRSYLTPGDSSSGWTAGAAAYYVGYLQPRTFLLKYNENGTITDAVDCAL | Prototypic<br>SARS-CoV-2<br>spike protein<br>ectodomain<br>without signal |

-continued

| SEQ ID NO. | SEQUENCE | DESCRIPTION |
|---|---|---|
| | DPLSETKCTLKSFTVEKGIYQTSNFRVQPTESIVRFPNITNLCPFGEVFNATRFAS<br>VYAWNRKRISNCVADYSVLYNSASFSTFKCYGVSPTKLNDLCFTNVYADSFVIRGD<br>EVRQIAPGQTGKIADYNYKLPDDFTGCVIAWNSNNLDSKVGGNYNYLYRLFRKSNL<br>KPFERDISTEIYQAGSTPCNGVEGFNCYFPLQSYGFQPTNGVGYQPYRVVVLSFEL<br>LHAPATVCGPKKSTNLVKNKCVNFNFNGLTGTGVLTESNKKFLPFQQFGRDIADTT<br>DAVRDPQTLEILDITPCSFGGVSVITPGTNTSNQVAVLYQDVNCTEVPVAIHADQL<br>TPTWRVYSTGSNVFQTRAGCLIGAEHVNNSYECDIPIGAGICASYQTQTNSPRRAR<br>SVASQSIIAYTMSLGAENSVAYSNNSIAIPTNFTISVTTEILPVSMTKTSVDCTMY<br>ICGDSTECSNLLLQYGSFCTQLNRALTGIAVEQDKNTQEVFAQVKQIYKTPPIKDF<br>GGFNFSQILPDPSKPSKRSFIEDLLFNKVTLADAGFIKQYGDCLGDIAARDLICAQ<br>KFNGLTVLPPLLTDEMIAQYTSALLAGTITSGWTFGAGAALQIPFAMQMAYRFNGI<br>GVTQNVLYENQKLIANQFNSAIGKIQDSLSSTASALGKLQDVVNQNAQALNTLVKQ<br>LSSNFGAISSVLNDILSRLDPPEAEVQIDRLITGRLQSLQTYVTQQLIRAAEIRAS<br>ANLAATKMSECVLGQSKRVDFCGKGYHLMSFPQSAPHGVVFLHVTYVPAQEKNFTT<br>APAICHDGKAHFPREGVFVSNGTHWFVTQRNFYEPQIITTDNTFVSGNCDVVIGIV<br>NNTVYDPLQPELDSFKEELDKYFKNHTSPDVDLGDISGINASVVNIQKEIDRLNEV<br>AKNLNESLIDLQELGKYEQ | peptide, proline mutant (986K/987V→986P/987P) |
| 30 | QCVNLTTRTQLPPAYTNSFTRGVYYPDKVFRSSVLHSTQDLFLPFFSNVTWFHAIH<br>VSGTNGTKRFDNPVLPFNDGVYFASTEKSNIIRGWIFGTTLDSKTQSLLIVNNATN<br>VVIKVCEFQFCNDPFLGVYYHKNNKSWMESEFRVYSSANNCTFEYVSQPFLMDLEG<br>KQGNFKNLREFVFKNIDGYFKIYSKHTPINLVRDLPQGFSALEPLVDLPIGINITR<br>FQTLLALHRSYLTPGDSSSGWTAGAAAYYVGYLQPRTFLLKYNENGTITDAVDCAL<br>DPLSETKCTLKSFTVEKGIYQTSNFRVQPTESIVRFPNITNLCPFGEVFNATRFAS<br>VYAWNRKRISNCVADYSVLYNSASFSTFKCYGVSPTKLNDLCFTNVYADSFVIRGD<br>EVRQIAPGQTGKIADYNYKLPDDFTGCVIAWNSNNLDSKVGGNYNYLYRLFRKSNL<br>KPFERDISTEIYQAGSTPCNGVEGFNCYFPLQSYGFQPTNGVGYQPYRVVVLSFEL<br>LHAPATVCGPKKSTNLVKNKCVNFNFNGLTGTGVLTESNKKFLPFQQFGRDIADTT<br>DAVRDPQTLEILDITPCSFGGVSVITPGTNTSNQVAVLYQDVNCTEVPVAIHADQL<br>TPTWRVYSTGSNVFQTRAGCLIGAEHVNNSYECDIPIGAGICASYQTQTNSPRRAA<br>SVASQSIIAYTMSLGAENSVAYSNNSIAIPTNFTISVTTEILPVSMTKTSVDCTMY<br>ICGDSTECSNLLLQYGSFCTQLNRALTGIAVEQDKNTQEVFAQVKQIYKTPPIKDF<br>GGFNFSQILPDPSKPSKRSFIEDLLFNKVTLADAGFIKQYGDCLGDIAARDLICAQ<br>KFNGLTVLPPLLTDEMIAQYTSALLAGTITSGWTFGAGAALQIPFAMQMAYRFNGI<br>GVTQNVLYENQKLIANQFNSAIGKIQDSLSSTASALGKLQDVVNQNAQALNTLVKQ<br>LSSNFGAISSVLNDILSRLDPPEAEVQIDRLITGRLQSLQTYVTQQLIRAAEIRAS<br>ANLAATKMSECVLGQSKRVDFCGKGYHLMSFPQSAPHGVVFLHVTYVPAQEKNFTT<br>APAICHDGKAHFPREGVFVSNGTHWFVTQRNFYEPQIITTDNTFVSGNCDVVIGIV<br>NNTVYDPLQPELDSFKEELDKYFKNHTSPDVDLGDISGINASVVNIQKEIDRLNEV<br>AKNLNESLIDLQELGKYEQ | Prototypic SARS-CoV-2 spike protein ectodomain without signal peptide, S1/S2 furin cleavage site 1 and proline mutant (685R→685A, 986K/987V→986P/987P) |
| 31 | QCVNLTTRTQLPPAYTNSFTRGVYYPDKVFRSSVLHSTQDLFLPFFSNVTWFHAIH<br>VSGTNGTKRFDNPVLPFNDGVYFASTEKSNIIRGWIFGTTLDSKTQSLLIVNNATN<br>VVIKVCEFQFCNDPFLGVYYHKNNKSWMESEFRVYSSANNCTFEYVSQPFLMDLEG<br>KQGNFKNLREFVFKNIDGYFKIYSKHTPINLVRDLPQGFSALEPLVDLPIGINITR<br>FQTLLALHRSYLTPGDSSSGWTAGAAAYYVGYLQPRTFLLKYNENGTITDAVDCAL<br>DPLSETKCTLKSFTVEKGIYQTSNFRVQPTESIVRFPNITNLCPFGEVFNATRFAS<br>VYAWNRKRISNCVADYSVLYNSASFSTFKCYGVSPTKLNDLCFTNVYADSFVIRGD<br>EVRQIAPGQTGKIADYNYKLPDDFTGCVIAWNSNNLDSKVGGNYNYLYRLFRKSNL<br>KPFERDISTEIYQAGSTPCNGVEGFNCYFPLQSYGFQPTNGVGYQPYRVVVLSFEL<br>LHAPATVCGPKKSTNLVKNKC | Prototypic SARS-CoV-2 spike protein NTD/RBD fragment without signal peptide |
| 32 | QCVNLTTRTQLPPAYTNSFTRGVYYPDKVFRSSVLHSTQDLFLPFFSNVTWFHAIH<br>VSGTNGTKRFDNPVLPFNDGVYFASTEKSNIIRGWIFGTTLDSKTQSLLIVNNATN<br>VVIKVCEFQFCNDPFLGVYYHKNNKSWMESEFRVYSSANNCTFEYVSQPFLMDLEG<br>KQGNFKNLREFVFKNIDGYFKIYSKHTPINLVRDLPQGFSALEPLVDLPIGINITR<br>FQTLLALHRSYLTPGDSSSGWTAGAAAYYVGYLQPRTFLLKYNENGTITDAVDCAL<br>DPLSETKCTLKSFTVEKGIYQTSNFRVQPTESIVRFPNITNLCPFGEVFNATRFAS<br>VYAWNRKRISNCVADYSVLYNSASFSTFKCYGVSPTKLNDLCFTNVYADSFVIRGD<br>EVRQIAPGQTGKIADYNYKLPDDFTGCVIAWNSNNLDSKVGGNYNYLYRLFRKSNL<br>KPFERDISTEIYQAGSTPCNGVEGFNCYFPLQSYGFQPTNGVGYQPYRVVVLSFEL<br>LHAPATVCGPKKSTNLVKNKCVNFNFNGLTGTGVLTESNKKFLPFQQFGRDIADTT<br>DAVRDPQTLEILDITPCSFGGVSVITPGTNTSNQVAVLYQDVNCTEVPVAIHADQL<br>TPTWRVYSTGSNVFQTRAGCLIGAEHVNNSYECDIPIGAGICASYQTQTNSP | Prototypic SARS-CoV-2 spike protein S1 fragment without signal peptide |
| 33 | SVASQSIIAYTMSLGAENSVAYSNNSIAIPTNFTISVTTEILPVSMTKTSVDCTMY<br>ICGDSTECSNLLLQYGSFCTQLNRALTGIAVEQDKNTQEVFAQVKQIYKTPPIKDF<br>GGFNFSQILPDPSKPSKRSFIEDLLFNKVTLADAGFIKQYGDCLGDIAARDLICAQ<br>KFNGLTVLPPLLTDEMIAQYTSALLAGTITSGWTFGAGAALQIPFAMQMAYRFNGI<br>GVTQNVLYENQKLIANQFNSAIGKIQDSLSSTASALGKLQDVVNQNAQALNTLVKQ<br>LSSNFGAISSVLNDILSRLDKVEAEVQIDRLITGRLQSLQTYVTQQLIRAAEIRAS<br>ANLAATKMSECVLGQSKRVDFCGKGYHLMSFPQSAPHGVVFLHVTYVPAQEKNFTT<br>APAICHDGKAHFPREGVFVSNGTHWFVTQRNFYEPQIITTDNTFVSGNCDVVIGIV<br>NNTVYDPLQPELDSFKEELDKYFKNHTSPDVDLGDISGINASVVNIQKEIDRLNEV<br>AKNLNESLIDLQELGKYEQ | Prototypic SARS-CoV-2 spike protein S2 fragment (cleaved at S1/S2, site 1) |

-continued

| SEQ ID NO. | SEQUENCE | DESCRIPTION |
|---|---|---|
| 34 | TMSLGAENSVAYSNNSIAIPTNFTISVTTEILPVSMTKTSVDCTMYICGDSTECSN<br>LLLQYGSFCTQLNRALTGIAVEQDKNTQEVFAQVKQIYKTPPIKDFGGFNFSQILP<br>DPSKPSKRSFIEDLLFNKVTLADAGFIKQYGDCLGDIAARDLICAQKFNGLTVLPP<br>LLTDEMIAQYTSALLAGTITSGWTFGAGAALQIPFAMQMAYRFNGIGVTQNVLYEN<br>QKLIANQFNSAIGKIQDSLSSTASALGKLQDVVNQNAQALNTLVKQLSSNFGAISS<br>VLNDILSRLDKVEAEVQIDRLITGRLQSLQTYVTQQLIRAAEIRASANLAATKMSE<br>CVLGQSKRVDFCGKGYHLMSFPQSAPHGVVFLHVTYVPAQEKNFTTAPAICHDGKA<br>HFPREGVFVSNGTHWFVTQRNFYEPQIITTDNTFVSGNCDVVIGIVNNTVYDPLQP<br>ELDSFKEELDKYFKNHTSPDVDLGDISGINASVVNIQKEIDRLNEVAKNLNESLID<br>LQELGKYEQ | Prototypic<br>SARS-CoV-2<br>spike protein<br>S2 fragment<br>(cleaved at<br>S1/S2, site 2) |
| 35 | SFIEDLLFNKVTLADAGFIKQYGDCLGDIAARDLICAQKFNGLTVLPPLLTDEMIA<br>QYTSALLAGTITSGWTFGAGAALQIPFAMQMAYRFNGIGVTQNVLYENQKLIANQF<br>NSAIGKIQDSLSSTASALGKLQDVVNQNAQALNTLVKQLSSNFGAISSVLNDILSR<br>LDKVEAEVQIDRLITGRLQSLQTYVTQQLIRAAEIRASANLAATKMSECVLGQSKR<br>VDFCGKGYHLMSFPQSAPHGVVFLHVTYVPAQEKNFTTAPAICHDGKAHFPREGVF<br>VSNGTHWFVTQRNFYEPQIITTDNTFVSGNCDVVIGIVNNTVYDPLQPELDSFKEE<br>LDKYFKNHTSPDVDLGDISGINASVVNIQKEIDRLNEVAKNLNESLIDLQELGKYE<br>Q | Prototypic<br>SARS-CoV-2<br>spike protein<br>S2 fragment<br>(cleaved at<br>S2') |
| 36 | QCVNLTTRTQLPPAYTNSFTRGVYYPDKVFRSSVLHSTQDLFLPFFSNVTWFHAIH<br>VSGTNGTKRFDNPVLPFNDGVYFASTEKSNIIRGWIFGTTLDSKTQSLLIVNNATN<br>VVIKVCEFQFCNDPFLGVYYHKNNKSWMESEFRVYSSANNCTFEYVSQPFLMDLEG<br>KQGNFKNLREFVFKNIDGYFKIYSKHTPINLVRDLPQGFSALEPLVDLPIGINITR<br>FQTLLALHRSYLTPGDSSSGWTAGAAAYYVGYLQPRTFLLKYNENGTITDAVDCAL<br>DPLSETKCTLKSFTVEKGIYQTSNFRVQPTESIVRFPNITNLCPFGEVFNATRFAS<br>VYAWNRKRISNCVADYSVLYNSASFSTFKCYGVSPTKLNDLCFTNVYADSFVIRGD<br>EVRQIAPGQTGNIADYNYKLPDDFTGCVIAWNSNNLDSKVGGNYNYLYRLFRKSNL<br>KPFERDISTEIYQAGSTPCNGVKGFNCYFPLQSYGFQPTYGVGYQPYRVVVLSFEL<br>LHAPATVCGPKKSTNLVKNKCVNFNFNGLTGTGVLTESNKKFLPFQQFGRDIADTT<br>DAVRDPQTLEILDITPCSFGGVSVITPGTNTSNQVAVLYQGVNCTEVPVAIHADQL<br>TPTWRVYSTGSNVFQTRAGCLIGAEHVNNSYECDIPIGAGICASYQTQTNSPRRAR<br>SVASQSIIAYTMSLGAENSVAYSNNSIAIPTNFTISVTTEILPVSMTKTSVDCTMY<br>ICGDSTECSNLLLQYGSFCTQLNRALTGIAVEQDKNTQEVFAQVKQIYKTPPIKDF<br>GGFNFSQILPDPSKPSKRSFIEDLLFNKVTLADAGFIKQYGDCLGDIAARDLICAQ<br>KFNGLTVLPPLLTDEMIAQYTSALLAGTITSGWTFGAGAALQIPFAMQMAYRFNGI<br>GVTQNVLYENQKLIANQFNSAIGKIQDSLSSTASALGKLQDVVNQNAQALNTLVKQ<br>LSSNFGAISSVLNDILSRLDKVEAEVQIDRLITGRLQSLQTYVTQQLIRAAEIRAS<br>ANLAATKMSECVLGQSKRVDFCGKGYHLMSFPQSAPHGVVFLHVTYVPAQEKNFTT<br>APAICHDGKAHFPREGVFVSNGTHWFVTQRNFYEPQIITTDNTFVSGNCDVVIGIV<br>NNTVYDPLQPELDSFKEELDKYFKNHTSPDVDLGDISGINASVVNIQKEIDRLNEV<br>AKNLNESLIDLQELGKYEQ | B.1.351 South<br>African variant<br>SARS-CoV-2<br>spike protein<br>ectodomain<br>without signal<br>peptide |
| 37 | QCVNLTTRTQLPPAYTNSFTRGVYYPDKVFRSSVLHSTQDLFLPFFSNVTWFHAIH<br>VSGTNGTKRFDNPVLPFNDGVYFASTEKSNIIRGWIFGTTLDSKTQSLLIVNNATN<br>VVIKVCEFQFCNDPFLGVYYHKNNKSWMESEFRVYSSANNCTFEYVSQPFLMDLEG<br>KQGNFKNLREFVFKNIDGYFKIYSKHTPINLVRDLPQGFSALEPLVDLPIGINITR<br>FQTLLALHRSYLTPGDSSSGWTAGAAAYYVGYLQPRTFLLKYNENGTITDAVDCAL<br>DPLSETKCTLKSFTVEKGIYQTSNFRVQPTESIVRFPNITNLCPFGEVFNATRFAS<br>VYAWNRKRISNCVADYSVLYNSASFSTFKCYGVSPTKLNDLCFTNVYADSFVIRGD<br>EVRQIAPGQTGNIADYNYKLPDDFTGCVIAWNSNNLDSKVGGNYNYLYRLFRKSNL<br>KPFERDISTEIYQAGSTPCNGVKGFNCYFPLQSYGFQPTYGVGYQPYRVVVLSFEL<br>LHAPATVCGPKKSTNLVKNKCVNFNFNGLTGTGVLTESNKKFLPFQQFGRDIADTT<br>DAVRDPQTLEILDITPCSFGGVSVITPGTNTSNQVAVLYQGVNCTEVPVAIHADQL<br>TPTWRVYSTGSNVFQTRAGCLIGAEHVNNSYECDIPIGAGICASYQTQTNSPRRAA<br>SVASQSIIAYTMSLGAENSVAYSNNSIAIPTNFTISVTTEILPVSMTKTSVDCTMY<br>ICGDSTECSNLLLQYGSFCTQLNRALTGIAVEQDKNTQEVFAQVKQIYKTPPIKDF<br>GGFNFSQILPDPSKPSKRSFIEDLLFNKVTLADAGFIKQYGDCLGDIAARDLICAQ<br>KFNGLTVLPPLLTDEMIAQYTSALLAGTITSGWTFGAGAALQIPFAMQMAYRFNGI<br>GVTQNVLYENQKLIANQFNSAIGKIQDSLSSTASALGKLQDVVNQNAQALNTLVKQ<br>LSSNFGAISSVLNDILSRLDKVEAEVQIDRLITGRLQSLQTYVTQQLIRAAEIRAS<br>ANLAATKMSECVLGQSKRVDFCGKGYHLMSFPQSAPHGVVFLHVTYVPAQEKNFTT<br>APAICHDGKAHFPREGVFVSNGTHWFVTQRNFYEPQIITTDNTFVSGNCDVVIGIV<br>NNTVYDPLQPELDSFKEELDKYFKNHTSPDVDLGDISGINASVVNIQKEIDRLNEV<br>AKNLNESLIDLQELGKYEQ | B.1.351 South<br>African variant<br>SARS-CoV-2<br>spike protein<br>ectodomain<br>without signal<br>peptide, S1/S2<br>furin cleavage<br>site 1 mutant<br>(685R→685A) |
| 38 | QCVNLTTRTQLPPAYTNSFTRGVYYPDKVFRSSVLHSTQDLFLPFFSNVTWFHAIH<br>VSGTNGTKRFDNPVLPFNDGVYFASTEKSNIIRGWIFGTTLDSKTQSLLIVNNATN<br>VVIKVCEFQFCNDPFLGVYYHKNNKSWMESEFRVYSSANNCTFEYVSQPFLMDLEG<br>KQGNFKNLREFVFKNIDGYFKIYSKHTPINLVRDLPQGFSALEPLVDLPIGINITR<br>FQTLLALHRSYLTPGDSSSGWTAGAAAYYVGYLQPRTFLLKYNENGTITDAVDCAL<br>DPLSETKCTLKSFTVEKGIYQTSNFRVQPTESIVRFPNITNLCPFGEVFNATRFAS<br>VYAWNRKRISNCVADYSVLYNSASFSTFKCYGVSPTKLNDLCFTNVYADSFVIRGD<br>EVRQIAPGQTGNIADYNYKLPDDFTGCVIAWNSNNLDSKVGGNYNYLYRLFRKSNL<br>KPFERDISTEIYQAGSTPCNGVKGFNCYFPLQSYGFQPTYGVGYQPYRVVVLSFEL<br>LHAPATVCGPKKSTNLVKNKCVNFNFNGLTGTGVLTESNKKFLPFQQFGRDIADTT | B.1.351 South<br>African variant<br>SARS-CoV-2<br>spike protein<br>ectodomain<br>without signal<br>peptide,<br>proline mutant<br>(986K/987V→986P/<br>987P) |

-continued

| SEQ ID NO. | SEQUENCE | DESCRIPTION |
|---|---|---|
| | DAVRDPQTLEILDITPCSFGGVSVITPGTNTSNQVAVLYQGVNCTEVPVAIHADQL TPTWRVYSTGSNVFQTRAGCLIGAEHVNNSYECDIPIGAGICASYQTQTNSPRRAR SVASQSIIAYTMSLGAENSVAYSNNSIAIPTNFTISVTTEILPVSMTKTSVDCTMY ICGDSTECSNLLLQYGSFCTQLNRALTGIAVEQDKNTQEVFAQVKQIYKTPPIKDF GGFNFSQILPDPSKPSKRSFIEDLLFNKVTLADAGFIKQYGDCLGDIAARDLICAQ KFNGLTVLPPLLTDEMIAQYTSALLAGTITSGWTFGAGAALQIPFAMQMAYRFNGI GVTQNVLYENQKLIANQFNSAIGKIQDSLSSTASALGKLQDVVNQNAQALNTLVKQ LSSNFGAISSVLNDILSRLDPPEAEVQIDRLITGRLQSLQTYVTQQLIRAAEIRAS ANLAATKMSECVLGQSKRVDFCGKGYHLMSFPQSAPHGVVFLHVTYVPAQEKNFTT APAICHDGKAHFPREGVFVSNGTHWFVTQRNFYEPQIITTDNTFVSGNCDVVIGIV NNTVYDPLQPELDSFKEELDKYFKNHTSPDVDLGDISGINASVVNIQKEIDRLNEV AKNLNESLIDLQELGKYEQ | |
| 39 | QCVNLTTRTQLPPAYTNSFTRGVYYPDKVFRSSVLHSTQDLFLPFFSNVTWFHAIH VSGTNGTKRFDNPVLPFNDGVYFASTEKSNIIRGWIFGTTLDSKTQSLLIVNNATN VVIKVCEFQFCNDPFLGVYYHKNNKSWMESEFRVYSSANNCTFEYVSQPFLMDLEG KQGNFKNLREFVFKNIDGYFKIYSKHTPINLVRDLPQGFSALEPLVDLPIGINITR FQTLLALHRSYLTPGDSSSGWTAGAAAYYVGYLQPRTFLLKYNENGTITDAVDCAL DPLSETKCTLKSFTVEKGIYQTSNFRVQPTESIVRFPNITNLCPFGEVFNATRFAS VYAWNRKRISNCVADYSVLYNSASFSTFKCYGVSPTKLNDLCFTNVYADSFVIRGD EVRQIAPGQTGNIADYNYKLPDDFTGCVIAWNSNNLDSKVGGNYNYLYRLFRKSNL KPFERDISTEIYQAGSTPCNGVKGFNCYFPLQSYGFQPTYGVGYQPYRVVVLSFEL LHAPATVCGPKKSTNLVKNKCVNFNFNGLTGTGVLTESNKKFLPFQQFGRDIADTT DAVRDPQTLEILDITPCSFGGVSVITPGTNTSNQVAVLYQGVNCTEVPVAIHADQL TPTWRVYSTGSNVFQTRAGCLIGAEHVNNSYECDIPIGAGICASYQTQTNSPRRAA SVASQSIIAYTMSLGAENSVAYSNNSIAIPTNFTISVTTEILPVSMTKTSVDCTMY ICGDSTECSNLLLQYGSFCTQLNRALTGIAVEQDKNTQEVFAQVKQIYKTPPIKDF GGFNFSQILPDPSKPSKRSFIEDLLFNKVTLADAGFIKQYGDCLGDIAARDLICAQ KFNGLTVLPPLLTDEMIAQYTSALLAGTITSGWTFGAGAALQIPFAMQMAYRFNGI GVTQNVLYENQKLIANQFNSAIGKIQDSLSSTASALGKLQDVVNQNAQALNTLVKQ LSSNFGAISSVLNDILSRLDPPEAEVQIDRLITGRLQSLQTYVTQQLIRAAEIRAS ANLAATKMSECVLGQSKRVDFCGKGYHLMSFPQSAPHGVVFLHVTYVPAQEKNFTT APAICHDGKAHFPREGVFVSNGTHWFVTQRNFYEPQIITTDNTFVSGNCDVVIGIV NNTVYDPLQPELDSFKEELDKYFKNHTSPDVDLGDISGINASVVNIQKEIDRLNEV AKNLNESLIDLQELGKYEQ | B.1.351 South African variant SARS-CoV-2 spike protein ectodomain without signal peptide, S1/S2 furin cleavage site 1 and proline mutant (685R→685A, 986K/987V→986P/987P) |
| 40 | QCVNFTNRTQLPSAYTNSFTRGVYYPDKVFRSSVLHSTQDLFLPFFSNVTWFHAIH VSGTNGTKRFDNPVLPFNDGVYFASTEKSNIIRGWIFGTTLDSKTQSLLIVNNATN VVIKVCEFQFCNYPFLGVYYHKNNKSWMESEFRVYSSANNCTFEYVSQPFLMDLEG KQGNFKNLSEFVFKNIDGYFKIYSKHTPINLVRDLPQGFSALEPLVDLPIGINITR FQTLLALHRSYLTPGDSSSGWTAGAAAYYVGYLQPRTFLLKYNENGTITDAVDCAL DPLSETKCTLKSFTVEKGIYQTSNFRVQPTESIVRFPNITNLCPFGEVFNATRFAS VYAWNRKRISNCVADYSVLYNSASFSTFKCYGVSPTKLNDLCFTNVYADSFVIRGD EVRQIAPGQTGTIADYNYKLPDDFTGCVIAWNSNNLDSKVGGNYNYLYRLFRKSNL KPFERDISTEIYQAGSTPCNGVKGFNCYFPLQSYGFQPTYGVGYQPYRVVVLSFEL LHAPATVCGPKKSTNLVKNKCVNFNFNGLTGTGVLTESNKKFLPFQQFGRDIADTT DAVRDPQTLEILDITPCSFGGVSVITPGTNTSNQVAVLYQGVNCTEVPVAIHADQL TPTWRVYSTGSNVFQTRAGCLIGAEYVNNSYECDIPIGAGICASYQTQTNSPRRAR SVASQSIIAYTMSLGAENSVAYSNNSIAIPTNFTISVTTEILPVSMTKTSVDCTMY ICGDSTECSNLLLQYGSFCTQLNRALTGIAVEQDKNTQEVFAQVKQIYKTPPIKDF GGFNFSQILPDPSKPSKRSFIEDLLFNKVTLADAGFIKQYGDCLGDIAARDLICAQ KFNGLTVLPPLLTDEMIAQYTSALLAGTITSGWTFGAGAALQIPFAMQMAYRFNGI GVTQNVLYENQKLIANQFNSAIGKIQDSLSSTASALGKLQDVVNQNAQALNTLVKQ LSSNFGAISSVLNDILSRLDKVEAEVQIDRLITGRLQSLQTYVTQQLIRAAEIRAS ANLAAIKMSECVLGQSKRVDFCGKGYHLMSFPQSAPHGVVFLHVTYVPAQEKNFTT APAICHDGKAHFPREGVFVSNGTHWFVTQRNFYEPQIITTDNTFVSGNCDVVIGIV NNTVYDPLQPELDSFKEELDKYFKNHTSPDVDLGDISGINASVVNIQKEIDRLNEV AKNLNESLIDLQELGKYEQ | P.1 Brazilian variant SARS-CoV-2 spike protein ectodomain without signal peptide |
| 41 | QCVNFTNRTQLPSAYTNSFTRGVYYPDKVFRSSVLHSTQDLFLPFFSNVTWFHAIH VSGTNGTKRFDNPVLPFNDGVYFASTEKSNIIRGWIFGTTLDSKTQSLLIVNNATN VVIKVCEFQFCNYPFLGVYYHKNNKSWMESEFRVYSSANNCTFEYVSQPFLMDLEG KQGNFKNLSEFVFKNIDGYFKIYSKHTPINLVRDLPQGFSALEPLVDLPIGINITR FQTLLALHRSYLTPGDSSSGWTAGAAAYYVGYLQPRTFLLKYNENGTITDAVDCAL DPLSETKCTLKSFTVEKGIYQTSNFRVQPTESIVRFPNITNLCPFGEVFNATRFAS VYAWNRKRISNCVADYSVLYNSASFSTFKCYGVSPTKLNDLCFTNVYADSFVIRGD EVRQIAPGQTGTIADYNYKLPDDFTGCVIAWNSNNLDSKVGGNYNYLYRLFRKSNL KPFERDISTEIYQAGSTPCNGVKGFNCYFPLQSYGFQPTYGVGYQPYRVVVLSFEL LHAPATVCGPKKSTNLVKNKCVNFNFNGLTGTGVLTESNKKFLPFQQFGRDIADTT DAVRDPQTLEILDITPCSFGGVSVITPGTNTSNQVAVLYQGVNCTEVPVAIHADQL TPTWRVYSTGSNVFQTRAGCLIGAEYVNNSYECDIPIGAGICASYQTQTNSPRRAA SVASQSIIAYTMSLGAENSVAYSNNSIAIPTNFTISVTTEILPVSMTKTSVDCTMY ICGDSTECSNLLLQYGSFCTQLNRALTGIAVEQDKNTQEVFAQVKQIYKTPPIKDF GGFNFSQILPDPSKPSKRSFIEDLLFNKVTLADAGFIKQYGDCLGDIAARDLICAQ KFNGLTVLPPLLTDEMIAQYTSALLAGTITSGWTFGAGAALQIPFAMQMAYRFNGI GVTQNVLYENQKLIANQFNSAIGKIQDSLSSTASALGKLQDVVNQNAQALNTLVKQ LSSNFGAISSVLNDILSRLDKVEAEVQIDRLITGRLQSLQTYVTQQLIRAAEIRAS | P.1 Brazilian variant SARS-CoV-2 spike protein ectodomain without signal peptide, S1/S2 furin cleavage site 1 mutant (685R→685A) |

| SEQ ID NO. | SEQUENCE | DESCRIPTION |
|---|---|---|
| | ANLAAIKMSECVLGQSKRVDFCGKGYHLMSFPQSAPHGVVFLHVTYVPAQEKNFTT<br>APAICHDGKAHFPREGVFVSNGTHWFVTQRNFYEPQIITTDNTFVSGNCDVVIGIV<br>NNTVYDPLQPELDSFKEELDKYFKNHTSPDVDLGDISGINASVVNIQKEIDRLNEV<br>AKNLNESLIDLQELGKYEQ | |
| 42 | QCVNFTNRTQLPSAYTNSFTRGVYYPDKVFRSSVLHSTQDLFLPFFSNVTWFHAIH<br>VSGTNGTKRFDNPVLPFNDGVYFASTEKSNIIRGWIFGTTLDSKTQSLLIVNNATN<br>VVIKVCEFQFCNYPFLGVYYHKNNKSWMESEFRVYSSANNCTFEYVSQPFLMDLEG<br>KQGNFKNLSEFVFKNIDGYFKIYSKHTPINLVRDLPQGFSALEPLVDLPIGINITR<br>FQTLLALHRSYLTPGDSSSGWTAGAAAYYVGYLQPRTFLLKYNENGTITDAVDCAL<br>DPLSETKCTLKSFTVEKGIYQTSNFRVQPTESIVRFPNITNLCPFGEVFNATRFAS<br>VYAWNRKRISNCVADYSVLYNSASFSTFKCYGVSPTKLNDLCFTNVYADSFVIRGD<br>EVRQIAPGQTGTIADYNYKLPDDFTGCVIAWNSNNLDSKVGGNYNYLYRLFRKSNL<br>KPFERDISTEIYQAGSTPCNGVKGFNCYFPLQSYGFQPTYGVGYQPYRVVVLSFEL<br>LHAPATVCGPKKSTNLVKNKCVNFNFNGLTGTGVLTESNKKFLPFQQFGRDIADTT<br>DAVRDPQTLEILDITPCSFGGVSVITPGTNTSNQVAVLYQGVNCTEVPVAIHADQL<br>TPTWRVYSTGSNVFQTRAGCLIGAEYVNNSYECDIPIGAGICASYQTQTNSPRRAR<br>SVASQSIIAYTMSLGAENSVAYSNNSIAIPTNFTISVTTEILPVSMTKTSVDCTMY<br>ICGDSTECSNLLLQYGSFCTQLNRALTGIAVEQDKNTQEVFAQVKQIYKTPPIKDF<br>GGFNFSQILPDPSKPSKRSFIEDLLFNKVTLADAGFIKQYGDCLGDIAARDLICAQ<br>KFNGLTVLPPLLTDEMIAQYTSALLAGTITSGWTFGAGAALQIPFAMQMAYRFNGI<br>GVTQNVLYENQKLIANQFNSAIGKIQDSLSSTASALGKLQDVVNQNAQALNTLVKQ<br>LSSNFGAISSVLNDILSRLDPPEAEVQIDRLITGRLQSLQTYVTQQLIRAAEIRAS<br>ANLAAIKMSECVLGQSKRVDFCGKGYHLMSFPQSAPHGVVFLHVTYVPAQEKNFTT<br>APAICHDGKAHFPREGVFVSNGTHWFVTQRNFYEPQIITTDNTFVSGNCDVVIGIV<br>NNTVYDPLQPELDSFKEELDKYFKNHTSPDVDLGDISGINASVVNIQKEIDRLNEV<br>AKNLNESLIDLQELGKYEQ | P.1 Brazilian variant SARS-CoV-2 spike protein ectodomain without signal peptide,

| SEQ ID NO. | SEQUENCE | DESCRIPTION |
|---|---|---|
| | GNFKNLREFVFKNIDGYFKIYSKHTPINLVRDLPQGFSALEPLVDLPIGINITRFQ<br>TLLALHRSYLTPGDSSSGWTAGAAAYYVGYLQPRTFLLKYNENGTITDAVDCALDP<br>LSETKCTLKSFTVEKGIYQTSNFRVQPTESIVRFPNITNLCPFGEVFNATRFASVY<br>AWNRKRISNCVADYSVLYNSASFSTFKCYGVSPTKLNDLCFTNVYADSFVIRGDEV<br>RQIAPGQTGKIADYNYKLPDDFTGCVIAWNSNNLDSKVGGNYNYLYRLFRKSNLKP<br>FERDISTEIYQAGSTPCNGVEGFNCYFPLQSYGFQPTYGVGYQPYRVVVLSFELLH<br>APATVCGPKKSTNLVKNKCVNFNGLTGTGVLTESNKKFLPFQQFGRDIADTTDA<br>VRDPQTLEILDITPCSFGGVSVITPGTNTSNQVAVLYQGVNCTEVPVAIHADQLTP<br>TWRVYSTGSNVFQTRAGCLIGAEHVNNSYECDIPIGAGICASYQTQTNSHRRAASV<br>ASQSIIAYTMSLGAENSVAYSNNSIAIPTNFTISVTTEILPVSMTKTSVDCTMYIC<br>GDSTECSNLLLQYGSFCTQLNRALTGIAVEQDKNTQEVFAQVKQIYKTPPIKDFGG<br>FNFSQILPDPSKPSKRSFIEDLLFNKVTLADAGFIKQYGDCLGDIAARDLICAQKF<br>NGLTVLPPLLTDEMIAQYTSALLAGTITSGWTFGAGAALQIPFAMQMAYRFNGIGV<br>TQNVLYENQKLIANQFNSAIGKIQDSLSSTASALGKLQDVVNQNAQALNTLVKQLS<br>SNFGAISSVLNDILSRLDKVEAEVQIDRLITGRLQSLQTYVTQQLIRAAEIRASAN<br>LAATKMSECVLGQSKRVDFCGKGYHLMSFPQSAPHGVVFLHVTYVPAQEKNFTTAP<br>AICHDGKAHFPREGVFVSNGTHWFVTQRNFYEPQIITTDNTFVSGNCDVVIGIVNN<br>TVYDPLQPELDSFKEELDKYFKNHTSPDVDLGDISGINASVVNIQKEIDRLNEVAK<br>NLNESLIDLQELGKYEQ | protein<br>ectodomain<br>without signal<br>peptide, S1/S2<br>furin cleavage<br>site 1 mutant<br>(685R→685A) |
| 46 | QCVNLTTRTQLPPAYTNSFTRGV -continued

| SEQ ID NO. | SEQUENCE | DESCRIPTION |
|---|---|---|
| | TPTWRVYSTGSNVFQTRAGCLIGAEHVNNSYECDIPIGAGICASYQTQTNSPRRAR<br>SVASQSIIAYTMSLGAENSVAYSNNSIAIPTNFTISVTTEILPVSMTKTSVDCTMY<br>ICGDSTECSNLLLQYGSFCTQLNRALTGIAVEQDKNTQEVFAQVKQIYKTPPIKDF<br>GGFNFSQILPDPSKPSKRSFIEDLLFNKVTLADAGFIKQYGDCLGDIAARDLICAQ<br>KFNGLTVLPPLLTDEMIAQYTSALLAGTITSGWTFGAGAALQIPFAMQMAYRFNGI<br>GVTQNVLYENQKLIANQFNSAIGKIQDSLSSTASALGKLQDVVNQNAQALNTLVKQ<br>LSSNFGAISSVLNDILSRLDKVEAEVQIDRLITGRLQSLQTYVTQQLIRAAEIRAS<br>ANLAATKMSECVLGQSKRVDFCGKGYHLMSFPQSAPHGVVFLHVTYVPAQEKNFTT<br>APAICHDGKAHFPREGVFVSNGTHWFVTQRNFYEPQIITTDNTFVSGNCDVVIGIV<br>NNTVYDPLQPELDSFKEELDKYFKNHTSPDVDLGDISGINASVVNIQKEIDRLNEV<br>AKNLNESLIDLQELGKYEQ | |
| 49 | QCVNLTTRTQLPPAYTNSFTRGVYYPDKVFRSSVLHSTQDLFLPFFSNVTWFHAIH<br>VSGTNGTKRFDNPVLPFNDGVYFASTEKSNIIRGWIFGTTLDSKTQSLLIVNNATN<br>VVIKVCEFQFCNDPFLGVYYHKNNKSWMESEFRVYSSANNCTFEYVSQPFLMDLEG<br>KQGNFKNLREFVFKNIDGYFKIYSKHTPINLVRDLPQGFSALEPLVDLPIGINITR<br>FQTLLALHRSYLTPGDSSSGWTAGAAAYYVGYLQPRTFLLKYNENGTITDAVDCAL<br>DPLSETKCTLKSFTVEKGIYQTSNFRVQPTESIVRFPNITNLCPFGEVFNATRFAS<br>VYAWNRKRISNCVADYSVLYNSASFSTFKCYGVSPTKLNDLCFTNVYADSFVIRGD<br>EVRQIAPGQTGKIADYNYKLPDDFTGCVIAWNSNNLDSKVGGNYNYLYRLFRKSNL<br>KPFERDISTEIYQAGSTPCNGVEGFNCYFPLQSYGFQPTNGVGYQPYRVVVLSFEL<br>LHAPATVCGPKKSTNLVKNKCVNFNFNGLTGTGVLTESNKKFLPFQQFGRDIADTT<br>DAVRDPQTLEILDITPCSFGGVSVITPGTNTSNQVAVLYQGVNCTEVPVAIHADQL<br>TPTWRVYSTGSNVFQTRAGCLIGAEHVNNSYECDIPIGAGICASYQTQTNSPRRAA<br>SVASQSIIAYTMSLGAENSVAYSNNSIAIPTNFTISVTTEILPVSMTKTSVDCTMY<br>ICGDSTECSNLLLQYGSFCTQLNRALTGIAVEQDKNTQEVFAQVKQIYKTPPIKDF<br>GGFNFSQILPDPSKPSKRSFIEDLLFNKVTLADAGFIKQYGDCLGDIAARDLICAQ<br>KFNGLTVLPPLLTDEMIAQYTSALLAGTITSGWTFGAGAALQIPFAMQMAYRFNGI<br>GVTQNVLYENQKLIANQFNSAIGKIQDSLSSTASALGKLQDVVNQNAQALNTLVKQ<br>LSSNFGAISSVLNDILSRLDKVEAEVQIDRLITGRLQSLQTYVTQQLIRAAEIRAS<br>ANLAATKMSECVLGQSKRVDFCGKGYHLMSFPQSAPHGVVFLHVTYVPAQEKNFTT<br>APAICHDGKAHFPREGVFVSNGTHWFVTQRNFYEPQIITTDNTFVSGNCDVVIGIV<br>NNTVYDPLQPELDSFKEELDKYFKNHTSPDVDLGDISGINASVVNIQKEIDRLNEV<br>AKNLNESLIDLQELGKYEQ | D614G variant SARS-CoV-2 spike protein ectodomain without signal peptide, S1/S2 furin cleavage site 1 mutant (685R-685A) |
| 50 | QCVNLTTRTQLPPAYTNSFTRGVYYPDKVFRSSVLHSTQDLFLPFFSNVTWFHAIH<br>VSGTNGTKRFDNPVLPFNDGVYFASTEKSNIIRGWIFGTTLDSKTQSLLIVNNATN<br>VVIKVCEFQFCNDPFLGVYYHKNNKSWMESEFRVYSSANNCTFEYVSQPFLMDLEG<br>KQGNFKNLREFVFKNIDGYFKIYSKHTPINLVRDLPQGFSALEPLVDLPIGINITR<br>FQTLLALHRSYLTPGDSSSGWTAGAAAYYVGYLQPRTFLLKYNENGTITDAVDCAL<br>DPLSETKCTLKSFTVEKGIYQTSNFRVQPTESIVRFPNITNLCPFGEVFNATRFAS<br>VYAWNRKRISNCVADYSVLYNSASFSTFKCYGVSPTKLNDLCFTNVYADSFVIRGD<br>EVRQIAPGQTGKIADYNYKLPDDFTGCVIAWNSNNLDSKVGGNYNYLYRLFRKSNL<br>KPFERDISTEIYQAGSTPCNGVEGFNCYFPLQSYGFQPTNGVGYQPYRVVVLSFEL<br>LHAPATVCGPKKSTNLVKNKCVNFNFNGLTGTGVLTESNKKFLPFQQFGRDIADTT<br>DAVRDPQTLEILDITPCSFGGVSVITPGTNTSNQVAVLYQGVNCTEVPVAIHADQL<br>TPTWRVYSTGSNVFQTRAGCLIGAEHVNNSYECDIPIGAGICASYQTQTNSPRRAR<br>SVASQSIIAYTMSLGAENSVAYSNNSIAIPTNFTISVTTEILPVSMTKTSVDCTMY<br>ICGDSTECSNLLLQYGSFCTQLNRALTGIAVEQDKNTQEVFAQVKQIYKTPPIKDF<br>GGFNFSQILPDPSKPSKRSFIEDLLFNKVTLADAGFIKQYGDCLGDIAARDLICAQ<br>KFNGLTVLPPLLTDEMIAQYTSALLAGTITSGWTFGAGAALQIPFAMQMAYRFNGI<br>GVTQNVLYENQKLIANQFNSAIGKIQDSLSSTASALGKLQDVVNQNAQALNTLVKQ<br>LSSNFGAISSVLNDILSRLDPPEAEVQIDRLITGRLQSLQTYVTQQLIRAAEIRAS<br>ANLAATKMSECVLGQSKRVDFCGKGYHLMSFPQSAPHGVVFLHVTYVPAQEKNFTT<br>APAICHDGKAHFPREGVFVSNGTHWFVTQRNFYEPQIITTDNTFVSGNCDVVIGIV<br>NNTVYDPLQPELDSFKEELDKYFKNHTSPDVDLGDISGINASVVNIQKEIDRLNEV<br>AKNLNESLIDLQELGKYEQ | D614G variant SARS-CoV-2 spike protein ectodomain without signal peptide, proline mutant (986K/987V→986P/987P) |
| 51 | QCVNLTTRTQLPPAYTNSFTRGVYYPDKVFRSSVLHSTQDLFLPFFSNVTWFHAIH<br>VSGTNGTKRFDNPVLPFNDGVYFASTEKSNIIRGWIFGTTLDSKTQSLLIVNNATN<br>VVIKVCEFQFCNDPFLGVYYHKNNKSWMESEFRVYSSANNCTFEYVSQPFLMDLEG<br>KQGNFKNLREFVFKNIDGYFKIYSKHTPINLVRDLPQGFSALEPLVDLPIGINITR<br>FQTLLALHRSYLTPGDSSSGWTAGAAAYYVGYLQPRTFLLKYNENGTITDAVDCAL<br>DPLSETKCTLKSFTVEKGIYQTSNFRVQPTESIVRFPNITNLCPFGEVFNATRFAS<br>VYAWNRKRISNCVADYSVLYNSASFSTFKCYGVSPTKLNDLCFTNVYADSFVIRGD<br>EVRQIAPGQTGKIADYNYKLPDDFTGCVIAWNSNNLDSKVGGNYNYLYRLFRKSNL<br>KPFERDISTEIYQAGSTPCNGVEGFNCYFPLQSYGFQPTNGVGYQPYRVVVLSFEL<br>LHAPATVCGPKKSTNLVKNKCVNFNFNGLTGTGVLTESNKKFLPFQQFGRDIADTT<br>DAVRDPQTLEILDITPCSFGGVSVITPGTNTSNQVAVLYQGVNCTEVPVAIHADQL<br>TPTWRVYSTGSNVFQTRAGCLIGAEHVNNSYECDIPIGAGICASYQTQTNSPRRAA<br>SVASQSIIAYTMSLGAENSVAYSNNSIAIPTNFTISVTTEILPVSMTKTSVDCTMY<br>ICGDSTECSNLLLQYGSFCTQLNRALTGIAVEQDKNTQEVFAQVKQIYKTPPIKDF<br>GGFNFSQILPDPSKPSKRSFIEDLLFNKVTLADAGFIKQYGDCLGDIAARDLICAQ<br>KFNGLTVLPPLLTDEMIAQYTSALLAGTITSGWTFGAGAALQIPFAMQMAYRFNGI<br>GVTQNVLYENQKLIANQFNSAIGKIQDSLSSTASALGKLQDVVNQNAQALNTLVKQ<br>LSSNFGAISSVLNDILSRLDPPEAEVQIDRLITGRLQSLQTYVTQQLIRAAEIRAS<br>ANLAATKMSECVLGQSKRVDFCGKGYHLMSFPQSAPHGVVFLHVTYVPAQEKNFTT | D614G variant SARS-CoV-2 spike protein ectodomain without signal peptide, S1/S2 furin cleavage site 1 and proline mutant (685R→685A, 986K/987V→986P/987P) |

| SEQ ID NO. | SEQUENCE | DESCRIPTION |
|---|---|---|
|  | APAICHDGKAHFPREGVFVSNGTHWFVTQRNFYEPQIITTDNTFVSGNCDVVIGIV<br>NNTVYDPLQPELDSFKEELDKYFKNHTSPDVDLGDISGINASVVNIQKEIDRLNEV<br>AKNLNESLIDLQELGKYEQ |  |
| 52 | SDLDRCTTFDDVQAPNYTQHTSSMRGVYYPDEIFRSDTLYLTQDLFLPFYSNVTGF<br>HTINHTFDNPVIPFKDGIYFAATEKSNVVRGWVFGSTMNNKSQSVIIINNSTNVVI<br>RACNFELCDNPFFAVSKPMGTQTHTMIFDNAFNCTFEYISDAFSLDVSEKSGNFKH<br>LREFVFKNKDGFLYVYKGYQPIDVVRDLPSGFNTLKPIFKLPLGINITNFRAILTA<br>FLPAQDTWGTSAAAYFVGYLKPTTFMLKYDENGTITDAVDCSQNPLAELKCSVKSF<br>EIDKGIYQTSNFRVVPSRDVVRFPNITNLCPFGEVFNATKFPSVYAWERKRISNCV<br>ADYSVLYNSTFFSTFKCYGVSATKLNDLCFSNVYADSFVVKGDDVRQIAPGQTGVI<br>ADYNYKLPDDFMGCVLAWNTRNIDATSTGNYNYKYRYLRHGKLRPFERDISNVPFS<br>PDGKPCTPPALNCYWPLNDYGFYTTTGIGYQPYRVVVLSFELLNAPATVCGPKLST<br>DLIKNQCVNFNFNGLTGTGVLTPSSKRFQPFQQFGRDVSDFTDSVRDPKTSEILDI<br>SPCSFGGVSVITPGTNASSEVAVLYQDVNCTDVSTAIHADQLTPAWRIYSTGNNVF<br>QTQAGCLIGAEHVDTSYECDIPIGAGICASYHTVSLLRSTSQKSIVAYTMSLGADS<br>SIAYSNNTIAIPTNFSISITTEVMPVSMAKTSVDCNMYICGDSTECANLLLQYGSF<br>CTQLNRALSGIAAEQDRNTREVFAQVKQMYKTPTLKDFGGFNFSQILPDPLKPTKR<br>SFIEDLLFNKVTLADAGFMKQYGECLGDINARDLICAQKFNGLTVLPPLLTDDMIA<br>AYTAALVSGTATAGWTFGAGAALQIPFAMQMAYRFNGIGVTQNVLYENQKQIANQF<br>NKAISQIQESLTTTSTALGKLQDVVNQNAQALNTLVKQLSSNFGAISSVLNDILSR<br>LDKVEAEVQIDRLITGRLQSLQTYVTQQLIRAAEIRASANLAATKMSECVLGQSKR<br>VDFCGKGYHLMSFPQAAPHGVVFLHVTYVPSQERNFTTAPAICHEGKAYFPREGVF<br>VFNGTSWFITQRNFFSPQIITTDNTFVSGNCDVVIGIINNTVYDPLQPELDSFKEE<br>LDKYFKNHTSPDVDLGDISGINASVVNIQEEIDRLNEVAKNLNESLIDLQELGKYE<br>Q | SARS-CoV-1<br>spike protein<br>ectodomain<br>without signal<br>peptide |
| 53 | MFIFLLFLTLTSG | SARS-CoV-1<br>spike protein<br>signal peptide |
| 54 | MFVFLVLLPLVSS | Prototypic<br>SARS-CoV-2<br>spike protein<br>signal peptide |
| 55 | MFVFLVLLPLVSSQCVNLTTRTQLPPAYTNSFTRGVYYPDKVFRSSVLHSTQDLFL<br>PFFSNVTWFHAIHVSGTNGTKRFDNPVLPFNDGVYFASTEKSNIIRGWIFGTTLDS<br>KTQSLLIVNNATNVVIKVCEFQFCNDPFLGVYYHKNNKSWMESEFRVYSSANNCTF<br>EYVSQPFLMDLEGKQGNFKNLREFVFKNIDGYFKIYSKHTPINLVRDLPQGFSALE<br>PLVDLPIGINITRFQTLLALHRSYLTPGDSSSGWTAGAAAYYVGYLQPRTFLLKYN<br>ENGTITDAVDCALDPLSETKCTLKSFTVEKGIYQTSNFRVQPTESIVRFPNITNLC<br>PFGEVFNATRFASVYAWNRKRISNCVADYSVLYNSASFSTFKCYGVSPTKLNDLCF<br>TNVYADSFVIRGDEVRQIAPGQTGKIADYNYKLPDDFTGCVIAWNSNNLDSKVGGN<br>YNYLYRLFRKSNLKPFERDISTEIYQAGSTPCNGVEGFNCYFPLQSYGFQPTNGVG<br>YQPYRVVVLSFELLHAPATVCGPKKSTNLVKNKCVNFNFNGLTGTGVLTESNKKFL<br>PFQQFGRDIADTTDAVRDPQTLEILDITPCSFGGVSVITPGTNTSNQVAVLYQDVN<br>CTEVPVAIHADQLTPTWRVYSTGSNVFQTRAGCLIGAEHVNNSYECDIPIGAGICA<br>SYQTQTNSPRRARSVASQSIIAYTMSLGAENSVAYSNNSIAIPTNFTISVTTEILP<br>VSMTKTSVDCTMYICGDSTECSNLLLQYGSFCTQLNRALTGIAVEQDKNTQEVFAQ<br>VKQIYKTPPIKDFGGFNFSQILPDPSKPSKRSFIEDLLFNKVTLADAGFIKQYGDC<br>LGDIAARDLICAQKFNGLTVLPPLLTDEMIAQYTSALLAGTITSGWTFGAGAALQI<br>PFAMQMAYRFNGIGVTQNVLYENQKLIANQFNSAIGKIQDSLSSTASALGKLQDVV<br>NQNAQALNTLVKQLSSNFGAISSVLNDILSRLDKVEAEVQIDRLITGRLQSLQTYV<br>TQQLIRAAEIRASANLAATKMSECVLGQSKRVDFCGKGYHLMSFPQSAPHGVVFLH<br>VTYVPAQEKNFTTAPAICHDGKAHFPREGVFVSNGTHWFVTQRNFYEPQIITTDNT<br>FVSGNCDVVIGIVNNTVYDPLQPELDSFKEELDKYFKNHTSPDVDLGDISGINASV<br>VNIQKEIDRLNEVAKNLNESLIDLQELGKYEQYIKWPWYIWLGFIAGLIAIVMVTI<br>MLCCMTSCCSCLKGCCSCGSCCKFDEDDSEPVLKGVKLHYT | Prototypic<br>SARS-CoV-2<br>full-length<br>spike protein,<br>1273 aa |
| 56 | MFVFLVLLPLVSSQCVNLTTRTQLPPAYTNSFTRGVYYPDKVFRSSVLHSTQDLFL<br>PFFSNVTWFHAIHVSGTNGTKRFDNPVLPFNDGVYFASTEKSNIIRGWIFGTTLDS<br>KTQSLLIVNNATNVVIKVCEFQFCNDPFLGVYYHKNNKSWMESEFRVYSSANNCTF<br>EYVSQPFLMDLEGKQGNFKNLREFVFKNIDGYFKIYSKHTPINLVRDLPQGFSALE<br>PLVDLPIGINITRFQTLLALHRSYLTPGDSSSGWTAGAAAYYVGYLQPRTFLLKYN<br>ENGTITDAVDCALDPLSETKCTLKSFTVEKGIYQTSNFRVQPTESIVRFPNITNLC<br>PFGEVFNATRFASVYAWNRKRISNCVADYSVLYNSASFSTFKCYGVSPTKLNDLCF<br>TNVYADSFVIRGDEVRQIAPGQTGKIADYNYKLPDDFTGCVIAWNSNNLDSKVGGN<br>YNYLYRLFRKSNLKPFERDISTEIYQAGSTPCNGVEGFNCYFPLQSYGFQPTNGVG<br>YQPYRVVVLSFELLHAPATVCGPKKSTNLVKNKCVNFNFNGLTGTGVLTESNKKFL<br>PFQQFGRDIADTTDAVRDPQTLEILDITPCSFGGVSVITPGTNTSNQVAVLYQDVN<br>CTEVPVAIHADQLTPTWRVYSTGSNVFQTRAGCLIGAEHVNNSYECDIPIGAGICA<br>SYQTQTNSPRRARSVASQSIIAYTMSLGAENSVAYSNNSIAIPTNFTISVTTEILP<br>VSMTKTSVDCTMYICGDSTECSNLLLQYGSFCTQLNRALTGIAVEQDKNTQEVFAQ<br>VKQIYKTPPIKDFGGFNFSQILPDPSKPSKRSFIEDLLFNKVTLADAGFIKQYGDC<br>LGDIAARDLICAQKFNGLTVLPPLLTDEMIAQYTSALLAGTITSGWTFGAGAALQI<br>PFAMQMAYRFNGIGVTQNVLYENQKLIANQFNSAIGKIQDSLSSTASALGKLQDVV | Prototypic<br>SARS-CoV-2<br>spike protein<br>ectodomain with<br>signal peptide |

| SEQ ID NO. | SEQUENCE | DESCRIPTION |
|---|---|---|
|  | NQNAQALNTLVKQLSSNFGAISSVLNDILSRLDKVEAEVQIDRLITGRLQSLQTYV TQQLIRAAEIRASANLAATKMSECVLGQSKRVDFCGKGYHLMSFPQSAPHGVVFLH VTYVPAQEKNFTTAPAICHDGKAHFPREGVFVSNGTHWFVTQRNFYEPQIITTDNT FVSGNCDVVIGIVNNTVYDPLQPELDSFKEELDKYFKNHTSPDVDLGDISGINASV VNIQKEIDRLNEVAKNLNESLIDLQELGKYEQ |  |
| 57 | VNLTTRTQLPPAYTNSFTRGVYYPDKVFRSSVLHSTQDLFLPFFSNVTWFHAIHVS GTNGTKRFDNPVLPFNDGVYFASTEKSNIIRGWIFGTTLDSKTQSLLIVNNATNVV IKVCEFQFCNDPFLGVYYHKNNKSWMESEFRVYSSANNCTFEYVSQPFLMDLEGKQ GNFKNLREFVFKNIDGYFKIYSKHTPINLVRDLPQGFSALEPLVDLPIGINITRFQ TLLALHRSYLTPGDSSSGWTAGAAAYYVGYLQPRTFLLKYNENGTITDAVDCALDP LSETKCTLKS | Prototypic SARS-CoV-2 spike protein NTD without signal peptide, 290 aa |
| 58 | PNITNLCPFGEVFNATRFASVYAWNRKRISNCVADYSVLYNSASFSTFKCYGVSPT KLNDLCFTNVYADSFVIRGDEVRQIAPGQTGKIADYNYKLPDDFTGCVIAWNSNNL DSKVGGNYNYLYRLFRKSNLKPFERDISTEIYQAGSTPCNGVEGFNCYFPLQSYGF QPTNGVGYQPYRVVVLSFELLHAP | Prototypic SARS-CoV-2 spike protein RBD, 192 aa |
| 59 | RRAR | Prototypic SARS-CoV-2 spike protein S1/S2 |
| 60 | GSAG | Prototypic SARS-CoV-2 spike protein S1/S2 mutant |
| 61 | SFIEDLLFNKVTLADAGF | Prototypic SARS-CoV-2 spike protein fusion peptide (FP) sequence |
| 62 | GIGVTQNVLYENQKLIANQFNSAIGKIQDSLSSTASALGKLQDVVNQNAQALNTLV KQLSSNFGAISSVLNDILSRLD | Prototypic SARS-CoV-2 spike protein heptad repeat 1 (HR1) |
| 63 | KVEAEVQIDRLITGRLQSLQTYVTQQLIRAAEIRASANLAATKMSECVLG | Prototypic SARS-CoV-2 spike protein central helix (CH) |
| 64 | TTAPAICHDGKAHFPREGVFVSNGTHWFVTQRNFYEPQIITTDNTFVSGNCDVVIG IVNNTVYDPL | Prototypic SARS-CoV-2 spike protein connector domain (CD) |
| 65 | EELDKYFKNHTSPDVDLGDISGINASVVNIQKEIDRLNEVAKNLNESLIDLQELGK YEQ | Prototypic SARS-CoV-2 spike protein heptad repeat 2 (HR2) |
| 66 | WPWYIWLGFIAGLIAIVMVTIML | Prototypic SARS-CoV-2 spike protein transmembrane (TM) domain |
| 67 | ANVVRDRDLEVDTTLKSLSQQIENIRSPEGSRKNPARTCRDLKMCHSDWKSGEYWI DPNQGCNLDAIKVFCNMETGETCVYPTQPSVAQKNWYISKNPKDKRHVWFGESMTD GFQFEYGGQGSDPADVAIQLTFLRLMSTEASQNITYHCKNSVAYMDQQTGNLKKAL LLQGSNEIEIRAEGNSRFTYSVTVDGCTSHTGAWGKTVIEYKTTKTSRLPIIDVAP LDVGAPDQEFGFDVGPVCFL | Trimerization peptide (Type I), QT version |

| SEQ ID NO. | SEQUENCE | DESCRIPTION |
|---|---|---|
| 68 | NGLPGPIGPPGPRGRTGDAGPVGPPGPPGPPGPPGPPSAGFDFSFLPQPPQEKAHD GGRYYRANDANVVRDRDLEVDTTLKSLSQQIENIRSPEGSRKNPARTCRDLKMCHS DWKSGEYWIDPNQGCNLDAIKVFCNMETGETCVYPTQPSVAQKNWYISKNPKDKRH VWFGESMTDGFQFEYGGQGSDPADVAIQLTFLRLMSTEASQNITYHCKNSVAYMDQ QTGNLKKALLLQGSNEIEIRAEGNSRFTYSVTVDGCTSHTGAWGKTVIEYKTTKTS RLPIIDVAPLDVGAPDQEFGFDVGPVCFL | Trimerization peptide (Type I), with glycine-X-Y repeats and D→N mutation at BMP-1 site, QT version |
| 69 | NGLPGPIGPPGPRGRTGDAGPVGPPGPPGPPGPPGPPSAGFDFSFLPQPPQEKAHD GGRYYRNDDANVVRDRDLEVDTTLKSLSQQIENIRSPEGSRKNPARTCRDLKMCHS DWKSGEYWIDPNQGCNLDAIKVFCNMETGETCVYPTQPSVAQKNWYISKNPKDKRH VWFGESMTDGFQFEYGGQGSDPADVAIQLTFLRLMSTEASQNITYHCKNSVAYMDQ QTGNLKKALLLQGSNEIEIRAEGNSRFTYSVTVDGCTSHTGAWGKTVIEYKTTKTS RLPIIDVAPLDVGAPDQEFGFDVGPVCFL | Trimerization peptide (Type I), with glycine-X-Y repeats and A→N mutation at BMP-1 site, QT version |
| 70 | RSNGLPGPIGPPGPRGRTGDAGPVGPPGPPGPPGPPGPPSAGFDFSFLPQPPQEKA HDGGRYYRANDTXNWRDRDLEVDTTLKSLSQQIENIRSPEGSRKNPARTCRDLKMC HSDWKSGEYWIDPNQGCNLDAIKVFCNMETGETCVYPTQPSVAQKNWYISKNPKDK RHVWFGESMTDGFQFEYGGQGSDPADVAIQLTFLRLMSTEASQNITYHCKNSVAYM DQQTGNLKKALLLQGSNEIEIRAEGNSRFTYSVTVDGCTSHTGAWGKTVIEYKTTK TSRLPIIDVAPLDVGAPDQEFGFDVGPVCFL | Trimerization peptide (Type I), with glycine-X-Y repeats and D→N mutation at BMP-1 site, QT version |
| 71 | GSNGLPGPIGPPGPRGRTGDAGPVGPPGPPGPPGPPGPPSAGFDFSFLPQPPQEKA HDGGRYYRANDTXNWRDRDLEVDTTLKSLSQQIENIRSPEGSRKNPARTCRDLKMC HSDWKSGEYWIDPNQGCNLDAIKVFCNMETGETCVYPTQPSVAQKNWYISKNPKDK RHVWFGESMTDGFQFEYGGQGSDPADVAIQLTFLRLMSTEASQNITYHCKNSVAYM DQQTGNLKKALLLQGSNEIEIRAEGNSRFTYSVTVDGCTSHTGAWGKTVIEYKTTK TSRLPIIDVAPLDVGAPDQEFGFDVGPVCFL | Trimerization peptide (Type I), with glycine-X-Y repeats and D→N mutation at BMP-1 site, QT version |
| 72 | ANVVRDRDLEVDTTLKSLSQQIENIRSPEGSRKNPARTCRDLKMCHSDWKSGEYWI DPNQGCNLDAIKVFCNMETGETCVYPTQPSVAQKNWYISKNPKDKRHVWFGESMTD GFQFEYGGQGSDPADVAIQLTFLRLMSTEASQNITYHCKNSVAYMDQQTGNLKKAL LLKGSNEIEIRAEGNSRFTYSVTVDGCTSHTGAWGKTVIEYKTTKSSRLPIIDVAP LDVGAPDQEFGFDVGPVCFL | Trimerization peptide (Type I), KS version |
| 73 | NGLPGPIGPPGPRGRTGDAGPVGPPGPPGPPGPPGPPSAGFDFSFLPQPPQEKAHD GGRYYRANDANVVRDRDLEVDTTLKSLSQQIENIRSPEGSRKNPARTCRDLKMCHS DWKSGEYWIDPNQGCNLDAIKVFCNMETGETCVYPTQPSVAQKNWYISKNPKDKRH VWFGESMTDGFQFEYGGQGSDPADVAIQLTFLRLMSTEASQNITYHCKNSVAYMDQ QTGNLKKALLLKGSNEIEIRAEGNSRFTYSVTVDGCTSHTGAWGKTVIEYKTTKSS RLPIIDVAPLDVGAPDQEFGFDVGPVCFL | Trimerization peptide (Type I) with glycine-X-Y repeats and D→N mutation at BMP-1 site, KS version |
| 74 | NGLPGPIGPPGPRGRTGDAGPVGPPGPPGPPGPPGPPSAGFDFSFLPQPPQEKAHD GGRYYRNDDANVVRDRDLEVDTTLKSLSQQIENIRSPEGSRKNPARTCRDLKMCHS DWKSGEYWIDPNQGCNLDAIKVFCNMETGETCVYPTQPSVAQKNWYISKNPKDKRH VWFGESMTDGFQFEYGGQGSDPADVAIQLTFLRLMSTEASQNITYHCKNSVAYMDQ QTGNLKKALLLKGSNEIEIRAEGNSRFTYSVTVDGCTSHTGAWGKTVIEYKTTKSS RLPIIDVAPLDVGAPDQEFGFDVGPVCFL | Trimerization peptide (Type I) with glycine-X-Y repeats and A→N mutation at BMP-1 site, KS version |
| 75 | RSNGLPGPIGPPGPRGRTGDAGPVGPPGPPGPPGPPGPPSAGFDFSFLPQPPQEKA HDGGRYYRANDANVVRDRDLEVDTTLKSLSQQIENIRSPEGSRKNPARTCRDLKMC HSDWKSGEYWIDPNQGCNLDAIKVFCNMETGETCVYPTQPSVAQKNWYISKNPKDK RHVWFGESMTDGFQFEYGGQGSDPADVAIQLTFLRLMSTEASQNITYHCKNSVAYM DQQTGNLKKALLLKGSNEIEIRAEGNSRFTYSVTVDGCTSHTGAWGKTVIEYKTTK SSRLPIIDVAPLDVGAPDQEFGFDVGPVCFL | Trimerization peptide (Type I) with glycine-X-Y repeats and D→N mutation at BMP-1 site, KS version |

| SEQ ID NO. | SEQUENCE | DESCRIPTION |
|---|---|---|
| 76 | GSNGLPGPIGPPGPRGRTGDAGPVGPPGPPGPPGPPGPPSAGFDFSFLPQPPQEKA HDGGRYYRANDANVVRDRDLEVDTTLKSLSQQIENIRSPEGSRKNPARTCRDLKMC HSDWKSGEYWIDPNQGCNLDAIKVFCNMETGETCVYPTQPSVAQKNWYISKNPKDK RHVWFGESMTDGFQFEYGGQGSDPADVAIQLTFLRLMSTEASQNITYHCKNSVAYM DQQTGNLKKALLLKGSNEIEIRAEGNSRFTYSVTVDGCTSHTGAWGKTVIEYKTTK SSRLPIIDVAPLDVGAPDQEFGFDVGPVCFL | Trimerization peptide (Type I) with glycine-X-Y repeats and D→N mutation at BMP-1 site, KS version |
| 77 | DEIMTSLKSVNGQIESLISPDGSRKNPARNCRDLKFCHPELKSGEYWVDPNQGCKL DAIKVFCNMETGETCISANPLNVPRKHWWTDSSAEKKHVWFGESMDGGFQFSYGNP ELPEDVLDVQLAFLRLLSSRASQNITYHCKNSIAYMDQASGNVKKALKLMGSNEGE FKAEGNSKFTYTVLEDGCTKHTGEWSKTVFEYRTRKAVRLPIVDIAPYDIGGPDQE FGVDVGPVCF | Trimerization peptide (Type III) |
| 78 | EPMDFKINTDEIMTSLKSVNGQIESLISPDGSRKNPARNCRDLKFCHPELKSGEYW VDPNQGCKLDAIKVFCNMETGETCISANPLNVPRKHWWTDSSAEKKHVWFGESMDG GFQFSYGNPELPEDVLDVQLAFLRLLSSRASQNITYHCKNSIAYMDQASGNVKKAL KLMGSNEGEFKAEGNSKFTYTVLEDGCTKHTGEWSKTVFEYRTRKAVRLPIVDIAP YDIGGPDQEFGVDVGPVCFL | Trimerization peptide (Type III) |
| 79 | SEPMDFKINTDEIMTSLKSVNGQIESLISPDGSRKNPARNCRDLKFCHPELKSGEY WVDPNQGCKLDAIKVFCNMETGETCISANPLNVPRKHWWTDSSAEKKHVWFGESMD GGFQFSYGNPELPEDVLDVQLAFLRLLSSRASQNITYHCKNSIAYMDQASGNVKKA LKLMGSNEGEFKAEGNSKFTYTVLEDGCTKHTGEWSKTVFEYRTRKAVRLPIVDIA PYDIGGPDQEFGVDVGPVCFL | Trimerization peptide (Type III) |
| 80 | RSEPMDFKINTDEIMTSLKSVNGQIESLISPDGSRKNPARNCRDLKFCHPELKSGE YWVDPNQGCKLDAIKVFCNMETGETCISANPLNVPRKHWWTDSSAEKKHVWFGESM DGGFQFSYGNPELPEDVLDVQLAFLRLLSSRASQNITYHCKNSIAYMDQASGNVKK ALKLMGSNEGEFKAEGNSKFTYTVLEDGCTKHTGEWSKTVFEYRTRKAVRLPIVDI APYDIGGPDQEFGVDVGPVCFL | Trimerization peptide (Type III) |

The invention claimed is:

1. An immunogenic composition comprising:
   a) a fusion polypeptide comprising a SARS-CoV-2 spike (S) ectodomain polypeptide and a C-propeptide of a human pro-collagen, wherein the C-propeptide is configured to form a disulfide bond-linked homotrimer; and
   b) one or more adjuvants.

2. The immunogenic composition of claim 1, wherein the human pro-collagen is selected from the group consisting of proa1(I), proa1(II), proa1(III), proa1(V), proa1(XI), proa2(I), proa2(V), proa2(XI), and proa3(XI).

3. The immunogenic composition of claim 1, wherein the fusion polypeptide further comprises a glycine-repeat triple helical region of collagen linked to the C-propeptide.

4. The immunogenic composition of claim 1, wherein the fusion polypeptide does not comprise a BMP-1 protease recognition sequence or comprises a mutated BMP-1 protease recognition sequence.

5. The immunogenic composition of claim 1, wherein the SARS-CoV-2 S ectodomain polypeptide comprises an S1 sequence and/or an S2 sequence.

6. The immunogenic composition of claim 1, wherein the SARS-CoV-2 S ectodomain polypeptide comprises a furin cleavage site mutation and/or one or more proline substitutions between an HR1 domain and a central helix domain.

7. The immunogenic composition of claim 1, wherein the SARS-CoV-2 S ectodomain polypeptide comprises a receptor binding domain (RBD) sequence and/or an N-terminal domain (NTD) sequence.

8. The immunogenic composition of claim 7, wherein the NTD sequence and the RBD sequence are independently selected from the group consisting of the NTD and RBD sequences of the B.1.526, B.1.1.143, P.2, B.1.351, P.1, B.1.1.7, B.1.617, and A.23.1 lineages of SARS-CoV-2.

9. The immunogenic composition of claim 8, wherein the NTD sequence is from a SARS-CoV-2 of the B.1.526 lineage, and the RBD sequence is from a SARS-CoV-2 of the B.1.351 lineage.

10. The immunogenic composition of claim 1, comprising a disulfide bond-linked homotrimer of the fusion polypeptide, wherein the disulfide bond-linked homotrimer comprises interchain disulfide bonds among the C-propeptide sequences.

11. The immunogenic composition of claim 10, wherein the fusion polypeptide comprises the sequence set forth in SEQ ID NO: 56.

12. The immunogenic composition of claim 10, wherein the fusion polypeptide comprises the sequence set forth in SEQ ID NO: 67.

13. The immunogenic composition of claim 10, wherein the fusion polypeptide comprises the sequence set forth in SEQ ID NO: 1.

14. The immunogenic composition of claim 1, wherein the one or more adjuvants comprise alum.

15. The immunogenic composition of claim 1, wherein the one or more adjuvants comprise a TLR3 agonist, a TLR4 agonist, a TLR5 agonist, a TLR7 agonist, a TLR8 agonist, and/or a TLR9 agonist.

16. The immunogenic composition of claim 14, wherein the one or more adjuvants comprise CpG.

17. The immunogenic composition of claim 1, wherein the one or more adjuvants comprise squalene, α-tocopherol and polysorbate 80.

18. The immunogenic composition of claim 1, wherein the one or more adjuvants comprise squalene, Span 85 and polysorbate 80.

19. The immunogenic composition of claim 1, wherein the one or more adjuvants comprise monophosphoryl lipid A (MPL).

20. The immunogenic composition of claim 1, wherein the one or more adjuvants comprise a saponin.

* * * * *